US010605808B2

(12) United States Patent
Logtenberg et al.

(10) Patent No.: US 10,605,808 B2
(45) Date of Patent: *Mar. 31, 2020

(54) ANTIBODY PRODUCING NON-HUMAN ANIMALS

(71) Applicant: Merus N.V., Utrecht (NL)

(72) Inventors: Ton Logtenberg, Utrecht (NL); Mark Throsby, Utrecht (NL); Robert A. Kramer, Utrecht (NL); Rui Daniel Pinto, Utrecht (NL); Cornelis A. Dekruif, De Bilt (NL); Erwin Houtzager, Zeist (NL)

(73) Assignee: Merus N.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/140,321

(22) Filed: Apr. 27, 2016

(65) Prior Publication Data

US 2016/0238600 A1 Aug. 18, 2016

Related U.S. Application Data

(63) Continuation of application No. 12/589,181, filed on Oct. 19, 2009, which is a continuation of application No. 12/459,285, filed on Jun. 29, 2009, now abandoned.

(60) Provisional application No. 61/133,274, filed on Jun. 27, 2008.

(51) Int. Cl.
C07K 16/10 (2006.01)
G01N 33/569 (2006.01)
C07K 16/00 (2006.01)
C07K 16/22 (2006.01)
C07K 16/32 (2006.01)
C07K 16/24 (2006.01)
C07K 16/28 (2006.01)

(52) U.S. Cl.
CPC ....... G01N 33/56966 (2013.01); C07K 16/00 (2013.01); C07K 16/005 (2013.01); C07K 16/10 (2013.01); C07K 16/22 (2013.01); C07K 16/248 (2013.01); C07K 16/2863 (2013.01); C07K 16/32 (2013.01); C07K 2317/10 (2013.01); C07K 2317/14 (2013.01); C07K 2317/21 (2013.01); C07K 2317/24 (2013.01); C07K 2317/31 (2013.01); C07K 2317/34 (2013.01); C07K 2317/51 (2013.01); C07K 2317/515 (2013.01); C07K 2317/52 (2013.01); C07K 2317/55 (2013.01); C07K 2317/56 (2013.01); C07K 2317/622 (2013.01); C07K 2317/64 (2013.01); C07K 2317/76 (2013.01); C07K 2317/94 (2013.01); C07K 2319/00 (2013.01)

(58) Field of Classification Search
CPC ................ C07K 16/00; C07K 2317/21; C07K 2317/515; C07K 2317/64; C07K 2317/51; C07K 2317/10; C07K 2317/14
See application file for complete search history.

(56) References Cited

U.S. PATENT DOCUMENTS

| 4,399,216 A | 8/1983 | Axel et al. |
| 4,599,311 A | 7/1986 | Kawasaki |
| 4,634,665 A | 1/1987 | Axel et al. |
| 4,801,687 A | 1/1989 | Ngo |
| 4,816,567 A | 3/1989 | Cabilly et al. |
| 4,868,103 A | 9/1989 | Stavrianopoulos et al. |
| 4,937,190 A | 6/1990 | Palmenberg et al. |
| 5,030,002 A | 7/1991 | North, Jr. |
| 5,137,809 A | 8/1992 | Loken et al. |
| 5,151,504 A | 9/1992 | Croze |
| 5,179,017 A | 1/1993 | Axel et al. |
| 5,223,409 A | 6/1993 | Ladner et al. |
| 5,385,839 A | 1/1995 | Stinski |
| 5,627,037 A | 5/1997 | Ward et al. |
| 5,631,169 A | 5/1997 | Thompson |
| 5,641,640 A | 6/1997 | Hanning |
| 5,667,988 A | 9/1997 | Barbas et al. |
| 5,667,998 A | 9/1997 | Dougherty et al. |
| 5,733,779 A | 3/1998 | Reff |
| 5,770,429 A | 6/1998 | Lonberg et al. |
| 5,772,997 A | 6/1998 | Hudziak et al. |
| 5,783,186 A | 7/1998 | Arakawa et al. |
| 5,789,208 A | 8/1998 | Sharon |
| 5,834,237 A | 11/1998 | Jacobs et al. |
| 5,885,827 A | 3/1999 | Wabl et al. |

(Continued)

FOREIGN PATENT DOCUMENTS

| AU | 2003250074 A1 | 2/2004 |
| CA | 2114353 A1 | 8/1994 |

(Continued)

OTHER PUBLICATIONS

Huang, Y., et al., 2007, An efficient and targeted gene integration system for high-level antibody expression, J. Immunol. Methods 322:28-39.*

Hartman, T. E., et al., 2007, Derivation and characterization of cholesterol-independent non-GS NS0 cell lines for production of recombinant antibodies, Biotechnol. Bioengineering 96(2):294-306.*

Rong et al., Tumorigenesis induced by coexpression of human hepatocyte growth factor and the human met protooncogene leads to high levels of expression of the ligand and receptor, Cell Growth Differ., Jul. 1993, pp. 563-569, vol. 4, No. 7.

Brady et al., Rapid specific amplification of rat antibody cDNA from nine hybridomas in the presence of myeloma light chains, Journal of Immunological Methods, Aug. 31, 2006, pp. 61-67, vol. 315.

(Continued)

Primary Examiner — Jeffrey S Parkin
(74) Attorney, Agent, or Firm — Sterne, Kessler, Goldstein & Fox P.L.L.C.

(57) ABSTRACT

Described are transgenic, non-human animals comprising a nucleic acid encoding an immunoglobulin light chain, whereby the immunoglobulin light chain is a common human, human-like, or humanized light chain. Further provided is methods for producing an immunoglobulin from the transgenic, non-human animal.

9 Claims, 110 Drawing Sheets
Specification includes a Sequence Listing.

(56) References Cited

U.S. PATENT DOCUMENTS

| | | | |
|---|---|---|---|
| 5,888,789 A | 3/1999 | Rodriguez | |
| 5,965,371 A | 10/1999 | Marasco et al. | |
| 6,004,940 A | 12/1999 | Marasco et al. | |
| 6,054,297 A | 4/2000 | Carter et al. | |
| 6,080,560 A | 6/2000 | Russell et al. | |
| 6,114,598 A | 9/2000 | Kucherlapati et al. | |
| 6,180,357 B1 | 1/2001 | Young et al. | |
| 6,207,446 B1 | 3/2001 | Szostak et al. | |
| 6,265,150 B1 | 7/2001 | Terstappen et al. | |
| 6,291,740 B1 | 9/2001 | Bremel et al. | |
| 6,303,341 B1 | 10/2001 | Hiatt et al. | |
| 6,335,163 B1 | 1/2002 | Sharon | |
| 6,586,251 B2 | 7/2003 | Economides et al. | |
| 6,596,541 B2 | 7/2003 | Murphy et al. | |
| 7,067,284 B1 | 6/2006 | Barbas et al. | |
| 7,105,348 B2 | 9/2006 | Murphy et al. | |
| 7,183,076 B2 | 2/2007 | Arathoon et al. | |
| 7,262,028 B2 † | 8/2007 | Van Berkel | |
| 7,329,530 B2 | 2/2008 | Houtzager et al. | |
| 7,429,486 B2 | 9/2008 | Van Berkel et al. | |
| 7,491,516 B2 | 2/2009 | Collinson et al. | |
| 7,579,446 B2 | 8/2009 | Bakker et al. | |
| 7,696,330 B2 | 4/2010 | Meulen et al. | |
| 7,740,852 B2 | 6/2010 | Bakker et al. | |
| 7,777,010 B2 | 8/2010 | Logtenberg | |
| 7,858,086 B2 | 12/2010 | Geuijen et al. | |
| 7,901,919 B2 | 3/2011 | Houtzager et al. | |
| 7,919,257 B2 | 4/2011 | Hoogenboom et al. | |
| 7,927,834 B2 | 4/2011 | Van Berkel et al. | |
| 7,932,360 B2 | 4/2011 | Van Berkel et al. | |
| 7,960,518 B2 | 6/2011 | Throsby et al. | |
| 7,968,092 B2 | 6/2011 | Throsby et al. | |
| 8,052,974 B2 | 11/2011 | Throsby et al. | |
| 8,106,170 B2 | 1/2012 | Ter Meulen et al. | |
| 8,148,497 B2 | 4/2012 | Bakker et al. | |
| 8,192,927 B2 | 6/2012 | Van Den Brink et al. | |
| 8,211,431 B2 | 7/2012 | Throsby et al. | |
| 8,241,631 B2 | 8/2012 | Throsby et al. | |
| 8,268,756 B2 | 9/2012 | Logtenberg et al. | |
| 8,470,327 B2 | 6/2013 | Throsby et al. | |
| 8,502,018 B2 | 8/2013 | Stevens | |
| 8,911,738 B2 | 12/2014 | Throsby et al. | |
| 9,012,371 B2 | 4/2015 | Logtenberg et al. | |
| 9,248,181 B2 | 2/2016 | De Kruif et al. | |
| 9,248,182 B2 † | 2/2016 | De Kruif | |
| 9,303,081 B2 | 4/2016 | Van Berkel et al. | |
| 9,358,286 B2 | 6/2016 | De Kruif et al. | |
| 2002/0088016 A1 | 7/2002 | Bruggemann | |
| 2002/0138857 A1 | 9/2002 | Ghayur | |
| 2003/0039958 A1 | 2/2003 | Holt et al. | |
| 2003/0077739 A1 | 4/2003 | Simmons et al. | |
| 2003/0091561 A1 | 5/2003 | van de Winkel et al. | |
| 2003/0093820 A1 | 5/2003 | Green et al. | |
| 2003/0096225 A1 | 5/2003 | Logtenberg | |
| 2003/0194403 A1 | 10/2003 | van de Winkel et al. | |
| 2003/0207346 A1 | 11/2003 | Arathoon et al. | |
| 2003/0215914 A1 | 11/2003 | Houtzager et al. | |
| 2003/0219829 A1 | 11/2003 | Logtenberg et al. | |
| 2003/0224408 A1 | 12/2003 | Hoogenboom et al. | |
| 2005/0014261 A1 | 1/2005 | Houtzager et al. | |
| 2005/0037001 A1 | 2/2005 | Germeraad et al. | |
| 2005/0037427 A1 | 2/2005 | Houtzager et al. | |
| 2005/0170398 A1 | 8/2005 | Van et al. | |
| 2006/0015949 A1 | 1/2006 | Lonberg et al. | |
| 2006/0015957 A1 | 1/2006 | Lonberg et al. | |
| 2006/0088520 A1 | 4/2006 | Germeraad et al. | |
| 2006/0160184 A1 | 7/2006 | Mattheus Hoogenboom et al. | |
| 2006/0177437 A1 | 8/2006 | Houtzager et al. | |
| 2006/0205077 A1 | 9/2006 | Schwenk et al. | |
| 2006/0257397 A1 | 11/2006 | Throsby et al. | |
| 2006/0292634 A1 | 12/2006 | Houtzager et al. | |
| 2007/0054362 A1 | 3/2007 | Van Berkel et al. | |
| 2007/0059766 A1 | 3/2007 | Logtenberg et al. | |
| 2007/0178552 A1 | 8/2007 | Arathoon et al. | |
| 2007/0280945 A1 | 12/2007 | Stevens et al. | |
| 2008/0070799 A1 | 3/2008 | Bakker et al. | |
| 2008/0241166 A1 | 10/2008 | Tomlinson et al. | |
| 2009/0017521 A1 | 1/2009 | Houtzager et al. | |
| 2009/0054254 A1 | 2/2009 | Throsby et al. | |
| 2009/0130652 A1 | 5/2009 | Throsby et al. | |
| 2009/0181855 A1 | 7/2009 | Vasquez et al. | |
| 2009/0263864 A1 | 10/2009 | Van Berkel et al. | |
| 2010/0069614 A1 | 3/2010 | Houtzager et al. | |
| 2010/0146647 A1 | 6/2010 | Logtenberg et al. | |
| 2010/0172917 A1 | 7/2010 | Ter Meulen et al. | |
| 2010/0297153 A1 | 11/2010 | Geuijen et al. | |
| 2010/0310572 A1 | 12/2010 | Bakker et al. | |
| 2010/0310586 A1 | 12/2010 | Dolcetti et al. | |
| 2010/0331527 A1 | 12/2010 | Davis et al. | |
| 2011/0177073 A1 | 7/2011 | Van Berkel et al. | |
| 2011/0195454 A1 | 8/2011 | McWhirter et al. | |
| 2011/0268739 A1 | 11/2011 | Throsby et al. | |
| 2012/0021409 A1 | 1/2012 | McWhirter et al. | |
| 2012/0039898 A1 | 2/2012 | Throsby et al. | |
| 2012/0058907 A1 | 3/2012 | Logtenberg et al. | |
| 2012/0076794 A1 | 3/2012 | Throsby et al. | |
| 2012/0093823 A1 | 4/2012 | Throsby | |
| 2012/0141493 A1 | 6/2012 | Throsby et al. | |
| 2012/0177637 A1 | 7/2012 | Hoogenboom et al. | |
| 2012/0192300 A1 | 7/2012 | Babb et al. | |
| 2012/0276115 A1 | 11/2012 | Throsby | |
| 2012/0315278 A1 | 12/2012 | Throsby et al. | |
| 2013/0145484 A1 | 6/2013 | Logtenberg et al. | |
| 2014/0314755 A1 | 10/2014 | Logtenberg et al. | |
| 2014/0317766 A1 | 10/2014 | Logtenberg et al. | |
| 2016/0238600 A1 | 8/2016 | Hoogenboom et al. | |

FOREIGN PATENT DOCUMENTS

| | | |
|---|---|---|
| CA | 2405961 | 11/2001 |
| CA | 2405961 A1 | 11/2001 |
| CA | 1341364 | 6/2002 |
| CA | 1341364 C | 6/2002 |
| CA | 2445255 | 10/2002 |
| CA | 2445255 A1 | 10/2002 |
| CA | 2114353 | 1/2006 |
| EP | 0120694 | 10/1984 |
| EP | 0120694 A2 | 10/1984 |
| EP | 0171142 A1 | 2/1986 |
| EP | 0314161 | 5/1989 |
| EP | 0314161 A1 | 5/1989 |
| EP | 0402029 | 12/1990 |
| EP | 0402029 A2 | 12/1990 |
| EP | 0445625 | 9/1991 |
| EP | 0445625 A1 | 9/1991 |
| EP | 0469025 A1 | 2/1992 |
| EP | 0469897 | 2/1992 |
| EP | 0469897 A2 | 2/1992 |
| EP | 0481790 | 4/1992 |
| EP | 0481790 A2 | 4/1992 |
| EP | 171142 A1 | 7/1992 |
| EP | 0523949 | 1/1993 |
| EP | 0523949 A1 | 1/1993 |
| EP | 469025 A1 | 8/1995 |
| EP | 0666868 A1 | 8/1995 |
| EP | 0724639 A1 | 8/1996 |
| EP | 0814159 | 12/1997 |
| EP | 0814159 A2 | 12/1997 |
| EP | 0724639 | 1/2001 |
| EP | 666868 | 4/2002 |
| EP | 1204740 | 5/2002 |
| EP | 1204740 A1 | 5/2002 |
| EP | 1349234 A2 | 10/2003 |
| EP | 1399575 A2 | 3/2004 |
| EP | 1439234 A1 | 7/2004 |
| EP | 1439234 | 11/2004 |
| EP | 1325932 | 4/2005 |
| EP | 1325932 B1 | 4/2005 |
| EP | 1399575 B1 | 7/2006 |
| EP | 2147594 | 1/2010 |
| EP | 2147594 B1 | 11/2013 |
| FR | 2817875 | 6/2002 |
| FR | 2817875 A1 | 6/2002 |
| JP | 5-68599 | 3/1993 |

(56) References Cited

FOREIGN PATENT DOCUMENTS

| | | |
|---|---|---|
| JP | 05-068599 A | 3/1993 |
| JP | 08-116978 A | 5/1996 |
| JP | 8116978 | 5/1996 |
| JP | 2004008214 | 8/2003 |
| JP | 2004-008214 A | 1/2004 |
| JP | 2004-008218 A | 1/2004 |
| JP | 20048218 | 1/2004 |
| JP | 2004-524841 | 8/2004 |
| JP | 2004-524841 A | 8/2004 |
| JP | 2006-109711 | 4/2006 |
| JP | 2006-109711 A | 4/2006 |
| JP | 2006-515503 | 6/2006 |
| JP | 2006-515503 A | 6/2006 |
| JP | 2001-523971 A | 11/2007 |
| JP | 2008-538912 | 11/2008 |
| JP | 2008-538912 A | 11/2008 |
| JP | 2010-505418 | 2/2010 |
| JP | 2010-505418 A | 2/2010 |
| JP | 2010-512749 | 4/2010 |
| JP | 2010-512749 A | 4/2010 |
| JP | 2011-525808 | 9/2011 |
| JP | 2011-525808 A | 9/2011 |
| JP | 2013-004215 A | 1/2013 |
| JP | 2013004215 A | 1/2013 |
| JP | 5749161 B2 | 4/2015 |
| JP | 5749161 | 5/2015 |
| RU | 2236127 C2 | 9/2004 |
| WO | 90/02809 A1 | 3/1990 |
| WO | 9002809 | 3/1990 |
| WO | 90/12878 A1 | 11/1990 |
| WO | 9012878 A1 | 11/1990 |
| WO | 91/00906 A1 | 1/1991 |
| WO | 9100906 | 1/1991 |
| WO | 9100906 A1 | 1/1991 |
| WO | 91/08216 A1 | 6/1991 |
| WO | 9108216 | 6/1991 |
| WO | 91/17271 A1 | 11/1991 |
| WO | 9117271 | 11/1991 |
| WO | 92/01047 A1 | 1/1992 |
| WO | 9201047 | 1/1992 |
| WO | 92/03918 A1 | 3/1992 |
| WO | 9203918 A1 | 3/1992 |
| WO | 92/09690 A2 | 6/1992 |
| WO | 9209690 | 6/1992 |
| WO | 92/15679 A1 | 9/1992 |
| WO | 9215679 | 9/1992 |
| WO | 92/18619 A1 | 10/1992 |
| WO | 9218619 | 10/1992 |
| WO | 92/20791 A1 | 11/1992 |
| WO | 9220791 | 11/1992 |
| WO | 93/01288 A1 | 1/1993 |
| WO | 9301288 | 1/1993 |
| WO | 93/12227 A1 | 6/1993 |
| WO | 9312227 A1 | 6/1993 |
| WO | 94/02602 A1 | 2/1994 |
| WO | 94/02610 A1 | 2/1994 |
| WO | 9402602 | 2/1994 |
| WO | 9402610 | 2/1994 |
| WO | 94/23046 A1 | 10/1994 |
| WO | 9423046 A1 | 10/1994 |
| WO | 94/25591 A1 | 11/1994 |
| WO | 9425591 | 11/1994 |
| WO | 95/17085 A1 | 6/1995 |
| WO | 95/17500 A1 | 6/1995 |
| WO | 9517085 | 6/1995 |
| WO | 9517500 | 6/1995 |
| WO | 95/20401 A1 | 8/1995 |
| WO | 9520401 | 8/1995 |
| WO | 96/27011 A1 | 9/1996 |
| WO | 9627011 | 9/1996 |
| WO | 97/42313 A1 | 11/1997 |
| WO | 9742313 | 11/1997 |
| WO | 97/47739 A1 | 12/1997 |
| WO | 9747739 | 12/1997 |
| WO | 98/15627 A1 | 4/1998 |
| WO | 98/15833 A1 | 4/1998 |
| WO | 9815627 | 4/1998 |
| WO | 9815833 | 4/1998 |
| WO | 98/24923 A1 | 6/1998 |
| WO | 9824923 A1 | 6/1998 |
| WO | 98/39416 A1 | 9/1998 |
| WO | 98/41645 A1 | 9/1998 |
| WO | 9839416 | 9/1998 |
| WO | 9841645 | 9/1998 |
| WO | 98/50431 A2 | 11/1998 |
| WO | 98/52976 A1 | 11/1998 |
| WO | 1998/050431 A2 † | 11/1998 |
| WO | 9850431 | 11/1998 |
| WO | 9852976 | 11/1998 |
| WO | 99/15684 A2 | 4/1999 |
| WO | 99/20749 A1 | 4/1999 |
| WO | 9915684 A2 | 4/1999 |
| WO | 9920749 | 4/1999 |
| WO | 99/23221 A2 | 5/1999 |
| WO | 9923221 | 5/1999 |
| WO | 99/26569 A1 | 6/1999 |
| WO | 9926569 A1 | 6/1999 |
| WO | 99/36569 A1 | 7/1999 |
| WO | 9936569 | 7/1999 |
| WO | 99/45962 A1 † | 9/1999 |
| WO | 1999/045962 A1 † | 9/1999 |
| WO | 9945962 | 9/1999 |
| WO | 99/50657 A1 | 10/1999 |
| WO | 1999050657 | 10/1999 |
| WO | 99/64582 A2 | 12/1999 |
| WO | 9964582 | 12/1999 |
| WO | 00/23540 A1 | 4/2000 |
| WO | 200023540 A1 | 4/2000 |
| WO | 00/44777 A1 | 8/2000 |
| WO | 44777 A1 | 8/2000 |
| WO | 00/63403 | 10/2000 |
| WO | 00/63403 A2 | 10/2000 |
| WO | 0063403 | 10/2000 |
| WO | 00/70023 A1 | 11/2000 |
| WO | 00/71694 A1 | 11/2000 |
| WO | 0070023 | 11/2000 |
| WO | 0071694 | 11/2000 |
| WO | 00/76310 A1 | 12/2000 |
| WO | 0076310 | 12/2000 |
| WO | 01/00245 A2 | 1/2001 |
| WO | 0100245 | 1/2001 |
| WO | 01/19394 A2 | 3/2001 |
| WO | 0119394 | 3/2001 |
| WO | 01/27279 A1 | 4/2001 |
| WO | 0127279 | 4/2001 |
| WO | 01/32901 A1 | 5/2001 |
| WO | 0132901 | 5/2001 |
| WO | 01/48485 A2 | 7/2001 |
| WO | 0148485 | 7/2001 |
| WO | 01/64929 A1 | 9/2001 |
| WO | 0164929 | 9/2001 |
| WO | 01/88132 A2 | 11/2001 |
| WO | 0188132 | 11/2001 |
| WO | 188132 A2 | 11/2001 |
| WO | 02/18948 A2 | 3/2002 |
| WO | 0218948 | 3/2002 |
| WO | 02/36789 A2 | 5/2002 |
| WO | 0236789 A2 | 5/2002 |
| WO | 02/43478 A2 | 6/2002 |
| WO | 02/46233 A1 | 6/2002 |
| WO | 0243478 | 6/2002 |
| WO | 0246233 | 6/2002 |
| WO | 02/59297 A2 | 8/2002 |
| WO | 02/66630 A | 8/2002 |
| WO | 02/066630 A1 † | 8/2002 |
| WO | 2059297 A2 | 8/2002 |
| WO | 02066630 | 8/2002 |
| WO | 02/74969 A2 | 9/2002 |
| WO | 02074969 | 9/2002 |
| WO | 02/96948 A2 | 12/2002 |
| WO | 02096948 | 12/2002 |
| WO | 03/04704 A2 | 1/2003 |
| WO | 2003/002609 A2 | 1/2003 |
| WO | 03002609 | 1/2003 |

(56) References Cited

FOREIGN PATENT DOCUMENTS

| | | |
|---|---|---|
| WO | 03004704 | 1/2003 |
| WO | 03/16501 A2 | 2/2003 |
| WO | 03016501 | 2/2003 |
| WO | 03/33670 A2 | 4/2003 |
| WO | 3033670 A2 | 4/2003 |
| WO | 03/46560 A2 | 6/2003 |
| WO | 03/48306 A2 | 6/2003 |
| WO | 03046560 | 6/2003 |
| WO | 03047336 A2 | 6/2003 |
| WO | 03048306 | 6/2003 |
| WO | 2003/102157 A2 | 12/2003 |
| WO | 2003/106674 A2 | 12/2003 |
| WO | 2003/106684 A2 | 12/2003 |
| WO | 03102157 | 12/2003 |
| WO | 3106674 A2 | 12/2003 |
| WO | 03106684 | 12/2003 |
| WO | 2004/003211 A1 | 1/2004 |
| WO | 2004/009618 A2 | 1/2004 |
| WO | 2004009618 | 1/2004 |
| WO | 2004003211 | 8/2004 |
| WO | 2004/106375 A1 † | 12/2004 |
| WO | 2004106375 | 12/2004 |
| WO | 2004106375 A1 | 12/2004 |
| WO | 2005/068622 A2 | 7/2005 |
| WO | 2005068622 | 7/2005 |
| WO | 2006/068953 A2 | 6/2006 |
| WO | 2006068953 A2 | 6/2006 |
| WO | 2006/117699 A2 | 11/2006 |
| WO | 2006117699 | 11/2006 |
| WO | 2007/117410 A2 | 10/2007 |
| WO | 2007117410 | 10/2007 |
| WO | 2008/054606 A2 | 5/2008 |
| WO | 2008054606 | 5/2008 |
| WO | 2008/076379 A2 | 6/2008 |
| WO | 2008076379 | 6/2008 |
| WO | 2009/018411 A1 | 2/2009 |
| WO | 2009018411 A1 | 2/2009 |
| WO | 2009/089004 A1 | 7/2009 |
| WO | 2009089004 A1 | 7/2009 |
| WO | 2009/157771 A2 | 12/2009 |
| WO | 2009157771 | 12/2009 |
| WO | 2011/014469 A1 | 2/2011 |
| WO | 2011014469 A1 | 2/2011 |
| WO | 2011/097603 A1 | 8/2011 |
| WO | 2011097603 | 8/2011 |
| WO | 2012/141798 A1 | 10/2012 |
| WO | 2012141798 | 10/2012 |
| WO | 2016/081923 A2 | 5/2016 |
| WO | 2016081923 A2 | 5/2016 |

OTHER PUBLICATIONS

Inlay et al., Roles of the Ig kappa light chain intronic and 3' enhancers in Igk somatic hypermutation, J. Immunol., 2006, pp. 1146-1151, vol. 177(2).

Novobrantseva et al., Rearrangement and expression of immunoglobulin light chain genes can precede heavy chain expression during normal B cell development in mice, J. Exp. Med., Jan. 4, 1999, pp. 75-88, vol. 189, No. 1.

Pasqualucci et al., BCL-6 mutations in normal germinal center B cells: evidence of somatic hypermutation acting outside Ig loci, Proc. Natl. Acad. Sci. USA, Sep. 1998, pp. 11816-11821, vol. 95.

Srinivas et al., Cre reporter strains produced by targeted insertion of EYFP and ECFP into the ROSA26 locus, BMC Dev. Bioi., Mar. 27, 2001, vol. 1 :4.

Mirick et al., A review of human anti-globulin antibody (HAGA, HAMA, HACA, HAHA) responses to monoclonal antibodies: not four letter words, Q. Nucl. Med. Mol. Imaging, Dec. 2004, pp. 251-257, vol. 48, No. 4.

De Haard, et al., A large non-immunized human Fab fragment phage library that permits rapid isolation and kinetic analysis of high affinity antibodies,J. Biol. Chem., 1999, pp. 18218-18230, vol. 274.

Flavell et al., Systemic Therapy with 3BIT, a Triple Combination Cocktail of Anti-CD 19, -CD22, and -CD38-Saporin Immunotoxins, Is Curative of Human B-Cell Lymphoma in Severe Combined Immunodeficient Mice, Cancer Research, Nov. 1997, pp. 4824-29, vol. 57.

Peeters et al., "Production of antibodies and antibody fragments in plants", Elsevier, Vaccine, vol. 19, 2001, pp. 2756-2761.

Segal et al., "Introduction: bispecific antibodies", Elsevier, Journal of Immunological Methods, vol. 248, 2001, pp. 1-6.

Vaughan et al., "Human Antibodies with Sub-nanomolar Affinities Isolated from a Large Non-immunized Phage Display Library", Nature Biotechnology, vol. 14, Mar. 1996, pp. 309-314.

Kasprzyk et al., "Therapy of an Animal Model of Human Gastric Cancer Using a Combination of Anti-erbB-2 Monoclonal Antibodies", Cancer Research, vol. 52, May 15, 1992, pp. 2771-2776.

Flavell et al., "Therapy of human T-cell acute lymphoblastic leukaemia with a combination of anti-CD7 and anti-CD38-SAPORIN immunotoxins is significantly better than therapy with each individual immunotoxin", British Journal of Cancer, vol. 84, No. 4, 2001, pp. 571-578.

Casellas et al., "Contribution of Receptor Editing to the Antibody Repertoire", Science, vol. 291, Feb. 23, 2001, pp. 1541-1544.

Radic et al., "Ig H and L Chain Contributions to Autoimmune Specificities[1]", The Journal of Immunology, vol. 146, No. 1, Jan. 1, 1991, pp. 176-182.

Wildt et al., "Analysis of Heavy and Light Chain Pairings Indicates that Receptor Editing Shapes the Human Antibody Repertoire", Journal of Molecular Biology, vol. 285, 1999, pp. 895-901.

EPO Communication of a notice of opposition for EP Application No. 10186063.3 and EP Patent No. 2314629, Jul. 21, 2014, EPO Form 2316, 01.12, one page.

EPO Brief Communication regarding the Opposition againts EP Application No. 10186063.3 and EP Patent No. 2314629, Oct. 24, 2014, EPO Form 2911O 01.12, one page.

EPO Acknowledgement of Receipt of the submission by the proprietor, EP Application No. 10186063.3 and EP Patent No. 2314629, dated Feb. 24, 2015, one page.

EPO Brief Communication regarding the Opposition against EP Application No. 10186063.3 and EP Patent No. 2314629, Feb. 27, 2015, EPO Form 2911O 01.12, one page.

Letter from Mr. C.M. Jansen of V.O. Patents & Trademarks to European Patent Office, Regarding Registration of the Association and change of address, dated Sep. 29, 2015, one page.

EPO Communication of amended entries concerning the representative (R. 143(1)(h) EPC), EP Application No. 10186063.3 and EP Patent No. 2314629, dated Oct. 8, 2015, EPO Form 2548, 08.13, one page.

EPO Communication to V.O., Acknowledgement of receipt of EPO Forms 2310 and 2043, EP Application No. 10186063.3 and EP Patent No. 2314629, dated Nov. 19, 2015, EPO Form 2936 08.10, one page.

V.O. communication to EPO, Executed Acknowledgement of receipt of EPO Form 2310 and 2043, EP Application No. 10186063.3 and EP Patent No. 2314629, dated Nov. 20, 2015, EPO Form 2936 08.10, one page.

EPO Submission in opposition proceedings, Acknowledgement of Receipt filed by David Power of J A Kemp, EP Application No. 10186063.3 and EP Patent No. 2314629, dated Nov. 20, 2015, two pages.

EPO Acknowledgement of receipt, Acknowledgement of Receipt, Application No. 10186063.3 and EP Patent No. 2314629, dated Nov. 27, 2015, one page.

J A Kemp communication to EPO, Executed Acknowledgement of receipt of EPO Form 2310 and 2043, EP Application No. 10186063.3 and EP Patent No. 2314629, dated Nov. 25, 2015, EPO Form 2936 08.10, one page.

EPO Letter accompanying subsequently filed items, Document concerning representation filed by C.M. Jansen of V.O., EP Application No. 10186063.3, Dec. 17, 2015, one page.

Correspondence from C.M. Jansen of V.O. to the European Patent Office regarding change of correspondence, EP Application No. 10186063.3 and EP Patent No. 2314629, dated Dec. 17, 2015, one page.

(56) References Cited

OTHER PUBLICATIONS

Correspondence from Dr. Fritz Lahrtz of Isenbruck Bösl Förschler LLP to the European Patent Office regarding Change ef correspondence, EP Application No. 10186063.3 and EP Patent No. 2314629, dated Jan. 8, 2016, one page.
Rong et al., Tumorigenicity of the met proto-oncogene and the gene for hepatocyte growth factor, Mol. Cell Biol., Nov. 1992, pp. 5152-5158, vol. 12, No. 11.
Jeffers et al., Enhanced tumorigenicity and invasion-metastasis by hepatocyte growth factor/scatter factor-met signalling in human cells concomitant with induction of the urokinase proteolysis network, Mol. Cell. Biol., Mar. 1996, pp. 1115-1125, vol. 16, No. 3.
Lu et al., Identification of the Residues in the Extracellular Region of KDR Important for Interaction with Vascular Endothelial Growth Factor and Neutralizing Anti-KDR Antibodies, J. Biol. Chem., May 12, 2000, pp. 14321-14330, vol. 275.
Zhu et al., Inhibition of vascular endothelial growth factor-induced receptor activation with anti-kinase insert domain-containing receptor single-chain antibodies from a phage display library, Cancer Res., Aug. 1998, pp. 3209-14, vol. 58, No. 15.
Eggan et al., Hybrid vigor, fetal overgrowth, and viability of mice derived by nuclear cloning and tetraploid embryo complementation, PNAS, May 22, 2001,pp. 6209-6214, vol. 98, No. 11.
Throsby, Isolation and Characterization of Human Monoclonal Antibodies from Individuals Infected with West Nile Virus, J. Virol., Jul. 2006, pp. 6982-92, vol. 80, No. 14.
Fendly et al., Characterization of Murine Monoclonal Antibodies Reactive to Either the Human Epidermal Growth Factor Receptor or HER2/neu Gene Product, Cancer Research, Mar. 1, 1990, pp. 1550-1558, vol. 50.
Xu et al., "Deletion of the Ig kappa light chain intronic enhancer/ matrix attachment region impairs but does not abolish V kappa J kappa rearrangement," Immunity (1996) 4:377-385.
F.T. Wunderlich (2004), "Generation of inducible Cre systems for conditional gene inactivation in mice," Inauguraldissertation zur Erlangung des Doktorgrades der Mathematisch Naturwissenschaftlichen Fakultät der Universität zu Köln; on the World Wide Web at deposit.ddb.de/cgi bin/dokserv?idn=97557230x&dok_var= d1&dok_ext=pdf&filename= 97557230x.pd.
Wen et al., Tricistronic viral vectors co-expressing interleukin-12 (1L-12) and CD80 (B7-1) for the immunotherapy of cancer: Preclinical studies in myeloma, Cancer Gene Therapy, 2001,pp. 361-370, vol. 8 No. 5.
De Wildt et al., Analysis of Heavy and Light Chain Pairings Indicates that Receptor Editing Shapes fhe Human Antibody Repertoire, J. Mol. Biol., 1999, pp. 895-901, vol. 285, No. 3.
De Chiara, Thomas M. et al., "VelociMouse: Fully ES Cell-Derived FO-Generation Mice Obtained from the Injection of ES Cells into Eight-Cell-Stage Embryos," Gene Knockout Protocols: Second Edition, Rail Kuhn (Ed.), Humana Press, vol. 530, Chapter 16, pp. 311-324 (2009).
Sasaki, Yoshiteru et al., "Canonical NF-kB Activity, Dispensable forB Cell Development, Replaces BAFF-Receptor Signals and Promotes B Cell Proliferation upon Activation," Immunity, vol. 24:729-739 (2006).
Van Doorn. S.T., Additional post-filing data and letter filed by the patentee, 1 page, dated Jun. 13, 2013.
Kling, Jim, "Big Pharma vies for mice," Nature Biotechnology, vol. 25 (6):613 (2007).
Reiter, Marc W. et al., "Receptor Editing Occurs Frequently during Normal B Cell Development," J. Exp. Med., vol. 188(7):1231-1238 (1998).
Attaelmannan, Mohammed et al., "Understanding and Identifying Monoclonal Gammopathies," Clinical Chemistry, vol. 46(88):1230-1238 (2000).
Yarilin, A.A., Osnovy Immunologii, [Fundamentals of Immunology], Meditsina, Moscow, p. 195 (1999).
Roitt, A. et al., Immunology, Mir, Moscow, pp. 134,214 (2000).
Yarilin, A.A. et al., Osnovy Immunologii, [Fundamentals of Immunology], Medilsina, Moscow, p. 194 (1999).
Aucouturier et al., Monoclonal Ig L Chain and L Chain V Domain Fragment Crystallization in Myeloma-Associated Fanconi's Syndrome, The Journal of Immunology, Apr. 5, 1993, pp. 3561-3568, vol. 150, No. 8.
Hiatt et al., Production of antibodies in transgenic plants, Nature, Nov. 2, 1989, pp. 76-78, vol. 342.
Radic et al., Ig H and L chain contributions to autoimmune specificities, The Journal of Immunology, Jan. 1, 1991, pp. 176-182, vol. 146, No. 1, The American Association of Immunologists.
EP Priority Document of EP Application No. 02077953.4, "Recombinant Production of Mixtures of Antibodies", submitted in International Application No. PCT/EP03107690, Sep. 5, 2003, 140 pages.
EP Priority Document of International Application No. PCT/EP03/ 50201, "Recombinant Production of Mixtures of Antibodies", submitted in International Application No. PCT/EP03/07690, Sep. 1, 2003, 168 pages.
Request for Grant of a European Patent for EP Application No. 10186063.3, dated Oct. 1, 2010, 6 pages.
Designation of Inventor Van Berkel Patricius Hendrikus, at least as early as Oct. 1, 2010, 1 page.
Designation of Inventor Logtenberg Ton, at least as early as Oct. 1, 2010, 1 page.
Drawings, at least as early as Oct. 1, 2010, 33 pages.
Sequence Listing, at least as early as Oct. 1, 2010, 18 pages.
EPO Communication pursuant to the Decision of the President of the European Patent Office on the filing of priority document, EP Application No. 10186063.3, dated Oct. 21, 2010, EPO Form 1195, 04.09 PRIO, 1 page.
EPO Invitation to remedy deficiencies pursuant to Rule 30(3) EPC / Rule 163(3) EPC, EP Application No. 10186063.3, dated Nov. 23, 2010, EPO Form 1128, 05.10, 3 pages.
EPO Communication pursuant to Rule 55 EPC, EP Application No. 10186063.3, dated Nov. 25, 2010, EPO Form 1047A, 11.09, 1 page.
Sequence Listing, Jan. 27, 2011, 12 pages.
Refund of Fees, EP Application No. 10186063.3, Jun. 4, 2011, EPO Form 2907, 12.07, 1 page.
EPO Communication pursuant to Rules 70(2) and 70a(2) EPC and reference to Rule 39(1) EPC, EP Application No. 10186063.3, dated May 2, 2011, EPO Form 1082, 04.10, 2 pages.
Response to Communication pursuant to Rules 70(2) and 70a(2) EPC and reference to Rule 39(1) EPC, EP Application No. 10186063. 3, dated Oct. 17, 2011, 16 pages.
EPO Communication regarding Applicant Address Change, EP Application No. 10186063.3, dated Jan. 26, 2012, EPO FOrm 2544, 04.10, 1 page.
EPO Communication pursuant to Article 94(3) EPC, Application No. 10186063.3, dated Jun. 11, 2012, EPO Form 2001, 12.10CSX, 3 pages.
Response to Communication pursuant to Article 94(3) EPC, EP Application No. 10186063.3, dated Jul. 19, 2012, 45 pages.
Notification to EPO regarding Request for recording a change in name of representative, EP Application No. 10186063.3, dated Mar. 23, 2013, 3 pages.
EPO communication, Client Database System (CDS)—clean up, EP Application No. 10186063.3, dated Apr. 23, 2013, EPO Form 2596C, 04.08, 1 page.
EPO Communication under rule 71(3) EPC, EP Application No. 10186063.3, dated Jun. 17, 2013, EPO Form 2004C, 34.12TRI, 196 pages.
Letter accompanying subsequently filed items regarding translations of claims, EP Application No. 10186063.3, dated Sep. 6, 2013, 13 pages.
EPO Transmission of the certificate for a European patent pursuant to Rule 74 EPC, EP Application No. 10186063.3, Oct. 18, 2013, EPO Form 2047, 12.07, 1 page.
Nicholson et al, "Antibody Repertoires of Four- and Five-Feature Translocus Mice Carrying Human Immunoglobulin Heavy Chain and k and λ Light Chain Yeast Artificial Chromosomes[1]", The American Assoication of Immunologists, 1999, 002-1767/99, pp. 6898-6906.

(56) References Cited

OTHER PUBLICATIONS

Mendez et al., "Functional transplant of megabase human immunoglobulin loci recapitulates human antibody response in mice", Nature genetics, vol. 15, Feb. 1997, pp. 146-156.
Merchant et al., "An efficient route to human bispecific IgG", Nature Biotechnology, vol. 16, Jul. 1998, pp. 676-681.
Larrick et al., "Producing proteins in transgenic plants and animals", Elsevier Science Ltd., Current Opinion in Biotechnology 2001, 12, pp. 411-418.
Wilmut et al., "Basic techniques for tansgenesis", AFRC Institute of Animal Physiology and Genetics Research, Journal of Reproduction & Fertility Ltd, 1991, pp. 265-275.
Schnieke et al., "Human Factor IX Transgenic Sheep Produced by Transfer of Nuclei from Transfected Fetal Fibroblasts", Science, vol. 278, Dec. 19, 1997, pp. 2130-2133.
EPO communication to Fritz Lahrtz of Isenbruck Bösl Höschler LLP, Communication of amended entries concerning the representative (R. 143(1)(h) EPC), EP Application No. 10186063.3 and EP Patent No. 2314629, dated Jan. 12, 2016, EPO Form 2548 08.13, one page.
EPO communication to Andrew Bentham of J A Kemp, Brief Communication regarding EPO Form 2548 dated Jan. 12, 2016, EP Application No. 10186063.3 and EP Patent No. 2314629, dated Jan. 12, 2016, EPO Form 291000 01.12, two pages.
Correspondence from Dr. Fritz Lahrtz of Isenbruck Bösl Förschler LLP to the European Patent Office regarding the Oral Proceedings on Jun. 22, 2016, EP Application No. 10186063.3 and EP U.S. Pat. No. 2314629, dated Feb. 16, 2016, one page.
EPO communication, Maintenance / Change of date / Cancellation of oral proceedings arranged for: Jun. 22, 2016 at 10.00 hrs, EP Application No. 10186063.3 and EP Patent No. 2314629, dated Feb. 22, 2016, EPO Form 2088 06.14, two pages.
EPO communication to Andrew Bentham of J A Kemp, Brief Communication regarding Oral Proceedings on Jun. 22, 2016 at 10:00 in S2.1., EP Application No. 10186063.3 and EP Patent No. 2314629, dated Feb. 25, 2016, EPO Form 291000 01.12, one page.
EPO communication to Fritz Lahrtz of Isenbruck Bösl Höschler LLP, Brief Communication regarding letter dated Feb. 16, 2016, EP Application No. 10186063.3 and EP Patent No. 2314629, dated Mar. 7, 2016, EPO Form 2310A 12.07, one page.
EPO communication to Andrew Bentham of J A Kemp, Brief Communication regarding Oral Proceedings on Jun. 22, 2016 and the Letter from the proprietor of the patent dated Feb. 16, 2016, EP Application No. 10186063.3 and EP Patent No. 2314629, dated Mar. 7, 2016, EPO Form 2310A 12.07, two pages.
EPO communication to Fritz Lahrtz of Isenbruck Bösl Höschler LLP, Brief Communication regarding Oral proceedings on Jun. 22, 2016 at 10:00 in S2.1, EP Application No. 10186063.3 and EP Patent No. 2314629, dated Apr. 26, 2016, EPO Form 29110 01.12, one page.
Auxiliary Request 1, EP Patent No. 2314629B1, May 20, 2016, five pages.
Auxiliary Request 2, EP Patent No. 2314629B1, May 20, 2016, five pages.
Auxiliary Request 3, EP Patent No. 2314629B1, May 20, 2016, five pages.
Auxiliary Request 4, EP Patent No. 2314629B1, May 20, 2016, five pages.
Auxiliary Request 5, EP Patent No. 2314629B1, May 20, 2016, five pages.
Auxiliary Request 6, EP Patent No. 2314629B1, May 20, 2016, five pages.
Auxiliary Request 7, EP Patent No. 2314629B1, May 20, 2016, five pages.
Auxiliary Request 8, EP Patent No. 2314629B1, May 20, 2016, five pages.
Auxiliary Request 9, EP Patent No. 2314629B1, May 20, 2016, five pages.
Auxiliary Request 10, EP Patent No. 2314629B1, May 20, 2016, five pages.
Auxiliary Request 12, EP Patent No. 2314629B1, May 20, 2016, three pages.
Auxiliary Request 13, EP Patent No. 2314629B1, May 20, 2016, five pages.
Auxiliary Request 14, EP Patent No. 2314629B1, May 20, 2016, five pages.
Main Request with annotations, EP Patent No. 2314629B1, May 20, 2016, five pages.
Auxiliary Request 1 with annotations, EP Patent No. 2314629B1, May 20, 2016, five pages.
Auxiliary Request 2 with annotations, EP Patent No. 2314629B1, May 20, 2016, five pages.
Auxiliary Request 4 with annotations, EP Patent No. 2314629B1, May 20, 2016, five pages.
Auxiliary Request 7 with annotations, EP Patent No. 2314629B1, May 20, 2016, seven pages.
Auxiliary Request 8 with annotations, EP Patent No. 2314629B1, May 20, 2016, seven pages.
Auxiliary Request 11 with annotations, EP Patent No. 2314629B1, dated May 20, 2016, five pages.
Auxiliary Request 12 with annotations, EP Patent No. 2314629B1, May 20, 2016, five pages.
Auxiliary Request 13 with annotations, EP Patent No. 2314629B1, May 20, 2016, five pages.
Auxiliary Request 14 with annotations, EP Patent No. 2314629B1, May 20, 2016, five pages.
Main Request, EP Patent No. 2314629B1, May 20, 2016, five pages.
Opposition Filed Against European Patent No. EP 2 314 629 B1 (European Patent Application No. 10186063.3) in the Name of Merus B.V., Declaration of Dr. Joel Martin, May 18, 2016, 13 pages.
Appeal Brief under 37 C.F.R. § 41.37 filed by Brenda Herschbach Jarrell, U.S. Appl. No. 13/948,818, Jul. 20, 2015, 26 pages.
Huls et al., "Antitumor Immune Effector Mechanisms Recruited by Phage Display-derived Fully Human IgG1 and IgA1 Monoclonal Antibodies", Cancer Research, vol. 59, Nov. 15, 1999, pp. 5778-5784.
Holliger et al., "Diabodies": Small bivalent and bispecific antibody fragments, Proc. Natl. Acad. Sci., Jul. 1993, pp. 3444-3448, vol. 90.
Kortt et al., Dimeric and trimeric antibodies: high avidity scFvs for cancer targeting, Biomol. Eng., Oct. 15, 2001, pp. 95-108, vol. 18, No. 3.
Ma et al., Assembly of monoclonal antibodies with IgG1 and IgA heavy chain domains in transgenic tobacco plants, Eur. J. Immunol., 1994, p. 131-38, vol. 24.
Warnaar et al., Hybridoma, 1994, pp. 519-526, vol. 13, No. 6.
Heintges et al., Cloning, Bacterial Expression and Sequencing of Human Antibody Fragments Against Hepatitis C Virus NS3 by Phage Display of a Combinatorial Phagemid Library, Hepatology, p. 497, vol. 28, No. 4, 1998.
Burioni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 29-35, vol. 288, No. 1.
Chen et al., Abstract, Selection and analysis of an optimized anti-VEGF antibody: crystal structure of an affinity-matured Fab in complex with antigen, Journal of Molecular Biology, Nov. 5, 1999, pp. 865-881, vol. 293, No. 4.
Champion et al., Abstract, the development of monoclonal human rabies virus-neutralizing antibodies as a substitute for pooled human immune globulin in the prophylactic treatment of rabies virus exposure, Abstract, Journal of Immunological Methods, Feb. 2000, pp. 81-90, vol. 235, No. 1-2, Elsevier Science Publishers B.V., Amsterdam, NL.
Lu et al., Selection of high affinity human neutralizing antibodies to VEGFR2 from a large antibody phage display library for antiangiogenesis therapy, Abstract, International Journal of Cancer, Jan. 20, 2002, pp. 393-399, vol. 97, No. 3.
Sidhu et al., Phage-displayed antibody libraries of synthetic heavy chain complementarily determining regions, Abstract, Journal of Molecular Biology, Apr. 23, 2004, pp. 299-310, vol. 338, No. 2.
Friedenson et al., Immunoglobulin G Antibodies from an Individual Rabbit in Which Several Heavy Chain Variants Are Paired with One

(56) References Cited

OTHER PUBLICATIONS

Light Chain Sequence, The Journal of Biological Chemistry, 1973, pp. 7073-7079, vol. 248, No. 20.
Skerra, Arne, 'Anticalins': A New Class of Engineered Ligand-Binding Proteins with Antibody-Like Properties, 2001, Reviews in Molecular Biotechnology, pp. 257-75, vol. 74, Elsevier.
Rojas et al. Phage antibody fragments library combining a single human light chain variable region with immune mouse heavy chain variable regions, Journal of Biotechnology, 2002, pp. 287-298, vol. 94.
Carmack et al, Influence of a Vkappa8 L Chain Transgene on Endogenous Rearrangements and the Immune Response to the HA(SB) Determinant on Influenza Virus The Journal of Immunology, 1991, vol. 147, No. 6, pp. 2024-2033.
Lenz, et al.; Expression of heterobispecific antibodies by genes transfected into producer hybridoma cellsGene; 87 Mar. 15, 1990, No. 2; pp. 213-218.
Morimoto et al., High level expression of a human rabies virus-neutralizing monoclonal antibody by a rhabdovirus-based vector, J. Immunol. Methods, Jun. 2001, pp. 199-206, vol. 1, No. 252(1-2).
Arai et al., Antibody responses induced by immunization with a Japanese rabies vaccine detennined by neutralization test and enzyme-linked immunosorbent assay, Vaccine, Jun. 2002, pp. 2448-2453, vol. 7, No. 20(19-20).
Perrin et al., In vitro rabies vaccine potency appraisal by ELISA: advent of the immunocapture method with a neutralizing anti-glycoprotein monoclonal antibody, Biologicals, Oct. 1990, pp. 321-330, vol. 18(4).
Conrath et al., Camel Single-domain Antibodies as Modular Building Units in Bispecific and Bivalent Antibody Constructs, The Journal of Biological Chemistry, 200 I, pp. 7346-7350, vol. 276, No. 10.
ECACC deposit, Deposit Reference 03041601 dated Apr. 16, 2003.
Flavell et al., Therapy of human T-cell acute lymphoblastic leukaemia with a combination of anti-CD7 and anti-CD38-SAPORIN immunotoxins is significantly better than therapy with each individual immunotoxin, British Journal of Cancer, Feb. 2001, pp. 571-578, vol. 84, No. 4.
Declaration of Peter Hudson, May 1, 2015, 52 pages.
Declaration of Andrew Murphy, Dec. 19, 2014, 18 pages.
Declaration of David Tarlinton, Dec. 21, 2014, 40 pages.
Second Declaration of Robert Brink, Jun. 2, 2015, 38 pages.
Second Declaration of Peter Hudson, Jun. 2, 2015, 81 pages.
Gonzales-Fernandez et al., Analysis of somatic hypennutation in mouse Peyer's patches using immunoglobulin K lightchain transgenes, Proc. Natl. Acad. Sci., Nov. 1993, pp. 9862-9866, vol. 90.
Goyenechea et al., Modifying the sequence of an immunoglobulin V-gene alters the resulting pattern of lypermutation, Proc. Natl. Acad. Sci. 1996, pp. 13979-13984, vol. 93.
Hengstschlager et al., A lambda 1 trans gene under the control of a heavy chain promoter and enhancer does not undergo somatic hypennutation, Eur. J. Immunol. 1994, pp. 1649-1656, vol. 24.
Klotz et al., Somatic Hypermutation of a lambda, Transgene Under the Control of the lambda, Enhancer or the Heavy Chain Intron Enhancer, The Journal oflnununology, 1996. pp. 4458-4463. vol. 157.
Kong et al., A lambda 3' Enhancer Drives Active and Untemplated Somatic Hypermutation of a lambda1 Trans gene, The Journal oflmmunology, 1998, pp. 294-301, vol. 161.
Mendez et al., Functional transplant of megabase human immunoglobulin loci recapitulates human antibody response in mice, Nature Genetics. 1997. pp. 146-156. vol. 15.
Sharpe et al., Somatic hypermutation of immunoglobulin kappa may depend on sequences 3' of C kappa and occurs on passengertransgenes, The EMBO.Ioumal. 1991. pp. 2139-2145, vol. 10, No. 8.
ImMunoGeneTics Information System, for analysed sequence CHEB VK, http://www.imgt.org/IMGT vguesVvguest, at east as early as Apr. 25, 2012.
NCBI, Aucouturier et al., Monoclonal IgL Claim and L chain V domain fragment crystallization in myeloma-associated Fanconi's syndrome, <http://www.ncbi.nlm.nib/gov/nuccore/M87478, at least as early as Apr. 25, 2012.
Third Party Observations Under Article 115 EPC Against European Parent Application No. 09075279.1 in the name of Merus B.V., dated Oct. 25, 2012.
European Patent Office Communication for Application No. 09075279.1 dated May 8, 2012.
Hochedlinger, Konrad et al., "Monoclonal mice generated by nuclear transfer from mature B and T donor cells," Nature, vol. 415:1 035-1 038 (2002).
Nissim et al., Antibody fragments from a 'single pot' phage display library as immunochemical reagents, The EMBO Journal, 1994, pp. 692-698, vol. 13. No. 3.
PCT International Search Report, PCT/NL2009/050381 dated Dec. 7, 2009.
PCT International Preliminary Report on Patentability, PCT/NL2009/050381 dated Jan. 5, 2011.
De Kruif et al., Human Immunoglobulin Repertoires against Tetanus Toxoid Contain a Large and Diverse Fraction of High-Affinity Promiscuous VH Genes, J. Mol. Bioi., 2009, pp. 548-558, vol. 387.
Homig-Holzel eta!., Constitutive CD40 signaling in B cells selectively activates the noncanonical NF-?B pathway and promotes lymphomagenesis, J. Exp. Med., 2008, pp. 1317-1329, vol. 205, No. 6.
Winter et al., Insertion of 2 kb of bacteriophage DNA between an immunoglobulin promoter and leader exon stops somatic hypermutation in a kappa trans gene, Molecular Immunology, Apr. 1997, pp. 359-666, vol. 34, No. 5.
Presta et al., Engineering of therapeutic antibodies to minimize immunogenicity and optimize function, Advanced Drug Delivery Reviews, Aug. 7, 2006, pp. 640-556, vol. 58, No. 5-6, Elsevier BV, Amsterdam, NL.
Smith-Gill et al., Contributions of immunoglobulin heavy and light chains to antibody specificity for lysozyme and two haptens, Journal of Immunology, Dec. 15, 1987, pp. 4135-4144, vol. 139, No. 12., Baltimore, MD, US.
Declaration of Anthony L. DeFranco, Dec. 21, 2014, 56 pages.
Ngo, T.-H., et al, Identification of functional synergism between monoclonal antibodies. Application to the enhancement of plasminogen activator inhibitor-1neutralizing effects, FEBS Letters, 1997, pp. 373-376, vol. 416.
Klagsbrun et al., Vascular endothelial growth factor and its receptors, Cytokine Rev., Oct. 1996, pp. 259-270, vol. 7, Issue 3, Abstract only.
Folkman, Angiogenesis in cancer, vascular, rheumatoid and other disease, J. Nat. Med., 1995, pp. 27-31, vol. 1, Abstract only.
Birchmeier et. al., Met, metastasis, motility and more, Nat. Rev. Mol. Cell Biol., Dec. 2003, pp. 915-925, vol. 1, Abstract only.
Cherrington et al., New paradigms for the treatment of cancer: The role of anti-angiogenesis agents, Adv. Cancer. Res., 2000, pp. 1-38, vol. 79, Abstract only.
Zhu et. al., Inhibition of Tumor Growth and Metastasis by Targeting Tumor-Associated Angiogenesis with Antagonists to the Receptors of Vascular Endothelial Growth Factor, Invest. New Drugs, Aug. 1999, pp. 195-212, vol. 17, Issue 3, Abstract only.
Lu et al., Acquired antagonistic activity of a bispecific diabody directed against two different epitopes on vascular endothelial growth factor receptor 2, J. Immunol. Methods, Nov. 19, 1999, pp. 159-171, vol. 230.
Ignatovich et al., Dominance of intrinsic genetic factors in shaping the human immunoglobulin V? repertoire, J. Mol. Biol., Nov. 26, 1999, pp. 457-465, vol. 294, Issue 2.
Desmet et al., Anchor profiles of HLA-specific peptides: Analysis by a novel affinity scoring method and experimental validation, Proteins, Jan. 1, 2005, pp. 53-69, vol. 58, Abstract only.
Green et al., Antigen-specific human monoclonal antibodies from mice engineered with human Ig heavy and light chain YACs, Nat. Genet., 1994, pp. 13-21, vol. 7, Abstract only.
Vlin Soo Kim et al., Comparative Analyses of Complex Formation and Binding Sites between Human Tumor Necrosis Factor-alpha

(56) References Cited

OTHER PUBLICATIONS and its Three Antagonists Elucidate their Different Neutralizing Mechanisms, JMB, Dec. 14, 2007, pp. 1374-1388, vol. 374, Issue 5.
Klitz et al., New HLA haplotype frequency reference standards: High-resolution and large sample typing of HLA DR-DQ haplotypes in a sample of European Americans, Tissue Antigens, 2003, pp. 296-307, vol. 62, Issue 4, Abstract only.
Eigenbrot et al., X-ray Structures of the Antigen-binding Domains from Three Variants of Humanized anti-p185HER2 Antibody 4D5 and Comparison with Molecular Modeling, J. Mol. Biol., Feb. 20, 1993, pp. 969-995, vol. 229, Issue 4, Elsevier, Abstract only.
Gerstner et al., Sequence Plasticity in the Antigen-binding Site of a Therapeutic Anti-HER2 Antibody, J. Mol. Biol., Aug. 30, 2002, pp. 851-862, vol. 321, issue 5, Elsevier, Abstract only.
Mostoslavsky et al., "Asynchronous replication and allelic exclusion in the immune system," Nature (2001) 414:221-225, Abstract only.
Ewert et al., Biophysical properties of human antibody variable domains, J. Mol. Biol., Jan. 17, 2003, pp. 531-553, vol. 325, Iss. 3.
Padlan et al., A possible procedure for reducing the immunogenicity of antibody variable domains while preserving their ligand-binding properties, Mol. Immunol., 1991, pp. 489-498, vol. 28, Abstract only.
Kaufman et al., Amplification and expression of sequences cotransfected with a modular dihydrofolate reductase complementary DNA gene, J. Mol. Biol., Aug. 25, 1982, pp. 601-621, vol. 159, Issue 4, Abstract only.
Gluzman, SV40-transformed simian cells support the replication of early SV40 mutants, Cell, Jan. 1981, pp. 175-182, vol. 23, Issue 1, Abstract only.
Burger et al., An integrated strategy for the process development of a recombinant antibody-cytokine fusion protein expressed in BHK cells, Appl. Microbiol. Biotechnol., Sep. 1999, pp. 345-353, vol. 52, Issue 3, Abstract only.
Allen, Ligand-targeted therapeutics in anticancer therapy, Nat. Rev. Cancer, 2002, 2:750-783, Abstract only.
Atwell et al., Stable heterodimers from remodeling the domain interface of a homodimer using a phage display library1, J. Mol. Biol., Jul. 4, 1997, pp. 26-35, vol. 270, Issue 1, Abstract only.
Hoogenboom, Designing and optimizing library selection strategies for generating high-affinity antibodies, Trends Ehotechnol., 1997, pp. 62-70, vol. 15, Issue 2, Abstract only.
Hoogenboom, et al., Natural and designer binding sites made by phage display technology, lmmunol. Today, Aug. 1, 2000, pp. 371-378, vol. 21, Issue 8, Abstract only.
Application for U.S. Patent, U.S. Appl. No. 15/090,505, sharing common inventors, available on the U.S. Patent Office website.
Priority Document dated Oct. 27, 2009, EP12175544.
Designation of inventor Erwin Houtzager dated Jul. 9, 2012, EP12175544.
Designation of inventor Pinto Rui Daniel dated Jul. 9, 2012, EP12175544.
Designation of inventor Ton Logtenberg dated Jul. 9, 2012, EP12175544.
Designation of inventor Mark Throsby dated Jul. 9, 2012, EP12175544.
Abstract dated Jul. 9, 2012, EP12175544.
Claims dated Jul. 9, 2012, EP12175544.
Drawings continued dated Jul. 9, 2012, EP12175544.
Approved Judgement in *Regeneron Pharmaceuticals Inc.vs Kymab Limited and Novo Nordisk A/S*, Case No. HP-2013-000001/HP-2014-000001 for Hearing dates: Nov. 18-20, 23-27,30 and Dec. 7 & 8, 2015.
EPO Sequence Listing dated Oct. 29, 2012, EP12175544.1.
EPO Notification of European publication No. dated Jan. 16, 2013, EP12175544.1.
EPO Communication: The extended European search report is enclosed dated Jun. 16, 2016, EP12175544.1.
Drew Murphy Statement dated Sep. 8, 2015, (5 pages).

Thomas et al., Site-Directed Mutagenesis by Gene Targeting in Mouse Embryo-Derived Stem Cells, Cells, Nov. 3, 1987, pp. 503-512, vol. 51.
Dascalho et al., A Quasi-Monoclonal Mouse, Science, Jun. 14, 1996, pp. 1649-1652, vol. 272.
Spillner et al., Paratope-based protein identification by antibody and peptide phage display, Analytical Biochemistry, 2003, pp. 96-104, vol. 321, Academic Press.
Staerz et al., Hybrid hybridoma producing a bispecific monoclonal antibody that can focus effector T-cell activity, Proc Natl Acad Sci U S A, 1986, vol. 83(5) pp. 1453-1457.
Translation of pertinent portions of the Action.
Annexes in respect of a request for a change from Merus B.V. to Merus N.V. dated May 19, 2016 (English version).
Verma et al., Antibody engineering: Comparison of bacterial, yeast, insect and mammalian expression systems, Journal of Immunological Methods, 1998, pp. 165-181, vol. 216.
Request for recordal of change of Proprietor from Merus B.V. to Merus N.V. filed by Isenbruck with European Patent Office dated May 27, 2016, 2 pages.
Response to the Summons to attend Oral Proceedings dated Nov. 29, 2015 and in preparation of the Hearing of Jun. 22, 2016, from Isenbruck to European Patent Office dated May 20, 2016.
Phelps et al., Expression and Characterization of a Chimeric Bifunctional Antibody with Therapeutic Applications, The Journal of Immunology, Aug. 15, 1990, pp. 1200-1204, vol. 145, No. 4.
Acknowledgement of receipt from European Patent Office for EP 10186063.3 dated May 20, 2016.
Letter regarding the opposition procedure (no time limit) dated Jun. 20, 2016 from Isenbruck to European Patent Office, 1 page, NUM537.
Letter from JA Kemp to the European Patent Office regarding Oral Proceedings scheduled for Jun. 22, 2016.
Brief Communication from European Patent Office to Isenbruck regarding EP 10186063.3 dated Jun. 13, 2016.
Opposition to Merus B.V.'s EP 2 314 629 B1 Consolidated List of Documents filed by All Parties, unknown author, undated, at least as early as Jun. 6, 2016.
Brief Communication from European Patent Office to Isenbruck regarding EP 10186063.3 dated Jun. 10, 2016 about oral proceedings on Jun. 22, 2016.
Brief communication from European Patent Office to JA Kemp about Opposition—Oral proceedings on Jun. 22, 2016.
Communication from the European Patent Office to Isenbruck regarding change to Merus N.V. dated Jun. 7, 2016.
Kingzette et al., Trans-chromosomal recombination within the Ig heavy chain switch region in B lymphocytes, Immunology, Proc. Natl. Acad. Sci, USA, Sep. 1998, pp. 11840-11845, vol. 95.
Karu et al., Recombinant Antibody Technology, ILAR Journal, pp. 132-141, http://ilarjournal.oxfordjournals.org/by guest on Apr. 6, 2014.
Seidl et al., Position-dependent inhibition of class-switch recombination by PGK-neo (Reg.) cassettes inserted into the immunoglobulin heavy chain constant region locus, Proc. Natl. Acad. Sci. USA, Immunology, Mar. 1999, pp. 3000-3005, vol. 96.
Yang et al., Homologous recombination based modification in *Esherichia coli* and germline transmission in transgenic mice of a bacterial artificial chromosome, Nature Publishing Group, Sep. 1997, pp. 859-865, vol. 15.
Clark, Mike, Antibody humanization: a case of the 'Emperor's new clothes'?, Aug., pp. 397-402, vol. 21, No. 8.
Annex I—Summary of Product Characteristics.
Documents associated with European Patent Application EP 02709544, dated Jul. 16, 2014, Letter regarding the opposition procedure (no time limit)—4.
Documents associated with European Patent Application EP 02709544, dated Dec. 4, 2015, Communication of the Board of Appeal (ex parte_ inter partes).
Documents associated with European Patent Application EP 02709544, dated May 24, 2016, Communication inviting the parties to file observations.
Documents associated with European Patent Application EP 02709544, dated Sep. 19, 2016, Letter regarding the opposition procedure (no time limit).

(56) References Cited

OTHER PUBLICATIONS

Japan Patent Office, Notice of Reasons for Rejection, Japanese Patent Application No. 2011-516168, dated Oct. 15, 2013, four pages.
SHIGA International Patent Office to Japan Patent Office, Amendments to claims made in response to notice of reasons for rejection, Japanese Patent Application No. 2011-516168, dated Jan. 14, 2014, three pages.
Japan Patent Office, Registration Fee Payment, Japanese Patent Application No. 2011-516168, dated May 13, 2015, one page.
Japan Patent Office, Certificate of Patent, Japanese Patent No. 5749161, Japanese Application No. 2011-516168, dated May 22, 2015.
Japan Patent Office, Final Notice of Reasons for Rejection, Japanese Patent Application No. 2011-516168, dated Jul. 28, 2014, six pages.
SHIGA Internation Patent Office to Japan Patent Office, Remarks in response to notice of reasons for rejection, Japanese Patent Application No. 2011-516168, dated Jan. 5, 2015, 16 pages.
SHIGA International Patent Office to Japan Patent Office, Amendments to claims made in response to notice of reasons for rejection, Japanese Patent Application No. 2011-516168, dated Jan. 5, 2015, three pages.
Japan Patent Office, Notice of Allowance, Japanese Patent Application No. 2011-516168, dated Apr. 13, 2015, four pages.
Janeway et al., Chapter 3: Structure of the Antibody Molecule and the Immunoglobulin Genes, ImmunoBiology The Immune System in Health and Disease, Fourth Edition, 1999, pp. 90-108, Elsevier Science Ltd/Garland Publishing.
Declaration of Proffessor Anthony DeFranco, European Patent No. 2147594 B1, European Patent Application No. 39075279.1, dated Aug. 24, 2016, 23 pages.
Canadian Patent Office, Completion Requirement, Submission of Sequence Listing , CA Application No. 2729095, dated Mar. 9, 2011, one page.
Canadian Patent Office, Information Letter, Foreign and non-patent references, CA Application No. 2729095, dated Mar. 9, 2011, two pages.
Canadian Patent Office, Statement and Declaration Under Rule 37, CA Application No. 2729095, dated Dec. 22, 2010, one page.
Canadian Intellectual Property Office, General Correspondence Form, CA Application No. 2729095, PCT Application No. PCT/NL2009/050381, dated Dec. 22, 2010, three pages.
Canadian Intellectual Property Office to Borden Ladner Gervais LLP, Requisition by the Examiner, CA Application No. 2729095, dated Apr. 16, 2013, seven pages.
Canadian Patent Office, Response to the Examiner's Report dated Apr. 16, 2013, CA Application No. 2729095, dated Oct. 15, 2013, 20 pages.
Canadian Intellectual Property Office to Blake Cassels & Graydon LLP, Protest Confirmation, Canadian Patent Application No. 2729095, dated Apr. 16, 2014, one page.
Canadian Intellectual Property Office to Borden Ladner Gervais LLP, Requisition by the Examiner, CA Application No. 2729095, dated Jun. 11, 2014, three pages.
Canadian Intellectual Property Office to Borden Ladner Gervais LLP, Advisement of protest filed, Ca Application No. 2729095, dated Nov. 2, 2015, one page.
Isenbruck Bosl Horschler LLP to European Patenr Office, Documents filed by Proprietor, Response to the summons to attend oral proceedings scheduled for Oct. 28, 2016 and to the preliminary opinion of the Opposition Division dated Jan. 19, 2016, EP 2147594 / 09075279.1-1405, dated Aug. 26, 2016, 32 pages.
Japan Patent Office, As-Filed English language application, Japanese Patent Application No. 2015-097258, dated May 12, 2015, 218 pages.
Canadian Patent Office, Statement of Support, CA Application No. 2729095, dated Mar. 9, 2011, one page.
Japan Patent Office, Request for Substantive Examination, Japanese Patent Application No. 2015-097258, dtaed Jun. 1, 2015, 1 page.

Borden Ladner Gervais LLP to Canadian Patent Office, Response to Official Action dated Nov. 10, 2015, Application No. 2729095, dated May 10, 2016, 12 pages.
Japan Patent Office, As-Filed Application, Japanese Patent Application No. 2015-097258, dated May 13, 2015, 270 pages.
Japan Patent Office, Acknowledgement of receipt, Japanese Patent Application No. 2015-097258, dated May 12, 2015, 1 page.
Correspondence from S.T. van Doorn of V.O. to European Patent Office regarding in vivo data, EP Application No. 39075279.1, dated Jun. 13, 2013, two pages.
Klöhn et al., "IBC's 23rd Annual Antibody Engineering, 10th Annual Antibody Therapeutics International Conferences and the 2012 Annual Meeting of The Antibody Society", mAbs, vol. 5, Issue 2, Dec. 3-6, 2012, pp. 178-201, Landes Bioscience.
Third Party Observations Against European Parent Application No. 09075279.1 in the name of Merus BV, Jul. 1, 2013, three pages.
EPO Communication pursuant to Rule 114(2) EPC, EP Application No. 09075279.1 and Patent No. 2147594, dated Jul. 2, 2013, EPO Form 2022 12.07, one page.
EPO Communication, Minutes, EP Application No. 09075279.1, dated Aug. 8, 2013, EPO Form 2906 01.91TRI, 25 pages.
Letter accompanying subsequently filed items regarding German and French translation of the claims, EP Application No. 09075279.1, dated Sep. 2, 2013, two pages.
EPO Communication under Rule 71(3) EPC, EP Application No. 09075279.1, dated Sep. 2, 2013, EPO Form 2004C06.13TRI, five pages.
EPO Communication, Annex to EPO Form 2004, Communication pursuant to Rule 71(3) EPC, EP Application No. 39075279.1, dated Sep. 2, 2013, EPO Form 2056, two pages.
French Translation of claims for EP Application No. 09075279.1, at least as early as Sep. 2, 2013, three pages.
EPO Acknowledgement of receipt of letter regarding French and German translated claims, EP Application No. 39075279.1, dated Sep. 2, 2013, one page.
EPO Acknowledgement of receipt of letter regarding request to hold application, EP Application No. 09075279.1, dated Sep. 3, 2013, one page.
EPO Communication, Consultation by telephone with the applicant / representative, EP Application No. 09075279.1, dated Oct. 9, 2013, EPO Form 2036 12.07TRI, one page.
EPO Communication, Result of consultation, EP Application No. 09075279.1, dated Oct. 14, 2013, EPO Form 2049A 12.07TRI, two pages.
EPO Communication, Decision to grant a European patent pursuant to Article 97(1) EPC, EP Application No. 39075279.1, dated Oct. 17, 2013, EPO Form 2006A 12.07, two pages.
EPO Communication, Notice of Opposition to a European Patent, EP Application No. 09075279.1 and EP Patent No. 2147594, dated Aug. 11, 2014, EPO Form 2300E, eight pages.
Nagle, "Regeneron helps make Sanofi VelcoImmue to its 'Weak' pipline", Outsourcing—Pharma.com, Dec. 3, 2007, two pages, William Reed Business Media SAS.
Stevens, "Human Antibody Discovery VelcoImmune—A novel platform", Pharma Focus Asia, Issue 8, 2008, pp. 72-74.
Sasaki et al., "Canonical NF-kB Activity, Dispensable for B Cell, Development, Replaces BAFF-Receptor Signals and Promotes B Cell Proliferation upon Activation", Immunity, vol. 24, Jun. 2006, pp. 729-739, Elsevier Inc.
Rickert et al., "B lymphocyte-specific, Cre-mediated mutagenesis in mice", Nucleic Acids Research, vol. 25, No. 6, 1997, pp. 1317-1318, Oxford University Press.
Logtenberg, "Antibody cocktails: next-generation biopharmaceuticals with improved potency", Trends in Biotechnology, vol. 25, No. 9, Aug. 6, 2007, pp. 390-394, Elsevier Ltd.
Dechiara et al., "Chapter 16: VelociMouse: Fully ES Cell-Derived F0-Generation Mice Obtained from the Injection of ES Cells into Eight-Cell-Stage Embryos", Gene Knockout Protocols, Second Edition, vol. 530, 2009, pp. 311-324, Humana Press.
Popov et al., "A Human Immunoglobulin λ Locus Is Similarly Well Expressed in Mice and Humans", The Journal of Experimental Medicine, vol. 189, No. 10, May 17, 1999, pp. 1611-1619, The Rockefeller University Press.

(56) References Cited

OTHER PUBLICATIONS

EPO Communication of a Notice of Opposition, EP Application No. 09075279.1 and EP Patent No. 2147594, dated Aug. 20, 2014, EPO Form 2316 01.12, one page.
Documents associated with European Patent Application EP 02709544, dated Apr. 24, 2014, Annex to the communication—opposition.
Johnston, et al., Complete Sequence Assembly and Characterization of the C57BL/6 Mouse Ig Heavy Chain V Region, J. Immunol., Jul 2, 2014, http://www.jimmunol.org/content/176/7/4221.
Meier et al., Short DNA sequences inserted for gene targeting can accidentally interfere with off-target gene expression, The FASEB Journal, Jun. 2010, pp. 1714-1724, vol. 24.
Documents associated with European Patent Application EP 02709544, dated Sep. 25, 2015, Forwarding of submissions to parties—1.
Documents associated with European Patent Application EP 02709544, dated Sep. 25, 2015, Forwarding of submissions to parties—2.
Documents associated with European Patent Application EP 02709544, dated Sep. 25, 2015, Forwarding of submissions to parties—3.
Documents associated with European Patent Application EP 02709544, dated Sep. 25, 2015, Cited document during appeal procedure.
Documents associated with European Patent Application EP 02709544, dated Sep. 25, 2015, Letter dealing with oral proceedings during the appeal procedure.
Documents associated with European Patent Application EP 02709544, dated Sep. 25, 2015, Claims—01.
Documents associated with European Patent Application EP 02709544, dated Sep. 25, 2015, Claims—02.
Documents associated with European Patent Application EP 02709544, dated Sep. 25, 2015, Claims—03.
Documents associated with European Patent Application EP 02709544, dated Sep. 25, 2015, Claims—04.
Documents associated with European Patent Application EP 02709544, dated Sep. 25, 2015, Claims—05.
Documents associated with European Patent Application EP 02709544, dated Sep. 25, 2015, Claims—06.
Documents associated with European Patent Application EP 02709544, dated Sep. 25, 2015, Claims—07.
Documents associated with European Patent Application EP 02709544, dated Sep. 25, 2015, Claims—08.
Documents associated with European Patent Application EP 02709544, dated Sep. 25, 2015, Claims—09.
Documents associated with European Patent Application EP 02709544, dated Sep. 25, 2015, Claims—10.
Documents associated with European Patent Application EP 02709544, dated Sep. 25, 2015, Claims—11.
Documents associated with European Patent Application EP 02709544, dated Sep. 25, 2015, Claims—12.
Documents associated with European Patent Application EP 02709544, dated Sep. 25, 2015, Amended claims with annotations—01.
Documents associated with European Patent Application EP 02709544, dated Sep. 25, 2015, Amended claims with annotations—02.
Documents associated with European Patent Application EP 02709544, dated Sep. 25, 2015, Amended claims with annotations—03.
Documents associated with European Patent Application EP 02709544, dated Sep. 25, 2015, Amended claims with annotations—04.
Documents associated with European Patent Application EP 02709544, dated Sep. 25, 2015, Amended claims with annotations—05.
Documents associated with European Patent Application EP 02709544, dated Sep. 25, 2015, Amended claims with annotations—06.
Documents associated with European Patent Application EP 02709544, dated Sep. 25, 2015, Amended claims with annotations—07.
Documents associated with European Patent Application EP 02709544, dated Sep. 25, 2015, Amended claims with annotations—08.
Documents associated with European Patent Application EP 02709544, dated Sep. 25, 2015, Amended claims with annotations—09.
Documents associated with European Patent Application EP 02709544, dated Sep. 25, 2015, Amended claims with annotations—10.
Documents associated with European Patent Application EP 02709544, dated Sep. 25, 2015, Amended claims with annotations—11.
Documents associated with European Patent Application EP 02709544, dated Sep. 25, 2015, Amended claims with annotations—12.
Documents associated with European Patent Application EP 02709544, dated Sep. 25, 2015, (Electronic) Receipt.
Documents associated with European Patent Application EP 02709544, dated Oct. 1, 2015, Forwarding of submissions to parties—1.
Documents associated with European Patent Application EP 02709544, dated Oct. 1, 2015, Forwarding of submissions to parties—2.
Documents associated with European Patent Application EP 02709544, dated Oct. 1, 2015, Forwarding of submissions to parties—3.
Documents associated with European Patent Application EP 02709544, dated Oct. 1, 2015, Cited document during appeal procedure.
Documents associated with European Patent Application EP 02709544, dated Oct. 1, 2015, Letter dealing with oral proceedings during the appeal procedure—2.
Documents associated with European Patent Application EP 02709544, dated Oct. 1, 2015, Letter dealing with oral proceedings during the appeal procedure.
Documents associated with European Patent Application EP 02709544, dated Oct. 2, 2015, Communication of the Board of Appeal (ex parte_ inter partes).
Documents associated with European Patent Application EP 02709544, dated Oct. 2, 2015, Cited document during appeal procedure—1.
Documents associated with European Patent Application EP 02709544, dated Oct. 2, 2015, Cited document during appeal procedure—2.
Documents associated with European Patent Application EP 02709544, dated Oct. 2, 2015, Cited document during appeal procedure—3.
Documents associated with European Patent Application EP 02709544, dated Oct. 5, 2015, Letter relating to Appeal Procedure.
Documents associated with European Patent Application EP 02709544, dated Oct. 9, 2015, Forwarding of submissions to parties—1.
Documents associated with European Patent Application EP 02709544, dated Oct. 9, 2015, Forwarding of submissions to parties—2.
Documents associated with European Patent Application EP 02709544, dated Oct. 9, 2015, Forwarding of submissions to parties—3.
Documents associated with European Patent Application EP 02709544, dated Oct. 12, 2015, Letter accompanying subsequently filed items.
Documents associated with European Patent Application EP 02709544, dated Oct. 12, 2015, Forwarding of submissions to parties—1.
Documents associated with European Patent Application EP 02709544, dated Oct. 12, 2015, Forwarding of submissions to parties—2.
Documents associated with European Patent Application EP 02709544, dated Oct. 12, 2015, Forwarding of submissions to parties—3.
Claims (amendments indicated), European Patent Application No. 09075279.1, Dec. 22, 2011, Reference No. 385231EPOO, five pages.
Correspondence from S. van Doorn of Vereenigde to the European Patent Office in response to the communication pursuant to Article 94(3) EPC, European Patent Application No. 09075279.1, dated Dec. 22, 2011, five pages.
Sirac et al., "Role of the monoclonal κ chain V domain and reversibility of renal damage in a transgenic model of acquired Fanconi syndrome", Immunobiology, Blood, A Transgenic Model of Acquired Fanconi Syndrome, Jul. 15, 2006, vol. 108, No. 2, pp. 536-543.
Detailed results for the IMGT/V-QUEST analysed sequences, The International Immunogenetics Information System, IMGT/V-QUEST programme version: 3.2.24, seven pages, at least as early as Apr. 25, 2012, http://www.ingtorg/IMGT_vquest/vquest.
Kong et al., "A λ3' Enhancer Drives Active and Untemplated Somatic Hypermutation of a $\lambda_1$ Transgene[1]", The Journal of Immunology, vol. 161, 1998, pp. 294-301, The American Association of Immunologists.
Klotz et al., "Somatic Hypermutation of a $\lambda_2$ Transgene Under the Control of the λ Enhancer of the Heavy Chain Intron Enhancer", The Journal of Immunology, vol. 157, 1996, pp. 4458-4463, The American Association of Immunologists.
Jolly et al., "Rapid methods for the analysis of immunoglobulin gene hypermutation: application to transgenic and gene targeted mice", Nucleic Acids Research, vol. 25, No. 10, 1997, pp. 1913-1919, Oxford University Press.
González-Fernández et al., "Analysis of somatic hypermutation in mouse Peyer's patches using immunoglobulin κ light-chain transgenes",

(56) References Cited

OTHER PUBLICATIONS

Immunology, vol. 90, Nov. 1993, pp. 9862-9866, Proceedings of the National Academy of Sciences, USA.
Hengstschläger et al., "A λ1 transgene under the control of a heavy chain promoter and enhancer does not undergo somatic hypermutation", European Journal of Immunology, vol. 24, 1994, pp. 1649-1656, VCH, Germany.
EPO Communication pursuant to Rule 114(2) EPC, EP Application No. 09075279.1 and U.S. Pat. No. 2,147,594, dated May 8, 2012, EPO Form 2022 12.07, one page.
EPO Communication pursuant to Article 94(3) EPC, EP Application No. 09075279.1, dated Jun. 29, 2012, EPO Form 2001 12.10CSX, six pages.
Response to communication pursuant Article 94(3) EPC, EP Application No. 09075279.1, dated Sep. 11, 2012, eleven pages.
Sharpe et al., "Somatic hypermutation of immunoglobulin χ may depend on sequences 3' of $C_χ$ and occurs on passenger transgenes", The EMBO Journal, vol. 10, No. 8, 1991, pp. 2139-2145, Oxford University Press.
Third Party Observations Under Article 115 EPC Against European Parent Application No. 09075279.1 in the name of Merus BV, Oct. 25, 2012, six pages.
EPO Communication pursuant to Rule 114(2) EPC, EP Application No. 09075279.1 and U.S. Pat. No. 2,147,594, dated Nov. 5, 2012, EPO Form 2022 12.07, one page.
EPO Communication regarding Preparation for oral Proceedings—Instructions to Support Service, EP Application No. 39075279.1, Feb. 5, 2013, EPO Form 2040 12.07TRI, two pages.
EPO Communication, Annex to Summons to attend oral proceedings pursuant to Rule 115(1) EPC, EP Application No. 39075279.1, Mar. 6, 2013, EPO form 2906 01.91TRI, six pages.
EPO Communication to Martin Hatzmann of Vereenigde, Acknowledgement of receipt of the document specified above, EP Application No. 09075279.1, dated Mar. 6, 2013, EPO Form 2936 08.10, one page.
Executed Acknowledgement of receipt of the document specified above, EP Application No. 09075279.1, dated Mar. 2013, EPO Form 2936 08.10, one page.
Letter accompanying subsequently filed items regarding amended claims with clean and annotated copies, EP Application No. 09075279. 1, dated Apr. 23, 2013, 2 pages.
EPO communication, Client Database System (CDS)—clean up, EP Application No. 19075279.1, dated Apr. 23, 2013, Form 2596C, 04.08, 1 page.
Auxiliary request 1, EP Application No. 09075279.1, Apr. 23, 2013, three pages.
Auxiliary request 2, EP Application No. 09075279.1, Apr. 23, 2013, three pages.
Auxiliary request 3, EP Application No. 09075279.1, Apr. 23, 2013, three pages.
Auxiliary request 5, EP Application No. 09075279.1, Apr. 23, 2013, three pages.
Auxiliary request 6, EP Application No. 09075279.1, Apr. 23, 2013, three pages.
Auxiliary request 4, EP Application No. 09075279.1, Apr. 23, 2013, three pages.
Auxiliary request 1 (amendments indicated), EP Application No. 09075279.1, Apr. 23, 2013, three pages.
Auxiliary request 2 (amendments indicated), EP Application No. 09075279.1, Apr. 23, 2013, three pages.
Letter accompanying subsequently filed items regarding oral proceedings, EP Application No. 09075279.1, Apr. 24, 2013, one page.
Correspondence from S.T. van Doorn to European Patent Office regarding written submissions filed Apr. 23, 2013, EP Application No. 09075279.1, dated Apr. 24, 2013, one page.
EPO Acknowledgement of receipt of written submissions, EP Application No. 09075279.1, dated Apr. 24, 2013, one page.

EPO communication, Executed Maintenance / Change of date / Cancellation of oral proceedings arranged for: May 23, 2013 at 10.00 hrs, EP Application No. 19075279.1, May 14, 2013, EPO Form 2088 04.10, two pages.
EPO communication to Martin Hatzmann of V.O., Brief Communication regarding the letter of Apr. 23, 2013, EP Application No. 09075279.1 and EP Patent No. 2147594, dated May 22, 2013, EPO Form 2008A 12.07, one page.
EPO communication, EP Application No. 19075279.1, dated May 22, 2013, EPO Form 2906 01.91TRI, one page.
Documents associated with European Patent Application EP 02709544, dated Jul. 2, 2015, Cited document during appeal procedure—11.
Gorczyca, W. et al., DNA strand breaks occurring during apoptosis—their early insitu detection by the terminal leoxynucleotidyl transferase and nick translation assays and prevention by serine protease inhibitors, Int J Oncol., 1992, 1(6), 639-648.
Gorczyca, W. et al., Detection of DNA strand breaks in individual apoptotic cells by the in situ terminal deoxynucleotidyl transferase and nick translation assays, Cancer Res., 1993, 53(8), 1945-1951.
Gram, H. et al., in vitro selection and affinity maturation of antibodies from a naive combinatorial immunoglobulin library, Proc Natl Acad Sci U S A, 1992, 89(8), 3576-3580.
Gräslund, T. et al., Integrated strategy for selective expanded bed ion-exchange adsorption and site-specific protein processing using gene fusion technology, J Biotechnol., 2002, 96(1), 93-102.
Gray, E et al., Secretion capture and report web: use of affinity derivatized agarose microdroplets for the selection of hybridoma cells, J Immunol Methods, 1995, 182(2), 155-163.
Greenberger, JS. et al., Demonstration of permanent factor-dependent multipotential (erythroid/neutrophil/basophil) hematopoietic progenitor cell lines, Proc Natl Acad Sci U S A, 1983, 80(10), 2931-2935.
Guéry, JC, Adorini, L., Dendritic cells are the most efficient in presenting endogenous naturally processed self-epitopes to class II-restricted T cells, J Immunol., 1995, 154(2), 536-544.
Hanes, J. et al., Selecting and evolving functional proteins in vitro by ribosome display, Methods Enzymol., 2000, 328, 404-430.
Hawkins, RE. et al., Selection of phage antibodies by binding affinity. Mimicking affinity maturation, J Mol Biol., 1992, 226(3), 889-896.
Hiatt A, et al., Production of antibodies in transgenic plants, Nature, 1989, 342(6245), 76-78.
Hitzeman, RA. et al., Isolation and characterization of the yeast 3-phosphoglycerokinase gene (PGK) by an immunological screening technique, J Biol Chem., 1980, 255(24), 12073-12080.
Holmes, P., Al-Rubeai, M., Improved cell line development by a high throughput affinity capture surface display echnique to select for high secretors, J Immunol Methods, 1999, 230(1-2), 141-147.
Huse, WD. et al., Generation of a large combinatorial library of the immunoglobulin repertoire in phage lambda, Science, 1989, 246(4935), 1275-1281.
Inaba, K. et al., Dendritic cells pulsed with protein antigens in vitro can prime antigen-specific, MHC-restricted T cells in situ, J Exp Med., 1990, 172(2), 631-640.
Jonasson, P. et al., Genetic design for facilitated production and recovery of recombinant proteins in *Escherichia coli*, Biotechnol Appl Biochem., 2002, 35(Pt 2), 91-105.
Jones, D., et al., High-level expression of recombinant IgG in the human cell line PER.CX, Biotechnol Prog, 2003, 19(1), 163-168.
Köhler, G., Milstein, C., Continuous cultures of fused cells secreting antibody of predefined specificity, Nature, 1975, 256(5517), 495-497.
Koide, A. et al., The fibronectin type III domain as a scaffold for novel binding proteins, J Mol Biol., 1998, 284(4), 1141-1151.
Korndorfer, IP. et al., Structural mechanism of specific ligand recognition by a lipocalin tailored for the complexation of digoxigenin, J Mol Biol., 2003, 330(2), 385-396.
Ku, J. et al., Alternate protein frameworks for molecular recognition, Proc Natl Acad Sci U S A, 1995, 92(14), 6552-6556.
Lobato MN., Rabbitts, TH., Intracellular antibodies and challenges facing their use as therapeutic agents, Trends Mol Med., 2003, 9(9), 390-396.
Japan, Argument, Jun. 21, 2016, 15 pages.

(56) References Cited

OTHER PUBLICATIONS

Japan, declaration of Ton Logtenberg, Sep. 15, 2015, 5 pages.
Japan, English translation and Opponents counter arguments, 25 pages.
EP, Instructions to the EPO to amend the application, Sep. 29, 2014, 7 pages.
Japan, Declaration of Peter Hudson, Jun. 17, 2016, 15 pages.
Japan, IMGT/LIGM-DB sequence, Jul. 26, 2016, 13 pages.
Japan, Information Sheet for Submitted Publications, 3 pages.
Japan, Notification 084747, 1 page.
Japan, Opponents Counterargument 2016-700031, 19 pages.
Japan, Notice of Reasons for Revocation, dated Mar. 17, 2016, 8 pages.
Roth, et al., Really Essential Medical Immunology, pp. 23-35, 17 pages.
Barnes, LM. et al, Characterization of the stability of recombinant protein production in the GS-NS0 expression system, Biotechnol Bioeng., 2001, 73(4), 261-270.
Bertagnolli, M., Herrmann, S., IL-7 supports the generation of cytotoxic T lymphocytes from thymocytes. Multiple lymphokines required for proliferation and cytotoxicity, J Immunol., 1990,145(6), 1706-1712.
Binz, H.K. et al., Designing repeat proteins: well-expressed, soluble and stable proteins from combinatorial libraries of consensus ankyrin repeat proteins, J Mol Biol., 2003, 332(2), 489-503.
Bode et al. 2001, Int. J. Gene Ther. Mol. Biol. 6:33-46.
Boder, ET., Wittrup, KD., Yeast surface display for screening combinatorial polypeptide libraries, Nat Biotechnol., 1997, 15(6), 553-557.
Brezinsky, Sc. Et al., A simple method for enriching populations of transfected CHO cells for cells of higher specific productivity. J Immunol Methods, 2003, 277(1-2),141-155.
Chesnut, J. et al., Selective isolation of transiently transfected cells from a mammalian cell population with vectors expressing a membrane anchored single-chain antibody, Journal of Immunological Methods, 1996 pp. 17-27.
Cockett MI, Bet al., High level expression of tissue inhibitor of metalloproteinases in Chinese hamster ovary cells using glutamate synthetase gene amplification, Biotechnology, 1990, 8(7), 662-667.
De Vries, P. et al., the effect of recombinant mast cell growth factor on purified murine hematopoietic stem cells, J Exp Med, 1991, 173(5), 1205-1211.
Desmyter, A. et al., Crystal structure of a camel single-domain VH antibody fragment in complex with lysozyme, Nat Struct Biol., 1996, 3(9), 803-811.
Eren, R. et al., Preclinical evaluation of two human anti-hepatitis B virus (HBV) monoclonal antibodies in the HBV-trimera mouse model and in HBV chronic carrier chimpanzees, Hepatology, 2000, 32(3), 588-596.
Feige, U. et. al., Anti-interleukin-1 and anti-tumor necrosis factor-alpha synergistically inhibit adjuvant arthritis in Lewis rats, Cell Mol Life Sci., 2000, 57(10), 1457-1470.
Fishwild DM, et al., High-avidity human IgG kappa monoclonal antibodies from a novel strain of minilocus transgenic mice, Nat Biotechnol, 1996, 14(7), 845-851.
Garber, K. Biotech industry faces new bottleneck, Nat Biotechnol., 2001, 19(3), 184-185.
Ghetie, M-A., et al., Homodimerization of tumor-reactive monoclonal antibodies markedly increases their ability to induce growth arrest or apoptosis of tumor cells, Proc Natl Acad Sci U S A, 1997, 94(14), 7509-7514.
Further to Notice of Opposition dated Jul. 8, 2016, EP2264163/10010741.6, 3 pages, Jul. 12, 2016.
Tanha, J. et al.,Selection by phage display of llama conventional V(H) fragments with heavy chain antibody V(H)H properties, J Immunol Methods, 2002, 263(1-2), 97-109.
Toki, J. et al., Analyses of T-cell differentiation from hemopoietic stem cells in the G0 phase by an in vitro method, Proc Natl Acad Sci U S A, 1991, 88(17), 7548-7551.

Urlaub, G. et al., Isolation of Chinese hamster cell mutants deficient in dihydrofolate reductase activity, Proc Natl Acad Sci U S A, 1980, 77(7), 4216-4220.
Vagner, S. et al, Alternative translation of human fibroblast growth factor 2 mRNA occurs by internal entry of ribosomes, Mol Cell Biol., 1995, 15(1), 35-44.
Valenzuela, DM., High-throughput engineering of the mouse genome coupled with high-resolution expression analysis, Nat Biotechnol, 2003, 21(6), 652-659.
Weinberger, O. et al., Cellular interactions in the generation of cytolytic T lymphocyte responses: role of Ia-positive splenic adherent cells in presentation in H-2 antigen, Proc Natl Acad Sci U S A, 1980,77(10), 6091-6095.
WHO Technical Series Report, 1994, vol. 848, p. 8.
Wilson TJ, Kola I., The LoxP/CRE system and genome modification, Methods Mol Biol., 2001, 158, 83-94.
Ye, X., et al., Ultrabithorax and Antennapedia 5' untranslated regions promote developmentally regulated internal translation initiation, Mol. Cell Biol., 1997, 17(3), 1714-17121.
Zacharchuk, CM. Et al., Programmed T lymphocyte death. Cell activation- and steroid-induced pathways are mutually antagonistic, J Immunol., 1990, 145(12), 4037-4045.
Zamai et al., Optimal detection of apoptosis by flow cytometry depends on cell morphology, Cytometry, 1993, 14(8), 391-897.
Zou, YR. et al, Cre-loxP-mediated gene replacement: a mouse strain producing humanized antibodies, Curr Biol, 1994; 4(12), 1099-1103.
Communication of further notices of opposition, Aug. 23, 2016.
Acknowledgement of receipt, dated Jul. 13, 2016.
Murphy, Statement of, Exhibit Murphy 1, Mar. 18, 2015, Defendant's Exhibit DX145, Case No. 14-CV-1650 (KBF).
Statement of Dr. Anne Corcoran dated Jul. 8, 2016 with listing of Literature Cited and curriculum vitae.
In The High Court of Justice, Chancery Division, Patents Court, Case No. HP-2013-000001/HP-2014-000001 dated Oct. 6, 2015, First Expert Report of Professor Sir Martin Evans FRS Ph.D., Report relates to a patent owned by Regeneron Pharmaceuticals, Inc., Report relates to patents owned by Regeneron Pharmaceuticals, Inc., EP 1 360 287 and 2 264 163.
Annex 1 to First Expert Report of Professor Sir Martin Evans FRS Ph.D., undated.
Annex 2 to First Expert Report of Professor Sir Martin Evans FRS Ph.D., undated.
Andrew, Simon dated Mar. 2, 2011, 9 pages.
Technical Primer, author unknown, undated, 9 pages.
Popov, Dr. Andrei, Statement by with curriculum vitae, undated.
Notice of Opposition with statement and facts dated Oct. 14, 2015.
Bruggemann, Transgenic Animals: generation and use, 6 pages, 1997, pp. 397-402, OPA.
Deng et al., Reexamination of gene targeting frequency as a function of the extent of homology between the targeting vector and the target locus, Mol Cell Biol., Aug. 12, 1992, 3365-3371, vol. 12, No. 8, Medline.
Ebert et al., The Distal VH Gene Cluster of the Igh Locus Contains Distinct Regulatory Elements with Pax5 Transcription Fator-Dependent Activity in Pro-B Cells, Immunity Articles,13 pages, Feb. 25, 2011, pp. 175-187, vol. 34, No. 2, Elsevier, Inc.
Gu, et al., Independent Control of Immunoglobulin Switch Recombination at Individual Switch Regions Evidenced through Cre-loxP Mediated Gene Targeting, Cell, 10 pages, Jun. 18, 1993, pp. 1155-1164, vol. 73, No. 6, Cell Press.
Hansen et al., Large-scale gene trapping in C57BL/6N mouse embryonic stem cells, Genome Research, 10 pages, 2008, pp. 1670-1679, vol. 18, Cold Spring Harbor Laboratory Press.
Hong et al., Long targeting arms do not increase the efficiency of homologous recombination in the beta-globin locus of murine embryonic stem cells, Red Cells, 3 pages, Aug. 15, 2003, pp. 1531-1533, vol. 102, No. 4, The American Society of Hematology.
Johnston et al., Complete sequence assembly and characterization of the C57BL/6 mouse Ig heavy chain V region, The Journal of Immunology, 13 pages, Apr. 1, 2006, vol. 176, No. 7, The American Society of Immunology.
Joyner, 2007, previously submitted.

(56) References Cited

OTHER PUBLICATIONS

Opponents Initial Supplementary Submissions, Australia Oct. 5, 2016, 7 pages.
Letter with Fee, Australia, dated May 18, 2015, 1 page.
Acknowledgment of Receipt of Notice of Opposition from the APO, Jun. 23, 2014, 1 page.
Annexure PH-4 referred to in Peter Hudson Jun. 2, 2015 Declaration, 37 pages—Part 1.
Annexure PH-4 referred to in Peter Hudson Jun. 2, 2015 Declaration, 37 pages—Part 2.
Section 27 Notice, Australia, Oct. 31, 2013.
Section 27 Notice, Australia, Mar. 18, 2014.
Applicant request for extension of time, Australia, May 18, 2015, 6 pages.
CD Marker Handbook, Australia.
Lai et al., (1998), Mouse Cell Surface Antigens: Nomenclature and Immunophenotyping, The American Association of Immunologists. 3861-3868.
Applicant Written Submission, Australia, Sep. 6, 2016, 49 pages.
Documents associated with European Patent Application EP 02709544, dated Sep. 9, 2014, Letter regarding the opposition procedure (no time limit).
Documents associated with European Patent Application EP 02709544, dated Sep. 11, 2014, Letter accompanying subsequently filed items.
Documents associated with European Patent Application EP 02709544, dated Sep. 11, 2014, Letter regarding the opposition procedure (no time limit).
Documents associated with European Patent Application EP 02709544, dated Sep. 15, 2014, Brief commmunication—Opposition proceedings—1.
Documents associated with European Patent Application EP 02709544, dated Sep. 15, 2014, Brief commmunication—Opposition proceedings—2.
Documents associated with European Patent Application EP 02709544, dated Sep. 15, 2014, Brief commmunication—Opposition proceedings—3.
Documents associated with European Patent Application EP 02709544, dated Sep. 15, 2014, Brief commmunication—Opposition proceedings—4.
Documents associated with European Patent Application EP 02709544, dated Sep. 15, 2014, Brief commmunication—Opposition proceedings—5.
Documents associated with European Patent Application EP 02709544, dated Sep. 15, 2014, Brief commmunication—Opposition proceedings—6.
Documents associated with European Patent Application EP 02709544, dated Sep. 15, 2014, Brief commmunication—Opposition proceedings—7.
Documents associated with European Patent Application EP 02709544, dated Sep. 15, 2014, Brief commmunication—Opposition proceedings—8.
Documents associated with European Patent Application EP 02709544, dated Sep. 15, 2014, Brief commmunication—Opposition proceedings—9.
Documents associated with European Patent Application EP 02709544, dated Aug. 12, 2014, Any annexes (other than citation) to an opposition letter.
Documents associated with European Patent Application EP 02709544, dated Aug. 12, 2014, Written submission in preparation to_during oral proceedings.
Documents associated with European Patent Application EP 02709544, dated Aug. 20, 2014, 1003—Authorisation of representative.
Murphy et al., Mice with megabase humanization of their immunoglobulin genes generate antibodies as efficiently as normal mice, PNAS, (sent for review Aug. 26, 2013), pp. 1-6, www.pnas.org/cgi/doi/10.1073/pnas.10324022111.
Wuerffel et al., S-S Synapsis during Class Switch Recombination Is Promoted by Distantly Located Transcriptional Elements and Activation-Induced Deaminase, Immunity, Nov. 2007, pp. 711-722, vol. 27.

Scapini et al., Myeloid cells, BAFF, and IFN-gamma establish an inflammatory loop that exacerbates autoimmunity in Lyn-deficient mice, JEM, Jul. 12, 2010, pp. 1757-1773, vol. 207, No. 8.
MeMO® transgenic mouse for improved antibody therapeutics information sheet from www.merus.nl, dated Sep. 2012.
Lee et al., Complete humanization of the mouse immunoglobulin loci enables efficient therapeutic antibody discovery, Nature Biotechnology, pub. Online Mar. 16, 2014; pp. 1-12, doi:10.1038/nbt.2825.
Documents associated with European Patent Application EP 02709544, dated Sep. 2, 2014, Letter regarding the opposition procedure (no time limit).
EP, Documets filed by Merus EPO form 2318, Jun. 29, 2016, 1 page.
EP, Notice of Opposition, May 25, 2016, 28 pages.
EP, Payment of Fees, May 25, 2016, 1 page.
EP, Claim Construction and Opinion Order, Nov. 21, 2014, 59 pages.
EP, So Ordered Joint Stipulation and Order on Invalidity, Feb. 25, 2015 7 pages.
EP, Opinion and Order, Nov. 2, 2015, 114 pages.
EP, Documents filed by the prop during opp—eot, May 7, 2016, 6 pages.
EPO Brief Communication to Fritz Lahrtz of Isenbruck Bösl Höschler LLP regarding the telephone conversation on the Opposition, EP Application No. 09075279.1 and Patent No. 2147594, Mar. 16, 2016, EPO Form 2911O 01.12, one page.
EPO Brief Communication to Andrew Bentham of J A Kemp regarding the telephone conversation on the Opposition, EP Application No. 09075279.1 and Patent No. 2147594, Mar. 16, 2016, EPO Form 2911O 01.12, one page.
EPO Brief Communication to Fritz Lahrtz of Isenbruck Bösl Höschler LLP regarding the Oral Proceedings on Oct. 13, 2016, EP Application No. 09075279.1 and Patent No. 2147594, Mar. 22, 2016, EPO Form 2310A 12.07, one page.
EPO Brief Communication to Andrew Bentham of J A Kemp regarding the Oral Proceedings on Oct. 13, 2016, EP Application No. 09075279.1 and Patent No. 2147594, Mar. 22, 2016, EPO Form 2310A 12.07, one page.
EPO Communication, Summons to Fritz Lahrtz of Isenbruck Bösl Höschler LLP to attend oral proceedings pursuant to Rule 115(1) EPC, EP Application No. 09075279.1 and EP Patent No. 2147594, Mar. 22, 2016, EPO Form 2310 12.14, one page.
EPO Communication to Fritz Lahrtz of Isenbruck Bösl Höschler LLP, Acknowledgement of receipt of EPO Forms 2310 and 2043, EP Application No. 09075279.1 and EP Patent No. 2147594, Mar. 22, 2016, EPO Form 2936 08.10, one page.
EPO Communication to Andrew Bentham of J A Kemp, Acknowledgement of receipt of EPO Forms 2310 and 2043, EP Application No. 090752791 and EP Patent No. 2147594, Mar. 22, 2016, EPO Form 2936 08.10, one page.
Fritz Lahrtz of Isenbruck Bösl Höschler LLP communication to EPO, Executed Acknowledgement, EP Application No. 09075279.1 and EP Patent No. 2147594, Mar. 29, 2016, EPO Form 2936 08.10, one page.
David Power of J A Kemp communication to EPO, Executed Acknowledgement, EP Application No. 09075279.1 and EP Patent No. 2147594, Mar. 22, 2016, EPO Form 2936 08.10, one page.
Deed of Conversion and Amendment of the Articles of Association for Mews BV (new name: Merus N.V.), dated May 19, 2016, 27 pages.
English translation of Deed of Conversion and Amendment of the Articles of Association for Merus BV (new name: Merus N.V.), dated May 19, 2016, 26 pages.
EPO Communication, Payment of fees and expenses, EP Application No. 09075279.1, dated May 30, 2016, EPO Form 101003.15, one page.
EPO Communication regarding the entries pertaining to the applicant / the proprietor (R. 143(1)(f) EPC), EP Application No. 09075279.1 and EP Patent No. 2147594, dated Jun. 13, 2016, EPO Form 2544 03.14, two pages.

(56) References Cited

OTHER PUBLICATIONS

EPO Brief Communication to Andrew Bentham of J A Kemp regarding the Opposition, EP Application No. 09075279.1 and Patent No. 2147594, dated Jun. 14, 2016, EPO Form 2911O 01.12, one page.
EPO Communication to Fritz Lahrtz of Isenbruck Bösl Förschler LLP, Refund of fees, EP Application No. 09075279.1 and Patent No. 2147594, dated Jun. 15, 2016, EPO Form 2907 04.14, one page.
Documents associated with European Patent Application EP 02709544, dated Jan. 28, 2014, Amended claims with annotations—2.
Documents associated with European Patent Application EP 02709544, dated Mar. 5, 2014, Communication to designated inventor—1.
Documents associated with European Patent Application EP 02709544, dated Mar. 5, 2014, Communication to designated inventor—2.
Documents associated with European Patent Application EP 02709544, dated Mar. 5, 2014, Communication to designated inventor—3.
Documents associated with European Patent Application EP 02709544, dated Mar. 5, 2014, Communication to designated inventor—4.
Documents associated with European Patent Application EP 02709544, dated Mar. 5, 2014, Communication to designated inventor—5.
Deng, et al., Reexamination of gene targeting frequency as a function of the extent of homology between the targeting vector and the target locus., Mol. Cell. Biol., 1992, pp. 3365-3371, vol. 12, No. 8.
Taki et al., Targeted Insertion of a Variable Region Gene into the Immunoglobulin Heavy Chain Locus, Science, Nov. 19, 1993, pp. 1268-1271, vol. 262.
Shi et al., The mapping of transgenes by fluorescence in situ mybridiation on G-banded mouse chromosomes, Mammalian Genome, 1994, pp. 337-341.
Niarayanan et al., Efficient and precise engineering of a 200 kb beta-globin human/bacterial artificial chromosome in E. coli DH10B using an inducible homologous recombination system, Gene Therapy, 1999, pp. 442-447, vol. 6.
Bruggemann, Marianne, Human Antibody Expression in Transgenic Mic, Archivum Immunologiae et Therapiae Experimentalis, 2001, pp. 203-208, vol. 49.
Stevens, Ph.D., Sean, Statement of.
Methods of Modifying Eukaryotic Cells.
Gene targeting in animal cells using isogenic DNA constructs.
Method of making transgenic mice lacking endogenous heavy chains.
U.S. Appl. No. 60/244,665, filed Oct. 13, 2000, Aris et al.
Production of Antibodies From Transgenic Animals.
Gezielte Ersetztung Eines Gens Ohne Endogene Und Selektienbare Restsequenzen.
Production of Antibodies Using CRE-Mediated Site-Specific Recombination.
Transgenic Mammals Having Human IG Loci Including Plural VH and V kappa Regions and Antibodies Produced Therefrom.
Documents associated with European Patent Application Ep 02709544, dated Jan. 28, 2014, Letter regarding the Dpposition procedure (no. time limit).
<Ouskoff et al., Cassette vectors directing expression of T cell receptor genes in transgenic mice, Journal of mmunological Methods (1995) pp. 273-280, Vol_ 180.
Murakami, T. et al, Splenic CD19-CD35+B220+ cells function as an inducer of follicular dendritic cell network formation, Blood, 2007,110(4), 1215-1224.
Opponent's (REGN) submissions filed on Oct. 19, 2016 in -AU10.
Orban, PC. et al, Tissue- and site-specific DNA recombination in transgenic mice, Proc Natl Aced Sci U S A, 1992, 89(15), 6861-6865.
Padlan et al., A possible procedure for reducing the immunogenicity of antibody variable domains while preserving their ligand-binding properties, Mol. Immunol., 1991, pp. 489-498, vol. 28.
ROITT, Immunology, Moscow, 2000.
Shaffer, AL. Et al., In vivo occupancy of the kappa light chain enhancers in primary pro- and pre-B cells: a model for kappa locus activation, Immunity, 1997, 6(2), 131-143.

Smith, EJ. et al., A novel, native-format bispecitic antibody triggering T-cell killing of B-cells is robustly active in mouse tumor models and cynomolgus monkeysSci Rep., 2015, 5: 17943.
Submissions filed by applicant on Oct. 19, 2016 in -AU10.
Submissions filed by applicant on Sep. 6, 2016 in -AU10.
Weiner, et al., Fully human therapeutic monoclonal antibodies, Journal of Immunotherapy, Jan. 1, 2006, pp. 1-9, vol. 29, No. 1, Lippincott Williams & Wilkins.
Yang, SY. Et al, Control of gene conversion and somatic hypermutation by immunoglobulin promoter and enhancer sequences, J Exp Med., 2006, 203(13), 2919-2928.
Yarilin, Fundamentals of Immunology, Moscow, 1999.
Zou, YR. et al, Generation of a mouse strain that produces immunoglobulin kappa chains with human constant regions, Science, 1993, 262(5137), 1271-1274.
Inlay et al., Essential roles of the kappa light chain intronic enhancer and 3' enhancer in kappa rearrangement and demethylation, Nat Immunol., Apr. 22, 2002, pp. 463-468, vol. 3.
Documents associated with European Patent Application EP 02709544, dated Oct. 12, 2015, Letter dealing with oral proceedings during the appeal procedure—.
Documents associated with European Patent Application EP 02709544, dated Oct. 22, 2015, receipt of Electronic Filings with U.S. District Court, Southern District of New York in Case No. 1:14-cv-1650-KBF.
Documents associated with European Patent Application EP 02709544, dated Oct. 22, 2015, receipt of Electronic Filings with U.S. District Court, Southern District of New York in Case No. 1:14-cv-1650-KBF, includes duration of transmission.
Documents associated with European Patent Application EP 02709544, Memorandum Decision & Order for U.S. District Court, Southern District of New York date filed Aug. 6, 2015, in Case No. 1:14-cv-1650-KBF, includes duration of transmission.
Documents associated with European Patent Application EP 02709544, dated Nov. 4, 2015, Letter accompanying subsequently filed items.
Documents associated with European Patent Application EP 02709544, dated Nov. 4, 2015, Oral Proccedings summons.
Documents associated with European Patent Application EP 02709544, dated Nov. 4, 2015, Amended claims with annotations.
Lucas, BK. et al, High-level production of recombinant proteins in CHO cells using a dicistronic DHFR intron expression vector, Nucleic Acids Res., 1996, 24(9), 1774-1779.
Macatonia, SE. et al., Dendritic cells produce IL-12 and direct the development of Th1 cells from naive CD4+ T cells, J Immunol., 1995, 154(10), 5071-5079.
Manen, D. et al., A sensitive reporter gene system using bacterial luciferase based on a series of plasmid cloning rectors compatible with derivatives of pBR322, Gene, 1997, 186(2), 197-200.
Massengale, WT et al., CD20-negative relapse of cutaneous B-cell lymphoma after anti-CD20 monoclonal antibody therapy, J Am Acad Dermatol., 2002, 46(3), 441-443.
McConnell, S.J., Hoess, Rh., Tendamistat as a scaffold for conformationally constrained phage peptide libraries, J Mol Biol., 1995, 250(4), 460-470.
Neumann, E., Gene transfer into mouse lyoma cells by electroporation in high electric fields, Embo J.,1982, 1(7), 841-845.
Office Action Response in U.S. Appl. No. 12/932,719 (dated Feb. 27, 2012) filed in protest against U.S. Appl. No. 15/158,543.
PI?ckthun, A. et al, In vitro selection and evolution of proteins. In: Adv. Prot. Chem., F.M. Richards et al, Eds, Academic Press, San Diego, 2001, vol. 55, 367-403.
Reiter, Y. et al., An antibody single-domain phage display library of a native heavy chain variable region: isolation of functional single-domain VH molecules with a unique interface, J Mol Biol., 1999, 290(3), 685-698.
Santini, C. et al., Efficient display of an HCV cDNA expression library as C-terminal fusion to the capsid protein D of bacteriophage lambda, J Mol Biol., 1998, 282(1), 125-135.
Schaffitzel, C. et al., Ribosome display: an in vitro method for selection and evolution of antibodies from libraries, J Immunol Methods, 1999, 231(1-2), 119-135.
Schaffitzel,C. et al., In vitro selection and evolution of protein-ligand interactions by ribosome display. In: Protein-Protein Inter-

(56) References Cited

OTHER PUBLICATIONS actions. A Molecular Cloning Manual, E. Golemis, Ed., Cold Spring Harbor Laboratory Press, New York, 2001, pp. 535-567.
Stijlemans, B. et al., Efficient targeting of conserved cryptic epitopes of infectious agents by single domain antibodies. African trypanosomes as paradigm, J Biol Chem., 2004, 279(2), 1256-1261.
Strelkauskas, AJ. Et al., Human monoclonal antibody: 2. Simultaneous expression of IgG and IgM with similar binding specificities by a human hybrid clone, Hybridoma, 1987, 6(5), 479-487.
Documents associated with European Patent Application EP02709544, dated Jul. 8, 2015, Forwarding of submissions to parties—1.
Documents associated with European Patent Application EP02709544, dated Jul. 8, 2015, Forwarding of submissions to parties—2.
Documents associated with European Patent Application EP02709544, dated Jul. 8, 2015, Forwarding of submissions to parties—3.
Documents associated with European Patent Application EP02709544, dated Jul. 8, 2015, Forwarding of submissions to parties—4.
Documents associated with European Patent Application EP02709544, dated Jul. 8, 2015, Forwarding of submissions to parties—5.
Documents associated with European Patent Application EP02709544, dated Jul. 8, 2015, Forwarding of submissions to parties—6.
Documents associated with European Patent Application EP02709544, dated Aug. 13, 2015, Oral proceedings order for summons—.
Documents associated with European Patent Application EP02709544, dated Aug. 31, 2015, Forwarding of submission to parties—2.
Documents associated with European Patent Application EP02709544, dated Jan. 22, 2015, Letter relating to Appeal Procedure—2.
Documents associated with European Patent Application EP02709544, dated Feb. 15, 2015, Annexes (other than sited documents) regarding appeal procedure.
Jones et al., Replacing the complementarity-determining regions in a human antibody with those from a mouse, Nature, May 1986, pp. 522-525, vol. 321.
Xu et al., Diversity in the CDR3 Region of V eta Is Sufficient for Most Antibody Specificities, Immunity, Jul. 2000, pp. 37-45, vol. 13.
Griffiths et al., Isolation of high affinity human antibodies directly from large synthetic repertoires, The EMBO Journal, 1994, pp. 3245-3260, vol. 13, No. 14.
Nelson et al., Development trends for human monoclonal antibody therapeutics, Nature Reviews, Oct. 2010, pp. 767-774, vol. 9.
Mortuza et al., Immunoglobulin heavy-chain gene rearrangement in adult acute lymphoblastic leukemia reveals preferential usage of J eta-proximal variable gene segments, Immunobiology, Blood, May 1, 2001, pp. 2716-2726, vol. 37, No. 9.
Yancopoulos et al., Preferential utilization of the most J eta-proximal V eta gene segments in pre-B-cell lines, Nature, Oct. 25, 1984, pp. 727-733, vol. 311.
Documents associated with European Patent Application EP02709544, dated Feb. 15, 2015, Patent Document sited during the appeal procedure—2.
Arnold, Lw., et al., Development of B-1 cells: segregation of phosphatidyl choline- specific B cells to the B-1 population 3c,curs after immunoglobulin gene expression, J Exp Med., 1994;179(5),1585-1595.
Attaelmannan, M., Understanding and identifying monoclonal gammopathies, Clin Chem., 2000, 46(8 Pt 2), 1230-1238.
Aucouturier et al., Monocloanl Ig L Chain and L Chain V Domain Fragment Crystallization in Myelloma-Associated Fanconi's Syndrome, and Aucouturier et al. Sequence alignment, The Journal of Immunology, 1993, 3561-3568.
Betz, AG. Elements regulating somatic hypermutation of an immunoglobulin kappa gene: critical role for the intron enhancer/matrix attachment region, Cell, 1994, 77(2), 239-248.
De Chiara 2009, Chapter 16 of Gene Knockout Protocols: 2nd Ed, vol. 530, Humana Press, 311-324.
Decision of US District Court about U.S. Pat. No. 8,502,018, *Regn* vs. *Menus B.V.*, dated Feb. 11, 2015.
Decl. Robert Brink (1st) Apr. 2015.
Decl. Robert Brink (2nd) Jun. 2015.
Decl. Robert Brink (4th), Oct. 19, 2016 (—AU10).
Decl. Anthony De Franco (1st) Dec 2014.
Decl. Anthony De Franco (2nd) Oct 2015.
Decl. Anthony De Franco (3rd) Oct. 4, 2016 (against—AU10).
Decl. Anthony De Franco (4th) Oct. 18, 2016 (against—AU10).
Decl. Anthony De Franco filed in Aug. 2016 (—EP).
Decl. Christopher Carl Goodnow (1st) Oct. 2015.
Decl. Christopher Carl Goodnow (2nd), Apr. 10, 2016 against—AU10.
Decl. Peter Hudson (1st) May 2015.
Decl. Peter Hudson (2nd) Jun. 2015.
Decl. John McWhirter incl. Sequence Alignment filed on Aug. 2, 2016.
Decl. David Tarlinton (2nd) Oct. 2015.
Desmet et al., Fast and accurate side-chain topology and energy refinement (FASTER) as a new method for protein structure optimization, Proteins, Jul. 1, 2002, pp. 31-43, vol. 48, Issue 1.
Desmet et al., Anchor profiles of HLA-specific peptides: Analysis by a novel affinity scoring method and experimental validation, Proteins, Jan. 1, 2005, pp. 53-69, vol. 58.
Fecteau, JF. et al., A new memory CD27− IgG+ B cell population in peripheral blood expressing VH genes with low frequency of somatic mutation, J Immunol., 2006, 177(6), 3728-3736.
Gen Bank Acc. No. DQ187586-1 2005.
Gen Bank Acc. No. X59315 (human Ig kappa LC variable region).
Green et al., Antigen-specific human monoclonal antibodies from mice engineered with human Ig heavy and light chain YACs, Nat. Genet., 1994, pp. 13-21, vol. 7.
Hengstschläger, M. et al, A lambda 1 transgene under the control of a heavy chain promoter and enhancer does not undergo somatic hypermutation., Eur J Immunol., 1994, 24(7), 1649-1656.
Hoogenboom et al., Selecting and screening recombinant antibody libraries, Nat. Biotechnol., Sep. 7, 2005, pp. 1105-1116, vol. 23.
Jakobovits A., The long-awaited magic bullets: therapeutic human monoclonal antibodies from transgenic mice, Expert Gpinion Investigating Drugs, 1998, 7(4), 607-614.
Jones et al., Replacing the complementarity-determining regions in a human antibody with those from a mouse, Nature, May 29, 1986, pp. 522-525, vol. 321.
Kim, MS. et al., Comparative analyses of complex formation and binding sites between human tumor necrosis factor-alpha and its three antagonists elucidate their different neutralizing mechanisms, J Mol Biol., 2007, 374(5), 1374-1388.
Kitamura D., A B cell-deficient mouse by targeted disruption of the membrane exon of the immunoglobulin mu chain gene, Nature, 1991, 350(6317), 423-426.
Lonberg, N., Human antibodies from transgenic animals, Nat Biotechnol., 2005, 23(9), 1117-1125.
Mao, X. et al., Activation of EGFP expression by Cre-mediated excision in a new ROSA26 reporter mouse strain, Blood, 2001, 97(1), 324-6.
Jul. 13, 2016 Refund of fees, 1 page.
Jun. 30, 2016 Communication regarding the transmission of the European search report, 1 page.
Jun. 30, 2016 European search opinion, 6 pages.
Jun. 30, 2016 European search report, 9 pages.
Jun. 30, 2016 Information on Search Strategy, 1 page.
Jun. 20, 2016 Communication of the registration of a transfer or change of name and/or address, 2 pages.
Jun. 16, 2016 General enquiry, 1 page.
Jun. 15, 2016 Search started, 1 page.
May 30, 2016 Annexes in respect of a request for a change, 53 pages.
May 30, 2016 Payment of fees and costs, 1 page.
May 30, 2016 Request for change of name—applicant, 1 page.
Dec. 23, 2015 Communication of amended entries concerning the representative, 1 page.
Dec. 22, 2015 Request for change of applicant's representative, 2 pages.
Dec. 17, 2015 (Electronic) Receipt, 1 page.
Dec. 17. 2015 Letter accompanying subsequently filed items, 1 page.

(56) References Cited

OTHER PUBLICATIONS

Dec. 17, 2015 Request for change of applicant's representative, 1 page.
Oct. 8, 2015 Communication of amended entries concerning the representative, 1 page.
Sep. 29, 2015 Request for change of applicant's representative, 1 page.
Apr. 23, 2013 CDS Clean up—amended data concerning the representative for the applicant, 1 page.
Apr. 2, 2013 Document concerning representation, 3 pages.
Jan. 6, 2013 Notification of forthcoming publication, 2 pages.
Oct. 29, 2012 Non-scannable object, 1 page.
Oct. 29, 2012 Reply to the invitation to remedy deficiencies, 2 pages.
Oct. 29, 2012 Sequence listing, 76 pages.
Aug. 31, 2012 Deficiencies in sequence listing, 2 pages.
Aug. 20, 2012 (Electronic) Receipt, 1 page.
Aug. 20, 2012 (Partial) description filed in response to formal objections, 8 pages.
Aug. 20, 2012 Drawings, 79 pages.
Aug. 20, 2012 Letter accompanying subsequently filed items, 1 page.
Jul. 9, 2012 Abstract, 1 page.
Jul. 9, 2012 Acknowledgement of receipt of electronic submission of the request for grant of a European patent, 2 pages.
Jul. 9, 2012 Claims, 6 pages.
Jul. 9, 2012 Description, 87 pages.
Jul. 9, 2012 Designation of inventor Daniel, 1 page.
Jul. 9, 2012 Designation of inventor Erwin, 1 page.
Jul. 9, 2012 Designation of inventor Ton, 1 page.
Jul. 9, 2012 Designation of inventor Mark, 1 page.
Jul. 9, 2012 Drawings, 72 pages.
Jul. 9, 2012 Request for grant of a European patent (divisional application), 6 pages.
Oct. 27, 2009 Priority document, 72 pages.
EPO Communication regarding Submission in opposition proceedings, Request for extension of time, EP Application No. 09075279.1 and Patent No. 2147594, Oct. 16, 2014, two pages.
EPO Acknowledgement of receipt of letter regarding request for extension of time, EP Application No. 09075279.1, date of receipt Oct. 16, 2014, one page.
EPO Brief Communication regarding the Opposition, EP Application No. 09075279.1 and Patent No. 2147594, Oct. 22, 2014, EPO Form 2911O 01.12, one page.
Correspondence from S.T. van Doorn of V.O. to European Patent Office in response to Communication under Rule 79 (1) EPC, EP Application No. 09075279.1 and Patent No. 2147594, Apr. 2, 2015, 32 pages.
EPO Brief Communication regarding the Opposition, EP Application No. 09075279.1 and Patent No. 2147594, Apr. 13, 2015, EPO Form 2911O 0112, one page.
EPO Brief Communication regarding the Opposition, EP Application No. 09075279.1 and Patent No. 2147594, Aug. 25, 2015, EPO Form 2911O 0112, one page.
EPO Communication of amended entries concerning the representative (R. 143(1)(h) EPC), EP Application No. 09075279.1 and Patent No. 2147594, Oct. 8, 2015, EPO Form 2548 08.13, one page.
EPO Acknowledgement of receipt of letter of inquiry, EP Application No. 09075279.1 and Patent No. 2147594, date of receipt Nov. 17, 2015, one page.
EPO Acknowledgement of receipt of change of representation, EP Application No. 09075279.1 and Patent No. 2147594, date of receipt Dec. 17, 2015, one page.
EPO communication to Fritz Lahrtz of Isenbruck Bösl Höschler LLP, Communication of amended entries concerning the representative (R. 143(1)(h) EPC), EP Application No. 09075279.1 and EP Patent No. 2147594, Jan. 12, 2016, EPO Form 2548 08.13, one page.
EPO communication to Andrew Bentham of J A Kemp, Brief Communication regarding EPO Form 2548 of Jan. 12, 2016, EP Application No. 09075279.1 and EP Patent No. 2147594, Jan. 12, 2016, EPO Form 2910O 01.12, two pages.
EPO communication, Preparation for oral proceedings—Instruction to Support Service, EP Application No. 09075279.1 and EP Patent No. 2147594, Jan. 14, 2016, EPO Form 2040 12.07TRI, two pages.
EPO Communication, Summons to Andrew Bentham of J A Kemp to attend oral proceedings pursuant to Rule 115(1) EPC, EP Application No. 09075279.1 and EP Patent No. 2147594, Jan. 19, 2016, EPO Form 2310 12.14, one page.
EPO Communication regarding Preliminary, Non-binding Opinion of the Opposition Division, EP Application No. 09075279.1, Jan. 19, 2016, EPO Form 2906 01.91TRI, 11 pages.
EPO Communication to Fritz Lahrtz of Isenbruck Bösl-Höschler LLP, Acknowledgement of receipt of EPO Forms 2310 and 2043, EP Application No. 09075279.1 and EP Patent No. 2147594, Jan. 19, 2016, EPO Form 2936 08.10, one page.
Fritz Lahrtz of Isenbruck Bösl Höschler LLP communication to EPO, Executed Acknowledgement, EP Application No. 09075279.1 and EP Patent No. 2147594, Jan. 25, 2016, EPO Form 2936 08.10, one page.
Submission in opposition proceedings by Andrew Bentham, EP Application No. 09075279.1 and Patent No. 2147594, Jan. 29, 2016, two pages.
EPO Acknowledgement of receipt of request to change date of oral proceedings, EP Application No. 09075279.1 and Patent No. 2147594, date of receipt Jan. 29, 2016, one page.
Correspondence from Fritz Lahrtz of Isenbruck Bösl Höschler LLP to European Patent Office regarding request for postponement of Oral Proceedings, EP Application No. 09075279.1 and EP Patent No. 2147594, Feb. 1, 2016, two pages.
EPO communication, Maintenance / Change of date / Cancellation of oral proceedings arranged for: 22.06.16 at 10.00 hrs, EP Application No. 09075279.1 and EP Patent No. 2147594, Feb. 4, 2016, EPO Form 2088 06.14, two pages.
EPO Brief Communication to Fritz Lahrtz of Isenbruck Bösl Höschler LLP regarding the Opposition and Oral Proceedings, EP Application No. 09075279.1 and Patent No. 2147594, Feb. 9, 2016, EPO Form 2911O 01.12, one page.
EPO Brief Communication to Andrew Bentham of J A Kemp regarding the Opposition and Oral Proceedings, EP Application No. 09075279.1 and Patent No. 2147594, Feb. 9, 2016, EPO Form 2911O 01.12, one page.
Advice of receipt to Fritz Lahrtz of Isenbruck Bösl Höschler LLP, Registration No. of item RD119029438NL, Mar. 14, 2016, one page.
Documents associated with European Patent Application EP 02709544, dated Feb. 20, 2015, (Electronic) Receipt—2.
Documents associated with European Patent Application EP 02709544, dated Feb. 26, 2015, Forwarding of submissions to parties—09.
Documents associated with European Patent Application EP 02709544, dated Feb. 26, 2015, Communication of amended entries in the Register of European Patents.
Documents associated with European Patent Application EP 02709544, dated Mar. 2, 2015, Letter accompanying subsequently filed items—1.
Documents associated with European Patent Application EP 02709544, dated Mar. 2, 2015, Letter accompanying subsequently filed items—2.
Documents associated with European Patent Application EP 02709544, dated Mar. 16, 2015, Forwarding of submissions to parties—1.
Documents associated with European Patent Application EP 02709544, dated Mar. 16, 2015, Forwarding of submissions to parties—2.
Documents associated with European Patent Application EP 02709544, dated Mar. 16, 2015, Forwarding of submissions to parties—3.
Documents associated with European Patent Application EP 02709544, dated Mar. 26, 2015, Forwarding of submissions to parties—2.
Particulars of Infringement, Jan. 3, 2014.
Documents associated with European Patent Application EP 02709544, dated Apr. 22, 2014, Notification concerning the date of oral proceedings—1.
Documents associated with European Patent Application EP 02709544, dated Apr. 22, 2014, Notification concerning the date of oral proceedings—2 .

(56) References Cited

OTHER PUBLICATIONS

Keane et al., Mouse genomic variation and its effect on phenotypes and gene regulation, Nature International Weekly Journal of Science, 6 pages, Sep. 15, 2011, pp. 289-294, vol. 477 Macmillan Publishers Limited.
Kwaks et al., 2003, previously submitted.
Lewis et al., A common Human β Globin Splicing Mutation Modeled in Mice, Blood Journal, 5 pages, Mar. 15, 1998, pp. 2152-2156, vol. 91, No. 6, The American Society of Hematology.
Lioudmila et al, Global Gene Expression profiling reveals similarities and differences among mouse pluripotent stem cells of different orgin and strains, Development Biology, 14 pages, Oct. 4, 2007, pp. 446-459, vol. 307, No. 2, NIH Public Access.
MacDonald et al., 2014, previously submitted.
Murphy et al., 2014, previously submitted.
Nagy et al., Derivation of completely cell culture-derived mice from early-passage embryonic stem cells, Development Biology, 5 pages, Sep. 15, 1993, pp. 8424-8428, vol. 90, No. 18, Proc Natl Acad Sci U S A.
gakatani et al., Abnormal Behavior in a Chromosome Engineered Mouse Model for Human 15q11-13 Duplication Seen in Austin, Cell, 12 pages, Jun. 26, 2009, pp. 1235-1246, vol. 137, No. 7, Elsevier Inc.
Pawlitzky et al., Identification of a Candidate Regulatory Element within the 5' Flanking Region of the Mouse Igh Locus Defined by Pro-B Cell-Specific Hypersensitivity Associated with Binding of PU.1, Pax5, and E2A, The Journal of Immunology, 13 pages, Jun. 1, 2006, pp. 6839-6851, vol. 176, No. 11, The American Association of Immunology.
Retter et al., Sequences and Characterization of the Ig Heavy Chain Constant and Partial Variable Region of the Mouse Strain 129S1, The Journal of Immunology, 9 pages, Aug. 15, 2007, pp. 2419-2427, vol. 179, No. 4, The American Association of Immunologists.
Riblet, R., A. Tutter, and P. Brodeur. 1986. Polymorphism and evolution of Igh-V gene families. Curr. Top. Microbial. Immunol. 127:168.
Sambrook 3rd ed pp. 1.2-1.16 (2001).
Sambrook 3rd Ed Chapter 1.21.
Sambrook 3rd Ed protocol 1, p. 12.10-12.13.
Sambrook 3rd ed Chapter 5 Protocols 15 and 19.
Sambrook 3rd ed vol. 3 p. 16.54-16.57.
Sambrook 3rd ed pp. 4.1-4.8 (2001).
Sambrook 3rd ed Protocol 7 4.48-4.52.
Sambrook 3d Ed 4.82-4.85.
Sambrook 3rd ed Chapter 5.3.
Sambrook 3rd ed, vol. 1 p. 6.3.
Sambrook 3rd Ed 8.95, Real time PCR.
Sambrook 3rd ed, Chapter 5, Protocol 13.
Sambrook 3rd ed, Chapter 6, Protocol 2.
Sambrook 3rd ed, Chapter 16.34, protocol 5.
Sauer, Brian, "Inducible gene targeting in mice using the Cre/loxSystem", Methods (1998), 14.4: 381-392.
Schindelhauer et al., HJ., Efficient combination of large DNA in vitro: in gel site specific recombination (IGSSR) of PAC fragments containing a satellite DNA and the human HPRT gene locus, Nucleic Acids Research, 1997, 25(11):2241-3.
Stevens et al., Poster 2006—VelocImmuneTM: Humanization of immunoglobulin loci using VelociGene® technology.
Xu,S. and Feiss, M., Structure of the bacteriophage lambda cohesive end site. Genetic analysis of the site (cosN) at which nicks are introduced by terminase, J Mol Biol., 1991, 220(2), 281-92.
Yang Y. et al., B., Site-specific gene targeting in mouse embryonic stem cells with intact bacterial artificial chromosomes, Nat Biotechnol., 2003, 21(4):447-51.
Zhao, S., A Comprehensive BAC Resource, Nucleic Acids Research, 2001, 29(1):141-3.
Kaufman, RJ., Overview of vector design for mammalian gene expression, Mol Biotechnol., 2000, 16(2), 151-160.

Kawasaki, K. et al; Evolutionary dynamics of the human immunoglobulin k locus and the germ line repertoire of the Vk genes, Eur J Immunol, 2001, 31(4):1017-28.
Kirschbaum, T. et al., The 3' part of the immunoglobulin kappa locus of the 1458-66 mouse, Eur J Immunol., 1998; 28(5), 1458-66.
Kirschbaum, T. et al., The central part of the mouse immunoglobulin kappa 2057-64. locus, Eur J Immunol., 1999, 29(7), 2057-64.
Kunkel, TA. et al, Rapid and efficient site-specific mutagenesis without phenotypic selection, Methods Enzymol., 1987, 154, 367-382.
Macdonald et al., Poster 2006—Velocigene® Technology Extended to Humanization of Several Megabases of Complex.
Mejia el al., The Assembly of Large BACs by in Vivo Recombination, Genomics, 2000, 70(2):165-70.
MeM□ the ingenious mouse for improved antibody therapeutics, www.merus.nl.
Mouse Genetics and Transgenics: A Practical Approach. I. J. Jackson and C. M. Abbott (eds). Oxford University Press, Oxford. 2000, chapter 7.
Mouse Genome Data available in public databases, Feb. 2001, NIH.
Murphy; KC., Use of Bacteriophage Lambda Recombination Functions to Promote Gene Replacement in *Escherichia coli*, J Bacterial, 1998, 180(8), 2063-71.
Muyrers JP. et al, ET-cloning: think recombination first, Genetic Engineering, 2000, 22:77-98.
NEB 1-Ceul datasheet and heat inactivation table.
NEB PI-SceI datasheet.
NIH website—Mouse BAC end sequencing project.
Orford M. et al., Engineering EGFP reporter constructs into a 200 kb human beta-globin BAC clone using GET Recombination; Nucleic Acids Res., 2000; 28(18), E84.
Potter H. et al., Enhancer-dependent expression of human Kc immunoglobulin genes introduced into mouse pre-B lymphocytes by electroporation, Proc Natl Acad Sci U S A, 1984, 81(22), 7161-5.
Potter H. et al., Transfection by Electroporation, Curr Prot Mol Biol., 2003, Chapter 9:Unit9.3. doi: 10.1002/0471142727.mb0903s92.
Presentation by Open Monoclonal Technology, Inc (Nov. 3, 2013), http://www.openmonoclonaltechnology.com/downloads.html.
Red/ET Recombination guide (Gene Bridges).
Abstract to 2006 Macdonald poster (1st International Mugen Conference Sep. 2006, Athens).
Abstract to 2006 Stevens poster (1st International Mugen Conference Sep. 2006, Athens).
Bio-Rad Cat No. 165-2105-Gene Pulser® II Electroporation System Instruction Manual.
Bitter, GA., Heterologous Gene Expression in Yeast, Methods Enzymol., 1987, 152, 673-684.
Boren J. et al; A Simple and Efficient Method for Making Site-directed Mutants, Deletions, and Fusions of Large DNA Such as PI and BAC Clones, Genome Res., 1996, 6(11), 1123-30.
Carson and Wu (1989) A linkage map of the mouse immunoglobulin lambda light chain.
Carter, R, Improving the efficacy of antibody-based cancer therapies, Nat Rev Cancer, 2001, 1(2), 118-129.
Declaration of Dr Werner Muller dated Dec. 22, 2016 in opposition proceedings EP2264163.
DNA Cloning 3, A Practical Approach, 2nd Ed, pp. 112-114.
DNA Sequencing Core Website, dated Nov. 21, 2015.
Email relating to Gene Bridges course on RedET recombination.
Eppig JT., Mouse Genome Informatics (MGI): reflecting on 25 years, Mamm Genome, 2015, 26(7-8):272-84. doi: 10.007/s00335-015-9589-4. Epub Aug. 4, 2015.
Factsheet from Opponent1 re MeMo mouse dated 2012.
Fuchs, P. et al., Targeting recombinant antibodies to the surface of *Escherichia coli*: fusion to a peptidoglycan associated lipoprotein, Biotechnology (N Y), 1991, 9(12), 1369-1372.
GeneBridges course invitation, 2003.
Hansen, S. et al., "Crescendo's Cash Fragments," BioCentury, The BernsteinReport on BioBusiness, Dec. 2, 2013, p. A13.
Hill, R et al., BAC Trimming: Minimizing Clone Overlaps; Genomics, 2000, 64(1):111-3.

(56) References Cited

OTHER PUBLICATIONS

Huetz, F. et al., Targeted disruption of the V(H) 81X gene: influence on the B cell repertoire, Eur J Immunol. Jan. 1997;27(1):307-14.
Documents associated with European Application EP 02709544, dated Sep. 17, 2013, Brief communication—Opposition Patent proceedings—2 .
Documents associated with European Patent Application EP 02709544, dated Sep. 17, 2013, Grant of extension of time limit (opposition procedure).
Documents associated with European Patent Application EP 02709544, dated Oct. 11, 2013, (Electronic) Receipt.
Documents associated with European Patent Application EP 02709544, dated Jan. 28, 2014, Brief communication—Opposition proceedings—2.
Molecular Biology of B Cells, 1st Ed., Reth et al., Elsevier, Feb. 19, 2004, http://store.elsevier.com/Molecular-Biology-of-B-Cells/isbn-9780120536412/, printed Jan. 22, 2014.
Open Monoclonal Technology, Inc., Nov. 3, 2013, 3 pages.
Ma et al., Human antibody expression in transgenic rats: Comparison of chimeric IgH lock with human V eta and J eta but bearing different rat C-gene regions, J. Immunol. Methods (2013), http://dx.doi.org/10.1016/j.jim.2013.10.007.
Green et al., Regulation of B Cell Development by Variable Gene Complexity in Mice Reconstituted with Human Immunoglobulin Yeast Artificial Chromosomes, J. Exp. Med. Aug. 3, 1998, pp. 483-495, vol. 188, Downloaded from www.jem.org on Feb. 22, 2007.
Hansen, Stephen, BioCentury, Kymab: More mAb diversity, Article Reprint from Feb. 27, 2012.
BioCentry, Dec. 23, 2013, p. A1, A13, vol. 21, No. 48.
News Release: Astellas Licenses Regeneron's Velocimmune® Technology for Discovering Human Monoclonal Antibodies (Mar. 30, 2007).
Regeneron and Columbia University Enter Into a Strategic VeloclmmuneR Agreement, Business Wire, (Sep. 16, 2008), http://www.businesswire.com/news/google/20080916005336/en, printed Jan. 23, 2014.
Statement of Sue Klapholz, M.D., Ph.D., Jan. 27, 2014.
Glanville et al., Naïve antibody gene-segment frequencies are heritable and unaltered by chronic lymphocyte ablation, PNAS, Dec. 13, 2011, pp. 20066-20071, vol. 108, No. 50.
First Auxilary Request.
Second Auxilary Request.
Third-Party Submission filed with the U.S. Patent Office on Aug. 29, 2016 in U.S. Appl. No. 15/140,321, 4 pages.
Documents listed in the Third-Party Submission include the following: U.S. Pat. No. 7,262,028 (previously submitted); Merchant et al., 1998 (previously submitted); Declaration of Dr. Joel Martin executed May 18, 2016 (previously submitted); U.S. Pat. No. 9,248,182 (previously submitted); WO 1998/050431 (previously submitted); Carter, 2001; WO 1999/045962 (previously submitted); Ritchie et al., 1984 (previously submitted); WO 02/066630 (previously submitted).
Canadian Intellectual Property Office—office action for Application No. 2,729,095 held by Merus B.V. dated Nov. 10, 2015 listing references considered: D8—Sirac et al., 2006 (previously submitted); D10—WO 2006/117699 (previously submitted); D12—WO 2004/106375 (previously submitted); D13—Wo 02/066630 (previously submitted); D14—US 2007/0280945 (previously submitted).
Defrancesco et al., Big Pharma vies for mice, Nature Biotechnology, 25/6, pp. 613-614, Jun. 2007.
Third-Party Opposition dated Sep. 16, 2015, for Canadian Application No. 2,729,095, and Protest and Submission of Prior Art, which lists the following documents D8, D9, D10, D11, D12, D13, D14, D15, D16, D17, D18, D19, D20.
The Third-Party Opposition of Sep. 16, 2015, indicates the following attachments: 1) Second Protest (13 pages); 2) D8—Sirac et al., 2006, 9 pages (previously submitted); 3) D9—US20060015957 (299 pages); 4) D10—WO 2006117699 (79 pages) (previously submitted); 5) D11—WO 2004009618 (186 pages); 6) D12—WO 2004106375 (189 pages) (previously submitted); 7) D13—WO 20066630 (74 pages) (previously submitted).
8) D14—US 20070280945 (71 pages) (previously submitted); 9) D15—WO2008076379 (37 pages) (previously submitted); 10) D16—WO 2008054606 (30 pages) (previously submitted); 11) D17—New in Brief 2007 (2 pages) (previously submitted); 12) D18—Scott et al., 2007 (3 pages) (previously submitted); 13) D19—Nagle et al., 2007 (2 pages) (previously submitted) and 14) D20—Sirac et al., 2011 (15 pages) (previously submitted).
Protest and Submission of Prior Art submitted by Blake, Cassels & Graydon LLP dated Apr. 8, 2014, indicates the following attachments: 1) Protest and Submission of Prior Art (13 pages); 2) D8—Sirac et al., 2006, 9 pages (previously submitted); 3) D9—Aucouturier et al. (8 pages) (previously submitted); D10—GenBank M87478 (1 page) (previously submitted); D11—Sequence Alignment of GenBank (7 pages) (previously submitted); D12—de Wildt (7 pages) (previously submitted); D13—US 20060015957 (299 pages) (previously submitted); D14—WO 2004106375, (Previously.
D17—WO 9850431 (70 pages) (previously submitted); D18—WO 02066630 (74 pages) (previously submitted); D19—US 20070280945 (71 Pp.) (previously submitted); D20—WO 2008076379 (37 pages) (previously submitted); D21—WO 2008054606 (30 pages) (previously submitted); D22—NIB 2007 (2 pages) (previously submitted); 23—Scott et al., 2007 (3 pages) (previously submitted); and D24—Nagle et al., 2007 (2 pages) (previously submitted).
Protest and Submission of Prior Art submitted by Blake, Cassels & Graydon LLP dated Sep. 16, 2015, indicates the following attachments: D8—Sirac et al., 2006, 9 pages (previously submitted); D9—US 20060015957 (299 pages) (previously submitted); D10—WO 2006117699 (previously submitted); D11—WO 2004009618 (previously submitted); D12—WO 2004106375 (previously submitted).
D13—WO 02066630 (previously submitted); D14—US 20070280945 (previously submitted); D15—WO 2008076379 (previously submitted); D16—2008054606 (previously submitted); D17—News in Brief Article (previously submitted); D18—Scott, (previously submitted); D19, Nagle, 2007 (previously submitted); D20, Sirac et al., 2011.
(Page 1) EPO Form 2906 regarding Patent Application No. 10 186 0613 dated Jul. 27, 2016, indicating the description needs to be brought in conformity with the claims, 1 page.
(Page 5-6) Letter from Isenbruck to the European Patent Office dated Jun. 20, 2016, indicating Ton Logtenberg will not be in attendance at the oral proceedings, 2 pages.
(Page 63-64) Letter dated May 27, 2016, accompanying the Deed of Conversion and Amendment, and Form 1010, 2 pages.
(Page 66-70) Main Request with annotations, EP Patent No. 2314629B1, May 20, 2016, five pages (previously submitted); (pp. 71-75) Auxiliary Request 1 with annotations, EP Patent No. 2314629B1, May 20, 2016, five pp. (previously submitted); (pp. 76-80) Auxiliary Request 2, EP Patent No. 2314629B1, May 20, 2016, five pages (previously submitted).
(Pages 81-85) Auxiliary Request 3 with annotations, EP Patent No. 231462961, May 20, 2016, five pages (previously submitted); (pp. 86-90) Auxiliary Request 4 with annotations, EP Patent No. 2314629B1, May 20, 2016, five pages (previously submitted); (pp. 91-95) Auxiliary Request 5 with annotations, EP Patent No. 2314629B1, May 20, 2016, five pages (previously submitted).
(Pages 96-100) Auxiliary Request 6 with annotations, EP Patent No. 231462961, May 20, 2016, five pages (previously submitted); (pp. 101-107) Auxiliary Request 7 with annotations, EP Patent No. 2314629B1, May 20, 2016, seven pages (previously submitted); (pp. 108-114) Auxiliary Request 8 with annotations, EP Patent No. 2314629B1, May 20, 2016, seven pages (previously submitted).
(Pages 115-123) Auxiliary Request 9 with annotations, EP Patent No. 2314629B1, May 20, 2016, nine pages (previously submitted); (pp. 124-132) Auxiliary Request 10 with annotations, EP Patent No. 2314629B1, May 20, 2016, nine pages (previously submitted); (pp. 133-137) Auxiliary Request 11 with annotations, EP Patent No. 2314629B1, May 20, 2016, five pages.
(Pages 138-142) Auxiliary Request 12 with annotations, EP Patent No. 2314629B1, May 20, 2016, five pages (previously submitted);

(56) References Cited

OTHER PUBLICATIONS (pp. 143-147) Auxiliary Request 13 with annotations, EP Patent No. 2314629B1, May 20, 2016, five pages; (Pages 148-152) Auxiliary Request 14 with annotations, EP Patent No. 2314629B1, May 20, 2016, five pages.
(Pages 153-157) Auxiliary Request 1, EP U.S. Pat. No. 2314629B1, May 20, 2016, five pages.
(Pages 158-162) Auxiliary Request 2, EP Patent No. 2314629B1, May 20, 2016, five pages; (previously submitted); (pp. 163-167) Auxiliary Request 4, EP Patent No. 2314629B1, May 20, 2016, five pages (previously submitted); (pp. 173-177); Auxiliary Request 5, EP Patent No. 2314629B1, May 20, 2016, five pages (previously submitted).
(Pages 178-182) Auxiliary Request 6, EP Patent No. 2314629B1, May 20, 2016, five pages (previously submitted); (pp. 183-197) Auxiliary Request 7, EP Patent No. 2314629B1, May 20, 2016, five pages (previously submitted); (pp. 188-192); Auxiliary Request 8, EP Patent No. 2314629B1, May 20, 2016, five pages (previously submitted).
(Pages 193-197) Auxiliary Request 9, EP Patent No. 2314629B1, May 20, 2016, five pages (previously submitted); (pp. 198-202) Auxiliary Request 10, EP Patent No. 2314629B1, May 20, 2016, five pages (previously submitted); (pp. 203-205) Auxiliary Request 11, EP Patent No. 2314629B1, May 20, 2016, three pages (previously submitted).
(Pages 206-208); Auxiliary Request 12, EP Patent No. 2314629B1, May 20, 2016, three pages (previously submitted); (pp. 209-213); Auxiliary Request 13, EP Patent No. 2314629B1, May 20, 2016, five pages (previously submitted); (pp. 214-218) Auxiliary Request 14, EP Patent No. 2314629B1, May 20, 2016, five pages.
(Pages 219-225) Logtenberg, Prof. Ton Declaration of, CEO, Merus B.V., dated May 4, 2016, 7 pages (previously submitted); (pp. 226-251) Appeal Brief under 37 C.F.R. § 41.37 filed by Brenda Herschbach Jarrell, U.S. Appl. No. 13/948,818, filed Jul. 20, 2015, 26 pages with Claims Appendix (previously submitted).
(Pages 252-267) Response to the Summons to attend Oral Proceedings dated Nov. 29, 2015 and in preparation of the Hearing of Jun. 22, 2016, from Isenbruck Bösl Förschler LLP to European Patent Office dated May 20, 2016.
(Pages 268-272) Main Request with annotations, EP U.S. Patent No. 2314629B1, Reference No. M70120EPEIN FLZ, May 20, 2016, five pages(previously submitted); (pp. 273-279) EPO communication to Fritz Lahrtz of Isenbruck Bösl Höschler LLP, Brief Communication regarding Oral proceedings on Jun. 22, 2016 at 10:00 in S2.1, EP Application No. 10186063.3 and EP Patent No. 2314629, dated Apr. 26, 2016, (previously submitted).
(Page 280) Correspondence trom Dr. Fritz Lahrtz of Isenbruck Bösl Förschler LLP to the European Patent Office regarding the Oral Proceedings on Jun. 22, 2016, EP Application No. 10186063.3 and EP Patent No. 2314629, Feb. 16, 2016, one page (previously submitted); (p. 281) EPO communication to Fritz Lahrtz of Isenbruck Bösl Höschler LLP, Communication of amended entries concerning the representative (R. 143(1)(h) EPC), EP Application No. 10186063.3 and EP Patent No. 2314629, dated Jan. 12, 2016, EPO Form 2548 08.13, one page (previously submitted).
(Page 282) Correspondence from Dr. Fritz Lahrtz of Isenbruck Bösl Förschler LLP to the European Patent Office regarding change of correspondence, EP Application No. 10186063.3 and EP Patent No. 2314629, Jan. 8, 2016, one page (previously submitted); (p. 283) EPO Acknowledgement of receipt, Application No. 10186063.3, dated Dec. 17, 2015, one page; (previously submitted).
(Page 284-285) EPO Letter accompanying subsequently filed items, Document concerning representation filed by C. M. Jansen of V.O., EP Application No. 10186063.3, dated Dec. 17, 2015, two pages (previously submitted); (pp. 286-287) EPO Communication to J A Kemp, Acknowledgement of receipt of EPO Forms 2310 and 2043, EP Application No. 10186063.3 and Ep Patent No. 2314629, dated Nov. 19, 2015, EPO Form 2936 08.10, one page; (previously submitted).
(Pages 288-298) EPO Communication regarding opposition, EP Application No. 101860613, Nov. 19, 2015, EPO Form 2906 01.91TRI with Consolidated list of documents, 11 pages (previously submitted).
(Page 306) EPO Communication of amended entries concerning the representative (R. 143(1)(h) EPC), EP Application No. 10186063.3 and EP Patent No. 2314629, dated Oct. 8, 2015, EPO Form 2548, Aug. 2013, one page (previously submitted); (p. 307) Correspondence from C.M. Jansen of V.O. to European Patent Office regarding the Registration of the Association and change of address, reference No. RvE/E100EPEP, Sep. 29, 2015, one page (previously submitted).
(Pages 311-330) Reply to Communication under Rule 79(1) EPC, EP Application No. 10186063.3 and EP Patent No. 2314629, dated Feb. 24, 2015, 20 pages (previously submitted).
(Page 331) EPO Extension of time limit pursuant to Rule 132 EPC, EP Application No. 10186063.3 and EP Patent No. 2314629, Oct. 24, 2014, EPO Form 2944C, Jun. 2012, one page.
(Page 332-335) EPO Communication regarding Submission in opposition proceedings, Request for extension of time, EP Application No. 10186063.3 and U.S. Patent 2314629, Oct. 16, 2014, four pages.
(Page 336) EPO Communication of a notice of opposition (R. 79(1) EPC), EP Application No. 10186063.3 and EP Patent No. 2314629, Aug. 22, 2014, EPO Form 2317A, Dec. 2007, one page (previously submitted).
Mead G.P. et al., Poster, Detection of Bence Jones myeloma and monitoring of myeloma chemotherapy using immunoassays specific for free immunoglobulin light chains, Clinical Laboratory, 2003, vol. 49, No. 1-2, 2003, p. 25-27.
Zhu et al., Remodeling domain interfaces to enhance heterodimerformation, Protein Science, Apr. 1997, pp. 781-788, vol. 6, Issue 4.
Canadian Patent Office, Completion Requirement, Submission of Sequence Listing , CA Application No. 2729095, Mar. 9, 2011, one page.
Third-Party Opposition dated Sep. 16, 2015, for Canadian Application No. 2,729,095, and Protest and Submission of Prior Art, which lists the following documents DB, D9, D10, D11, D12, D13, D14, D15, D16, D17, D18, D19, D20.
Canadian Patent Office, Response to the Office Action dated Jun. 11, 2014, CA Application No. 2729095, dated Dec. 10, 2014, 24 pages.
U.S. Provisional Patent Application filed Oct. 13, 2000, Aris et al., U.S. Appl. No. 60/244,665.
Documents associated with European Patent Application EP 02709544, dated Apr. 4, 2014, Patent document cited during the opposition procedure—1.
Office Action Response in U.S. Appl. No. 12/932,719 (dated Aug. 10, 2013) filed in protest against U.S. Appl. No. 15/158,543.
Documents associated with European Patent Application EP 02709544, dated Apr. 4, 2014, Patent document cited during the opposition procedure—2.
Documents associated with European Patent Application EP 02709544, dated Jul. 9, 2015, Forwarding of submissions to parties—1.
Documents associated with European Patent Application EP 02709544, dated Jul. 9, 2015, Forwarding of submissions to parties—2.
Documents associated with European Patent Application EP 02709544, dated Jul. 9, 2015, Forwarding of submissions to parties—3 .
Johansson, BM. et al., Evidence for involvement of activin A and bone morphogenetic protein 4 in mammalian mesoderm and hematopoietic development, Mol Cell Biol., 1995, 15(1), 141-151.
Urlaub et al., Isolation of Chinese hamster cell mutants deficient in dihydrofolate reductase activity, PNAS, Jul. 1, 1980, pp. 4216-4220, vol. 77, No. 7.
Frengen, E. et al., A modular, positive selection bacterial artificial chromosome vector with multiple cloning sites, Genomics, 1999, 58(3), 250-3.
EPO Communication regarding Submission in opposition proceedings, Reply of the patent proprietor to the notice(s) of opposition, EP Application No. 09075279.1 and Patent No. 2147594, Apr. 2, 2015, two pages.
Documents associated with European Patent Application EP 02709544, dated Mar. 10, 2014, Letter accompanying subsequently filed items.

(56) References Cited

OTHER PUBLICATIONS

Japan Patent Office, As-Filed Application, Japanese Patent Application No. 2015-097258, May 13, 2015, 270 pages.
Documents associated with European Patent Application EP 02709544, dated Sep. 8, 2015, Advice of delivery.
Giraldo et al., Size matters: use of YACs, BACs and PACs in transgenic animals, Transgenic Research, 2001, pp. 83-103, vol. 10.
Bruggemann, Marianne, Human Monoclonal Antibodies from Translocus Mice, Elsevier Science (USA), Molecular Biology of B Cells, (2004) Ch. 34, pp. 547-561.
Statement of Facts and Arguments in support of Opposition, EP Application No. 09075279.1 and Ep Patent No. 2147594, at least as early as Aug. 11, 2014, 46 pages.
Documents associated with European Patent Application EP 02709544, dated Feb. 28, 2014, Preparation for oral proceedings.
Ye, X., et al., Ultrabithorax and Antennapedia 5' untranslated regions promote developmentally regulated internal ranslation initiation, Mal. Cell Biol., 1997, 17(3), 1714-17121.
Min Soo Kim et al., Comparative Analyses of Complex Formation and Binding Sites between Human Tumor Necrosis Factor-alpha and its Three Antagonists Elucidate their Different Neutralizing Mechanisms, JMB, Dec. 14, 2007, pp. 1374-1388, vol. 374, Issue 5.
EPO Communication pursuant to Article 94(3) EPC, Application No. 10186063.3, Dec. 12, 2011, EPO Form 2001, 12.10CSX, 5 pages.
Shiga Internation Patent Office to Japan Patent Office, Remarks in response to notice of reasons for rejection, Japanese Patent Application No. 2011-516168, dated Jan. 14, 2014, six pages.
Hudziak et al., p185HER2 monoclonal antibody has antiproliferative effects in vitro and sensitizes human breast tumor cells to tumor necrosis factor, Mol. Cell. Biol., Mar. 1989, pp. 1165-1172, vol. 9. No. 3.
Documents associated with European Patent Application EP 02709544, dated Apr. 4, 2014, Intervention of the assumed infringer.
Documents associated with European Patent Application EP 02709544, dated Nov. 3, 2015, Letter dealing with oral proceedings during the appeal procedure—2.
Documents associated with European Patent Application EP 02709544, dated Mar. 9, 2015, Letter accompanying subsequently filed items.
Aug. 8, 2016 Invitation to confirm maintenance of the application and to correct deficiencies in the Written Opinion/amend application, 2 pages.
Attaelmannan, Mohammed et al., "Understanding and Identifying Monoclonal Gammopathies," Clinical Chemistry, vol. 46(8B):1230-1238 (2000).
Documents associated with European Patent Application EP 02709544, dated Nov. 3, 2015, Letter dealing with oral proceedings during the appeal procedure—1.
Zou, YR. et al, Generation of a mouse strain that produces immunoglobulin kappa chains with human constant egions, Science, 1993, 262(5137), 1271-1274.
Throsby, Isolation and Characterization of Human Monoclonal Antibodies from Individuals Infected with West Nile Virus, J. Virol., Jul. 2006, pp. 6982-6992, vol. 80, No. 14.
De Graaf et al., Expression of scFvs and scFv Fusion Proteins in Eukaryotic Cells, Antibody Phage Display Methods and Protocals, Methods in Molecular Biology, 2002, pp. 379-387, vol. 178.
Retter, Marc W. et al., "Receptor Editing Occurs Frequently during Normal B Cell Development," J. Exp. Med., vol. 188(7):1231-1238 (1998).
Specification of International Application No. PCT/EP03/07690, "Recombinant Production of Mixtures of Antibodies", at Least as early as Oct. 1, 2010, 122 pages.
Lofgren et al., Comparing ELISA and Surface Plasmon Resonance for Assessing Clinical Immunogenicity of Panitumumab, J Immunol., 2007, pp. 7467-7472, vol. 178.
Akerstrom, B. et al., On the interaction between single chain Fv antibodies and bacterial immunoglobulin-binding proteins, J Immunol Methods., 1994, 177(1-2), 151-163.

Janeway et al., Chapter 3: Structure of the Antibody Molecule and the Immunoglobulin Genes, ImmunoBiology The Immune System in Health and Disease, Fourth Edition, 1999, pp. 90-108, Elsevier Science Lid/Garland Publishing.
Documents associated with European Patent Application EP 02709544, dated Jun. 6, 2013, Notice of opposition—2.
Documents associated with European Patent Application EP 02709544, dated Jun. 6, 2013, Notice of opposition—1.
Statement of Facts and Arguments in Support of Opposition, Patent No. EP2147594 B1, 46 pages, dated Aug. 11, 2014.
Documents associated with European Patent Application EP 02709544, dated Jun. 6, 2013, Notice of opposition—3.
EPO Communication to Andrew Bentham of J A Kemp, Acknowledgement of receipt of EPO Forms 2310 and 2043, EP Application No. 09075279.1 and EP Patent No. 2147594, dated Mar. 22, 2016, EPO Form 2936 08.10, one page.
Conn et al., Purification of a glycoprotein vascular endothelial cell mitogen from a rat glioma-derived cell line, Proc. Natl. Acad. Sci. U.S.A., Feb. 1, 1990, pp. 1323-1327, vol. 87, No. 4.
EPO Communication to Martin Hatzmann of Vereenigde, Summons to attend oral proceedings pursuant to Rule 115(1 EPC, EP Application No. 09075279.1, Mar. 6, 2013, EPO form 2008 12.12, one page.
Documents associated with European Patent Application EP 02709544, dated Jan. 28, 2014, Amended claims wilt annotations—2.
Tarlinton, David, Declaration filed Against Australian Application No. 2009263082 in the name of Merus B.V., executed Dec. 21, 2014.
Larrick et al., Producing proteins in transgenic plants and animals, Current Opinion in Biotechnology, Aug. 1, 2001, pp. 411-418, vol. 12, Issue 4.
Canadian Patent Office, Voluntary Amendment , CA Application No. 2729095, dated Dec. 5, 2011, thirteen pages.
Documents associated with European Patent Application EP 02709544, dated Feb. 9, 2015, Letter relating to Appeal Procedure.
EPO Acknowledgement of receipt of letter of inquiry, EP Application No. 09075279.1 and Patent No. 2147594, dated Nov. 17, 2015, one page.
Deficiencies in application documents dated Jul. 20, 2012, EP12175544.1.
Regeneron partners VelocImmune with University of Texas, Elsevier BusinessIntelligence, http://www.elsevierbi.com/deals/200920210?p+1, printed Jan. 23, 2014.
Fishwild OM, et al., High-avidity human IgG kappa monoclonal antibodies from a novel strain of minilocus transgenic mice, Nat Biotechnol, 1996, 14(7), 845-851.
Next generation trangenic mice for therapeutic human antibodies, MeMo—the ingenious mouse, at least as early as Aug. 11, 2014, two pages, www.merus.nl.
Kroesen et al., Bispecific antibodies for treatment of cancer in experimental animal models and man, Department of Clinical Immunology, 1998 pp. 105-129.
Presentation by Cecile Geuijen, May 27, 2013: Full length human IgG bispecific antibodies for cancer therapy.
EPO Acknowledgement of receipt of possible dates for oral proceedings, EP Application No. 09075279.1 and Patent No. 2147594, date of receipt Feb. 15, 2016, one page.
EPO Communication, Decision to grant a European patent pursuant to Article 97(1) EPC, EP Application No. 09075279.1, dated Oct. 17, 2013, EPO Form 2006A 12.07, two pages.
Fukita, Y. et al., Somatic hypermutation in the heavy chain locus correlates with transcription, Immunity, 1998, 9(1), 105-14.
Takeda et al., Construction of chimaeric processed immunoglobulin genes containing mouse variable and human Constant region sequences, Nature, Apr. 4, 1985, pp. 452-454, vol. 314.
Documents associated with European Patent Application EP 02709544, dated Nov. 9, 2015, Oral Proceedings_ Minutes (Appellant_ Proprietor).
EP Acknowledgement of Receipt for Request for Grant of EP Application No. 10186063.3, dated Oct. 1, 2010, 2 pages.
Barmes, LM. et al, Characterization of the stability of recombinant protein production in the GS-NS0 expression system Biotechnol Bioeng., 2001, 73(4), 261-270.

(56) References Cited

OTHER PUBLICATIONS

Mayer, MP., A new set of useful cloning and expression vectors derived from pBlueScript, Gene, 1995, 163(1), 41-46.
Marie-Paule Lefranc and Gerard Lefranc, The Immunoglobulin Facts Book, Academic press, 2001, p. 52-58.
Harjunpaa, A., et al, Rituximab (anti-CD20) therapy of B-cell lymphomas: direct complement killing is superior to Cellular effector mechanisms. Scand J Immunol., 2000, 51(6), 634-641.
Hay, BN. et al., Bacteriophage cloning and *Escherichia coli* expression of a human IgM Fab, Hum Antibodies Hybridomas, 1992, 3(2), 81-85.
Documents associated with European Patent Application EP 02709544, dated Jul. 16, 2014, Patent document cited during the opposition procedure—2.
Abuin et al., Recycling Selectable Markers in Mouse Embryonic Stem Cells, Molecular and Cellular Biology, 6 pages, Apr. 1996, pp. 1851-1856, vol. 16. No. 4, American Society of Microbiology.
Documents associated with European Patent Application EP 02709544, dated Jul. 16, 2014, Patent document cited during the opposition procedure—4.
Documents associated with European Patent Application EP 02709544, dated Jul. 16, 2014, Patent document cited during the opposition procedure—6.
Statement of Grounds and Particulars submitted in opposition to Australian Patent Application 2009263082, filed Sep. 22, 2014, 35 pages.
Prosser et al., A resource of vectors and ES cells for targeted deletion of MicroRNAs in mice, Nature Biotechnology, 6 pages, Aug. 7, 2011, pp. 840-845, vol. 29, No. 9, Nature America Inc.
Correspondence from A. Bentham of J A Kemp to The European Patent Office regarding request to change date of Oral Proceedings, EP Patent No. 2147594, Jan. 29, 2016, two pages.
Eren, R. et al., Preclinical evaluation of two human anti-hepatitis B virus (HBV) monoclonal antibodies in the HBV-trimera mouse model and in HBV chronic carrier chimpanzees, Hepalology, 2000, 32(3), 588-596.
EPO communication, Executed Maintenance / Change of date / Cancellation of oral proceedings arranged for: May 23, 2013 at 10.00 hrs, EP Application No. 19075279.1, dated May 14, 2013, EPO Form 2088 04.10, two pages.
Bogen, Bjarne et al., "A rearranged lambda 2 light gene chain retards but does not exclude kappa and lambda 1 expression," Eur. J. Immunol., vol. 21:2391-2395 (1991).
"Big Pharma vies for mice", Nature Biotechnology, vol. 25, No. 6, Jun. 2007, pp. 613-614, Nature Publishing Group.
Ritchie et al., Allelic exclusion of control of endogenous immunoglobin gene rearrangement in kappa transgenic mice, Nature, Dec. 1984, pp. 517-520, vol. 312, Nature Publishing Group.
Documents associated with European Patent Application EP 02709544, dated Jun. 12, 2013, Letter regarding the Opposition procedure (no time limit)—2.
Documents associated with European Patent Application EP 02709544, dated Jun. 12, 2013, Letter regarding the Opposition procedure (no time limit)—1.
Cheong et al., Affinity Enhancement of Bispecific Antibody Against Two Different Epitopes in the Same Antigen, Biochemical and Biophysical Research Communications, vol. 173, No. 3, 1990, pp. 795-800.
Griffiths et al., Isolation of high affinity human antibodies directly from large synthetic repertoires, EMBO J., Jul. 15, 1994, pp. 3245-3260, vol. 13, No. 14.
SHIGA Internation Patent Office to Japan Patent Office, Remarks in response to notice of reasons for rejection, Japanese Patent Application No, 2011-516168, dated Jan. 5, 2015, 16 pages.
Documents associated with European Patent Application EP 02709544, dated Mar. 17, 2016, Advice of delivery.
Stijlemans, B. et al., Efficient targeting of conserved cryptic epitopes of infectious agents by single domain antibodies. I\frican trypanosomes as paradigm, J Biol Chem 2004, 279(2), 1256-1261.

Holt, L.J. et al., Domain antibodies: proteins for therapy, Trends Biotechnol., 2003, 21(11), 484-490.
Mccafferty; Hoogenboom; Chiswell: Antibody engineering : a practical approach, 1996, Oxford University press.
Kouskoff et al., Cassette vectors directing expression of T cell receptor genes in transgenic mice, Journal of Immunological Methods (1995) pp. 273-280, vol. 180.
Documents associated with European Patent Application EP 02709544, dated Jul. 2, 2015, Annexes (other than cited documents) regarding appeal procedure—2.
Documents associated with European Patent Application EP 02709544, dated Jul. 2, 2015, Annexes (other than cited documents) regarding appeal procedure—1.
EPO Acknowledgement of receipt of change of representation, EP Application No. 09075279.1 and Patent No. 2147594, dated Dec. 17, 2015, one page.
Documents associated with European Patent Application EP 02709544, dated Jul. 2, 2015, Cited document during appeal procedure—02.
Documents associated with European Patent Application EP 02709544, dated Jul. 2, 2015, Cited document during appeal procedure—01.
Galy, AH. et al., Delineation of T-progenitor cell activity within the CD34+ compartment of adult bone marrow, Blood, 1995, 85(10), 2770-2778.
Documents associated with European Patent Application EP 02709544, dated Jul. 2, 2015, Cited document during appeal procedure—08.
Documents associated with European Patent Application EP 02709544, dated Jul. 2, 2015, Cited document during appeal procedure—07.
EPO Communication under rule 71(3) EPC, EP Application No. 10186063.3, dated Jun. 17, 2013, EPO Form 2004C, 04.12TRI, 196 pages.
Documents associated with European Patent Application EP 02709544, dated—Nov. 9, 2015—Amended claims with annotations—1.
Documents associated with European Patent Application EP 02709544, dated Jul. 2, 2015, Cited document during appeal procedure—09.
Documents associated with European Patent Application EP 02709544, dated Jul. 2, 2015, Cited document during appeal procedure—04.
Brink MF, et al., Developing efficient strategies for the generation of transgenic cattle which produce biopharmaceuticals in milk, Theriogenology, 2000, 53(1), 139-148.
Documents associated with European Patent Application EP 02709544, dated Jul. 2, 2015, Cited document during appeal procedure—03.
Documents associated with European Patent Application EP 02709544, dated Jul. 2, 2015, Cited document during appeal procedure—06.
Documents associated with European Patent Application EP 02709544, dated Jul. 2, 2015, Cited document during appeal procedure—05.
Documents associated with European Patent Application EP 02709544, dated Mar. 2, 2015, (Electronic) Receipt—2.
EPO Brief Communication regarding the Opposition, EP Application No. 09075279.1 and Patent No. 2147594, Dec. 9, 2015, EPO Form 29110 01.12, one page.
Documents associated with European Patent Application EP 02709544, dated Mar. 2, 2015, (Electronic) Receipt—1.
De Vries, P. et al., The effect of recombinant mast cell growth factor on purified murine hemalopoielic stem cells, J Exp Med, 1991, 173(5), 1205-1211.
Phan, TG., High affinity germinal center B cells are actively selected into the plasma cell compartment, J Exp Med., 2006 203(11); 2419-2424.
Storb, Ursula et al., "Transgenic Mice with mu and kappa Genes Encoding Antiphosphorylcholine Antibodies," J. Exp. Med., vol. 164:627-641 (1986).
Ma et al., Assembly of monoclonal antibodies with IgG1 and IgA heavy chain domains in transgenic tobacco plants, Eur. J_ Immunol., 1994, p. 131-138, vol. 24.
Reply letter of proprietor in response to the opposition proceedings against EP 2264163 B1, dated Dec. 30, 2016.
Soriano, P., Generalized IacZ expression with the ROSA26 Cre reporter strain, Nat Genet. 1999;21(1), 70-71.
EPO Communication pursuant to Rule 114(2) EPC, EP Application No. 09075279.1 and Patent No. 2147594, dated Jun. 14, 2013, EPO Form 2022 12.07, one page.

(56) References Cited

OTHER PUBLICATIONS

Lenz, et al.; Expression of heterobispecific antibodies by genes transfected into producer hybridoma cellsGene; 87 ( 1990) Mar. 15, No. 2; pp. 213-218.
Documents associated with European Patent Application EP 02709544, dated Jan. 22, 2015, Letter relating to Appeal Procedure—1.
Documents associated with European Patent Application EP 02709544, dated Jan. 22, 2015, Letter relating to Appeal Procedure—.
Feige, U. el. al., Anti-interleukin-1 and anti-tumor necrosis factor-alpha synergistically inhibit adjuvant arthritis in Lewis rats, Cell Mol Life Sci., 2000, 57(10), 1457-1470.
Documents associated with European Patent Application EP 02709544, dated Nov. 4, 2015, oral Proceedings_summons.
Documents associated with European Patent Application EP 02709544, dated Dec. 9, 2014, Letter accompanying subsequently filed items.
Documents associated with European Patent Application EP 02709544, dated Sep. 19, 2016, Any annexes (other than citation) to an opposition letter—1.
Keane et al., Mouse genomic variation and its effect an phenotypes and gene regulation, Nature International Weekly Journal of Science, 6 pages, Sep. 15, 2011, pp. 289-294, vol. 477 Macmillan Publishers Limited.
Documents associated with European Patent Application EP 02709544, dated Sep. 19, 2016, Any annexes (other than citation) to an opposition letter—2.
In the High Court of Justice, Chancery Division, Patents Court, Case No. HP-2013-000001/HP-2014-000001 dated Nov. 12, 2015, Third Expert Report of Professor Sir Martin Evans FRS Ph.D., Report relates to patents owned by Regeneron Pharmaceuticals, Inc., EP 1 360 287 and 2 264 163.
Schedl A. et al., Transgenic mice generated by pronuclear injection of a yeast artificial chromosome, Nucleic Acids Res., 1992, 20(12): 3073-3077.
Application for U.S. Appl. No. 15/090,505, sharing common inventors, available on the U.S. Patent Office, website (no copy provided).
EPO Communication regarding the cancelling of the Summons for Oral Proceedings dated Oct. 13, 2016, EP Application No. 09075279.1, Mar. 17, 2016, EPO Form 2088 06.14, one page.
Documents associated with European Patent Application EP 02709544, dated Dec. 3, 2015, Forwarding of submissions to parties—2.
Zhu et al., Inhibition of vascular endothelial growth factor-induced receptor activation with anti-kinase insert domain-containing receptor single-chain antibodies from a phage display library, Cancer Res., Aug. 1998, pp. 3209-3214, vol. 58, No. 15.
Opponents submissions filed on Jan. 15, 2016 (oppo JP5749161).
Documents associated with European Patent Application EP 02709544, dated Dec. 3, 2015, Forwarding of submissions to parties—3.
Documents associated with European Patent Application EP 02709544, dated Sep. 22, 2015, Communication of the Board of Appeal (ex parte_ inter partes)—3.
Binz, H.K. et al., Designing repeat proteins: well-expressed, soluble and stable proteins from combinatorial libraries of Consensus ankyrin repeat proteins, J Mal Biol., 2003, 332(2), 489-503.
Documents associated with European Patent Application EP 02709544, dated Sep. 22, 2015, Communication of the Board of Appeal (ex parte_ inter partes)—4.
Documents associated with European Patent Application EP 02709544, dated Sep. 22, 2015, Communication of the Board of Appeal (ex parte_ inter partes)—5.
Arai et al., Abstract, Antibody responses induced by immunization with a Japanese rabies vaccine detennined by neutralization test and enzyme-linked immunosorbent assay, Vaccine, Jun. 2002, pp. 2448-53, vol. 7, No. 20(19-20).
Documents associated with European Patent Application EP 02709544, dated Apr. 10, 2014, Brief communication—Opposition proceedings—1.
Bono et al., VH Gene Segments in the Mouse and Human Genomes, JMB, 3 pages, Sep. 3, 2004, pp. 131-143, vol. 342, No. 1, Elsevier Ltd.

Middendorp et al., Cellular Maturation Defects in Bruton's Tyrosine Kinase-Deficient Immature B Cells Are Amplified by Premature B Cell Receptor Expression and Reduced by Receptor Editing, J. Immunol., Feb. 1, 2004, pp. 1371-1379, vol. 172, No. 3.
Murphy et al., Mice with megabase humanization of their immunoglobulin genes generate antibodies as efficiently as normal mice, PNAS, 2013, 6 pages, Early Edition.
Documents associated with European Patent Application EP 02709544, dated Sep. 4, 2015, Acknowledgement of receipt Board of Appeal.
Greenberger, JS. et al., Demonstration of permanent factor-dependent multipotential (erythroid/neutrophil/basophil) hematopoietic progenitor cell lines, Proc Nall Acad Sci USA, 1983, 80(10), 2931-2935.
Documents associated with European Patent Application EP 02709544, dated Apr. 10, 2014, Brief communication—Opposition proceedings—3.
Documents associated with European Patent Application EP 02709544, dated Sep. 22, 2015, Communication of the Board of Appeal (ex parte_ inter partes)—1.
Documents associated with European Patent Application EP 02709544, dated Sep. 22, 2015, Communication of the Board of Appeal (ex parte_ inter partes)—2.
Documents associated with European Patent Application EP 02709544, dated Sep. 15, 2014, Letter accompanying subsequently filed items.
Canadian Protest and Submission of Prior Art for Application No. 2,729,095, 16 pages, dated Apr. 8, 2014.
Kakitani et al., "A novel transgenic chimaeric mouse system for the rapid functional evaluation of genes encoding secreted proteins," Nucleic Acids Research (2005) 33(9):e85.
EPO Communication of a notice of opposition (R. 79(1) EPC), EP Application No. 10186063.3 and EP Patent No. 2314629, Aug. 22, 2014, EPO Form 2317A, 12.07, one page.
Desmet et al., Fast and accurate side-chain topology and energy refinement (FASTER) as a new method for protein structure optimization, Proteins, Jul. 1, 2002, pp. 31-43, vol. 48, Issue 1, Abstract only.
Documents associated with European Patent Application EP 02709544, dated Jan. 29, 2014, Brief communication—Opposition proceedings—2.
Declaration of Dr Lynn Macdonald dated Dec. 20, 2016 in opposition proceedings EP2264163.
Japan Patent Office, Opposition against Patent, JP Patent No. 5749161, Jan. 15, 2016, 55 pages.
Documents associated with European Patent Application EP 02709544, dated Oct. 22, 2015, receipt of Electronic rilings with U.S. District Court, Southern District of New York in Case No. 1:14-cv-1650-KBF.
Holliger et al., "Diabodies": Small bivalent and bispecific antibody fragments, Proc. Natl. Acad. Sci., Jul. 1993, pp. 6444-6448, vol. 90.
Documents associated with European Patent Application EP 02709544, dated Jul. 16, 2014, Letter regarding the opposition procedure (no time limit)—3.
Documents associated with European Patent Application EP 02709544, dated Jul. 16, 2014, Letter regarding the opposition procedure (no time limit)—1.
Documents associated with European Patent Application EP 02709544, dated Jul. 16, 2014, Letter regarding the opposition procedure (no time limit)—2.
Rickert, RC. et al., Impairment of T-cell-dependent B-cell responses and B-1 cell development in CD19-deficient mice, Nature, 1995, 376(6538), p. 352-355.
Nusbaum, C. et al; A YAC-based physical map of the mouse genome, Nature Genetics, 1999, 22(4):388-93.
Documents associated with European Patent Application EP 02709544, dated Sep. 11, 2014, Letter ccompanying subsequently filed items.
Lu et al., Acquired antagonistic activity of a bispecific diabody directed against two different epitopes on vascular endolhelial growth factor receptor 2, J. Immunol. Methods, Nov. 19, 1999, pp. 159-71, vol. 230.
Letter submitting declarations of Peter Hudson and Robert Brink dated Jun. 2, 2015, Australian Application No. 2009263082, 1 page.

(56) References Cited

OTHER PUBLICATIONS

Documents associated with European Patent Application EP 02709544, dated Jul. 17, 2014, Letter regarding the opposition procedure (no time limit)—1.

Documents associated with European Patent Application EP 02709544, dated Jul. 17, 2014, Letter regarding the opposition procedure (no time limit)—2.

Auxiliary request 6, EP Application No. 09075279.1, Reference No. P85261EP00, Apr. 23, 2013, three pages.

Green, Larry, Antibody engineering via genetic engineering of the mouse: XenoMouse strains are a vehicle for the facile generation of therapeutic human monoclonal antibodies, Journal of Immunological Methods, 1999, pp. 11-23, vol. 231.

Documents associated with European Patent Application EP 02709544, dated Nov. 28, 2014, Processing of an ppeal.

Clark, Michael, IgG Effector Mechanisms, Chem Immunol., 1997, pp. 88-110, vol. 65.

Correspondence from A. Bentham of J A Kemp to the European Patent Office regarding inquiry on status of Opposition, EP Application No. 09075279.1, Nov. 17, 2015, one page.

Pl?ckthun, A. et al, In vitro selection and evolution of proteins. In: Adv. Prat. Chem., F.M. Richards et al, Eds, I \cademic Press, San Diego, 2001, vol. 55, 367-403.

Second Declaration of Anthony L. Defranco dated Oct. 18, 2015, Australian application No. 2009263082, 31 pages.

Janeway, C. A. J., Travers, P., Walport, M. and Capra, J. D. Immunobiology: the immune system in health and : disease, Current Biology Publications, 4th edition, 1999, chapter 3, pp. 79-113.

Detailed results for the IMGTN-QUEST analysed sequences, The International Immunogenetics Information System, IMGTN-QUEST programme version: 3.2.24, seven pages, at least as early as Apr. 25, 2012, http://www.imgl.org/IMGT_vquesl/vquest.

Huang, AY. et al., Role of bone marrow-derived cells in presenting MHC class I-restricted tumor antigens, Science, 1994, 264(5161), 961-965.

Epo Communication, Provision of the minutes in accordance with Rule 124(4) EPC, EP Application No. 09075279.1, dated Aug. 8, 2013, EPO Form 2042 12.07TRI, one page.

Documents associated with European Patent Application EP 02709544, dated Jul. 2, 2015, Cited documents during appeal procedure—11.

Documents associated with European Patent Application EP 02709544, dated Jul. 2, 2015, Cited document during appeal procedure—10.

Documents associated with European Patent Application EP 02709544, dated Jul. 2, 2015, Cited document during appeal procedure—13.

Documents associated with European Patent Application EP 02709544, dated Jul. 2, 2015, Cited document during appeal procedure—12.

EPO Communication regarding important information concerning oral proceedings, at least as early as Nov. 19, 2015, EPO Form 2043 02.09, three pages.

Documents associated with European Patent Application EP 02709544, dated Jul. 2, 2015, Cited document during appeal procedure—18.

Jones et al., "High-Level Expression of Recombinant IgG in the Human Cell Line PER.C6", Biotechnology Progress, vol. 19, 2003, pp. 163-168.

Documents associated with European Patent Application EP 02709544, dated Jul. 16, 2014, Auxiliary request during Opposition procedure—09.

Documents associated with European Patent Application EP 02709544, dated Jul. 2, 2015, Cited document during appeal procedure—15.

EPO Notification of European Publication Number and Information on the application of Article 67(3) EPC, EP Application No. 10186063.3, dated Mar. 3, 2011, EPO Form 1133, 05.10, 1 page.

Documents associated with European Patent Application EP 02709544, dated Jul. 2, 2015, Cited document during appeal procedure—14.

Documents associated with European Patent Application EP 02709544, dated Jul. 2, 2015, Cited document during appeal procedure—17.

Documents associated with European Patent Application EP 02709544, dated Jul. 2, 2015, Cited document during appeal procedure—16.

Letter accompanying subsequently filed items regarding revocation procedure, EP Application No. 09075279.1, Aug. 20, 2015, one page.

Documents associated with European Patent Application EP 02709544, dated Jul. 16, 2014, Auxiliary request during Opposition procedure—05.

Declaration and CV of Anthony De Franco originally submitted for the EP1360287 Opposition, dated Sep. 2, 2014.

Zamai et al., Optimal detection of apoptosis by flow cytometry depends on cell morphology, Cytometry, 1993, 14(8), 891-897.

Documents associated with European Patent Application EP 02709544, dated Jul. 16, 2014, Auxiliary request during Opposition procedure—06.

Radie et al., Ig Hand L chain contributions to autoimmune specificities, The Journal of Immunology, Jan. 1, 1991, pp. 176-182, vol. 146, No. 1, The American Association of Immunologists.

Documents associated with European Patent Application EP 02709544, dated Jul. 16, 2014, Auxiliary request during Opposition procedure—07.

Documents associated with European Patent Application EP 02709544, dated Jul. 16, 2014, Auxiliary request during Opposition procedure—08.

Documents associated with European Patent Application EP 02709544, dated Jul. 16, 2014, Auxiliary request during Opposition procedure—01.

Documents associated with European Patent Application EP 02709544, dated Jul. 16, 2014, Auxiliary request during Opposition procedure—02.

(Page 7) EPO Brief Communication regarding the Opposition against EP Application 10186063.3, dated Jun. 13, 2016, 1 page.

Documents associated with European Patent Application EP 02709544, dated Jul. 16, 2014, Auxiliary request during Opposition procedure—03.

Documents associated with European Patent Application EP 02709544, dated Jul. 16, 2014, Auxiliary request during Opposition procedure—04.

EPO Acknowledgement of Receipt of the submission by the proprietor, EP Application No. 10186063.3 and EP Patent No. 2314629, date of receipt Feb. 24, 2015, one page.

Logtenberg, Ton, Antibody cocktails: Next-Generation Biopharmaceuticals with Improved Potency, Trends in Biotechnology, 2007, pp. 390-394, vol. 25, No. 9, Science Direct.

Conrath et al., Camel Single-domain Antibodies as Modular Building Units in Bispecific and Bivalent Antibody Constructs, The Journal of Biological Chemistry, 2001, pp. 7346-7350, vol. 276, No. 10.

Second Declaration of Ton Logtenberg Under 37 C.F.R. 1.132, U.S. Appl. No. 13/750,753 dated Dec. 18, 2015, ten pages.

Documents associated with European Patent Application EP 02709544, dated Nov. 28, 2014, Minutes of the oral proceedings (Opposition Division)—conclusion of the proceedings—1.

Documents associated with European Patent Application EP 02709544, dated Mar. 5, 2014, Advice of delivery.

Kaufman et al., Amplification and expression of sequences cotransfected with a modular dihydrofolate reductase complementary DNA gene, J_ Mal. Biol., Aug. 25, 1982, pp. 601-621, vol. 159, Issue 4, Abstract only.

Wilke et al., Diagnosis of Haploidy and Triploidy Based on Measurement of Gene Copy Number by Real-Time PCR, Human Mutation, 2000, pp. 431-436, vol. 16.

(Pages 309-310) EPO Communication regarding Submission in opposition proceedings, Reply of the patent proprietor to the notice(s) of opposition, EP Application No. 10186063.3 and Patent No. 2314629, Oct. 16, 2013, two pages.

Documents associated with European Patent Application EP 02709544, dated Mar. 16, 2016, Advice of delivery.

Auxiliary request 5 (amendments indicated), EP Application No. 09075279.1, Apr. 23, 2013, three pages.

Letter accompanying subsequently filed items regarding oral proceedings, EP Application No. 09075279.1, Apr. 24, J013, one page.

Reply to Communication under Rule 79(1) EPC, EP Application No. 10186063.3 and EP Patent No. 2314629, dated Feb. 24, 2015, 20 pages.

(56) References Cited

OTHER PUBLICATIONS

EPO Brief Communication to Fritz Lahrlz of lsenbruck Bosl Hoschler LLP regarding the telephone conversation on the Opposition, EP Application No. 09075279.1 and Patent No. 2147594, Mar. 16, 2016, EPO Form 29110 01.12, one age.
Documents associated with European Patent Application EP02709544, Memorandum Decision & Order for U.S. District Court, Southern District of New York date filed Aug. 6, 2015, in Case No. 1:14-cv-1650-KBF.
Retter et al., Sequences and Characterization of the Ig Heavy Chain Constant and Partial Variable Region of the Mouse Strain 129S1, The Journal of Immunology, 9 pages, Aug. 15, 2007, pp. 2419-2427, vol. 179, No. 4, The American Association of Immunologists.
Documents associated with European Patent Application EP02709544, dated Sep. 5, 2014, Letter accompanying subsequently filed items.
Srinivas et al., "Cre reporter strains produced by targeted insertion of EYFP and ECFP into the ROSA26 locus," BMC Dev. Biol. (2001) 1:4.
Angrand et al., Simplified generation of targeting constructs using ET recombination, Nucleic Acids Res., 1999, 27 (17), e16.
Declaration of Prof. Ton Logtenberg, CEO, Merus B.V., European Patent No. EP 2 314 629 B1, May 4, 2016, seven pages.
PCT International Search Report, PCT/NL2005/000036, dated Jan. 19, 2005.
Immunoglobulin Genes, Honjo et al., Academic Press Limited, Copyright 1989.
Acknowledgemenl of receipt from European Patent Office for EP 10186063.3 dated May 20, 2016.
Yang et al., Homologous recombination based modification in *Esherichia coli* and germline transmission in transgenic of a bacterial artificial chromosome, Nature Publishing Group, Sep. 1997, pp. 859-865, vol. 15. mice.
Canadian Patent Office, Statement and Declaration Under Rule 37, CA Application No. 2729095, Dec. 22, 2010, one page.
Gonzalez-Fernandez et al., "Analysis of somatic hypermutation in mouse Peyer's patches using immunoglobulin K light-chain transgenes", Immunology, vol. 90, Nov. 1993, pp. 9862-9866, Proceedings of the National Academy of Sciences, USA.
Auxiliary request 3, EP Application No. 09075279.1, Reference No. P85261EP00, Apr. 23, 2013, three pages.
Documents associated with European Patent Application EP02709544, dated Feb. 24, 2015, Forwarding of submissions to parties.
Dekruif et al., Rapid selection of cell subpopulation-specific human monoclonal antibodies from a synthetic phage antibody library, Proc. Natl. Acad. Sci., USA, Apr. 1995, pp. 3938-3942, vol. 92.
Smith et al., A site-directed chromosomal translocation induced in embryonic stem cells by Cre-loxP recombination, Nature Genetics, 10 pages, Apr. 1995, pp. 376-385, vol. 9, No. 4, Nature Publishing Group.
Urlaub, G. et al., Isolation of Chinese hamster cell mutants deficient in dihydrofolate reductase activity, Proc Nall Acad Sci US A, 1980, 77(7), 4216-4220.
EPO Communication of further notices of opposition Rule 79(2) EPC, EP Application No. 09075279.1 and Patent No. 2147594, Sep. 25, 2014, EPO Form 2318 01.12, one page.
Jessen et al., Modification of bacterial artificial chromosomes through Chi-stimulated homologous recombination and its application in zebrafish transgenesis, Proc. Natl. Acad. Sci., Apr. 1998, pp. 5121-5126, vol. 95.
Documents associated with European Patent Application EP02709544, dated Sep. 2, 2014, Letter accompanying subsequently filed items—2.
Documents associated with European Patent Application EP02709544, dated Sep. 2, 2014, Letter accompanying subsequently filed items—1.
EPO Acknowledgement of receipt of letter regarding request to hold application, EP Application No. 09075279.1, date of receipt Sep. 3, 2013, one page.

Toyooka et al., Identification and characterization of subpopulations in undifferentiated ES cell Culture, Development, 10 pages, Mar. 2008, pp. 909-918 vol. 135, No. 5.
Ward et al., Nature, 1989, pp. 544-546, vol. 341.
EPO Communication, After communication under Rule 71(3) EPC (IGRA) but before decision to grant (EPO Form 2006A), EP Application No. 09075279.1, dated Sep. 5, 2013, EPO Form 2092C 04.12, two pages.
Documents associated with European Patent Application EP02709544, dated Mar. 5, 2015, Letter dealing with oral proceedings during the appeal procedure—2.
Documents associated with European Patent Application EP02709544, dated Mar. 5, 2015, Letter dealing with oral proceedings during the appeal procedure—1.
GenBank Accession No. M87478, "Human rearranged IgK mRNA VJC region," 1 page (1994).
Documents associated with European Patent Application EP02709544, dated Aug. 14, 2015, Oral Proceedings_ summons.
Gu,, H. et al., Most Peripheral B Cells in Mice Are Ligand Selected, J Exp Med., 1991, 173(6), 1357-71.
Frykman, S. et al, Quantitating secretion rates of individual cells: design of secretion assays, Biotechnol Bioeng., 1998,59(2), 214-226.
Komdorfer, IP. et al., Structural mechanism of specific ligand recognition by a lipocalin tailored for the complexation of digoxigenin, J Mol Biol., 2003, 330(2), 385-396.
Houshmand, H. et al., Use of bacteriophage T7 displayed peptides for determination of monoclonal antibody specificity and biosensor analysis of the binding reaction, Anal Biochem., 1999, 268(2), 363-370.
Nissim, Ahuva et al., "Antibody fragments from a 'single pot' phage display library as immunochemical reagents," The EMBO Journal, vol. 13(3):692-698 (1994).
Presentation by Open Monoclonal Technology, Inc (Nov. 3, 2013), http://www.ppenmonoclonaltechnology.com/downloads.html.
EPO Model-Sheet dated Oct. 29, 2012, EP12175544.1.
EPO Acknowledgement of receipt of letter regarding French and German translated claims, EP Application No. 09075279.1, date of receipt Sep. 2, 2013, one page.
Abedi, M.R. et al., Green, fluorescent protein as a scaffold for intracellular presentation of peptides, Nucleic Acids Res., 1998, 26(2), 623-630.
Documents associated with European Patent Application EP02709544, dated Mar. 18, 2014, Letter accompanying subsequently filed items.
Gerbert et al., Vascular endothelial growth factor regulates endothelial cell survival through the phosphatidylinositol 3'-kinase/Akt signal transduction pathway. Requirement for Flk-1/KDR activation, J Biol. Chem., Nov. 13, 1998, pp. 30336-30343, vol. 273.
Auxiliary request 2 (amendments indicated), EP Application No. 09075279.1, Reference No. P85261EP00, Apr. 23, 2013, three pages.
Documents associated with European Patent Application EP02709544, dated Sep. 5, 2014, (Electronic) Receipt.
Retter, MW., Nemazee, D., Receptor editing: genetic reprogramming of autoreactive lymphocytes, Cell Biochem Biophys., 1999, 31(1), 81-88.
Documents associated with European Patent Application EP02709544, dated Aug. 24 2015, Advice of delivery.
Online Response of Regeneron Pharmaceuticals, Inc. for European Patent Application No. 12173456.0 dated Apr. 12, 2013.
Janeway's Immunobiology, Murphy, Travers, Walport eds, Seventh Edition, 2008 (pp. 144-155).
Janeway's Immunobioloby, Murphy, Travers, Walport eds, Seventh Edition, 2008 (pp. 266-267).
Sugita, et al., Int. J. Cancer, 1986, pp. 351-357, vol. 37.
Documents associated with European Patent Application EP02709544, dated Oct. 26, 2015, Forwarding of submissions to parties.
Seidl et al., Position-dependent inhibition of class-switch recombination by PGK-neo(Registered) cassettes inserted into he immunoglobulin heavy chain constant region locus, Proc. Natl. Acad. Sci. USA, Immunology, Mar. 1999, pp. 3000-3005, vol. 96.
Documents associated with European Patent Application EP02709544, dated Sep. 18, 2014, Notice of appeal.

(56) References Cited

OTHER PUBLICATIONS

Documents associated with European Patent Application EP 02709544, dated May 30, 2016, Annexes in respect of a request for a change—2.
Teaching of U.S. Appl. No. 12/589,181 (MeMo), submitted in U.S. Appl. No. 12/589,181 (Jun. 20, 2012).
Documents associated with European Patent Application EP 02709544, dated Dec. 10, 2014, Communication of the file number to the parties.
Documents associated with European Patent Application EP 02709544, dated May 30, 2016, Annexes in respect of a request for a change—1.
Merus, "MeMo—the ingenious mouse, for improved antibody therapeutics," www.merus.nl, 3 pages (2011).
Giusti et al., Hypermutation is Observed Only in Antibody H Chain V Region Transgenes That Have Recombined with Endogenous Immunoglobulin H DNA: Implications for the Location of cis-acting Elements Required for Somatic Mutation, J Exp. Med, Mar. 1993, pp. 797-809, vol. 177.
Documents associated with European Patent Application EP 02709544, dated Feb. 26, 2014, Letter concerning the inventor.
EPO Communication concerning the registration of amendments relating to entries pertaining to the applicant/the proprietor dated Jun. 20, 2016, EP12175544.1.
Smith, CA., Rennick, DM., Characterization of a murine lymphokine distinct from interleukin 2 and interleukin 3 (IL-3) possessing a T-cell growth factor activity and a mast-cell growth factor activity that synergizes with IL- 3, Proc Natl Acad Sci US A, 1986, 83(6), 1857-1861.
Documents associated with European Patent Application EP 02709544, dated Jul. 2, 2015, Letter relating to Appeal Procedure.
Shizuya H. et al., Cloning and stable maintenance of 300-kilobase-pair fragments of human DNA in *Escherichia coli* using an F-factor-based vector; Proc Natl Acad Sci US A, 1992, 89(18):8794-7.
EPO Request for change of applicant's representative dated Sep. 29, 2015, EP12175544.1.
Stoneley, M., et al., C-Myc 5' untranslated region contains an internal ribosome entry segment, Oncogene, 1998, 16 3), 423-428.
Documents associated with European Patent Application EP 02709544, dated Jan. 28, 2014, (Electronic) Receipt—1.
Documents associated with European Patent Application EP 02709544, dated Jan. 28, 2014, (Electronic) Receipt—2.
Appeal Brief under 37 C.F.R, sctn. 41.37 filed by Brenda Herschbach Jarrell, U.S. Appl. No. 13/948,818, Jul. 20, 2015, 26 pages.
Taki et al., Targeted insertion of a Variable Region Gene into the Immunoglobulin Heavy Chain Locus, Science, 4 pages, Nov. 19, 1993, pp. 1268-1271, vol. 262, No. 5137.
Documents associated with European Patent Application EP 02709544, dated Nov. 4, 2015, Claims—1.
Documents associated with European Patent Application EP 02709544, dated Nov. 4, 2015, Claims—2.
Matzuk et al., a-Inhibin is a tumor-suppressor gene with gonadal specificity in mice, Nature, 7 pages, Nov. 26, 1992, pp. 313-319, vol. 360, Nature Publishing Group.
Roschenthaler, F. et al., the 5' part of the mouse immunoglobulin kappa locus as a continuously cloned structure, Eur J Immunol., 2000, 30(12): 3349-54.
Mostoslavsky et al., "Asynchronous replication and allelic exclusion in the immune system," Nature (2001) 414:221-225.
Documents associated with European Patent Application EP 02709544, dated Oct. 27, 2015, Forwarding of submissions to parties—3.
Amendment, Australian patent application No. 2009263082, dated Jan. 23, 2014, 22 pages.
Documents associated with European Patent Application EP 02709544, dated Oct. 27, 2015, Forwarding of submissions to parties—4.
Documents associated with European Patent Application EP 02709544, dated Oct. 27, 2015, Forwarding of submissions to parties—1.
Documents associated with European Patent Application EP 02709544, dated Oct. 27, 2015, Forwarding of submissions to parties—2.

Japan Patent Office, As-Filed english language application, Japanese Patent Application No. 2015-097258, May 12, 2015, 218 pages.
Documents associated with European Patent Application EP 02709544, dated Sep. 2, 2014, Letter regarding he opposition procedure (no lime limit).
Auxiliary Request 4 with annotations, EP Patent No. 231462961, May 20, 2016, five pages.
Letter accompanying subsequently filed items regarding documents filed during examination procedure, EP Application No. 09075279.1, Sep. 3, 2013, one page.
JA Kemp to The European Patent Office of Final Written Submissions for Oral Proceedings scheduled for Jun. 22, 2016 in Opposition to Merus BV's EP 2 314 629 B1 dated May 20, 2016.
Miller, Ten years of gene targeting: targeted mouse mutants, from vector design to phenotype analysis, Mechanisms of Development, 19 pages, Jan. 21, 1999, pp. 3-21, vol. 82, No. 1-2, Elsevier Inc.
Third Party Observations Under Article 115 EPC Against European Parent Application No. 09075279.1 in the name of Merus B.V., dated Oct. 25, 2012. 6 pages.
Documents associated with European Patent Application EP 02709544, dated May 24, 2016, Annex to the communication—opposition.
Documents associated with European Patent Application EP 02709544, dated Mar. 24, 2014, Brief communication—Opposition proceedings—3.
Documents associated with European Patent Application EP 02709544, dated Mar. 24, 2014, Brief communication—opposition proceedings—2.
Documents associated with European Patent Application EP 02709544, dated Mar. 24, 2014, Brief communication Opposition proceedings—1.
Documents associated with European Patent Application EP 02709544, dated Aug. 20 2015, Request for change of opponent's representative.
Documents associated with European Patent Application EP 02709544, dated Feb. 26, 2014, (Electronic) Receipt.
Documents associated with European Patent Application EP 02709544, dated Feb. 15, 2015, Annexes (other than cited documents) regarding appeal procedure.
O'Connor, M. et al; Construction of Large DNA Segments in *Escherichia coli*, Science, 1989, 244(4910):1307-12.
Documents associated with European Patent Application EP 02709544, dated Aug. 12, 2014, Written submission in reparation to during oral proceedings.
Communication from copending European patent application No. 05704566.8 dated Jun. 6, 2013.
Manen, D. et al., A sensitive reporter gene system using bacterial luciferase based on a series of plasmid cloning vectors compatible with derivatives of pBR322, Gene, 1997, 186(2), 197-200.
Wang, G. et al, AT cell-independent antitumor response in mice with bone marrow cells retrovirally transduced with an antibody/Fc-gamma chain chimeric receptor gene recognizing a human ovarian cancer antigen, Nat Med., 1998, 4 2), 168-172.
Thiebe et al., The variable genes and gene families of the mouse immunoglobulin? locus, European Journal of Immunology, Jul. 1999, pp. 2072-2081, vol. 29, Issue 7.
Documents associated with European Patent Application EP 02709544, dated Nov. 9, 2015, Amended claims with annotations—2.
Cho et al., Structure of the extracellular region of HER2 alone and in complex with the Herceptin Fab, Nature, Feb. 13, 2003, pp. 756-760, vol. 421, Abstract only.
Documents associated with European Patent Application EP 02709544, dated Nov. 28, 2014, Minutes of the oral proceedings (Opposition Division)—conclusion of the proceedings—2.
Ebert et al., The Distal VH Gene Cluster of the Igh Locus Contains Distinct Regulatory Elements with Pax5 Transcription Falor-Dependent Activity in Pro-B Cells, Immunity Articles,13 pages, Feb. 25, 2011, pp. 175-187, vol. 34, No. 2, Elsevier, Inc.
EPO Communication pursuant to Article 94(3) EPC, Application No. 10186063.3, Jun. 11, 2012, EPO Form 2001, 12.10CSX, 3 pages.

(56) References Cited

OTHER PUBLICATIONS

Muller, Ulrike, Ten years of gene targeting: targeted mouse mutants, from vector design to phenotype analysis, Jan. 1999, pp. 3-21, vol. 82.
Decision of US District Court about U.S. Pat. No. 8,502,018, *REGN* vs. *Merus B.V.*, dated Feb. 11, 2015.
Figini et al., Panning Phage Antibody Libraries on Cells: Isolation of Human Fab Fragments against Ovarian Carcinoma Using Guided Selection, Cancer Research, Mar. 1, 1998, pp. 991-996, vol. 58.
Response to Invitation to remedy deficiencies pursuant to Rule 30(3) EPC / Rule 163(3) EPC, EP Application No. 10186063.3, Jan. 27, 2011, 2 pages.
De Heard, et al., A large non-immunized human Fab fragment phage library that permits rapid isolation and kinetic analysis of high affinity antibodies, J. Biol. Chem., 1999, pp. 18218-18230, vol. 274.
Lonberg, Nils et al., "Antigen-specific human antibodies from mice comprising four distinct genetic modificaitons," Nature, vol. 368:856-859 (1994).
Reichert, Janice M., Monoclonal antibodies in the clinic, Nature Publishing Group, 2001, pp. 819-822, vol. 19.
EPO Communication regarding the preparation for oral proceedings—Instructions to Support Service dated Nov. 11, 2015, EP Application No. 10186063.3 and EP Patent No. 2314629, EPO Form 2040 12.01TRI, two pages.
Graham, FL., van der Eb,AJ., A new technique for the assay of infectivity of human adenovirus 5 DNA, Virology, 1973, 52(2), 456-467.
Documents associated with European Patent Application EP 02709544, dated Jul. 16, 2014, Auxiliary request during Opposition procedure—12.
Documents associated with European Patent Application EP 02709544, dated May 24, 2016, Communication inviting parties to file observations.
Documents associated with European Patent Application EP 02709544, dated Jul. 16, 2014, Auxiliary request during Opposition procedure—13.
Documents associated with European Patent Application EP 02709544, dated Jul. 16, 2014, Auxiliary request during Opposition procedure—14.
In the High Court of Justice, Chancery Division, Patents Court, Case No. HP-2013-000001/HP-2014-000001 dated Oct. 6, 2015, Expert Report of Adrian Francis Stewart, Report relates to a patent owned by Regeneron Pharmaceuticals, Inc., Ep 1 360 287.
Documents associated with European Patent Application EP 02709544, dated Jul. 16, 2014, Auxiliary request during Opposition procedure—10.
Auxiliary Request 11 with annotations, EP Patet No. 2314629B1, May 20, 2016, Five pages.
Ewert et al., Biophysical properties of human antibody variable domains, J_ Mal. Biol., Jan. 17, 2003, pp. 531-553, vol. 325, Iss. 3.
Documents associated with European Patent Application EP 02709544, dated Jul. 16, 2014, Auxiliary request during Opposition procedure—11.
Meyer, Kerstin B. et al., "The importance of the 3'-enhancer region in immunoglobulin kappa gene expression," Nucleic Acids Research, vol. 18(19):5609-5615 (1990).
Marks et al., By-passing immunization: Human antibodies from V-gene libraries displayed on phage, J. Mol. Biol., Dec. 5, 1991, pp. 581-597, vol. 222, Issue 3, Abstract only.
Documents associated with European Patent Application EP 02709544, dated Sep. 5, 2014, Letter regarding the opposition procedure (no time limit).
EPO Payment of fees and expenses dated May 30, 2016, EP12175544.1.
Tan et al, "Superhumanized" Antibodies: Reduction of Immunogenic Potential by Complementarity-Determining Region Grafting with Human Germline Sequences: Application to an Anti-CD281, J. Immunol., Jul. 15, 2002, pp. 1119-1125, vol. 169, No. 2.
Designation of Inventor Brus Ronald Hendrik Peter, at least as early as Oct. 1, 2010, 1 page.
Claims, Replacement pp. 125-129, at least as early as Oct. 1, 2010, 5 pages.
Bader, ET., Wittrup, KO., Yeast surface display for screening combinatorial polypeptide libraries, Nat Biolechnol., 1997, 15(6), 553-557.
Mcclanahan, T. et al., Hematopoietic growth factor receptor genes as markers of lineage commitment during in vitro development of hematopoietic cells, Blood, 1993, 81(11), 2903-2915.
Bertagnolli, MM. et al., IL-12 augments antigen-dependent proliferation of activated T lymphocytes, J Immunol., 1992, 149(12), 3778-3783.
Documents associated with European Patent Application EP 02709544, dated Mar. 21, 2014, Advice of delivery.
Refund of Fees, EP Application No. 10186063.3, Nov. 17, 2010, EPO Form 2907, 12.07, 1 page.
Documents associated with European Patent Application EP 02709544, dated Nov. 28, 2014, Acknowledgement of a document—2.
Documents associated with European Patent Application EP 02709544, dated Feb. 13, 2015, Forwarding of submissions to parties—1.
Documents associated with European Patent Application EP 02709544, dated Nov. 28, 2014, Acknowledgement of a document—3.
Documents associated with European Patent Application EP 02709544, dated Nov. 28, 2014, Acknowledgement of a document—4.
Documents associated with European Patent Application EP 02709544, dated Feb. 13, 2015, Forwarding of submissions to parties—3.
Documents associated with European Patent Application EP 02709544, dated Feb. 13, 2015, Forwarding of submissions to parties—2.
Ignalovich et al., Dominance of intrinsic genetic factors in shaping the human immunoglobulin V? repertoire, J. Mal. Biol., Nov. 26, 1999, pp. 457-465, vol. 294, Issue 2.
Mejia et al., Retrofitting Vectors for *Escherichia coli*-Based Artificial Chromosomes (PACs and BACs) with Markers for Transfection Studies; Genome Research, 1997; 7(2):179-86.
Hitzeman, RA. et al., Isolation and characterization of the yeast 3-phosphoglycerokinase gene (PGK) by an mmunological screening technique, J Biol Chem., 1980, 255(24), 12073-12080.
Lee et al., Complete humanization of the mouse immunoglobulin loci enables efficient therapeutic antibody discovery, Nature Biotechnology, 8 days, Mar. 16, 2014, pp. 356-363, vol. 32, No. 4, Nature America Inc.
(Page 331) EPO Extension of time limit pursuant to Rule 132 EPC, EP Application No. 10186063.3 and EP Patent No. 2314629, Oct. 24, 2014, EPO Form 2944C, 06.12, one page.
Desmet et al., Computation of the binding of fully flexible peptides to proteins with flexible side chains, FASEB J., Feb. 1997, pp. 164-172, vol. 11, No. 2.
Correspondence from A Bentham of J A Kemp to European Patent Office regarding an opposition, EP Patent No. 2147594, Aug. 11, 2014, one page.
Taylor, Lisa D. et al., "Human immunoglobulin transgenes undergo rearrangement, somatic mutation and class switching in mice that lack endogenous IgM," International Immunology, vol. 6(4):579-591 (1994).
Flavell et al., Systemic Therapy with 3BIT, a Triple Combination Cocktail of Anti-CD 19, CD22, and -CD38-Saporin Immunotoxins, Is Curative of Human B-Cell Lymphoma in Severe Combined Immunodeficient Mice, Cancer Research, Nov. 1997, pp. 4824-4829, vol. 57.
Documents associated with European Patent Application EP 02709544, dated Apr. 3, 2014, Patent document cited during the opposition procedure—2.
Documents associated with European Patent Application EP 02709544, dated Apr. 3, 2014, Patent document cited during the opposition procedure—1.
In the High Court of Justice, Chancery Division, Patents Court, Case No. HP-2013-000001/HP-2014-000001 dated Nov. 17, 2015, Third Expert Report of Adrian Francis Stewart, Report relates to a patent owned by Regeneron Pharmaceuticals, Inc., EP 1 360 287.
Documents associated with European Patent Application EP 02709544, dated Aug. 3, 2015, (Electronic) Receipt.
Peled, Jonathan U. et al., "The Biochemistry of Somatic Hypermutation," Annu. Rev. Immunol., vol. 26:481-511 (2008).

(56) References Cited

OTHER PUBLICATIONS

EPO Communication, Result of consultation, EP Application No. 09075279.1, Oct. 14, 2013, EPO Form 2049A 12.07TRI, two pages.
Epo Communication of amended entries concerning the representation dated Dec. 23, 2015, EP12175544.1.
In the High Court of Justice, Chancery Division, Patents Court, Case No. HP-2013-000001/HP-2014-000001 dated Oct. 6, 2015, First Expert Report of Professor Hiddie L Ploegh, Report relates to patents owned by Regeneron Pharmaceuticals, Inc., EP 1 360 287 and 2 264 163.
Description dated Jul. 9, 2012, EP12175544.
Correspondence from Dr. Fritz Lahrtz of Isenbruck Bosl Forschler LLP to the European Patent Office regarding change of representation, EP Application No. 09075279.1 and EP Patent No. 2147594, Jan. 8, 2016, one page.
Documents associated with European Patent Application EP 02709544, dated Sep. 7, 2015, Advice of delivery.
Correspondence from A. Bentham of J A Kemp to the European Patent Office regarding the reply to the Patentees response to Opposition, EP Application No. 09075279.1, Aug. 20, 2015, eight pages.
Cao et al., Neutralizing monoclonal antibodies to hepatocyte growth factor/scatter factor (HGF/SF) display antitumor activity in animal models, Proc. Natl. Acad. Sci. U.S.A., Jun. 19, 2001, pp. 7443-7448, vol. 98, No. 13.
EPO Communication of amended entries concerning the representative (R. 143(1)(h) EPC), EP Application No. 10186063.3 and EP Patent No. 2314629, Oct. 8, 2015, EPO Form 2548, 08.13, one page.
Riblet, R., A. Tuller, and P. Brodeur. 1986. Polymorphism and evolution of Igh-V gene families. Curr. Top. Microbiol. Immunol. 127:168.
Documents associated with European Patent Application EP 02709544, dated Jul. 16, 2014, (Electronic) Receipt—1.
Documents associated with European Patent Application EP 02709544, dated Jul. 16, 2014, (Electronic) Receipt—2.
David Namazee, "Receptor Editing in B Cells", Advances in Immunology, vol. 74, 0065-2776/00, 2000, pp. 89-126.
Documents associated with European Patent Application EP 02709544, dated Jul. 16, 2014, (Electronic) Receipt—3.
Dietzschold et al., Delineation of putative mechanisms involved in antibody-mediated clearance of rabies virus from the central nervous system, PNAS, 1992, pp. 7252-7256, vol. 89, No. 15.
Lcioudmila et al, Global Gene Expression profiling reveals similarities and differences among mouse pluripotent stem cells of different orgin and strains, Development Biology, 14 pages, Oct. 4, 2007, pp. 446-459, vol. 307, No. 2, NIH Public Access.
Auxiliary Request 5, EP Patent No. 2314629B1, May 20, 2016, ffive pages.
Notice of Opposition dated Jul. 8, 2016, EP2264163 10010741.6.
Prak, Eline Lunning, Light Chain Replacement: A new model for antibody gene rearrangement, J_ Exp. Med., Aug. 1995, pp. 541-548, vol. 182, The Rockefeller University Press.
Documents associated with European Patent Application EP 02709544, dated Mar. 26, 2015, Letter accompanying subsequently filed items.
Nakatani et al., Abnormal Behavior in a Chromosome Engineered Mouse Model for Human 15q11-13 Duplication Seen in Austin, Cell, 12 pages, Jun. 26, 2009, pp. 1235-1246, vol. 137, No. 7, Elsevier Inc.
In The High Court of Justice, Chancery Division, Patents Court, Case No. HP-2013-000001/HP-2014-000001 dated Nov. 3, 2015, Second Expert Report of Professor Sir Martin Evans FRS Ph.D., Report relates to patents owned by Regeneron Pharmaceuticals, Inc., EP 1 360 287 and 2 264 163.
Glanville et al., Narve antibody gene-segment frequencies are heritable and unaltered by chronic lymphocyte ablation, PNAS, Dec. 13, 2011, pp. 20066-20071, vol. 108, No. 50.
Vang Y. et al., B., Site-specific gene targeting in mouse embryonic stem cells with intact bacterial artificial Chromosomes, Nat Biotechnol., 2003, 21(4):447-51.
Sambrook 3rd ed pp. 2.110-2.111 (2001).
Glaser S. et al., Current issues in mouse genome engineering, Nat Genet., 2005, 37(11), 1187-93.
Declaration of Robert Brink, Apr. 30, 2015, 34 pages.
Klohn, Peter-Christian et al., "IBC's 23rd Annual Antibody Engineering, 1oth Annual Antibody Therapeutics International Conferences and the 2012 Annual Meeting ofThe Antibody Society," mAbs, vol. 5(2):178-201 (2013).
Murphy, "Chapter 8: The Development and Survival of Lymphocytes", Janeway's Immunobiology, Eight Edition, Jul. 24, 2011, pp. 275-290.
Koide, A. et al., The fibronectin type III domain as a scaffold for novel binding proteins, J Mal Biol., 1998, 284(4), 1141-1151.
Weigert, M., and R. Riblet. 1978. The genetic control of antibody variable regions in the mouse, Springer Seminars in Immunopathology. 1:133-169, 1978.
Documents associated with European Patent Application EP 02709544, dated Mar. 11, 2014, Bibliographic data of the European patent application.
Klotz, EL. et al, Somatic hypermutation of an artificial test substrate within an Ig kappa transgene, J Immunol., 1998;161(2); 782-790.
Opponent Objects to the Allowability of the Ext, Australia, May 4, 2015.
English translation of Deed of Conversion and Amendment of the Articles of Association for Merus BV (new name: Merus NV.), May 19, 2016, 26 pages.
Eigenbrot et al., X-ray Structures of the Antigen-binding Domains from Three Variants of Humanized anti-p185HER2 Antibody 4D5 and Comparison with Molecular Modeling, J_ Mal. Biol., Feb. 20, 1993, pp. 969-995, vol. 229 ssue 4, Elsevier, Abstract only.
Griffiths, et al., Human anti-self antibodies with high specificity from phage display libraries, EMBO J., Feb. 1993, pp. 725-734, vol. 12, No. 2.
Documents associated with European Patent Application EP 02709544, dated Mar. 19, 2015, Authorisation of representative.
EPO Communication regarding opposition, EP Application No. 10186063.3, Nov. 19, 2015, EPO Form 290601.91TRI, 11 pages.
EPO Acknowledgement of Receipt of the Notice of Opposition against EP Application No. 10186063.3 and EP Patent No. 2314629, date of receipt Jul. 15, 2014, three pages.
Kaufman, "Overview of Vector Design for Mammalian Gene Expression," Mol Biotechnol (2000) 16(2):151-160.
Documents associated with European Patent Application EP 02709544, dated Feb. 11, 2014, Brief communication—Opposition proceedings—1.
Documents associated with European Patent Application EP 02709544, dated Feb. 11, 2014, Brief communication—Opposition proceedings—2.
Documents associated with European Patent Application EP 02709544, dated Feb. 28, 2014, Summons to attend oral proceedings—3.
Documents associated with European Patent Application EP 02709544, dated Feb. 28, 2014, Summons to attend oral proceedings—2.
Documents associated with European Patent Application EP 02709544, dated Feb. 28, 2014, Summons to attend oral proceedings—1.
Response to office action for Canadian Application No. 2,729,095 dated May 10, 2016, 12 pages.
Documents associated with European Patent Application EP 02709544, dated Mar. 9, 2015, (Electronic) Receipt.
Smith, G.P., Filamentous fusion phage: Novel expression vectors that display cloned antigens on the virion surface. Science, Jun. 14, 1985, pp. 1315-1317, vol. 228, Issue 4705, Abstract only.
Japan Patent Office, Final Notice of Reasons for Rejection, Japanese Patent Application No. 2011-516168, Jul. 28, 2014, six pages.
Borden Ladner Gervais LLP to Canadian Patent Office, Response to Official Action of Nov. 10, 2015, Application No. 2729095, dated May 10, 2016, 12 pages.
MeMO (Registered) transgenic mouse for improved antibody therapeutics information sheet from www.merus.nl, dated Sep. 2012.
Bruggemann, Marianne, Human Antibody Expression in Transgenic Mic, Archivum Immunologiae et Therapiae Experimenlalis, 2001, pp. 203-208, vol. 49.
Potter H. et al., Transfection by Electroporation, Curr Prot Mal Biol., 2003, Chapter 9:Unit9.3. doi: 10.1002/0471142727. mb0903s92.

(56) References Cited

OTHER PUBLICATIONS

Weiner, et al., Abstract, Fully human therapeutic monoclonal antibodies, Journal of Immunotherapy, Jan. 1, 2006, pp. 1-9, vol. 29, No. 1, Lippincott Williams & Wilkins, Hagerstown, MD, US.
Documents associated with European Patent Application EP 02709544, dated Aug. 27 2015, (Electronic) Receipt.
Documents associated with European Patent Application EP 02709544, dated Jan. 28, 2014, Reply of the patent proprietor to the notice(s) of opposition—1.
Documents associated with European Patent Application EP 02709544, dated Dec. 12, 2014, Composition of the board (T)—1.
Designation of inventor Mark Throsby dated Jul. 9, 2012, User Reference: P85261EP10, EP12175544.
Little, M., Recombinant antibodies for immunotherapy, chapter 7; 8; 2009, Cambridge Univ. Press.
Documents associated with European Patent Application EP 02709544, dated Jan. 28, 2014, Reply of the patent proprietor to the notice(s) of opposition—2.
Documents associated with European Patent Application EP 02709544, dated Feb. 24, 2015, Setting time limit for reply file observations to appeal (inter partes).
Documents associated with European Patent Application EP 02709544, dated Jan. 30, 2015, Letter regarding the Opposition procedure (no time limit).
Documents associated with European Patent Application EP 02709544, dated Feb. 15, 2015, Statement of grounds of appeal.
Jakobovits, Aya, Production of fully human antibodies by transgenic mice, Current Biotechnology, 1995, pp. 561-566, vol. 6.
Auxiliary Request 12, EP Patent No. 2314529B1, Reference No. M70120EPEIN FLZ, May 20, 2016, three pages.
Documents associated with European Patent Application EP 02709544, dated Dec. 12, 2014, Composition of the board (T)—2.
Warnaar et al., Hybridoma, 1994, pp. 519-26, vol. 13, No. 6.
Van den Beucken et al., Building novel binding ligands to B7.1 and B7.2 based on human antibody single variable light chain domains, J. Mol. Biol., Jul. 13, 2001, pp. 591-601, vol. 310, Issue 3, Abstract only.
Stacy et al., Use of Double Replacement Gene Targeting to Replace the Murine a-Lactalbumin Gene with Its Human Counterpart in Embryonic Stem Cells and Mice, Molecular and Cellular Biology,8 pages, Feb. 1994, pp. 1009-1016, vol. 14, No. 2, American Society for Microbiology.
EPO communication to Andrew Bentham of J A Kemp, Brief Communication regarding Oral Proceedings on Jun. 22, 2016 at 10:00 in S2.1., EP Application No. 10186063.3 and EP Patent No. 2314629, Feb. 25, 2016, EPO rorm 291000 01.12, one page.
Jul. 20, 2012 Deficiencies in application documents—annex Band C, 4 pages.
Riechmann, L., Winter, G., Novel folded protein domains generated by combinatorial shuffling of polypeptide segments, Proc Natl Acad Sci US A, 2000, 97(18), 10068-10073.
Regeneron and Columbia University Enter Into a Strategic VelocImmuneR Agreement, Business Wire, (Sep. 16, 2008), http://www.businesswire.com/news/google/20080916005336/en, printed Jan. 23, 2014.
Documents associated with European Patent Application EP 02709544, dated Oct. 3, 2016, Written submission in Preparation to_during oral proceedings.
Mirick et al., A review of human anti-globulin antibody (HAGA, HAMA, HAGA, HAHA) responses to monoclonal antibodies: not four letter words, Q Nucl. Med. Mol. Imaging, Dec. 2004, pp. 251-257, vol. 48, No. 4.
Muyrers, JP. et al; Point mutation of bacterial artificial chromosomes by ET recombination, EMBO Reports, 2000, 1(3):239-43.
Murphy, Andrew, Statement of, Jan. 27, 2014.
Documents associated with European Patent Application EP 02709544, dated Dec. 9, 2014. (Electronic) Receipt.
Segal et al., Introduction: bispecific antibodies, Journal of Immunological Methods, 2001, pp. 1-6, vol. 248, Elsevier.

Protest and Submission of Prior Art submitted by Blake, Cassels & Graydon LLP dated Sep. 16, 2015, indicates the following attachments: D8-Sirao et al., 2006, 9 pages (previously submitted); D9-US 20060015957 (299 pages) (previously submitted); D10-WO 2006117699 (previously submitted); D11-WO 2004009618 (previously submitted); D12-WO 2004106375 (previously submitted).
Canadian Intellectual Property Office, General Correspondence Form, CA Application No. 2729095, PCT Application No. PCT/NL2009/050381, Dec. 22, 2010, three pages.
GenBank Accession No. DQ187586-1, Protein ID ABA26122.1, Rabquer, B.J. et al., "Differential variable gene usage between pneumococcal polysaccharide specific B cells isolated 5-10 days and 4-6 weeks post-vaccination," 1 page (2005).
Friedenson el al., Immunoglobulin G Antibodies from an Individual Rabbit in Which Several Heavy Chain Variants Are Paired wilh One Light Chain Sequence, The Journal of Biological Chemistry, 1973, pp. 7073-7079, vol. 248, No. 20.
Documents associated with European Patent Application EP 02709544, dated Feb. 12, 2014, Request for acceleration of the opposition procedure.
Yancopoulos et al., Preferential utilization of the most J eta-proximal Veta gene segments in pre-B-<:ell lines, Nature, Oct. 25, 1984, pp. 727-733, vol. 311.
Macdonald, LE. et al, Precise and in situ genetic humanization of 6 Mb of mouse immunoglobulin genes, Proc Natl Acad Sci USA, 2014, 111(14):5147-5152.
Shields, RL, et al., High resolution mapping of the binding site on human IgGI for FcgRI, FcgRII, FcgRIII and FcRn and design of IgGI variants with improved binding to the FcgR, J Biol Chem., 2001, 276(9), 6591-6604.
Aranda, A., Pascual, A., Nuclear hormone receptors and gene expression, Physiol Rev., 2001, 81(3), 1269-1304.
Sirac et al., Light chain inclusion permits terminal B cell differentation and does not necessarily result in autoreactivity, PNAS, May 16, 2006, pp. 7747-7752, vol. 103, No. 20.
Smith et al., Genomic Analysis of Transgenic Animals, Southern Blotting, Chapter 37, Methods in Molecular Biology, vol. 18, Transgenesis Techniques, Principles and Protoc0ls, 1993, pp. 323-327.
Vollmer et al., Antigen contacts by Ni-reactive TCR: typical alphabeta chain cooperation versus alpha chain-dominated specificity, International Immunology, 2000, pp. 1723-1731, vol. 12, No. 12.
Bruggemann, M and Neuberger, MS, Strategies for expressing human antibody repertoires in transgenic mice, Immunology Today, 1996, 17(8):391-7.
Jolly et al.. Rapid methods for the analysis of immunoglobulin gene hypennutation: application to transgenic and gene targeted mice, Nucleic Acids Research, 1997, pp. 1913-1919, vol. 25, No. 10.
Documents associated with European Patent Application EP 02709544, dated Oct. 14, 2013, Brief communication Opposition proceedings—1.
Aggarwal, AK. and Wah, DA., Novel site-specific DNA endonucleases, Curr Opin Struct Biol., 1998, 8(1):19-25.
Keller, G. et al., Hematopoietic commitment during embryonic stem cell differentiation in culture, Mol Cell Biol., 1993, 13(1), 473-486.
Documents associated with European Patent Application EP 02709544, dated Aug. 27, 2015, Letter accompanying subsequently filed items.
Documents associated with European Patent Application EP 02709544, dated Nov. 28, 2014, Acknowledgement of a document—1.
AstraZeneca Licenses Regeneron's VelocImmune Technology for Discovering Human Monoclonal Antibodies (Feb. 5, 2007), Drugs.com, http://www.drugs.com/news/astrazeneca-licenses-regenron-s-velocimmune-technolo printed Jan. 23, 2014.
Documents associated with European Patent Application EP 02709544, dated Mar. 26, 2015, Amended claims with annotations—4.
Documents associated with European Patent Application EP 02709544, dated Mar. 26, 2015, Amended claims with annotations—5.
Goyenechea et al., "Modifying the sequence of an immunoglobulin V-gene alters the resulting pattern of hypermutation", Immunology, vol. 93, Nov. 1996, pp. 13979-13984, Proceedings of the National Academy of Sciences, USA.
Extract from Fundamental Immunology, 4th Edition, Paul, W.E., Lippincott-Raven (1999).

(56) References Cited

OTHER PUBLICATIONS

Documents associated with European Patent Application EP 02709544, dated Mar. 26, 2015, Amended claims with annotations—2.
EPO communication, Maintenance/ Change of date/ Cancellation of oral proceedings arranged for: May 23, 2013 at 10.00 hrs, EP Application No. 19075279.1, Apr. 25, 2013, EPO Form 2088 04.10, two pages.
Kramer et al., A novel helper phage that improves phage display selection efficiency by preventing the amplification of phages without recombinant protein, Nucleic Acids Res., 2003, e59, vol. 31, No. 11.
Documents associated with European Patent Application EP 02709544, dated Mar. 26, 2015, Amended claims with annotations—3.
Dougier et al., Interallelic class switch recombination can reverse allelic exclusion and allow trans-complementation of an IgH locus switching defect, Eur. J Immunol., pp. 2181-2191, vol. 36.
Auxiliary Request 13, EP Patent No. 2314629B1, Reference No. M70120EPEIN FLZ, May 20, 2016, ffive pages.
Chothia, et al., Canonical Structures for the Hypervariable Regions of Immunoglobulins, J Mol. Biol., Aug. 20, 1987, pp. 901-917, vol. 196, Issue 4.
Documents associated with European Patent Application EP 02709544, dated Mar. 26, 2015, Amended claims with annotations—1.
Reiter, Y. et al., An antibody single-domain phage display library of a native heavy chain variable region: isolation of unctional single-domain VH molecules with a unique interface, J Mol Biol., 1999, 290(3), 685-698.
Documents associated with European Patent Application EP 02709544, dated Jan. 20, 2015, Communication of The Board of Appeal (ex parte_ inter partes).
De Jong, G., Mammalian artificial chromosome pilot production facility: large-scale isolation of functional satellite DNA-based artificial chromosomes, Cytometry, 1999, 35(2), 129-133.
Nord, K. et al., Recombinant human factor VIII-specific affinity ligands selected from phage-displayed combinatorial libraries of protein A, Eur J Biochem., 2001, 268(15), 4269-4277.
Documents associated with European Patent Application EP 02709544, dated Nov. 5, 2015, Forwarding of submissions to parties—2.
Documents associated with European Patent Application EP 02709544, dated Nov. 5, 2015, Forwarding of submissions to parties—1.
Yang, X.W. et al., "Homologous recombination based modification in *Escherichia coli* and germline transmission in transgenic mice of a bacterial artificial chromosome," Nat. Biotechnol., vol. 15(9):859-865 (1997).
Summons to Attend Oral Proceedings, EP Patent No. 2147594, at least as early as Feb. 1, 2016, five pages.
Documents associated with European Patent Application EP 02709544, dated Sep. 19, 2016, Letter regarding he opposition procedure (no time limit).
Thykjaer et al., Gene targeting approaches using positive-negative selection and large flanking regions, Plant Molecular Biology, 1997, pp. 523-530, vol. 35.
Communication from European Patent Office: Rejection of the opposition against EP 2147594, dated Oct. 28, 2016, 1 page.
Inlay et al., Essential roles of the kappa light chain intronic enhancer and 3' enhancer in kappa rearrangement and demethylation, Nat Immunol., Apr. 22, 2002, pp. 463-468, vol. 3, Abstract only.
Notice of Third Party Submission filed with the U.S. Patent Office on Aug. 29, 2016 in U.S. Appl. No. 15/140,321, 2 pages.
Declaration of Prof. Ton Logtenberg dated Sep. 15, 2015 filed in U.S. Appl. No. 13/750,753, four pages.
Neumann, E., Gene transfer into mouse lyoma cells by electroporation in high electric fields, EMBO J.,1982, 1(7), g41-845.
European Search Report for European patent application No. 10189886.4 dated Nov. 20, 2012.
Muyldermans, Reviews in Molecular Biotechnology, 2001, pp. 277-302, vol. 72.
Documents associated with European Patent Application EP 02709544, dated Mar. 18, 2014, Letter concerning the inventor.
Lang, A.B. et al, Immunotherapy with Human Monoclonal Antibodies, Journal of Immunology, Jul. 1993, pp. 466-472, vol. 151, No. 13.
Zambrowicz et al., Disruption and sequence identification of 2,000 genes in mouse embryonic stem cells, Nature, 4 pages Apr. 9, 1998, pp. 608-611, vol. 392, Nature Macmillan Publishing.
Documents associated with European Patent Application EP 02709544, dated Nov. 25, 2015, Letter relating to Appeal Procedure.
Waterhouse et al., Combinatorial infection and in vivo recombination: a strategy for making large phage antibody repertoires, Nucleic Acids Research, 1993, pp. 2265-2266, vol. 21, No. 9.
Documents associated with European Patent Application EP 02709544, dated Feb. 15, 2015, Claims—03.
Documents associated with European Patent Application EP 02709544, dated Feb. 15, 2015, Claims—04.
EPO Communication pursuant to Article 94(3) EPC, EP Application No. 09075279.1, Jun. 29, 2012, EPO Form 2001 12.10CSX, six pages.
Documents associated with European Patent Application EP 02709544, dated Feb. 15, 2015, Claims—05.
De Wildt, Ruud M.T. et al., "Analysis of Heavy and Light Chain Pairings Indicates that Receptor Editing Shapes the Human Antibody Antibody Repertoire," J. Mol. Biol., vol. 285:895-901 (1999).
Documents associated with European Patent Application EP 02709544, dated Feb. 15, 2015, Claims—06.
Documents associated with European Patent Application EP 02709544, dated Feb. 15, 2015, Claims—01.
Documents associated with European Patent Application EP 02709544, dated Feb. 15, 2015, Claims—02.
Szabo et al., Surface plasmon resonance and its use in biomolecular interaction analysis {BIA), Curr. Opin. Struct. Biol., Oct. 1995, pp. 699-705, vol. 5, Issue 5, Abstract only.
Sambrook 3rd ed, Chapter 16.34, protocol 5, 2001.
Santini, C. et al., Efficient display of an HCV cDNA expression library as C-terminal fusion to the capsid protein D of bacteriophage lambda, J Mal Biol., 1998, 282(1), 125-135.
McMahon et al., The Wnt-1 (int-1)Proto-Oncogene Is Required for Development of a Large Region of the Mouse Brain, Cell, 13 pages, Sep. 21, 1990, pp. 1073-1085, vol. 62, No. 6, Cell Press.
Almagro et al., Humanization of antibodies, Frontiers in Bioscience, Jan. 1, 2008, pp. 1619-1633, vol. 13.
Meyer et al., The Igk 3'-enhancer triggers gene expression in early B lymphocytes but its activity in enhanced on B cell activation, Int. Immunol., 1996, pp. 1561-1568, vol. 8, No. 10.
Letter regarding the opposition procedure (no time limit) dated Jun. 20, 2016 from Isenbruck to European Patent Office, 1 page, NUM536.
French, et al., Cancer Research, 1991, pp. 2353-2361, vol. 51.
EPO Brief Communication to Andrew Bentham of J A Kemp regarding the telephone conversation on the Opposition, EP Application No. 09075279.1 and Patent No. 2147594, Mar. 16, 2016, EPO Form 29110 01.12, one page.
Brief Communication from European Patent Office to JA Kemp regarding EP 10186063.3 dated Jun. 13, 2016.
Hochedlinger et al, Nature 415:1035-1338, 2002.
Kruse PF and Patterson MK (eds) Tissue Culture. Methods and Applications, 1973, Academic Press, New York, no pages provided.
Fussenegger et al., Genetic optimization of recombinant glycoprotein production by mammalian cells, Reviews, Tibtech, Jan. 1999, pp. 35-42, vol. 17.
Yoshio-Hoshino, N. et al., Establishment of a new interleukin-6 {IL-6) receptor inhibitor applicable to the gene therapy or IL-6-dependent tumor, Cancer Res., 2007, 67(3), 871-875.
Documents associated with European Patent Application EP 02709544, dated Nov. 4, 2015, Amended claims ,vith annotations.
Kohler and Milstein, Continuous cultures of fused cells secreting antibody of predefined specificity, Nature, Aug. 7, 1975, pp. 495-497, vol. 256.
Request for Grant of a European Patent for EP Application No. 10186063.3, Oct. 1, 2010, 6 pages.
Wilmut et al., Viable offspring derived from fetal and adult mammalian cells, Nature, Feb. 27, 1997, pp. 810-813, vol. 385, Issue 6619.

(56) References Cited

OTHER PUBLICATIONS

Esposito, Gloria et al., "Phage display of a human antibody against Clostridium tetani toxin," Gene, vol. 148:167-168 (1994).
Gavilondo et al., Antibody Engineering at the Millennium, BioTechniques, Jul. 2000, pp. 128-145, vol. 29.
Aucouturier et al., Monoclonal Ig L Chain and L Chain V Domain Fragment Crystallization in Myeloma-Associated Fanconi's Syndrome, The Journal of Immunology, Apr. 15, 1993, pp. 3561-3568, vol. 150, No. 8.
Designation of Inventor Van Berkel Patricius Hendrikus, User Reference No. P61090EP20, at least as early as Oct. 1, 2010, 1 page.
Documents associated with European Patent Application EP02709544, dated Jul. 21, 2014, Brief communication—opposition proceedings—1.
Documents associated with European Patent Application EP02709544, dated Jul. 21, 2014, Brief communication—opposition proceedings—2.
Documents associated with European Patent Application EP02709544, dated Jul. 21, 2014, Brief communication—opposition proceedings—4.
Popov et al., "A Human Immunoglobulin J.. Locus Is Similarly Well Expressed in Mice and Humans", The Journal of Experimental Medicine, vol. 189, No. 10, May 17, 1999, pp. 1611-1619, The Rockefeller University Press.
Documents associated with European Patent Application EP02709544, dated Sep. 30, 2016, Letter accompanying subsequently filed items.
Documents associated with European Patent Application EP02709544, dated Sep. 19, 2016, Letter accompanying subsequently filed items.
Documents associated with European Patent Application EP02709544, dated Feb. 11, 2014, Brief cornmunicatior Opposition proceedings—1.
Documents associated with European Patent Application EP02709544, dated Jan. 23, 2015, Forwarding of submissions to parties—2.
Documents associated with European Patent Application EP02709544, dated Jan. 23, 2015, Forwarding of submissions to parties—1.
Documents associated with European Patent Application EP02709544, dated Feb. 15, 2015, Patent Document cited during the appeal procedure—1.
Documents associated with European Patent Application EP02709544, dated Feb. 15, 2015, Patent Document cited during the appeal procedure—2.
Documents associated with European Patent Application EP02709544, dated Mar. 9, 2015, Letter dealing with oral proceedings during the appeal procedure.
Documents associated with European Patent Application EP02709544, dated Aug. 19, 2014, Brief communication—opposition proceedings—1.
Richards-Smith, BA. et al., Deletion mapping of the mouse ornithine decarboxylase-related locus Odc-rs8 within Igh-V, Mammalian Genome, 1992, 3(10):568-74.
Documents associated with European Patent Application EP02709544, Memorandum Decision & Order for U.S. District Court, Southern District of New York date filed Aug. 6, 2015, in Case No. 1:14-cv-1650-KBF, includes :luration of transmission.
EPO Brief Communication to Fritz Lahrlz of Isenbruck Bosl Hoschler LLP regarding the Opposition and Oral Proceedings, EP Application No. 09075279.1 and Patent No. 2147594, Feb. 9, 2016, EPO Form 29110 01.12, one page.
Documents associated with European Patent Application EP02709544, dated Jul. 16, 2014, 05.
Documents associated with European Patent Application EP02709544, dated Jul. 16, 2014, 06.
Documents associated with European Patent Application EP02709544, dated Jul. 16, 2014, 07.
Documents associated with European Patent Application EP02709544, dated Jul. 16, 2014, 08.
Documents associated with European Patent Application EP02709544, dated Jun. 12, 2013, Appendix 2: Third Party Observations filed during prosection (D12).

Galun et al., Clinical evaluation (Phase I) of a combination of two human monoclonal antibodies to HBV: Safety and antiviral properties., Hepatology, Mar. 2002, pp. 673-679, vol. 35, Issue 3.
Documents associated with European Patent Application EP02709544, dated Jul. 16, 2014, 09.
Lonberg et al., Human antibodies from transgenic animals, Nature Biotechnology, Sep. 1, 2005, pp. 1117-1125, vol. 23, No. 9, Nature Publishing Group, New York, NY, US.
Documents associated with European Patent Application EP02709544, dated Jul. 16, 2014, 01.
Documents associated with European Patent Application EP02709544, dated Jul. 16, 2014, 02.
Documents associated with European Patent Application EP02709544, dated Jul. 16, 2014, 03.
Documents associated with European Patent Application EP02709544, dated Jul. 16, 2014, 04.
Carter et al.,Humanization of anti-p185her2 antibody for human cancer therapy, PNAS, 1992, pp. 4285-4289, vol. 89.
EPO communication, EP Application No. 19075279.1, at least as early as May 22, 2013, EPO Form 2906 01.91TRI, one page.
Gorman, C., Bullock, C., Site-specific gene targeting for gene expression in eukaryotes, Curr Opin Biotechnol., 2000, 11(5), 455-460.
Documents associated with European Patent Application EP02709544, dated Aug. 7, 2015, Forwarding of submissions to parties—1.
Documents associated with European Patent Application EP02709544, dated Aug. 7, 2015, Forwarding of submissions to parties—2 .
Documents associated with European Patent Application EP02709544, dated Aug. 7, 2015, Forwarding of submissions to parties—3.
Documents associated with European Patent Application EP02709544, dated Sep. 12, 2014, Any annexes (other than citation) to an opposition letter—2.
Kitamura et al., A B cell-deficient mouse by targeted disruption of the membrane exon of the immunoglobulin mu chain gene, Nature, Apr. 4, 1991, pp. 423-426, vol. 350.
Documents associated with European Patent Application EP02709544, dated Sep. 12, 2014, Any annexes (other than citation) to an opposition letter—1.
European Search Report for EP Application No. 10186063, dated Mar. 16, 2011, EPO Form 1503, 03.82, 2 pages.
Documents associated with European Patent Application EP02709544, dated Jul. 16, 2014, 10.
Documents associated with European Patent Application EP02709544, dated Jul. 16, 2014, 11.
Documents associated with European Patent Application EP02709544, dated Jul. 16, 2014, 12.
U.S. Priority Document of U.S. Appl. No. 60/397,066, "Recombinant Production of Mixtures of Antibodies", submitted in International Application No. PCT/EP03/07690, Sep. 1, 2003, 140 pages.
Documents associated with European Patent Application EP02709544, dated Jul. 16, 2014, 13.
Gelpi, E., Biomedical and biochemical applications of liquid chromatography-mass spectrometry, J Chromatogr A, 1995, 703(1-2), 59-80, Abstract Only.
Ringrose et al., Quantitative comparison of DNA Looping in vitro and in vivo: chromatin increases effective DNA flexibility at short distances, The EMBO Journal, 12 pages, Dec. 1, 1999, pp. 6630-6641, vol. 18, No. 23, European Molecular Biology Organization.
Schaffilzel, C. et al., Ribosome display: an in vitro method for selection and evolution of antibodies from libraries, J mmunol Methods, 1999, 231(1-2), 119-135.
Nemazee, "Receptor editing in lymphocyte development and central tolerance", Nature Reviews Immunology, vol. 6, Oct. 2006, pp. 728-740, Nature Publishing Group.
Kortt et al., Abstract, Dimeric and trimeric antibodies: high avidity scFvs for cancer targeting, Biomol. Eng., Oct. 15, 2001, pp. 95-108, vol. 18, No. 3.
Schlehuber et al., Tuning ligand affinity, specificity, and folding stability of an engineered lipocalin variant—a so-called anticalin—using a molecular random approach, Biophysical Chemistry 96 (2002) 213-228.

(56) References Cited

OTHER PUBLICATIONS

Documents associated with European Patent Application EP 02709544, dated Sep. 10, 2014, Brief communication—Opposition proceedings—3.
Documents associated with European Patent Application EP 02709544, dated Sep. 10, 2014, Brief communication—Opposition proceedings—2.
Documents associated with European Patent Application EP 02709544, dated Sep. 10, 2014, Brief communication—Opposition proceedings—1.
Mortuza et al., Immunoglobulin heavy-chain gene rearrangement in adult acute lymphoblastic leukemia reveals preferential usage of J eta-proximal variable gene segments, Immunobiology, Blood, May 1, 2001, pp. 2716-2726, vol. 7, No. 9.
Documents associated with European Patent Application EP 02709544, dated Feb. 10, 2014, Letter accompanying subsequently filed items.
PCT International Search Report, PCT/EP03/07690, dated Apr. 16, 2004.
Shmerling, D. et al., Strong and ubiquitous expression of transgenes targeted into the beta-actin locus by Cre/lox cassette replacement, Genesis: The Journal of Genetics and Development, 2005, vol. 42, No. 4, p. 229-235.
Huelz, F. et al., Targeted disruption of the V(H) 81X gene: influence on the B cell repertoire, Eur J Immunol. Jan. 1997;27(1):307-14.
Acknowledgement of receipt of European Patent Office regarding EP 10186063.3 dated Jun. 6, 2016, 2 pages.
Documents associated with European Patent Application EP 02709544, dated Dec. 3, 2015, Forwarding of submissions to parties—1.
Gram, H. et al., In vitro selection and affinity maturation of antibodies from a naive combinatorial immunoglobulin ibrary, Proc Nall Acad Sci US A, 1992, 89(8), 3576-3580.
Documents associated with European Patent Application EP 02709544, dated Mar. 26, 2015, Letter relating to Appeal Procedure.
Documents associated with European Patent Application EP 02709544, dated Aug. 19, 2014, Brief communication—opposition proceedings—3.
Documents associated with European Patent Application EP 02709544, dated Aug. 19, 2014, Brief communication—opposition proceedings—2.
Correspondence from C.M. Jansen of V.O. to the European Patent Office regarding change of correspondence, EP Application No. 10186063.3 and EP Patent No. 2314629, Dec. 17, 2015, one page.
Vaughan et al., Human Antibodies with Sub-nanomolar Affinities Isolated from a Large Non-immunized Phage Display Library, Nature Biotechnology, Mar. 1996, pp. 309-314, vol. 14.
Statement of Dr Yancopoulos, first witness statement in UK litigation (The High Court of Justice, Chancery Division, Patents Court, Case No. HP-2013-000001/HP-2014-000001 dated Oct. 2, 2015, Report relates to a patent owned by Regeneron Pharmaceuticals, Inc., EP 2264163).
Documents associated with European Patent Application EP 02709544, dated Sep. 16, 2013, Letter accompanying subsequently filed items.
Bethke et al., Segmental genomic replacement by ere-mediated recombination: genotoxic stress activation of the p53 Promoter in single-copy transformants, Nucleic Acids Res., 1997, 25(14):2828-34.
Documents associated with European Patent Application EP 02709544, dated Sep. 11, 2014, Letter regarding he opposition procedure (no time limit).
Waterston, RH. et al., Initial sequencing and comparative analysis of the mouse genome, Nature, 2002, 420(6915):520-62.
Bruggemann, Marianne, The Preparation of Human Antibodies from Mice Harbouring Human Immunoglobulin Loci, Transgenic animals: generation and use, Louis Marie Houdebine, 1997, Ch. 58, Part IV, Sectdion A, pp. 397-402.
Japan Patent Office, Registration Fee Payment, Japanese Patent Application No. 2011-516168, May 13, 2015, one page.
Cockett MI, Bel al., High level expression of tissue inhibitor of melalloproleinases in Chinese hamster ovary cells using Jlutamale synthelase gene amplification, Biotechnology, 1990, 8(7), 662-667.

Wilmut et al., "Viable offspring derived from fetal and adult mammalian cells", Roslin Institute (Edinburgh), Letters to Nature, vol. 385, Feb. 27, 1997, pp. 810-200.
Hooper, D., "Rabies Virus," In: Manual of Clinical Laboratory Immunology, Part II, 5 ed., N.R. Rose (Ed.), ASM Press, wash. D.C., pp. 755-760, (1997).
EPO Communication regarding important information concerning oral proceedings, at least as early as Jan. 19, 2016, EPO Form 2043 02.09, three pages.
Documents associated with European Patent Application EP 02709544, dated Oct. 30, 2015, oral proceedings_order for summons—1.
(Pages 288-298) EPO Communication regarding opposition, EP Application No. 10186063.3, Nov. 19, 2015, EPO Form 2906 01.91 TRI with Consolidated list of documents, 11 pages (previously submitted).
Documents associated with European Patent Application EP 02709544, dated Oct. 30, 2015, oral proceedings_order for summons—2.
Documents associated with European Patent Application EP 02709544, dated Nov. 6, 2015, Forwarding of submissions to parties.
Correspondence from the Canadian Intellectual Property Office in Canadian Application No. 2,729,095 to Blake, Cassels & Graydon LLP dated Apr. 16, 2014, regarding filed protest, 1 page.
Documents associated with European Patent Application EP 02709544, dated Sep. 2, 2014, Document concerning representation—1.
Documents associated with European Patent Application EP 02709544, dated Sep. 2, 2014, Document concerning representation—2.
EPO Communication, Summons to J A Kemp to attend oral proceedings pursuant to Rule 115(1) EPC, EP Application No. 10186063.3 and EP Patent No. 2314629, Nov. 19, 2015, EPO Form 2310 12.14, one page.
Documents associated with European Patent Application EP 02709544, dated Oct. 25, 2015, Letter dealing with oral proceedings during the appeal procedure—1.
Documents associated with European Patent Application EP 02709544, dated Sep. 9, 2014, Any annexes (other than citation) to an opposition letter.
Documents associated with European Patent Application EP 02709544, dated Oct. 25, 2015, Letter dealing with oral proceedings during the appeal procedure—2.
Documents associated with European Patent Application EP 02709544, dated Aug. 13, 2015, Oral proceedings_order for summons—1.
Documents associated with European Patent Application EP 02709544, dated Aug. 13, 2015, Oral proceedings_order for summons—2.
Documents associated with European Patent Application EP 02709544, dated Mar. 14, 2014, Brief communication—opposition proceedings—1.
Documents associated with European Patent Application EP 02709544, dated Mar. 14, 2014, Brief communication—opposition proceedings—2.
Lu et al,. Complete Inhibition of vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor, Cancer Res., Oct. 1, 2001, pp. 7002-7008, vol. 61.
EPO Notification of European publication number dated Jan. 16, 2013, EP12175544.1.
Shaffer, AL. El al., In vivo occupancy of the kappa light chain enhancers in primary pro- and pre-B cells: a model for kappa locus activation, Immunity, 1997, 6(2), 131-143.
Documents associated with European Patent Application EP 02709544, dated Mar. 14, 2014, Brief communication—opposition proceedings—3.
EPO Communication, Payment ofees and expenses, EP Application No. 09075279.1, May 30, 2016, EPO Form 1010 03.15, one page.
Zheng et al., Engineering a mouse balancer chromosome, Nature Genetics, 4 pages, Aug. 1999, pp. 375-378, vol. 22, No. 4, Nature America Inc.
Inaba, M. et al., Distinct mechanisms of neonatal tolerance induced by dendritic cells and thymic B cells, J Exp Med., 1991, 173(3), 549-559.
D15—WO 2008/076379 {previously submitted); D16—WO 2008/054606 {previously submitted); D17—DeFrancesco et al., 2007 (listed separately); D18—Scott, et al., 2007 (previously submitted);

(56) References Cited

OTHER PUBLICATIONS

D19—Nagle, 2007 (previously submitted); Examination Search Report lists Family Members EP2147594B1 and AU2009263082B9.
Documents associated with European Patent Application EP02709544, dated Jul. 15, 2014, Letter regarding the opposition procedure (no time limit).
Documents associated with European Patent Application EP02709544, dated Feb. 12, 2014, (Electronic) Receipt—2.
Notification to EPO regarding Applicant Address Change, EP Application No. 10186063.3, dated Jan. 4, 2012, 1 page.
Documents associated with European Patent Application EP02709544, dated Feb. 12, 2014, (Electronic) Receipt—1.
Hanes, J. et al., Picomolar affinity antibodies from a fully synthetic naive library selected and evolved by ribosome display, Nat Biotechnol., 2000, 18(12), 1287-1292.
Bendig MM., The production of foreign proteins in mammalian cells, Genet Eng, 1988;(7); 91-127.
Jeffers et al., Enhanced tumorigenicity and invasion-metastasis by hepatocyte growth factor/scatter factor-met signalling in human cells concomitant with induction of the urokinase proteolysis network, Mal. Cell. Biol., Mar. 1996, pp. 1115-1125, vol. 16, No. 3.
EPO Submission in opposition proceedings, Request for extension of time, EP Application No. 10186063.3 and EP Patent No. 2314629, Oct. 16, 2014, two pages.
Documents associated with European Patent Application EP02709544, dated Oct. 14, 2016, Internal form—Opposition_addressees.
Kuehn et al., A potential animal model for Lesch Nyhan syndrome through introduction of HPRT mutations into mice, Letters to Nature, 4 pages, Mar. 19, 1987, pp. 295-298, vol. 326, Nature Publishing Group.
Lazar et al., A molecular immunology approach to antibody humanization and functional optimization, Mol Immunol., Mar. 2007, pp. 1986-1998, vol. 44, Issue 8.
Documents associated with European Patent Application EP02709544, dated Mar. 10, 2016, Decision of the Board of Appeal.
EPO communication, Preparation for oral proceedings—Instruction to Support Service, EP Application No. 09075279.1 and EP Patent No. 2147594, Jan. 14, 2016, EPO Form 2040 12.07TR1, two pages.
Presta et al., Engineering of therapeutic antibodies to minimize immunogenicity and optimize function, Advanced Drug Delivery Reviews, Aug. 7, 2006, pp. 640-56, vol. 58, No. 5-6, Elsevier BV, Amsterdam, NL.
Nobrega et al., Megabase deletions of gene deserts result in viable mice, Nature, 6 pages, Oct. 21, 2004, pp. 988-993 vol. 431, Nature Publishing Group.
Chinwalla et al., The mouse genome, Nature 420, 510, Dec. 5, 2002, p. 510-511 (Nature Genome Timeline).
Kontermann,RE, Dual targeting strategies with bispecific antibodies, 2012, mAbs 4(2), pp. 182-197.
Perlot et al., Analysis of Mice Lacking DNaseI Hypersensitive Sites at the 5' End of the IgH Locus, PLoS One, 11 pages, Nov. 15, 2010, pp. 1-10, vol. 5, No. 11.
EPO Acknowledgement of receipt dated Aug. 20, 2012, EP12175544. 1.
(Page 4) The communication was printed for and notified to each of the representatives/parties, regarding EP Application 10186063.3, at least as early as Jul. 27, 2016, 1 page.
Lefranc, Marie-Paule, Nomenclature of the Human Immunoglobulin Kappa (IGK) Genes, Exp Clin Immunogenet, 2001, pp. 161-174, vol. 18, Karger.
Second Declaration by David Tarlington dated Oct. 15, 2015, Australian patent application No. 2009263082, 24 pages.
Hardy et al., B Cell Development Pathways, Annu. Rev. Immunol., 2001, pp. 595-621, vol. 19.
Documents associated with European Patent Application EP02709544, dated Jun. 12, 2013, Communication of a notice of opposition—first information to patent proprietor.
In The High Court of Justice, Chancery Division, Patents Court, Case No. HP-2013-000001/HP-2014-000001 dated Nov. 3, 2015, Second Expert Report of Professor Jonathan Charles Howard, Report relates to patents owned by Regeneron Pharmaceuticals, Inc., EP 1 360 287 and 2 264 163.
Rees, S. et al, Bicistronic vector for the creation of stable mammalian cell lines that predisposes all antibiotic-resistant cells to express recombinant protein, Biotechniques, 1996, 20(1), 102-4, 106, 108-10.
Jakobovits et al., Analysis of homozygous mutant chimeric mice: deletion of the immunoglobulin heavy-chain joining region blocks B-cell development and antibody production, Proc. Natl. Acad. Sci. U.S.A., Mar. 1993, pp. 2551-2555, vol. 90.
Letter from Mr. T.J. Elmore of V.O. Patents & Trademarks to European Patent Office, at least as early as Oct. 16, 2014, accompanying subsequently filed items, one page.
Perrin et al., Abstract, In vitro rabies vaccine potency appraisal by ELISA: advant of the immunocapture method with a neutralizing anti-glycoprotein monoclonal antibody, Biologicals, Oct. 1990, pp. 321-30, vol. 18(4).
EPO Communication, Minutes of the oral proceedings before the Examining Division, EP Application No. 09075279.1 and Patent No. 2147594, May 23, 2013, EPO Form 2009.1 12.07TRI, two pages.
Documents associated with European Patent Application EP02709544, dated Dec. 5, 2014, Advice of delivery.
Documents associated with European Patent Application EP02709544, dated Aug. 22, 2014, Letter accompanying subsequently filed items.
Neuberger, M.S. et al., "Isotype exclusion and transgene down-regulation in immunoglobulin-lambda transgenic mice," Nature, vol. 338:350-352 (1989).
Ferrara, N., Vascular endothelial growth factor: molecular and biological aspects., Curr. Top. Microbiol. Immunol., 1999, 237:1-30.
Flavell et al., Therapy of human T-cell acute lymphoblastic leukaemia with a combination of anti-CD? and anti-CD38-SAPORIN immunotoxins is significantly better than therapy with each individual immunotoxin, British Journal of Cancer, Feb. 2001, pp. 571-578, vol. 84, No. 4.
Documents associated with European Patent Application EP02709544, dated Sep. 19, 2016, (Electronic) Receipt.
Sheng, Y., et al., Transformation of *Escherichia coli* with large DNA molecules by electroporation, Nucleic Acids Res., 1995, 23(11), 1990-6.
David Nemazee, Receptor Editing in B Cells, Advances in Immunology, 2000, pp. 89-126, vol. 74, Academic Press.
Lu et al., Selection of high affinity Inman neutralizing antibodies to VEGFR2 from a large antibody phage display library for antiangiogenesis therapy, Abstract, International Journal of Cancer, Jan. 20, 2002, pp. 39399, vol. 97, No. 3.
Documents associated with European Patent Application EP02709544, dated Oct. 30, 2015, Advice of delivery—1.
EPO General enquiry dated Jun. 16, 2016, EP12175544.1.
Chan, A., Mak, TW., Genomic organization of the T cell receptor, Cancer Detect Prev., 1989,14(2), 261-267.
Documents associated with European Patent Application EP02709544, dated Oct. 30, 2015, Advice of delivery—2.
Response in Appeal Proceedings for EP1360287 patent filed Jul. 2, 2015 by Kymab (present Opponent 2).
Documents associated with European Patent Application EP02709544, dated Sep. 9, 2014, (Electronic) Receipt.
(Page 8) EPO Brief Communication regarding the Opposition against EPApplication 10186063.3, dated Jun. 10, 2016, 1 page.
Hoogenboom et al., Antibody phage display technology and its applications, Immunotechnology,1998, pp. 1-20, vol. 4.
Documents associated with European Patent Application EP02709544, dated Apr. 3, 2014, Letter concerning fees and payments.
Novobrantseva et al., Rearrangement and expression of immunoglobulin light chain Jenes can precede heavy chain expression during normal B cell development in mice, J Exp. Med., Jan. 4, 1999, pp. 75-88, vol. 189, No. 1.
EP Priority Document of EP Application No. 02077953.4, "Recombinant Production of Mixtures of Antibodies", submitted in International Application No. PCT/EP03/07690, dated Sep. 5, 2003, 140 pages.

(56) References Cited

OTHER PUBLICATIONS

Torres et al., "Chapter 10: LoxP-containing transgenes", Laboratory Protocols for Conditional Gene Targeting, 1997, pp. 42-53, Oxford University Press Inc., New York, USA.
Nagle, "Regeneron helps make Sanofi Velcolmmue to its 'weak' pipline", Outsourcing—Pharma.com, Dec. 3, 2007, two pages, William Reed Business Media SAS.
Struhl, K. et al., High-frequency transformation of yeast: autonomous replication of hybrid DNA molecules, Proc Natl Acad Sci U S A, 1979, 76(3), 1035-1039.
Jonassen, P. et al., Genetic design for facilitated production and recovery of recombinant proteins in *Escherichia coli*, Biotechnol Appl Biochem., 2002, 35(Pt 2), 91-105.
Documents associated with European Patent Application EP 02709544, dated Sep. 15, 2014, Brief communication—Opposition proceedings—4.
Documents associated with European Patent Application EP 02709544, dated Sep. 15, 2014, Brief communication—Opposition proceedings—5.
Documents associated with European Patent Application EP 02709544, dated Sep. 15, 2014, Brief communication—Opposition proceedings—6.
Documents associated with European Patent Application EP 02709544, dated Sep. 15, 2014, Brief communication—Opposition proceedings—7.
Gonzales-Fernandez et al., Analysis of somatic hypennutation in mouse Peyer's patches using immunoglobulin K light-chain transgenes, Proc. Natl. Acad. Sci., Nov. 1993, pp. 9862-66, vol. 90.
Nahta et al.,The HER-2-Targeting Antibodies Trastuzumab and Pertuzumab Synergistically inhibit the Survival of Breast Cancer Cells, Cancer Research, Apr. 1, 2004, pp. 2343-2346, vol. 64.
Documents associated with European Patent Application EP 02709544, dated Sep. 15, 2014, Brief communication—Opposition proceedings—1.
Documents associated with European Patent Application EP 02709544, dated Sep. 15, 2014, Brief communication—Opposition proceedings—2.
Documents associated with European Patent Application EP 02709544, dated Sep. 15, 2014, Brief communication—Opposition proceedings—3.
Moldenhauer et al., Bispecific antibodies from hybrid hybridoma, in R.E. Kontermann (ed): Bispecific antibodies, Berlin Heidelberg, Springer Verlag, 2011, pp. 29-46.
Documents associated with European Patent Application EP 02709544, dated Sep. 15, 2014, Brief communication—Opposition proceedings—8.
Documents associated with European Patent Application EP 02709544, dated Sep. 15, 2014, Brief communication—Opposition proceedings—9.
Carmack et al, Influence of a VK8 L Chain Transgene on Endogenous Rearrangements and the Immune Response to the HA(SB) Determinant on Influenza Virus the Journal of Immunology, 1991, vol. 147, No. 6, pp. 2024-2033.
Documents associated with European Patent Application EP 02709544, dated Jun. 20, 2016, Communication of amended entries.
EPO Acknowledgement of receipt dated Jul. 9, 2012, Application No. EP12175544.1.
Inaba, K. et al., Dendritic cells pulsed with protein antigens in vitro can prime antigen-specific, MHC-restricted T cells n situ, J Exp Med., 1990, 172(2), 631-640.
Molecular Biology of B Cells, 1st Ed., Reth et al., Elsevier, Feb. 19, 2004, http://store.elsevier.com/Molecular-Biology-Jf-B-Cells/isbn-9780120536412/, printed Jan. 22, 2014.
Documents associated with European Patent Application EP 02709544, dated Sep. 15, 2014, 1003- Authorisation of representative—2.
Documents associated with European Patent Application EP 02709544, dated Sep. 15, 2014, 1003—Authorisation of representative—1.
Documents associated with European Patent Application EP 02709544, dated Sep. 23, 2016, Brief communication—Opposition proceedings—1.
Documents associated with European Patent Application EP 02709544, dated Sep. 23, 2016, Brief communication—Opposition proceedings—2.
Nemazee, David, "Receptor editing in lymphocyte development and central tolerance," Nature, vol. 6(10):728-740 (2006).
Attaelmannan et al., "Understanding and Identifying Monoclonal Gammopathies", Clinical Chemistry, vol. 46, No. 8, 2000, pp. 1230-1238.
Documents associated with European Patent Application EP 02709544, dated Sep. 23, 2016, Brief communication—Opposition proceedings—3.
EPO Communication pursuant to Rule 55 EPC, EP Application No. 10186063.3, Nov. 25, 2010, EPO Form 1047A, 11.09, 1 page.
De Kruif et al., "Rapid selection of cell subpopulation-specific human monoclonal antibodies from a synthetic phage antibody library", Proceedings of the National Academy of Sciences Usa, vol. 92, Apr. 1995, pp. 3938-3942.
De Wildt et al., "Analysis of Heavy and Light Chain Pairings Indicates that Receptor Editing Shapes the Human Antibody Repertoire", Journal of Molecular Biology, vol. 285, No. jmbi.1998.2396, 1999, pp. 895-901, Academic Press.
EPO Communication regarding Extension of time limit pursuant to Rule 132 EPC, EP Application No. 09075279.1 and Patent No. 2147594, Oct. 22, 2014, one page.
Tomizuka et al., Double trans-chromosomic mice: Maintenance of two individual human chromosome fragments Containing Ig heavy and kappa loci and expression of fully human antibodies, PNAS, Jan. 18, 2000, pp. 722-727, vol. 97, No. 2.
Documents associated with European Patent Application EP 02709544, dated Aug. 17 2015, Advice of delivery—2.
Documents associated with European Patent Application EP 02709544, dated Sep. 17, 2013, Grant of extensior of time limit (opposition procedure).
Nuerffel et al,, S-S Synapsis during Class Switch Recombination Is Promoted by Distantly Located Transcriptional Elements and Activation-Induced Deaminase, Immunity, Nov. 2007, pp. 711-722, vol. 27.
Lucas, BK. et al, High-level production of recombinant proteins in CHO cells using a dicistronic DHFR intron xpression vector, Nucleic Acids Res., 1996, 24(9), 1774-1779.
Documents associated with European Patent Application EP 02709544, dated Apr. 1, 2015, Forwarding of submissions to parties—3.
Documents associated with European Patent Application EP 02709544, dated Apr. 1, 2015, Forwarding of submissions to parties—2.
Gascan et al., Human B cell clones can be induced to proliferate and to switch to IgE and IgG4 synthesis by interleukin-4 and a signal provided by activated CD4C T cell clones. J Exp Med. 1991;173:747-750.
Documents associated with European Patent Application EP 02709544, dated Apr. 1, 2015, Forwarding of submissions to parties—1.
EPO Reply to the invitation to remedy deficiencies dated Oct. 29, 2012, EP12175544.1.
Documents associated with European Patent Application EP 02709544, dated Aug. 17 2015, Advice of delivery—1.
Dinnyes et al., "Somatic Cell Nuclear Transfer: Recent Progress and Challenges", Cloning and Stem Cells, vol. 4, No. 1, 2002, pp. 81-90.
Documents associated with European Patent Application EP 02709544, dated Jul. 16, 2014, Amended claims with annotations—07.
EPO Communication, Notice of Opposition to a European Patent, EP Application No. 09075279.1 and EP Patent No. 2147594, Aug. 11, 2014, Epo Form 2300E, eight pages.
Documents associated with European Patent Application EP 02709544, dated Jul. 16, 2014, Amended claims with annotations—06.
Documents associated with European Patent Application EP 02709544, dated Jul. 16, 2014, Amended claims with annotations—05.
Kling, Jim, "Big Pharma view for mice," Nature Biotechnology, vol. 25 (6):613 (2007).
Documents associated with European Patent Application EP 02709544, dated Oct. 11, 2013, Request for cceleration of the opposition procedure.
Documents associated with European Patent Application EP 02709544, dated Jul. 16, 2014, Amended claims with annotations—04.
Documents associated with European Patent Application EP 02709544, dated Jul. 16, 2014, Amended claims with annotations—03.

(56) References Cited

OTHER PUBLICATIONS

Documents associated with European Patent Application EP 02709544, dated Jul. 16, 2014, Amended claims with annotations—02.
Documents associated with European Patent Application EP 02709544, dated Jul. 16, 2014, Amended claims with annotations—01.
European Patent Office Communication for Application No. 09075279.1 dated Nov. 5, 2012.
Barbas, CF. et al., Assembly of combinatorial antibody libraries on phage surfaces: the gene III site, Proc Natl Acad Sci US A, 1991, 88(18), 7978-7982.
Desmet et al., The dead-end elimination theorem and its use in protein side-chain positioning, Nature, Apr. 9, 1992, pp. 539-542, vol. 356.
Documents associated with European Patent Application EP 02709544, dated Nov. 3, 2015, Fax relating to Appeal procedure—2.
Documents associated with European Patent Application EP 02709544, dated Jan. 28, 2014, Letter accompanying subsequently filed items—1.
Documents associated with European Patent Application EP 02709544, dated Nov. 3, 2015, Fax relating to Appeal procedure—1.
Documents associated with European Patent Application EP 02709544, dated Jan. 28, 2014, Letter accompanying subsequently filed items—2.
EPO Information on Search Strategy dated Jun. 30, 2016, EP12175544.1.
Documents associated with European Patent Application EP 02709544, dated Nov. 3, 2015, Fax relating to Appeal procedure—3.
Documents associated with European Patent Application EP 02709544, dated Jul. 6, 2015, Data sheet for the decision.
Scott, Christopher Thomas, "Mice with a human touch," Nature Biotechnology, vol. 25:1075-1077 (2007).
Japan Patent Office, Certificate of Patent, Japanese U.S. Pat. No. 5749161, Japanese Application No. 2011-516168, dated May 22, 2015.
Van der Vuurst de Vries A, Logtenberg T, Dissecting the human peripheral B-cell compartment with phage display-derived antibodies, Immunology, 1999, 98(1), 55-62.
Liang et al., Extensive genomic copy number variation in embryonic stem cell, pnas, 4 pages, Nov. 11, 2008, pp. 17453-17456, vol. 105, No. 45, Genetic Society of America.
Skarnes et al., A conditional knock out resource for the genome-wide study of mouse gene function, Nature, 6 pages, Jun. 16, 2011, pp. 337-342, vol. 474, MacMillan Publishers.
Documents associated with European Patent Application EP 02709544, dated Jul. 16, 2014, Amended claims with annotations—14.
Documents associated with European Patent Application EP 02709544, dated Jul. 16, 2014, Amended claims with annotations—13.
Documents associated with European Patent Application EP 02709544, dated Jul. 16, 2014, Amended claims with annotations—12.
Valenzuela, OM., High-throughput engineering of the mouse genome coupled with high-resolution expression analysis, Nat Biotechnol, 2003, 21(6), 652-659.
Documents associated with European Patent Application EP 02709544, dated Jul. 16, 2014, Amended claims with annotations—11.
Documents associated with European Patent Application EP 02709544, dated Feb. 15, 2015, Letter accompanying subsequently filed items.
Documents associated with European Patent Application EP 02709544, dated Jul. 16, 2014, Amended claims with annotations—10.
EPO Communication of further notices of opposition pursuant to Rule 79(2) EPC, EP Application No. 10186063.3 and EP Patent No. 2314629, Aug. 22, 2014, EPO Form 2318, 01.12, one page.
Documents associated with European Patent Application EP 02709544, dated Nov. 5, 2015, Advice of delivery—2.
Documents associated with European Patent Application EP 02709544, dated Nov. 5, 2015, Advice of delivery—1.
Takai, Y. et al., Requirement for three distinct lymphokines for the induction of cytotoxic T lymphocytes from thymocytes, J Immunol., 1986,137(11), 3494-3500.
Davis et al., A null c-myc mutation causes lethality before 10.5 days of gestation in homozygotes and reduced fertility in heterozygous female mice, Genes & Development, 12 pages, Apr. 7, 1993, pp. 671-682, vol. 7, No. 4, Cold Spring Harbor Laboratory Press.
EPO Brief Communication regarding the Opposition, EP Application No. 09075279.1 and Patent No. 2147594, Apr. 13, 2015, EPO Form 29110 01.12, one page.
Documents associated with European Patent Application EP 02709544, dated Feb. 26, 2014, Letter ccompanying subsequently filed items.
Franconi et al., Functional expression in bacteria and plants of an scFv antibody fragment against tospoviruses, Immunotechnology, 1999, pp. 189-201, vol. 4.
EPO Payment of fees and expenses dated Oct. 29, 2012, EP12175544.1.
Canadian Patent Office, Information Letter, Foreign and non-patent references, CA Application No. 2729095, dated March 9, 2011, two pages.
United States District Court Southern District of New York, *Regeneron Pharmaceuticals, Inc.*, Plaintiff v. *Merus B.V.*, Defendant, 14 Civ. 1650 (KBF) Opinion & Order dated Nov. 2, 2015.
European Search Opinion, EP Application No. 10186063.3, at least as early as Mar. 24, 2011, EPO Form 1703, 01,91TRI, 3 pages.
List of references in Opposition to Merus B.V.'s EP 2 314 29 B1, Consolidated List of Documents, undated, one page.
Documents associated with European Patent Application EP 02709544, dated Sep. 8, 2014, Brief communication—Opposition proceedings—1.
Documents associated with European Patent Application EP 02709544, dated Sep. 8, 2014, Brief communication—Opposition proceedings—3.
Wen et al., Tricistronic viral vectors co-expressing interleukin-12 (1L-12) and Cobo {B7-1) for the immunotherapy of Cancer: Preclinical studies in myeloma, Cancer Gene Therapy, 2001,pp. 361-70, vol. 8 No. 5.
Documents associated with European Patent Application EP 02709544, dated Sep. 12, 2014, Letter regarding the opposition procedure (no time limit).
SHIGA International Patent Office to Japan Patent Office, Amendments to claims made in response to notice of reasons for rejection, Japanese Patent Application No. 2011-516168, Jan. 14, 2014, three pages.
Documents associated with European Patent Application EP 02709544, dated Feb. 25, 2015, Forwarding of submissions to parties.
Documents associated with European Patent Application EP 02709544, dated Sep. 17, 2014, 2341—Information about the result of oral proceedings.
Documents associated with European Patent Application EP 02709544, dated Jul. 16, 2014, Written submission in preparation to during oral proceedings—1.
(Page 302-303) EPO Communication in preparation for oral proceedings dated Jun. 22, 2016, EP Application No. 10186063.3, EPO Form 2040, two pages.
Klitz et al., New HLA haplotype frequency reference standards: High-resolution and large sample typing of HLA DR-DQ haplotypes in a sample of European Americans, Tissue Antigens, 2003, pp. 296-307, vol. 62, Issue 4, Abstract.
Documents associated with European Patent Application EP 02709544, dated Jul. 25, 2014, Brief communication—opposition proceedings—2.
Documents associated with European Patent Application EP 02709544, dated Jul. 25, 2014, Brief communication—opposition proceedings—3.
Statement of Professor Anthony De Franco, first witness statement in UK litigation (The High Court of Justice, Chancery Division, Patents Court, Case No. HP-2013-000001/HP-2014-000001 dated Oct. 3, 2015, Report relates to a patent owned by Regeneron Pharmaceuticals, Inc., EP 2264163).
Murphy; KC., Use of Bacteriophage Lambda Recombination Functions to Promote Gene Replacement in *Escherichia oli*, J Bacteriol, 1998, 180(8), 2063-71.
Documents associated with European Patent Application EP 02709544, dated Jul. 25, 2014, Brief communication—opposition proceedings—1.
Little et al., Human antibody libraries in *Escherichia coli*, Journal of Biotechnology, 1995, pp. 187-195, vol. 41, Elsevier.

(56) References Cited

OTHER PUBLICATIONS (Pages 219-225) Logtenberg, Prof. Ton Declaration of, CEO, Merus B.V., dated May 4, 2016, 7 pages (previously submitted); (pp. 226-251) Appeal Brief under 37 C.F.R. .Sctn. 41.37 filed by Brenda Herschbach Jarrell, U.S. Appl. No. 13/948,818, filed Jul. 20, 2015, 26 pages with Claims Appendix (previously submitted).
Inlay et al., "Roles of the Ig kappa light chain intronic and 3' enhancers in Igk somatic hypermutation," J. Immunol. (2006) 177(2):1146-1151.
EPO communication to Andrew Bentham of J A Kemp, Brief Communication regarding EPO Form 2548 of Jan. 12, 2016, EP Application No. 09075279.1 and EP Patent No. 2147594, Jan. 12, 2016, EPO Form 291000 J1.12, two pages.
EP Application No. 09075279.1 with annotations, Aug. 3, 2010, 170 pages.
Correspondence from S.T. van Doorn to European Patent Office regarding written submissions filed Apr. 23, 2013, EP Applicalion No. 09075279.1, dated Apr. 24, 2013, one page.
Auerbach et al., Angiogenesis Assays: A Critical Overview, Clin. Chemistry, Jan. 2003, pp. 32 40, vol. 49, No. 1.
Rong et al., Tumorigenesis induced by coexpression of human hepatocyte growth factor and the human met protooncogene leads to high levels of expression of the ligand and receptor, Cell Growth Differ., Jul. 1993, pp. P63-P569, vol. 4, No. 7.
Mendel et al., The Angiogenesis Inhibitor SU5416 Has Long-lasting Effects on Vascular Endothelial Growth Factor Receptor Phosphorylation and Function, Clin. Cancer Res., Dec. 2000, pp. 4848-4858, vol. 6.
Documents associated with European Patent Application EP 02709544, dated Feb. 28, 2014, Annex to the communication—opposition.
Third Party Observations Under Article 115 EPC Against European Parent Application No. 09075279.1 in the name of Merus BV, Apr. 25, 2012, six pages.
Documents associated with European Patent Application EP 02709544, dated Jul. 2, 2015, Reply to 1.
Documents associated with European Patent Application EP 02709544, dated Sep. 12, 2014, Letter accompanying subsequently filed items.
Graslund, T. et al., Integrated strategy for selective expanded bed ion-exchange adsorption and site-specific protein rocessing using gene fusion technology, J Biotechnol., 2002, 96(1), 93-102.
Documents associated with European Patent Application EP 02709544, dated Jul. 2, 2015, Reply to 2.
Documents associated with European Patent Application EP 02709544, dated Jul. 2, 2015, Reply to 3.
Haines et al., Germline diversity of the expressed BALB/c VhJ558 gene family, Molecular Immunology, 10 pages, May 22, 2001, pp. 9-18 vol. 38, No. 1, Elsevier Science Ltd.
Main request, EP Application No. 09075279.1, Apr. 23, 2013, three pages.
Documents associated with European Patent Application EP 02709544, dated Jan. 30, 2015, (Electronic) Receipt—2.
Auxiliary Request 10 with annotations, EP Patent No. 2314629B1, May 20, 2016, nine pages.
Documents associated with European Patent Application EP 02709544, dated Sep. 12, 2014, (Electronic) Receipt.
Documents associated with European Patent Application EP 02709544, dated Jan. 30, 2015, (Electronic) Receipt—3.
Third Party Observation for U.S. Appl. No. 15/140,321, Sep. 2, 2016, two pages.
Documents associated with European Patent Application Ep 02709544, dated Jan. 30, 2015, (Electronic) Receipt—1.
Documents associated with European Patent Application EP 02709544, dated Dec. 9, 2014, Acknowledgement of a document.
Auxiliary Request 6 with annotations, EP Patent No. 2314629B1, May 20, 2016, Five pages.
Stevens, Sean, "Human Antibody Discovery, VelocImmune—A novel platform," Pharma Focus Asia, issue 8, pp. 72-74 (2008).
Arnold, LW., et al., Development of B-1 cells: segregation of phosphalidyl choline-specific B cells to the B-1 populalion occurs after immunoglobulin gene expression, J Exp Med., 1994;179(5),1585-1595.

V.O. communication to EPO, Executed Acknowledgement of receipt of EPO Form 2310 and 2043, EP Application No. 10186063.3 and EP Patent No. 2314629, Nov. 20, 2015, EPO Form 2936 08.10, one page.
EPO communication, Client Database System (CDS)—clean up, EP Application No. 19075279.1, Apr. 23, 2013, EPO For, 2596C, 04.08, 1 page.
Documents associated with European Patent Application EP 02709544, dated Feb. 15, 2015, Claims—07.
Documents associated with European Patent Application EP 02709544, dated Feb. 15, 2015, Claims—08.
EPO Client Database System—clean up dated Apr. 23, 2013, EP12175544.1.
Correspondence from T.J. Elmore of V.O. to European Patent Office regarding request for extension of time, EP Application No. 09075279.1 and Patent No. 2147594, Oct. 16, 2014, one page.
Declaration of Professor Anthony Defranco, European Patent No. 2147594 B1, European Patent Application No. 09075279.1, dated Aug. 24, 2016, 23 pages.
Macatonia, SE. et al., Dendritic cells produce IL-12 and direct the development of Th1 cells from naive CD4+ T cells, J mmunol., 1995, 154(10), 5071-5079.
Macejak, DG., Sarnow, P., Internal initiation of translation mediated by the 5' leader of a cellular mRNA, Nature, 1991, 353(6339), 90-94.
Materials from examination of a European Patent Application No. 09075279.1 in the name of O1, Apr. 23, 2013.
Letter from European Patent Office to Mr. Andrew Bentham of JA Kemp dated Jun. 6, 2016, accompanying subsequently filed items, one page.
Auxiliary request 4 (amendments indicated), EP Application No. 09075279.1, Apr. 23, 2013, three pages.
Ren et al., Targeted Insertion Results in a Rhombomere 2-Specific Hoxa2 Knockdown and Ectopoic Activation of Hoxa1 Expression, Developmental Dynamics, 2002, pp. 305-315, vol. 225.
Moreau, JF. et al., Leukaemia inhibitory factor is identical to the myeloid growth factor human interleukin for DA cells, Nature, 1988, 336(6200), 690-692.
Kunkel et al., Rapid and efficient site-specific mutagenesis without phenotypic selection, Methods in Enzymol., 1987, pp. 367-382, vol. 154.
Thomas et al., Site-Directed Mutagenesis by Gene Targeting in Mouse Embryo-Derived Stern Cells, Cells, Nov. 6, 1987, pp. 503-512, vol. 51.
Borden Ladner Gervais LLP in the Canadian Patent Office, Voluntary Amendment, Application No. 2729095, dated May 12, 2016, two pages.
Christophe Sirac; Sirac et al. (2006) Role of the monoclonal kappa chain V domain and reversibility of renal damage in a transgenic model of acquired Fanconi syndrome, Blood 108:536-543.
Documents associated with European Patent Application EP 02709544, dated Sep. 15, 2014, (Electronic) Receipt.
Attaelmannan, M Understanding and identifying monoclonal gammopathies, Clin Chem., 2000, 46(8 Pl 2), 1230-1238.
In The High Court of Justice, Chancery Division, Patents Court, Case No. HP-2013-000001/HP-2014-000001 dated Nov. 15, 2015, Third Witness Statement of Andrew Joseph Murphy, Report relates to patent owned by Regeneron Pharmaceuticals, Inc., EP 1 360 287.
Bitter, "Heterologous gene expression in yeast," Methods Enzymol (1987) 152:673-684.
EP, Third Party Observation for Application No. EP20120783456, Jun. 16, 2016, 3 pages.
Kirschbaum, T. et al., The 3' part of the immunoglobulin kappa locus of the mouse, Eur J Immunol., 1998; 28(5), 1458-66.
Johnston et al., Complete sequence assembly and characterization of the C57BU6 mouse Ig heavy chain V region, The Journal of Immunology, 13 pages, Apr. 1, 2006, vol. 176, No. 7, The American Society of Immunology.
Zhao, S., A Comprehensive BAG Resource, Nucleic Acids Research, 2001, 29(1):141-3.
Concise Description of Relevance in Third Party Submission filed with the U.S. Patent Office on Aug. 29, 2016 in U.S. Appl. No. 15/140,321, 6 pages.

(56) References Cited

OTHER PUBLICATIONS

EP Priority Document of International Application No. PCT/EP03/50201, "Recombinant Production of Mixtures of Antibodies", submitted in International Application No. PCT/EP03/07690, dated Sep. 1, 2003, 168 pages.
Voluntary Amendment filed by Borden Ladner Gervais LLP dated May 12, 2016 in Canadian Application No. 2,729,095, 2 pages.
Roitt, I.M. et al., Anti-idiotypes as surrogate antigens: structural considerations, Immunol Today, 1985, 6(9), 265-267.
Documents associated with European Patent Application EP 02709544, dated Jun. 20, 2016, Brief communication—: Opposition proceedings—2.
Documents associated with European Patent Application EP 02709544, dated Jun. 20, 2016, Brief communication—: Opposition proceedings—1.
EPO Request for recording a change in name of representative dated Apr. 2, 2013, EP12175544.1.
Documents associated with European Patent Application EP 02709544, dated Jun. 20, 2016, Brief communication—: Opposition proceedings—3.
Lie, Y.S. et al., "Advances in quantitative PCR technology: 5' nuclease assays," Curr. Opin. Biotechnol., vol. 9 (1):43-48 (1998).
Submission in opposition proceedings by Andrew Bentham, Letter providing alternated dates for Oral Proceedings, EP Application No. 09075279.1 and Patent No. 2147594, Feb. 15, 2016, one page.
Documents associated with European Patent Application EP 02709544, dated Feb. 26, 2014, Letter accompanying subsequently filed items.
Japan Patent Office, Notice of Reasons for Rejection, Japanese Patent Application No. 2011-516168, Oct. 15, 2013, four pages.
In The High Court of Justice, Chancery Division, Patents Court, Case No. HP-2013-000001/HP-2014-000001 dated Oct. 6, 2015, Expert Report of Professor Jonathan Charles Howard, Report relates to patents owned by Regeneron Pharmaceuticals, Inc., EP 1 360 287 and 2 264 163.
Documents associated with European Patent Application EP 02709544, dated Apr. 24, 2014, Acknowledgement of a document—3.
Documents associated with European Patent Application EP 02709544, dated Apr. 24, 2014, Acknowledgement of a document—2.
Documents associated with European Patent Application EP 02709544, dated Apr. 24, 2014, Acknowledgement of a document—1.
Nefedov M. et al., Insertion of disease-causing mutations in BACs by homologous recombination in E coli.Nucleic Acids Res., 2000, 28(17), E79.
Notification to EPO regarding Request for recording a change in name of representative, EP Application No. 10186063.3, Mar. 23, 2013, 3 pages.
Documents associated with European Patent Application EP 02709544, dated Apr. 24, 2014, Acknowledgement of a document—4.
Bertagnolli, MM. et al., IL-4-supported induction of cytolytic T lymphocytes requires IL-2 and IL-6, Cell Immunol., 1991 133(2), 327-341.
Documents associated with European Patent Application EP 02709544, dated Feb. 28, 2014, Preparation for oral roceedings.
Sequence Listing, Reference No. P61909EP20, Jan. 27, 2011, 12 pages.
EPO Acknowledgement of receipt of letter regarding in vivo data, EP Application No. 09075279.1, dated Jun. 13, 2013, one page.
Pelanda et al., A prematurely expressed Ig(kappa) transgene, but not V(kappa)J(kappa) gene segment targeted into the Ig(kappa) locus, can rescue B cell development in lambdaS-deficient mice, Immunity, Sep. 1996, pp. 229-239, vol. 5, No. 3.
Documents associated with European Patent Application EP 02709544, dated Mar. 19. 2014, Bibliographic data of the European patent application.
Documents associated with European Patent Application EP 02709544, dated Mar. 26, 2015, (Electronic) Receipt.
Correspondence from A. Bentham of J A Kemp to the European Patent Office regarding possible dates for Oral Proceedings, EP Patent No. 2147594, Feb. 15, 2016, one page.
Response to communication pursuant Article 94(3) EPC, EP Application No. 09075279.1, dated Sep. 11, 2012, Reference No. P85231Ep00, eleven pages.
Van der Heijden et al., Structural and functional studies on a unique linear neutralizing antigenic site (G5) of the rabies virus glycoprotein, J.Gen. Virol., Aug. 1993, pp. 1539-1545, vol. 74, Issue 8.
Documents associated with European Patent Application EP 02709544, dated Nov. 2, 2015, Advice of delivery.
Japan Patent Office, Official Action, Japan Patent Application No. 2015-097258, dated Mar. 31, 2016, seven pages.
Wilmut et al., "Basic techniques for tansgenesis", AFRC Institute of Animal Physiology and Genetics Research, Journa of Reproduction & Fertility Ltd, 1991, pp. 266-275.
Documents associated with European Patent Application EP 02709544, dated May 2, 2014, Letter accompanying subsequently filed items.
EPO Decision to grant a European patent pursuant to Article 97(1) EPC, EP Application No. 10186063.3, dated Sep. 19, 2013, EPO Form 2006A, 12.07, 2 pages.
McBurney, MW. et al., Evidence for repeat-induced gene silencing in cultured Mammalian cells: inactivation of tandem repeats oftransfected genes, Exp Cell Res., 2002, 274(1), 1-8.
Phelps et al., Expression and Characterization of a Chimeric Bifunclional Antibody with Therapeutic Applications the Journal of Immunology, Aug. 15, 1990, pp. 1200-1204, vol. 145, No. 4.
Documents associated with European Patent Application EP 02709544, dated Feb. 26, 2015, Forwarding of submissions to parties—08.
Documents associated with European Patent Application EP 02709544, dated Feb. 26, 2015, Forwarding of submissons to parties—09.
Documents associated with European Patent Application EP 02709544, dated Feb. 26, 2015, Forwarding of submissions to parties—06.
Houldsworth et al., Comparative Genomic Hybridization: An Overview, American Journal of Pathology, Dec. 1994, pp. 1253-1260, vol. 145. No. 6.
Documents associated with European Patent Application EP 02709544, dated Feb. 26, 2015, Forwarding of submissions to parties—07.
Documents associated with European Patent Application EP 02709544, dated Feb. 26, 2015, Forwarding of submissions to parties—04.
Auxiliary Request 7 with annotations, EP Patent No. 2314629131, Reference No. M70120EPEIN FLZ, May 20, 2016, seven pages.
Documents associated with European Patent Application EP 02709544, dated Feb. 26, 2015, Forwarding of submissions to parties—05.
Documents associated with European Patent Application EP 02709544, dated Feb. 26, 2015, Forwarding of submissions to parties—02.
Documents associated with European Patent Application EP 02709544, dated Feb. 26, 2015, Forwarding of submissions to parties—03.
Gorczyca, W. et al., Detection of DNA strand breaks in individual apoptotic cells by the in situ terminal deoxynucleotidy ransferase and nick translation assays, Cancer Res., 1993, 53(8), 1945-1951.
Documents associated with European Patent Application EP 02709544, dated Feb. 26, 2015, Forwarding of submissions to parties—01.
Sasaki, Yoshiteru et al., "Canonical NF-κB Activity, Dispensable for B Cell Development, Replaces BAFF-Receptor Signals and Promotes B Cell Proliferation upon Activation," Immunity, vol. 24:729-739 (2006).
Li et al., Stable expression of three genes from a tricistronic retroviral vector containing a picornavirus and 9-nt cellular internal ribosome entry site elements, J. Virol. Methods, Feb. 2004, pp. 137-144, vol. 115, Issue 2.
Koopman G, et al., Annexin V for Flow Cytometric Detection of Phosphatidylserine Expression on B Cells Undergoing Apoptosis, The Blood Journal, 1994, pp. 1415-1420.
Patel AK, Boyd, PN., An improved assay for antibody dependent cellular cytotoxicity based on time resolved fluorometry, J Immunol Methods, 1995, 184(1), 29-38.
Hoogenboom, et al., Natural and designer binding sites made by phage display technolgy, Immunol. Today, Aug. 1, 2000, pp. 371-378, vol. 21, Issue 8, Abstract only.
Hamers-Casterman, C. et al., Naturally occurring antibodies devoid of light chains, Nature, 1993, 363(6428), 446-448.
Goyenechea, Beatriz et al., "Cells strongly expressing Igk transgenes show clonal recruitment of hypermutation: a role for both MAR and the enhancers," The EMBO Journal, vol. 16(13):3987-3994 (1997).

(56) References Cited

OTHER PUBLICATIONS

Fine, JS. et al., Interleukin-10 enhances gamma delta T cell development in the murine fetal thymus, Cell Immunol., 1994, 155(1), 111-122.
Carter, Paul, "Bispecific human IgG by design," Journal of Immunological Methods, vol. 248:7-15 (2001).
Morrison, Sherie L., Transfectomas Provide Novel Chimeric Antibodies, Science, Sep. 20, 1985, pp. 1202-1207, vol. 229.
Documents associated with European Patent Application EP 02709544, dated Jul. 16, 2014, Written submission in preparation to_during oral proceedings—4.
Opposition Filed Against European Patent No. 2147594 (European Patent Application No. 09075279.1) in the Name of Merus N.V., Declaration of Professor Anthony Defranco, dated Aug. 24, 2016, 23 pages.
Documents associated with European Patent Application EP 02709544, dated Jul. 16, 2014, Written submission in preparation to_during oral proceedings—3.
Documents associated with European Patent Application EP 02709544, dated Jul. 16, 2014, Written submission in preparation to_during oral proceedings—2.
Documents associated with European Patent Application EP 02709544, dated Mar. 26, 2015, Forwarding of submissions to parties—3.
Documents associated with European Patent Application EP 02709544, dated Mar. 26, 2015, Forwarding of submission to parties—2.
Documents associated with European Patent Application EP 02709544, dated Jan. 28, 2014, Brief communication—Opposition proceedings—1.
Documents associated with European Patent Application EP 02709544, dated Jul. 16, 2014, Written submission in preparation to_during oral proceedings—5.
Auxiliary request 2, EP Application No. 09075279.1, Reference No. P85261EP00, Apr. 23, 2013, three pages.
EPO Request for change of applicant's representation dated Dec. 17, 2015, EP12175544.1.
Dammacco et al., Immunoglobulin secretion by peripheral blood and bone marrow B cells in patients with multiple myeloma. Studies by the reverse haemolytic plaque assay, Clin. Exp. Immunol., Sep. 1984, pp. 743-751, vol. 57, No. 3.
EPO Communication to J A Kemp, Submission in opposition proceedings made following summons to attend oral proceedings, Patent No. EP 2147594, Application No. EP09075279.1, dated Aug. 26, 2016, two pages.
Ghetie, M -A., et al., Homodimerization of tumor-reactive monoclonal antibodies markedly increases their ability to nduce growth arrest or apoptosis of tumor cells, Proc Natl Acad Sci US A, 1997, 94(14), 7509-7514.
Wilson TJ, Kola I., The LoxP/CRE system and genome modification, Methods Mal Biol., 2001, 158, 83-94.
Bell, AC. et al., Insulators and boundaries: versatile regulatory elements in the eukaryotic genome, Science, 2001, 291 (5503), 447-450.
Third Party Observations Under Article 115 EPC Against European Parent Application No. 09075279.1 in the name of Merus B.V., dated Apr. 25, 2012.
Documents associated with European Patent Application EP 02709544, dated Jun. 12, 2013, Notice of opposition—3.
Documents associated with European Patent Application EP 02709544, dated Jun. 12, 2013, Notice of opposition—2.
Documents associated with European Patent Application EP 02709544, dated Jun. 12, 2013, Notice of opposition—1.
Geuijen, Cecile, merus Full length human IgG bispecific antibodies for cancer therapy, May 27, 2013, Merus-RABs and Bispecific Antibodies, pp. 1-33.
Rickert et al., "B lymphocyte-specific, ere-mediated mutagenesis in mice", Nucleic Acids Research, vol. 25, No. 6, 1997, pp. 1317-1318, Oxford University Press.
Documents associated with European Patent Application EP 02709544, dated Nov. 28, 2014, Annex to the communication-opposition.

Reh et al., Gene Targeting by Homologous Recombination, eLS, 11 pages, Apr. 15, 2014, pp. 1-10, vol. 10, No. 2, John Wiley & Sons Ltd.
Letter accompanying subsequently filed items regarding Document concerning representation, EP Application No. 09075279.1, Submitted by C.M. Jansen of V.O., Dec. 17, 2015, one page.
Herring CD., Vector-Hexamer PCR Isolation of All Insert Ends from a YAC Contig of the Mouse Igh Locus, Genome Research, 1998, 8(6):673-81.
Padlan et al., A possible procedure for reducing the immunogenicity of antibody variable domains while preserving heir ligand-binding properties, Mol. Immunol., 1991, pp. 489-498, vol. 28, Abstract only.
Lee, EC. et al; A Highly Efficient *Escherichia coli*-Based Chromosome Engineering System Adapted for Recombinogenic Targeting and Subcloning of BAC DNA, Genomics, 2001, 73(1), 56-65.
Chen et al., Selection and analysis of an optimized antiVEGF antibody: crystal structure of an affinitymatured Fab in complex with antigen, Abstract, Journal of Molecular Biology, Nov. 5, 1999, p. 865-81, vol. 293, No. 4.
Documents associated with European Patent Application EP 02709544, dated Dec. 10, 2014, Advice of delivery.
Documents associated with European Patent Application EP 02709544, dated Jul. 2, 2015, Letter accompanying subsequently filed items.
Matsuda, F. et al, The complete nucleotide sequence of the human immunoglobulin heavy chain variable region locus, J. Exp. Med., 1998, 188 (11), 2151-2162.
Giddings et al., "Transgenic plants as factories for biopharmaceuticals", Institue of Biological Sciences, University of Wales, Nature Biotechnology, vol. 18, Nov. 2000, pp. 1150-1155.
Documents associated with European Patent Application EP 02709544, dated Nov. 28, 2014, Decision revoking the European patent.
Antica, M. et al., Thymic stem cells in mouse bone marrow, Blood, 1994, 84(1), 111-117.
Documents associated with European Patent Application EP 02709544, dated Feb. 10, 2014, (Electronic) Receipt).
Documents associated with European Patent Application EP 02709544, dated Sep. 30, 2016, Reply to an examination report in opposition proceedings.
Canadian Intellectual Property Office, Office Action, Application No. 2729095, dated Nov. 10, 2015, eight pages.
Documents associated with European Patent Application EP 02709544, dated Jun. 20, 2013, Brief communication—Opposition proceedings.
Documents associated with European Patent Application EP 02709544, dated Aug. 22, 2014, (Electronic) Receipt.
EPO Submission in opposition proceedings, Reply of the patent proprietor to the notice(s) of opposition, EP Application No. 10186063.3 and EP Patent No. 2314629, Feb. 24, 2015, two pages.
Hoogenboom et al., Selecting and screening recombinant antibody libraries, Nat. Biotechnol., Sep. 7, 2005, pp. 1105-1116, vol. 23, Abstract only.
EPO Communication regarding Submission in opposition proceedings, Request for extension of time, EP Application No. 09075279.1 and Patent No. 2147594, dated Oct. 16, 2014, two pages.
Hanes, J. et al., Selecting and evolving functional proteins in vitro by ribosome display, Methods Enzymol., 2000, 328, 104-430.
Documents associated with European Patent Application EP 02709544, dated Dec. 23, 2014, Annexes (other than cited documents) regarding appeal procedure—1.
Murphy, Andrew, Declaration filed Against Australian Application No. 2009263082 in the name of Merus B.V., executed Dec. 19, 2014.
Documents associated with European Patent Application EP 02709544, dated Dec. 23, 2014, Annexes (other than cited documents) regarding appeal procedure—2.
Documents associated with European Patent Application EP 02709544, dated Mar. 5, 2014, Bibliographic data of the European patent application.
Main Request with annotations, EP Patent No. 2314629B1, Reference No. M70120EPEIN FLZ, May 20, 2016, five pages.
Arnold et al., Development of B-1 Cells: Segregation of Phosphatidyl Choline-specific B Cells to the B-1 Population Occurs After Immu-

(56) References Cited

OTHER PUBLICATIONS noglobulin Gene Expression, J. Exp. Med., May 1994, pp. 1585-1595, vol. 179, The Rockefeller University Press.
Jakobovits et al., From XenoMouse technology to panitumumab, the first fully human antibody product from transgenic mice, Nature Biotechnology, Oct. 2007, pp. 1134-1143, vol. 25, No. 10.
EPO communication, Maintenance / Change of date / Cancellation of oral proceedings arranged for: Jun. 22, 2016 at 10.00 hrs, EP Application No. 10186063.3 and EP Patent No. 2314629, Feb. 22, 2016, EPO Form 2088 06.14, two pages.
Takahashi et al., Induction of Pluripotent Stem Cells from Mouse Embryonic and Adult Fibroblast Cultures by Defined Factors, Cell, 4 pages, Aug. 25, 2006, pp. 663-676, vol. 126, No. 4, Elsevier, Inc.
Smith, GP. et al., Small binding proteins selected from a combinatorial repertoire of knottins displayed on phage, J Mol Biol., 1998, 27, 277(2), 317-332.
Documents associated with European Patent Application EP 02709544, dated Jul. 16, 2014, Amended claims with annotations—08.
Hengstschlager, Markus et al., "A lambda1 transgene under the control of a heavy chain promoter and enhancer does not undergo somatic hypermutation," Eur. J. Immunol., vol. 24:1649-1656 (1994).
Documents associated with European Patent Application EP 02709544, dated Mar. 9, 2015, Forwarding of submissions to parties—9.
Human rearranged IgK mRNA VJC region, GenBank Accession No. M87478, NCBI, Apr. 13, 2012, one page.
Statement of Professor Ishida submitted in the UK High Court, first witness statement in UK litigation (The High Court of Justice, Chancery Division, Patents Court, Case No. HP-2013-000001/HP-2014-000001 dated Sep. 3, 2015, Report relates to a patent owned by Regeneron Pharmaceuticals, Inc., EP 2264163).
Campbell et al., Sheep cloned by nuclear transfer from a cultured cell line, Nature, Mar. 7, 1996, pp. 64-66, vol. 380, Nature Publishing Group.
Yu et al., A mouse model of Down syndrome trisomic for all human chromosome 21 synthetic regions, Human Molecular Genetics, 12 pages May 12, 2010, pp. 1-12, Oxford University Press.
Nikolic, T. et al, A subtraction of B220(+) cells in murine bone marrow and spleen does not belong to the B cell lineage but has dendritic cell characteristics, Eur J Immunol., 2002, 32(3), 686-692.
Epo Communication to Fritz Lahrlz of Isenbruck Bosl Hoschler LLP, Acknowledgement of receipt of EPO Forms 2310 and 2043, EPApplication No. 09075279.1 and Ep Patent No. 2147594, dated Jan. 19, 2016, EPO Form 2936 08.10, one Jage.
Documents associated with European Patent Application EP 02709544, dated Aug. 3, 2015, Letter relating to Appeal Procedure.
Sharpe, Melanie et al., "Somatic hypermutation of immunoglobulin kappa may depend on sequences 3' of C kappa and occurs on passenger transgenes," The EMBO Journal, vol. 10(8):2139-2145 (1991).
Documents associated with European Patent Application EP 02709544, dated Mar. 9, 2015, Forwarding of submissions to parties—1.
Documents associated with European Patent Application EP 02709544, dated Mar. 9, 2015, Forwarding of submissions to parties—2.
Liu, et al., Trisomy Eight in ES Cells Is a Common Potential Problem in Gene Targeting and Interferes With Germ Line Transmission, Development Dynamics, 7 pages, May 1997, pp. 85-91, vol. 209, No. 1, Wiley Liss, Inc.
EPO communication to Fritz Lahrlz of Isenbruck Bosl Hoschler LLP, Brief Communication regarding letter dated Feb. 16, 2016, EP Application No. 10186063.3 and EP Patent No. 2314629, dated Mar. 7, 2016, EPO Form 2310A 12.07, one page.
Documents associated with European Patent Application EP 02709544, dated Mar. 9, 2015, Forwarding of submissions to parties—3.
EPO communication to Andrew Bentham of J A Kemp, Brief Communication regarding EPO Form 2548 dated Jan. 12, 2016, EP Application No. 10186063.3 and Ep Patent No. 2314629, dated Jan. 12, 2016, EPO Form 29100001.12, two pages.
Concise Description of Relevance in Third Party Submission filed with the U.S. Patent Office on Aug. 29, 2016 in U.S. Appl. No. 15/140,321, 46 pages.

Boren J. et al; A Simple and Efficient Method for Making Site-directed Mutants, Deletions, and Fusions of Large DNA Such as PI and BAG Clones, Genome Res., 1996, 6(11), 1123-30.
Statement of Fact and Arguments in Support of Opposition dated Jul. 15, 2014 for EP 2 314 629 B1.
Klotz et al., Somatic Hypermutation of a Lambda2 Transgene Under the Control of the Lambda Enhancer or the Heavy Chain Intron Enhancer, The Journal of Immunology, 1996, pp. 4458-4463, vol. 157.
Response to Communication pursuant to Rules 70(2) and 70a(2) EPC and reference to Rule 39(1) EPC, EP \pplication No. 10186063. 3, dated Oct. 17, 2011, 16 pages.
Bruggemann et al., Strategies for expressing human antibody repertoires in transgenic mice, Immunology Today, Aug. 1996, pp. 18-35, vol. 17, No. 8.
Chevillard et al., A Three-Megabase Yeast Artificial Chromosome Contig Spanning the C57BL Mouse Igh Locus, The Journal of Immunology, 8 pages, Jun. 1, 2002, pp. 5659-5666 vol. 168, No. 11 The American Association of Immunology.
Documents associated with European Patent Application EP 02709544, dated Jul. 18, 2013, Communication of a notice of opposition and request to file observations.
Documents associated with European Patent Application EP 02709544, dated Oct. 12, 2015, (Electronic) Receipt.
German Translation of claims for EP Application No. 09075279.1, at least as early as Sep. 2, 2013, four pages.
Morrison et al., Chimeric human antibody molecules: mouse antigen-binding domains with human constant region domains, Proc. Natl. Acad. Sci. USA, Nov. 1, 1984, pp. 6851-6855, vol. 81, No. 21.
Zhang Y. et al; DNA cloning by homologous recombination in Escherichia coli, Nat Biotechnol., 2000, 18(12):1314-7.
EPO Acknowledgement of receipt dated Dec. 17, 2015, EP12175544. 1.
Gerstein et al., Isotype Switching of an Immunoglobulin Heavy Chain Transgene Occurs by DNA Recombination between Different Chromosomes, Cell, Nov. 2, 1990, pp. 537-548, vol. 63.
Bruggemann et al., The Immunogenicity of Chimeric Antibodies, J Exp. Med., Dec. 1, 1989, pp. 2153-2157, vol. 170, downloaded from jem.rupress.org on Jul. 11, 2014.
Documents associated with European Patent Application EP 02709544, dated Nov. 28, 2014, Processing of an appeal.
EPO Communication, Transmission of the certificate for a European patent pursuant to Rule 74 EPC, EP Application No. 09075279.1, dated Nov. 13, 2013, EPO Form 2047 12.07, one page.
Queen et al., A humanized antibody that binds to the interleukin 2 receptor, Proc. Natl. Acad. Sci. U.S.A., Dec. 1, 1989, pp. 10029-10033, vol. 86, No. 24.
Documents associated with European Patent Application EP 02709544, dated Oct. 11, 2013, Letter accompanying subsequently filed items.
Third Party Observation for Application No. EP20090075279, 16 pages, Jun. 14, 2013.
EPO Acknowledgement of receipt of claim requests, EP Application No. 09075279.1, dated Apr. 23, 2013, two pages.
Defrancesco et al., Big Pharma vies for mice, Nature Biotechnology, 25/6, pp. 613-14, Jun. 2007.
Decision of UK High Court of Justice (REGN against Kymab Limited; Novo Nordisk) dated Feb. 2, 2016.
Bitter et al., Expression and Secretion Vectors for Yeast, in Methods in Enzymology, Ed. Wu & Grossman, Acad. Press, N.Y. 153:516 544 (1987) Abstract only.
Gorczyca, W. et al., Induction of DNA strand breaks associated with apoptosis during treatment of leukemias, Leukemia, 1993, 7(5), 659-670.
Thotakura, NR., Blithe, DL., Glycoprotein hormones: glycobiology of gonadotrophins, thyrotrophin and free alpha subunit, Glycobiology, 1995, 5(1), 3-10.
Zhu el. al., Inhibition of Tumor Growth and Metastasis by Targeting Tumor-Associated Angiogenesis with Antagonists to the Receptors of Vascular Endothelial Growth Factor, Invest. New Drugs, Aug. 1999, pp. 195-212, vol. 17, ssue 3, Abstract only.
Documents associated with European Patent Application EP 02709544, dated Sep. 21, 2015, Letter dealing with oral proceedings during the appeal procedure.

(56) References Cited

OTHER PUBLICATIONS

Epo communication to Fritz Lahrtz of Isenbruck Bosl Hoschler LLP, Communication of amended entries concerning the representative (R. 143(1)(h) EPC), EP Application No. 09075279.1 and EP Patent No. 2147594, dated Jan. 12, 2016, EPO Form 2648 08.13, one page.
Bruggemann, M. et al, Human antibody production in transgenic mice: expression from 100 kb of the human IgH locus, EurJ Immunol., 1991, 21(5), 1323-6.
EPO Communication to J A Kemp, Acknowledgement of receipt of EPO Forms 2310 and 2043, EP Application No. 10186063.3 and EP Patent No. 2314629, dated Nov. 19, 2015, EPO Form 2936 08.10, one page.
Hynes, RO., Cell adhesion: old and new questions, Trends Cell Biol., 1999, 9(12), M33-37.
Murakami, T. et al, Splenic CD19-CD35+B220+ cells function as an inducer of follicular dendritic cell network ormation, Blood, 2007,110(4), 1215-1224.
Pollock et al., "Transgenic milk as a method for the production of recombinant antibodies", Elsevier, Journal of Immunological Methods, 231 (1999), pp. 147-157.
Auxiliary Request 3, EP Patent No. 2314629B1, Reference No. M70120EPEIN FLZ, May 20, 2016, ffive pages.
Klohn et al., "IBC's 23rd Annual Antibody Engineering, 1oth Annual Antibody Therapeutics International Conferences and the 2012 Annual Meeting of The Antibody Society", mAbs, vol. 5, Issue 2, Dec. 3-6, 2012, pp. 178-201, andes Bioscience.
Auxiliary request 4, EP Application No. 09075279.1, Reference No. P85261EP00, Apr. 23, 2013, three pages.
Third Party Observations Against European Parent Application No. 09075279.1 in the name of Merus BV, at least as early as Sep. 5, 2013, four pages.
Schmitz et al., Phage Display: A Molecular Tool for the Generation of Antibodies—A Review, Placenta, 2000, pp. S106-S112, Supplement A, Trophoblast Research, vol. 14.
EPO Communication regarding Preliminary, Non-binding Opinion of the Opposition Division, EP Application No. 09075279.1, dated Jan. 19, 2016, EPO Form 2906 01.91TRI, 11 pages.
Letter accompanying subsequently filed items regarding examination, EP Application No. 09075279.1, dated Jun. 13, 2013, one page.
Third Party Observation for application No. EP20090075279, Anonymous, at least as early as Sep. 5, 2013, seven pages.
Muyrers JP. et al, ET-doning: think recombination first, Genetic Engineering, 2000, 22:77-98.
Burger et al., An integrated strategy for the process development of a recombinant antibody-cytokine fusion protein expressed in BHK cells, Appl. Microbial. Biotechnol., Sep. 1999, pp. 345-53, vol. 52, Issue 3, Abstract only.
Documents associated with European Patent Application EP 02709544, dated Sep. 11, 2014, (Electronic) Receipt.
David Power of J A Kemp communication to EPO, Executed Acknowledgement, EP Application No. 09075279.1 and EP Patent No. 2147594, dated Mar. 22, 2016, EPO Form 2936 08.10, one page.
Documents associated with European Patent Application EP 02709544, dated Mar. 19, 2015, Letter relating to Appeal Procedure.
Brief Communication from European Patent Office to JA Kemp regarding EP 10186063.3 dated Jun. 7, 2016.
Documents associated with European Patent Application EP 02709544, dated Aug. 27 2015, Advice of delivery.
Wallace et al., Manipulating the mouse genome to engineer precise functional syntenic replacements with human sequence, Cell, 12 pages, Jan. 12, 2007, pp. 197-209, vol. 128, No. 1, Elsevier Inc.
EPO Acknowledgement of receipt, request, Application No. 10186063. 3, dated Dec. 17, 2015, one page.
Cheung et al., A recombinant human Fab expressed in *Escherichia coli* neutralizes rabies virus, J.Virol., Nov. 1992, pp. 6714-6720, vol. 66, No. 11.
Refund of Fees, EP Application No. 10186063.3, dated Jun. 4, 2011, EPO Form 2907, 12.07, 1 page.

Documents associated with European Patent Application EP 02709544, dated Aug. 12, 2014, (Electronic) Receipt.
(Page 65) EPO Brief Communication regarding the Opposition against EP Application 10186063.3, dated May 26, 2016, 1 page.
Third Party Observation for Application No. 2009263082, 25 pages, dated Oct. 21, 2013.
Documents associated with European Patent Application EP 02709544, dated Feb. 28, 2014, Acknowledgement of a document—1.
McGinnes, K., B-lineage colonies from normal, human bone marrow are initiated by B cells and their progenitors, Blood, 1991, 77(5), 961-970.
Epo Communication pursuant to Rule 114(2) EPC, EP Application No. 09075279.1, dated Oct. 10, 2013, EPO Form 2022 12.07, one page.
(Pages 299-301) EPO Communication regarding important information concerning oral proceedings, requesting information by Apr. 20, 2016, EPO Form 2043 02.09, three pages (previously submitted).
De Kruif et al., Human Immunoglobulin Repertoires against Tetanus Toxoid Contain a Large and Diverse Fraction of High-Affinity Promiscuous VH Genes, J. Mol. Biol., 2009, pp. 548-58, vol. 387.
Documents associated with European Patent Application EP 02709544, dated Feb. 26, 2014, 1002—Designation of nventor—2.
Olpposition Filed Against European Patent No. EP 2 314 629 B1 (European Patent Application No. 10186063.3) in the Name of Merus B.V., Declaration of Dr. Joel Martin, May 18, 2016, 13 pages.
Documents associated with European Patent Application EP 02709544, dated Apr. 22, 2014, Notification concerning he date of oral proceedings—1.
Documents associated with European Patent Application EP 02709544, dated Apr. 22, 2014, Notification concerning he date of oral proceedings—2.
Documents associated with European Patent Application EP 02709544, dated Jul. 21, 2014, Brief communicationopposition proceedings—3.
EPO Communication regarding important information concerning oral proceedings, at least as early as Mar. 22, 2016, EPO Form 2043 02.09, three pages.
Hoogenboom et al., By-passing immunisation. Human antibodies from synthetic repertoires of germline VH gene segments rearranged in vitro, J Mol Biol., Sep. 20, 1992, pp. 381-388, vol. 227, Issue 2, Abstract only.
Documents associated with European Patent Application EP 02709544, dated Feb. 28, 2014, Acknowledgement of a document—3.
Documents associated with European Patent Application EP 02709544, dated Feb. 28, 2014, Acknowledgement of a document—2.
Schoonjans et al., A new model for intermediate molecular weight recombinant bispecific and trispecific antibodies by efficient heterodimerization of single chain variable domains through fusion to a Fab-chain, Biomolecular Engineering 17 (2001) 193-202.
Seibler et al., Rapid generation of inducible mouse mutants, Nucleic Acids Res., Feb. 15 2003, e12, vol. 31, No. 4.
Documents associated with European Patent Application EP 02709544, dated Jul. 2, 2015, (Electronic) Receipt.
EPO Communication regarding The oral proceedings dated Jun. 22, 2016, EP Application No. 10186063.3, EPO Form 2341 09.14, one page.
Davies, J Riechmann, L., Antibody VH domains as small recognition units, Biotechnology (NY), 1995, 13(5), 475-479.
Documents associated with European Patent Application EP 02709544, dated Mar. 26, 2015, Forwarding of submissions to parties—1.
EPO Communication, Summons to V.O. to attend oral proceedings pursant to Rule 115(1) EPC, EP Application No. 10186063.3 and EP Patent No. 2314629, Nov. 19, 2015, EPO Form 2310 12.14, one page.
Fendly et al., Characterization of Murine Monoclonal Antibodies Reactive to Either the Human Epidermal Growth Fractor Receptor or HER2/neu Gene Product, Cancer Research, Mar. 1, 1990, pp. 1550-1558, vol. 50.
Documents associated with European Patent Application EP 02709544, dated Feb. 26, 2015, Forwarding of submissions to parties—11.
Documents associated with European Patent Application EP 02709544, dated Aug. 20, 2014, 1003—Authorisation of epresentative.

(56) References Cited

OTHER PUBLICATIONS

Documents associated with European Patent Application EP 02709544, dated Feb. 26, 2015, Forwarding of submissions to parties—12.

Porgador, A. et al., Bone marrow-generated dendritic cells pulsed with a class I-restricted peptide are potent inducers of cytotoxic T lymphocytes, J Exp Med., 1995, 182(1), 255-260.

Documents associated with European Patent Application EP 02709544, dated Feb. 26, 2015, Forwarding of submissions to parties—10.

EPO Submission in opposition proceedings, Acknowledgement of Receipt filed by David Power of J A Kemp, EP Application No. 10186063.3 and EP Patent No. 2314629, Nov. 20, 2015, two pages.

Jones et al., Replacing the complementarity-determining regions in a human antibody with those from a mouse, Nature, May 29, 1986, pp. 522-525, vol. 321, Abstract only.

Conrath K.E. et al., Emergence and evolution of functional heavy-chain antibodies in Camelidae.Development & Comparative Immunology., 2003, 27(2), 87-103.

Documents associated with European Patent Application EP 02709544, dated Dec. 23, 2014, (Electronic) Receipt.

EPO Annexes in respect of a request fora change dated May 30, 2016, EP12175544.1.

Response to Communication pursuant to Article 94(3) EPC, EP Application No. 10186063.3, dated Dec. 21, 2011, 13 pages.

Hengstschlager et al., A lambda 1 trans gene under the control of a heavy chain promoter and enhancer does not undergo somatic hypennutation, Eur. J. Immunol. 1994, pp. 1649-56, vol. 24.

Hawkins, RE. et al., Selection of phage antibodies by binding affinity. Mimicking affinity maturation, J Mal Biol., 1992, 226(3), 889-896.

Documents associated with European Patent Application EP 02709544, dated Nov. 28, 2014, Internal form—opposition addressees—1.

Zahn Zabel et al., Development of stable cell lines for production or regulated expression using matrix attachment regions, J. Biotechnology, Apr. 27, 2001, pp. 29-42, vol. 87, Issue 1.

Taylor, Lisa D. et al., "A transgenic mouse that expresses a diversity of human sequence heavy and light chain immunoglobulins," Nucleic Acids Research, vol. 20(23):6287-6295 (1992).

Documents associated with European Patent Application EP 02709544, dated Aug. 31, 2015, Forwarding of submissions to parties—3.

Documents associated with European Patent Application EP 02709544, dated Aug. 31, 2015, Forwarding of submissions to parties—1.

Documents associated with European Patent Application EP 02709544, dated Aug. 31, 2015, Forwarding of submissions to parties—2.

Documents associated with European Patent Application EP 02709544, dated Feb. 5, 2015, Forwarding of submissions to parties—2.

Documents associated with European Patent Application EP 02709544, dated Feb. 5, 2015, Forwarding of submissions to parties—1.

Rajewsky et al., Conditional gene targeting, J Clin Invest, Aug. 1, 1996, pp. 600-603, vol. 98, No. 3.

Smith, EJ. et al., A novel, native-formal bispecific antibody triggering T-cell killing of B-cells is robustly active in mouse umor models and cynomolgus monkeysSci Rep., 2015, 5: 17943.

Marasco, WA., Intrabodies as antiviral agents, Curr Top Microbiol Immunol., 2001, 260, 247-270.

Documents associated with European Patent Application EP 02709544, dated Sep. 16, 2015, Cited document during appeal procedure.

Documents associated with European Patent Application EP 02709544, dated Apr. 4, 2014, Notice of opposition.

Documents associated with European Patent Application EP 02709544, dated Apr. 22, 2014, Notification concerning the date of oral proceedings—3.

Roberts and Szostak, RNA-peptide fusions for the in vitro selection of peptides and proteins, Proc. Natl. Acad. Sci. U.S.A., Nov. 1997, pp. 12297-12302, vol. 94.

EPO Acknowledgement of receipt of request to change date of oral proceedings, EP Application No. 09075279.1 and U.S. Pat. No. 2147594, dated Jan. 29, 2016, one page.

Documents associated with European Patent Application EP 02709544, dated Jan. 22, 2015, Letter accompanying subsequently filed items—2.

Gerstner et al., Sequence Plasticity in the Antigen-binding Site of a Therapeutic Anti-HER2 Antibody, J. Mal. Biol., Aug. 30, 2002, pp. 851-862, vol. 321, issue 5, Elsevier, Abstract only.

Documents associated with European Patent Application EP 02709544, dated Jan. 22, 2015, Letter accompanying subsequently filed items—1.

Letter accompanying subsequently filed items regarding German and French translation of the claims, EP Application No. 09075279.1, Sep. 2, 2013, two pages.

Cvetkovic et al., Appropriate Tissue- and Cell-specific Expression of a Single Copy Human Angiotensinogen Transgene Specifically Targeted Upstream of the HPRT Locus by Homologous Recombination, The Journal of Biological Chemistry, Jan. 14, 2000, pp. 1073-1078, vol. 275, No. 2, The American Society for Biochemistry and Molecular Biology, Inc.

Rottgen, P., Collins, J_ et al., A human pancreatic secretory trypsin inhibitor presenting a hypervariable highly Constrained epitope via monovalent phagemid display, Gene, 1995, 164(2), 243-250.

Rojas et al. Phage antibody fragments library combining a single human light chain variable region with immune mouse heavy chain variable regions, Journal of Biotechnology, 2002, pp. 287-98, vol. 94.

Champion et al., The development of monoclonal human rabies virumeutralizing antibodies as a substitute for pooled human immune globulin in the prophylactic treatment ofabies virus exposure, Abstract, Journal of Immunological Methods, Feb. 2000, pp. 81-90, vol. 235, No. 1-2, Elsevier Science Publishers B.V., Amsterdam, NL.

Auxiliary request 5, EP Application No. 09075279.1, Reference No. P85261EP00, Apr. 23, 2013, three pages.

Documents associated with European Patent Application EP 02709544, dated Nov. 28, 2014, Decision of the opposition Division and instruction.

Documents associated with European Patent Application EP 02709544, dated Oct. 3, 2016, (Electronic) Receipt.

Broach; JR. et al., Transformation in yeast: development of a hybrid cloning vector and isolation of the CAN1 gene, Gene, 1979, 8(1), 121-133.

Kingzette et al., Trans-chromosomal recombination within the Ig heavy chain switch region in B lymphocytes, mmunology, Proc. Natl. Acad. Sci, USA, Sep. 1998, pp. 11840-11845, vol. 95.

Appel RD, et al., A new generation of information retrieval tools for biologists: the example of the ExPASy WWW server, 1994, Trends Biochem. Sci., 19, 258-260.

Cherrington et al., New paradigms for the treatment of cancer: The role of anli-angiogenesis agents, Adv. Cancer. Res., 2000, pp. 1-38, vol. 79, Abstract only.

Documents associated with European Patent Application EP 02709544, dated Sep. 30, 2016, Clean description pages in the opposition procedure.

Spiridon CI,et al., Tartgeting multiple Her-2 epitopes with monoclonal antibodies results in improved antigrowth activity of a human breast cancer cell line in vitro and in vivo, Clin Cancer Res., 2002, 8(6), 1720-1730.

Opposition Summary, Australian Application No. 2009263082, May 18, 2015, 11 pages.

(Page 62) EPO Payment of fees and expenses for EP Application 10186063.3 dated May 27, 2016, 1 page.

Documents associated with European Patent Application EP 02709544, dated Feb. 10, 2014, Letter regarding the Jpposition procedure (no time limit).

Scapini et al., Myeloid cells, BAFF, and IFN-gamma establish an inflammatory loop that exacerbates autoimmunity in yn-deficient mice, JEM, Jul. 12, 2010, pp. 1757-1773, vol. 207, No. 8.

Dietrich et al, A comprehensive genetic map of the mouse genome, Nature, 1996, vol. 380, pp. 149-152.

Sambrook, Fritsch and Maniatis, Molecular Cloning: A Laboratory Manual, 2nd edition, 1989.

Mejia et al., "The Assembly of Large BACs by in Vivo Recombination," Genomics (2000) 70(2):165-70.

Yu, D. et al; An efficient recombination system for chromosome engineering in *Escherichia coli*, Proc Natl Acad Sci U S A., 2000, 97(11), 5978-83.

(56) References Cited

OTHER PUBLICATIONS

Documents associated with European Patent Application EP02709544, dated Jul. 16, 2014, Letter regarding the Jpposition procedure (no time limit)—4.
D'Eustachio, P. and Riblet, R, Mouse Chromosome 12, Mammalian Genome 8, 1998, S241-S257.
Documents associated with European Patent Application EP02709544, dated Apr. 24, 2014, Summons to attend oral proceedings—4.
Documents associated with European Patent Application EP02709544, dated Apr. 24, 2014, Summons to attend oral proceedings—3.
Correspondence from Dr. Fritz Lahrtz of Isenbruck Bosl Forschler LLP to the European Patent Office regarding change of correspondence, EP Application No. 10186063.3 and EP Patent No. 2314629, Jan. 8, 2016, one page.
Documents associated with European Patent Application EP02709544, dated Apr. 24, 2014, Summons to attend oral proceedings—2.
Documents associated with European Patent Application EP02709544, dated Apr. 24, 2014, Summons to attend oral proceedings—1.
Documents associated with European Patent Application EP02709544, dated Nov. 4, 2015, Letter dealing with oral proceedings during the appeal procedure—1.
Documents associated with European Patent Application EP02709544, dated Nov. 4, 2015, Letter dealing with oral proceedings during the appeal procedure—2.
Documents associated with European Patent Application EP02709544, dated Sep. 2, 2014, (Electronic) Receipt—1.
Documents associated with European Patent Application EP02709544, dated Sep. 2, 2014, (Electronic) Receipt—2.
Documents associated with European Patent Application EP02709544, dated Nov. 28, 2014, Provision of the minutes—opposition procedure.
Ezzell, C., Magic bullets fly again, Sci Am., 2001, 285(4), 34-41.
Guery, JC, Adorini, L., Dendritic cells are the most efficient in presenting endogenous naturally processed self-epitopeio class II-restricted T cells, J Immunol., 1995, 154(2), 536-544.
Wigler, M. et al.,Biochemical transfer of single-copy eucaryotic genes using total cellular DNA as donor, Cell, 1978, 14 (3), 725-731.
Third Party Observations for Application No. 09075279.1, 8 pages, May 16, 2013.
Corcoran et al., The interleukin-7 receptor a chain transmits distinct signals for proliferation and differentiation during a lymphopoiesis, The EMBO Journal, 9 pages, Apr. 15, 1996, pp. 1924-1932, vol. 15, No. 8, Oxford University Press.
Kasprzyk et al., Therapy of an Animal Model of Human Gastric Cancer Using a Combination of Anti-erbB-2 Monoclonal Antibodies, Cancer Research, May 15, 1992, pp. 2271-2776, vol. 52.
Popov, Andrei V. et al., "A Human Immunoglobulin lambda Locus Is Similarly Well Expressed in Mice and Humans," J. Exp. Med., vol. 189(10):1611-1619 (1999).
Norderhaug et al., Balanced expression of single subunits in a multisubunit proteins, achieved by cell fusion of individual transfectants, European Journal of Biochemistry, 2002, pp. 3205-3210, vol. 269.
Kang et al., Linkage of recognition and replication functions by assembling combinatorial antibody Fab libraries along phage surfaces, Proc. Natl. Acad. Sci., May 1991, pp. 4363-4366, vol. 88.
EPO Communication to Martin Hatzmann of Vereenigde, Acknowledgement of receipt of the document specified above, EP Application No. 09075279.1, Mar. 6, 2013, EPO Form 2936 08.10, one page.
Skerra, Arne, 'Anticalins': A New Class of Engineered Ligand-Binding Proteins with Antibody-Like Properties, 2001, Reviews in Molecular Biotechnology, pp. 257-275, vol. 74, Elsevier.
EPO Communication pursuant to Rules 70(2) and 70a(2) EPC and reference to Rule 39(1) EPC, EP Application No. 10186063.3, May 2, 2011, EPO Form 1082, 04.10, 2 pages.
Documents associated with European Patent Application EP02709544, dated Oct. 22, 2015, receipt of Electronic Filings with U.S. District Court, Southern District of New York in Case No. 1:14-cv-1650-KBF, includes duration of tansmission.
EPO Communication of notices of opposition (R. 79(1) EPC), EP Application No. 09075279.1 and Patent No. 2147594 Sep. 25, 2014, EPO Form 2317A 12.07, one page.
Chesnul, J et al., Selective isolation of transiently transfecled cells from a mammalian cell population with vectors expressing a membrane anchored single-chain antibody, Journal of Immunological Methods, 1996 pp. 17-27.
Kwaks et al., Identification of anti-repressor elements that confer high and stable protein production in mammalian cells, Nature Biotechnology, 2003, pp. 553-558, vol. 269.
Advice of receipt to Fritz Lahrtz of Isenbruck Bosl Hoschler LLP, Registration No. of item RD118911257NL, May 25, 2016, one page.
Documents associated with European Patent Application EP02709544, dated Jul. 18, 2013, Notice of further oppositions to opponent(s)—1.
Documents associated with European Patent Application EP02709544, dated Jul. 18, 2013, Notice of further oppositions to opponent(s)—2.
Documents associated with European Patent Application EP02709544, dated Feb. 12, 2014, Letter regarding the opposition procedure (no time limit).
Documents associated with European Patent Application EP02709544, dated Sep. 30, 2016, Amended description with annotations.
EPO Acknowledgement of receipt of letter regarding reply patentee's response to opposition, EP Application No. 09075279.1 and Patent No. 2147594, date of receipt Aug. 20, 2015, one page.
Response to Communication pursuant to Article 94(3) EPC, EP Application No. 10186063.3, Jul. 19, 2012, 45 pages.
Letter accompanying subsequently filed items regarding translations of claims, EP Application No. 10186063.3, Sep. 6, 2013, 13 pages.
Letter accompanying subsequently filed items regarding acknowledgement, EP Application No. 09075279.1, Submitted by David Power of J A Kemp, Apr. 12, 2016, one page.
Jakobovits et al., Germ-line transmission and expression of a human-derived yeast artificial chromosome, Nature, Mar. 18, 1993, pp. 255-258, vol. 362, Abstract only.
Shen et al., A General Method to Modify BACs to Generate Large Recombinant DNA Fragments, Molecular Biotechnology, 6 pages, Nov. 3, 2005, pp. 181-186, vol. 31, No. 3, Humana Press Inc.
Documents associated with European Patent Application EP02709544, dated Oct. 22, 2015, Letter dealing with oral proceedings during the appeal procedure.
EPO Communication pursuant to Rule 114(2) EPC, EP Application No. 09075279.1 and Patent No. 2147594, Nov. 5, 2012, EPO Form 2022 12.07, one page.
Auxiliary Request 14, EP Patent No. 2314629B1, Reference No. M70120EPEIN FLZ, May 20, 2016, ffive pages.
Heintges et al.. Cloning, Bacterial Expression and Sequencing of Human Antibody Fragments Against Hepatitis C Virus NS3 by Phage Display of a Combinatorial Phagernid Library, Hepatology, p. 497, vol. 28, No. 4, 1998.
EPO Communication, Summons to Fritz Lahrtz of Isenbruck Bosl Hoschler LLP to attend oral proceedings pursuant to Rule 115(1) EPC, EPApplication No. 09075279.1 and EP Patent No. 2147594, Jan. 19, 2016, EPO Form 2310 12.14, one page.
Kawasaki, K. et al; Evolutionary dynamics of the human immunoglobulin k locus and the germ line repertoire of the Vk Jenes, Eur J Immunol, 2001, 31(4):1017-28.
Huls, G., et al., Antitumor Immune Effector Mechanisms Recruited by Phage Display-derived Fully Human IgG1 and IgA1 Monoclonal Antibodies, Cancer Research, Nov. 15, 1999, pp. 5778-5784, vol. 59.
Kenter et al., Three-dimensional architecture of the IgH locus facilitates class switch recombination, Annals of the New York Academy of Sciences, 2012, pp. 86-94.
EP Priority Document of International Application No. PCT/EP2003/07690, "Recombianant Production of Mixtures of Antibodies", Oct. 25, 2010, 186 pages.
EPO Acknowledgement of receipt—Opposition proceedings in relation to EP09075279.1 dated Aug. 26, 2016, two pages.

(56) References Cited

OTHER PUBLICATIONS

Designation of inventor Ton Logtenberg dated Jul. 9, 2012, User Reference: P85261EP10, EP12175544.
Documents associated with European Patent Application EP02709544, dated May 30, 2016, Request for change of name—applicant.
Auxiliary request 1, EP Application No. 09075279.1, Reference No. P85261EP00, Apr. 23, 2013, three pages.
Description of relevance of Third Party Submission in U.S. Appl. No. 15/090,505 dated Feb. 24, 2017.
Osoegawa K. et al., Bacterial Artificial Chromosome Libraries for Mouse Sequencing and Functional Analysis, GenomE Research, 2000, 10(1):116-28.
Van Etten, WJ. et al; Radiation hybrid map of the mouse genome, Nature Genetics, 1999, 22(4):384-7.
Shimizu et al., Trans-Splicing as a Possible Molecular Mechanism for the Multiple Isotype Expression of the immunoglobulin Gene, J Exp. Med. Jun. 1991, pp. 1385-1393, vol. 173.
Ma et al., Human antibody expression in transgenic rats: Comparison of chimeric IgH lock with human V eta and J eta out bearing different rat C-gene regions, J Immunol. Methods (2013), http://dx.doi.org/10.1016/j.jim.2013.10.007.
Campbell et al., "Sheep cloned by nuclear transfer from a cultured cell line", Roslin Institute (Edinburgh), Letters to Nature, vol. 380, Mar. 7, 1996, pp. 64-66.
Call et al., A Cre-lox recombination system for the targeted integration of circular yeast artificial chromosomes into embryonic stem cells, Hum Mol Genet., 2000, 9(12), 1745-51.
Auxiliary Request 8 with annotations, EP Patent No. 2314629B1, Reference No. M70120EPEIN FLZ, May 20, 2016, seven pages.
(Pages 2-3) EPO Document regarding Patent Application No. 10 186 063.3 dated Jul. 27, 2016, Communication pursuant to Article 101(1) and Rule 81(2) to (3) EPC 2 pages.
Folkman, Angiogenesis in cancer, vascular, rheumatoid and other disease, J. Nat. Med., 1995, pp. 27-31, vol. 1, Abslract only.
PCT International Search Report, PCT/NL2004/000386 dated Nov. 23, 2004.
Documents associated with European Patent Application EP02709544, dated Dec. 23, 2014, Letter accompanying subsequently filed items.
Documents associated with European Patent Application EP02709544, dated Jun. 12, 2013, Payment of fees and costs.
Documents associated with European Patent Application EP02709544, dated Apr. 10, 2014, Brief communication—Opposition proceedings—2.
Karu et al., Recombinant Antibody Technology, ILAR Journal, 10 pages, 1995, pp. 132-141, vol. 37, No. 3, Oxford Journals.
Torres, Raul M. et al., Laboratory Protocols for Conditional Gene Targeting, Oxford University Press, Oxford, Chapters 10-11, pp. 42-53 (1997).
Documents associated with European Patent Application EP02709544, dated Jan. 28, 2014, Amended claims with annotations—1.
Tanaka et al., De novo production of diverse intracellular antibody libraries, Nucleic Acids Research, 2003, e23, pp. 1-10, vol. 31, No. 5.
Documents associated with European Patent Application EP02709544, dated May 30, 2016, Payment of fees and costs.
Second Declaration of Craig Bassing (Bassing II), originally submitted for the EP1360287 Opposition, dated Sep. 2, 2014.
Documents associated with European Patent Application EP02709544, dated Aug. 20, 2014, Letter accompanying subsequently filed items.
Dinnyes et al., Somatic Cell Nuclear Transfer: Recent Progress and Challenges, Cloning and Stem Cells, Jul. 5, 2004, vol. 4, Issue 1.
Documents associated with European Patent Application EP02709544, dated Jul. 6, 2015, Reply to appeal.
Documents associated with European Patent Application EP02709544, dated Oct. 3, 2016, Letter accompanying subsequently filed items.
Wright A, Morrison SL., Effect of glycosylation on antibody function: implications for genetic engineering, Trends Biotechnol., Jan. 1997;15(1):26-32.
Peeters et al., Production of antibodies and antibody fragments in plants, Vaccine, Mar. 21, 2001, pp. 2756-2761, vol. 19, Issues 17-19, Elsevier.
Vajdos et al., Comprehensive Functional Maps of the Antigen-binding Site of an Anti-ErbB2 Antibody Obtained with Shotgun Scanning Mutagenesis, J Mol. Biol., Jul. 5, 2002, pp. 415-428, vol. 320, issue 2, Elsevier.
Kwaks et al., Employing epigenetics to augment the expression of therapeutic proteins in mammalian cells, Trends in Biotechnology, Mar. 1, 2006, pp. 137-142, vol. 24, No. 3, Elsevier Publications, Cambridge, GB.
Documents associated with European Patent Application EP02709544, dated Mar. 18, 2016, Advice of delivery.
Green et al., Regulation of B Cell Development by Variable Gene Complexity in Mice Reconstituted with Human immunoglobulin Yeast Artificial Chromosomes, J Exp. Med. Aug. 3, 1998, pp. 483-495, vol. 188, Downloaded from , vww.jem.org on Feb. 22, 2007.
Bagchi et al., CHD5 Is a Tumor Supp.ressor at Human 1p36, Cell, 17 pages,Feb. 9, 2007, pp. 459-475, vol. 128, No. 3, Elsevier Inc.
Lefranc, MP., Nomenclature of the human immunoglobulin lambda (IGL) genes, Exp Clin Immunogenet, 2001, 184):242-54.
Documents associated with European Patent Application EP02709544, dated Sep. 18, 2014, Brief communication—Opposition proceedings—1.
Letter of Protest filed by Regeneron against U.S. Appl. No. 15/158,543 on Oct. 14, 2016.
Documents associated with European Patent Application EP02709544, dated Sep. 18, 2014, Brief communication—Opposition proceedings—2.
McMurry et al., Enhancer Control of Local Accessibility to V(D)J Recombinase, Mulecular and Cellular Biology, Aug. 1997, pp. 4553-4561, vol. 17, No. 8.
Documents associated with European Patent Application EP02709544, dated Sep. 18, 2014, Brief communication—Opposition proceedings—3.
Schnieke et al., Human Factor IX Transgenic Sheep Produced by Transfer of Nuclei from Transfected Fetal Fibroblasts, Science, Dec. 19, 1997, pp. 2130-2133, vol. 278, Issue 5346.
Documents associated with European Patent Application EP02709544, dated Sep. 18, 2014, Brief communication—Opposition proceedings—4.
EPO Acknowledgement of receipt of letter regarding reply to opposition, EP Application No. 09075279.1 and Patent No. 2147594, date of receipt Apr. 2, 2015, one page.
Page 337) EPO Communication of a notice of opposition EP Application No. 10186063.3 and EP Patent No. 2314629 Jul. 21, 2014, EPO Form 2316, one page.
Lindhofer et al., Preferential Species-Restricted Heavy/Light Chain Pairing in Rat/Mouse Quadromas, Journal of Immunology, 1995, pp. 219-225, vol. 155.
Sirac et al., "Toward Understanding Renal Fanconi Syndrome: Step by Step Advances through Experimental Models", Contributions to Nephrology, Experimental Models of Renal Fanconi Syndrome, vol. 169, 2011, pp. 247-261.
Vagner, S., et al, Alternative translation of human fibroblast growth factor 2 mRNA occurs by internal entry of ribosomes, Mal Cell Biol., 1995, 15(1), 35-44.
Documents associated with European Patent Application EP02709544, dated Oct. 13, 2015, Letter dealing with oral proceedings during the appeal procedure.
Documents associated with European Patent Application EP02709544, dated Sep. 18, 2014, Brief communication—Opposition proceedings—5.
Roschenthaler, F. et al., The 5' part of the mouse immunoglobulin kappa locus, Eur J Immunol., 1999, 29(7), 2065-71.
Documents associated with European Patent Application EP02709544, dated Sep. 18, 2014, Brief communication—Opposition proceedings—6.
ECACC deposit, Deposit Ref. 96022940 dated Feb. 29, 1996.
Lonberg, N., Fully human antibodies from transgenic mouse and phage display platforms, Curr Opin Immunol, 2008, 20(4), pp. 450-459.

(56) References Cited

OTHER PUBLICATIONS

Sidhu et al., Phage display for selection of novel binding peptides, Methods Enzymol., 2000 328:333 363.
Lonberg, N., Human Monoclonal Antibodies from Transgenic Mice, Handb Exp Pharmacol., 2008, (181):69-97.
Bradley et al., Embryonic stem cells: proliferation and differentiation, Cell Biology, 6 pages, 1990, pp. 1013-1017, Current Biology Ltd.
EP, Annex to TPO against EP2627773, Jun. 16, 2016, 3 pages.
Desmet et al., Anchor profiles of HLA-specific peptides: Analysis by a novel affinity scoring method and experimental validation, Proteins, Jan. 1, 2005, pp. 53-69, vol. 58, Abstract only.
Strelkauskas et al., Human Monoclonal Antibody: 2. Simultaneous Expression of IgG and IgM with Similar Binding Specificities by a Human Hybrid Clone, Hybridoma, 1987, pp. 479-487, vol. 6, No. 5, Mary Ann Liebert, Inc., Publishers.
In The High Court of Justice, Chancery Division, Patents Court, Case No. HP-2013-000001/HP-2014-000001 dated Nov. 3, 2015, Second Expert Report of Professor Hiddie L Ploegh, Report relates to patents owned by Regeneron Pharmaceuticals, Inc., EP 1 360 287 and 2 264 163.
Frenken, LG. et al., Isolation of antigen specific llama VHH antibody fragments and their high level secretion by *Saccharomyces cerevisiae*, J Biotechnol., 2000, 78(1), 11-21.
Kong, Qingzhong et al., "A lambda 3' Enhancer Drives Active and Untemplated Somatic Hypermutation of a lambda1 Transgene," The Journal of Immunology, vol. 161:294-301 (1998).
Documents associated with European Patent Application EP02709544, dated Feb. 9, 2015, Letter accompanying subsequently filed items.
Takai, Y. et al., B cell stimulatory factor-2 is involved in the differentiation of cytotoxic T lymphocytes, J Immunol., 1988, 140(2), 508-512.
Nagy A. et al., Cre Recombinase: The Universal Reagent for Genome Tailoring, Genesis, 2000, 26(2), 99-109.
Claims (amendments indicated), European Patent Application No. 09075279.1, Dec. 22, 2011, Reference No. P85231EP00, five pages.
In The High Court of Justice, Chancery Division, Patents Court, Case No. HP-2013-000001/HP-2014-000001 dated Oct. 6, 2015, First Expert Report of Professor Sir Martin Evans FRS Ph.D., Report relates to a patent owned by Regeneron Pharmaceuticals, Inc., Report relates to patents owned by Regeneron Pharmaceuticals, Inc., EP 1 360 281 and 2 264 163.
Casellas et al., Contribution of Receptor Editing to the Antibody Repertoire, Science, Feb. 23, 2001, pp. 1541-1544, vol. 291, Issue 5508.
De Kruif et al., Selection and Application of Human Single Chain Fv Antibody Fragments from a Semi-synthetic Phage Antibody Display Library with Designed CDR3 Regions, Journal of Molecular Biology, 1995, pp. 97-105, vol. 248.
Franklin et al., Insights into ErbB signaling from the structure of the ErbB2-pertuzumab complex, Cancer Cell, Apr. 2004, pp. 317-328, vol. 5, issue 4.
Muyrers et al., Rapid modification of bacterial artificial chromosomes by ET-recombination, Oxford University Press, 1999, pp. 1555-1557, vol. 27, No. 6.
Sirac et al., Role of the monoclonal kappa chain V domain and reversibility of renal damage in a transgenic model of acquired Fanconi syndrome, Blood, Jul. 15, 2006, pp. 536-543, vol. 108, No. 2.
Declaration and CV of Craig Bassing, originally submitted for the EP1360287 Opposition, dated Jul. 16, 2014.
Documents associated with European Patent Application EP02709544, Opinion & Order in U.S. District Court, Southern District of New York date filed Nov. 2, 2015, in Case No. 1:14-cv-1650-KBF, 114 pages.
Drawings dated Jul. 9, 2012, EP12175544.
Blankenstein et al., Immunoglobulin Veta region genes of the mouse are organized in overlapping clusters, Eur. J immunol., 1987, pp. 1351-1357, vol. 17.

Documents associated with European Patent Application EP 02709544, dated May 17, 2014, Advice of delivery.
Documents associated with European Patent Application EP 02709544, dated Sep. 16, 2013, (Electronic) Receipt.
Documents associated with European Patent Application EP 02709544, dated Apr. 24, 2014, Preparation for oral proceedings.
Correspondence from S.T. van Doom to European Patent Office regarding written submissions in response to the summons to attend oral proceedings dated Mar. 6, 2013, EP Application No. 09075279.1, Apr. 23, 2013, 15 pages.
Grosveld, F., Activation by locus control regions?, Curr Opin Genet Dev., 1999, 9(2),152-157.
In The High Court of Justice, Chancery Division, Patents Court, Case No. HP-14A00007 dated Jan. 3, 2014, between Regeneron Pharmaceuticals Inc., Claimant and Novo Nordisk A/S, Defendant, Particulars of Infringement, relates to a patent owned by Regeneron Pharmaceuticals, Inc., EP 1 360 287, with accompanying Annex 1 to the Particulars of Infringement, 8 pages.
Wu et al., A protocol for constructing gene targeting vectors: generating knockout mice for the cadherin family and beyond, Natures Protocol, 20 pages, May 29, 2008, pp. 1056-1076, vol. 3, No. 6, Nature Publishing.
Groeneveld EH., Burger EH., Bone morphogenetic proteins in human bone regeneration, Eur J Endocrinol., 2000, 1421), 9-21.
Correspondence from Dr. Fritz Lahrtz of Isenbruck Bosl Forschler LLP to the European Patent Office regarding change of name for Proprietor, EP Application No. 09075279.1 and EP Patent No. 2147594, May 30, 2016, one page.
Kawasaki, K. et al., One-megabase sequence analysis of the human immunoglobulin lambda gene locus, Genome Res., 1997, 7(3), 250-61.
Correspondence from the Canadian Intellectual Property Office in Canadian Application No. 2,729,095 to Borden Ladner Gervais LLP dated Apr. 16, 2014, advising that a protest has been filed by Blake Cassels & Graydon LLP, 1 page.
Documents associated with European Patent Application EP 02709544, dated Jun. 12, 2013, Any annexes (other than Citation) to an opposition letter—2.
Oh, SK., et al., Homeotic gene Antennapedia mRNA contains 5'-noncoding sequences that confer translational initiation by internal ribosome binding, Genes Dev., 1992, 6(9), 1643-1653.
Notice of Opposition, Australian application No. 2009263082, Jun. 20, 2014, 1 page.
Third Party Observations Against European Parent Application No. 09075279.1 in the name of Merus BV, May 16, 2013, eight pages.
Huang et al., Association of telomere length with authentic pluripotency of ES/iPS cells, Cell Research, 13 pages, Feb. 2011, pp. 779-792, vol. 21, No. 5.
Documents associated with European Patent Application EP 02709544, dated Aug. 20, 2014, (Electronic) Receipt.
Lekkerkerker, Phage antibodies against human dendritic cell subpopulations obtained by flow cytometry-based selection on freshly isolated cells, Journal of Immunological Methods, 1999, pp. 53-63, vol. 231.
Declaration of Dr Andrew Murphy dated Dec. 21, 2016 in opposition proceedings EP2264163.
Correspondence from C.M. Jansen of V.O. to European Patent Office regarding change of representation, EP Patent No. 2147594, Dec. 17, 2015, one page.
Monaco et al., YACs, BACs, PACs and MACs: artificial chromosomes as research tools, Tibtech, Jul. 1994, pp. 280-286, vol. 12.
EPO communication to Martin Hatzmann of V.O., Brief Communication regarding the letter of Apr. 23, 2013, EP Application No. 09075279.1 and EP Patent No. 2147594, May 22, 2013, EPO Form 2008A 12.07, one page.
EPO communication to Andrew Bentham of J A Kemp, Brief Communication regarding Oral Proceedings on Jun. 22, 2016 and the Letter from the proprietor of the patent of Feb. 16, 2016, EP Application No. 10186063.3 and EP Patent No. 2314629, Mar. 7, 2016, EPO Form 2310A 12.07, two pages.
EPO Acknowledgement of receipt, Acknowledgement of Receipt, Application No. 10186063.3 and EP Patent No. 2314629, Nov. 27, 2015, one page.

(56) References Cited

OTHER PUBLICATIONS

Dumoulin, M. et al., Single-domain antibody fragments with high conformational stability, Protein Sci., 2002, 11(3), 500-515.
Winter et al., Insertion of 2 kb of bacteriophage DNA between an immunoglobulin promoter and leader exon stops somatic hypermutation in a kappa transgene, Molecular Immunology, Apr. 1997, pp. 359-366, vol. 34, No. 5.
Documents associated with European Patent Application EP 02709544, dated Apr. 4, 2014, Letter concerning fees and payments.
EPO Partial description filed in response to formal objections dated Aug. 20, 2012, EP12175544.1.
EPO Authorisation of Johan Renew regarding Oral Proceedings, EP Application No. 09075279.1, Dec. 2, 2015, one page.
Ramirez-Solis et al., Gene Targeting in Embryonic Stem Cells, Methods Enzymol., 1993, 225:855-78.
Documents associated with European Patent Application EP 02709544, dated Mar. 10, 2014, Letter concerning the inventor.
Odegard et al., Targeting of somatic hypermutation, Nature Reviews, Immunology, Aug. 2006, pp. 573-583, vol. 6, No. 8.
Documents associated with European Patent Application EP 02709544, dated Jun. 12, 2013, Any annexes (other than Citation) to an opposition letter—1.
Karu et al., Recombinant Antibody Technology, ILAR Journal, pp. 132-141, http://ilarjournal.oxfordjournals.org/by guest on Apr. 6, 2014.
Stein, I., et al., Translation of vascular endothelial growth factor mRNA by internal ribosome entry: implications for translation under hypoxia, Mol Cell Biol., 1998, 18(6), 3112-3119.
Bolland et al., Antisense intergenic transcription in V (D) J recombination, Nature Immunology, 8 pages, Apr. 25, 2004, pp. 630-637, vol. 5, No. 6, Nature Publishing Group.
Hardy, R., Hayakawa, K., B cell development pathways, Annu Rev Immunol., 2001, 19, 595-621.
Winter et al., Making antibodies by phage display technology, Annu. Rev. Immunol., Apr. 1994, pp. 433-455, vol. 12, Abstract only.
EPO Communication to V.O., Acknowledgement of receipt of EPO Forms 2310 and 2043, EP Application No. 10186063.3 and EP Patent No. 2314629, Nov. 10, 2015, EPO Form 2936 08.10, one page.
Epo Extension of time limit pursuant to Rule 132 EPC, EP Application No. 10186063.3 and EP Patent No. 2314629, Oct. 24, 2014, EPO Form 2944C, 06.12, one page.
Documents associated with European Patent Application EP 02709544, dated Oct. 7, 2016, Brief communication—Opposition proceedings—6.
Hill, F. et al., BAC Trimming: Minimizing Clone Overlaps; Genomics, 2000, 64(1):111-3.
Approved Judgement in *Regeneron Pharmaceuticals Inc.vs Kymab Limited and Novo Nordisk A/S*, Case No. HP-2013-000001/HP-2014-000001 for Hearing dales: Nov. 18-20, 23-27,30 and Dec. 7 & 8, 2015.
Aucouturier et al., "Monoclonal Ig L Chain and L Chain V Domain Fragment Crystallization in Myeloma-Associated Fanconi's Sydrome", The Journal of Immunology, vol. 150, No. 8, Apr. 15, 1993, pp. 3561-3568, The American Association of Immunologists, USA.
Documents associated with European Patent Application EP 02709544, dated Oct. 7, 2016, Brief communication—Opposition proceedings—2.
Documents associated with European Patent Application EP 02709544, dated Oct. 7, 2016, Brief communication—Opposition proceedings—3.
Documents associated with European Patent Application EP 02709544, dated Oct. 7, 2016, Brief communication—Opposition proceedings—4.
EPO Communication regarding Preparation for oral Proceedings—Instructions to Support Service, EP Application No. 09075279.1, Feb. 5, 2013, EPO Form 2040 12.07TRI, two pages.
Documents associated with European Patent Application EP 02709544, dated Sep. 30, 2016, (Electronic) Receipt.
EPO Invitation to remedy deficiencies pursuant to Rule 30(3) EPC / Rule 163(3) EPC, EP Application No. 10186063.3, Nov. 23, 2010, EPO Form 1128, 05.10, 3 pages.
Letter accompanying subsequently filed items regarding amended claims with clean and annotated copies, EP Application No. 09075279.1, Apr. 23, 2013, 2 pages.
Documents associated with European Patent Application EP 02709544, dated Sep. 17, 2014, Brief communication—Opposition proceedings—1.
Documents associated with European Patent Application EP 02709544, dated Sep. 17, 2014, Brief communication—Opposition proceedings—2.
Documents associated with European Patent Application EP 02709544, dated Sep. 17, 2014, Brief communication—Opposition proceedings—3.
Narayanan et al., Efficient and precise engineering of a 200 kb beta-globin human/bacterial artificial chromosome in *E.coli* DH10B using an inducible homologous recombination system, Gene Therapy, 1999, pp. 442-447, vol. 6.
Hiatt et al., "Production of antibodies in transgenic plants", Department of Molecular Biology, Letters to Nature, vol. 342, Nov. 2, 1989, pp. 76-78.
Toledo, F, et al., RMCE-ASAP: a gene targeting method for ES and somatic cells to accelerate phenotype analyses, Nucleic Acids Research, 2006, vol. 34 No. 13, pp. e92-1.
Murphy, Chapter 6: Antigen Presentation to T Lymphocytes, Janeway's Immunobiology, Eighth Edition, 2012, 31 pages.
Garnick, RL., Peptide mapping for detecting variants in protein products, Dev Biol Stand., 1992, 76, 117-130.
Lobato MN., Rabbits, TH., Intracellular antibodies and challenges facing their use as therapeutic agents, Trends Mal Med., 2003, 9(9), 390-396.
Documents associated with European Patent Application EP 02709544, dated Oct. 12, 2015, Letter dealing with oral proceedings during the appeal procedure—2.
Documents associated with European Patent Application EP 02709544, dated Oct. 12, 2015, Letter dealing with oral proceedings during the appeal procedure—3.
Mao, Xiaohong et al., "Activation of EGFP expression by ere-mediated excision in a new ROSA26 reporter mouse strain," Blood, vol. 97(1):324-326 (2001).
Documents associated with European Patent Application EP 02709544, dated Oct. 12, 2015, Letter dealing with oral proceedings during the appeal procedure—1.
International Preliminary Report on Patentability and Written Opinion for Application No. PCT/NL2009/050381, 11 pages dated Jan. 5, 2011.
Xu,S. and Feiss, M., Structure of the bacteriophage lambda cohesive end site. Genetic analysis of the site (cosN) at , which nicks are introduced by terminase, J Mal Biol., 1991, 220(2), 281-92.
Documents associated with European Patent Application EP 02709544, dated Mar. 21, 2016, Letter accompanying subsequently filed items.
Documents associated with European Patent Application EP 02709544, dated Aug. 22, 2014, Written submission in preparation to during oral proceedings.
Third Party Observations for Application No. EP09075279.1, 6 pages, dated Oct. 25, 2012.
EPO Brief Communication to Andrew Bentham of J A Kemp regarding the Opposition, EP Application No. 09075279.1 and Patent No. 2147594, Jun. 14, 2016, EPO Form 29110 01.12, one page.
EPO Letter accompanying subsequently filed items dated Aug. 20, 2012, EP12175544.1.
Weinberger, O. et al., Cellular interactions in the generation of cytolytic T lymphocyte responses: role of Ia-positive splenic adherent cells in presentation in H-2 antigen, Proc Natl Acad Sci US A, 1980,77(10), 6091-6095.
Holmes, P., Al-Rubeai, M., Improved cell line development by a high throughput affinity capture surface display technique to select for high secretors, J Immunol Methods, 1999, 230(1-2), 141-147.
Documents associated with European Patent Application EP 02709544, dated Sep. 2, 2014, Any annexes (other than citation) to an opposition letter—3.

(56) References Cited

OTHER PUBLICATIONS

Cascalho et al., A Quasi-Monoclonal Mouse, Science, Jun. 14, 1996, pp. 1649-1652, vol. 272.
Japan Patent Office, Acknowledgement of receipt, Japanese Patent Application No. 2015-097258, May 12, 2015, 1 page.
EPO Communication, EPApplication No. 10186063.3, dated Mar. 3, 2011, EPO Form 1507N, 08.10, 1 page.
Payment of fees and expenses for EP Application No. 10186063.3 dated May 27, 2016, one page.
Documents associated with European Patent Application EP 02709544, dated Sep. 2, 2014, Any annexes (other than citation) to an opposition letter—2.
Documents associated with European Patent Application EP 02709544, dated Sep. 2, 2014, Any annexes (other than citation) to an opposition letter—1.
EPO Letter accompanying subsequently filed items dated Dec. 17, 2015, EP12175544.1.
EPO Invitation to remedy deficiencies dated Aug. 31, 2012, EP12175544.1.
Statement of Fact and Argument in Support of Opposition filed against EP Patent No. 2314629, at least as early as Jul. 15, 2014, 30 pages.
Lewis et al., A common Human B Globin Splicing Mutation Modeled in Mice, Blood Journal, 5 pages, Mar. 15, 1998, pp. 2152-2156, vol. 91, No. 6, The American Society of Hematology.
Documents associated with European Patent Application EP 02709544, dated Sep. 18, 2014, Payment offees and costs.
Fedorov et al., A comparison of the germline potential of differently aged ES cell lines and their transfected descendants, Transgenic Research, 9 pages, May 6, 1997, pp. 223-231, vol. 6, No. 3 Chapman & Hall.
Correspondence from Fritz Lahrlz of Isenbruck Bosl Hoschler LLP to European Patent Office regarding request for Postponement of Oral Proceedings, EPApplication No. 09075279.1 and EP Patent No. 2147594, Feb. 1, 2016, two pages.
Staerz et al, Hybrid hybridoma producing a bispecific monoclonal antibody that can focus effector T-cell activity, Proc Natl Aced Sci US A, 1986, vol. 83(5) pp. 1453-1457.
Sirac et al., "Role of the monoclonal k chain V domain and reversibility of renal damage in a transgenic model of acquired Fanconi syndrome", Immunobiology, Blood, vol. 108, No. 2, Jul. 15 2006, pp. 536-543, The American Society of Hematology.
Brief communication in Opposition proceedings in EP 10186063.3 dated May 26, 2016.
Seidl et al., An expressed neo gamma cassette provides required functions of the Igamma2b exon for class switching, International Immunology, 1998, pp. 1683-1692, vol. 10, No. 11.
Brief communication in opposition proceedings for EP application 10186063.3 dated May 31, 2016, one page.
Designation of Inventor Bout Abraham, at least as early as Oct. 1, 2010, 1 page.
Mead G.P. et al., Poster, Detection of Bence Jones myeloma and monitoring of myeloma chemotherapy using mmunoassays specific for free immunoglobulin light chains, Clinical Laboratory, 2003, vol. 49, No. 1-2, 2003, p. 25-27.
Klotz, EL. Storb, U, Somatic hypermutation of a lambda 2 transgene under the control of the lambda enhancer or the heavy chain intron enhancer, J Immunol, 1996, 157(10), 4458-4463.
Documents associated with European Patent Application EP 02709544, dated Mar. 7, 2014, Advice of delivery.
Shvarts et al., A senescence rescue screen identifies BCL6 as an inhibitor of anti-proliferative p19(ARF)-p53 signaling, Genes Dev., Mar. 15, 2002, pp. 681-686, vol. 16(6).
Macdonald et al., Precise and in situ genetic humanization of 6 Mb of mouse immunoglobulin genes, PNAS, 2013, (6 Pages), Early Edition.
Goyenechea et al., Modifying the sequence of an immunoglobulin V-gene alters the resulting pattern of hypermutation, Proc. Natl. Acad. Sci. 1996, pp. 13979-84, vol. 93.
Auxiliary Request 4, EP Patent No. 2314629B1, May 20, 2016, ffive pages.
EPO Acknowledgement of receipt of written submissions, EP Application No. 09075279.1, date of receipt Apr. 24, 2013, one page.
Bebbington, CR. et al, High-level expression of a recombinant antibody from myeloma cells using a glutamine synthetase gene as an amplifiable selectable marker, Biotechnology (N Y), 1992, 10(2), 169-175.
Documents associated with European Patent Application EP 02709544, dated Jun. 12, 2013, Document concerning representation.
Rideout et al., Generation of mice from wild-type and targeted ES cells by nuclear cloning, Nat Genetics; 2000, 24 2):109-110.
Documents associated with European Patent Application EP 02709544, dated Nov. 9, 2015, Amended description with annotations.
Documents associated with European Patent Application EP 02709544, dated Oct. 14, 2016, Communication inviting the parties to file observations.
Herault et al., Engineering chromosomes in mice through targeted meiotic recombination (TAMERE), Nature Genetics, 4 pages, Dec. 20, 1998, pp. 381-384, vol. 20, Nature America Inc.
Lonberg, N., Human antibodies from transgenic animals, Nat Bioteohnol., 2005, 23(9), 1117-1125.
Mansour SL., Disruption of the proto-Oncogene int-2 in mouse embryo-derived stem cells: a general strategy for targeting mutations to non-selectable genes, Nature, 1988, 336(6197), 348-52.
Nagle, Mike, "Regeneron helps make Sanofi VelocImmune to its 'weak' pipeline," Outsourceing—Pharma.com, 2 pages (2007).
Documents associated with European Patent Application Ep 02709544, dated Mar. 2, 2015, Letter dealing with oral proceedings during the appeal procedure—1.
Documents associated with European Patent Application EP 02709544, dated Mar. 2, 2015, Letter dealing with oral proceedings during the appeal procedure—2.
Application for U.S. Patent, U.S. Appl. No. 11/645,238, sharing common inventors, available on the U.S. Patent Office , website.
Auxiliary Request 5 with annotations, EP Patent No. 2314629B1, May 20, 2016, Five pages.
Bruggemann et al., A Repertoire of Monoclonal Antibodies with Human Heavy Chains from Transgenic Mice, Proc. Natl. Acad. Sci., Sep. 1989, pp. 6709-6713, vol. 86, USA.
Documents associated with European Patent Application EP 02709544, dated Sep. 15, 2014, Letter regarding the opposition procedure (no time limit).
Documents associated with European Patent Application EP 02709544, dated Sep. 9, 2014, Letter regarding he opposition procedure (no time limit).
Ramirez-Solis et al., Chromosome engineering in mice, Nature, 5 pages, Dec. 14, 1995, pp. 720-724, vol. 378, Nature Publishing Group.
Documents associated with European Patent Application EP 02709544, dated May 24, 2016, Internal form—: Opposition_addressees.
EPO Request for grant of a European patent dated Jul. 9, 2012, Application No. EP12175544.1.
Documents associated with European Patent Application EP 02709544, dated Mar. 18, 2014, (Electronic) Receipt.
Rong et al., Tumorigenicity of the met proto-0ncogene and the gene for hepatocyte growth factor, Mol. Cell Biol., Nov. 1992, pp. 5152-5158, vol. 12, No. 11.
Scott, "Mice with a human touch", Nature Biotechnology, vol. 25, No. 10, Oct. 2007, pp. 1075-1077, Nature Publishing Group.
Japan Patent Office, Notice of Allowance, Japanese Patent Application No. 2011-516168, Apr. 13, 2015, four pages.
Fritz Lahrlz of Isenbruck Bosl Hoschler LLP communication to EPO, Executed Acknowledgement, EP Application No. 09075279.1 and EP Patent No. 2147594, Mar. 29, 2016, EPO Form 2936 08.10, one page.
Third Party citation for application No. 14163642.3, 3 pages, dated Jan. 29, 2016.
J A Kemp communication to EPO, Executed Acknowledgement of receipt of EPO Form 2310 and 2043, EP Application No. 10186063.3 and EP Patent No. 2314629, Nov. 25, 2015, EPO Form 2936 08.10, one page.

(56) References Cited

OTHER PUBLICATIONS

Clark, Mike, Antibody humanization: a case of the 'Emperor's new clothes'?, 2000p,397-402, vol. 21, No. 8.
Xu et al., "Deletion of the Ig kappa light chain intronic enhancer/matrix attachment region impairs but does not abolish V kaooa J kaooa rearrangement," Immunity (1996) 4:377-385.
A.L. Joyner, Gene Targeting: A Practical Approach, The Practical Approach Series, 2005, (196 pages), Second Edition, Oxford University Press.
Davies, Nicholas P. et al., "Creation of Mice Expressing Human Antibody Light Chains by Introduction of a Yeast Artificial Chromosome Containing the Core Region of the Human Immunoglobulin kappa Locus," Bio/Technology, vol. 11:911-914 (1993).
Kuroiwa et al., Sequential targeting of the genes encoding immunoglobulin µ and prion protein in cattle, Nature Genetics, 5 pages, Jun. 6, 2004, pp. 775-780, vol. 36, No. 7, Nature Publishing Group.
Betz, AG. Elements regulating somatic hypermutation of an immunoglobulin kappa gene: critical role for the inIron nhancer/malrix attachment region, Cell, 1994, 77(2), 239-248.
Documents associated with European Patent Application EP 02709544, dated Nov. 16, 2015, Advice of delivery.
Auxiliary Request 7, EP Patent No. 2314629B1, May 20, 2016, ffive pages.
Correspondence from S.T. van Doorn of V.O. to European Patent Office regarding in vivo data, EP Application No. 09075279.1, Jun. 13, 2013, two pages.
EPO Communication under Rule 71(3) EPC, EP Application No. 09075279.1, Sep. 2, 2013, EPO Form 2004C 06.13TRI, five pages.
Rosenberg A., et al., T7Select Phage Display System: A Powerful New Protein Display System Based on Bacteriophage T7, 1996, Innovations 6, 1-6.
Documents associated with European Patent Application EP 02709544, dated Mar. 4, 2015, Letter dealing with oral proceedings during the appeal procedure.
Bode et al. 2001, Int. J Gene Ther. Mal. Biol. 6:33-46.
Documents associated with European Patent Application EP 02709544, dated Mar. 18, 2014, Advice of delivery.
Documents associated with European Patent Application EP 02709544, dated Oct. 28, 2015, Letter dealing with oral proceedings during the appeal procedure.
EPO Communication of a Notice of Opposition, EP Application No. 09075279.1 and EP Patent No. 2147594, Aug. 20, 2014, EPO Form 2316 01.12, one page.
Documents associated with European Patent Application EP 02709544, dated Jan. 22, 2015, (Electronic) Receipt—2.
Documents associated with European Patent Application EP 02709544, dated Jan. 22, 2015, (Electronic) Receipt—1.
Ku et al., Diversity in the CDR3 Region of Veta Is Sufficient for Most Antibody Specificities, Immunity, Jul. 2000, pp. 37-45, vol. 13.
Documents associated with European Patent Application EP 02709544, dated Nov. 4, 2015, Letter ccompanying subsequently filed items.
Documents associated with European Patent Application EP 02709544, dated Nov. 4, 2015, (Electronic) Receipt.
Documents associated with European Patent Application EP 02709544, dated Apr. 3, 2014, Intervention of the assumed infringer.
Ku, J et al., Alternate protein frameworks for molecular recognition, Proc Nall Acad Sci US A, 1995, 92(14), 5552-5556.
Third Party Observation for application No. EP20090075279, Anonymous, at least as early as Jun. 24, 2013, nine pages.
Gan, W. et al, Functional characterization of the internal ribosome entry site of elF4G mRNA, J Biol Chem., 1998, 273 (9), 5006-5012.
Desmyter, A. et al., Crystal structure of a camel single-domain VH antibody fragment in complex with lysozyme, Nat Struct Riol., 1996, 3(9), 803-811.
Communication from Japanese Patent Office: Opposition decision (Opp.—No. 2016-700031) for JP 5749161, dated Sep. 7, 2016, 50 pages.
Documents associated with European Patent Application EP 02709544, dated Sep. 25, 2015, Letter accompanying subsequently filed items.
International Search Report for Application No. PCT/NL2009/050381, 5 pages, dated Dec. 7, 2009.
Bertagnolli, M., Herrmann, S., IL-7 supports the generation of cytotoxic T lymphocytes. Multiple ymphokines required for proliferation and cytotoxicity, J Immunol., 1990,145(6), 1706-1712.
Auxiliary Request 9 with annotations, EP Patent No. 2314629B1, May 20, 2016, nine pages.
Advice of receipt to Fritz Lahrlz of Isenbruck Bosl Hoschler LLP, Registration No. of item RD119029438NL, Mar. 14, 2016, one page.
Documents associated with European Patent Application EP 02709544, dated Jul. 14, 2015, Forwarding of submissions to parties—1.
Documents associated with European Patent Application EP 02709544, dated Jul. 14, 2015, Forwarding of submissions to parties—2.
Documents associated with European Patent Application EP 02709544, dated Jul. 14, 2015, Forwarding of submissions to parties—3.
Canadian Intellectual Property Office to Blake Cassels & Graydon LLP, Protest Confirmation, Canadian Patent Application No. 2729095, Apr. 16, 2014, one page.
Executed Acknowledgement of receipt, EP Application No. 09075279. 1, Mar. 7, 2013, EPO Form 2936 08.10, one page.
(Page 332-335) EPO Communication regarding Submission in opposition proceedings, Request for extension of lime, EP Application No. 10186063.3 and Patent No. 2314629, Oct. 16, 2014, four pages.
Opposition to Merus B.V.'s EP 2 314 629 B1 Consolidated Lisi of Documents filed by All Parties, unknown author, undated, at least as early as Jun. 6, 2016.
Cleary et al , Disruption of an imprinted gene cluster by a targeted chromosomal translocation in mice, Nature Genetics, 5 pages, Aug. 20, 2001, pp. 78-82, vol. 29, No. 1, Nature Publishing Group.
Documents associated with European Patent Application EP 02709544, dated Oct. 28, 2015, Forwarding of submissions to parties—1.
Nelson, AL. et al., Development trends for human monoclonal antibody therapeutics, Nat Rev Drug Discov, 2010, 9 10), pp. 767-774.
Documents associated with European Patent Application EP 02709544, dated Aug. 28, 2014, Brief communication- opposition proceedings—2.
Documents associated with European Patent Application EP 02709544, dated Aug. 28, 2014, Brief communication—opposition proceedings—3.
Documents associated with European Patent Application EP 02709544, dated Aug. 28, 2014, Brief communication opposition proceedings—1.
Yang, SY. El al, Control of gene conversion and somatic hypermutation by immunoglobulin promoter and enhancer sequences, J Exp Med., 2006, 203(13), 2919-2928.
Brief Communication from European Patent Office to Isenbruck Bosl Forschler LLP regarding EP 10186063.3 dated Jun. 13, 2016.
F.T. Wunderlich (2004), "Generation of inducible Cre systems for conditional gene inactivation in mice," inauguraldissertation zur Erlangung des Doktorgrades der Mathematisch Naturwissenschaftlichen Fakultat der Universitat zu Koln; on the World Wide Web at deposit.ddb.de/cgi bin/dokserv?dn=97557230x&dok_var= d1&dok_ext=pdf&filename= 97557230x.pd.
Clackson, T. et al., Making antibody fragments using phage display libraries, Nature, 1991, 352(6336), 624-628.
Melvyn Little, Antibodies for Immunotherapy, Cambridge University Press, 2009. 23 pages.
Documents associated with European Patent Application EP 02709544, dated Mar. 5, 2014, Brief communication—opposition proceedings—3.
Documents associated with European Patent Application EP 02709544, dated Mar. 5, 2014, Brief communication—opposition proceedings—2.
Documents associated with European Patent Application EP 02709544, dated Feb. 9, 2015, (Electronic) Receipt.
Documents associated with European Patent Application EP 02709544, dated Mar. 5, 2014, Brief communication—opposition proceedings—1.

(56) References Cited

OTHER PUBLICATIONS

Mouse Genetics and Transgenics: A Practical Approach. I. J. Jackson and C. M. Abbott (eds). Oxford University Press Olxford. 2000, chapter 7.
Third Party Opposition filed in Canadian Intellectual Property Office, Application No. 2729095, dated Sep. 16, 2015, 15 pages.
Documents associated with European Patent Application EP 02709544, dated Dec. 4, 2014, Acknowledgement of a document.
Hong et al., Long targeting arms do not increase the efficiency of homologous recombination in the beta-globin locus of rnurine embryonic stem cells, Red Cells, 3 pages, Aug. 15, 2003, pp. 1531-1533, vol. 102, No. 4, The American Society of Hematology.
Auxiliary Request 9, EP Patent No. 2314629B1, May 20, 2016, ffive pages.
Documents associated with European Patent Application EP 02709544, dated Sep. 9, 2014, Letter accompanying subsequently filed items.
PCT International Preliminary Examination Report, PCT/EP03/07690, dated Nov. 11, 2004.
EPO European search opinion dated Jun. 30, 2016, EP12175544.1.
Schindelhauer et al., HJ., Efficient combination of large DNA in vitro: in gel site specific recombination (IGSSR) of PAC ragments containing a satellite DNA and the human HPRT gene locus, Nucleic Acids Research, 1997, 25 (11):2241-3.
Mattheakis, LC. et al., An in vitro polysome display system for identifying ligands from very large peptide libraries, Proc Natl Acad Sci U S A, 1994, 91(19), 9022-9026.
Roholt et al, Antibodies of Limited Heterogeneity: L. Chains of a Single Mobility, Immunochemistry, Pergamon Press, 1970, vol. 7, pp. 329-340.
Auxiliary Request 3 with annotations, EP Patent No. 2314629B1, May 20, 2016, Five pages.
Opinion & Order in *Regeneron Pharmaceuticals, Inc.*, v *Merus B.V.*, Case 1:14-cv-01650-KBF filed Nov. 2, 2015.
Eggan et al., Hybrid vigor, fetal overgrow1h, and viability of mice derived by nuclear cloning and tetraploid embryo Complementation, PNAS, May 22, 2001,pp. 6209-6214, vol. 98, No. 11.
(Page 304-305) Summons to Attend Oral Proceedings, EP Application No. 10186063.3, dated Nov. 19, 2015, two pages.
Kelley et al, Antigen Binding Thermodynamics and Antiproliferative Effects of Chimeric and Humanized anti-p185HER2 Anitbody Fab Fragments, 1992 Biochemistry 31:5435-5441.
EPO European Search Report dated Jun. 16, 2016, EP12175544.
Defranco, Anthony L., Declaration filed Against Australian Application No. 2009263082 in the name of Merus B.V., executed Dec. 21, 2014.
Pau et al, The human cell line PER.C6 provides a new manufacturing system for the production of influenza vaccines, Vaccine, 2001, pp. 2716-2721, vol. 19.
Hoogenboom et al., Multi-subunit proteins on the surface of filamentous phage: methodologies for displaying antibody Fab heavy and light chains, Nucl. Acids Res., 1991, pp. 4133-4137, vol. 19, Issue 15.
Murphy, Kenneth, "The Development and Survival of Lymphocytes," Janeway's Immunobioloby, 8th Edition, Taylor & Francis, Chapter 8, pp. 275-290 (2011).
Nguyen et al., Heavy-chain only antibodies derived from dromedary are secreted and displayed by mouse B cells, Immunology, 2003, pp. 93-101, vol. 109.
Documents associated with European Patent Application EP 02709544, dated Jun. 20, 2013, Letter regarding the opposition procedure (no time limit).
Documents associated with European Patent Application EP 02709544, dated Oct. 14, 2013, Brief communication—Opposition proceedings—2.
Canadian Intellectual Property Office to Borden Ladner Gervais LLP, Requisition by the Examiner, CA Application No. 2729095, Jun. 11, 2014, three pages.
Documents associated with European Patent Application EP 02709544, dated Dec. 4, 2015, Communication of he Board of Appeal (ex parte_ inter partes).
Ngo, T.-H., et al, Identification of functional synergism between monoclonal antibodies. Application to the enhancemen of plasminogen activator inhibitor-1neutralizing effects, FEBS Letters, 1997, pp. 373-376, vol. 416.
EPO Request for recordation of a transfer dated May 30, 2016, EP12175544.1.
Epo communication to Fritz Lahrlz of Isenbruck Bosl Hoschler LLP, Brief Communication regarding Oral proceedings on Jun. 22, 2016 at 10:00 in S2.1, EP Application No. 10186063.3 and EP Patent No. 2314629, Apr. 26, 2016, EPO Form 29110 01.12, one page.
Third Party Observations Against European Parent Application No. 09075279.1 in the Name of Merus BV, 3 pages, dated Jul. 1, 2013.
Hoogenboom, Designing and optimizing library selection strategies for generating high-affinity antibodies, Trends Biotechnol., 1997, pp. 62-70, vol. 15, Issue 2, Abstract only.
Japan, Third Party Observation 2011-516168, 14 pages.
Homig-Holzel et al., Constitutive CD40 signaling in B cells selectively activates the noncanonical NF-KB pathway and promotes lymphomagenesis, J. Exp. Med., 2008, pp. 1317-1329, vol. 205, No. 6.
Mainville, M. et al; Deletion al Mapping of Fifteen Mouse VH Gene Families Reveals a Common Organization for Three Igh Haplotypes, Journal of Immunology, 1996, 156(3):1038-46.
News Release: Astellas Licenses Regeneron's Velocimmune(Registereci) Technology for Discovering Human Monoclonal Antibodies (Mar. 30, 2007).
Sanger et al., DNA sequencing with chain-terminating inhibitors, PNAS, Dec. 1, 1997, pp. 5463-5467, vol. 74, No. 12.
Thomassen Y. et al, Large-scale production of VHH antibody fragments by *Saccharomyces cerevisiae*, 2002, Enzyme Microb. Technol., 30, 273-278.
Declaration of Sir Martin Evans dated Dec. 23, 2016 in opposition proceedings EP2264163.
Yelverton E, et al., Rabies virus glycoprotein analogs: biosynthesis in *Escherichia coli*, Science, 1983, 219(4585), 614-620.
Burjoni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 2-935, vol. 288, No. 1.
Persic, L. et al. An integrated vector system for the eukaryotic expression of antibodies or their fragments after selection from phage display libraries, Gene, Mar. 10, 1997, pp. 9-18, vol. 187, Issue 1.
EPO Communication of amended entries concerning the representative dated Oct. 8, 2015, EP12175544.1.
Documents associated with European Patent Application EP 02709544, dated Mar. 2, 2015, Communication of the Board of Appeal (ex parte_ inter partes).
Documents associated with European Patent Application EP 02709544, dated Aug. 3, 2015, Annexes (other than cited documents) regarding appeal procedure.
EPO Communication, Consultation by telephone with the applicant/representative, EP Application No. 09075279.1, Oct. 9, 2013, EPO Form 2036 12.07TRI, one page.
Feeney, AJ. and Riblet, R., Dst4: a new, and probably the last, functional Dh gene in the BALB/c mouse, Immunogenetics, 1993, 37(3):217-21.
Wade-Martins, R. et al, Long-term stability of large insert genomic DNA episomal shuttle vectors in human cells, Nucleic Acids Res., 1999, 27(7), 1674-82.
Singer et al., Genes & Genomes A Changing Perspective, University Science Books, Mill Valley, California, 1991, 134-145.
Knight, Jonathan, Mouse genome effort 'on course', Nature, 2001, vol. 411, p. 121.
Zacharchuk, CM. El al., Programmed T lymphocyte death. Cell activation- and steroid-induced pathways are mutually antagonistic, J Immunol., 1990, 145(12), 4037-4045.
Documents associated with European Patent Application EP 02709544, dated Jan. 30, 2015, Letter accompanying subsequently filed items—1.
In The High Court of Justice, Chancery Division, Patents Court, Case No. HP-2013-000001/HP-2014-000001 dated Oct. 2, 2015,

(56) References Cited

OTHER PUBLICATIONS

First Witness Statement of Andrew Joseph Murphy, Report relates to patent owned by Regeneron Pharmaceuticals, Inc., EP 1 360 287, 19 pages.
*Homo sapiens* immunoglobulin light chain variable region protein, GenBank Accession No. ABA26122.1, Aug. 8, 2014, one page.
Gu et al., Independent Control of Immunoglobulin Switch Recombination at Individual Switch Regions Evidenced through Cre-loxP-Mediated Gene Targeting, Cell, Jun. 18, 2993, pp. 1155-1164, vol. 73.
Documents associated with European Patent Application EP 02709544, dated Jan. 30, 2015, Letter accompanying subsequently filed items—2.
Documents associated with European Patent Application EP 02709544, dated Feb. 26, 2014, 1002—Designation of inventor—1.
Documents associated with European Patent Application EP 02709544, dated Feb. 26, 2014, 1002—Designation of inventor—2.
Documents associated with European Patent Application EP 02709544, dated Feb. 26, 2014, 1002—Designation of inventor—3.
Hurle et al., Protein engineering techniques for antibody humanization, Biotechnology, 1994, pp. 428-433, vol. 5.
Documents associated with European Patent Application EP 02709544, dated Feb. 26, 2014, 1002—Designation of inventor—4.
Documents associated with European Patent Application EP 02709544, dated Feb. 26, 2014, 1002—Designation of inventor—5.
Brady et al., Rapid specific amplification of rat antibody cDNA from nine hybridomas in the presence of myeloma light hains, Journal of Immunological Methods, Aug. 31, 2006, pp. 61-67, vol. 315.
Notice of Opposition to a European patent, EP Patent No. 2314629, EP Application No. 10186063.3, Jul. 14, 2014, EPO Form 2300E, 8 pages.
EPO Communication, Annex to EPO Form 2004, Communication pursuant to Rule 71(3) EPC, EP Application No. 09075279.1, Sep. 2, 2013, EPO Form 2056, two pages.
Macatonia, SE. et al., Primary stimulation by dendritic cells induces antiviral proliferative and cytotoxic T cell responses in vitro, J Exp Med., 1989,169(4), 1255-1264.
Morimoto et al., Abstract, High level expression of a human rabies virus-neutralizing monoclonal antibody by a rhabdovirus-based vector, J. Immunol. Methods, Jun. 2001, pp. 199-206, vol. 1, No. 252(1-2).
Abstract, "Recombinant Production of Mixtures of Antibodies", at least as early as Oct. 1, 2010, 1 page.
Huls, G. A., et al., A recombinant, fully human monoclonal antibody with antitumor activity constructed from phage-displayed antibody fragments, Nat Biotechnol., 1999, 17(3), 276-281.
Catalano, CE. et al., Virus DNA packaging: the strategy used by phage lambda, J Mol Biol., 1991, 20; 220(2): 281-92.
Kirschbaum, T. et al., The central part of the mouse immunoglobulin kappa locus, Eur J Immunol., 1999, 29(7), 2057-64.
Huse, WO. et al., Generation of a large combinatorial library of the immunoglobulin repertoire in phage lambda, Science, 1989, 246(4935), 1275-1281.
Sequence Alignment and Declaration of Dr. John McWhirter, European Patent Application No. 09075289.1, European Patent No. 2147594 B1, dated Aug. 2, 2016, four pages.
Japan Patent Office, Third Party Observation, Japanese Patent Application No. 2011-516168, May 9, 2014, 14 pages.
Documents associated with European Patent Application EP 02709544, dated Nov. 18, 2015, Oral Proceedings_ Forwarding minutes.
EPO Request for change of applicant's representation dated Dec. 22, 2015, EP12175544.1.
Trucksis M. et al., The Vibrio cholerae genome contains two unique circular chromosomes, Proc Natl Acad Sci U SA, 1998, 95(24), 14464-9.
Declaration of Professor Kenan Murphy dated Dec. 29, 2016 in opposition proceedings EP2264163.
Gray, F. et al., Secretion capture and report web: use of affinity derivatized agarose microdroplets for the selection of hybridoma cells, J Immunol Methods, 1995, 182(2), 155-163.
Atwell et al., Stable heterodimers from remodeling the domain interface of a homodimer using a phage display library1, J. Mal. Biol., Jul. 4, 1997, pp. 26-35, vol. 270, Issue 1, Abstract only.
Drawings dated Aug. 20, 2012, EP12175544.1.
Houston, M.E., Jr. et al., Use of a conformationally restricted secondary structural element to display peptide libraries: a two-stranded alpha-helical coiled-coil stabilized by lactam bridges, J Mol Biol., 1996, 262(2), 270-282.
Documents associated with European Patent Application EP 02709544, dated Jan. 29, 2014, Brief communication Opposition proceedings—1.
Documents associated with European Patent Application EP 02709544, dated Jun. 12, 2013, (Electronic) Receipt—2.
Documents associated with European Patent Application EP 02709544, dated Jun. 12, 2013, (Electronic) Receipt—1.
EPO Communication regarding the entries pertaining to the applicant/ the proprietor (R. 143(1)(f) EPC), EP Application No. 09075279.1 and EP Patent No. 2147594, Jun. 13, 2016, EPO Form 2544 03.14, two pages.
Main Request with annotations, EP U.S. Pat. No. 2314629B1, May 20, 2016, ffive pages.
Documents associated with European Patent Application EP 02709544, dated Oct. 11, 2013, Request for acceleration of the opposition procedure.
Third Party Observation for Application No. 09075279.1,4 pages, dated Oct. 10, 2013.
Auxiliary Request 2, EP U.S. Pat. No. 2314629B1, May 20, 2016, ffive pages.
Documents associated with European Patent Application EP 02709544, dated Oct. 7, 2016, Brief communication—Opposition proceedings—5.
Verma et al., Antibody engineering: Comparison of bacterial, yeast, insect and mammalian expression systems, Journal of Immunological Methods, 1998, pp. 165-81, vol. 216.
Documents associated with European Patent Application EP 02709544, dated Oct. 7, 2016, Brief communication—Opposition proceedings—1.
EPO Brief Communication regarding the Opposition against EP Application No. 10186063.3 and EP Patent No. 2314629, Feb. 27, 2015, EPO Form 29110 01.12, one page.
Documents associated with European Patent Application EP 02709544, dated Feb. 23, 2015, Request for change of opponent's representative.
Documents associated with European Patent Application EP 02709544, dated Jul. 17, 2014, Patent document cited during the opposition procedure.
EPO Communication pursuant to the Decision of the President of the European Patent Office on the filing of priority document, EPApplication No. 10186063.3, Oct. 21, 2010, EPO Form 1195, 04.09 PRIO, 1 page.
Auxiliary request 3 (amendments indicated), EP Application No. 09075279.1, Apr. 23, 2013, three pages.
Hansen, S. et al., "Crescendo's Cash Fragments," BioCentury, The BernsteinReporton BioBusiness, Dec. 23, 2013, p. A13.
Itoh, N. et al., The polypeptide encoded by the cDNA for human cell surface antigen Fas can mediate apoptosis, Cell, 1991, 66(2), 233-243.
Documents associated with European Patent Application EP 02709544, dated Jul. 28, 2014, Brief communication—opposition proceedings—3.
Documents associated with European Patent Application EP 02709544, dated Apr. 24, 2014, Information concerning oral proceedings.
Documents associated with European Patent Application EP 02709544, dated Jul. 28, 2014, Brief communication—Opposition proceedings—1.
Correspondence from S.T. van Doom of V.O. to European Patent Office in response to Communication under Rule 79(1) EPC, EP Application No. 09075279.1 and Patent No. 2147594, Apr. 2, 2015, 32 pages.
Documents associated with European Patent Application EP 02709544, dated Jul. 28, 2014, Brief communication—opposition proceedings—2.

(56) References Cited

OTHER PUBLICATIONS

In The High Court of Justice, Chancery Division, Patents Court, Case No. HP-2013-000001/HP-2014-000001 dated Nov. 2, 2015, Second Expert Report of Adrian Francis Stewart, Report relates to a patent owned by Regeneron Pharmaceuticals, Inc., EP 1 360 287.
Documents associated with European Patent Application EP 02709544, dated Dec. 11, 2014, Advice of delivery.
In The High Court of Justice, Chancery Division, Patents Court, Case No. HP-2013-000001/HP-2014-000001 dated Nov. 3, 2015, Second Witness Statement of A. J.Murphy, Report relates to patent owned by Regeneron Pharmaceuticals, Inc., EP 1 360 287.
Documents associated with European Patent Application EP 02709544, dated Feb. 28, 2014, Information concerning oral proceedings.
Nissim et al., "Antibody fragments from a 'single pot' phage display library as immunochemical reagents", The EMBO Journal, vol. 13, No. 3, 1999, pp. 692-698.
Tada et al., Expression and characterization of a chimeric bispecific antibody against fibrin and against urokinase-type plasminogen activator, Journal of Biotechnology, 1994, pp. 157-174, vol. 33.
Klagsbrun, M., D'Amore PA.,Vascular endothelial growth factor and its receptors, Cytokine Growth Factor Rev,, 1996, 7 (3), 259 270.
Annexes in respect of a request fora change from Merus B.V. to Merus N.V. dated May 19, 2016 (in Dutch; English Version is also attached).
Repp, R. et al., Phase I clinical trial of the bispecific antibody MDX-H210 {anti-FcgammaRI x anti-HER-2/neu) in Combination with Filgrastim (G-CSF) for treatment of advanced breast cancer, Br J Cancer, 2003,89(12), 2234-2243.
EPO Brief Communication to Andrew Bentham of J A Kemp regarding the Oral Proceedings on Oct. 13, 2016, EP Application No. 09075279.1 and Paten No. 2147594, Mar. 22, 2016, EPO Form 2310A 12.07, one page.
Documents associated with European Patent Application EP 02709544, dated Jan. 30, 2015, Annexes (other than cited documents) regarding appeal procedure.
Castelli et al., HLA-DP4, the Most Frequent HLA II Molecule, Defines a New Supertype of Peptide-Binding Specificity, J. Immunol., Dec. 15, 2002, pp. 6928-6934, vol. 169, No. 12.
NCBI, Aucouturier et al., Monoclonal IgL Claim and L chain V domain fragment crystallization in myeloma-associated Fanconi's syndrome, syndrome, <http://www.ncbi.nlm.nib/gov/nuccore/M87478, at least as early as Apr. 25, 2012.
Tan et al., A Human-Mouse Chimeric Immunoglobulin Gene With a Human Variable Region is Expressed in Mouse Myeloma Cells, The Journal of Immunology, Nov. 1985, pp. 3564-3568, vol. 5.
Pawlilzky et al., Identification of a Candidate Regulatory Element within the 5' Flanking Region of the Mouse Igh Locus Defined by Pro-B Cell-Specific Hypersensitivity Associated with Binding of PU.1, Pax5, and E2A, The Journal of Immunology, 13 pages, Jun. 1, 2006, pp. 6839-6851, vol. 176, No. 11, The American Association of Immunology.
Correspondence from C.M. Jansen of V.O. to European Patent Office regarding the Registration of the Association and change of address, reference No. RvE/E100EPEP, Sep. 29, 2015, one page.
Garrard, L J. et al., Fab assembly and enrichment in a monovalent phage display system, Biotechnology (NY), 1991, 9(12), 1373-1377.
Documents associated with European Patent Application EP 02709544, dated Jan. 9, 2015, Forwarding of submissions to parties—3.
Documents associated with European Patent Application EP 02709544, dated Jan. 9, 2015, Forwarding of submissions to parties—2.
Documents associated with European Patent Application EP 02709544, dated Jan. 9, 2015, Forwarding of submissions to parties—1.
EPO Communication to Andrew Bentham of J A Kemp, Acknowledgement of receipt of EPO Forms 2310 and 2043, EP Application No. 09075279.1 and EP Patent No. 2147594, Jan. 19, 2016, EPO Form 2936 08.10, one page.
Paul Carter, "Bispecific human IgG by design", Elsevier, Journal of Immunological Methods, vol. 248, 2001, pp. 7-15.
Eppig JT., Mouse Genome Informatics (MGI): reflecting on 25 years, Mamm Genome, 2015, 26(7-8):272-84. doi: 10.1007/s00335-015-9589-4. Epub Aug. 4, 2015.
EPO Communication to Fritz Lahrtz of Isenbruck Bosl Forschler LLP, Refund of fees, EP Application No. 09075279.1 and Patent No. 2147594, Jun. 15, 2016, EPO Form 2907 04.14, one page.
Fuchs, P. et al., Targeting recombinant antibodies to the surface of *Escherichia coli*: fusion to a peptidoglycan ssociated lipoprotein, Biotechnology (NY), 1991, 9(12), 1369-1372.
Documents associated with European Patent Application EP 02709544, dated May 2, 2014, (Electronic) Receipt.
Hwang et al., Immunogenicity of engineered antibodies, Methods, May 2005, pp. 3-10, vol. 36, Issue 1.
Schaffilzel,C. et al., In vitro selection and evolution of protein-ligand interactions by ribosome display. In: Protein-Protein Interactions. A Molecular Cloning Manual, E. Golemis, Ed., Cold Spring Harbor Laboratory Press, New York, 2001, pp. 535-567.
Letter disclosing in vivo data dated Jun. 13, 2013, European patent application No. 09075279.1, 2 pages.
Judgement in Preliminary Relief Proceedings of Aug. 14, 2015 with English translation, Case No. C/09/480452/KG ZA 15-9, 33 pages.
Bhardwaj, N. et al., Influenza virus-infected dendritic cells stimulate strong proliferative and cytolytic responses from human CD8+T cells, J Clin Invest., 1994; 94(2), 797-807.
Documents associated with European Patent Application EP 02709544, dated Jul. 16, 2014, Letter accompanying subsequently filed items.
Shiga International Patent Office to Japan Patent Office, Amendments to claims made in response to notice of reasons for rejection, Japanese Patent Application No. 2011-515168, Jan. 5, 2015, three pages.
EPO Search has started dated Jun. 15, 2016, EP12175544.1.
Krebs et al., High-throughput generation and engineering of recombinant human antibodies, Journal of Immunological Methods, 2001, pp. 67-84, vol. 254.
Documents associated with European Patent Application EP 02709544, dated Dec. 23, 2014, Letter relating to Appeal Procedure.
Documents associated with European Patent Application EP 02709544, dated Feb. 12, 2014, Letter accompanying subsequently filed items—1.
Documents associated with European Patent Application EP 02709544, dated Feb. 12, 2014, Letter accompanying subsequently filed items—2.
Toki, J. et al., Analyses of T-cell differentiation from hemopoietic stem cells in the GO phase by an in vitro method, Proc Natl Acad Sci US A, 1991, 88(17), 7548-7551.
Alber, T., Kawasaki, G., Nucleotide sequence of the triose phosphate isomerase gene of *Saccharomyces cerevisiae*, J Mol Appl Genet., 1982, 1(5), 419-434.
J A Kemp to European Patent Office, Final Written Submissions Oral Proceedings Scheduled for Oct. 28, 2016, Opposition to Merus N.V.'s EP2147594 dated Aug. 26, 2016, 40 pages.
Documents associated with European Patent Application EP 02709544, dated Jun. 20, 2013, Letter accompanying subsequently filed items.
Letter from Mr. Andrew Bentham of JA Kemp to European Patent Office dated Jul. 15, 2014, accompanying subsequently filed items, one page.
Zheng, B. et al., Engineering Mouse Chromosomes with Cre-loxP: Range, Efficiency, and Somatic Applications, Mol Cel Bio, 2000, 20(2):648-55.
Auxiliary Request 8, EP Patent No. 2314629B1, May 20, 2016, ffive pages.
Corsaro, CM., Pearson, ML., Enhancing the efficiency of DNA-mediated gene transfer in mammalian cells, Somatic Cell Genet., 1981, 7(5), 603-616.
Documents associated with European Patent Application EP 02709544, dated Mar. 26, 2015, Claims—1.
Documents associated with European Patent Application Ep 02709544, dated Mar. 26, 2015, Claims—3.
Documents associated with European Patent Application EP 02709544, dated Mar. 26, 2015, Claims—2.
Documents associated with European Patent Application EP 02709544, dated Mar. 26, 2015, Claims—5.

(56) References Cited

OTHER PUBLICATIONS

Documents associated with European Patent Application EP 02709544, dated Mar. 26, 2015, Claims—4.
Documents associated with European Patent Application EP 02709544, dated May 2, 2014, Advice of delivery—3.
Auxiliary Request 11, EP Patent No. 2314629B1, May 20, 2016, three pages.
Documents associated with European Patent Application EP 02709544, dated May 2, 2014, Advice of delivery—2.
Bowman, MR. et al., The cloning of CD70 and its identification as the ligand for CD27, J Immunol., 1994, 152(4), 1756-1761.
Documents associated with European Patent Application EP 02709544, dated May 2, 2014, Advice of delivery—1.
Spillner et al., Paratope-based protein identification by antibody and peptide phage display, Analytical Biochemistry, 2003 p. 96-104, vol. 321, Academic Press.
Documents associated with European Patent Application EP 02709544, dated Apr. 3, 2014, Notice of opposition.
Huse et al., Purification of antibodies by affinity chromatography, Journal of Biochemical and Biophysical Methods, 2002, pp. 217-231, vol. 51.
Weinberger, O. et al, Cellular interactions in the generation of cytolytic T lymphocyte responses. Analysis of the helper T cell pathway, Eur J Immunol., 1981, 11(5), 405-411.
Declaration of Joel Martin filed May 18, 2016 in EP2314629B.
Epo communication, Client Database System (CDS)-clean up, EP Application No. 10186063.3, Apr. 23, 2013, EPO Form 2596C, 04.08, 1 page.
Deng, et al., Reexamination of gene targeting frequency as a function of the extent of homology between the targeting vector and the target locus., Mal. Cell. Biol., 1992, pp. 3365-3371, vol. 12, No. 8.
Isenbruck Bosl Horschler LLP to European Patenr Office, Documents filed by Proprietor, Response to the summons to attend oral proceedings scheduled for Oct. 28, 2016 and to the preliminary opinion of the Opposition Division datec Jan. 19, 2016, EP 2147594 / 09075279.1-1405, dated Aug. 26, 2016, 32 pages.
Spanopoulou et al., Functional immunoglobulin transgenes guide ordered B-cell differentiation in Rag-1-deficient mice, Genes & Development, 1994, pp. 1030-1042, vol. 8.
Office Action Response in U.S. Appl. No. 12/932,719 {dated Nov. 6, 2014) filed in protest against U.S. Appl. No. 15/158,543.
Nair, S. et al., Induction of primary, antiviral cytotoxic, and proliferative responses with antigens administered via dendritic cells, J Virol., 1993, 67(7), 4062-4069.
Vasicek, T. et al, B-less: a Strain of Profoundly B Cell-deficient Mice Expressing a Human lambda Transgene, J Exp Med., 1992, 175(5), 1169-80.
Pollock et al., Transgenic milk as a method for the production of recombinant antibodies, Journal of Immunological Methods, Dec. 10, 1999, pp. 147-157, vol. 231, Issues 1-2.
Documents associated with European Patent Application EP 02709544, dated Apr. 30, 2014, Advice of delivery.
Auxiliary request 6 (amendments indicated), EP Application No. 09075279.1, Apr. 23, 2013, three pages.
Canadian Patent Office, Response to the Examine s Report dated Apr. 16, 2013, CA Application No. 2729095, Oct. 15, 2013, 20 pages.
Documents associated with European Patent Application EP 02709544, dated Jul. 3, 2015, Reply to appeal.
EPO Communication pursuant to Rule 114(2) EPC, EP Application No. 09075279.1 and Patent No. 2147594, May 8, 2012, EPO Form 2022 12.07, one page.
Allien, Ligand-targeted therapeutics in anticancer therapy, Nat. Rev. Cancer, 2002, 2:750-783, Abstract only.
Dumoulin, M. et al., A camelid antibody fragment inhibits the formation of amyloid fibrils by human lysozyme, Nature, 2003 424(6950), 783-788.

Zhang et al., A new logic for DNA engineering using recombination in *Escherichia coli*, nature genetics, Oct. 20, 2998, pp. 123-128, vol. 20.
Fox et al., Fluorescent in situ hybridization (FISH) to mouse chromosomes, Mouse Genetics and Transgenics: A practical approach, I.J. Jackson, C.M. Abbott (Eds.), Oxford University Press, London (2000), pp. 154-168.
Singer, Maxine et al., "Transcription: The Transfer of DNA Sequence Information to RNA," Genes & Genomes, University Science Books, CA, Chapter 3.2, pp. 134-145 (1991).
Ammerer, G., Expression of genes in yeast using the ADCI promoter, Methods Enzymol., 1983, 101, 192-201.
EPO Brief Communication regarding the Opposition againts EP Application No. 10186063.3 and EP Patent No. 2314629, Oct. 24, 2014, EPO Form 29110 01.12, one page.
Reyrat, JM. et al; Counterselectable Markers: Untapped Tools for Bacterial Genetics and Pathogenesis, Infect Immun., 1998; 66(9):4011-7.
Auxiliary Request 10, EP Patent No. 2314629B1, May 20, 2016, ffive pages.
Xiang, Yougui et al., "The Downstream Transcriptional Enhancer, Ed, Positively Regulates Mouse Igk Gene Expression and Somatic Hypermutation," J. Immunol., vol. 180(10):6725-6732 (2008).
Australian Office Action for Application No. 2009263082, 8 pages, dated Mar. 18, 2014.
EPO Communication pursuant to Rule 114(2) EPC, EP Application No. 09075279.1 and Patent No. 2147594, Jul. 2, 2013, EPO Form 2022 12.07, one page.
Documents associated with European Patent Application EP 02709544, dated Jan. 28, 2014, Letter regarding the opposition procedure (no time limit).
Storb et al., Immunoglobulin transgenes as targets for somatic hypermutation, Int. J Dev. Bioi., 1998, pp. 977-982, vol. 42(7).
Japan Patent Office, Notification of Third Party Observation, Japanese Patent Application No. 2011-516168, May 20, 2014, one page.
Nicholson et al., Antibody Repertoires of Four- and Five-Feature Translocus Mice Carrying Human Immunoglobulin Heavy Chain and kappa and lambda Light Chain Yeast Artificial Chromosomes, the Journal of Immunology, 1999, pp. 6898-6906, vol. 163.
Merchant et al., An efficient route to human bispecific IgG, Nature Biotechnology, Jul. 1998, pp. 677-681, vol. 16.
Orban, PC. et al, Tissue- and site-specific DNA recombination in transgenic mice, Proc Natl Acad Sci U S A, 1992, 89 15), 6861-6865.
Canadian Intellectual Property Office to Borden Ladner Gervais LLP, Requisition by the Examiner, CA Application No. 2729095, Apr. 16, 2013, seven pages.
EPO Acknowledgement of Receipt of the submission by the proprietor, EP Application No. 10186063.3 and EP Patent No. 2314629, date of receipt Oct. 16, 2014, one page.
Pasqualucci et al., "BCL-6 mutations in normal germinal center B cells: evidence of somatic hypermutation acting outside Ig loci," Proc. Natl. Acad. Sci. USA (1998) 95(20):11816-11821.
Middendorp et al., Impaired Precursor B Cell Differentiation in Bruton's Tyrosine Kinase-Deficient Mice, J. Immunol., Mar. 15, 2002, pp. 2695-2703, vol. 168 No. 6.
Lefranc, M.-P., Immunogenetics, Human (*Homo sapiens*) IGH locus on chromosome 14, http://www.imgt.org/IMGTrepertoire/index.php?sectdion+LocusGene, printed Mar. 30, 2012.
Giddings et al., Transgenic plants as factories for biopharmaceuticals, Nature Biotechnology, 2000, pp. 1151-1155, vol. 18, Nature America Inc.
Marvin, J.S., et al., Recombinant approaches to IgG-like bispecific antibodies, Acta Pharmacologica Sinica, Jun. 2005 pp. 649-658, vol. 26.
ImMunoGeneTics Information System, for analysed sequence CHEB VK, http://www.imgt.org/IMGT_vguest/vquest, at least as early as Apr. 25, 2012.
In the High Court of Justice, Chancery Division, Patents Court, Case No. HP-2013-000001/HP-2014-000001 dated Jan. 2, 2016, between Regeneron Pharmaceuticals Inc., Claimant and Kymab Limited and Novo Nordisk A/S, Defendants, Mr. Justice Henry Carr, Approved Judgment.

(56) References Cited

OTHER PUBLICATIONS

Documents associated with European Patent Application EP 02709544, dated Sep. 8, 2015, Cited document during appeal procedure—2.
Schlake et al., Use of Mutated FLP Recognition Target (FRT) Sites for the Exchange of Expression Cassettes at Defined Chromosomal Loci, Biochemistry, 1994, pp. 12746-12751, vol. 33.
(Page 308) EPO Acknowledgement of Receipt of the submission by the proprietor, EP Application No. 10186063.3 and EP Patent No. 2314629, dated Feb. 24, 2015, one page (previously submitted).
Orford M. et al., Engineering EGFP reporter constructs into a 200 kb human beta-globin BAC clone using GET Recombination; Nucleic Acids Res., 2000; 28(18), E84.
Documents associated with European Patent Application EP 02709544, dated Mar. 21, 2016, Advice of delivery.
Documents associated with European Patent Application EP 02709544, Letter from Allen & Overy to Powell Gilbert LLP dated Jun. 23, 2015 transmitting a letter from UK Intellectual Property Office regarding amendment to Patent application EP 1 360 287.
Documents associated with European Patent Application EP 02709544, dated Sep. 16, 2013, Request for extension of time limit.
Documents associated with European Patent Application EP 02709544, dated Sep. 10, 2015, Advice of delivery.
Documents associated with European Patent Application EP 02709544, dated Sep. 8, 2015, Cited document during appeal procedure—1.
Japan Patent Office, Request for Substantive Examination, Japanese Patent Application No. 2015-097258, dated Jun. 1, 2015, 1 page.
A new target and technology have Regeneron's future looking bright, The Barnes Report (Apr. 30, 2007), http://www.imakenews.com/barnesreport/e_article000807331.cfm?=b11,0,w, printed Jan. 23, 2014.
Aya Jakobovits, The long-awaited magic bullets: therapeutic human monoclonal antibodies from transgenic mice, Exp. Opin. Invest. Drugs, 1998, pp. 607-614, vol. 7, No. 4, Ashley Publications Ltd.
Kitamura D., AB cell-deficient mouse by targeted disruption of the membrane exon of the immunoglobulin mu chain Jene, Nature, 1991, 350(6317), 423-426.
Sjolander and Urbaniczky, Integrated fluid handling system for biomolecular interaction analysis, Anal. Chem., 1991, pp. 2338-2345, vol. 63, No. 20, Abstract only.
EPO Communication, Annex to EPO Form 2004, Communication pursuant to Rule 71(3) EPC, Bibliographical data of EP Application No. 10186063.3, dated Jun. 5, 2013, EPO Form 2056, 11.08, 1 page.
Nanbru, C. et al., Alternative translation of the proto-oncogene c-myc by an internal ribosome entry site, J Biol Chem., 1997, 272(51), 32061-32066.
Kim SJ, et al., Characterization of chimeric antibody producing CHO cells in the course of dihydrofolate reductase-mediated gene amplification and their stability in the absence of selective pressure, Biotechnol Bioeng., 1998, 58(1), 73-84.
Correspondence from S. van Doom of Vereenigde to the European Patent Office in response to the communication pursuant to Article 94(3) EPC, European Patent Application No. 09075279.1, dated Dec. 22, 2011, five pages.
Simmons et al., Expression of full-length immunoglobulins in *Escherichia coli*: rapid and efficient production of aglycosylated antibodies, J. Immunol. Methods, May 1, 2002, pp. 133-147, vol. 263.
Documents associated with European Patent Application EP 02709544, dated Aug. 12, 2014, Letter accompanying subsequently filed items.
Boel et al., Functional human monoclonal antibodies of all isotypes constructed from phage display library-derived single-chain Fv antibody fragments, Journal of Immunological Methods, 2000, pp. 153-166, vol. 239.
Fecteau, Jessie F. et al., "A New Memory CD27 IgG+ B Cell Population in Peripheral Blood Expressing VH Genes with Low Frequency of Somatic Mutation," The Journal of Immunology, vol. 177:3728-3736 (2006).
Mendez et al., Functional transplant of megabase human immunoglobulin loci recapitulates human antibody response in mice, Nature Genetics. 1997. pp. 146-56. vol. 15.

(Pages 9-61) Deed of Conversion and Amendment of the Articles of Association for Merus B.V. (new name: Merus N.V.), first in Dutch and then in English (Dutch version previously submitted without English translation).
EPO Communication of amended entries concerning the representative (R. 143(1)(h) EPC), EP Application No. 09075279.1 and Patent No. 2147594, dated Oct. 8, 2015, EPO Form 2548 08.13, one page.
Johnston, et al., Complete Sequence Assembly and Characterization of the C57BL/6 Mouse Ig Heavy Chain V Region, J Immunol., Jul 2, 2014, htttp://www.jimmunol.org/content/176/7/4221.
Documents associated with European Patent Application EP 02709544, dated Sep. 12, 2014, Brief communication—Opposition proceedings—1.
Documents associated with European Patent Application EP 02709544, dated Sep. 12, 2014, Brief communication—Opposition proceedings—2.
Documents associated with European Patent Application EP 02709544, dated Feb. 10, 2014, Letter regarding the opposition procedure (no time limit).
Page 336) EPO Communication of a notice of opposition {R. 79(1) EPC), EP Application No. 10186063.3 and EP Patent No. 2314629, dated Aug. 22, 2014, EPO Form 2317A, 12.07, one page {previously submitted).
Documents associated with European Patent Application EP 02709544, dated Sep. 12, 2014, Brief communication—Opposition proceedings—3.
Documents associated with European Patent Application EP 02709544, dated Sep. 12, 2014, Brief communication—Opposition proceedings—4.
Sidhu et al., Phage-displayed antibody libraries of synthetic heavy chain complementarity determining regions, Abstract, Journal of Molecular Biology, Apr. 23, 2004, pp. 299310, vol. 338, No. 2.
Documents associated with European Patent Application EP 02709544, dated Sep. 12, 2014, Brief communication—Opposition proceedings—5.
Documents associated with European Patent Application EP 02709544, dated Sep. 12, 2014, Brief communication—Opposition proceedings—6.
Hansen et al., Large-scale gene trapp.ing in C57BL/6N mouse embryonic stem cells, Gename Research, 10 pages, 2008, pp. 1670-1679, vol. 18, Cold Spring Hamor Laboratory Press.
Deed of Conversion and Amendment of the Articles of Association for Merus BV (new name: Merus NV.), May 19, 2016, 27 pages.
Fleischer et al., Reactivity of mouse T-cell hybridomas expressing human Vbeta gene segments with staphylococcal and streptococcal superantigens, Infect. Immun., Mar. 1996, pp. 987-994.
Submission in opposition proceedings by Andrew Bentham, EP Application No. 09075279.1 and Patent No. 2147594, dated Jan. 29, 2016, two pages.
Jespers LS, et al., Guiding the selection of human antibodies from phage display repertoires to a single epitope of an antigen, Biotechnology (NY), 1994, 12(9), 899-903.
Auxiliary Request 6, EP Patent No. 2314629B1, Reference No. M70120EPEIN FLZ, May 20, 2016, ffive pages.
Documents associated with European Patent Application EP 02709544, dated Nov. 28, 2014, Internal form—opposition_addressees—2.
Documents associated with European Patent Application EP 02709544, dated Nov. 28, 2014, Minutes of the oral proceedings (Opposition Division)—introduction of the parties.
Mccafferty et al., Antibody Engineering, PAS, 2002, 178 Pages, Oxford University Press.
Rebar, EJ. et al., Phage display methods for selecting zinc finger proteins with novel DNA-binding specificities, Methods Enzymol., 1996, 267, 129-149.
Documents associated with European Patent Application EP 02709544, dated Aug. 3, 2015, Letter accompanying subsequently filed items.
Soukharev et al., Segmental genomic replacement in embryonic stem cells by double lox targeting, Nucleic Acids Research, 1999, pp. e21, vol. 27, No. 18.
Documents associated with European Patent Application EP 02709544, dated Apr. 3, 2014, Cover sheet for fax transmission.

(56) References Cited

OTHER PUBLICATIONS

Marks, JD., Deciphering antibody properties that lead to potent botulinum neurotoxin neutralization, Mov Disord., 2004, 19 Suppl 8, S101-108.
Documents associated with European Patent Application EP 02709544, dated Dec. 18, 2014, Advice of delivery—1.
Documents associated with European Patent Application EP 02709544, dated Dec. 18, 2014, Advice of delivery—2.
Documents associated with European Patent Application EP 02709544, dated Jul. 16, 2014, 1003—Authorisation of representative.
Canadian Intellectual Property Office to Borden Ladner Gervais LLP, Advisement of protest filed, CA Application No. 2729095, Nov. 2, 2015, one page.
Kuhlman, B. et al, Design of a novel globular protein fold with atomic-level accuracy, Science, 2003, 302(5649), 1364-1368.
EPO Brief Communication regarding the Opposition, EP Application No. 09075279.1 and Patent No. 2147594, dated Oct. 22, 2014, EPO Form 29110 01.12, one page.
EPO Acknowledgement of receipt of executed acknowledgment, EP Application No. 09075279.1 and Patent No. 2147594, dated Apr. 12, 2016, one page.
Documents associated with European Patent Application EP 02709544, dated May 7, 2014, Advice of delivery.
Wilmut et al., Basic techniques for transgenesis, Journals of Reproduction and Fertility, 1991, pp. 265-275, vol. 43, Journals of Reproduction & Fertility LTD.
EP Acknowledgement of Receipt for EP Application No. 10186063. 3, dated Sep. 6, 2013, 1 page.
Massengale, WT et al., CD20-negative relapse of cutaneous B-cell lymphoma after anti-CD20 monoclonal antibody herapy, J Am Acad Derrnatol., 2002, 46(3), 441-443.
EPO communication, Maintenance/ Change of date/ Cancellation of oral proceedings arranged for: Jun. 16, 2016 at 10.00 hrs, EP Application No. 09075279.1 and EP Patent No. 2147594, Feb. 4, 2016, EPO Form 2088 06.14, two Jages.
Documents associated with European Patent Application EP 02709544, dated Mar. 14, 2016, Advice of delivery.
Documents associated with European Patent Application EP 02709544, dated Apr. 11, 2014, Findings upon submissions relating to oral proceedings.
(Page 1) EPO Form 2906 regarding Patent Application No. 10 186 063.3 dated Jul. 27, 2016, indicating the description needs to be brought in conformity with the claims, 1 page.
Documents associated with European Patent Application EP 02709544, dated Oct. 26, 2015, Letter dealing with oral proceedings during the appeal procedure.
Auxiliary Request 2 with annotations, EP Patent No. 2314629B1, Reference No. M70120EPEIN FLZ, May 20, 2016, Five pages.
Documents associated with European Patent Application EP 02709544, dated Mar. 10, 2014, (Electronic) Receipt.
Documents associated with European Patent Application EP 02709544, dated Mar. 21, 2016, (Electronic) Receipt.
Dechiara, Thomas M. et al., "VelociMouse: Fully ES Cell-Derived F0-Generation Mice Obtained from the Injection of ES Cells into Eight-Cell-Stage Embryos," Gene Knockout Protocols: Second Edition, Ralf Kuhn (Ed.), Humana Press, vol. 530, Chapter 16, pp. 311-324 (2009).
Epo Communication, Summons to Andrew Bentham of J A Kemp to attend oral proceedings pursuant to Rule 115(1) EPC, EP Application No. 09075279.1 and EP Patent No. 2147594, Mar. 22, 2016, EPO Form 2310 12.14, one page.
Further to Notice of Opposition dated Jul. 8, 2016, EP2264163/ 10010741.6, 3 pages, dated Jul. 12, 2016.
Sarber, K. Biotech industry faces new bottleneck, Nat Biotechnol., 2001, 19(3), 184-185.
Storb et al., Ig gene expression and regulation in Ig transgenic mice, Immunoglobin Genes, 19 pages, 1995, pp. 345-363, Elsevier Ltd.

United States District Court Southern District of New York, *Regeneron Pharmaceuticals, Inc.*, Plaintiff v. *Merus B.V.*, Defendant, 14 Civ. 1650 (KBF) Opinion & Order (Claim Construction) dated Nov. 21, 2014.
Documents associated with European Patent Application EP 02709544, dated Jun. 20, 2013, (Electronic) Receipt).
Submission in opposition proceedings by Andrew Bentham, EP Application No. 09075279.1 and Patent No. 2147594, Nov. 17, 2015, two pages.
Murphy et al., Mice with megabase humanization of their immunoglobulin genes generate antibodies as efficiently a normal mice, PNAS, (sent for review Aug. 26, 2013), pp. 1-6, www.pnas.org/cgi/doi/10.1073/pnas.10324022111.
Transue, TR. et al., Camel single-domain antibody inhibits enzyme by mimicking carbohydrate substrate, Proteins, 1998, 32(4), 515-522.
Zou et al., Cre-loxP-mediated gene replacement: a mouse strain producing humanized antibodies, Current Biology, 1994, pp. 1099-1103, vol. 4.
Ee et al., Complete humanization of the mouse immunoglobulin loci enables efficient therapeutic antibody discovery, Nature Biotechnology, pub. Online Mar. 16, 2014; pp. 1-12, doi:10.1038/nbt.2825.
Correspondence from S. van Doorn to European Patent Office regarding request to hold application, EP Application No. 09075279. 1, dated Sep. 3, 2013, one page.
Koochekpour et. al., Met and Hepatocyte Growth Factor/Scatter Factor Expression in Human Gliomas, Cancer Res., Dec. 1, 1997, pp. 5391-5398, vol. 57.
Declaration from Professor Allen Bradley in Respect of the opposition to EP2264163 filed by Kymab Limited, dated Jul. 7, 2016, with curriculum vitae.
Documents associated with European Patent Application EP 02709544, dated Jul. 16, 2014, Letter regarding the opposition procedure (no time limit).
O'Brien, RL., Somatic hypermutation of an immunoglobulin transgene in kappa transgenic mice, Nature, 1987, 326 6111), 405-409.
Liu, et al., Embryonic Lethality and Tumorigenesis Caused by Segmental Aneuploidy on Mouse Chromosome 11, 14 pages, Nov. 1998, pp. 1155-1168, vol. 150, No. 3, The Genetic Society of America.
Documents associated with European Patent Application EP 02709544, dated Oct. 16, 2015, Forwarding of submissions to parties—5.
Carter, P., Improving the efficacy of antibody-based cancer therapies, Nat Rev Cancer, 2001, 1(2), 118-129.
Documents associated with European Patent Application EP 02709544, dated Mar. 11, 2016, Notification(s) of the decision—4.
Documents associated with European Patent Application EP 02709544, dated Mar. 11, 2016, Notification(s) of the decision—3.
Documents associated with European Patent Application EP 02709544, dated Mar. 11, 2016, Notification(s) of the decision—2.
Documents associated with European Patent Application EP 02709544, dated Mar. 11, 2016, Notification(s) of the decision—1.
Documents associated with European Patent Application EP 02709544, dated Sep. 17, 2013, Brief Communication—Opposition proceedings—2.
Documents associated with European Patent Application EP 02709544, dated Sep. 17, 2013, Brief Communication—Opposition proceedings—1.
Third Party Observation for Application No. 09075279.1, 12 pages, dated Sep. 12, 2013.
Brief Communication from European Patent Office to Isenbruck Bosl Forschler LLP regarding EP 10186063.3 dated Jun. 10, 2016 about Oral proceedings on Jun. 22, 2016.
Shi et al., The mapping of transgenes by fluorescence in situ mybridiation on G-banded mouse chromosomes, Mammalian Genome, 1994, pp. 337-341.
Nowakowski et al., Potent neutralization of botulinum neurotoxin by recombinant oligoclonal antibody, PNAS, Aug. 20, 2002, pp, 11346-11350, vol. 99, No. 17.
Fujieda et al., Multiple Types of Chimeric Germ-Line Ig Heavy Chain Transcripts in Human B Cells, Evidence for trans-Splicing of Human Ig RNA, The Journal of Immunology, 1996, pp. 3450-3460.

(56) References Cited

OTHER PUBLICATIONS

EPO Brief Communication to Fritz Lahrlz of Isenbruck Bosl Hoschler LLP regarding the Oral Proceedings on Oct. 13, 2016, EP Application No. 09075279.1 and Patent No. 2147594, Mar. 22, 2016, EPO Form 2310A 12.07, one page.
Documents associated with European Patent Application EP 02709544, dated Mar. 9, 2015, Forwarding of submissions to parties—4.
Documents associated with European Patent Application EP 02709544, dated Mar. 9, 2015, Forwarding of submissions to parties—5.
Documents associated with European Patent Application EP 02709544, dated Mar. 9, 2015, Forwarding of submissions to parties—6.
Documents associated with European Patent Application EP 02709544, dated Mar. 9, 2015, Forwarding of submissions to parties—7.
Documents associated with European Patent Application EP 02709544, dated Mar. 9, 2015, Forwarding of submissions to parties—8.
Baker et al., Adaptation of TCR Expression Vectors for the Construction of Mouse-Human Chimeric MBP-Specific TCR Transgenes, Journal of Neuroscience Research, 1996, pp. 487-491, vol. 45.
Documents associated with European Patent Application EP 02709544, dated Jul. 16, 2014, Amended claims with annotations—09.
Documents associated with European Patent Application EP 02709544, dated Sep. 8, 2014, Brief communication—Opposition proceedings—2.
Reply letter of proprietor in response to the opposition proceedings against EP 2501817 B1, dated Dec. 23, 2016.
Roebroek, Anton J_ et al., Mutant Lrp1 Knock-In mice generated by recombinase-mediated cassette exchange reveal differential importance of the NPXY motifs in the intracellular domain on LRP1 for normal fetal development, Molecular and Cellular Biology, 2006, vol. 26, No. 2, p. 605-616.
Muyldermans, S., Single domain camel antibodies: current status, J Biotechnol., 2001, 74(4), 277-302.
G. Neufeld et al., Vascular endothelial growth factor (VEGF) and its receptors, FASEB J., Jan. 1999, pp. 9-22, vol. 13, No. 1.
Epo Acknowledgement of receipt of Notice of Opposition, EP Application No. 09075279.1 and EP Patent No. 2147594, dated Aug. 11, 2014, two pages.
Tucker et al., Mouse IgA heavy chain gene sequence: Implications for evolution of immunoglobulin hinge exons, Proc. Natl. Acad. Sci. USA, Dec. 1981, pp. 7684-7688, vol. 78, No. 12.
EPO Acknowledgement of receipt of letter regarding request for extension of time, EP Application No. 09075279.1, dated Oct. 16, 2014, one page.
Sharpe et al., "Somatic hypermutation of immunoglobulin x may depend on sequences 3' of Cx and occurs on passenger transgenes", The EMBO Journal, vol. 10, No. 8, 1991, pp. 2139-2145, Oxford University Press.
Logtenberg, "Antibody cocktails: next-generation biopharmaceuticals with improved potency", Trends in Biotechnology, vol. 25, No. 9, Aug. 6, 2007, pp. 390-394, Elsevier Lid.
Meier et al., Short DNA sequences inserted for gene targeting can accidentally interfere with off-target gene xpression, The FASEB Journal, Jun. 2010, pp. 1714-1724, vol. 24.
Documents associated with European Patent Application EP 02709544, dated Nov. 28, 2014, Scanned annex to a communication—opposition procedure—2.
Third Party Observation for application No. EP20120783456, Anonymous, Jun. 16, 2016, three pages.
Documents associated with European Patent Application EP 02709544, dated Nov. 28, 2014, Scanned annex to a communication—opposition procedure—1.
Nagy et al., Derivation of completely cell culture-derived mice from early-passage embryonic stem cells, Development Biology, 5 pages, Sep. 15, 1993, pp. 8424-8428, vol. 90, No. 18, Proc Nall Acad Sci U S A.
EPO Brief Communication regarding the Opposition, EP Application No. 09075279.1 and Patent No. 2147594, dated Aug. 25, 2015, EPO Form 29110 01.12, one page.
Askew et al., Site-Directed Point Mutations in Embryonic Stem Cells: a Gene-Targeting Tag- and Exchange Strategy, Molecular and Cellular Biology, 10 pages, Jul. 1993, pp. 4115-4124 vol. 13, No. 7, American Society of Microbiology.
Documents associated with European Patent Application EP 02709544, dated Nov. 28, 2014, Grounds for the decision (Annex)—opposition.
EPO Letter accompanying subsequently filed items, Documents filed during examination procedure and Letter dealing with Oral proceedings filed by David Power of J A Kemp, EP Application No. 10186063.3, May 20, 2016, one page.
Gorczyca, W. et al., DNA strand breaks occurring during apoptosis—their early insitu detection by the terminal deoxynucleotidyl transferase and nick translation assays and prevention by serine protease inhibitors, Int J Oncol., 1992, 1(6), 639-648.
Documents associated with European Patent Application EP 02709544, dated Jul. 18, 2013, Notice of further Jppositions to opponent(s)—1.
Documents associated with European Patent Application EP 02709544, dated Jan. 30, 2015, Letter relating to Appeal Procedure—1.
Blair et al., The Liberation of Embryonic Stem Cells, PLoS Genetics, 6 pages, Apr. 2011,pp. 1-6, vol. 7, No. 4.
Documents associated with European Patent Application EP 02709544, dated Sep. 5, 2014, Any annexes (other than citation) to an opposition letter.
Figini et al.. In Vitro Assembly of Repertoires of Antibody Chains on the Surface of Phage by Renaturation, Journal of Molecular Biology, 1994, pp. 68-78, vol. 239.
Valenzuela et al., High Through put engineering of the mouse genome coupled with high resolution expression analysis, 13 pages, Nature Biotechnology, May 5, 2003, pp. 652-659, vol. 21, No. 6, Nature Publishing Group.
Komdorfer, IP. et al., Crystallographic analysis of an "anticalin" with tailored specificity for fluorescein reveals high structural plasticity of the lipocalin loop region, Proteins, 2003, 53(1), 121-129.
Documents associated with European Patent Application EP 02709544, dated Jan. 30, 2015, Letter relating to Appeal Procedure—3.
Documents associated with European Patent Application EP 02709544, dated Jan. 30, 2015, Letter relating to Appeal Procedure—2.
Documents associated with European Patent Application EP 02709544, dated Nov. 4, 2015, Fax relating to Appeal procedure.
Gluzman, SV40-transforrmed simian cells support the replication of early SV40 mutants, Cell, Jan. 1981, pp. 175-182, vol. 23, Issue 1, Abstract only.
Jain et al., Engineering antibodies for clinical applications, Trends in Biotechnol., Jul. 2007, pp. 307-316, vol. 25, Issue 7.
Declaration of Professor Hidde Ploegh dated Dec. 23, 2016 in opposition proceedings EP2264163.
Rickert, Robert C. et al., "B lymphocyte-specific, ere-mediated mutagenesis in mice," Nucleic Acids Research, vol. 25(6):1317-1318 (1997).
Yoo EM et al., Structural requirements for polymeric immunoglobulin assembly and association with J chain, J Biol Chem., 1999, 274(47), 33771-33777.
McConnell, S.J., Hoess, Rh., Tendamistat as a scaffold for conformationally constrained phage peptide libraries, J Mal Biol., 1995, 250(4), 460-470.
EPO Communication to Fritz Lahrlz of Isenbruck Bosl Hoschler LLP, Acknowledgement of receipt of EPO Forms 2310 and 2043, EP Application No. 09075279.1 and EP Patent No. 2147594, dated Mar. 22, 2016, EPO Form 2936 08.10, one age.
Nord, K. et al., A combinatorial library of an alpha-helical bacterial receptor domain, Protein Eng., 1995, 8(6), 601-608.
Documents associated with European Patent Application EP 02709544, dated Oct. 16, 2015, Forwarding of submissions to parties—2.
Documents associated with European Patent Application EP 02709544, dated Oct. 16, 2015, Forwarding of submissions to parties—1.
Documents associated with European Patent Application EP 02709544, dated Oct. 16, 2015, Forwarding of submissions to parties—4.
Documents associated with European Patent Application EP 02709544, dated Oct. 16, 2015, Forwarding of submissions to parties—3.
Darzynkiewicz, Z. et al., Features of apoptotic cells measured by flow cytometry, Cytometry, 1992,13(8), 795-808.

(56) References Cited

OTHER PUBLICATIONS

Ritchie, et al. Allelic Exclusion and Control of Endogenous Immunoglobulin Gene Rearrangement in k Transgenic Mice. Nature 312(6): 517-520, 1984.†
Carter. Bispecific Human IgG by Design. J. Immunol. Methods 248: 7-15, 2001.†
Declaration of Dr. Joel Martin; Executed May 18, 2016; Submitted May 20, 2016, and entered into public record in European Patent No. 2314629.†
Merchant, et al. An Efficient Route to Human Bispecific IgG. Nat. Biotech. 16: 677-681, 1998.†
Written Submissions in Response to Summons to Attend Oral Proceedings, EP Patent Application No. 09075279.1.†
Ritchie, et al. , Allelic Exclusion and Control of Endogenous Immunoglobulin Gene Rearrangement in kappa Transgenic Mice, Nature, 312(6):517-520, 1984.†
In re Chu, 66 F.3d 292 (Fed. Cir. 1995).†

\* cited by examiner
† cited by third party

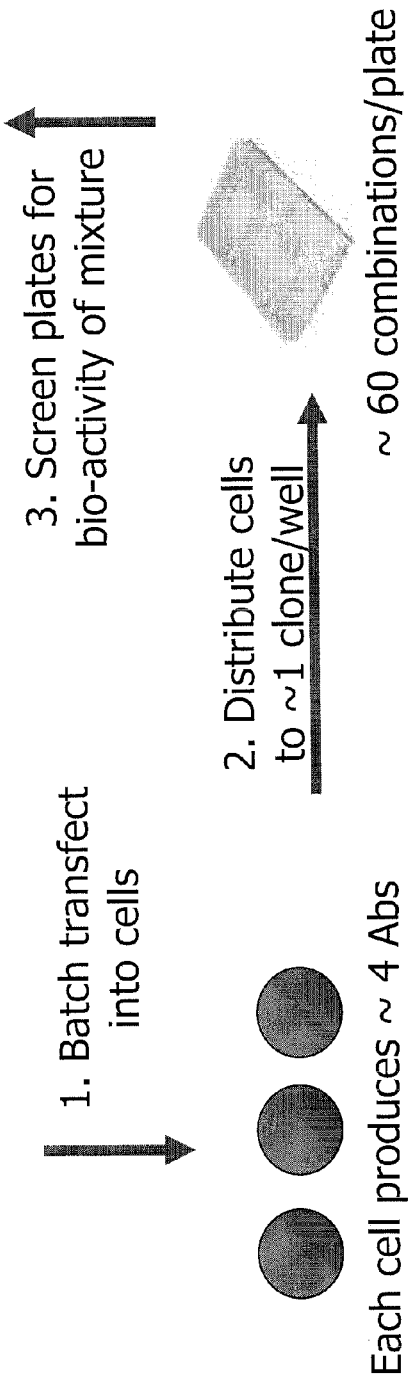
FIG. 9 pSCFV polylinker sequence

```
--pel B leader ---------      -- VH insertion ---      ----linker----
  A   A   P   A   M   A    Q   V   Q   L   Q   V   T   V   S   S   G   G   G
 GCG GCC CAG CCG GCC ATG   GCA CAG GTC CAG CTG CAG GTC ACC GTC TCG AGT GGT GGA GGC
---Sfil--------                   --PstI--                       --XhoI--
        --NcoI---                              --BstNI--

----linker----                              ---- VL insertion --------
 G   S   G   G   G   S   G   G   G   G   S   D   I   E   L   T   E   I   K
GGT TCA GGC GGA GGT GGC TCT GGC GGT GGC GGA TCG GAT ATC GAG CTC ACT GAG ATC AAA
                                            -EcoRV-  -SalI- ---------- c-myc tag ----------
 R   A   A   A   E   Q   K   L   I   S   E   E   D   L   N   *       (SEQ ID NO:47)
CGG GCG GCC GCA GAA CAA AAA CTC ATC TCA GAA GAG GAT CTG AAT TAA      (SEQ ID NO:46)
---NotI---
```

- The polylinker sequence of pSCFV, a pUC119-based plasmid suitable for stepwise cloning of antibody variable regions and expression of scFv fragments.

Enzyme sites :
SfiI : GGCCNNNN/NGGCC (SEQ ID NO:149)
NotI : GC/GGCCGC (SEQ ID NO:150)
ApaLI: GTGCA/C (SEQ ID NO:151)
XhoI : C/TCGAG (SEQ ID NO:152)
SacI : GAGCT/C (SEQ ID NO:153)
PstI : CTGCA/G (SEQ ID NO:154)
NcoI : C/CATGG (SEQ ID NO:155)
SalI :GTCGAC (SEQ ID NO:156)
BstEII: GGTNACC (SEQ ID NO:157)
EcoRV : GAT/ATC (SEQ ID NO:158)

FIG. 13

Comparison of light chains of three hybridomas

```
Clone      CDR1                                                    CDR2                                CDR3
JA : EIVLTQSPATLSLSPGERATLAC RASQTASRYLA    WYQQKPGQAPRLLIY DTSNRAT GIPARFSGSGSGTDFTLSISSLEPEDFAVYYC QQRFNWPWT  FGQGTKVEFKRT
                                                                                                                (SEQ ID NO:110)
JB : SYVLTQPPSVSVAPGKTARINC GGNNIEYRSVH     WYQQKSGQAPVAVIY DNSDRPS GIPERFSGSKSGNTATLTISRVEAGDEADYYC QVWDISSDVV FGGGTKLTVL
                                                                                                                (SEQ ID NO:112)
M57: QSALTQPRSVSGSPGQSVTISC TGTSSDIGGYNFVS  WYQQHPGKAPKLMIY DATKRPS GVPDRFSGSKSGNTASLTISGLQAEDEADYYC CSYAGDYTPGVV FGGGTKLTVL
                                                                                                                (SEQ ID NO:114)
```

FIG. 16

CDR1        CDR2
EVQLLESGGGLVQPGGSLRLSCAASGFTFS NYAMS WVRQAPGKGLEWVS AISASGHSTYLADSVKG

CDR3
RFTISRDNSKNTLYLQMNSLRAEDTAVYYCAK DREVTMIVLNGGFDY WGQGTRVTVSS (SEQ ID NO:109)

FIG. 18A

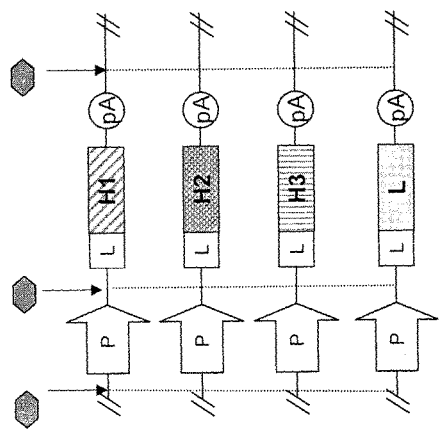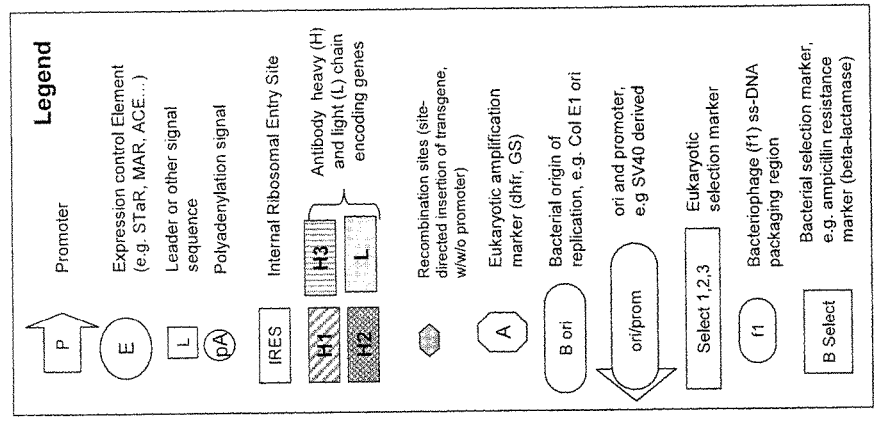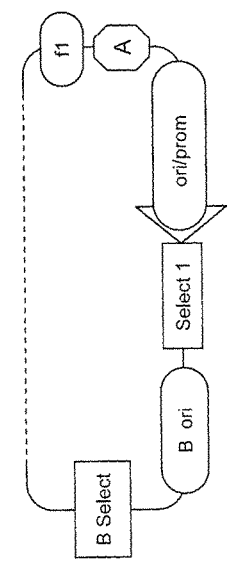
FIG. 20

Design of a hybrid light chain library for h4D5v8 and 2C4 :

```
             CDR1                                   CDR2
             24      30                             53
h4D5: DIQMTQSPSSLSASVGDRVTITC RASQDVNTAVA WYQQKPGKAPKLLIY SASFLYS (SEQ ID NO:160)
2C4 : --------------------- K-----SIG-  --------------- ---YR-T
HYB1: --------------------- X-----XXX-  --------------- ---XX-X
HYB2: --------------------- ------S---  --------------- ---XX-X

CDR3
                                       91   95
h4D5: GVPSRFSGSRSGTDFTLTISSLQPEDFATYYCQQ HYTTPPT FGQGTKVEIKR
2C4 : --------------------------------- Y-IY-Y- ----------
HYB1: --------------------------------- X-XX-X- ----------
HYB2: --------------------------------- F------ ----------
```

*FIG. 23* human germline IGKV1-39/J DNA (SEQ ID NO:84)
  1  GAC ATC CAG ATG ACC CAG AGC CCC AGC AGC CTG AGC GCC AGC GTG GGC GAC AGA GTG ACC ATC ACC TGC AGA GCC AGC
 79  CAG AGC ATC AGC AGC TAC CTG AAC TGG TAT CAG CAG AAG CCC GGC AAG GCC CCC AAG CTG CTG ATC TAC GCC GCC AGC
157  TCC CTG CAG AGC GGC GTG CCC AGC AGA TTC AGC GGC AGC GGC TCC GGC ACC GAC TTC ACC CTG ACC ATC AGC AGC CTG
235  CAG CCC GAG GAC TTC GCC ACC TAC TGC CAG CAG AGC TAC AGC ACC CCC ACC TTC GGC CAG GGC ACC AAG GTG
313  GAG ATC AAG human germline IGKV1-39/J Protein (SEQ ID NO:85)
  1  DIQMTQSPSS LSASVGDRVT ITCRASQSIS SYLNWYQQKP GKAPKLLIYA
 51  ASSLQSGVPS RFSGSGSGTD FTLTISSLQP EDFATYCQQ  SYSTPPTFGQ
101  GTKVEIK human germline IGLV2-14/J DNA (SEQ ID NO:86)
  1  CAG TCT GCC CTG ACC CAG CCC GCC TCT GTG TCC GCC AGC CCT GGC CAG CCC AAG GCC ACC ATC AGC TGC ACC GGC ACC
 79  AGC GAC GTG GGC GGC TAC AAC TAC GTG TCC TGG TAT CAG CAG CAC CCT GGC TAT TTC AGC CCC AAG CTG ATG ATC TAC GAG
157  GTG TCC AAC AGA CCC AGC GGC GTG AGC AAC AGA TTC AGC GGC AGC AAG AGC GGC AAC ACC GCC AGC CTG ACC ATC AGC
235  GGC CTC CAG GCT GAG GAC GAG GCC GAC TAC TAC TGC AGC AGC TAC ACC AGC TCC AGC ACC CTG GTG TTT GGC GGC GGA
313  ACA AAG CTG ACC GTG CTG human germline IGLV2-14/J Protein (SEQ ID NO:87)
  1  QSALTQPASV SGSPGQSITI SCTGTSSDVG GYNYVSWYQQ HPGKAPKLMI
 51  YEVSNRPSGV SNRFSGSKSG NTASLTISGL QAEDEADYYC SSYTSSSTLV
101  FGGGTKLTVL Rat IGCK allele a DNA (SEQ ID NO:88)
  1  AGA GCC GAC GCC GCT CCC ACC CCC GTG TCC ATC TTC CCC CCC AGC ATG GAA CAG CTG ACC TCT GGC GGA GCC ACC GTG GTC
 79  TGC TTC GTG AAC AAC TTC TAC CCC AGA GAC ATC AGC GTG AAG TGG AAG ATC GAC GGC AGC AGG CAG GAC GGC GTG
157  CTG GAC AGC GTG ACC GAC CAG GAC AGC AAG GAC AGC ACC TAC AGC ATG AGC AGC ACC CTG ACC CTG ACC AAG GTG GAG
235  TAC GAG AGG CAC AAC CTG TAC ACC TGC GAG GTG GTG CAC AAG ACC AGC TCC AGC CCC GTC GTC AAG AGC TTC AAC CGG
313  AAC GAG TGT

*FIG. 37A*

Rat IGCK allele a protein (SEQ ID NO:89)
  1 RADAAPTVSI FPPSMEQLTS GGATVVCFVN NFYPRDISVK WKIDGSEQRD
 51 GVLDSVTDQD SKDSTYSMSS TLSLTKVEYE RHNLYTCEVV HKTSSSPVVK
101 SFNRNEC IGKV1-39/J-Ck (SEQ ID NO:90)
  1 GGT ACC GCG GCC ACC ATG GAC ATG AGA GTG CCC GCC CAG CTC CTG GGG CTC CTG CTA CTC TGG CTC CGA GGT AAG
 79 GAT GGA GAA CAC TAG GAA TTT ACT TGT TTT TAT GTT TCC AAT CAT CTC AGG TGC TCA GTA CTG GGA AAG GAT AAC ATG
157 ATT AAT AGT AAG CGC GAG CCC TGG CAG CCC CAA GAG CAT CAC CCA GAG ATG CAG AGC CAG CCA GAT CAG CCC GAA CTG
235 CAG CCT GAG CGC CGT CGG CGA CAC CCC CAA CTT GAT GCT CAC CCT GCA CGC CAG AGC CGG CAG CTT CGC GCC CAG CAG
313 GTA TCA GCA GAA CAG GCC CTC CGG CAC CCC CGG CCA CAT CGG GAT CAA GGT GGA AGC CGA CGC CGC TCC
391 ATT CAG CGG CAG GAG CTA CAC CAC CCC CAG CAT GGA GAA GCT GAC CTT GGT CGT GCT CTG GAA CGA CGC CAA CTT
469 CTG CCA GCA GAG CTC CAT CTT CCC CCC CGT CAC GTG CAG ACA GAT GAG CAG CGG GCA GAG GGA CAA GAG CGT GAC CGA
547 CAC CGT GTC CAG AGA CAT CAG GAA CAT CTA CAC CTA CAG CAT GAG CAT GAG CAT GGA GTA CGA GCA CAA CCT
625 CTA CCC CAG CAA GGA GAA CTA GGA GAA CTC CGT CAC CAG GAA GTG GAA GAT GAG CAG CCT GAG CAC CCT CGT GAA TAG
703 CCA GGA CAG CAC AGA CAA CAG CTA CAG GGA CTC CAC CAT CAG GGA CAG CAC CCT GAG CAT CAG CCT GAG CAA CAA CCT
781 GTA CAC CTG CGA GGT GGT GCA CAA GAC CTC CAA CCC CGT CAA CCG GAA CGA CAA CCG GAA CGA GTG TAG AGC TAG
859 CGA GCT C IGLV2-14/J-Ck (SEQ ID NO:91)
  1 GGT ACC GCG GCC ACC ATG GAC ATG AGA GTG CCC GCC CAG CTC CTG GGG CTC CTG CTA CTC TGG CTC CGA GGT AAG
 79 GAT GGA GAA CAC TAG GAA ATT TGT TTT TAT GTT TCC AAT CTC AGG TGC CCT GAC ATG TCA AAG TTC TCT GAT AAC ATG
157 ATT AAT AGT AAG CCC TGG CAG AAT CAT CAC CGG CAC CGG CAG ATG TCA GTC TCA GTC TGC CCT GAC GTC CGG CAA GCC CGC CTC
235 TGT GTC CAG AGA CCC GCA CGG CAG GAT CTA CAC CAG GAT CTG CAA GCT CAG GAT CTA CAC CAG GAA CCA GAG CAG CGG CGG CTA CGT
313 GTC CTG GTA TCA GCA GAA CCC CGG CAA GAG CCC CAA GCT CCT CAT CTA CCG GAA CAA CCA GCG GCC TGA CGA AGC CGT GAG CGG CGT GAG
391 CAA CAG CTA CTG CAG CAG ATT CAG CGG CAG CTA CAC CAG CAC CAC CGC CCT GGT GTT TGG CGG AAC GCT GAC CGT GCT GGC AGC CGA
469 CTA CGC TCC CAC CGT GTC CAG CGT CCC GGG GAC CTC TGG GCA GCA GAG GGA CGA GAG CGG GGA CGT CTT CGT
547 CGC CAA CTT CTA CCC CAG AGA CAT CAG CGT GAA GTG GAA GAT CGA GAT GAG CAG CCT GAG CAC CCT CGT GGA GTA CGA GAG
625 GAA CAA CTT CGA CAG CAC CGA GGA CTC CAC CAC CAG CAG CAG CAT CAG CCT GAG CAC CCT GAG CCT GGA GTA CGA GAG
703 CGT GAC CGT GTA CAG CGA CAA CTG CGA GGT GCA CAA CAG CAA GGT CAA CCG GAA CGA GTG
781 GCA CAA CCT GTA CAC CTG CGA CAA CTC CAA CCC CGT CAA CGG GAA CCG GAA CGA GTG
859 TTG AGC TAG CGA GCT C

FIG. 37B

VkP-IGKV1-39/J-Ck (SEQ ID NO:92)

```
12637 CCA TAT CTC CCC ACC CAT CCC CCA TAC CAG ACT GGT TAT TGA TTT TCA TGG TGA CTG GCC TGA GAA GAT TAA AAA AAG
12715 TAA TGC TAC CTT ATT GGG AGT GTC CCA TGG ACC AAG ATA GCA CTC GTC ACC GTC TCC AAC AGC CTG AGA
12793 AGA CCC TTT GAG GAA CTG AAA ACA CCT TAG GCA CAT CTG CTT TCG CCT ACC CCA GCA TCC GGC CAA GGC TGT ATC
12871 GGT GCA CTC CAC ACC CTT TCA AGT TTC CAA CTC ATA TCT TGT TTG ATA TTA CTC AAG GCA AAT CTA TAG CAG
12949 CAG CAC TGG GAT AAT GAT GAA AAT CCA ACT CAA CTT GGA ATA ATC AGT AGT GAA GAC TTC TGA TAT GGT AGT CCC GCC
13027 TCC CAA TCA TGC TTT TGC ACA GTC AAA GAT GTT TCA TGG GCT TCA TGG ACG TTC TGA TAC CTG AGA GTG GCA AAA
13105 CAT ATA CCA TAT AAG TGT GCT AAA TAG TTT GGC CAT CTT TAG GCT GAG AGA AAT ACA GCG ATG AGC ATT GCA
13183 AAT AGT AGT TTG TCA GTA AAC ACC CCA CAA CCC ATA ACA GAA GTA TTC TCT TCT ATC CCT TTT CCA TCC ATG TAG
13261 GGA TAG CTC TTC ATA TTT GTT CTA GAC CGG CC
13339 ATG

VkP-IGKV1-39/J-Ck-∆1 (SEQ ID NO:93)
   1 GGC CGG CCC ACA TGA AAC AAT GGG AAC CAT GTG ACA ATC ACA GAG GTG TTG TTA CTA TAG CAA AAG GGA TTG TTA CTC
  79 TCC ACA TCC CTT TAA GTA ACT TGA AGG CCT ATC CAA CCC CTC ATT AGA CAT TTT CTA CGA ATG TTT GTT
 157 ATA CTC TCC TGT ATA CTC CCA ATA CAA CCT CTC TCA AGA GAA ATA TTC AGT AGC TCC CTC CAG AGC CTG TGC GAC
 235 TTT TTT CCT TCA AAA TAT CTC TTG GGG GAC ATT GCC CCT GTG AGT TAC ACA GCC CTC TGA TAA CAT CTA TGC TCA
 313 GCT GGT CTG ACC TGG CCC TGC TGA TTG ATT TGC ATG AGT TTC CAG AGC ACA GCC CCC TGC CCT GAA GAC TTC TAT ATG GGC TGG
 391 GCC TGC TGC ATG CCC TGA TTT TCA GTC TCA GTC GAG AGC CAC CTA GGA TAC TGA AGT CTG GTC GTG CCA GCT CCT
 469 TCG CAC CCT GTG GCT CCT GTG TAA CAT GAT TAT TTT TTA TGT CAA TCT CAG GTG CCA GAT GTG ACA
 547 GCT AGG GAA GTT CTC TGA GTT CCC CCC TGA CAT TAG CGG TGG CCG ACA GAG TGA CCA TCA CCT GCA GCC AGA
 625 TCC AGA CCC AGC ACT TCT TAG CAT GAT TAT GCG AAG AGC CCC CCA AGC TGC TGA TCT ACG CCG CCA GCT CCC
 703 AGA TCA GCA GCT ACC TGA ACT GGT ATC AGC AGA AAG GCA AGC GCT ACA AGC ACT TCA CCC TGA GCT CAC AGC AGC
 781 GCA TCA GCA GCT ACC GCG ACT GCT AGC ACT GCG AGC GCG AGC AGG CCG GCT ACA CCT CGA CCT CGA GAC GTG ATG TGG GCT
 859 TGC AGA GCG ACT TCG CCA ACT CAG TCT TTC ACA CAG CAT TAC GTC AGT GGT TAT CAT CGA GAC CTG AGC
 937 CCG AGG GCT TCA TCG CCG GTA ACT CGG CCC CTG GGG ATT GTT CTG ACG ACT TCA CTT TAC ACA ATC ATC
 1015 TCA AAC GTA AGT ACA CTT TTC TCA ATT ATG TGT AAG CAG CAG TGG AAT TAC AGT AAA CAG GTT AAG GTC AGT TCA
 1093 GAA AAT CTT GAG AAA ATG GAG AGG GCT TTT AGT TGA GAG GAA AGT TGA GAG GAA TCA GAG ACG AGT CTG AGA ATT GGG AGA
 1171 GTG AGA TTA GGG GCA AAA AGA AGA GGC ATT GTT GAA ATC CAA GAT ATA CCG TAC TGG TCT TTA AGA GAT TGG AGA
 1249 GGA GAA TAA GCA TGA ATT CTG AGT TCG AGG ATA GAA CAA AGT CGT GGA AGG CCA TCA TAC AGT CGG ATG AGA
 1327 TTT GGA GGG GAT GAG ATA AAC TGA AGG AGG ATG AAG CAG CAG AGT CAG TCA TCT GTA AAG AGG CTC TGA GAA
 1405 GAG AAG ACT CAT CCG TGT TGA GTT TCC ACA AGT ACT CTG AGT TTT GCA ATA AAA CAG TGG GGA TAG CAG AGT TGA
 1483 GAG AAG GAG CGT AGG CTG TCT CTC ATT TGT CTC CTA AGT TAT GAC AAA AAT CAG TAA GTC CTG AAA TAA
 1561 GTG AGC CTG AGG AGG TAA GTA TGA AAA GCC ATG TAG TGG CTT AAA TGG GAA TAA CAG TTC CAG AGA GTG TGA CTC
 1639 TCA TTA AGC TGT TTG AAA GTA TGA CTC CTT GTG CTT GCG ATG GCC AGT TAG CTA GGA ACG AGT CCT TGA CAG ACA GCT CAA GGG GTT
 1717 TTA TTC TAA AAT TTG TCA CAA AAT CAT GTC AGA AAT TGA TAA ATT TGA AAT GAT CTT TTT GTT TCC CTA AAA ACA GTT GGG
 1795 TTT TTC CTT CTT ATT TCT ACA ACG ACT TTG TAA GAC GTT TGG TCC TTA CTG TAT GTT ATT ACT CGA TTG TAA
 1873 TTT GAA CTA TAT GTT TTA ATG GCC AAT GGA CTG AAA CGG ACC TCT TTA CAT CCC TAG CAC CTC GTG CCA GCC
 1951 TAT ATC GCC AGC CCC TGC CCC GCC TCA AGC AAT GGA AAT ACT TCC GCA TGT GAA CCC CCG TAG CAC CTT CCT
 2029 ATT TGG CGT TCA GGG CCA TAA GGG CTG TAA GCC CAC TAA TCT GAA AAC AGA GAC TAC ACT AAT GTG AGA AAA ACA
 2107 GAG GCA CAG TGA GAA TAG CAC AGC CAC CAG CAG
```

```
7957  AGT TAA ATA AGT TAT ATT GTA GAA AAG GTA GAG AGG AGA ATA GTG GAA AGA GAT AAG GAG ACT TCA AAA GGA GTG
8035  GAC GGA GAT AGA CAG GAT GGA GAA AGC AGA AGC TGA CTT TCT AAT GGC TGA TAG ACA CAG GAA CAG AAA AGA GGA
8113  AGC CAG GGG TAT TTC GCC TAT CTG CTT TCT GCA CAT AAC AGT CTC ATG CCC AAT TAT TGA GTT CAA GGC TTA ATT
8191  CTT CAC CTT GCC CTC AAC AGA GTC TTT TTA TAG GTT GGT AAC TTT GTG AAG TGC ACA CTG AGA TGT GTA TCA GGT CCT
8269  CTT ATC TCC TTA TAG CTA TGT TTA TAA CTG GGT AAC TTT GTG AAG TGC ACA CTG AGA TGT GCT ACA
8347  ACT TTT TAA TAC AAA ATT TTG AAG AGT TTG TAC AAT GTA TGT ATA ATT ATA TAT TTA ATT GCA CTT TAG ATT TTG
8425  ATT TCA ACT CAA GAT ACT TCT ATA TAT AGT GGT TAA ATC CCT GGA ACC TTT GTA GAC CAG GCT GGC CTC
8503  TAT TGT GGT TTT CGA GAC AGG GTT TCT CTG TGT AGC CCT GGC TGT CCT GCC TCT GCC TCT GCC TCT
8581  AAA CTC AGA AAC CTA CCT GCC TCT GCC TCT GCC TCT GCC TCT GCC TCT GCC TCT TGG AAT TAA AGA TTT GCG CCA CCA CGC GTG
8659  GCC TCT GCC TCT ATA TAT GTC TCA TTC TAT CAG ATA GGA CTG TGT AGA CTG TGC TAA ACT AAT AAA TGT
8737  GCC AGA AAC CTA CCT GCC TCT ATA TAT GTC TCA TTC TAT CAG ATA GGA CTG TGT AGA CTG TGC TAA ACT AAT AAA TGT
8815  AAA TTT TTA AAC TTT GCT TGT TGT TTT GCT TTG CTT TGC TTT CTT TTG CTT TTG GGT
8693  GCC CTC AAA AGT AAT CGC AAG TTG CTT GCT TTG CTT ACT CTT AAG CTC ATG AAG CTC TGG GAA CTC ACT ATA TAG ATC
8971  TGC TTT GCT TTC CCG GGG GAG CGA TGG AGA AAG AAT CTT ACT ATG AAG CTC ATG AAG CTC TGG GAA CTC ACT ATA TAG ATC
9049  TTT TTT GCT TGT TAT GCT TGG AGA AAG AAT CTT ACT ATG AAG CTC ATG AAG CTC TGG GAA CTC ACT ATA TAG ATC
9127  AGG CTT GAT TCA ACT CAT AGA GAT CTG CCT TCT GCC TCC CAA CTG CTG GGA ATA AAG GCA TAC ACC TCC ATG CCC
9205  AGA TAG TGA TCC CAA GTT TTA GCA ATA GTT TCT AGA CTT AGA TAG ACA TAG AGA TAG AGT CAA AGA
9283  ACT AAT GTG GAG TTT ACC TGA ATC ATA CTC TAT ACT TTA TCA GAG ATT CTT CAG AGT CTT ATA CTG TGT GGG GCA ATA
9361  TAC AGG CAC CAT ATA CAG ATG AGA ATG ACC TTT GCC ATC ATG CAT AGG CTT ACT GGT TAG TTC ATA TTG TTA AAG CCA TTG GGG GCA ATA
9439  TTA CTC ATT ATA CAG ATG AGA ATG ACC TTT GCC ATC ATG CAT AGG CTT ACT GGT TAG TTC ATA TTG TGA GCA
9517  TTA ACC TTT TAC TTT GCT GTA TTT TAA TGT ATA ATT TTA CCA CTG ATT TTT ATT TTT AAC ATT TAT
9595  AAG AAA TAA ATG AAA TAC ATG GAC AAA ATA CAA TAT GAT ATT TTT TTA TTA CAA CCC TTT TTT ATT TTC ATT TCA AAT
9673  AAA GAA AAA AGT CTT TGA TAA GAT TCA GAT TTG TCT CTA TAA CTC CTT CCA TGG GTA TTT TGT TCC CTG GCA TTC
9751  GCT ATC CCC AAA GCC TAT ACC TTC CCC TAT GAT CTT CAA AAA ACC AAG GGC CTC TCC TCT CAT ATT AGG CCA TCT TTT
9829  CTC TGT ACT GAG GCA TAT GAT CTT CAA AAA ACC AAG GGC CTC TCC TCT CAT ATT AGG CCA TCT TTT
9907  GCT ACA TAT GCA ACT AGA GAC ACA GTG GGG ACT GGT ACT CTT TCC ATC AGT TGG TTA AGT TGC AGA
9985  CCC CTT TAG CTC CTT GGA TAC TTT CTC GGA TTC CCT CAT TAG GGG TTC CTT CAA TCC AGA CTG TGA GCA
10063 TCC ACT TCT GTA TTT GCC AGG CAC TGG CAT AGC CTC ACG AGA AAG AGA CTA TGT CAG GAG CTA CCT GTC AGT AAA ATC
10141 TTT CTG GCA TAT GCA ATA GTA TCT GGG TTT GGT GGT TGT ATA TCC CCA AGT TGC GTC TCT GAA TGG
10219 TCC TTC CTT CCA TCT CAG CTC CAA ACT TTG TCT CTA TAA CTC CTT CCA TGG GTA TTT TGT TCC CTG GCA TTC
10297 GTG AAG AAT CCC AAA GCC TAT ACC TTC CCC TAT GAT CTT CAA AAA ACC AAG GGC CTC TCC TCT CAT ATT AGG CCA TCT TTT
10375 ATA TCC ACG TAT CAG TGA GTG GCA GTT GTT ATT TTG GTT ATG TGT GTT ACT CTA GGT ATA TGC GGA GAA TTG CTG GAT CTT
10453 ATG CAT ATC CCA TTT GCC CAT CAT CAG AGA TTC ACT GCT TTT AAT TGC TGA AAT TGT GTA AAT GTA CCA
10531 CAT TAT TTT CTG CAT TCC CTT GGT GTC CTC ATT CTT CCT AGT GGT ACT GGA GAG AAC ATA TTC CAA CAT AAT
10609 GAG CAT AGC GGA GCA CAA TGC ACA AGG TTG GAA AGC TCT AGA AGG ACT CTA AGA AGG ACT ATA AGC TCC ATT AAA ATC AGA
10687 CCG GTA GTA CCA TCA TGT CTT AAT AAA ACC CCT GTA GGC CAC CAA TAT ATA AAA CCA TTA TCC ATT AAA ATC AGA
10765 AAA GCT TAT GTA TGA TCA ACT ACT CCT ATT TGT ATG AGC ATT AGC ATT TGG AAA TAA AGG AAT TGG CAA TGC GGA ATA
10843 GGA CTG CCC ACT ATC CCT ACT TCT AAA TTG GTC ATA TAT GAT GAT TTA TAC ATC TTA ACC TCA AAT TTT GAC
10921 CAA ATG GGA AAA TAT TGT CTC AAA TTT CAG CAA AGT GTT ATG ATG CAC CAG CTT CAC ATT CTT CCC AGC TTC
10999 TAG AAA AAT TGT CTC TCT TCT TGC CTT TCA TCC TTT CTG TCC TCT GCA CTC CCT TTG TCT CAA GAC TGA GTG CAG
```

|      |     |     |     |     |     |     |     |     |     |     |     |     |     |     |     |
|------|-----|-----|-----|-----|-----|-----|-----|-----|-----|-----|-----|-----|-----|-----|-----|
| 3901 | AAA | GGC | CAG | CAA | AAG | GCC | AGG | AAC | CGT | AAA | AAG | GCC | GCG | TTG | CTG | GCG |
| 3979 | CAT | CAC | AAA | AAT | CGA | CGC | TCA | AGT | CAG | AGG | TGG | CGA | AAC | CCG | ACA | GGA |
| 4057 | AGC | TCC | GTG | CGC | TCT | CAT | AGC | TCA | CGC | TGT | AGG | TAT | CTC | AGT | TCG | GTG |
| 4135 | GCG | CTT | TCT | CAT | AGC | TCA | CGC | TGT | TGC | GCC | TTA | TCC | GGT | AAC | TAT | CGT |
| 4213 | CCC | GTT | CAG | CCC | GAC | CGC | TGC | GCC | TTA | TCC | GGT | AAC | TAT | CGT | CTT | GAG |
| 4291 | CCA | CTG | GCA | GCA | GCC | ACT | GGT | AAC | AGG | ATT | AGC | AGA | GCG | AGG | TAT | GTA |
| 4369 | CCT | AAC | TAC | GGC | TAC | ACT | AGA | AGA | ACA | GTA | TTT | GGT | ATC | TGC | GCT | CTG |
| 4447 | GGT | AGC | TCT | TGA | TCC | GGC | AAA | CAA | ACC | ACC | GCT | GGT | AGC | GGT | GGT | TTT |
| 4525 | AAA | AAA | GGA | TCT | CAA | GAA | GAT | CCT | TTG | ATC | TTT | TCT | ACG | GGG | TCT | GCT |
| 4603 | ATT | TTG | GTC | ATG | GCT | AGT | TAA | TTA | ACA | TTT | AAA | TCA |     |     |     |     | pSelect-IGLV2-14/J-Ck (SEQ ID NO:97)

|      |     |     |     |     |     |     |     |     |     |     |     |     |     |     |     |     |
|------|-----|-----|-----|-----|-----|-----|-----|-----|-----|-----|-----|-----|-----|-----|-----|-----|
| 1    | GCG | GCC | GCA | ATA | AAA | TAT | CTT | TAT | TTT | CAT | TAC | ATC | TGT | GTG | TTG | GTT |
| 79   | TCC | ATC | AAA | ACA | AAA | CGA | AAC | AAC | AAC | TAG | ACA | AAC | TAG | AGG | TCC | CAA |
| 157  | TCT | ATC | GAA | GGA | TCT | GCG | ATC | GCT | GCC | GTG | CCT | AGT | GGT | GGG | CAG | CAT |
| 235  | GGG | GAG | GGG | TCG | GCA | ATT | GAA | CGG | GTG | CCT | AGA | CGT | ATA | GGT | GTA | ACT |
| 313  | TCC | GCC | TTT | TTC | CCG | AGG | GTG | GGG | GAG | AAC | GTT | TAA | TAG | GGA | CTA | GTG |
| 391  | TTG | CCG | CCA | GAA | CAC | AGC | TGA | AGC | TTC | GAG | GGG | TCT | CTC | CTT | GCA | TCT |
| 469  | ATC | CAC | GCC | GGT | TGA | GTC | GCG | TTC | TGC | CGC | CTC | GCG | TGT | GGA | TCC | CCT |
| 547  | TAA | AGC | TCA | GGT | CGA | GAC | CGG | GCC | TTT | CGT | TTT | CTG | TTA | GAG | CCC | CCA |
| 625  | GCC | TGA | CCC | TGC | TTG | CTC | AAC | TCT | ACG | TGG | CCA | TGA | AGA | CTC | AGC | TGC |
| 703  | CGC | CTA | CCT | GAG | ATC | ACC | GGC | GTG | GGC | CCA | AAC | ACT | AGG | AAT | TTA | CTC |
| 781  | TCT | GGC | TCC | GAG | GTA | AGG | ATG | GAG | AAC | ACT | AGA | ATA | TTT | GTT | TTT | ATG |
| 859  | AGT | TCT | CTG | ATA | ACA | TGA | TTA | AGA | ATA | GTA | TCT | GGC | AGC | CCT | CAG | ATC |
| 937  | CTG | ACC | CAG | CCC | GCC | TCT | GTG | TCC | TAT | GAG | CAG | CAC | AAG | CCC | GGC | CAG |
| 1015 | GGC | TAC | AAC | TAC | CTG | TCC | TGG | TAT | CAG | TTC | TAC | CCA | GCA | GCC | CCC | AAG |
| 1093 | AGA | CCC | AGC | GGC | GTG | AGC | GAC | AGA | TTC | TGC | GGC | AGC | AAG | AGC | GGC | AAC |
| 1171 | GCT | GAG | GAC | GAG | GCC | GAC | TAC | TAC | TGC | AGC | TCC | TAC | GTG | TCC | AGC | AGC |
| 1249 | ACC | GTG | GTC | TTC | GGC | GGA | GGA | ACC | AAG | CTG | ACC | GTG | CTA | TTC | CCA | CCA |
| 1327 | GAC | GGC | GTG | TGC | CTG | GAC | AGC | GGC | GTG | CAC | CTG | GTG | GTG | TGC | CTG | ATC |
| 1405 | AAG | GTG | GAG | TAC | GAG | TGT | TGA | GCT | AGC | TGG | CCA | GAC | ATG | ATA | AGA | TAC |
| 1483 | TTC | AAC | CGG | TAC | AGC | GCC | TCT | GTG | TCC | TGG | TCT | CCT | CAG | CAC | CAA | ACC |
| 1561 | CTG | ACT | CAG | CCT | TAT | AAC | GTC | TCC | TCT | CAT | GTT | TGT | GAT | ACC | ATG | ACC |
| 1015 | GGT | GGT | TAT | AAC | GGG | TTT | TCT | AAT | GCT | TCA | TAT | ACA | TCC | AAA | ATC | ATG |
| 1093 | CGG | CCC | TCA | GGG | GTT | TCT | GAT | TAT | TAC | TGC | TCA | TAT | ACA | AGC | AGC | AGC |
| 1171 | GCT | GTG | GAC | GCT | GAT | GCT | GCA | AAC | TTC | GTA | TAA | TGT | ATG | CTA | TAC | GAA |
| 1249 | ACC | GTC | CTA | CGG | TGC | GTG | AAC | ATC | AGT | GTC | GAA | CAG | ATT | GAT | GGC | AGT |
| 1327 | ACA | GTC | GTG | TTC | GGC | TCA | GGA | ACC | AAG | CTG | ACC | GTC | CTA | GGT | CAG | CCC |
| 1405 | GAT | GGT | GTC | CTG | GAC | AGT | GTT | ACT | GAT | CAG | GAC | AAA | GAC | AGC | ACC | TAC |

MV1043 (SEQ ID NO:98)

```
   1 CTT GAT TTG GGT GAT GGT TCA CGT AGT GGG CCA TCG CCC TGA TAG ACG GTT TTT CGC CCT TTG ACG TTG GAG TCC ACG
  79 TTC TTT AAT AGT GGA CTC TTC TAT GGC CAA ACT GGA ACA ACA CTC AAC TCT ATC TCG GGC TAT TCT TTT GAT TAA GGG
 157 ATT TTG CCG GTC ATT TCG GTC TTA AAA CTG ATT GAG CTG TAA CAA TTT AAC GCG AAT TTT AAC CGA CCC CAC ATA TTA
 235 ACG TTT ACA ATT TGG TGC AGT CTC AGT TGC TCT GCA ATC TCT GAT GCC GCA TAG TTA AGC CCC GTG ACC GTC TCC GGG CCA
 313 ACA CCC GCT GAC GCG ACG TGT CTG CGG CTG GCT TGT CCG CGG CCG AGA CAA GCT GTG AGG CTC GTA TTT TTA TAG
 391 TGC ATG TGT CAG AGG TTT TCA CGA TCA ATG GTT TCT TAG ACG GGC ATG AGA CGA ATA CGC GGA ACC CCT ATT TGT
 469 GTT AAT GTC ATG ATA ATA CAT TCA AAT ATG CCG CTC ATG GGC AGA CAA CCC TGA TAA ATG CAA TAA TAT TGA AAA
 547 TTA TTT TTC TAA AGT ATG AGT ATT CAA CAT TTC CGT GCC CTT ATT CCC TTT TTT GCA CTT TCT CCT GTT TTT GCT
 625 AGG AAG CCA GAA ACG CTG GTG AAA GTA AAA GAT GCT CAG CGT GGT GCC CGA GTG GGT TAC ATC GAA CTG GAT CTC
 703 AAC AGC GGT AAG ATC CTT GAG AGT TTT CGC GGG GAA GTT AGC ACT TAT TCT CAG AAT GAC TTG GTT
 781 GGC GCG GTA TTA TCC CGT ATT GAC AAG CCC CAA ACG GGT ATA CAC TAT TCT CAG AAT GAC TTG GTT
 859 GAG TAC TCA CCA GTC ACA AAG GCC AAC TTA CTT CTG ACA ACG ATC GGA AGA CCG CTA ACC AAC ACC ACG
 937 GAG TAC TCA CCA GTC ACA AAG GCC AAC TTA CTT CTG ACA ACG ATC GGA AGA CCG CTA ACC AAC ACC ACG
1015 AGT GAT AAC ACT GCG GCC CTT GAT CGT TGG GCA CTA ACA GCC GAA GAA ATA CCA AAC CAA TTT GCT GAT
1093 GGG GAT CAT GTA ACT GTA ACT CGC CTT GAT CGT TGG GCA CTA ACA GCC GAA GAA ATA CCA AAC CAA TTT GCT GAT
1171 ATG CCT GTA GCA ATG GCA GTT GCA ACG TTG CGC AAA CTA TTA ACT GGC GAA CTA CTT ACT CTA GCT GAG ACC CAA TTA
1249 ATA GAC TGG ATG GCG GAT AAA GTT GCG GCA GGA CAA CTT CTG GCC CTT CCG GCT GGC TGG TTT ATT GCT GAT
1327 AAA TCT GCT CTG CTA CTA GTG GCT GGG TCT CTT ACC GAT AAG TCG TGT CTT ACC AGC ATC GTA GCA CCG CCT ATC GTA
1405 GTT ATC TAC ACG GGG AGT CAG CGG CAG AAT TAG ATT GAT TTA AAA CTT TAA TTT AAA AGG
1483 AAG CAT TGG TCA GAC CTG CAA GTT TAC TCA ATG ACC AAA ATC CCT TAA CGT GAG TTT CAT CTT TAT AGT CCT GTC
1561 ATC TAG GTG AAG ATC AAA GGA TCT TTT CTG CGC GTA ATC TGC TGC TTG CAA ACA AAA AAA CCA
1639 CCC GTA GAA AAG CAC GTG GTT TGT TTG CCG GAT CAA GAG CTA CCA ACT CTT TTT CCG AAG GTA ACG GCG
1717 CCG CTA CCA GCG GTG GTT TGT TTG CCG GAT CAA GAG CTA CCA ACT CTT TTT CCG AAG GTA ACG GCG
1795 CAG ATA CCA AAT ACT GTT CTT CTA GTG CCG GAT CAA GAG CTA CCA ACT CTT TTT CCG AAG GTA ACG GCG
1873 CTC GCT CTG CTA ATC CTG TTA CCA GTG GCT GCT CCG AGT GGT GCT ATA CAG CCC AGC TTG GAG CGA ACG ACC TAC
1951 TAG TTA CCG GAT AAG GCG AGC AGG CCA CAG CGT GAG CTT ATG AAA GCG AGA AAG GCG GAC AGG TAT CCG
2029 ACC GAA CTG AGA TAC CTA CAG GAG TCG ACA GGA GCG CTT CCA GGG CCA GTG TAT CTT TAT AGT CCT GTC
2107 GTA AGC GGC AGG GTC GGA ACA GGA GAG CGC ACG AGG GCG TGG ACG CAT CAT TAT GGT GAA AAC GCC AGC
2185 CGG GGG TTT CGC CAC CTC TGA CTT GAG CGT CGA TTT TTG TGA TGC TCG TCA GGG GGG TTC CCT TAA TGC AGG CAC
2263 AAC GCG GCC TTT TTA CGG TTC CTG GCC TTT TGC TGG CGC ATG ACC AGC AGT CCA CTA CTC ACC CCT GAT TCT
2341 GTG GAT AAC CGT ATT ACC GCC TTT GAG TGA GCT GAT ACC GCT CGC CGC AGC CGA ACG ACC GAG TCA GTG
2419 AGC GAG GAA GCG GAA GAG CGC CCA ATA CGC AAA CCG CCT CTC CCC GCG CGT TGG CCG ATT CAT TAA TGC AGC TGG CAC
2497 CAG AGG CAG TTT CAC GAC CTT CTG ATG GCG CGG AGT TAG CGC GTG TGT GGA ATT GTG AGC GGA TAA CAA TTT CAC ACA GGA AAC AGC TAT
2575 GCT TTA GAC CAT CTA GAG GTC GAC CTC GAG GGG GGG CCC GGT ACC CAG CTT TTG TTC CCT TTA GTG AGG GTT AAT TTC GAG CTT GGC GTA ATC ATG GTC ATA GCT GTT TCC
2653 GAC CAT GAT TAC GCC AAG CTT GCA TGC CTG CAG GTC GAC TCT AGA GGA TCC CCG GGT ACC GAG CTC GAA TTC ACT GGC CGT CGT TTT ACA ACG TCG TGA CTG GGA AAA CCC TGG CGT TAC CCA ACT TAA TCG
2731 AGT TGT TTA CAC TTT ATG CTT CCG GCT CGT ATG TTG TGT GGA ATT GTG AGC GGA TAA CAA TTT CAC ACA GGA AAC AGC TAT GAC CAT GAT TAC GCC AAG CTT
2809 CAG AGT CAG CAC CAC TTG CCG TGC ATC GCA GAG TTT CCC AAT CTT AAG TTA AAC AAA ATT AAC CTA GCA GAA GCC AGG AAC CGT TAA GAA AGC
2887 CCC TAA GCT CCT GAT CTA TGC ATC TGA ACC TGA AGA TTT ATC ACA TTA CTG GAT CTT CAG GAT CTT CAG AAG AGT TTA CAG AGA
2965 AGA TTT CAC CAT CAC CAT CAC CAT CAC TAA TAG ACG TTC CTA CTG TCA CTG TCA CTG ACC TTA CAG GAC
3043 TCC AAC GTT CGG CCA AGG CAA CAA GCT CTT CCA AGC TCA GTT CTC CGT GAC TCT GAC TTG AGA TGG TTA
```

```
8893  GTT CGG TGT AGG TCG TTC GCT CCA AGC TGG GCT GTG TGC ACG AAC CCC CAC TGG TTC AGC CCG ACC GCT GCG CCT TAT CCG
8971  GTA ACT ATC GTC TTG AGT CCA ACC CGG TAA GAC ACG ACT TAT CGC CAG CCA ACA GAA AAA GGA CAG TTA GCA
9049  GAG CGA GGT ATG TAG CCG GTG CTA CAG AGT TCT GGC AGT TGA ACT ACG GCT GAT CCG CTA GAA CTA CCG TAT TTG
9127  GTA TCT GCG CTC TGC TGA AGC CAG TTA CCT TCG GAA AAA GAG TTG GTA GCT CTT AAG GCA AAC CTT TGA TCT TTT
9205  GTA GCG GTG GTT TTT TTG ACG AGC TTG GCA AGC AGA ACT CGC GTT AAG GAT CTC AAG GAT TAT CAA AAA CCG CTG
9283  CTA CGG GGT CTG ACG CTG AGT GGA AAA ACT CAC GTT TGG TCA TGA GAT TAT CTG ACA GTT ACC
9361  CCT AGA TCC TTT TAA ATT GAA GTT TTA AAT GTA TCT CAA GTA TAT TTC CAT CCA TAG TTG CCT GAC TCC CCG TCG TGT
9439  AAT GCT TAA TCA GTG AGG CAC CTA TCT CAG CGA TCT GTC TAT TTC GTT CAA GTG CTG CAA TGA TAC CGC GAG ACC CAC CGG CTC
9517  AGA TAA CTA CGA TAC GGG AGG GCT TAC CAT CTG GCC CCA GTC CTG CAA GTG AGC CCG GAA GGG CCG CAA CTT TAT CCG CCT CCA TCC
9595  CAG ATT TAT CAG CAA TAA ACC AGC CAG CCG GAA GGG CTA GAG AGT GTG CAG GTT CGC GCA ACG TTG TTG CCA TTG CTA
9673  AGT CTA TTA ATT GTT GCC GGG AAG CTA GAG TTG GTA TGG CTT CGT CAT TCA GCT CCG GTT CCG AAC GAT CAA GGC GAG TTA CAT
9751  CAG GCA TCG TGG TGT TGT GCA AAA CGG TTA GAA GTA AGT GCT TTT CTG TGA CTG GTG
9829  GAT CCC CCA CCA TGG TTA AAG CAC TGC ATA ATT CTC TTA CTG TCA TGC CAT CCG TAA TGC GCT CGG CGT CAA TAC GGG ATA ATA
9907  TAT CAC TCA TGG TTA CAG CAT TCT GAG CAT GTA TGC GGC CGA CGA GTT GCT CTT CGG GGC GAA AAC TCT CAA GGA TCT TAC
9985  AGT ACT CAA CCA AGT CAT TAA AAG TGC TCA TTG CAC CCA CTC GTG GAA AAC GTT CTT CAG CAT CTT TTA CTT TCA CCA GCG TTT
10063 CCG CGC CAC ATA GCA GAA CTT CGA TGT CGA CTT TAA AAC TGT GAA TAA CAC CGA CAC TAA AGG GAA AAT GTT GAA TAC TCA
10141 CGC TGA GAT CCA GTT CGA GAA CAG GAA GGC AAA ATG CCG CAA
10219 CTG GGT GAG CAA AAA CAG GAA GGC AAA ATG CCG CAA
```

*FIG. 37Z*

SEQ ID NO:100

```
   1 atccaggcgc ggatcaataa aagatcatta ttttcaatag atctgtgtgt tggttttttg
  61 tgtgccttgg gggagggggga ggccagaatg aggcgcggcc aaggggagg gggaggccag
 121 aatgaccttg ggggagggggg aggccagaat gaccttgggg gaggggagg ccagaatgag
 181 gcgcggatcc ggagaagttc ctattccgaa gttcctattc ttcaaatagt ataggaactt
 241 cgctcgaggg atcggccatt gaacaagatg gattgcacgc aggttctccg gccgcttggg
 301 tggagaggct attcggctat gactgggcac aacagacaat cggctgctct gatgccgccg
 361 tgttccggct gtcagcgcag gggcgcccgg ttcttttttgt caagaccgac ctgtccggtg
 421 ccctgaatga actgcaggac gaggcagcgc ggctatcgtg gctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccggc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga agttttcct gtcatacttt
1141 gttaagaagg gtgagaacag agtacctaca ttttgaatgg aaggattgga gctacgggg
1201 tggggtgggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 ccccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc cccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 ccccctcccca cccccaattt tgtatttatt tattttttaa ttatttgtg cagcgatggg
2041 ggcggggggg ggggggggcgc gcgccaggcg gggcggggcg gggcgagggg cgggcgggg
2101 cgaggcggag aggtgcggcg cagccaaatc agagcggcgc gctccgaaag tttccttttg
2161 tggcgaggcg gcggcggcgg cggccctata aaagcgaag cgcgcggcgg cgggagtcg
2221 ctgcgttgcc ttcgccccgt gccccgctcc gcgccgcctc gcgccgcccg ccccggctct
```

FIG. 38B-1

```
2281 gactgaccgc gttactccca caggtgagcg ggcgggacgg cccttctcct ccgggctgta
2341 attagcgctt ggtttaatga cggctcgttt cttttctgtg gctgcgtgaa agccttaaag
2401 ggctccggga gggccctttg tgcgggggg agcggctcgg ggggtgcgtg cgtgtgtgtg
2461 tgcgtggga gcgccgcgtg cggcccgcgc tgcccggcgg ctgtgagcgc tgcgggcgcg
2521 gcgcggggct ttgtgcgctc cgcgtgtgcg cgaggggagc gcggccgggg gcggtgcccc
2581 gcggtgcgga ggggctgcga ggggaacaaa ggctgcgtgc ggggtgtgtg cgtgggggg
2641 tgagcagggg gtgtgggcgc ggcggtcggg ctgtaaccc ccctgcacc cctccccg
2701 agttgctgag cacggcccgg cttcgggtgc ggggctccgt gcggggcgtg gcgcggggct
2761 cgccgtgccg ggcgggggt ggcggcaggt ggggtgccg ggcggggcgg ggccgcctcg
2821 ggccggggag ggctcggggg aggggcgcgg cggccccgga gcgccggcgg ctgtcgaggc
2881 gcggcgagcc gcagccattg cctttatgg taatcgtgcg agagggcgca gggacttcct
2941 ttgtcccaaa tctgtgcgga gccgaaatct gggaggcgcc gccgcacccc ctctagcggg
3001 cgcggggcga agcggtgcgg cgccggcagg aaggaaatgg gcggggaggg ccttcgtgcg
3061 tcgccgcgcc gccgtcccct tctccctctc cagcctcggg gctgtccgcg ggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tcttttttgtt gtcaagcttg aggtgtggca
3361 ggcttgagat ctggccatac acttgagtga cattgacatc cactttgcct ttctctccac
3421 aggtgtccac tcccagggcg gcctccggag cgatcgccga tccgcctagg caattgttta
3481 aatcggccgg ccataacttc gtataatgta tgctatacga agttatggat cctcacagta
3541 ggtggcatcg ttcctttctg actgcccgcc ccccgcatgc cgtcccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg ttttttgtgt gccttgggg
3841 aggggaggc cagaatgagg cgcggccaag ggggaggggg aggccagaat gaccttgggg
3901 gaggggagg ccagaatgac cttggggag ggggaggcca gaatgaggcg cgccctccgt
3961 cgacctataa cttcgtataa tgtatgctat acgaagttat ggcggccgcc accatggaca
4021 tgagagtgcc cgcccagctc ctgggctcc tgctactctg gctccgaggt aaggatggag
4081 aacactagga atttactcag ccagtgtgct cagtactgac tggaacttca gggaagttct
4141 ctgataacat gattaatagt aagaatattt gttttatgt ttccaatctc aggtgccaga
4201 tgtgacatcc agatgaccca gagcccagc agcctgagcg ccagcgtggg cgacagagtg
4261 accatcacct gcagagcag ccagagcatc agcagctacc tgaactggta tcagcagaag
4321 cccggcaagg cccccaagct gctgatctac gccgccagct ccctgcagag cggcgtgccc
4381 agcagattca gcggcagcgg ctccggcacc gacttcaccc tgaccatcag cagcctgcag
4441 cccgaggact tcgccaccta ctactgccag cagagctaca gcacccccc caccttcggc
```

FIG. 38B-2

```
4501 caggqcacca aggtggagat caagagagcc gacgccgctc ccaccgtgtc catcttcccc
4561 cccagcatgg aacagctgac ctctggcgga gccaccgtgg tctgcttcgt gaacaacttc
4621 taccccagag acatcagcgt gaagtggaag atcgacggca gcgagcagag ggacggcgtg
4681 ctggacagcg tgaccgacca ggacagcaag gactccacct acagcatgag cagcaccctg
4741 agcctgacca aggtggagta cgagaggcac aacctgtaca cctgcgaggt ggtgcacaag
4801 accagctcca gccccgtggt caagtccttc aaccggaacg agtgttgagc tagcttaaga
4861 tttaaatagg ccggccgcgt cgacctcgag atccaggcgc ggatcaataa aagatcatta
4921 ttttcaatag atctgtgtgt tggttttttg tgtgccttgg gggaggggga ggccagaatg
4981 aggcgcggcc aaggggagg gggaggccag aatgaccttg ggggagggg aggccagaat
5041 gaccttgggg gaggggagg ccagaatgag gcgcgccccc gggtaccgag ctcgaattag
5101 tggatcctca cagtaggtgg catcgttcct ttctgactgc ccgccccccg catgccgtcc
5161 cgcgatattg agctccgaac ctctcgccct gccgccgccg gtgctccgtc gccgccgcgc
5221 cgccatggaa tcgcgccggt aaccgaagtt cctatacttt ctagagaata ggaacttcgg
5281 aataggaact tcaagccggt acccagcttt tgttcccttt agtgagggtt aatttcgagc
5341 ttggcgtaat catggtcata gctgtttcct gtgtgaaatt gttatccgct cacaattcca
5401 cacaacatac gagccgggag cataaagtgt aaagcctggg gtgcctaatg agtgagctaa
5461 ctcacattaa ttgcgttgcg ctcactgccc gctttccagt cgggaaacct gtcgtgccag
5521 ctgcattaat gaatcggcca acgcgcgggg agaggcggtt tgcgtattgg gcgctcttcc
5581 gcttcctcgc tcactgactc gctgcgctcg gtcgttcggc tgcggcgagc ggtatcagct
5641 cactcaaagg cggtaatacg gttatccaca gaatcagggg ataacgcagg aaagaacatg
5701 tgagcaaaag gccagcaaaa ggccaggaac cgtaaaaagg ccgcgttgct ggcgtttttc
5761 cataggctcc gcccccctga cgagcatcac aaaaatcgac gctcaagtca gaggtggcga
5821 aacccgacag gactataaag ataccaggcg tttccccctg gaagctccct cgtgcgctct
5881 cctgttccga ccctgccgct taccggatac ctgtccgcct ttctcccttc gggaagcgtg
5941 gcgctttctc atagctcacg ctgtaggtat ctcagttcgg tgtaggtcgt tcgctccaag
6001 ctgggctgtg tgcacgaacc cccgttcag cccgaccgct gcgccttatc cggtaactat
6061 cgtcttgagt ccaacccggt aagacacgac ttatcgccac tggcagcagc cactggtaac
6121 aggattagca gagcgaggta tgtaggcggt gctacagagt tcttgaagtg gtggcctaac
6181 tacggctaca ctagaaggac agtatttggt atctgcgctc tgctgaagcc agttaccttc
6241 ggaaaaagag ttggtagctc ttgatccggc aaacaaacca ccgctggtag cggtggtttt
6301 tttgtttgca agcagcagat tacgcgcaga aaaaaggat ctcaagaaga tcctttgatc
6361 ttttctacgg ggtctgacgc tcagtggaac gaaaactcac gttaagggat tttggtcatg
6421 agattatcaa aaaggatctt cacctagatc cttttaaatt aaaaatgaag ttttaaatca
6481 atctaaagta tatatgagta aacttggtct gacagttacc aatgcttaat cagtgaggca
6541 cctatctcag cgatctgtct atttcgttca tccatagttg cctgactccc cgtcgtgtag
6601 ataactacga tacgggaggg cttaccatct ggccccagtg ctgcaatgat accgcgagac
6661 ccacgctcac cggctccaga tttatcagca ataaaccagc cagccggaag ggccgagcgc
```

*FIG. 38B-3*

```
6721 agaagtggtc ctgcaacttt atccgcctcc atccagtcta ttaattgttg ccgggaagct
6781 agagtaagta gttcgccagt taatagtttg cgcaacgttg ttgccattgc tacaggcatc
6841 gtggtgtcac gctcgtcgtt tggtatggct tcattcagct ccggttccca acgatcaagg
6901 cgagttacat gatcccccat gttgtgcaaa aaagcggtta gctccttcgg tcctccgatc
6961 gttgtcagaa gtaagttggc cgcagtgtta tcactcatgg ttatggcagc actgcataat
7021 tctcttactg tcatgccatc cgtaagatgc ttttctgtga ctggtgagta ctcaaccaag
7081 tcattctgag aatagtgtat gcggcgaccg agttgctctt gcccggcgtc aatacgggat
7141 aataccgcgc cacatagcag aactttaaaa gtgctcatca ttggaaaacg ttcttcgggg
7201 cgaaaactct caaggatctt accgctgttg agatccagtt cgatgtaacc cactcgtgca
7261 cccaactgat cttcagcatc ttttactttc accagcgttt ctgggtgagc aaaaacagga
7321 aggcaaaatg ccgcaaaaaa gggaataagg gcgacacgga aatgttgaat actcatactc
7381 ttcctttttc aatattattg aagcatttat cagggttatt gtctcatgag cggatacata
7441 tttgaatgta tttagaaaaa taaacaaata ggggttccgc gcacatttcc ccgaaaagtg
7501 ccacctaaat tgtaagcgtt aatattttgt taaaattcgc gttaaatttt tgttaaatca
7561 gctcattttt taaccaatag gccgaaatcg gcaaaatccc ttataaatca aagaataga
7621 ccgagatagg gttgagtgtt gttccagttt ggaacaagag tccactatta agaacgtgg
7681 actccaacgt caaaggcga aaaaccgtct atcaggcga tggcccacta cgtgaaccat
7741 caccctaatc aagttttttg gggtcgaggt gccgtaaagc actaaatcgg aaccctaaag
7801 ggagccccg atttagagct tgacggggaa agccggcgaa cgtggcgaga aggaaggga
7861 agaaagcgaa aggagcgggc gctagggcgc tggcaagtgt agcggtcacg ctgcgcgtaa
7921 ccaccacacc cgccgcgctt aatgcgccgc tacagggcgc gtccattcg ccattcaggc
7981 tgcgcaactg ttgggaaggg cgatcgtgc gggcctcttc gctattacgc cagctggcga
8041 aaggggatg tgctgcaagg cgattaagtt gggtaacgcc agggttttcc cagtcacgac
8101 gttgtaaaac gacggccagt gagcgcgcgt aatacgactc actatagggc gaattggggg
8161 taactaagta aggatcgag
```

*FIG. 38B-4*

SEQ ID NO:101

```
   1 atccaggcgc ggatcaataa aagatcatta ttttcaatag atctgtgtgt tggtttttg
  61 tgtgccttgg gggaggggga ggccagaatg aggcgcggcc aaggggagg gggaggccag
 121 aatgaccttg ggggagggg aggccagaat gaccttgggg gaggggagg ccagaatgag
 181 gcgcggatcc ggagaagttc ctattccgaa gttcctattc ttcaaatagt ataggaactt
 241 cgctcgaggg atcgccatt gaacaagatg gattgcacgc aggttctccg gccgcttggg
 301 tggagaggct attcggctat gactgggcac aacagacaat cggctgctct gatgccgccg
 361 tgttccggct gtcagcgcag gggcgcccgg ttcttttgt caagaccgac ctgtccggtg
 421 ccctgaatga actgcaggac gaggcagcgc ggctatcgtg gctggccacg acgggcgttc
 481 cttgcgcagc tgtgctcgac gttgtcactg aagcgggaag ggactggctg ctattgggcg
 541 aagtgccggg gcaggatctc ctgtcatctc accttgctcc tgccgagaaa gtatccatca
 601 tggctgatgc aatgcggcgg ctgcatacgc ttgatccggc tacctgccca ttcgaccacc
 661 aagcgaaaca tcgcatcgag cgagcacgta ctcggatgga agccggtctt gtcgatcagg
 721 atgatctgga cgaagagcat caggggctcg cgccagccga actgttcgcc aggctcaagg
 781 cgcgcatgcc cgacggcgag gatctcgtcg tgacccatgg cgatgcctgc ttgccgaata
 841 tcatggtgga aaatggccgc ttttctggat tcatcgactg tggccggctg ggtgtggcgg
 901 accgctatca ggacatagcg ttggctaccc gtgatattgc tgaagagctt ggcggcgaat
 961 gggctgaccg cttcctcgtg ctttacggta tcgccgctcc cgattcgcag cgcatcgcct
1021 tctatcgcct tcttgacgag ttcttctgag gggatcgatc cgctgtaagt ctgcagaaat
1081 tgatgatcta ttaaacaata aagatgtcca ctaaaatgga agttttcct gtcatacttt
1141 gttaagaagg gtgagaacag agtacctaca ttttgaatgg aaggattgga gctacgggg
1201 tgggggtggg gtgggattag ataaatgcct gctctttact gaaggctctt tactattgct
1261 ttatgataat gtttcatagt tggatatcat aatttaaaca agcaaaacca aattaagggc
1321 cagctcattc ctcccactca tgatctatag atctatagat ctctcgtggg atcattgttt
1381 ttctcttgat tcccactttg tggttctaag tactgtggtt tccaaatgtg tcagtttcat
1441 agcctgaaga acgagatcag cagcctctgt tccacataca cttcattctc agtattgttt
1501 tgccaagttc taattccatc agaagctgac tctagatggc gcgtatgcag gttttcgaca
1561 ttgattattg actagttatt aatagtaatc aattacgggg tcattagttc atagcccata
1621 tatggagttc cgcgttacat aacttacggt aaatggcccg cctggctgac cgcccaacga
1681 cccccgccca ttgacgtcaa taatgacgta tgttcccata gtaacgccaa tagggacttt
1741 ccattgacgt caatgggtgg agtatttacg gtaaactgcc cacttggcag tacatcaagt
1801 gtatcatatg ccaagtacgc ccctattga cgtcaatgac ggtaaatggc ccgcctggca
1861 ttatgcccag tacatgacct tatgggactt tcctacttgg cagtacatct acgtattagt
1921 catcgctatt accatggtcg aggtgagccc cacgttctgc ttcactctcc ccatctcccc
1981 cccctcccca cccccaattt tgtatttatt tattttttaa ttattttgtg cagcgatggg
2041 ggcggggggg ggggggcgc gcgccaggcg gggcgggcgg gggcgagggg cggggcgggg
2101 cgaggcggag aggtgcggcg gcagccaatc agagcggcgc gctccgaaag tttccttta
```

FIG. 40B-1

```
2161 tggcgaggcg gcggcggcgg cggccctata aaaagcgaag cgcgcggcgg gcgggagtcg
2221 ctgcgttgcc ttcgccccgt gccccgctcc gcgccgcctc gcgccgcccg ccccggctct
2281 gactgaccgc gttactccca caggtgagcg ggcgggacgg ccttctcctc ccgggctgta
2341 attagcgctt ggtttaatga cggctcgttt cttttctgtg gctgcgtgaa agccttaaag
2401 ggctccggga gggccctttg tgcggggggg agcggctcgg ggggtgcgtg cgtgtgtgtg
2461 tgcgtgggga gcgccgcgtg cggcccgcgc tgcccggcgg ctgtgagcgc tgcgggcgcg
2521 gcgcggggct ttgtgcgctc cgcgtgtgcg cgaggggagc gcggccgggg gcggtgcccc
2581 gcggtgcggg ggggctgcga gggaacaaa ggctgcgtgc ggggtgtgtg cgtgggggg
2641 tgagcagggg gtgtgggcgc ggcggtcggg ctgtaaccc cccctgcacc cccctccccg
2701 agttgctgag cacggcccgg cttcgggtgc ggggctccgt gcggggcgtg gcgcggggct
2761 cgccgtgccg ggcgggggt ggcggcaggt ggggtgccg ggcggggcgg ggccgcctcg
2821 ggccggggag ggctcggggg aggggcgcgg cggccccgga gcgccggcgg ctgtcgaggc
2881 gcggcgagcc gcagccattg ccttttatgg taatcgtgcg agagggcgca gggacttcct
2941 ttgtcccaaa tctgtgcgga gccgaaatct gggaggcgcc gccgcaccc ctctagcggg
3001 cgcggggcga agcggtgcgg cgccggcagg aaggaaatgg gcggggaggg ccttcgtgcg
3061 tcgccgcgcc gccgtccct tctcctctc cagcctcggg gctgtccgcg ggggacggc
3121 tgccttcggg ggggacgggg cagggcgggg ttcggcttct ggcgtgtgac cggcggctct
3181 agaagcgttg gggtgagtac tccctctcaa aagcgggcat gacttctgcg ctaagattgt
3241 cagtttccaa aaacgaggag gatttgatat tcacctggcc cgcggtgatg cctttgaggg
3301 tggccgcgtc catctggtca gaaaagacaa tcttttgtt gtcaagcttg aggtgtggca
3361 ggcttgagat ctggccatac acttgagtga cattgacatc cactttgcct ttctctccac
3421 aggtgtccac tcccagggcg gcctccggag cgatcgccga tccgcctagg caattgttta
3481 aatcggccgg ccataacttc gtataatgta tgctatacga agttatggat cctcacagta
3541 ggtggcatcg ttcctttctg actgcccgcc ccccgcatgc cgtcccgcga tattgagctc
3601 cgaacctctc gccctgccgc cgccggtgct ccgtcgccgc cgcgccgcca tggaatcgaa
3661 gccaccatgg atcttaccgg aaaactcgac gcaagaaaaa tcagagagat cctcataaag
3721 gtcaagaagg gcggaaagat cgccgtgtaa ttctagaccg gttcgagatc caggcgcgga
3781 tcaataaaag atcattattt tcaatagatc tgtgtgttgg tttttgtgt gccttggggg
3841 agggggaggc cagaatgagg cgcggccaag ggggagggg aggccagaat gaccttgggg
3901 gagggggagg ccagaatgac cttggggag ggggaggcca gaatgaggcg cgccctccgt
3961 cgacctataa cttcgtataa tgtatgctat acgaagttat ggcggccgcc accatggaca
4021 tgagagtgcc cgcccagctc ctggggctcc tgctactctg gctccgaggt aaggatggag
4081 aacactagga atttactcag ccagtgtgct cagtactgac tggaacttca gggaagttct
4141 ctgataacat gattaatagt aagaatattt gttttatgt ttccaatctc aggtgccaga
4201 tgtcagtctg ccctgaccca gcccgcctct gtgtctggca gccctggcca gagcatcacc
4261 atcagctgca ccggcaccag cagcgacgtg ggcggctaca actacgtgtc ctggtatcag
4321 cagcaccccg gcaaggcccc caagctgatg atctacgagg tgtccaacag acccagcggc
```

*FIG. 40B-2*

```
4381 gtgagcaaca gattcagcgg cagcaagagc ggcaacaccg ccagcctgac catcagcggc
4441 ctccaggctg aggacgaggc cgactactac tgcagcagct acaccagcag ctccaccctg
4501 gtgtttggcg gcggaacaaa gctgaccgtg ctgagagccc acgccgctcc caccgtgtcc
4561 atcttccccc ccagcatgga acagctgacc tctggcggag ccaccgtggt ctgcttcgtg
4621 aacaacttct accccagaga catcagcgtg aagtggaaga tcgacggcag cgagcagagg
4681 gacggcgtgc tggacagcgt gaccgaccag gacagcaagg actccaccta cagcatgagc
4741 agcaccctga gcctgaccaa ggtggagtac gagaggcaca acctgtacac ctgcgaggtg
4801 gtgcacaaga ccagctccag ccccgtggtc aagtccttca accggaacga gtgttgagct
4861 agcttaagat ttaataggc cggccgcgtc gacctcgaga tccaggcgcg gatcaataaa
4921 agatcattat tttcaataga tctgtgtgtt ggttttttgt gtgccttggg ggaggggggag
4981 gccagaatga ggcgcggcca aggggaggg ggaggccaga atgaccttgg gggaggggga
5041 ggccagaatg accttggggg aggggaggc cagaatgagg cgcgccccg ggtaccgagc
5101 tcgaattagt ggatcctcac agtaggtggc atcgttcctt tctgactgcc cgcccccgc
5161 atgccgtccc gcgatattga gctccgaacc tctcgccctg ccgccgccgg tgctccgtcg
5221 ccgccgcgcc gccatggaat cgcgccggta accgaagttc ctatactttc tagagaatag
5281 gaacttcgga ataggaactt caagccgta cccagctttt gttcccttta gtgagggtta
5341 atttcgagct tggcgtaatc atggtcatag ctgtttcctg tgtgaaattg ttatccgctc
5401 acaattccac acaacatacg agccgggagc ataaagtgta aagcctgggg tgcctaatga
5461 gtgagctaac tcacattaat tgcgttgcgc tcactgcccg ctttccagtc gggaaacctg
5521 tcgtgccagc tgcattaatg aatcggccaa cgcgcgggga gaggcggttt gcgtattggg
5581 cgctcttccg cttcctcgct cactgactcg ctgcgctcgg tcgttcggct gcggcgagcg
5641 gtatcagctc actcaaaggc ggtaatacgg ttatccacag aatcagggga taacgcagga
5701 aagaacatgt gagcaaaagg ccagcaaaag gccaggaacc gtaaaaaggc cgcgttgctg
5761 gcgtttttcc ataggctccg ccccctgac gagcatcaca aaaatcgacg ctcaagtcag
5821 aggtggcgaa acccgacagg actataaaga taccaggcgt ttccccctgg aagctccctc
5881 gtgcgctctc ctgttccgac cctgccgctt accggatacc tgtccgcctt tctcccttcg
5941 ggaagcgtgg cgctttctca tagctcacgc tgtaggtatc tcagttcggt gtaggtcgtt
6001 cgctccaagc tgggctgtgt gcacgaaccc cccgttcagc ccgaccgctg cgccttatcc
6061 ggtaactatc gtcttgagtc aacccggta agacacgact tatcgccact ggcagcagcc
6121 actggtaaca ggattagcag agcgaggtat gtaggcggtg ctacagagtt cttgaagtgg
6181 tggcctaact acggctacac tagaaggaca gtatttggta tctgcgctct gctgaagcca
6241 gttaccttcg gaaaaagagt tggtagctct tgatccggca aacaaaccac cgctggtagc
6301 ggtggttttt tgtttgcaa gcagcagatt acgcgcagaa aaaaggatc tcaagaagat
6361 cctttgatct tttctacggg gtctgacgct cagtggaacg aaaactcacg ttaagggatt
6421 ttggtcatga gattatcaaa aaggatcttc acctagatcc ttttaaatta aaaatgaagt
6481 tttaaatcaa tctaaagtat atatgagtaa acttggtctg acagttacca atgcttaatc
6541 agtgaggcac ctatctcagc gatctgtcta tttcgttcat ccatagttgc ctgactcccc
```

```
6601 gtcgtgtaga taactacgat acgggagggc ttaccatctg gccccagtgc tgcaatgata
6661 ccgcgagacc cacgctcacc ggctccagat ttatcagcaa taaaccagcc agccggaagg
6721 gccgagcgca gaagtggtcc tgcaacttta tccgcctcca tccagtctat taattgttgc
6781 cgggaagcta gagtaagtag ttcgccagtt aatagtttgc gcaacgttgt tgccattgct
6841 acaggcatcg tggtgtcacg ctcgtcgttt ggtatggctt cattcagctc cggttcccaa
6901 cgatcaaggc gagttacatg atcccccatg ttgtgcaaaa aagcggttag ctccttcggt
6961 cctccgatcg ttgtcagaag taagttggcc gcagtgttat cactcatggt tatggcagca
7021 ctgcataatt ctcttactgt catgccatcc gtaagatgct tttctgtgac tggtgagtac
7081 tcaaccaagt cattctgaga atagtgtatg cggcgaccga gttgctcttg cccggcgtca
7141 atacgggata ataccgcgcc acatagcaga actttaaaag tgctcatcat tggaaaacgt
7201 tcttcgggc gaaaactctc aaggatctta ccgctgttga tccagttc gatgtaaccc
7261 actcgtgcac ccaactgatc ttcagcatct tttactttca ccagcgtttc tgggtgagca
7321 aaaacaggaa ggcaaaatgc cgcaaaaaag ggaataaggg cgacacggaa atgttgaata
7381 ctcatactct cctttttca atattattga agcatttatc agggttattg tctcatgagc
7441 ggatacatat ttgaatgtat ttagaaaaat aaacaaatag gggttccgcg cacatttccc
7501 cgaaaagtgc cacctaaatt gtaagcgtta atattttgtt aaaattcgcg ttaaatttt
7561 gttaaatcag ctcatttttt aaccataggg ccgaaatcgg caaaatccct tataaatcaa
7621 aagaatagac cgagataggg ttgagtgttg ttccagtttg gaacaagagt ccactattaa
7681 agaacgtgga ctccaacgtc aaagggcgaa aaaccgtcta tcagggcgat ggcccactac
7741 gtgaaccatc acctaatca gttttttgg ggtcgaggtg ccgtaaagca ctaaatcgga
7801 accctaaagg gagcccccga tttagagctt gacggggaaa gccggcgaac gtggcgagaa
7861 aggaagggaa gaaagcgaaa ggagcgggcg ctagggcgct ggcaagtgta gcggtcacgc
7921 tgcgcgtaac caccacaccc gccgcgctta atgcgccgct acagggcgcg tcccattcgc
7981 cattcaggct gcgcaactgt tgggaagggc gatcggtgcg ggcctcttcg ctattacgcc
8041 agctggcgaa agggggatgt gctgcaaggc gattaagttg ggtaacgcca gggttttccc
8101 agtcacgacg ttgtaaaacg acggccagtg agcgcgcgta atacgactca ctatagggcg
8161 aattggggt aactaagtaa ggatcgag
```

*FIG. 40B-4*

ANTIBODY PRODUCING NON-HUMAN ANIMALS

CROSS-REFERENCE TO RELATED APPLICATIONS

This application is a continuation of co-pending U.S. patent application Ser. No. 15/140,321, filed Apr. 27, 2016, which is a continuation of U.S. patent application Ser. No. 12/589,181, filed Oct. 19, 2009, pending, which application is a continuation of U.S. patent application Ser. No. 12/459,285, filed Jun. 29, 2009, now abandoned, which applications claim the benefit, under 35 U.S.C. § 119(e), to U.S. Provisional Patent Application Ser. No. 61/133,274, filed Jun. 27, 2008, the entire contents of each of which are hereby incorporated herein by this reference.

STATEMENT ACCORDING TO 37 C.F.R. § 1.821(c) or (e)—SEQUENCE LISTING SUBMITTED AS A TXT FILE

Pursuant to 37 C.F.R. § 1.821(c) or (e), files containing a TXT version of the Sequence Listing has been submitted concomitant with this application, the contents of which are hereby incorporated by reference.

TECHNICAL FIELD

The application relates to the field of molecular biology, in particular, to medical molecular biology.

BACKGROUND

Specific recognition plays an important role in modern medical biology. Receptor-ligand interactions, immune responses, infections, enzymatic conversions are all based on specific recognition between molecules. Of particular interest are specific protein-protein interactions, which give a vast array of possibilities to interfere in all kinds of biological processes. Throughout nature, biological processes are found that depend on more than one (simultaneous) protein-interaction. At the present time, it seems that interfering at more than one point in a biological process is going to be more effective than a single interference. Particularly in antibody therapy, it is seen that one (monoclonal) antibody is often not effective enough for treating a particular disorder and/or disease. Therefore, the attention of many medical researchers is now focused on combination therapies. Well-known examples of combinations of antibodies that are presently clinically pursued are for the treatment of non-Hodgkin's lymphoma, the combination of the already approved anti-CD20 antibody Rituxan with the anti-CD22 antibody Epratuzumab from AmGen, and for the treatment of Hepatitis B, a combination of two human antibodies being developed by XTL Pharmaceuticals (E. Galun et al., *Hepatology* (2002) 35:673-679). However, the combination of multiple (two or more) drugs (be it antibodies or other) has a number of technical, practical and regulatory drawbacks. The drugs were typically not designed as combinations and development with optimal clinical efficacy and compatibility may be a problem. As an example, conditions for stabilizing the one may be detrimental to stability of the other(s). Furthermore, multiple sources of recombinant production lead to multiple sources of risks, such as, viral contamination, prion contamination and the like.

B cells mediate humoral immunity by producing specific antibodies. The basic structural subunit of an antibody (Ab) is an immunoglobulin (Ig) molecule. Ig molecules consist of a complex of two identical heavy (H) and two identical light (L) polypeptide chains. At the amino terminus of each H chain and L chain is a region that varies in amino acid sequence named the variable (V) region. The remaining portion of the H and L chains is relatively constant in amino acid sequence and is named the constant (C) region. In an Ig molecule, the H and L chain V regions (VH and VL) are juxtaposed to form the potential antigen-binding site. The genes that encode H and L chain V regions are assembled somatically from segments of germline DNA during precursor B (pre-B) cell differentiation: V, D and J gene segments for the H chain and V and J gene segments for the L chain. Within Ig V regions are three regions of greatest amino acid sequence variability that interact to form the antigen-recognition site and are thus referred to as complementarity determining regions (CDRs).

The V gene segment encodes the bulk of the V region domain, including CDR1 and CDR2. Diversity in CDR1 and CDR2 derives from sequence heterogeneity among multiple different germline-encoded V segments. CDR3 is encoded by sequences that are formed by the joining of H chain V, D, and J gene segments and L chain V and J segments and by mechanisms that create nucleotide sequence heterogeneity where these segments are combined. Additional diversity may be derived from pairing of different H and L chain V regions. Collectively these processes yield a primary repertoire of antibodies encoded by germline gene segments and expressed by newly formed B cells.

An additional source of antibody diversity is imposed on top of the diversity generated by recombination of Ig gene segments. B cells are able to introduce mutations into the antibody V regions that they express, a process called somatic hypermutation. Thus, when an animal first encounters an antigen, the antigen binds to a specific B cell which happens to carry antibodies which have a V domain which binds the antigen. This primary response may activate this B cell to go on to secrete the cognate antibody. These activated B cells can also now target a somatic mutation process to their rearranged antibody gene segments and thus allow the production of daughter cells which make variants of the antibodies of the primary response. A selection process amplifies those variant B cell descendants which make an antibody of improved affinity of the antigen. In B cells, somatic hypermutations are targeted to a restricted genomic region including both the rearranged VH and VL genes. Thus somatic mutation allows affinity maturation—the production and selection of high affinity antibodies. Therefore, somatic mutation is important for the generation of high affinity antibodies.

The exquisite specificity and high affinity of antibodies and the discovery of hybridoma technology allowing the generation of monoclonal antibodies (mAbs) has generated great expectations for their utilization as targeted therapeutics for human diseases. MAbs are identical because they are produced by a single B cell and its progeny. MAbs are made by fusing the spleen cells from a mouse that has been immunized with the desired antigen with myeloma cells to generate immortalized hybridomas. One of the major impediments facing the development of in vivo applications for mAbs in humans is the intrinsic immunogenicity of non-human Igs. Patients respond to therapeutic doses of mouse mAbs by making antibodies against the mouse Ig sequences (Human Anti Mouse Antibodies; HAMA), causing acute toxicity, alter their biodistribution and accelerate clearance, thus reducing the efficacy of subsequent administrations (Mirick et al. (2004), *Q. Nucl. Med. Mol. Imaging* 48:251-257).

To circumvent the generation of HAMA, antibody humanization methods have been developed in an attempt to produce mAbs with decreased immunogenicity when applied to humans. These endeavors have yielded various recombinant DNA-based approaches aimed at increasing the content of human amino acid sequences in mAbs while retaining the specificity and affinity of the parental non-human antibody. Humanization began with the construction of mouse-human chimeric mAbs (S. L. Morrison et al. (1984), *Proc. Natl. Acad. Sci. USA* 81:6851-5), in which the Ig C regions in murine mAbs were replaced by human C regions. Chimeric mAbs contain 60-70% of human amino acid sequences and are considerably less immunogenic than their murine counterparts when injected into humans, albeit that a human anti-chimeric antibody response was still observed (W. Y. Hwang et al. (2005), *Methods* 36:3-10).

In attempts to further humanize murine mAbs, CDR grafting was developed. In CDR grafting, murine antibodies are humanized by grafting their CDRs onto the VL and VH frameworks of human Ig molecules, while retaining those murine framework residues deemed essential for specificity and affinity (P. T. Jones et al. (1986), *Nature* 321:522). Overall, CDR-grafted antibodies consist of more than 80% human amino acid sequences (C. Queen et al. (1989), *Proc. Natl. Acad. Sci. U.S.A.* 86:10029; P. Carter et al. (1992), *Proc. Natl. Acad. Sci. U.S.A.* 89:4285). Despite these efforts, CDR-grafted, humanized antibodies were shown to still evoke an antibody response against the grafted V region (W. Y. Hwang et al. (2005), *Methods* 36:3).

Subsequently to CDR grafting, humanization methods based on different paradigms such as resurfacing (E. A. Padlan et al. (1991), *Mol. Immunol.* 28:489), superhumanization (P. Tan D. A. et al. (2002), *J. Immunol.* 169:1119), human string content optimization (G. A. Lazar et al. (2007), *Mol. Immunol.* 44:1986) and humaneering have been developed in an attempt to further decrease the content of non-human sequences in therapeutic mAbs (J. C. Almagro et al. (2008), *Frontiers in Bioscience* 13:1619). As in CDR grafting approaches, these methods rely on analyses of the antibody structure and sequence comparison of the non-human and human mAbs in order to evaluate the impact of the humanization process into immunogenicity of the final product. When comparing the immunogenicity of chimeric and humanized antibodies, humanization of variable regions appears to decrease immunogenicity further (W. Y. Hwang et al. (2005), *Methods* 36:3-10).

De-immunization is another approach developed to reduce the immunogenicity of chimeric or mouse antibodies. It involves the identification of linear T-cell epitopes in the antibody of interest, using bioinformatics, and their subsequent replacement by site-directed mutagenesis to human or non-immunogenic sequences (WO 09852976A1, the contents of which are incorporated by this reference). Although de-immunized antibodies exhibited reduced immunogenicity in primates, compared with their chimeric counterparts, some loss of binding affinity was observed (M. Jain et al. (2007), *Trends in Biotechnol.* 25:307).

The development of phage display technology complemented and extended humanization approaches in attempts to obtain less immunogenic mAbs for therapy in humans. In phage display, large collections ("libraries") of human antibody VH and VL regions are expressed on the surface of filamentous bacteriophage particles. From these libraries, rare phages are selected through binding interaction with antigen; soluble antibody fragments are expressed from infected bacteria and the affinity of binding of selected antibodies is improved by mutation (G. Winter et al. (1994), *Annu. Rev. Immunol.* 12:433). The process mimics immune selection, and antibodies with many different bindings specificities have been isolated using this approach (H. R. Hoogenboom et al. (2005), *Nat. Biotechnol.* 23:1105). Various sources of H and L chain V regions have been used to construct phage display libraries including those isolated from non-immune or immune donors. In addition, phage display libraries have been constructed of V regions that contain artificially randomized synthetic CDR regions in order to create additional diversity. Often, antibodies obtained from phage display libraries are subjected to in vitro affinity maturation to obtain high affinity antibodies (H. R. Hoogenboom et al. (2005), *Nat. Biotechnol.* 23:1105).

The creation of transgenic mouse strains producing human antibodies in the absence of mouse antibodies has provided another technology platform for the generation of specific and high affinity human mAbs for application in humans. In these transgenic animals, the endogenous mouse antibody machinery is inactivated and replaced by human Ig loci to substantially reproduce the human humoral immune system in mice (A. Jakobovits et al. (2007), *Nat. Biotechnol.* 25:1134; N. Lonberg (2005), *Nat. Biotechnol.* 23:1117). B cell development as well as Ig diversification by recombination of gene segments is faithfully reproduced in these mice, leading to a diverse repertoire of murine B cells expressing human Igs. By immunizing these mice with antigens, it was further demonstrated that these transgenic animals accumulated somatic mutations in the V regions of both heavy and light chains to produce a wide diversity of high-affinity human mAbs (N. Lonberg (2005), *Nat. Biotechnol.* 23:1117).

The question, whether "fully human" mAbs such as derived from phage display libraries or transgenic mice are less immunogenic than humanized mAbs cannot be answered yet, because full immunogenicity data are available for just two human mAbs. An anti-tumor necrosis factor mAb, developed from phage-displayed human libraries induced antibody responses in 12% of patients—at the higher end of the incidence of anti-antibody responses of the humanized antibodies (W. Y. Hwang et al. (2005), *Methods* 36:3-10).

Evaluation of the immunogenicity of the first registered human mAb generated by the transgenic approach demonstrated that mAb treatment resulted in the generation of antibodies in approximately 5.5% of treated cancer patients (A. Jakobovits et al. (2007), *Nat. Biotechnol.* 25:1134; J. A. Lofgren et al. (2007), *J. Immunol.* 178:7467)

SUMMARY OF THE INVENTION

Described are combinations of specific binding proteins, such as immunoglobulins, that are designed to be true combinations, essentially all components of the combination being functional and compatible with each other. By producing true combinations, an avenue of further improvements in both the production and properties of the combinations has been opened up.

Disclosed are methods for producing a composition comprising at least two different proteinaceous molecules comprising paired variable regions, the at least two proteinaceous molecules having different binding specificities, comprising contacting at least three different variable regions under conditions allowing for pairing of variable regions and harvesting essentially all proteinaceous molecules having binding specificities resulting from the pairing. Binding specificities are defined as interactions between molecules that can be distinguished from background interactions. Typically, specific interactions between molecules have higher binding affinity than background interactions between molecules.

Specific binding molecules, which for an important part are made up of amino acid residues (proteinaceous molecules), often require the pairing of different amino acid sequences in order to build a binding site. An amino acid sequence that pairs with another amino acid sequence to build a binding site is referred to as a "variable region" herein. Of course, such a sequence may be part of a larger amino acid sequence, which may again be part of a larger proteinaceous molecule, e.g., as a subunit. As an example, in an antibody a complementarity-determining region (CDR) may be a variable region, but a combination of three CDRs with their framework regions may also be considered as a variable region. As decribed herein, at least two different binding sites may be built in one system, in one method. Thus, variable regions (amino acid sequences or "peptides") are brought together under conditions in which they may pair to build two different binding sites. This requires at least three variable regions, of which one is capable of pairing with both other variable regions, thus building two specific binding sites. The two specific binding sites may be in one proteinaceous molecule or in different proteinaceous molecules, or both.

In antibodies of the IgG isotype, for example, this would be an antibody having two identical or two different binding sites. By producing the two desired binding specificities in one system, there is only one source of the products and thereby less risk of contamination with viruses, prions and the like. Such a system may be a cell-free system, such as a wheat germ system, but the described methods may be carried out inside a cell, or more cells of the same origin, or of the origin of the subjects to be treated, typically human. For production and selection purposes, other cells, such as, bacteria, insect cells, yeasts and other eukaryotes may be used.

If the pairing of the variable regions takes place in a cell, then the production of the variable regions may also take place in a cell, including the same cell. A particularly useful way of producing variable regions is through the expression of nucleic acids encoding these variable regions. In certain embodiments, all variable regions in one cell are produced by such expression, it is, however, also possible to produce a number of variable regions in this manner and have other variable regions brought in, based on different techniques of production, or the same means of production, but in another cell. For most purposes, the nature of the nucleic acid is not critical, it may be RNA or DNA, may be episomal or integrated, part of a viral vector or a plasmid, etc. However, for the final production system of the combination of proteins having different binding specificities, the nucleic acid or acids encoding the variable regions may be stably integrated into the host genome. Production of variable regions through expression of nucleic acids encoding them gives the possibility to manipulate the encoding sequences, thereby enabling the designing of new binding specificities, better pairing properties, exchanging useful sequences from one encoding sequence to another and the like. It also gives the possibility for selection for improved or different binding and/or pairing properties after alterations have been made, giving rise to the creation of libraries of many different nucleic acids in systems with easy selection mechanisms.

In this manner, the number of variable regions to be expressed for obtaining different binding sites may be reduced. One may design and/or select for a so-called "promiscuous" variable region, which is capable of pairing with more than one different binding region. "Pairing" is defined herein as any kind of coming together to build a binding site, be it through covalent or noncovalent bonding, conformational arrangement, folding, dimerization, multimerization or any other way. It thus encompasses terms such as associating, assembling, binding, combining and the like, be it directly or indirectly. Particularly when more than two different binding specificities are made in one cell, it is useful to have promiscuous variable regions in such a system, reducing the number of different nucleic acids that have to be expressed. In such a system, the promiscuous variable region should not contribute significantly to the binding specificity of the paired regions. In embodiments, the promsicous variable region it is mostly involved in folding and stability of the binding site, thereby, of course, indirectly influencing the binding specificity.

Apart from reducing the number of nucleic acids to be expressed, by choosing one or more promiscuous variable regions, the number of paired variable regions which are not functional can be reduced to essentially zero.

Particularly in the field of immunoglobulins, which typically comprise two pairs of two different paired variable regions, the production of more than one immunoglobulin inside the same cell often leads to pairing of variable regions that does not lead to a desired binding specificity. As decribed herein, pairs may be designed such that in one system essentially all variable regions can pair with another in the system to form a useful specific binding site. In methods of the prior art wherein four variable regions were expressed in hybrid-hybridomas or quadromas, the result was a low percentage of desired bispecific antibodies, a percentage of either original antibodies and a substantial percentage of paired regions without significant useful binding specificity. Bispecific antibodies may be produced with the described methods, either together with or without the concomitant production of the original antibodies, but typically essentially without production of non-functional pairs. In addition, mixtures of multiple monoclonal and multiple bispecific antibodies may be produced with the methods.

The methods as disclosed in the detailed description provide for adaptation of the nucleic acids encoding variable regions to the desired end result. Using promiscuous pairing or the opposite, monogamous pairing, the end result can be designed. Where bispecific antibodies or other certain pairings are to be excluded, the use of pairs of variable regions that can pair only with each other is used. Further, methods as disclosed in the detailed description provide for adaptation of the nucleic acids encoding the constant regions to lead to a preferential pairing of the binding sites formed by the variable regions when attached to the constant regions.

Antibodies are intended to refer to all variations of immunoglobulins that retain specific binding, such as Fabs, Fab'2, scFvs, but typical for antibodies described herein is the presence of a pair of amino acid sequences (at least two CDRs) that are paired to form a binding site. Thus, the also provided is a method wherein the variable regions are derived from heavy chains and/or light chains of immunoglobulins, engineered versions of variable regions with elements of heavy and/or light chains of immunoglobulins and/or a method wherein the proteinaceous molecules are antibodies, fragments and/or derivatives of antibodies.

The methods provided are typically for the production of multiple (i.e., three or more) binding specificities in one system. Because of the specific design of the contributing variable regions this has now become technically and commercially feasible.

Production may be controlled by placing the expression of different variable regions under control of different elements such as promoters, (trans) activators, enhancers, terminators, anti-repressors, repressors, and the like. These control elements may be inducible or repressible. Thus, the production of variable regions can be regulated, thus optimizing pairing conditions as desired. Different combinations of variable regions can be made by separation in time of expression of various variable regions and/or ratios between different paired variable regions may be manipulated by regulating expression levels. Variations are described in the detailed description. Also provided is an expression system comprising nucleic acids encoding variable regions together with all elements required for gene expression and pairing, such an expression system may comprises at least one recombinant cell, such as a bacterium, a yeast cell, a fungal cell, an insect cell, a plant cell or another eukaryotic cell, in particular, a mammalian cell, more in particular, a human cell or a mouse cell.

Such a system can be provided with all necessary and useful control elements as disclosed herein before and as well known in the art. Selection elements and suicide elements may also be introduced into such a system as desired.

A collection of expression systems comprising a variety of combinations of different specificities is also provided, typically as a library for use in selecting desired combinations of variable regions.

Also disclosed are methods and means for producing molecules comprsing variable regions that are specific for their targets, but are less immunogenic. Described herein, the reduction of immunogenicity is at least partially achieved by providing a nucleic acid molecule encoding at least an immunoglobulin light chain or heavy chain, wherein the heavy- or light chain encoding sequence is provided with a means that renders it resistant to DNA rearrangements and/or somatic hypermutations. In certain embodiments, the nucleic acid molecule can be provided cells that are used to generate a transgenic non-human mammal. In other embodiments, the nucleic acid molecule can be provided to other cells from such a transgenic non-human animal. The non-human mammal may be, e.g., a rodent, or, more specifically, may be a mouse. In certain embodiments, the nucleic acid encodes a human, human-like, or humanized immunoglobulin chain.

In the remainder of this specification, mice are typically used as examples of non-human mammals. The transgenic, non-human, mammalian hosts are capable of mounting an immune response to an antigen, where the response produces antibodies having primate, particularly human, variable regions. Various transgenic hosts may be employed, particularly murine, lagomorpha, ovine, avine, porcine, equine, canine, feline, or the like. Mice have been used for the production of B-lymphocytes for immortalization for the production of antibodies. Since mice are easy to handle, can be bred in large numbers, and are known to have an extensive immune repertoire, mice will usually be the animal of choice. Therefore, in the following discussion, the discussion will refer to mice, but it should be understood that other animals, particularly non-primate mammals, may be readily substituted for the mice, following the same procedures.

A reason for preventing rearrangements and hypermutation is that in this manner, a non-immunogenic polypeptide can be chosen beforehand knowing that this polypeptide chain will remain non-immunogenic. At least one of the chains of the resulting immunoglobulin is thus less immunogenic. The resulting antibody needs to have (usually) both a light- and a heavy chain. The non-immunogenic chain must therefore be capable of pairing with the other chain. The other chain may be an endogenous chain, an exogenous chain or a hybrid of both. For human therapy, the non-immunogenic chain should be as close to human as possible.

A means for rendering a gene encoding an immunoglobulin chain (or chains) resistant to DNA rearrangement and/or mutation is removal of all genetic elements responsible for the rearrangement and/or mutation. The drawback thereof is that the variability of the two chains is eliminated, whereas the transgenic non-human mammal may retain the variability in one chain (for example the heavy chain) and inhibits and/or prevents the rearrangement-mutation of the other chain (for example the light chain).

The elements for rearrangement and/or hypermutation characterized so far are located within the loci for immunoglobulins. Therefore, the means for rendering the immunoglobulin encoding sequence resistant to DNA rearrangement and/or mutation is inserting the gene in a locus outside the immunoglobulin loci.

Thus, as described herein, a transgenic non-human mammal is provided wherein the light/heavy chain encoding sequences are integrated in the genome of the non-human mammal in a locus outside the immunoglobulin loci. In certain embodiments, the insertion is in a locus that is resistant to gene silencing. As described herein, the integration may be in the Rosa-locus or a comparable locus.

In certain embodiments, provided is an expression cassette that can be inserted into a Rosa locus of the non-human animal or comparable locus with a means that allows expression of the immunoglobulin chain(s) essentially limited to cells of B cell lineage, for example with a means that allows expression of the light chain encoding nucleic acid during a certain stage of the development of B cells. The term "essentially limited expression" indicates that expression is predominantly in cells of the B-cell lineage, but that lower levels of expression in other cells, as compared to the level of expression in B-cells, is possible. In certain embodiments, the term "essentially limited expression" indicates that the expression is exclusively present in cells of the B-cell lineage. Such means typically include B cell (developmental stage) specific promoters such as CD19, CD20, μHC (all V-genes), VpreB1, VpreB2, VpreB3, λ5, Igα, Igβ, κLC (all genes), λLC (all genes), BSAP (Pax5). Although it is very well possible to direct the expression of the DNA rearrangement and/or mutation resistant chain by such promoters, they are relatively weak. A strong promoter will typically be required to ensure adequate surface expression of the B cell receptor (made up of the membrane attached Ig H and L chain) and to compete with the expression and pairing of endogenous chains (if present) through allelic exclusion. Such a promoter, however is usually not tissue specific. To confer tissue specificity, an indirect system employing Cre/lox or the like may be sued. The desired chain is put under control of a strong promoter inhibited by an element that can be removed by the action of a Cre-protein, leading to activation of the desired immunoglobulin encoding gene. This system is described in detail in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultät der Universität zu Köln; on the internet at deposit.ddb.de/cgi-bin/dokserv?idn=97557230x&dok_var=d &dok_ext=pdf&filename=97557230x.pdf.

In certain embodiments, the immunoglobulin chain produced in a manner resistant to rearrangements and hypermutation is a light chain capable of pairing with different heavy chains encoded by the non-human mammal. The light chain will then be the same (and less immunogenic) in all antibodies, but variety in specificity is retained through rearrangements and hypermutations in the heavy chains. It may in that case be desirable to silence at least one of the endogenous loci encoding a light chain, although allelic exclusion may render this unnecessary.

According to this embodiment, the endogenous kappa (κ) light chain locus may be functionally silenced.

If the endogenous κ light chain locus is silenced, but also for other reasons, it is desireable that the resistant light chain is a κ light chain, desireably a light chain that has a germline-like sequence. As described herein, such a light chain would lead to an antibody with reduced immunogenicity. One example of a germline sequence is based on the human IGKV1-39 (O12) as this light chain is very frequently observed in the human repertoire (de Wildt et al. 1999, *J. Mol. Biol.* 285(3):895) and has superior thermodynamic stability, yield and solubility (Ewert et al. 2003, *J Mol. Biol.* 325(3):531).

The following description gives more specific embodiments of the expression cassette with which the non-human animal can be provided described herein. Although this is typically advantageous for immunoglobulins, other genes of interest are also contemplated.

Thus, provided in a specific embodiment is a transgenic non-human mammal wherein the light chain encoding nucleic acid comprises in 5'-3' direction: a B cell specific promoter, a leader, a rearranged human V gene, optionally a MoEκi enhancer, a constant region (κ) and optionally a (truncated) MoEκ3' enhancer. Neuberger identified and examined a novel B-cell specific enhancer located downstream of the kappa constant region (EPO patent application EP004690251, the contents of which are incorporated herein by this reference). This enhancer has been shown to play a crucial role in the expression of kappa genes as removal of the 808 bp enhancer strongly reduced expression. Deletion of the 3' kappa enhancer also strongly reduced the level of somatic hypermutations (SHM). In transgenic and cell expression studies it has been revealed that reduced, mutated or deleted 3' kappa enhancers not only lowered expression levels but also decreased the level of somatic hypermutations. Currently, it cannot be determined whether the 3' kappa enhancer is involved in SHM processes, expression regulation or both (review V. H. Odegard et al. (2006), *Nat. Rev. Immunol.* 6:573; M. Inlay et al. (2002), *Nat. Immunol.* 3:463.).

Detailed expression studies using engineered variants of the 3' kappa enhancer indicated that a 50 nucleotide region is sufficient to drive expression. However for proper expression a reduced sequence of 145 nucleotides may be used (EP04690251; K. B. Meyer et al. (1990), *Nucleic Acids Res.* 18(19):5609-15).

Thus, in one aspect is provided a nucleic acid for insertion into the genome of a non human animal that is an expression cassette for the expression of a desired proteinaceous molecule in cells developing into mature B cells during a certain stage of development, the cassette comprising means for preventing silencing of expression of the desired proteinaceous molecule after introduction into a host cell, and means for timing expression of the desired proteinaceous molecule with the desired developmental stage of the host cell.

An expression cassette is defined as a nucleic acid molecule that has been provided with all elements necessary for expression of the gene in a host cell, although in certain embodiments some of such elements may be present on a second nucleic acid to be introduced, whereby these elements act in trans. Elements necessary for expression in a host cell include promoters, enhancers and other regulatory elements. Only those elements are necessary that are not provided by the host cell. Further, an expression cassette may comprise means for introduction into the genome of a host cell, such as sequences that allow for homologous recombination with a certain site in the genome. Usually, the nucleic acid molecule will be DNA, typically double stranded. Typically, the expression cassette will be provided to the cell in a vector from which it is transferred to the genome of the cell.

The expression of a gene of interest should not be silenced in the genome of the host cell, especially not in the development stage where expression is required. This can be done by various means, such as insertion into the endogenous locus or by providing the cassette with nucleic acid elements that prevent silencing (Kwaks et al. (2006), *Trends Biotechnol.* 24(3):137-142, which is incorporated herein by reference). In certain emobidments, the expression cassette is inserted in a locus that is not silenced in the host cells (EP 01439234; which is incorporated herein by reference).

Means for preventing silencing comprise STabilizing Anti-Repression-sequences (STAR®-sequences) and Matrix Attachment Regions (MARs). A STAR sequence is a nucleic acid molecular sequence that has a capacity to influence transcription of genes in cis. Typically, although not necessarily, a STAR sequence does not code by itself for a functional protein element. In one embodiment, one STAR element is used. In certain embodiments, however, more than one STAR element is used. In a particular embodiment, an expression cassette described herein is provided with two STAR sequences; one STAR sequence at the 5' side of the coding sequence of the immunoglobulin gene and one STAR sequence at the 3' side of the coding sequence of the immunoglobulin gene. MARs are DNA sequences that are involved in anchoring DNA/chromatin to the nuclear matrix and they have been described in both mammalian and plant species. MARs possess a number of features that facilitate the opening and maintenance of euchromatin. MARs can increase transgene expression and limit position-effects.

In certain embodiments, expression from the cassette may only occur during a certain period in the development of a cell, in particular a developing B cell, more in particular a B cell in a transgenic non-human animal, in particular a mouse. The developmental period may be chosen such that the expression of the gene from the cassette (typically a light- or heavy chain-like polypeptide) does not significantly interfere with the normal differentiation and/or maturation of the cell and when applicable, allows for pairing of the polypeptide chain produced with its counterpart.

This may, in one embodiment, be achieved by providing a nucleic acid molecule described herein, wherein the means for timing expression is a promoter of which the activity is essentially limited to the certain stage of development. In a developing B cell, which, e.g., after immunization is maturing and/or differentiating, the expression of the gene of interest, when it is one of the polypeptide chains of an immunoglobulin, must not interfere (significantly) with the maturation and/or differentiation and it needs to be timed such that the resulting polypeptide can pair with its counterparts. Therefore, provided is a nucleic acid molecule as described herein wherein the certain stage starts at a stage immediately preceding or coinciding with the onset of the expression of light chain molecules by the cells at a certain stage of development into a mature B cell. This may be achieved by selecting a promoter that is active only during the suitable period. Such a promoter may be a CD19 promoter, the Ig-α promoter, the Ig-β promoter, the μhc (all genes) promoter, the Vk promoter or analogues or homologues thereof.

In a specific embodiment, the promoter as disclosed herein does not drive the expression of the gene of interest directly. Instead, it drives the expression of a gene of which the product activates in trans the expression of the gene of interest. Such an activating gene may be a gene encoding a so-called Cre recombinase or Cre-like protein. The expression cassette for the gene of interest may, e.g., be provided with a sequence that inhibits expression of the gene of interest. The sequence can be removed by the action of the Cre recombinase, which is under control of the desired promoter (active during the proper stage of development). In this embodiment a set of expression cassettes is required.

Therefore, provided is a set of nucleic acid molecules that are expression cassettes, wherein one nucleic acid molecule comprises an expression cassette encoding a Cre-like protein under control of a promoter active during the desired stage of development of the host cell and the second nucleic acid comprises a sequence encoding a desired proteinaceous molecule under control of a constitutive promoter which can be activated by the action of a Cre-like protein. The activation may be achieved by removal of a stop sequence flanked by loxP sites. The Cre/lox system is described in detail in Rajewsky et al. (1996), *J. Clin. Invest.* 98:600-603, which is incorporated herein by reference. Such systems are reviewed in F. T. Wunderlich (2004), "Generation of inducible Cre systems for conditional gene inactivation in mice," Inauguraldissertation zur Erlangung des Doktorgrades der Mathematisch-Naturwissenschaftlichen Fakultat der Universitat zu Koln; on the World Wide Web at deposit.ddb.de/cgi-bin/dokserv?idn=97557230x&dok_var=d1&dok_ext=pdf&filename=97557230x.pd, which is incorporated herein by reference.

Further provided is a transgenic non-human animal that has been provided with an expression cassette hereof, wherein the desired proteinaceous molecule is a polypeptide chain of an immunoglobulin. One example of a polypeptide chain is a light chain. A more specific example of a polypeptide is a germline or germline-like light chain. An even more specific polypeptide is O12. In certain embodiments, the rearranged germline kappa light chain IGKV1-39*01/IGKJ1*01 (nomenclature according to the IMGT database, at [worldwideweb].imgt.org).

In certain embodiments, the polypeptide chain is rendered essentially incapable of rearrangement and/or of excluded of any sequence modification such as normally operating on Ig during the process of B cell affinity maturation. Therefore, provided is a transgenic non-human animal that has been provided with an expression cassette described herein, wherein the rearrangement and/or sequence modifications are prevented by the absence of elements at least partially responsible for somatic hypermutation such as, for example, the MoEκi enhancer.

One example of an expression cassette described herein comprises means for prevention of silencing. In one embodiment, the means for prevention of silencing are means for insertion into a locus in the genome of the host cell that is resistant to silencing. The means for insertion may be means for homologous recombination into the site resistant to silencing. An example locus when the non-human animal is a mouse is the rosa-locus.

A further example of an expression cassette described herein comprises in 5'-3' direction: a Vκ promoter, a mouse leader, a human V gene, optionally a MoEκi enhancer, a rat constant region (Cκ) and optionally a (truncated) MoEκ3' enhancer.

Yet a further example of an expression cassette described herein comprises in 5'-3' direction: a Vκ promoter, a human leader, a human V gene, optionally a MoEκi enhancer, a rat constant region (Cκ) and optionally a (truncated) MoEκ3' enhancer.

Certain antibodies produced as described herein may be be used in human therapeutics and diagnostics. Thus, provided is a method for producing a desired antibody comprising exposing a non-human mammal described herein to an antigen such that an antibody response is induced and isolating the antibodies specific for the antigen.

In certain embodiments, provided are methods for producing a desired antibody, the method comprising exposing a non-human mammal described herein to an antigen such that an antibody response is induced and isolating cells producing such antibodies, culturing and optionally immortalizing the cells and harvesting the antibodies.

In certain embodiments, provided is a method for producing a desired antibody comprising exposing a non-human mammal described herein to an antigen such that an antibody response is induced and isolating a nucleic acid encoding at least part of such an antibody, inserting the nucleic acid or a copy or a derivative thereof in an expression cassette and expressing the antibody in a host cell.

The methods for producing antibodies from transgenic mice are known to a person skilled in the art. Examples are methods for production of mixtures of antibodies from one cell, whereby the nucleic acids encoding these antibodies have been derived from mice described herein.

These so-called OLIGOCLONICS® are disclosed in WO 04106375 and WO 05068622, which are incorporated herein by reference.

Described herein are transgenic non-human mammals, such as mice, capable of generating specific and high affinity hybrid mouse-human antibodies with, for example, human immunoglobulin light chain variable (VL) regions in or near germline configuration and, for example, murine immunoglobulin heavy chain variable (VH) regions that may have accumulated somatic mutations during the process of antigen-driven affinity maturation. It is envisaged that the murine VH regions of the hybrid antibodies may be subjected to humanization procedures to yield mAbs that have reduced immunogenicity when applied in humans based on germline or near-germline VL regions and murine VH regions that have been humanized.

In particular, shown is that transgenic mice that harbor a DNA expression construct that encodes a rearranged human VL region under the control of cis-acting genetic elements that provide timely and regulated expression of the transgene on a significant proportion of B cells during B cell development, yet lack elements that direct the somatic hypermutation machinery to the transgene, are capable of generating specific and high affinity mouse-human hybrid antibodies with essentially unmutated L chains. It is shown that the rearranged human transgene is capable of pairing with a diversity of endogenous murine immunoglobulin H chains to form mouse-human hybrid immunoglobulins expressed on the surface of B cells and to sufficiently facilitate murine B cell development to obtain a sizeable and diverse peripheral B cell compartment.

In certain embodiments, the transgene expression construct harbors the coding sequences of a human rearranged L chain V region under the control of a human VL promoter to direct B-cell specific expression. In addition, the construct harbors the murine 3' Ck enhancer sequence for B cell specific and inducible and high level expression of the transgene. Furthermore, the construct is designed to lack regulatory elements that facilitate the recruitment of the somatic hypermutation machinery to the transgene, such as the intron enhancer and the 3' C-kappa enhancer.

In a related embodiment, the rearranged human VL gene is inserted in the murine Rosa26 locus by site-specific integration. The Rosa26 locus is useful in the context of the "targeted transgenesis" approach for efficient generation of transgenic organisms (such as mice) with a predictable transgene expression pattern.

In certain embodiments, the rearranged human VL region is selected for its capacity to pair with many different murine VH genes so as to ensure the generation of a population of B cells with a diverse VH gene repertoire. A method of obtaining such VL regions comprises amplifying a repertoire of rearranged VH genes from the B cells of mice and a repertoire of human rearranged germline VL regions from the B cells of humans and cloning them into phagemid display vectors to prepare diverse libraries of hybrid immunoglobulins in bacteria. By nucleotide sequence analysis of collections of unselected and antigen-selected VH/VL pairs, human germline VL genes that pair with many different murine VH genes are identified. A collection of human germline VL genes with this capacity is described.

In one embodiment, it is shown that upon immunization with antigen, the B cells are capable of mounting an immune response, leading to the generation of B cells that secrete hybrid antibodies with high specificity and affinity. The V regions encoding these antibodies are characterized by the human transgenic light chain that harbors no or very few mutations and a murine heavy chain that harbors a variable number of mutations introduced by the somatic hypermutation machinery.

In a related embodiment, strategies to obtain high affinity hybrid monoclonal antibodies from the transgenic mice by hybridoma and display technologies are contemplated as well as procedures to humanize the murine VH regions to obtain less immunogenic antibodies for application in humans.

In one embodiment, provided is an immunoglobulin L chain transgene construct comprising DNA sequences that encode a human immunoglobulin VL region in combination with a light chain constant region (CL) of an animal immunoglobulin protein, which sequences are operably linked to transcription regulatory sequences that, when integrated in a non-human transgenic animal, produce an Ig VL-CL polypeptide with a human VL region that is not or marginally subject to somatic hypermutation. The Ig VL is capable of pairing with rearranged VH-CH polypeptides that are generated during B cell development in the non-human transgenic animal, with the VH-CH polypeptides retaining the capacity to undergo somatic hypermutation upon stimulation. The CL region may be of any animal species and is generally capable of pairing with the CH regions of the non-human transgenic animal.

Also included is the use of a transgene construct as above in producing a transgenic non-human animal capable of the production of hybrid antibodies consisting of VL-CL polypeptides and VH-CH polypeptides in which the VL region is of human origin and the CL, VH and CH may be of any animal species, including human. Upon immunization, these transgenic animals are capable of generating high affinity antibodies encoded by somatically hypermutated VH genes and essentially non-mutated VL genes encoded by the transgene.

In another aspect, provided is a process for the production of a transgenic non-human animal capable of the production of hybrid antibodies in response to antigenic challenge, comprising functionally disrupting the endogenous immunoglobulin light chain locus and inserting into the animal genome a transgene construct described herein.

Included is the use of animals obtainable by this process in the production of B cells that produce immunoglobulin having human VL light chain. In another aspect there is provided a process for the production of B cells that produce immunoglobulin having human VL and binding to a selected antigen, comprising challenging an animal obtainable by a process as above with the antigen and screening for B cells from the animal that bind the antigen. Further included are B cells obtainable by this process and hybridomas obtainable by immortalizing such B cells, e.g., hybridomas obtained by fusing B cells as above with myeloma cells. Also included is a process for producing monoclonal antibody comprising cultivating such a hybridoma. In yet a further aspect, provided is the use of the above B cells in producing a hybridoma or corresponding monoclonal antibody.

Described herein is a process for the producing immunoglobulin(s) having human VL chain and binding to a selected antigen, the process comprising challenging an animal obtainable as aforementioned with the antigen and obtaining immunoglobulin therefrom.

In one strategy, as an individual step, a rearranged VL region encoded by human germline V and J gene segments and a light chain constant region of any animal species. For example, a murine constant region is introduced into the mouse germ line. The transgene DNA may be introduced into the pronuclei of fertilized oocytes or embryonic stem cells. The integration may be random or homologous depending on the particular strategy to be employed. For example, the VL transgene may be introduced by random insertion, resulting in mice that bear one or multiple copies of the transgene in the genome. Alternatively, the human VL transgene may be targeted to a specific genomic locus using site-specific recombination as described in the art.

In certain embodiments, the VL transgene is targeted to the murine ROSA26 locus which is a suitable integration site allowing strong and predictable expression of inserted transgenes (European Patent Office document EP 1,439,234 A1, the contents of which are incorporated herein by this reference). The targeting vector allows insertion of a single copy of a gene expression cassette, thus avoiding modulation of transgene expression by the arrangement of multiple copies. By choosing the autosomal Rosa26 locus as insertion site, the expression pattern of the inserted transgene in the non-human animal is predictable. Furthermore, random X inactivation and/or modulation by chromosomal position effects are avoided. This also eliminates the need to generate and analyze multiple transgenic strains for any given transgene. Finally, the Rosa26 targeting vector for the site-specific integration can be used for multiple gene expression cassettes. Thus, it may be envisaged that two or more different rearranged germline human VL regions are inserted into the Rosa26 locus to further increase the diversity of the repertoire of hybrid or human antibodies.

In another embodiment, a rearranged human VL region may be targeted to the murine Ig kappa or lambda light chain locus so as to functionally inactivate the endogenous locus or mice containing the rearranged human VL region may be bred with mice that lack functional kappa or lambda Ig loci or both. Thus, by using transformation, using repetitive steps or in combination with breeding, transgenic animals may be obtained which are able to produce antibodies harboring the human VL transgene in the substantial absence of endogenous host immunoglobulin light chains.

In one embodiment, a human VL transgene is selected for its capacity to pair with a substantial portion of murine VH regions to form a diverse repertoire of functional mouse-human hybrid antibodies expressed on the surface of B cells. By a substantial portion of murine VH regions is meant that the human VL pairs with at least with 0.1%, 1%, or 10% of the murine VH regions generated during B cell development. Methods to identify human VL genes with this characteristic include randomly pairing a repertoire of human VL regions with a repertoire of murine VH regions, co-expression of VH and VL regions in appropriate eukaryotic or prokaryotic expression vectors and screening for human VL regions that pair with a substantial portion of murine VH regions. In one embodiment, phagemid vectors may be used to direct expression of mouse-human antibody fragments in bacterial cells or to the surface of filamentous phage and analysis of binding capacity of antibody fragments by methods known in the art.

In another embodiment, a human VL transgene is selected for its capacity to pair with a substantial portion of human VH regions to form a diverse repertoire of human antibodies expressed on the surface of B cells. By a substantial portion of human VH regions is meant that the human VL pairs with at least with 0.1%, 1%, or 10% of the human VH regions generated during B cell development.

In the latter embodiment, the human VL transgenic mice are crossed with mice that harbor functional rearranged or non-rearranged human H chain immunoglobulin loci and functionally inactivated endogenous H chain Ig loci as described in the art. The functional inactivation of the two copies of each of the three host Ig loci (heavy chain, kappa and lambda light chain), where the host contains the human IgH and the rearranged human VL transgene would allow for the production of purely human antibody molecules without the production of host or host human chimeric antibodies. Such a host strain, by immunization with specific antigens, would respond by the production of mouse B-cells producing specific human antibodies, which B-cells are subsequently fused with mouse myeloma cells or are immortalized in any other manner for the continuous stable production of human monoclonal antibodies. Alternatively, the population of B cells is used as a source of VH regions that can be obtained by constructing cDNA libraries or by PCR amplification using primers for human VH regions as is known in the art.

A human rearranged VL gene is reconstructed in an appropriate eukaryotic or prokaryotic microorganism and the resulting DNA fragments can be introduced into pronuclei of fertilized mouse oocytes or embryonic stem cells. Various constructs that direct B cell specific expression of VL transgenes have been described in the art and have the following general format: a leader sequence and relevant upstream sequences to direct B cell specific expression of the transgene, a coding sequence of a human VL transgene, an enhancer sequence that directs B cell specific and high level expression of the transgene and a murine constant region gene. In one format, the enhancer is the C-kappa 3' enhancer because it directs high level expression in B-lineage cells, but does not recruit somatic hypermutation when used in transgene constructs.

In one embodiment, animals, for example, mice, comprising one or multiple copies of the transgene in the genome are isolated and analyzed for stable expression. Animals are selected that show stable expression of the transgene over longer periods of time, for example in B-cells. If required, different animal lines comprising independent insertions of one or multiple copies of the transgene, for example on different chromosomes, are crossed to obtain animals with different insertions of one or multiple copies of the transgene to increase expression of the transgene in animals, for example in B-cells.

Further provided is progeny of a transgenic non-human animal described herein, the progeny comprising, at least in its B-cell lineage, a heavy- or light chain encoding sequence together with a means that renders the sequence resistant to DNA rearrangements and/or somatic hypermutations.

Further provided is progeny of a transgenic non-human animal described herein, the progeny comprising an expression cassette for the expression of a desired proteinaceous molecule in cells during a certain stage of development in cells developing into mature B cells.

In addition, provided is a cell that is isolated from a transgenic non-human animal described herein, the cell comprising a heavy- or light chain encoding sequence together with a means that renders the sequence resistant to DNA rearrangements and/or somatic hypermutations. In addition, provided is a cell that is isolated from a transgenic non-human animal described herein, the cell comprising an expression cassette for the expression of a desired proteinaceous molecule in cells during a certain stage of development in cells developing into mature B cells. A cell described herein, for example an antibody-producing B-cell or a cell that is capable of differentiating or maturing into an antibody-producing B-cell, can be used for in vitro production of antibodies, as is known to the skilled person, for example, from Gascan et al. 1991, *J. Exp. Med.* 173: 747-750. Methods for immortalization of a cell described herein are known in the art and include the generation of hybridomas, for example, by fusion with a myeloma cell, transformation with Epstein Barr Virus; expression of the signal transducer of activation and transcription (STAT), activation via CD40 and IL4 receptor signaling, and/or expression of Bcl6 (Shvarts et al. 2002, *Genes Dev.* 16:681-686).

In a separate step, the endogenous Kappa and Lambda light chain loci are rendered essentially non-functional such that at least the majority of B cells in the transgenic mice bear Ig receptors that contain the transgenic human VL region. Inactivation of the endogenous mouse immunoglobulin loci is achieved by targeted disruption of the appropriate loci by homologous recombination in mouse embryonic stem cells. The targeted disruption comprises alteration of the genomic sequence such that substantially no functional endogenous mouse immunoglobulin Kappa and/or Lambda light chain is produced. The term "substantially no functional endogenous immunoglobulin" indicates that the endogenous Kappa and/or Lambda light chain loci are functionally silenced such that the level of functional protein expression of the endogenous Kappa and/or Lambda light chain loci is reduced to about 20%, about 10%, about 5%, about 2% or about 1% of the level of expression in a reference mouse. In one embodiment, the level of functional protein expression of the endogenous Kappa and/or Lambda light chain loci is reduced to 0%. The level of functional protein expression can be determined by means known to the skilled person, including western blotting and pairing with a mouse heavy chain. The reference mouse is a mouse in which the endogenous Kappa and/or Lambda light chain loci is not disrupted. The alteration comprises mutation and/or deletion of gene sequences that are required for functional expression of the endogenous immunoglobulin genes. Alternatively, the alteration comprises insertion of a nucleic acid into the endogenous mouse immunoglobulin Kappa and/or Lambda light chain loci such that the functional expression of the endogenous immunoglobulin genes is reduced. In one embodiment, the nucleic acid comprises a silencing element resulting in transcriptional silencing of the endogenous immunoglobulin gene. In a further embodiment, or in addition, the nucleic acid comprises a sequence that disrupts splicing and/or translation of the endogenous immunoglobulin gene, for example, by introducing an exon that renders a frame shift in the coding sequence, or that comprises a premature stop codon. In each case chimeric animals are generated which are derived in part from the modified embryonic stem cells and are capable of transmitting the genetic modifications through the germ line. The mating of mouse strains with human immunoglobulin loci to strains with inactivated mouse loci yields animals which produce antibodies comprising essentially only human light chains.

A construct for homologous recombination is prepared by means known in the art and any undesirable sequences are removed, e.g., procaryotic sequences. Any convenient technique for introducing a construct for homologous recombination into a target cell may be employed. These techniques include spheroplast fusion, lipofection, electroporation, calcium phosphate-mediated DNA transfer or direct microinjection. After transformation or transfection of the target cells, target cells are selected by means of positive and/or negative markers, for example, by neomycin resistance and/or acyclovir and/or gancyclovir resistance. Those cells which show the desired phenotype may then be further analyzed by restriction analysis, electrophoresis, Southern analysis, PCR, or the like. By identifying fragments which show the presence of the lesion(s) at the target locus, cells in which homologous recombination has occurred to inactivate a copy of the target locus are identified.

Furthermore, it is shown that upon immunization, the murine and human VH regions in the afore-mentioned transgenic mice but not the VL regions are capable of undergoing somatic hypermutations to generate high affinity antibodies. Advantageously, these antibodies encoded by germline VL regions are predicted to contribute to lower immunogenicity when applied in humans and result in more stable antibodies that are less prone to aggregation and thus safer for therapeutic use in humans.

MAbs derived from the afore-mentioned non-human transgenic animals or cells all share the same identical human VL regions. It has been described that mAbs that share the same identical VL region may be co-expressed in a single clonal cell for the production of mixtures of recombinant antibodies with functional binding sites (see, the incorpoarated WO 04106375 and WO 05068622). Thus, provided is a platform for the generation of specific and high affinity mAbs that constitute the basis for mixtures of mAbs produced by clonal cells.

In certain embodiments mAbs derived from the afore-mentioned non-human transgenic animals or cells are directed against cellular targets. Examples of targets are human surface-expressed or soluble proteins or carbohydrate molecules. Further, examples of targets are surface-expressed proteins or carbohydrate molecules that are expressed on the surface of bacteria, viruses, and other pathogens, especially of humans.

More specifically, example targets include cytokines and chemokines, including but not limited to InterLeukin 1beta (ILIbeta), IL2, IL4, IL5, IL7, IL8, IL12, IL13, IL15, IL18, IL21, IL23 and chemokines such as, for example, CXC chemokines, CC chemokines, C chemokines (or γ chemokines) such as XCL1 (lymphotactin-α) and XCL2 (lymphotactin-ß), and CX3C chemokines. Further examples of targets are receptor molecules of the cytokines and chemokines, including type I cytokine receptors such as, for example, the IL-2 receptor, type II cytokine receptors such as, for example, interferon receptors, immunoglobulin (Ig) superfamily receptors, tumor necrosis factor receptor family including receptors for CD40, CD27 and CD30, serine/threonine-protein kinase receptors such as TGF beta receptors, G-protein coupled receptors such as CXCR1-CXCR7, and tyrosine kinase receptors such as fibroblast growth factor receptor (FGFR) family members, EGF receptor family members including erbB1 (EGF-R; HER1), erbB2, (HER2), erbB3 (HER3), and erbB4 (HER4), insulin receptor family members including IGF-R1 and IGF-RII, PDGF receptor family members, Hepatocyte growth factor receptor family members including c-Met (HGF-R), Trk receptor family members, AXL receptor family members, LTK receptor family members, TIE receptor family members, ROR receptor family members, DDR receptor family members, KLG receptor family members, RYK receptor family members, MuSK receptor family members, and vascular endothelial growth factor receptor (VEGFR) family members.

Further example targets are targets that are over-expressed or selectively expressed in tumors such as, for example, VEGF, CD20, CD38, CD33, CEA, EpCAM, PSMA, CD54, Lewis Y, CD52, CD40, CD22, CD51/CD61, CD74, MUC-1, CD38, CD19, CD262 (TRAIL-R2), RANKL, CTLA4, and CD30; targets that are involved in chronic inflammation such as, for example, CD25, CD11a, TNF, CD4, CD80, CD23, CD3, CD14, IFNgamma, CD40L, CD50, CD122, TGFbeta and TGFalpha.

Surface-expressed proteins or carbohydrate molecules that are expressed on the surface of bacteria, viruses, and other parasitic pathogens, especially of humans, include surface markers of influenza A and B viruses such as hemagglutinin (HA) and neuraminidase (NA), filoviruses such as Ebola virus, rabies, measles, rubella, mumps, flaviviruses such as Dengue virus types 1-4, tick-borne encephalitis virus, West Nile virus, Japanese encephalitis virus, and Yellow fever virus, Paramyxoviruses including Paramyxovirus such as Parainfluenza 1, 3, Rubulavirus such as Mumpsvirus and Parainfluenza 2, 4, Morbillivirus, and Pneumovirus such as Respiratory syncytial virus, Vaccinia, small pox, coronaviruses, including Severe Acute Respiratory Syndrome (SARS) virus, hepatitis virus A, B and C, Human Immunodeficiency Virus, herpes viruses, including cytomegalovirus, Epstein Barr virus, herpes simplex virus, and Varicella zoster virus, parvoviruses such as, for example, B19; *Legionella pneumophila; Listeria monocytogenes; Campylobacter jejuni; Staphylococcus aureus; E. coli O157:H7; Borrelia burgdorferi; Helicobacter pylori; Ehrlichia chaffeensis; Clostridium difficile; Vibrio cholera; Salmonella enterica* Serotype *Typhimurium; Bartonella henselae; Streptococcus pyogenes* (Group A Strep); *Streptococcus agalactiae* (Group B Strep); Multiple drug resistant *S. aureus* (e.g., MRSA); *Chlamydia pneumoniae; Clostridium botulinum; Vibrio vulnificus; Parachlamydia pneumonia; Corynebacterium amycolatum; Klebsiella*

*pneumonia*; Linezolid-resistant enterococci (*E. faecalis* and *E. faecium*); and Multiple drug resistant *Acinetobacter baumannii*.

Additional examples of targets are IL-6 and its receptor, IL-6Ralpha, glycoprotein-denominated gp130, RSV, especially the surface proteins F, G and SH and non-structural proteins such as N and M, and receptor tyrosine kinases, in particular erbB1 (EGF-R; HER1), erbB2, (HER2), erbB3 (HER3), erbB4 (HER4), IGF-R1 and IGF-RII, c-Met (HGF-R).

Therefore, provided is a platform for the generation of specific and high affinity mAbs against the above mentioned targets that constitute the basis for mixtures of mAbs produced by clonal cells. In certain embodiments, the specific and high affinity mAbs comprise mAbs that are directed against different epitopes on at least one of the targets. In a further embodiment, the specific and high affinity mAbs comprise mAbs that are directed against different targets, such as, for example, one or more members of the EGF-receptor family, including erbB1 (EGF-R; HER1), erbB2, (HER2), erbB3 (HER3) and erbB4 (HER4).

Unless otherwise defined, scientific and technical terms used in connection with this disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al. *Molecular Cloning: A Laboratory Manual* (3rd edition, Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Selection methods are also described herein. In one embodiment, provided is a method for selecting combinations of proteinaceous molecules having specific affinity for at least two target epitopes, the method comprising contacting a collection with the two target epitopes and selecting combinations showing the specific affinity.

Such methods are particularly useful when the two target epitopes are associated with one disease or disorder. In certain embodiments, it is possible to combine such a method with subjecting a selected combination of proteinaceous molecules to a biological assay indicative of an effect of the combination on the disease and/or disorder.

Compositions obtainable by the methods described herein are also included. Examples are compositions comprising at least three different paired variable regions, having different binding specificities, in particular, those wherein the variable regions are derived from immunoglobulin light chains and/or immunoglobulin heavy chains. A combination composition that targets both TNF-α as well as IL-1β is an exemplary combination. In such typical therapeutic uses, it is important that the combination preparations do not lead to severe immune responses in the subject to be treated. At least some of the antigenic parts of the binding molecules, such as the constant regions in antibodies should be of human origin. In the alternative, antigenic parts may be omitted or masked by molecules such as PEG. Thus, also provided in one embodiment is a composition, which is a pharmaceutical composition. Although antibodies have found use in other areas, and antibody combinations as describd herein can be used in other areas, such as the pharmaceutical use of the combinations, both diagnostic and therapeutic. However, in industrial applications the combinations may also be superior to existing separation techniques, because of ease of production, consistency of production and the availability of many combinations of specificities, capable of separating almost anything from any mixture. In testing, be it in pharmaceutical diagnostics or in any other field (environmental, agricultural, to name a few) the combinations can be used advantageously as well. Both partners of a sandwich assay can be made in one cell. Agglutination mixtures can be made in one cell. When using the IgG format, the expression in the same cell will lead to a substantial fraction of bispecific compounds, which offer unique applications in combination with the monoclonals present in the same mix. For example, when a monoclonal antibody can only bind with one arm to an antigen, a bispecific molecule with binding sites capable of binding to two different epitopes on the same antigen, may more consistently than the monoclonal antibody mixture immobilize or trap antigen. Again, ease and consistency of production, as well as the diversity of specificities is an asset of the combinations. These advantages of course also apply in selecting and producing combinations of specificities for therapeutic and/or prophylactic use, with additional advantages in ease of selection, efficacy of selected combinations and the mentioned safety aspects.

A simple combination starts with two specificities present in the combination. When a promiscuous variable region is present, such a combination requires only three different variable regions. The combination can be made such that all resulting paired variable regions in one proteinaceous molecule have the same specificity, giving monospecific molecules, or the variable or, if appropriate, the constant regions can be designed such that bispecific molecules are also present. It can also be designed such that one monospecific and one bispecific molecule are present, but that the other possible monospecific molecule does not arise, because the variable regions cannot assemble in that manner. Thus, one embodiment comprises a composition comprising at least one monospecific antibody and at least one bispecific antibody produced in one cell for use as a pharmaceutical. In some applications, bispecific molecules, especially antibodies, may be advantageous for bringing two antigens together on a cell surface. Such aggregation events are often required in biology for transduction of a signal to the inside of a cell. Bispecific antibodies in the mixture may also be used to connect effector molecules with target cells. The uses envisaged for bispecific antibodies in the prior art are also envisaged for bispecific molecules. The most advantageous compositions comprise more than two different monospecific binding molecules, optionally together with the different possible combinations of bispecific or multispecific molecules that may result from the different possible pairing events. These multispecific mixtures resemble polyclonal mixtures in their efficacy for recognizing antigens, but without the drawbacks of many irrelevant specificities in the mixture. The mixtures resemble monoclonal antibodies in their defined constitution, ease of production and high specificities, but without the concomitant loss of efficacy. The mixtures are referred to as OLIGOCLONICS®. OLIGOCLONICS® can thus contain two, three, or more different binding specificities, and can exist in various formats. In the simplest form, OLIGOCLONICS® in the IgG format contain a mixture of different monospecific antibodies and bispecific antibodies in a particular given ratio. In the Fab format, OLIGOCLONICS® contain a mixture of different Fab molecules which are the product of correctly paired variable regions. In the mixed format, OLIGOCLONICS® contain a mixture of antibodies and antibody fragments.

As disclosed herein, the methods and means in one embodiment are the production of combinations of specificities. Before production of combinations, suitable combinations must be designed and/or selected. These methods for designing and selection are also part of the present disclosure. Thus, in a further embodiment, provided is a method for producing nucleic acids encoding variable regions for use in a method for production of combinations of specificities comprising synthesizing nucleic acids encoding variable regions, expressing the nucleic acids and allowing the expression products to pair and selecting nucleic acids encoding variable regions having desired pairing behavior.

In an alternative embodiment, provided is a method for producing nucleic acids encoding variable regions for use in a method for production of combinations of specificities comprising altering existing nucleic acids encoding variable regions, expressing the nucleic acids and allowing the expression products to pair and selecting nucleic acids encoding variable regions having desired pairing behavior. Of course, both methods may be combined and/or repeated in any order. Synthesis, alteration and selection methods are disclosed in more detail in the detailed description.

Nucleic acid molecules for use in producing combinations of specificities may be those encoding immunoglobulin polypeptides. Of course, all types of immunoglobulins, especially antibodies (IgM, IgE, IgGs, etc.), but also fragments (scFv, Fab, single-domain, engineered variants) can be used. Variable regions can, for example, be derived from either immunoglobulin heavy chain variable regions, or immunoglobulin light chain variable regions, but can also be engineered hybrids of heavy and light chain variable regions (with, for example, swapped CDR regions or FR regions). Variable regions can, for example, be obtained from hybridomas, by cloning from immune or non-immune donors or can be synthetically constructed variable regions. Even hybrids can be produced using nucleic acids and methods described herein. For example, hybrids with different yet functional binding sites can be made by providing elements from different isotypes, for example, IgM and IgG, or IgM and IgA. It should be born in mind that T cell receptors resemble antibodies in many respects. Thus, the methods can also be applied advantageously with T cell receptors, their variable regions and their encoding nucleic acids. The methods may be carried out using immunoglobulins having different chains (T cell receptors), especially antibodies having light chains and/or heavy chains or parts/derivatives thereof. Of course part and/or derivatives are such parts and/or derivatives that do have specific binding properties comparable to immunoglobulins.

This means that variable regions should at least comprise an element which resembles a complementarity-determining region of an antibody (CDR). In certain embodiments, the variable regions have more than a CDR, and/or a variable region resembles in size and physicochemical properties a VH or VL of an antibody. The detailed description describes using antibodies as an exemplary embodiment.

BRIEF DESCRIPTION OF THE DRAWINGS

FIG. 9: Screening antibody mixtures produced by the same host cell for optimal bio-activity. Mixtures are made by transfecting heavy chain genes encoding the antibodies of interest (here number is 10) together with optimally paired light chain, followed by cloning of cell lines, selecting stably producing cell lines, and eventually screening the resulting antibody mixtures for optimal bio-activity.

FIG. 13: The sequence of pSCFV (SEQ ID NO:148 of the SEQUENCE LISTING, incorporated herein by this reference), a pUC119-based plasmid suitable for stepwise cloning of antibody variable regions and expression of scFv fragments.

FIG. 16: Sequence alignment of the three light chains amino acid sequences of antibodies JA (Kappa) (SEQ ID NO:110), and JB (SEQ ID NO:112) and M57 (SEQ ID NO:114) (both lambdas). The position of the CDRs is indicated.

FIGS. 18A-18F: Mutagenesis of heavy chain variable region of the JA antibody (SEQ ID NO: 109); underlined region was mutagenized. Other regions known to be important for the interaction with the VL: the residues at the positions marked in color (bottom) or with the boxes around the JA-VH sequence are, alternatively, suitable for mutagenesis (based on data from worldwideweb.biochem.unizh.ch/antibody/Structures/DimContacts/VHDimHistFrame.html).

FIG. 20: Outline of the expression cassette and expression vectors for use with eukaryotic cells. The legend of the vector elements is depicted on the right. On the left hand side top panel are depicted, as examples, four eukaryotic expression cassettes for three antibody heavy chains and one light chain. The elements found in an expression cassette for a single antibody chain encoding gene or nucleic acid typically comprises a promoter, a Leader sequence, an open reading frame encoding the antibody chain of interest, a polyadenylation region and terminator, all in operable configuration. Further sites/regions used for site-directed and in some cases homologous, recombination, are shown (are also optional; indicated on top of the first expression cassette). On the bottom panel is depicted an exemplary vector backbone used for insertion of the top panel cassette(s). This scheme displays the typical elements of a eukaryotic expression vector, comprising a bacterial origin of replication (such as Col E1), a bacterial selection marker (B-Select, such as the ampicillin resistance gene), a eukaryotic selection marker (Select, such as gpt, neo, zeo, etc., see text; useful when stable integration into the host cell's genome is envisaged), and additional optional elements such as a bacteriophage packaging region (for ss-DNA production, such as f1), and an optional amplification marker (such as DHFR). Optional are other expression controlling elements (such as BEs, STAR, LCRs, MARs and the like, see below) and IRES; these are included in later figures.

FIG. 23: Design of a hybrid light chain library for identifying a pairing-compatible light chain for h4D5v8 and 2C4. The amino acid sequences used by Herceptin (trastuzumab, h4D5v8) and pertuzumab (Omnitarg, 2C4) are compared to one another, and to two designer light chain libraries, HYB1 and HYB2 (see, Example 17 for details of the design). Residues identical to those of Herceptin are indicated with a dash; amino acids are encoded by the single-letter consensus; X means positions to be targeted for diversification in a library approach. Numbers indicated for the most relevant residue positions (see, text for more details).

FIGS. 37A-37Z: Overview of the sequences used or referred to in this application: Human germline IGKV1-39/J DNA (SEQ ID NO:84); human germline IGKV1-39/J Protein (SEQ ID NO:85); human germline IGLV2-14/J DNA (SEQ ID NO:86); human germline IGLV2-14/J Protein (SEQ ID NO:87); Rat IGCK allele a DNA (SEQ ID NO:88); Rat IGCK allele a protein (SEQ ID NO:89); IGKV1-39/J-Ck (SEQ ID NO:90); IGLV2-14/J-Ck (SEQ ID NO:91); VkP-IGKV1-39/J-Ck (SEQ ID NO:92); VkP-IGKV1-39/J-Ck-Δ1 (SEQ ID NO:93); VkP-IGKV1-39/J-Ck-Δ2 (SEQ ID NO:94); VkP-IGLV2-14/J-Ck (SEQ ID NO:95); pSELECT-IGKV1-39/J-Ck (SEQ ID NO:96); pSelect-IGLV2-14/J-Ck (SEQ ID NO:97); MV1043 (SEQ ID NO:98); and MV1057 (SEQ ID NO:99).

FIGS. 38A-38C: Generation of Rosa26-IgVkl-39 KI allele. (FIG. 38A) Schematic drawing of the pCAGGS-IgVK1-39 targeting vector. (FIGS. 38B-1-38B-4) Nucleotide sequence of the pCAGGS-IgVK1-39 targeting vector (SEQ ID NO: 100). (FIG. 38C) Targeting strategy.

(FIG. 39A) Southern blot analysis of genomic DNA of ES clones comprising an insertion of the pCAGGS-IgVK1-39 targeting vector. Genomic DNA of four independent clones was digested with AseI and probed with 5e1 indicating the 5'-border of the targeting vector. All clones comprise a correct insertion of the targeting vector at the 5' end. (FIG. 39B) Southern blot analysis of genomic DNA of ES clones comprising an insertion of the pCAGGS-IgVK1-39 targeting vector. Genomic DNA of four independent clones was digested with MscI and probed with 3e1 indicating the 3'-border of the targeting vector. All clones comprise a correct insertion of the targeting vector at the 3' end. (FIG. 39C) Southern blot analysis of genomic DNA of ES clones comprising an insertion of the pCAGGS-IgVK1-39 targeting vector. Genomic DNA of four independent clones was digested with BamHI and probed with an internal Neo probe indicating the 5'-border of the targeting vector. All clones comprise a correct, single insertion of the targeting vector.

FIGS. 40A-40C: Generation of Rosa26-IgV12-14 KI allele. (FIG. 40A) Schematic drawing of the pCAGGS-IgVL2-14 targeting vector. (FIGS. 40B-1-40B-4) Nucleotide sequence of the pCAGGS-IgVL2-14 targeting vector containing the CAGGS expression insert (SEQ ID NO:101)

based on the rearranged germline IGLV2-14/J V lambda region (IGLV2-14/J-Ck). (FIG. 40C) Targeting strategy.

FIG. 41A displays the binding strength for DRB1 allotypes, while FIG. 41C displays the binding strength for DRB3/4/5, DQ and DP allotypes. The values in the figure represent dissociation constants (Kds) and are plotted on a logarithmic scale in the range 0.01 µM-0.1 µM (very strong binders may have run off the plot). For medium binding peptides, qualitative values are given only, and weak and non-binders are not shown. Values are plotted on the first residue of the peptide in the target sequence (the peptide itself extends by another nine residues). Importantly, only the strongest binding receptor for each peptide is shown: cross-reacting allotypes with lower affinity are not visible in this plot. The strongest binding receptor is indicated by its serotypic name. Finally, any germline-filtered peptides are plotted with a lighter color in the epitope map (in this case, no non-self epitopes were found). FIG. 41B shows the HLA binding promiscuity for every decameric peptide (Y-axis: the number of HLA allotypes recognizing critical epitopes in each of the peptides starting at the indicated residue shown on the X-axis). The promiscuity is measured as the number of allotypes out of the total of 47 for which the peptide is a critical binder. White columns refer to self-peptides, and black columns (absent here) to non-self peptides.

(FIG. 43A) Targeting strategy. (FIG. 43B) Schematic drawing of the pIgKappa targeting vector.

(FIG. 44A) First step of the targeting strategy. (FIG. 44B) Second step of the targeting strategy.

(FIG. 45A) pVkP-O12 (VkP-IGKV1-39/J-Ck); (FIG. 45B) pVkP-O12-del1 (VkP-IGKV1-39/J-Ck-Δ1); (FIG. 45C) pVkP-O12-del2 (VkP-IGKV1-39/J-Ck-Δ2).

(FIG. 46A) VkP-O12 (VkP-IGKV1-39/J-Ck); (FIG. 46B) VkP-O12-del1 (VkP-IGKV1-39/J-Ck-Δ1); (FIG. 46C) VkP-O12-del2 (VkP-IGKV1-39/J-Ck-Δ2).

FIGS. 51A-1, 51A-2, 51B-1, and 51B-2: Transgenic human Vk1 light chain is not expressed in pro- and pre-B cells but is expressed in the immature and recirculating populations B cells in the bone marrow. (FIGS. 51A-1 and 51A-2) Gating of bone marrow cells. (FIGS. 51B-1 and 51B-2) Histograms of transgene expression with overlay from one WT control.

DETAILED DESCRIPTION OF THE INVENTION

Figure 1:
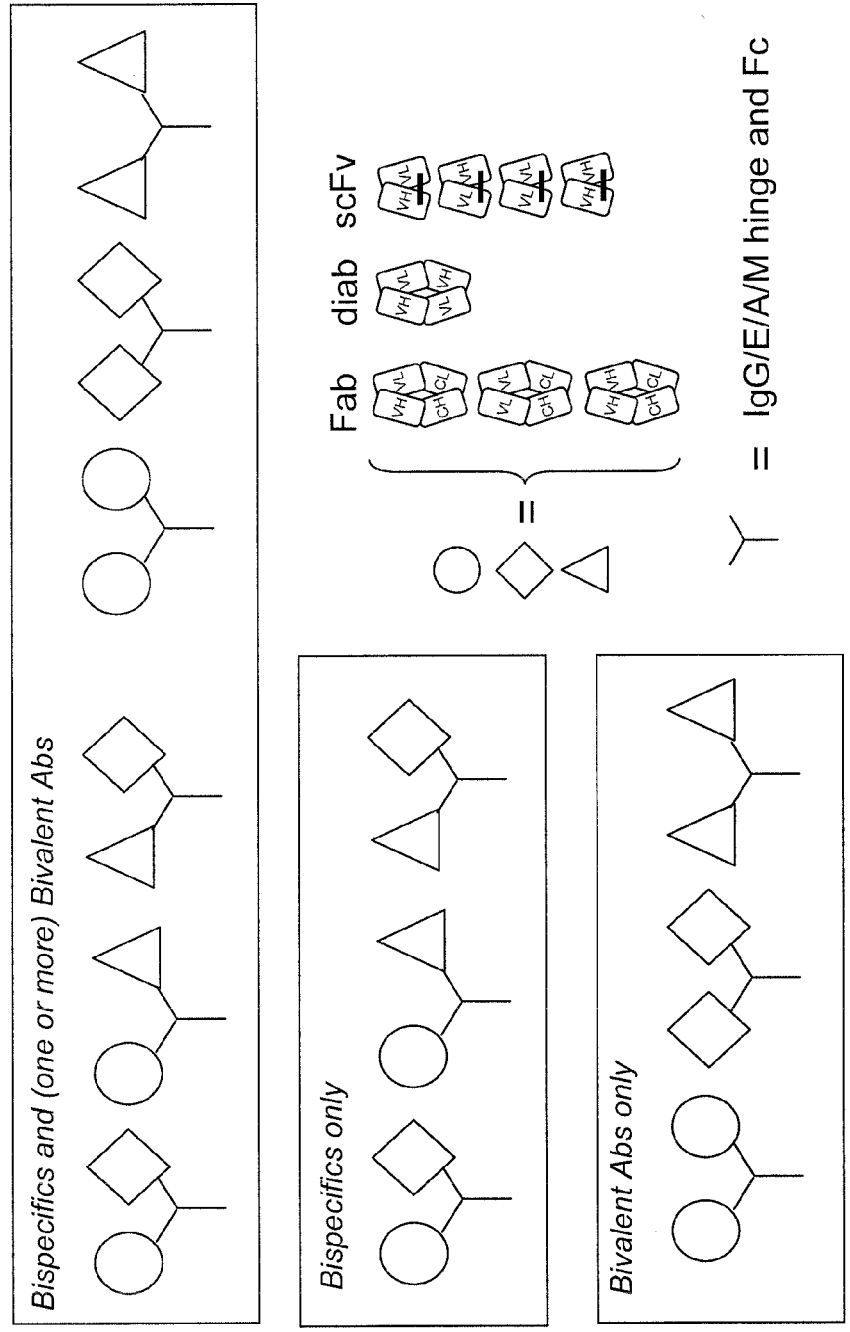
FIG. 1: Examples of composition of three or six proteinaceous molecules with three different binding specificities. The use of antibodies with appropriate pairing between the variable regions yields mixtures of antibodies that are bispecific or monospecific and bivalent (top panel). By appropriate engineering to manipulate the pairing between the variable regions, mixtures of only bispecifics or bivalent molecules arise (left hand side panels). In the legend on the right panel (grey box) it is indicated that the three symbols, the circle, triangle and square, represent binding sites consisting each of variable regions.

In the fight against infection, the immune system creates a cellular and humoral response that can specifically combat the infectious agent. The humoral immune response is based on immunoglobulins, or antibodies, which contact antigens and mediate certain effector functions to clear the infection ((I. M. Roit, et al. (1985)) and all references herein). In the immune system, antibodies are generated by B-lymphocytes. Antibodies consist of heavy and light chains that are assembled via inter-domain pairing and interchain disulphide bonds to form multivalent molecules. Various isotypes of natural antibodies exist, including IgG (within humans, four subclasses, IgG1, IgG2, IgG3, IgG4), IgM, IgD, IgA and IgE. An IgG molecule contains two heavy (H) and two light (L) chains, both with a variable (V) and constant (C) regions. A typical IgG antibody comprises two heavy (H) chain variable regions (abbreviated herein as VH), and two light (L) chain variable regions (abbreviated herein as VL). The VH and VL regions can be further subdivided into regions of hypervariability, termed "complementarity-determining regions" ("CDR"), interspersed with regions that are more conserved, termed "framework regions" (FR). The extent of the framework region and CDRs has been precisely defined (see, E. A. Kabat, et al. (1991) *Sequences of Proteins of Immunological Interest, Fifth Edition*, U.S. Department of Health and Human Services, NIH Publication No. 91-3242, and C. Chothia, et al. (1987) *J. Mol. Biol.* 196:901-917, which are incorporated herein by reference).

In the generation of the primary immune response, the pairing of heavy and light variable region sequences of antibodies is a random process. The variable region genes are first assembled by recombining of a set randomly picked V. (D) and J genetic elements represented in the genome as a diverse gene pool. The recombined heavy and light variable regions are then spliced towards their respective constant region genes and the chains expressed, assembled and secreted as immunoglobulin. In this combinatorial library, in principle every heavy chain can pair with every light chain, to create a vast repertoire of different antigen specificities, with diversity derived from the rearrangement process (which also introduces further diversity at some of the segment junctions) and from the combinatorial assembly of the heavy and light chain variable regions. In principle, B-cells produce only one antibody specificity, encoded by one antibody heavy and one antibody light chain sequence. The immune system selects via an efficient antigen-selection process those antibodies that can bind to a given antigen, in particular, when the antigen is foreign and part of a pathogen.

In natural immunoglobulins, the light chain which consists of two domains, is paired to the heavy chain, which consists of at least four domains and a hinge region: non-covalent interactions occur between VH and VL, and between CH1 and CL; between the latter a disulphide bridge provides a covalent linkage between heavy and light chains. Furthermore, the heavy chains are found paired to one another, i.e., in the IgG format, and sometimes further associate with additional elements such as J-chains (e.g., in the IgM format). A strong non-covalent interaction occurs between the CL and CH1 domains, a frequently weaker interaction is present between VL and VH. The heavy chains are paired via interactions in the hinge region (often covalently associated via one or more disulphide bridges) and between the CH2 and CH3 domains. By sequencing large pools of antibody variable genes from isolated B-cell and comparing the frequency of the pairings of VH and VL segments, it was confirmed that this pairing between VH and VL regions is on average a random process. However, since the variable regions are genetically diverse and some of this diversity at the amino acid level is structurally situated at the predicted interface region between the two domains, the pairing of one given VH to another VL is not any more random. For example, pairing of a given VH with another VL than the molecule was initially selected with, may lead to loss of affinity of binding for the antigen, but may also lead to a reduced pairing efficiency. Within one B-cell, typically and normally only one light and one heavy chain is expressed, but in the few instances that other light or heavy chains are expressed (such as in two fused B-cells), mispairing between the chains will occur, and antigen binding is lost in this fraction of the antibody preparation. For example, in the past, the expression of multiple antibody variable domains, as in quadromas or cells transfected with multiple heavy and/or light chain genes, typically yields a large fraction of pairings of variable regions that are not functional. In order to build bispecific antibodies, the pairing of different antibody heavy and light chains when expressed in the same cell was investigated intensively. From studies of the pairing in antibodies derived from hybrid hybridomas made by fusing two antibody-producing hybridomas, the pairing was shown to be based on a random association of light and heavy chains with some cases where a certain level of preferential pairing was seen, but not enough to prevent mispairing to occur.

Described herein are a variety of methods to select antibodies with optimal pairing behavior of antibody chains. With such methods, compositions of multiple antibodies with different binding specificities can be made.

1. Antibodies with Pairing-Compatible Variable Regions
   a. Summary

Herein, disclosed are methods and means for obtaining antibodies with pairing-compatible variable regions. The presence of such variable regions facilitate the predictability and functionality of the resulting pairing between the antibody variable regions. Two antibodies contain pairing-compatible variable regions when the pairing of the variable regions in a mixture of all variable regions combined, occurs in such manner that predominantly functional binding sites arise as a result of the pairing. Two antibodies have pairing-compatible variable regions when, for example, the variable light chain domains of both antibodies can be exchanged by the one of the other antibody, without drastically altering the antigen-binding affinity of the two antibodies. Another example of when antibodies have pairing-compatible variable regions, is when they share an identical or closely related variable region. In that case, pairing of the two partner domains to this shared region will lead to the formation of functional binding sites.

Methods for the identification of antibodies that have pairing-compatible variable regions are described. In the simplest form, pairing-compatible variable regions in sets of antibodies are identified by virtue of the sequence identity of the V-regions. In another approach, pairing compatible variable regions are identified by empirical exchange of V-genes or V-gene fragments between given antibodies, and testing antigen binding. In another approach, antibodies with a high likelihood of containing pairing-compatible variable regions can be enriched from antibody repertoires by combinations of selections and re-shuffling. Using appropriate selection strategies, antibody pairing may be selected to become promiscuous or exclusive in the context of the desired multiple antibody variable genes. A method is also described for providing a given antibody with pairing-compatible variable sequencing, using various mutagenesis and selection technologies. In another approach, antibodies with pairing-compatible variable regions are selected from synthetic antibody libraries with a high probability of identifying antibodies with such elements (for example, from a library with only one variegated variable domain). Further, antibodies with pairing-compatible variable regions are created by first selecting an antigen-specific single-domain antibody, and then providing this with a second domain that will pair with the first one to form a two-domain molecule.

Pairing-compatible variable regions can be identified in order to replace sequences in an antibody by the equivalent sequences of another antibody that are thought to mediate more favorable characteristics. The transfer of pairing-compatible variable regions between antibodies can be used to alter the pairing capability and pairing strength of the antibody chains, but it can also be envisaged to alter the immunogenicity, idiotype and expression yield of antibodies. Antibodies bearing such elements are also highly suitable for making pharmaceutical compositions of antibodies with multiple binding sites, for example, for making mixtures of antibodies containing such elements, by co-expression in the same host cell. In particular, when the variable regions share a full variable domain (such as the light chain), co-expression will yield functional binding sites only. Antibodies with pairing-compatible variable regions are suitable for the creation of mixtures of antibodies, in which the antibodies are either solely monospecific, or bispecific, or a mixture of mono- and bispecific antibodies, or even, depending on the choice of isotypes with more than two binding sites (e.g., sIgA, IgM), combinations of multiple specificities within the same antibody molecule. Such approaches provide a means to have in the same pharmaceutical preparation antibodies with multiple specificities, and, if required, combinations of specificities within the same molecule.

b. Sources of Antibodies

Suitable antibodies can be derived from a variety of sources, including monoclonal antibodies, phage antibodies, antibodies from transgenic animals, etc. Monoclonal antibodies are obtained from a population of substantially homogeneous antibodies using a hybridoma method first described by Kohler and Milstein, Nature 256:495 (1975) or may be made by recombinant DNA methods. In the hybridoma method, a mouse or other appropriate host animal, is immunized to elicit lymphocytes that are capable of producing antibodies that will specifically bind to the antigen used for immunization. Alternatively, lymphocytes may be immunized in vitro. Lymphocytes are fused with myeloma cells using a suitable fusing agent, such as polyethylene glycol, to form a hybridoma cell. Antibodies can also be isolated from transgenic animals that harbor human immunoglobulin genes.

Antibodies or antibody fragments can also be isolated using display-based antibody library technology, wherein antibody fragments are selected by exposing a library of such antibodies displayed on the surface of phage, yeast or other host cell, to the antigen of interest, and isolating those antibody fragments which bind to the antigen preparation. A display library is a collection of entities; each entity includes an accessible polypeptide component and a recoverable component that encodes or identifies the peptide component. Many antibody fragments have been displayed on the surface of entities that carry the genetic material encoding the antibody fragment inside the entity, such as bacteriophages. This format is termed "phage display." Phage display is described, for example, in Ladner et al., U.S. Pat. No. 5,223,409; Smith (1985) *Science* 228:1315-1317. Other display formats utilize peptide-nucleic acid fusions. Polypeptide-nucleic acid fusions can be generated by the in vitro translation of mRNA that includes a covalently attached puromycin group, e.g., as described in Roberts and Szostak (1997) *Proc. Natl. Acad. Sci. U.S.A.* 94:12297-12302, and U.S. Pat. No. 6,207,446. The mRNA can then be reverse transcribed into DNA and cross-linked to the polypeptide. In still another display format the library is a cell-display library. Proteins are displayed on the surface of a cell, e.g., a eukaryotic or prokaryotic cell. Exemplary prokaryotic cells include *E. coli* cells, *B. subtilis* cells, spores, exemplary eukaryotic cells include yeast such as *Saccharomyces cerevisiae, Hansenula polymorpha, Pichia pastoris, Kluyveromyces lactis*, insect cells, and mammalian cells. Methods for the display of antibody fragments and the construction of antibody libraries in a variety of formats are well described in the literature and known to those skilled in the art.

c. Identifying Pairing-Compatible Elements in Panels of Antigen-Reactive Antibodies Antibodies with pairing-compatible variable region sequences and, therefore, suitable pairing behavior of variable regions, are identified by a variety of methods that are disclosed within this document. In a first approach, antibodies with pairing-compatible variable regions are selected from panels of antigen-specific antibodies (in which the antigen can be one defined target antigen but also a collection of different antigens, and the panel contains at least two antibodies), as follows. The sequences of heavy and light variable regions are determined and inspected to find clones with identical or highly similar light or heavy chain variable domains. If the amino acid sequence of part of or the complete variable region is identical for two antibodies, the two given antibodies have a pairing-compatible variable region.

In another approach, pairing-compatible variable regions are identified in amino acid sequences that appear related yet have amino acid differences: for example, if there are differences in the amino acid sequence but the same or related germ line segment is used, or when highly similar CDR regions are used, or if similar canonical folds in some CDR regions are found yet different germ line segments are used, the variable regions may still comprise pairing-compatible variable regions. This is confirmed by swapping the variable region(s) between the antibodies in the panel, and measuring antigen binding of the new pairs. Experimentally light and heavy chains or parts thereof can be exchanged by recombinant DNA methods such as restriction enzyme-based DNA cloning, oligonucleotide-based mutagenesis, gene synthesis and PCR-mediated mutagenesis, methods which are widely available in the art. Binding assays that can be used are well established in the art and known to those skilled in the art; some are described below. This method may identify cases in which both variable regions can be exchanged between two antibodies, such as two related light chains that can be swapped with no or an acceptable effect on the affinity. It can also identify cases in which only one of the variable regions of the two antibodies can tolerate the exchange, for example, one light chain that functionally pairs with one of two heavy chains only, while the other light chain can functionally pair with both heavy chains. In that case the latter light chain can be used to replace the former non-matching one and, thus, create two antibodies with pairing-compatible variable regions. Functional pairing means that the variable region pairing has ideally no effect on antigen-binding affinity or specificity, but allowable may also be a <10-fold reduction in affinity, and at the most a 100-fold reduction in affinity, or any improvement of affinity.

Figure 2:
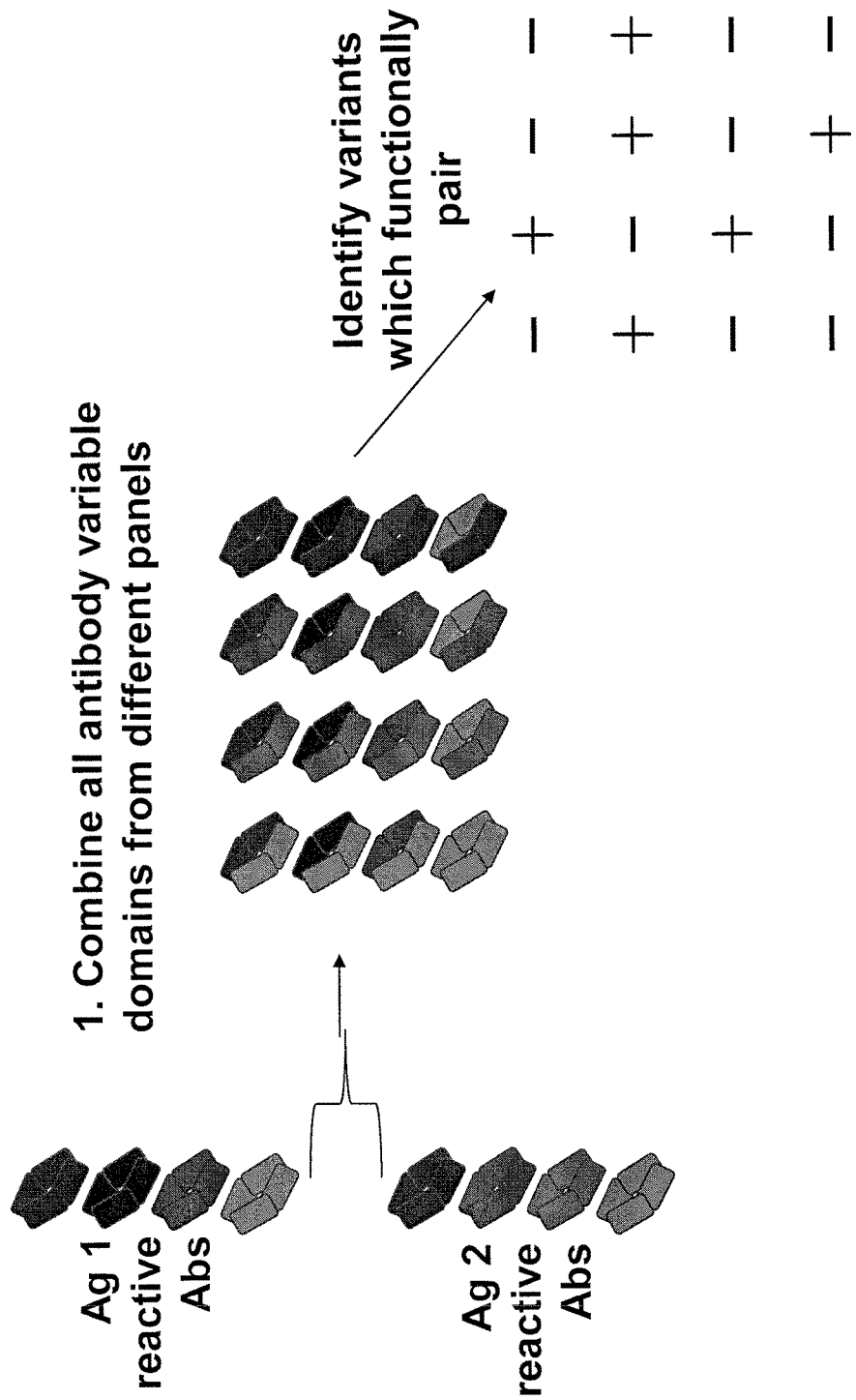
FIG. 2: Method to identify antibodies with pairing-compatible elements by empirical analysis of antibody variable region combinations.

In another embodiment, pairing-compatible variable regions are identified in panels of antibodies without knowing or using the sequence of the variable regions of the antibodies. First a collection of antibody variants is created in which all variable regions are combined with the other partner variable regions of the antibodies in the panel. Then, the effect on antigen binding is established empirically, to identify those antibodies with can functionally pair to the variable regions of the other antibodies in the panel (FIG. 2). This method identifies pairing-compatible variable regions that are not immediately identified by sequence comparison. Instead of using the partner variable regions derived of the antibodies in the panel, also other partner variable regions can be used. For example, the heavy chain variable region of each of the antibodies in the panel is combined with a set of chosen light chain variable regions, for example, consisting of mainly germ line encoded segments representative of one or more of the light chain kappa or lambda gene families. Pairing-compatible variable regions are then identified by screening the combinations for antigen binding and scoring whether one common variable region provides antigen binding for the desired set of antibodies in the panel. These methods can be based on assessment of antigen binding of individual combination of the variable region genes, thus co-expression of two variable regions in the desired antibody format, or of antigen binding of multiple combinations of variable regions derived from co-expression in the same host cell. For example, two antibody heavy chain variable regions can be expressed inside the same host cell as Fd chain, and co-expressed with one light chain, and antigen binding for both antibody binding sites assessed. Further, by differentially tagging the two heavy chains, for example, with epitope tags such as tags derived from c-myc, VSV, HA, etc., the pairing of the two H-L combinations can be followed. Such an approach is suitable for finding pairing-compatible variable regions if a limited number of starting antibodies is available and allows the screening of large collections of partner variable regions.

Examples of pairing-compatible variable regions are V-regions based upon highly homologous germ line segments, or V-regions that differ by changes in the amino acid sequence (e.g., with somatic or other mutations, minor deletions, additions, substitutions). In such case, the effect of the exchange of the homologous region in the first antibody may differ from the effect seen with the exchange of the homologous region in the second antibody; e.g., there are cases where the affinity is changed to an allowable level for only one of the two antibodies, and cases where this occurs for both antibodies. In one embodiment, the pairing-compatible variable region comprises the light chain variable region or part of the light chain variable region. In another embodiment, the pairing-compatible variable regions comprise the heavy chain variable region or part of the heavy chain variable region.

Another embodiment of an approach to identify pairing-compatible variable regions in a panel of antibodies is the following. First the variable region of each of the antibodies is co-expressed with a partner variable region derived from the other antibodies in the panel, and a screen carried out that will detect the presence of intact antibody (thus, not antigen binding). The formation of intact antibody indicates pairing between the two variable regions; if no intact antibody is retrieved, this will indicate that the two variable regions are not pairing inside the host cell. The screening can be used to identify antibodies that display variable regions that cannot pair with one another in the chosen antibody format, i.e., as Fab fragments expressed in *E. coli* or as IgG molecules expressed in eukaryotic cells. When co-expressing the four variable region genes, only the cognate interactions occur, and the variable region genes are pairing-compatible.

d. Antibodies with Pairing-Compatible Variable Regions from Antibody Libraries

In certain embodiments, antibodies with pairing-compatible variable regions are selected from synthetic antibody libraries with a high probability of identifying antibodies with such elements. Synthetic antibody libraries are collections of antibodies that have been synthetically diversified (e.g., using site-directed mutagenesis or PCR-based gene synthesis using mutagenized oligonucleotides) in defined regions/locations within their variable regions. In one embodiment, the design of the diversity introduced into the primary antibody repertoire is such that at least a portion of a variable region and, for example, a complete variable region is not diversified, while the remaining area contains the diversity (examples in FIGS. 3, 4(*a*), 4(*c*) and 4(*d*)). Examples of such libraries are libraries based on human variable region genes, for example, a set of 49 different heavy chain genes with diversity introduced in the VH-CDR3, all combined with a single light chain (H. R. Hoogenboom, et al. (1992) *J. Mol. Biol.* 227:381-388). Antibodies selected from such repertoires will contain by design pairing-compatible variable regions. Such repertoires can be created by recombinant DNA methods and displayed on the surface of phage, cells, spores, ribosomes, or can be created in transgenic mice carrying only partial diversity in the V-gene composition. Synthetic diversity can be introduced in all CDR residues, in a subset of CDR residues, i.e., those with significant solvent exposure, and can be designed to encode all or a subset of amino acids, i.e., those that are commonly observed in natural antibody CDRs. An example of such tailored antibody library, with a single heavy chain variable domain scaffold and a fixed light chain variable domain, and with a limited number of heavy chain CDR residues variegated with a limited number of encoding amino acids is described in *J. Mol. Biol.* 338:299-310 and in WO 03/102157A2. Alternatively, to libraries with synthetic diversity in one variable region, also libraries with natural diversity, or combinations of natural and synthetic diversity (e.g., synthetic diversity in CDR1 and CDR2 and natural diversity in CDR3) in one variable region may be used.

Figure 4:
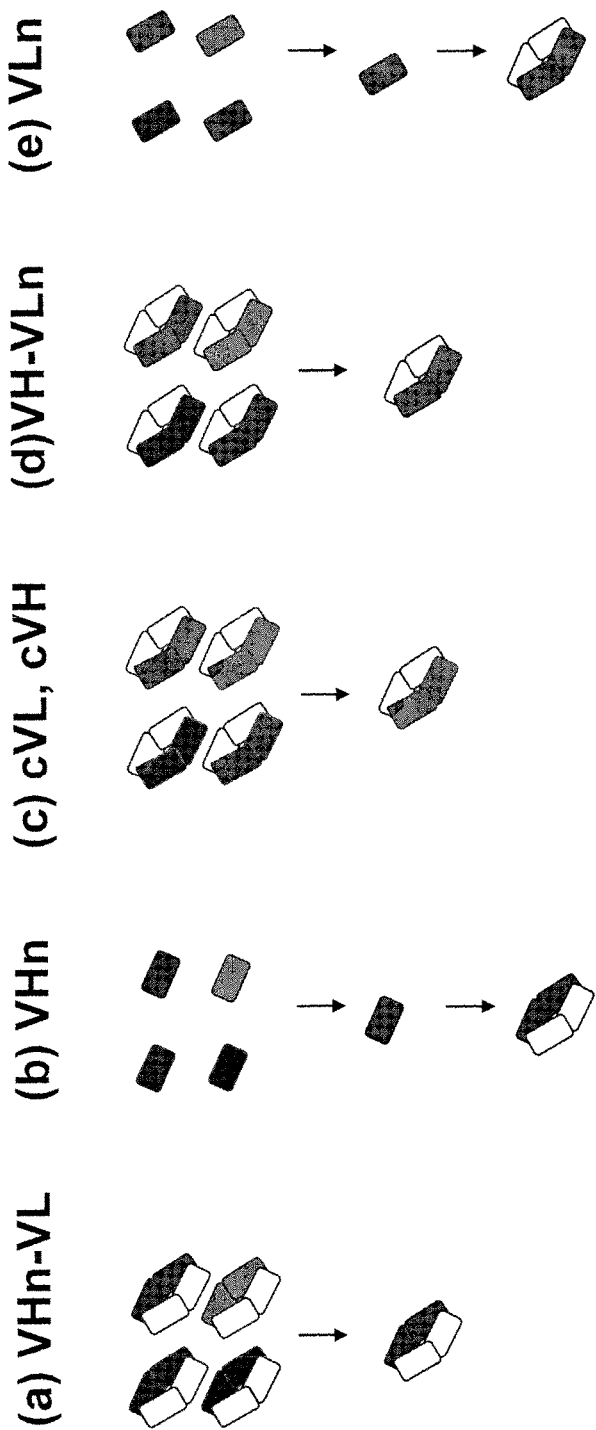
FIG. 4: Different approaches to select antibodies with appropriate pairing behavior. (a) selection of Fab library with constant light chain, and equivalent for Fab library with diversity in light chain only in (d); (b) selection of antigen-binding single-domain antibody from heavy chain only library, and equivalent for VL in (e); (c) selection of library of chimeric chains of VH and VL (in which, for example, some CDR elements are swapped).
Figure 5:
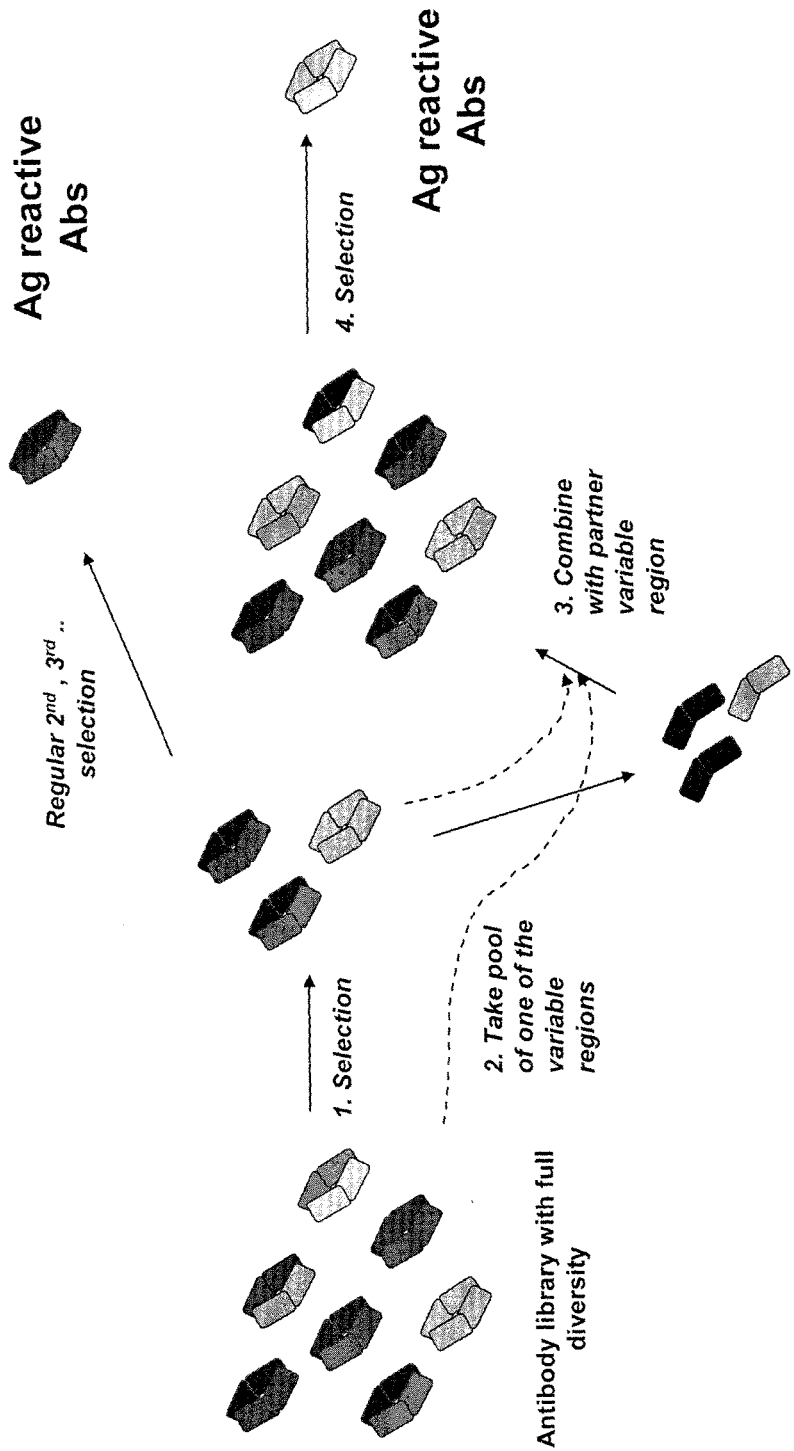
FIG. 5: Selecting antibodies with pairing-compatible variable regions by re-shuffling one chain. Starting point of the method is a repertoire of antibody binding sites, with paired variable regions, such as in this example, an Fab repertoire. Similarly single chain Fv libraries can be used. In a typical selection (top) the initially present pairing of variable regions is maintained throughout the iterative selection process; in the selection followed by reshuffling (steps 1-3), one of the two variable regions (for example the heavy chain) of the pairs that have been selected on antigen, is combined with partner domains (for example light chains) derived from either the selected population or from the original population). After this the selection (step 4), and the subsequent procedure are repeated. Eventually, individual antigen-reactive antibodies are identified by screening methods.

In one embodiment, antibodies with pairing-compatible variable regions are obtained by first selecting an antigen-specific single-domain antibody, and then providing this with a second domain that will pair with the first one to form a two-domain molecule (examples in FIG. 4, columns (b) and (e)). Single-domain antibodies may be isolated from in vitro display repertoires made from single-domain repertoire of certain human variable region fragments, such as human VH or human VL repertoires. In another embodiment, single domain antibodies are isolated from non-immunized, immunized or synthetic VHH repertoires, based on antibody heavy chain domains naturally devoid of light chains (e.g., camel, lama or some shark antibodies). Single-domain VH-based antibodies with antigen-binding activity can be combined via recombinant DNA technology with a single, a small repertoire, a chosen collection or a large repertoire of light chains, for example of human nature. Antigen-binding variants of single-domains now forced to contain a paired light chain, may be isolated using display technology based or equivalent methods. In another embodiment, single-domain VL-based antibodies with antigen-binding activity are combined via recombinant DNA technology with a single, a small repertoire, a chosen collection or a large repertoire of heavy chains, for example of human nature. Antigen-binding variants of single-domains now forced to contain a paired heavy chain, may be isolated using display technology-based or equivalent methods. In the embodiments of FIG. 5, the variants derived from the same route of isolation will always share a variable region sequence, thus will be able to provide functional pairing when brought into the context of pairing multiple variable regions.

If at least a portion of a variable region and a complete variable region is not diversified, while the rest of the variable region(s) contain the diversity, the selected antigen-binding antibodies coming from such repertoires will contain by design pairing-compatible variable regions. In many of the approaches in the literature used for building high affinity antibodies from synthetic antibody libraries, diversity in the initial library is built up throughout the antibody variable region genes and, in particular, in most of the six CDRs. Depending on the genetic make-up of these libraries, there will be a higher or lower probability of identifying antibodies with pairing-compatible variable regions. Libraries can be designed to fit specifically this new application, by introducing diversity in one variable region only, and not further diversifying the shared variable region, even in further affinity maturation processes. Libraries may be used in which the diversity is restricted to the three CDRs in one chain. The partner-variable region may then be, for example, one or a small set of germ line gene-encoded regions without any further diversity. In the primary library or follow-up libraries, diversity can be introduced in those areas of the antibody V-regions that are less likely to interact with the partner chain, so as to increase the chances of finding antigen-binding antibodies with high affinity, yet well pairing variable regions.

Antibodies with a high likelihood of containing pairing-compatible variable regions can also be enriched from antibody repertoires not biased in their genetic make-up, by combinations of selections and re-shuffling of, for example, the complete V-region of a given population or clone (exemplified in FIG. 5). This will enrich for those antigen-specific antibodies with a high likelihood of containing pairing-compatible variable regions, for example, because they are tolerant in their pairing with the shuffled region yet retain antigen-binding, or because the shuffled region is less likely to contribute to antigen binding. For example, an antibody Fab library is first enriched on antigen, and the selected heavy chains obtained after one or more rounds of selection are then recombined with the selected or unselected light chain repertoire (dashed lines in FIG. 5), and selected again on antigen (FIG. 5, step 4). In this way the selected antibody variable heavy chain domains will have the propensity to bind to the antigen relatively independently of the light chain to which it is paired. Antibodies to a first and second antigen can be identified by using the above-described selection and re-shuffling experiment, followed by a screening as before, to detect antigen binding of the selected heavy chains in combination with a collection of light chains. One may then identify those antibodies that bind either the first or the second antigen relatively independently of the light chain, or in the present of a related light chain family member. Due to the dominance of the heavy chain in antigen binding in these antibodies, many of the light chains are likely to functionally pair with the multiple heavy chain variable regions. Co-expression of antibodies with a pairing-tolerant variable region that is mediating antigen binding (such as the VH), and in which the partner domain is not involved or not important for antigen binding (such as the VL), will similarly lead to the formation of mainly or only functional binding sites.

In another embodiment, described is a method to obtain antibodies with heavy and light variable regions that preferentially or in the best case, exclusively, pair to one another and not to the respective light and heavy variable regions of one or more other antibodies, for example, those that are co-expressed in the same host. Such selection can be done by display methodology, but also using an intracellular selection route that relies on co-expression of antibody light and Fd chains in the same cell, allowing competition between the chains, and rescue of the intended combination via phage display or any other suitable route. The preferential or ideally exclusive pairing that is encountered in faithful antibodies will aid in the formation of mainly or only functional binding sites when such antibodies are co-expressed. This method essentially allows a high level of functional antibody binding sites to form even when variable region genes are used that have very distinct compositions.

A method for identifying antibodies with desired pairing behavior based on competition selection is described here. Antibodies are selected from a library of antibody fragments, by carrying out a selection directly in a host cell that co-expresses different antibodies. For example, when applied to using bacteriophage libraries, this concept is the following: bacteria are provided with a phage or phagemid genome that carries the genes encoding a Fab fragment in such manner that upon expression, one of the chains will be anchored to a phage particle. In the same host cell, other antibody light and/or heavy chain Fd fragments are co-expressed, for example, the Fab genes encoding a given antibody, or any set of multiple antibodies. For example, consider co-expression of two Fabs in the same cell, one of which is anchored via its heavy chain (Fd fragment, essentially VH-CH1) to the phage coat protein. As a consequence of this co-expression, competition occurs inside the same cell (in this case in the periplasm) between the two light chains for the pairing to the phage-anchored Fd chain. Further, the soluble heavy chain of the competing Fab will be able to pair with both light chains present in the same cell. In this system, phage particles with antigen binding activity will occur with different types of pairings. First, if the correct light chain will pair with its partner heavy chain on the phage only (exclusive pairing), and second, if the heavy chain on the phage surface is dominant in antigen binding and tolerant for pairing, yielding antigen binding virtually irrespective of which light chain it pairs with. Functionally such antibody pairs will behave in the same manner. In the case of the first situation, the lesser interactions between the partners of the two respective antibody pairs, the higher the proportion of functional Fab on phage.

The method described can be further biased towards antibodies with an exclusive pairing, by providing tags on the chains and enriching or depleting for particular combinations (e.g., depleting for those phage that carry the competitor light chains via a unique tag present on these chains). This method when applied to the isolation of antibodies via the selection of a phage library of Fabs, will yield a high frequency of antibodies that will have an appropriate pairing behavior and high functional yield when produced as mixture by co-expression. The use of competition-selection to bias selected antibodies towards being co-expression compatible, may also be applied to other display libraries (e.g., yeast display libraries), and to in vitro library systems based on ribosome display or mRNA display (Puromycin system), with methods of screening or selection of antibodies that recognize antigen as extensively described in the art. Further, the described method of competition-selection of antibody fragments for improved pairing (or antigen-selection and compatible pairing) using phage display can be readily translated into an intracellular (periplasmic) selection system based on protein-or enzyme complementation. In such approaches, fragmented, complementary or self-inhibitory enzymes are used to drive the selection of interacting molecules that are fused to the components of the selection system. Only when there is an interaction of a minimal strength will the protein or enzyme become activated, and under appropriate selection conditions, will the cells survive. Such methods have, for example, been described for the enzymes beta-lactamase and DHFR, with its applications in the selection of antibodies or expressed cDNA fragments that display a particular binding behavior. For example, competitive selection has been described for the affinity maturation of antibodies in the TACZYME system from Kalobios Inc. Herein, it is not the antigen binding but the pairing strength that can be made the selective force for a given population of antibodies presented in such system.

Figure 6:
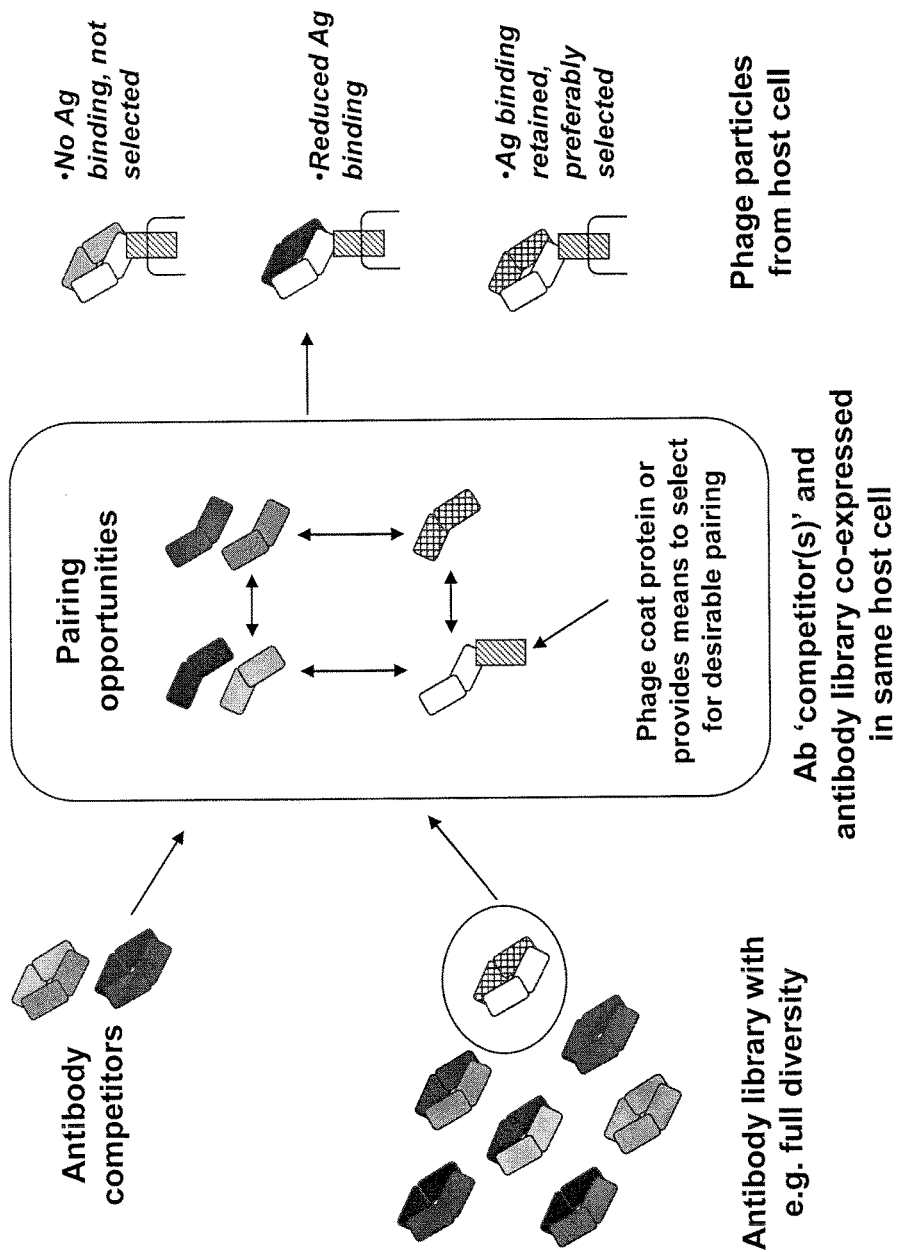
FIG. 6: Example of a competitive selection of antibodies with a desirable pairing behavior. The method involves the co-expression of one or more competing antibodies (top, left) in the same host cell as a member of an antibody library (bottom, left). Depicted is the method for Fab fragments, as described in the text. The result of the pairing opportunities of VHCH1 (white boxes) chain when co-expressed with two other Fab fragments is depicted. The original combination of the VH with its cognate light chain (hatched box), will retain its original binding affinity for antigen and can thus be selected.

In some embodiments, the method is used to identify new antibodies from phage libraries that show pairing-compatible variable regions with an existing antibody that has given variable region sequences. The antibody with the known antigen specificity is cloned for co-expression as Fab fragment in host cell that collectively express a phage display library of human Fab antibodies. This can be done by providing the Fab expression cassette onto a plasmid that is compatible with the presence of a phage or phagemid genome, such as the pBR322-based plasmid. Host cells harboring this plasmid are then infected with the phage particles encoding a library of human Fabs cloned into, for example, a phagemid vector such as pUC119, or a phage vector such as fd-tet-DOG1. While the competing Fab fragment is expressed, new phage particles are harvested (after helper phage infection if appropriate) from this culture. These particles are used for selection on antigen, and the resulting phage reinfected into cells harboring the competitor Fab fragment. After a few iterative rounds, the phage Fabs are screened for antigen binding in a binding assay; the pairing behavior between the reactive Fabs and the variable regions of the competing Fab can be further tested by co-expression and binding assays. One example of a format for this selection is the Fab format and not the scFv format, mainly because for most applications whole IgG-type antibodies will need to be established that have interactions between the chains that harbor the variable regions that mimic those seen in the Fab format. FIG. 6 depicts an example of how this method works for two Fabs competing with antibodies in a phage library.

This method requires some optimization steps, e.g., the use of a CH1-mutant with reduced affinity for its CL, and Fabs that do not display an intermolecular disulphide bridge such that the pairing will remain noncovalent. Residues positioned at the CH1-CL interface region may be mutated such that affinity between these two domains is reduced, for example, 10-fold or 100-fold, and as a result in the Fab format the pairing of the variable domains will become more dominant in driving the two chains together. Antibodies selected from such mutated Fab libraries, or from Fv libraries in which there is no covalent association between the two variable regions, may be biased towards having a preferential pairing behavior.

In a further embodiment, described is the creation of antibody libraries in which provisions are made to mediate unique pairing between the heavy and light chains, such that they are unlikely to interact with antibodies derived from a "regular" or non-purposely biased composition. An example of such provision is a knobs-into-holes engineered CH3-CH3 pair, in which one domain is provided with an amino acid with a large, bulky side chain (e.g., a tyrosine; the knob) that pokes out into the interface region, while the other domain at the equivalent structural position, carries one or more mutations (e.g., three) to create a hole into which the "knob" will fit. Examples of such engineered domain interfaces have also been published for variable regions (Zhu et al. (1997) *Protein Science* 6:781-788). It was shown that the effects of domain interface mutants are context (antibody) dependent, which provides also an opportunity to engineer the variable region domain interactions in an antibody-specific manner, in such way that when multiple antibody variable gene pairs are allowed to pair, mainly or only the cognate pairings are retrieved. Alternatively, installing a disulphide bond between the domains may mediate a preferential pairing. Alternatively, charge replacements are introduced in the framework regions, or combinations of these with sterically complementary mutations, to disfavor mispairing with one, and/or favorable pairing with the other partner variable region. Selection systems for such mutant libraries have been described earlier, and include the selection of the domain libraries on antigen via phage display of the paired variable regions (in scFv or Fab or, IgG format), or ribosome display of the scFv fragments, or selections based on the interaction itself instead of that with antigen. An example of the latter is described for selecting heterodimers of the immunoglobulin gamma-1 CH3 domain (Atwell et al. (1997) *J. Mol. Biol.* 270:26-35), which is applicable as follows: on of the two variable regions that should or should not interact (depending on what one would like to select for, repulsion or attraction/pairing) is displayed on phage (for example as VLCL or as VHCH1 chain), while the other is genetically tagged and produced in solution (for example as VHCH1 or as VLCL). The interaction between the two variable regions can than be selected for, using standard phage selection protocols and anti-tag reagents. Co-expression with a pair of non-tagged competitor variable regions as described earlier can be used to drive the selection towards variable region pairs that exclusively pair with one another.

In another embodiment of selecting binding sites with appropriate pairing behavior, described here are the use of antibodies derived from VH-VH libraries on the one hand and VL-VL libraries on the other; or the use of chimeric libraries in which elements (one or more CDR regions) are swapped between VH and VL. In another embodiment, comprised is the creation of two antibody libraries with such provisions made to mediate unique pairing between the heavy and light chains, such that when antibodies from these libraries are co-expressed, they will likely preferentially pair with the right partner.

Cited libraries of antibodies can take various forms. As a source of antibodies, a naive human library may be used, such as the antibody libraries described by Griffiths (A. D. Griffiths, et al. (1993) *EMBO J.* 12:725-734), Vaughan (T. J. Vaughan, et al. (1996) *Nat. Biotechnol.* 14:309-314), or de Haard (H. J. de Haard, et al. (1999) *J. Biol. Chem.* 274: 18218-18230). Both heavy and light chains in these libraries are derived from the repertoires of rearranged V-genes derived from the mRNA of peripheral blood lymphocytes (PBLs) from unimmunized humans and are, therefore, highly diverse. Alternatively, as a source of antibodies an immunized host or patient with biased humoral response (e.g., patients with infections, autoimmune diseases, etc.) is used. In immune libraries made from a hapten-immunized animal, it was shown that many of the clones were promiscuous and allowed pairing of the originally selected heavy and light chains with partner chains derived from other selected clones. Thus, antibodies with pairing-compatible variable regions may be more frequent in such immune libraries than in non-immune libraries.

Cited selection and screening technologies of recombinant antibodies and their fragments are well established in the field. Antigen-specific polypeptides can be identified from display libraries by direct screening of the library, or can be first selected on antigen to increase the percentage of antigen-reactive clones. The selection process may be accomplished by a variety of techniques well known in the art, including by using the antigen bound to a surface (e.g, a plastic surface, as in panning), or by using the antigen bound to a solid phase particle which can be isolated on the basis of the properties of the beads (e.g., colored latex beads or magnetic particles), or by cell sorting, especially fluorescence-activated cell sorting (FACS). As will be apparent to one of skill in the art, the antigen-specific affinity reagent may be bound directly or indirectly (e.g., via a secondary antibody) to the dye, substrate, or particle. Selection procedures have been extensively described in the literature (see, e.g., Hoogenboom (1997) *Trends Biotechnol.* 15:62-70). Other publications describe the production of high affinity (nanomolar range) human antibodies from very large collections of antibodies, and the affinity maturation of these antibodies by chain shuffling or other approaches (reviewed in, e.g., H. R. Hoogenboom, et al. (2000) *Immunol. Today* 21:371-378). Binding of antibodies to their respective antigens may be carried out using antibody-based assay techniques, such as ELISA techniques, Western blotting, immunohistochemistry, Surface Plasmon Resonance (SPR) analysis, affinity chromatography and the like, according to methods known to those skilled in the art (see, for example, Sambrook et al., 1989, *Molecular Cloning: A Laboratory Manual*, 2nd Ed., Cold Spring Harbor Laboratory Press). These techniques are viable alternatives to the traditional hybridoma techniques for isolation of "monoclonal" antibodies (especially when human antibodies are required), which are encompassed herein.

The following describes possible embodiments of exemplary assays for binding assays: ELISA. Polypeptides encoded by a display library can also be screened for a binding property using an ELISA assay. For example, each polypeptide is contacted to a microtiter plate whose bottom surface has been coated with the target, e.g., a limiting amount of the target. The plate is washed with buffer to remove non-specifically bound polypeptides. Then the amount of the polypeptide bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The polypeptide can be purified from cells or assayed in a display library format, e.g., as a fusion to a filamentous bacteriophage coat. In another version of the ELISA assay, each polypeptide of a library is used to coat a different well of a microtiter plate. The ELISA then proceeds using a constant target molecule to query each well.

Surface Plasmon Resonance (SPR). The binding interaction of a molecule isolated from library of diversity strands with a target can be analyzed using SPR. For example, after sequencing of a display library member present in a sample, and optionally verified, e.g., by ELISA, the displayed polypeptide can be produced in quantity and assayed for binding the target using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance). The changes in the refractivity generate a detectable signal, which are measured as an indication of real-time reactions between biological molecules. Methods for using SPR are described, for example, in U.S. Pat. No. 5,641,640; Raether (1988) *Surface Plasmons*, Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $k_{on}$ and $k_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $k_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $k_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos et al., U.S. Pat. No. 4,868,103). Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding. The homogenous assays can be performed while the candidate polypeptide is attached to the display library vehicle, e.g., a bacteriophage.

Automated screening. The methods and compositions provided herein are also suitable for automated screening of diversity libraries for finding clones with likely pairing-compatible variable regions. For example, a display library of Fabs or scFvs can be screened for members that bind to a target molecule. The library can be screened directly or first selected on antigen once or several times. Binders from a first round of screening can be amplified and rescreened, one or more times. Binders from the second or subsequent rounds are individually isolated, e.g., in a multi-well plate. Each individual binder can then be assayed for binding to the target molecule, e.g., using ELISA, a homogenous binding assay, or a protein array. These assays of individual clones can be automated using robotics. Sequences of the selected clones can be determined using robots and oligonucleotide primers that allow to read the variable region sequences of the selected clones. Results of the assay and the sequences can be stored in a computer system and evaluated by eye or by using software, e.g., to identify clones which meet particular parameters (e.g., for binding affinity and/or specificity, and for sequence homology).

e. Forcing Appropriate Pairing of Antibody Variable Regions Via Mutation and Selection There are instances where antibodies with given variable region sequences, antigen specificity and affinity are available, but where no pairing behavior can be achieved with the existing sequences. Some of the methods mentioned earlier can be applied to solve this, in particular, the screening of a combinatorial panel of variable region pairs to find fortuitously compatible pairs, or the selection of new antibodies that do have the desirable pairing behavior, for example, using competition selection with one of the antibodies of defined specificity. In those instances where this is not a desirable option and the existing antibodies are used, the following methods may be used to create pairing-compatible variable regions for the set of antibodies to be produced as an OLIGOCLONICS® mixture.

First of all the pairing can be biased by using single-chain Fv variants of the antibodies. The provision of a linker between heavy and light chain variable region will increase the chance that the two domains will pair with one another, instead of pairing with unlinked molecules or with other single chain Fv molecules of the same or different specificity present in the same cell. If such molecules are fused to Fc regions and co-expressed in the same host cell, the result is a mixture of scFv-Fc molecules which are paired via the heavy chain Fc region, forming monovalent and bispecific molecules. There is also an alternative solution that does not rely on pairing in the scFv format. With a set of, for example, three given antibodies, an antibody mixture consisting essentially of IgG-formatted molecules can be made by making the variable region genes compatible with one another. First the sequence of the antibody light chains is determined, and the chain that is the most common to the sequence of the two other light chain variable regions, or the closest to its germ line amino acid sequence identified. For the two antibodies that carry the different light chain, a library of heavy chains is created that is diverse in the CDRs including the CDR3 that produces a substantial fraction of the interactions between heavy and light variable region sequences. These heavy chains are combined with the chosen, non-mutated light chain in a format that provides expression and screening, or display and selection capabilities. In such manner, the two remaining antibodies are forced to accept the new light chain, which could affect pairing and affinity; the provision of mutations in the heavy chains and the selection (either separately as scFv or Fab fragments, or as Fab in competition with their original light chain in a method described above for competition selection), will enrich for variants that have corrected a possible deficiency in pairing efficiency and/or affinity loss.

f. Antibodies with Pairing-Compatible Variable Regions from Transgenic Mice

It is possible to produce transgenic animals (e.g., mice) that are capable, upon immunization, of producing a full repertoire of human antibodies in the absence of endogenous immunoglobulin production. Transfer of the human germline immunoglobulin gene array in mutant mice that carry a homozygous deletion of the antibody heavy chain joining region (JH) gene and, therefore, do not anymore produce murine antibodies, results in the production of human antibodies upon antigen challenge. See, e.g., Jakobovits et al., *Proc. Natl. Acad. Sci. U.S.A.* 90:2551-255 (1993); Jakobovits et al., *Nature* 362:255-258 (1993). Antibodies with pairing-compatible variable regions may be identified from panels of antibodies made in these animals, or from such antibodies and antibodies derived from other methods. It is envisaged that antibodies with pairing-compatible variable regions may be identified even more readily in transgenic mice carrying only the heavy or only the light chain locus, and only a single or a limited set of chosen partner chains; in that case immunization would lead to the generation of antibodies which all carry a compatible common chain. Antibodies with pairing-compatible variable regions are then identified using the methods described herein. The efficiency with which such antibodies can be identified can be further increased by reducing the extent of somatic hypermutation of the partner chain or chains. This can, for example, be done by removing regulatory sequences surrounding the variable regions, or by mutating the variable region codons such that the gene becomes a less likely substrate for the cellular hypermutation machinery, or by harvesting the B-cells earlier after immunizations.

One further approach is to combine the heavy chains of the three antibodies with a repertoire of highly diverse light chains, and screen the pairings, if necessary after selection on antigen, for light chains that maintain functional pairing (and antigen binding) and share a common sequence. This can be readily carried out using automated facilities for high throughput ELISA screening and sequencing, as presented earlier.

g. Uses of Antibodies with Pairing-Compatible Variable Regions

Antibodies with pairing-compatible variable regions have many applications. It is disclosed herein that the preparation of a desired functional antibody mixture is feasible when the composition of the variable heavy or light chains of the various antibodies is carefully selected to contain antibody variable regions that carry pairing-compatible variable regions such that the pairing of the antibody variable regions yield predominantly functional binding sites. After selection of antibodies with pairing-compatible variable regions as described above, the antibody variable region genes can be cloned into expression vectors that will direct the expression of an antibody of the desired format, e.g., IgG, IgA, IgM. In one embodiment, described is the production of mixtures of antibodies through the co-expression of variable region genes operably linked to constant region genes, in which these variable region genes encode different antibodies with pairing-compatible variable regions. Without the selection of appropriately pairing antibodies with pairing-compatible variable region, co-expression would lead to the formation of a mixture of antibodies with many non-functional heavy-light chain combinations. When appropriate pairing-compatible variable regions have been defined, a high level of functional antibody combining sites will arise. In one embodiment, the heavy chain variable region is operably linked to the first domain of the heavy chain constant region, followed by a hinge region, followed by the remaining domains of the heavy chain constant region. The variable region of the light chain on the other hand is operably linked to an appropriate constant domain of the kappa or lambda family.

In certain embodiments, the pairing-compatible variable region is an identical light chain. In that case the co-expression of this light chain and, for example, two different heavy chains derived from antibodies with as pairing-compatible variable region the full light chain, in the same cell will yield a mixture of the two expected bivalent molecules and one bispecific molecule. Similarly, when co-expressing this light chain with more than two heavy chains derived from antibodies that all have functional antigen binding sites when paired to that same light chain, the mixture will contain in a certain fraction each of the bivalent molecules, and a number of bispecific molecules with combinations of all binding sites, e.g., three when three antibody heavy chains are introduced, six when four antibody heavy chains are introduced, ten when five antibody heavy chains are introduced, etc. In this case, the affinity of the monomeric binding sites in these various species is expected to be very similar to the affinity of the original binding sites. In another embodiment, antibodies share a pairing-compatible variable region, but the sequence of this element is different between the two antibodies and, upon swapping, the affinity of one or both of the antibodies may be altered. If such antibodies are used for co-expression, the final antibody mixture will contain antibodies with the original and the altered binding affinity in all of the species that were mentioned above. In some embodiments, such antibodies share a compatible common light chain. In another embodiment, antibodies share a compatible common heavy chain. The expression levels of the individual components can be chosen or can be manipulated to alter the fraction of the species of antibodies containing that component.

2. Protein Mixtures with Optimally Paired Variable Regions

Using the methods described herein, antibodies with a pairing behavior suitable for the preparation of well-defined biopharmaceutical mixtures are obtained. Traditionally before use for human therapy, protein drugs are expressed and purified to homogeneity, consisting of one major molecular species. In some cases, therapy is more efficacious with combinations of proteins or other drugs. Embodiments include methods to make a proteinaceous mixture that will contain at least two major molecular species, composed of at least three variable regions, and such that some variable regions pair to form a functional binding site. The large-scale manufacturing of the proteinaceous mixture is a prerequisite for their clinical use, and a simple purification procedure is an important feature of the development process. The presence of inappropriately paired variable regions would inevitably lead to a more complicated purification procedure. In one embodiment, the genes encoding the components of the two proteinaceous compounds are co-expressed in the same host cell, and the different major molecular species that are present in the mixture and have a functional binding specificity purified using biochemical/biophysical techniques well known in the art. In one embodiment, the method is used to make a mixture of a defined number of antibodies. The major molecular species that comprise one or more different binding specificities could share a minimal proportion of their encoding genetic information (e.g., an Fc region, a common tag, or another shared domain or feature); such shared feature will provide a common mechanism/assay for following the individual compounds in the mixture. In another embodiment, the major molecular species are co-purified due to a similar biophysical/biochemical behavior, or due to a shared domain that mediates co-purification (e.g., an Fc). In another approach, the major molecular species are fused to a subunit of a protein such that they can multimerize with each other (e.g., CH2-OH3 region). Also provided are biopharmaceutical mixtures produced using this method. In some embodiments, the application is the co-expression of antibodies, with the choice of the V-genes and pairing behavior between VH and VL domains such that mainly or only functional binding sites are made, and the purification of the mix can occur via the shared feature, an Fc region. Methods for purification of immunoglobulin are well known in the art, including protein A, protein G and other affinity matrices. Other proteinaceous mixtures that could be envisaged to have paired variable regions are fusion proteins between antibodies or antibody fragments and other molecules, single domain antibodies derived from camel, llama or engineered single domain antibodies from murine or human variable region genes, receptor extracellular domains, peptides, proteins equipped with an engineered binding site, or cytokines. In some embodiments, the proteinaceous compounds share a feature (like by further fusion to an immunoglobulin Fc region; methods well known in the art), such that they can be co-purified using the same procedures. The optimal pairing of the variable regions in the different proteinaceous compounds will also lead to an optimal level of functional binding sites on these compounds, thus minimizing the number of purification steps required to obtain the active component of the protein mixture.

3. Selecting Antigen-Specific Proteinaceous Compounds Using Mixtures of Encoding DNA In certain embodiments, the proteinaceous compounds are antibodies. Antibodies are identified in collections or pools of genetically diverse antibodies, in which the pairing of the variable genes is optimized in such manner that upon co-expression of at least two antibodies inside the same cell an optimal pairing arises, providing a maximal amount of functional binding sites. In some embodiments, the pairing of all binding sites is optimized due to the use of a shared variable region gene, for example the light chain. The diversity of the other elements in the library will be such that antibodies with high affinity can still be selected. Due to this choice of the genetic make up of the variable regions, the pairing of the antibody variable regions will be such that a very high level of functional binding sites will be present when multiple variable regions forming more then one antibody binding site are contacted with one another, for example, when expressed in the same cell. In one embodiment, first a library or collection of different antibody heavy chain genes is made, and cloned into an eukaryotic cell expression vector. This library is introduced into host cells in such a manner that each host cell will be making multiple different antibody heavy chains. In particular embodiments, "anti-repressor elements" (Kwaks et al., 2003, *Nat. Biotechnol.* 21:553) are cloned at one or both ends of the antibody heavy chain gene. Such elements confer stable and high level expression of a given transgene as shown in this citation, and herein describe is its use to mediate stable and high level expression for each individual copy of the transgene (see, also below).

Figure 7:
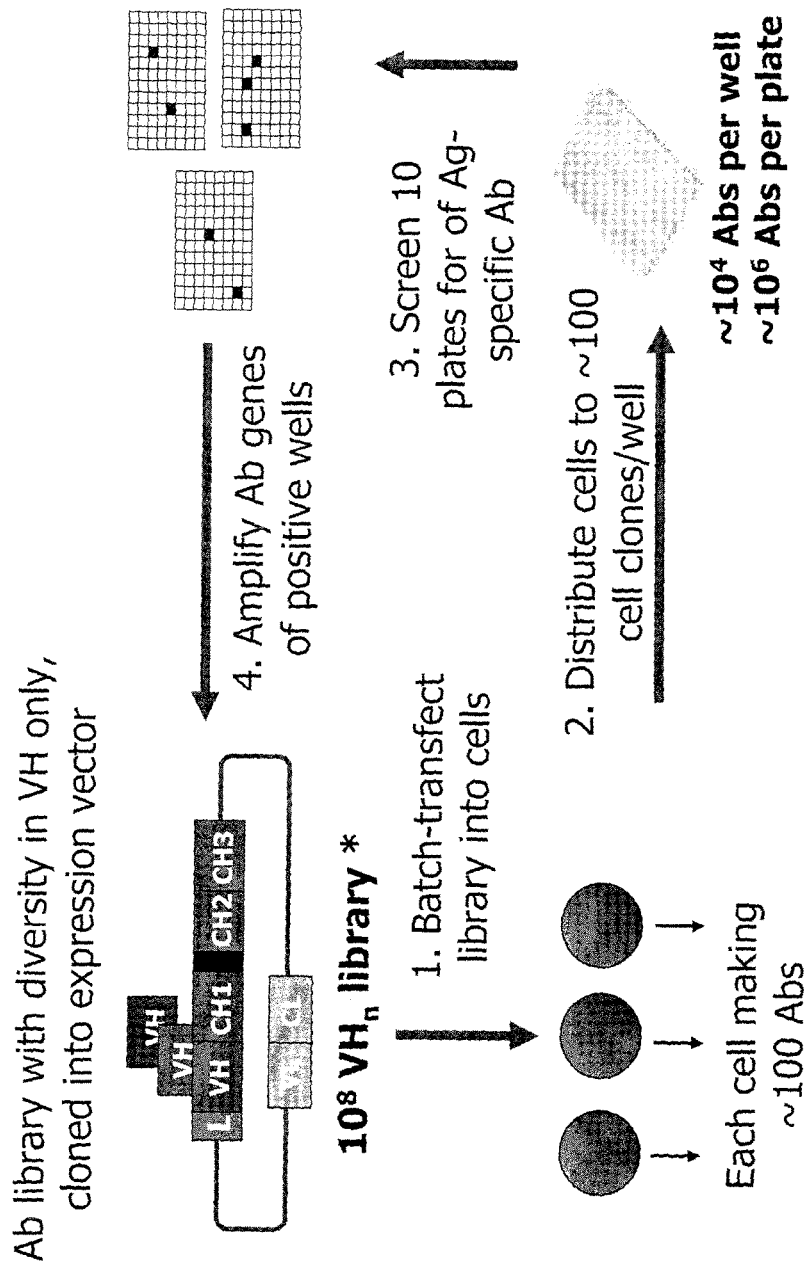
FIG. 7: Identifying antigen-specific antibodies by co-transfecting heavy chain gene libraries with an invariant light chain gene and screening the resulting antibody mixtures for antigen reactive antibodies. With every cycle of transfection and screening, the diversity of the VH library is reduced (at position *), to eventually yield a population of antigen-reactive heavy chain variable genes. The numbers indicate that sampling of a library of $10^8$ different heavy chains can be carried out by screening the wells often 96-well tissue culture with each 100 clones per well.
Figure 8:
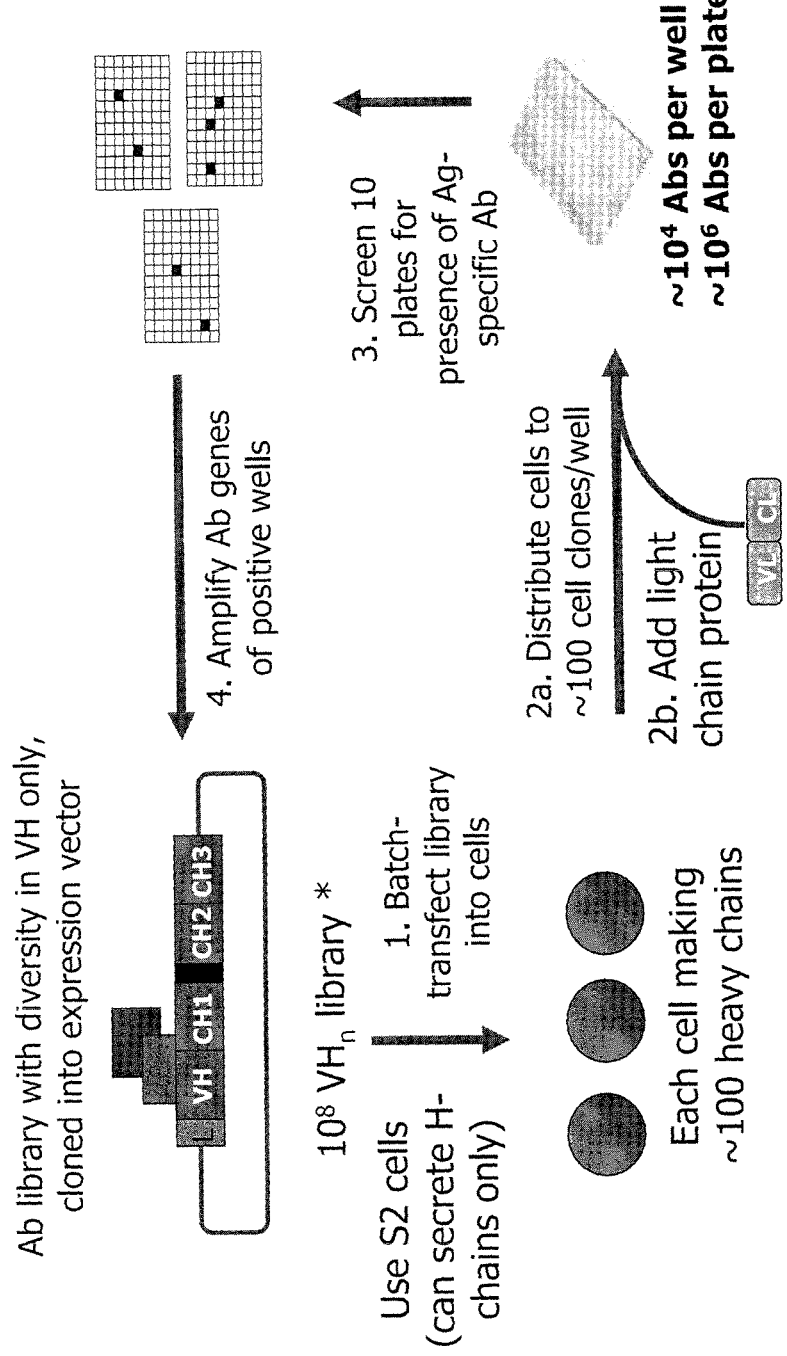
FIG. 8: Identifying antigen-specific antibodies by transfecting secretable heavy chain gene libraries, assembly with an invariant light chain and screening the resulting antibody mixtures for antigen reactive antibodies. With every cycle of transfection and screening, the diversity of the VH library is reduced (at position *), to eventually yield a population of antigen-reactive heavy chain variable genes.

In one embodiment, depicted in FIGS. 7 and 8, the variable region or regions with optimized pairing behavior for the other variable regions is or are also genetically encoded in an appropriate expression vector, and introduced into the host cell, either before, during or after the introduction of the other variable region. The expression cassette with the variable regions can also be part of a viral system such that high levels of transfection/infection efficiency can be achieved. In the case that the pool of first variable regions are antibody heavy chains, the second variable region with optimized pairing behavior can be one or more light chains.

The host cells which are transfected with both partners of the pairing, e.g., the mix of antibody heavy chains and set of light chains, are expanded and grown under conditions which allow the expression of heavy chains and light chains. In some embodiments, only one light chain is used, as exemplified in FIG. 7. For example, the expansion can occur in tissue culture wells, in such a manner that the tissue culture wells will contain between 10-1000 different originally transfected clones, each of the clones expressing multiple pairings of the antibody variable regions. Antigen-specific antibodies can be retrieved amongst these clones and wells by various methods, for example by ELISA or equivalent test of the antibody mixtures of each well (see, also earlier description of binding assays). If stable transfection is used, with the possibility to select transfected cell lines for stably integrated copies of the antibody encoding DNAs, the relevant antibody or antibodies may be cloned via limiting dilution. Alternatively, the DNA encoding the relevant antibody variable genes can be retrieved by amplifying and sequencing the antibody genes from the cells in the well using methods know in the art. If required, the antibody-heavy chain encoding DNA can be also amplified, recloned for expression in the same system, the DNA amplified and then used to repeat the transfection, expression and screening experiment. With this cycle of transfection and screening, after a few rounds, an antigen-reactive antibodies start dominating the population. At every round, the complexity of the mixture produced by an individual cell can be reduced by reducing the complexity of the DNA introduced into the cell, to eventually become a oligoclonal population. From the transfected wells, the antibody's V-gene can be rescued directly (e.g., via PCR) and further analysis and/or screening in this system, eventually at conditions that provide expression of the monoclonal antibody. Alternatively, the variable regions from reactive wells can be cloned into other systems for rapid screening of the binding specificity of the individual pairs of variable regions, e.g., via bacterial expression of antibody fragments or whole IgG, expression in other hosts, via in vitro display methods, bacteriophage display methods etc.

In certain embodiments, the heavy chains may be secreted by the host cell into the supernatant, where they can be reconstituted into functional antigen binding fragments, by the addition of and pairing with a partner light chain. This can be a small family of related chains, but may be one chain only. In this approach, cells are used that do not prevent secretion of the non-paired heavy chain. This embodiment is depicted in FIG. 8. *Drosophila* S2 cells have been described that contain a BiP (Binding Protein) homologue, hsc72, that specifically interacts with immunoglobulin heavy chains, but does not prevent their secretion. Alternatively, the heavy chains will need to carry amino acid mutations in such a manner that cells that normally retain heavy chains when they are not paired to light chains, will not mediate retention anymore. For example, mutations can be provided for or, selected within, the major recognition sites for BiP sites which are located in the heavy chain CH1 domain. For example, the CH1 domain can be replaced (e.g., by a CL or CH3 region) as long as the light chain can pair with this form of the molecule (or other variants, see also section on antibody cross-over variants), or mutated to avoid retention by BiP. The results of such variations are that the different heavy chains are secreted by the host cell. The chains are then reconstituted with one or more partner chains carrying the partner variable region(s). Methods to establish this have been extensively reviewed in literature on the biochemical analysis and assembly of antibody molecules. Antigen-reactive variable region pairs can be identified in the same way as described for the other embodiment.

In yet another embodiment, the first partner of the two paired variable regions (such as the heavy chain for an antibody) is anchored onto a eukaryotic cell surface, and the other variable region provided by expression in the same host cell or via reconstitution on the cell-surface. This set-up allows a direct screening for antigen-binding on the host cell surface, for example, via flow cytometry with fluorescently-labeled antigen, or a direct selection, for example, via cell sorting methods.

Methods to identify antigen-reactive antibodies from B-cell populations have been described in the literature and can be applied to these transfection-based systems also. In such described systems, random combinatorial diversity is sampled, and antibody variable gene pairing is also not optimized or biased. Use of such random combinatorial pairs of variable regions does not guarantee that upon production of an antibody mixture, the pairing will be optimal; on the contrary, mispaired variable regions will be a substantial fraction of the produced proteinaceous compounds. This random combinatorial diversity is limited by reducing the diversity of one of the variable region genes. The diversity that is present in the resulting paired repertoire originates mainly from one of the variable regions. For example, it may be one or a small set of light chains. As a consequence, in the iterative process of selecting the antigen-reactive variable regions, only one of the two partners of the pair will need to be identified. It is not necessary to retrieve both the heavy and light chain variable region sequence from the same cell. Another important difference is that multiple antibody genes are introduced and expressed from the same host cell. When using random diversity, such a feature would lead to a multiplication of the diversity and reduction of the quantity of the individual combinations to the extent that detection let alone cloning of the responsible antibody gene combination would become very difficult, if not impossible. Consider the case in which the cell would be making multiple combinations of heavy and light chain pairs, then the chance to retrieve the correct combination of the antibody that mediates antigen reactivity, would be become smaller as the cell is making a higher number of different chains. If the cell were expressing ten different heavy and light chains, the combinatorial diversity generated by this one cell would be a 100 different types of antibody binding sites; only ¹/₁₀ of the antibody variable genes amplified from such cell will be the relevant one, thus the chance to be able to clone the correct antibody genes is very low. As a consequence of this reduced combinatorial diversity, there will also be a higher quantity of each of the individual antibodies, which makes a more sensitive detection possible. Thus, the expression of the different antibodies in the same host cell is a desired feature. First as explained above, it is an important feature for the antigen-selection system to find antigen-reactive antibodies when using transfected cell populations. Second, the methods are directed towards the production of mixtures of proteins and more in particular, antibodies or their fragments, which requires optimal pairing of the variable regions, in particular, when producing such mixtures by co-expression in the same host cell. In the method described above, co-transfection of variable region genes inside the same cells leads to the expression of multiple antibodies in the same host cell. The methods are thus useful to select individual antibody variable region pairs that are reactive with a given target epitope, but also to select a mixture of different variable region pairs all reactive with a given target epitope (in the process of the screening, multiple antibody variable region pairs will be selected or identified, but when iterating the process, these antibodies are likely to be eventually mixed and end up in the same host cell). Further if the screening or selection of the mixture is carried out with targets with multiple epitopes, or multiple targets, the mixture can also contain antibodies to multiple epitopes or targets, yet with co-expression-compatible pairing of the variable region genes.

The methods are also suitable for the screening of mixtures of proteins with paired variable regions that have a defined binding specificity (FIG. 9). The genes encoding these compounds are introduced as a mixture into a host cell as above (in FIG. 9 examples is given of ten different antibodies), and individual clones that have integrated some or multiple copies of the genes encoding the various variable regions expanded. In the way described above, applied to antibodies, the supernatants of the resulting cell lines are screened for reactivity towards the various antigens. The levels of each of the individual antibody pairs may vary, and, when the antibody format is the IgG isotype, also the level of the bispecific antibodies resulting from the co-expression may be highly variable. Cells that secrete the mixture comprising the desired composition are identified and used as a stable production host for this mixture. Provided is a method to quickly screen hundreds of mixtures of different antibodies. The optimized pairing of the heavy and light variable regions will secure a high level of functional binding sites in the antibodies present in such mixtures.

Figure 10:
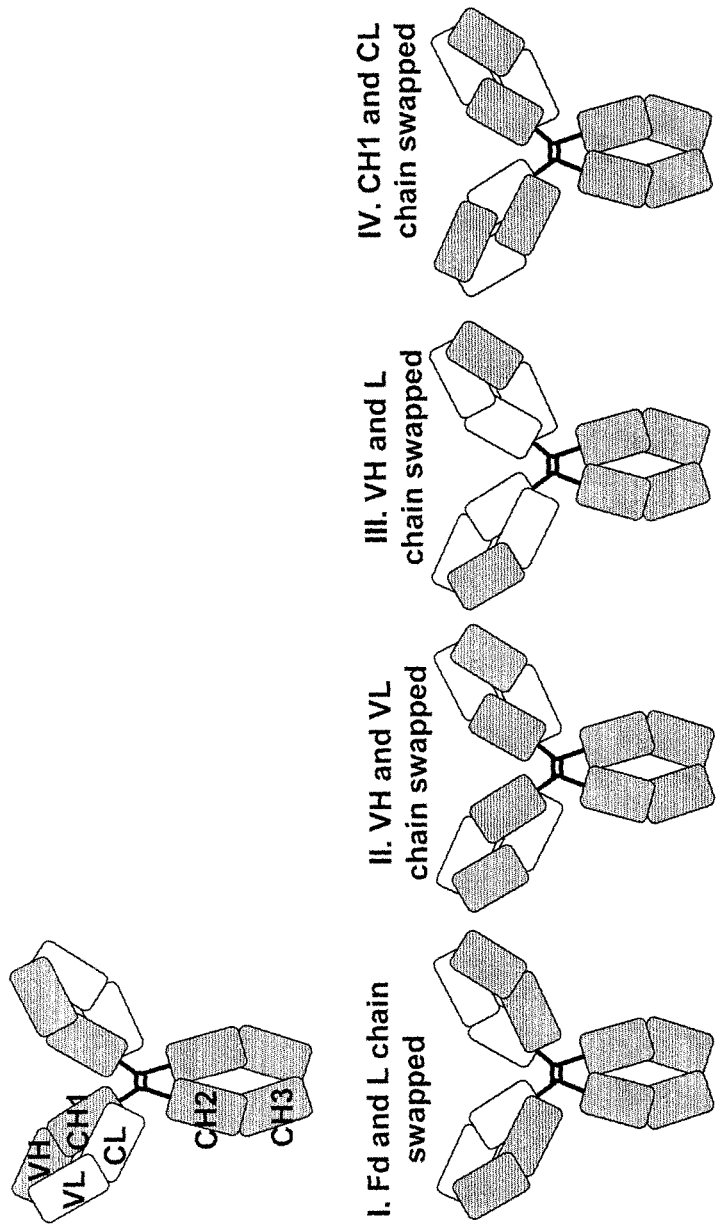
FIG. 10: Examples of antibodies with cross-over domains. Heavy chain domains (grey striped boxes) and light chain domains (white boxes).

4. Antibody-Based Compounds with Paired Variable Regions and Cross-Over or Mutations in the Constant Regions The pairing of the variable and constant regions of an antibody can be further engineered by crossing-over domains. Antibodies are made by "crossing-over" or swapping or replacing elements within the Fab region of the antibody (or the antibody heavy chain Fd region and the antibody light chain region), and combining the appropriate elements to establish a binding site in the context of an immunoglobulin molecule (examples are given in FIG. 10). In its simplest format, the L chain and H chain Fd region are swapped. A VL-CL-hinge-CH2-CH3 chain is thus paired to a VH-CH1 domain. In a second format, the constant region genes between H and L are swapped. In another form, the CH1 is replaced by a CL. In another form, the VH and VLs are swapped. In another form, one or more of the CDR regions between VH and VL are swapped. The pairing efficiency can be monitored in such cross-over variants, such that suitable combinations of non-cross-over antibodies with cross-over antibodies, or combinations of different cross-over antibodies, can be used to mediate optimal pairing when making mixtures of at least two antibody molecules (with antibody also including here cross-over variants as described above). In another form, the effect of mispairing between different VHs and/or VLs is reduced by linking the VH and VL via a linker to a single-chain Fv variant, which will favor the association between these two domains. Alternatively, the pairing between variable regions can be manipulated by the introduction at the appropriate positions of cysteines which upon pairing of the variable heavy and light variable domains can form a disulphide bridge. Also provided are methods for selecting antibody fragments that will bind antigen in an appropriate cross-over format, by selecting from appropriately formatted libraries, or by screening one or more antigen-binding antibodies for the activity in the cross-over format. Antibodies in which the CH1 domain is not part of the heavy chain may be secreted as free molecules not paired to light chains, allowing alternative approaches for the production of antibodies and new fusion formats. Antibodies in which the variable regions are swapped may be functionally non-equivalent and yield a more diverse, unnatural or different spectrum of antigen-binding or biological activity (the positioning of the heavy and light chain variable regions is expected to not always be completely equivalent). Besides effects of the exchange of the heavy and light chain genes on affinity and/or specificity, the swapping may alter the antibody flexibility and impact the biological behavior. Finally, an antibody binding site with chimeric VH-VL regions (with CDR or FR regions swapped between the two variable domains) may also yield an alternative, possibly larger but structurally non-overlapping set of antibody paratopes.

Second, selective engineering of the constant regions or the interaction of variable regions with constant regions may also affect the pairing behavior of the variable region genes. By modifying the antibody heavy chain constant region, the fraction of functional bispecific antibodies can be increased or decreased. In this approach, antibody heavy chains can be engineered to drive hetero- or homodimerization. This can be done by introducing sterically complementary mutations in the CH3 domain interface, for example, as has been described in the literature for increasing the percentage of functional bispecific antibodies in the mixture of antibodies arising from the co-expression of two heavy and two light chains. The pairing of the antibody binding site variable region may thus be influenced by the pairing of variegated constant regions, of heavy and light constant region domains.

5. Extracellular Pairing of Proteinaceous Mixtures

Figure 11:
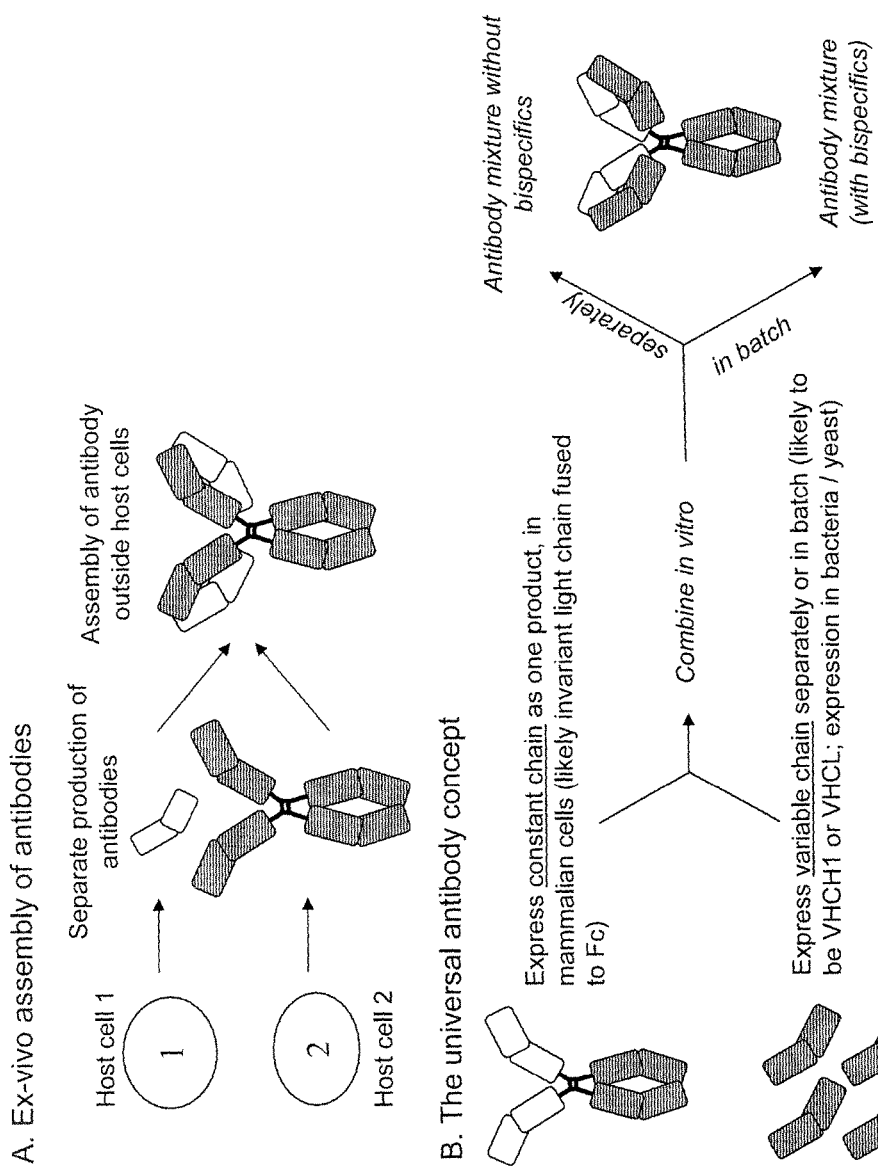
FIG. 11: Ex vivo assembly of antibodies (A) and the universal antibody concept (B). Antibodies are produced as separate chains and then combined to form a functional antibody. This is in particularly interesting when making mixtures of antibodies, as indicated in (B), where depending on the input of the chains and the separation of the mixing reactions.

Provided are methods for making whole antibodies using an in vitro pairing procedure of heavy and light chains produced in different host cells. In one embodiment, one of the two antibody chains is expressed in a first host cell and the other chain is expressed in a second host cell (FIG. 11, section A). The antibody chains are then brought together under conditions in which pairing of the two domains will occur, thus outside of the cell. In one embodiment, the pairing occurs in vitro, with purified chains and under conditions that are optimized for the pairing of the desired variable regions. In another embodiment, the expression occurs via the use of one or two dummy-chains, temporarily paired to the respective variable regions, removing the dummies from their partner via a mild and controllable process, and pairing the appropriate unpaired variable regions to one another to form a functional binding site. In one embodiment applied to antibodies, this association is made easier by using heavy-light chain pairs mutated in one or the other chain to facilitate the process of the pairing, e.g., mutated in the cysteine residue that normally forms the bridge between H and L chains (either both mutated, for example, to Ser, or only one mutated and not the other), or mutations that have altered the affinity of one chain for the other or mutations in the dummy chain used for the temporary pairing, in particular, the one that pairs with the heavy chain; thus such dummy light chain will pair with a native, non-mutated heavy chain, and may carry mutations such that it can be readily removed from the purified antibody.

An extension of this concept is that it is possible to produce antibodies using universal antibody chains (FIG. 11, section B). Provided are methods for expressing a shared, invariant variable region contained into the appropriate chain format (e.g., a VL-CL light chain) in a given host cell, and the other chain (e.g., a heavy chain consisting of VH-CH1 or VH-CH1-hinge-CH2-CH3) that is dominant in or provides most or all of the specificity, in another host cell. For production of two antibodies, three chains need to be made, which can be assembled in vitro to form two different antibodies. For example, if the light chain is identical, only one VL-CL domain will have to be made, and two VH-containing heavy chains. These can then be assembled extracellularly, for example, in vitro. Pairing of the variable regions will have to be optimal such that the proteinaceous mixture yields a high level of functional binding sites. The light chain can be used universally for all antibodies that will accommodate it (and antibodies accordingly selected if required). The heavy chain can be expressed in mammalian cells to provide a suitable glycosylation; for the light chains any suitable expression host cell can be chosen. When using the cross-over variants described in the previous section, in which the light chain is fused to the hinge and Fc, and the heavy chain variable region is provided as the lightest chain (as VH-CH1 or VH-CL), an important advantage of this set-up is apparent: the light chain fused to the Fc (depicted as "constant" chain in FIG. 11, section B), with its functionally important glycosylation features, can be made as the universal chain. The heavy chain can carry the dominant features for the specificity, and a mixture of heavy chains which will mediate different binding specificities can now be made in a different host cell that does not need to provide glycosylation. Such a feature makes the production of mixtures possible in two steps: a cheaper prokaryotic expression can be used to make mixtures of variable regions each encoding a unique binding specificity, while the more expensive production of the other variable region that also requires most fine analysis, can be done in a eukaryotic host. All antibodies that can pair with the latter variable gene without inflicting their overall specificity and affinity, can be produced by extracellular pairing with the same universal chain. The latter can be designed to be optimized for pharmaceutical applications: a broadly expressed, relatively common variable region, with a minimal number of MHC Class II epitopes, of human origin, and germ line in sequence. This procedure of mixing can be done with separate heavy chain mixtures or with a mix of the different heavy chains; when applied to the IgG format as depicted in FIG. 11, section B, the result is an antibody mixture without or with bispecifics, respectively. Manual mixing and pairing of variable region genes further provides much more control over the pairing, it can be done in a stepwise manner, per antibody, per group of antibodies etc. For some applications, for example, where there is an absolute necessity to avoid the formation of bispecific antibodies in a complex mixture with three or more antibodies, this method has an advantage over the cell line-based approach.

6. Controlling the Expression of Variable Regions in the Context of the Production of Multiple Pairing Variable Regions in the Same Host Cell Nucleic acid molecules encoding variable region, e.g., from antibodies, can be co-expressed in the same cell to make mixtures of different functional binding sites. With appropriate pairing behavior, a high level of functional binding sites will be present. It will however also be important to control the expression of the individual variable regions and their expression ratios, because this will effect the composition of the final antibody mixture. The expression level and the stability of the expression is a function of the site of integration of the transgene: if the transgene is integrated close to or within inaccessible chromatin, it is likely that its expression will be silenced. Described is the use for the production of mixtures of antibodies in the same cell, of elements that, when flanking the antibody genes, will increase the predictability of the expression level, the yield, and improve stability. Such elements can, for example, do this by counteracting chromatin-associated gene repression. Such anti-repressor elements provide a high level of predictability of expression, high levels of expression and stable expression overtime, of the antibody mixture (Kwaks et al., 2003, *Nat. Biotechnol.* 21:553). Such elements confer stable and high level expression of a given transgene as shown in this citation, and herein described is its use to mediate stable and high level expression for each individual copy of a mixture of transgenes, encoding multiple variable regions. A variety of such elements and other systems to achieve a similar result have been identified in the art, including Locus control regions (LCRs), chromatin opening elements, artificial chromosomes (e.g., ACE technology from Chromos Molecular Systems Ltd.), and Ubiquitous Chromatin Opening Elements. For example, LCRs are transcriptional regulatory elements which possess a dominant chromatin remodeling and transcriptional activating capability conferring full physiological levels of expression on a gene linked in cis, when integrated into the host cell genome. In the following section, "anti-repressor elements" are described but other, different control elements such as the ones mentioned and inasmuch as they provide the opportunity to regulate the high-level expression of multiple genes, may be equally suitable to achieve a controlled expression of the different variable regions.

In one embodiment, antibody mixtures are made from variable region pairs in which one dominates the binding, and the other is a shared variable region. In certain embodiments, the first variable region one is the heavy chain, and the second is the light chain. In certain embodiments, at least one of the antibody heavy chains is flanked by one anti-repressor element, or by two identical or two different anti-repressor elements located at either end of the heavy chain gene; in another embodiment, more than one or possibly all of the heavy chain genes that need to be expressed are flanked by anti-repressor elements. In one embodiment, the heavy chains are based on the same plasmid, in another they are on separate plasmids. In another embodiment, CHO cells are used as host; in another embodiment, PER. C6® cells are used.

The manufacture of mixtures of antibodies expressed in the same cell line will require appropriate variable region pairing and also a stable expression level of all of the antibody chains involved, as well as a stable ratio of the various chains, in such manner that the resulting antibody mixture after manufacture even at GMP conditions, has a stable composition. Such stable compositions can then translate into stable biological activity and stable toxicity profile. If the expression of only one antibody chain would change, it could affect the composition and, therefore, also alter its biological activity. The provision of elements that yield a more predictable and copy-number associated expression level is also important to build cell lines that express similar or even equimolar levels of different antibodies. If, for example, five antibody heavy chains have to be expressed, it will be very difficult to build a cell line that expresses all of these chains at similar quantities when using a random integration and selection approach without the anti-repressor elements. By using such elements, a higher copy number of antibody chains can be introduced without compromising the stability of the resulting cell line. Thus, multiple antibody heavy chains can be introduced, where the number of integrated copies for each heavy chain will also to some level reflect its absolute expression level. With such elements it will be much easier and more rapid to alter the ratios of expression levels between the heavy chains, for example, by manipulating the ratios of the DNAs encoding the heavy chains at the time of the transfection.

This also explains embodimeints including incorporation of such anti-repressor elements in vectors to be used for creating antibody libraries and select antigen reactive antibodies from these pools (see, section 4); anti-repressor elements which may be inserted in the expression vectors that incorporate the heavy chain, on FIGS. 7, 8 and 9.

7. Expression Systems for Multiple Variable Regions in the Context of the Production of Multiple Regions in the Same Host Cell When expressing multiple variable regions inside the same cell, maximal productivity will be achieved only if the partners that need to be paired are co-expressed at an equivalent level, such that there is little chance on what is essentially waste: the non-paired variable region. The composition of the mixture is influenced by manipulating any one of the parameters that affect the expression level achieved in the host cell. The expression level of a given component is a function of many factors including the regulatory sequences that drive the expression of the component, when the component is a heavy chain also the expression levels of the light chains, the choice of the host cell, the method of expression (transient or stable), and, for stable expression, the copy number and site of integration. The expression levels can further be affected by many parameters including choice of the transcriptional regulatory elements (including choice of promoter, enhancer, insulators, anti-repressors, etc.). The expression of the two light and heavy chains of the antibodies that are to be assembled from the mixture of the chains can be done independently for each of the chains, or made dependent from each other.

The expression vector or vectors comprising the antibody genes of interest contain regulatory sequences, including, for example, a promoter, operably linked to the nucleic acid(s) of interest. Large numbers of suitable vectors and promoters are known to those of skill in the art and are commercially available for generating the recombinant constructs herein. Appropriate cloning and expression vectors for use with prokaryotic and eukaryotic hosts are described by Sambrook et al., in *Molecular Cloning: A Laboratory Manual, Second Edition*, Cold Spring Harbor, N.Y. (1989), the disclosure of which is hereby incorporated herein by reference. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, and pRIT5 (Pharmacia). Eukaryotic: pWLneo, pSV2cat, pOG44, PXTI, pSG (Stratagene) pSVK3, pBPV, pMSG, and pSVL (Pharmacia). Promoter regions can be selected from any desired gene using CAT (chloramphenicol transferase) vectors or other vectors with selectable markers. Two appropriate vectors are pKK232-8 and pCM7. Particular bacterial promoters include lacI, lacZ, T3, T7, gpt, lambda P, and trc. Eukaryotic promoters include CMV immediate early, HSV thymidine kinase, Elongation-factor-1α, early and late SV40, LTRs from retrovirus, mouse metallothionein-I, and various art-known tissue-specific promoters. Methods well known to those skilled in the art can be used to construct vectors containing a polynucleotide as described herein and appropriate transcriptional/translational control signals.

Mammalian expression vectors will comprise an origin of replication, a suitable promoter and also any necessary ribosome-binding sites, polyadenylation site, splice donor and acceptor sites, transcriptional termination sequences, and 5' flanking non-transcribed sequences. Expression regulatory sequences may comprise promoters, enhancers, scaffold-attachment regions, negative regulatory elements, transcriptional initiation sites, regulatory protein binding sites or combinations of the sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules. In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr⁻ host cells with methotrexate selection/amplification) and the neo gene (for G418 selection).

In an exemplary system for recombinant expression of a modified antibody, or antigen-binding portion thereof, a recombinant expression vectors encoding at least one antibody heavy or light chain is introduced into dhfr⁻ CHO cells by calcium phosphate-mediated transfection. Within the recombinant expression vector, the antibody heavy or light chain gene is operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy or light chains. In many instances the expression vector may contain both heavy and light chain genes, and co-transfection will lead to the production of intact antibody, recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

The host may also be a yeast or other fungi. In yeast, a number of vectors containing constitutive or inducible promoters may be used. For a review, see, *Current Protocols in Molecular Biology*, Vol. 2, Ed. Ausubel et al., Greene Publish. Assoc. & Wiley Interscience, Ch. 13 (1988); Grant et al., *Expression and Secretion Vectors for Yeast, in Methods in Enzymology*, Ed. Wu & Grossman, Acad. Press, N.Y. 153:516-544 (1987); Glover, *DNA Cloning*, Vol. II, IRL Press, Wash., D. C., Ch. 3 (1986); Bitter, *Heterologous Gene Expression in Yeast*, in *Methods in Enzymology*, Eds. Berger & Kimmel, Acad. Press, N.Y. 152:673-684 (1987); and *The Molecular Biology of the Yeast Saccharomyces*, Eds. Strathern et al., Cold Spring Harbor Press, Vols. I and II (1982). The host may also be a prokaryotic organism, such as *E. coli*. As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

Introduction of the recombinant construct into the host cell can be effected, for example, by calcium phosphate transfection, DEAE, dextran mediated transfection, or electroporation (L. Davis, et al., *Basic Methods in Molecular Biology* (1986)).

DNA encoding the antibodies is readily isolated and sequenced using conventional procedures for cloning, DNA preparation and sequencing as described by Sambrook, et al., in *Molecular Cloning: A Laboratory Manual*, Second Edition, Cold Spring Harbor, N.Y. (1989), the disclosure of which is hereby incorporated by reference. For sequencing, oligonucleotide probes can be used that are capable of binding specifically to genes encoding the heavy and light chains of antibodies or to the vector sequences surrounding the gene fragments, and the DNA sequence determined by dideoxy-based sequencing (F. Sanger, et al. (1977) *PNAS* 74:5463-5467). Once isolated, the DNA encoding appropriate regions of the antibody may be placed into expression vectors, which are then transfected into host cells. The host cell can be a higher eukaryotic host cell, such as a mammalian cell, a lower eukaryotic host cell, such as a yeast cell, or the host cell can be a prokaryotic cell, such as a bacterial cell.

In some embodiments, antibodies with pairing-compatible variable regions are produced in mammalian cells. Examples of mammalian host cells for expressing the clone antibodies or antigen-binding fragments thereof include Chinese Hamster Ovary (CHO cells) (including dhfr⁻ CHO cells, described in G. Urlaub et al. (1980) *PNAS* 77:4216-4220), used with a DHFR selectable marker, e.g., as described in (R. J. Kaufman et al. (1982) *J. Mol. Biol.* 159:601-621), lymphocytic cell lines, e.g., NSO myeloma cells and SP2 cells, C127, 3T3, CHO, human epidermal A431 cells, Jurkat, U937, HL-60, mouse L-cells, Baby Hamster Kidney cells, COS or CV-1 cells, PER. C6® cells (M. G. Pau et al. (2001) *Vaccine* 19:2716-2721), other transformed primate cell lines, normal diploid cells, cell strains derived from in vitro culture of primary tissue, primary explants, and a cell from a transgenic animal, e.g., a transgenic mammal. For example, the cell is a mammary epithelial cell. Other cell types suitable for expression, in particular, for transient expression, are simian COS cells (Y. Gluzman (1981) *Cell* 23:175-182), and Human embryonic Kidney cells of lineages 293, 295T and 911 (Hek293, 295T, 911).

Alternatively, it may be possible to produce the antibody as fragment or as whole antibody in lower eukaryotes such as yeast or in prokaryotes such as bacteria (L. C. Simmons et al. (2002) *J. Immunol. Methods* 263:133-147). Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the full antibody is made in yeast or bacteria as IgG, it may be necessary to modify the protein produced therein, for example, by phosphorylation or glycosylation of the appropriate sites, in order to obtain the functional protein. Such covalent attachments may be accomplished using known chemical or enzymatic methods. Recombinant polypeptides and proteins produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine. The recombinant polypeptides encoded by a library of diversity strands can then be purified using affinity chromatography. Microbial cells employed in expression of proteins can be disrupted by any convenient method, including freeze-thaw cycling, sonication, mechanical disruption, or use of cell lysing agents.

Figure 12:
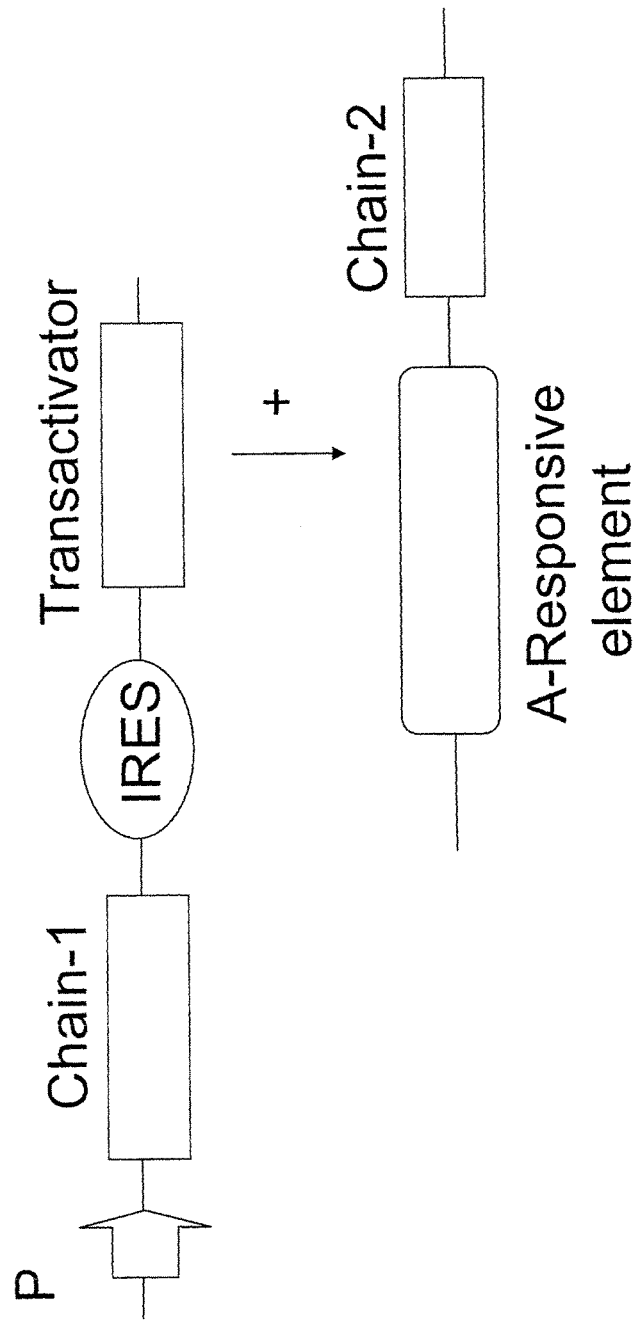
FIG. 12: Dependent expression of Ig chains. Chain-1 is typically the heavy chain, which is under control of a promoter (P). The IRES sequence links the expression of the heavy chain with that of a transactivator; this activates a responsive promoter to induce expression of Chain-2, typically the light chain (see, text for details).

Described herein is a method to directly relate the expression of the two partner variable regions that are required to pair in such manner that there is minimal waste (FIG. 12). The nucleic acid molecule encoding the first variable region is cloned into an expression cassette, such that it will be under the control of a given promoter (typically the strong CMV promoter or other), and such that its coding sequence is followed by an Internal Ribosome Entry Site (IRES) and the coding sequence of the transactivator of the tet responsive element (TRE) fused to the activation domain of the herpes simplex VP16 protein (tTa). The nucleic acid molecule encoding the second variable region is cloned into an expression cassette such that its expression is regulated via an inducible promoter, for example, the tet responsive element (TRE), existing of seven copies of the prokaryotic tetracycline operator site fused to a minimal CMV promoter. When introducing both expression cassettes into the same cell (on different vectors or on same vectors, at the same time or one before the other), the following relation between the expression of the two variable regions will exist: expression of the first variable region, which is under control of, for example, a constitutive promoter, will lead to the expression of the tTa protein. This protein activates the TRE-based promoter which will drive the expression of the second variable region. Thus, the production of the second variable region is now dependent on the production of the first variable region. If these regions are required to pair, the production of the individual components of the pairing can be made dependent.

When antibodies of the IgG-type are produced via a heavy and light chain, the production of the light chain can be made dependent on the production of the heavy chain. Consider the embodiment including the production in the same host cell of a mixture of antibodies which all share a pairing-compatible light chain. The light chain gene is cloned under control of the TRE element, while the heavy chains are all provided with the IRES and tTa gene, as described above. In the host cell, every individual heavy chain that is expressed will then trigger the production of more partner light chain. This is important, because with multiple heavy chains being expressed, it is likely that the level of light chain may become limiting, and that the excess of unpaired heavy chain will induce possible toxicity in the host cell (as has been described for B-cells). This concept is also applicable to the embodiment described in section 4, for the selection of antigen-reactive antibodies from pools made in eukaryotic cells. Other promoter-transactivator systems have been described and are applicable in this concept also. In the same application field, in those cases where the ratios of two particular heavy chains need to be controlled or fixed, this method of dependent-expression may be used to link the expression of two heavy chains.

Figure 21:
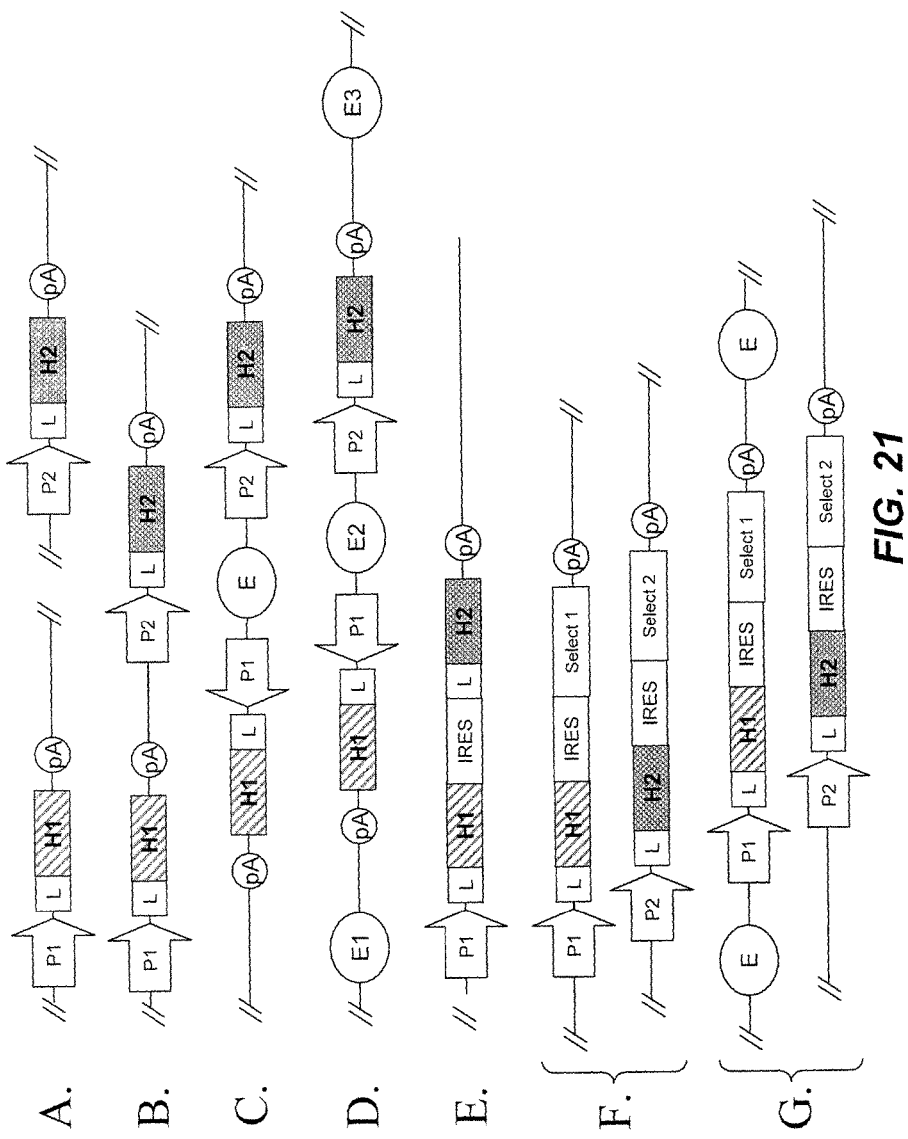
FIG. 21: Schemes depicting different formats for the co-expression of antibody chain encoding genes, exemplified here for the case in which two antibodies that share a common light chain (not shown) have to be co-expressed. (A) The basic individual cassettes, as separate cassettes and cloned into separate expression vectors. (B) This cassette contains the two Heavy chain (H) genes cloned in tandem, but their expression is individually regulated, via two different promoters, P1 and P2. (C) The two H genes are cloned into transcriptionally opposite directions and in this example separated by an element that influences the expression/stability/integration frequency (further examples are given in the text). (D) Same as B, but now additional E-elements are included at the 3' end of each of the two transcriptional units. (E) For cases in which two binding proteins should be present in the mixture at roughly similar quantities, an IRES is inserted between two H genes. (F and G) Expression cassettes for mediating the expression of two H chains, in which each of the H genes are linked via an IRES element to a selection marker (which is then selected for instead of using the vector-backbone-based marker), without (G) or with (H) additional elements in one cassette to influence expression.

Generally, a large number of suitable vectors and promoters are known to those of skill in the art and are commercially available for generating the recombinant constructs described herein. The following vectors are provided, by way of example, for the expression in eukaryotic cells of two or three antibodies that share a light chain sequence. The antibody chain encoding genes are cloned into expression cassettes that provide all regulatory and secretion signals which are typically used for antibody expression, as depicted in FIG. 20. In a first embodiment, the expression of multiple antibody heavy chains is made dependent on one another in the following way. In the first embodiment, the nucleic acid encoding the first heavy chain (H1) is cloned into an expression cassette, such that it will be under the control of a given promoter (typically the strong CMV promoter or other), and such that its coding sequence is followed by an Internal Ribosome Entry Site (IRES). This is immediately followed by a second antibody heavy chain coding region (H2, as depicted in FIG. 21). The P1 promoter will now drive the expression of H1 and H2, leading to an approximate 1:1 expression ratio between these two proteins; often though the second coding region is slightly less well expressed. Thus, if the expression ratio has to be steered towards a predefined range, the use of IRES sequences is particularly useful. This predefined range is influenced among other factors by the nature of the IRES sequence, and different IRES sequences will mediate different final ratios. Similarly, the expression ratio between three antibody heavy chains can be linked to one another by using a tricistronic expression cassette, in which the previous described cassette is followed by another IRES and Heavy chain coding region. Examples of tricistronic expression systems and of IRES sequences and configurations are described for other systems in the literature (Li et al., *J. Virol. Methods* 115:137.44; When et al., *Cancer Gene Therapy* 8:361-70; Burger et al. 1999, *Appl. Microbiol. Biotechnol.* 52:345-53). In these embodiments, the shared antibody light chain can be provided on a separate expression plasmid, on one or more of the vectors that carry on or multiple the antibody heavy chains, or can be already expressed by the host cell used for the transfection with the heavy chain expression vector or vectors.

In another embodiment, antibody heavy genes are sequentially transfected into the host cell. First, the embodiment for libraries of cells that produce mixes of two antibodies are considered. Cells are transfected with the two antibody genes cloned into different vectors but the transfection is done sequentially in time. For example, the antibody heavy and light chain encoding regions of the first antibody are introduced into the host cell, and stable transfectants expressing this antibody identified and isolated. The antibody genes encoding a second antibody, in which the variable regions are pairing-compatible, are transfected into the host cell that already expresses the first antibody genes at high level. This procedure of carrying out sequential transfections (and if appropriate selections of integration in between) is also suitable for making collections of mixture with up to four to five different antibodies. To increase the number of cell clones expressing multiple antibodies, the vectors carrying the genes encoding the antibody genes, also carries a unique selection marker, such that transfected cells that have integrated the vector sequence can be readily selected and antibody expressing clones identified. As an alternative embodiment for making cells that express multiple antibodies with compatible pairing, the following procedure is used. First, as before, cell clone is produced that expresses one set of antibody chains (this can be one H and one L or multiple H and one L, for example) and is selected on the basis of a first selection marker. In parallel, a cell clone is produced that expresses another subset of antibody chains (for example, one or more other H and one L) and that is selected on the basis of a different selection marker (for example, neo, gpt, zeo, bdl, etc.). These cell clones are then fused and selected for the presence of both of the selective markers. Methods for cell fusion are extensively described in the literature and known to those working in the field; they are similar to those described in Norderhaug et al., 2002, *Eur. J. Biochem.* 269:3205-10. The hybrid cells have the potential to express all of the antibody chains. Similarly, this procedure can be repeated if collections of larger numbers of antibody chains have to be made. Further, the use of cell populations rather than cell clones, in this sequential transfection or cell-fusion approach, provides a method for achieving large collections of cells that express the antibody chains at different ratios.

In one embodiment, the proteinaceous molecule's coding region or regions are flanked by sequences that mediate site-directed integration into the host cell genome (as depicted in FIG. 20). Without these, integration of transgenes occurs at random and, usually, several copies of the transgene are integrated at the same time, sometimes in the form of a head-to-tail tandem, with the site of integration and the number of copies integrated varying from one transfected cell to another. The use of recombination sites as depicted in FIG. 20 allows the precise site of integration to be targeted by homologous recombination between vector and host cell genome. This provides a means to insert the coding region into a site of high transcriptional activity, with the option to provide a promoter in the transgene or use the one that is present at the site of integration. With random or homologous recombination-mediated insertion of the antibody chain encoding nucleic acids is meant any insertion into the genome of the host cell, or into the nucleic acids in a subcellular organel, or into an artificial chromosome.

Some embodiments are to employ (per expression vector used in the library construction) not more than three antibody heavy chain coding regions and may have two per vector. In certain embodiments, some plasmids do not contain more than three promoters and three IRES sequences and not more than six STAR or MAR elements. In some instances, the expression vector's size may be limited to 20 kb and if more than five binding sites are required in the mix, and these cannot be functionally encoded in a plasmid that is less than 20 kb in size, to use two or more different plasmids.

MARs and STARs can be positioned on either side of the DNA sequence to be transcribed. For example, the elements can be positioned about 200 bp to about 1 kb, 5' from the promoter, and at least about 1 kb to 5 kb from the promoter, at the 3' end of the gene of interest. In addition, more than one element can be positioned 5' from the promoter or at the 3' end of the transgene. For example, two or more elements can be positioned 5' from the promoter. The element or elements at the 3' end of the transgene can be positioned at the 3' end of the gene of interest, or at the 5' end of a 3' regulatory sequence, e.g., a 3' untranslated region (UTR) or a 3' flanking sequence. Chromatin opening elements can be flanking on both ends of the expression cassette (FIG. 21, row D), or placed 5' of the expression cassette (FIG. 21, row C). In particular, when multiple regulatory elements such as STAR and UCOs have to be introduced into one and the same plasmids, elements may be used that have activity towards both ends of the element such that they can be provided in the middle of an expression cassette (FIG. 21, row C). Since MARs have also been reported to function when co-transfected in trans with the transgene (Zahn-Zabel et al. (2001) *J. Biotechnology* 87:29-42), they have the advantage that no DNA-cloning step is required to physically link them to SPCBP expression cassette(s). In that case, size of the MAR element or of the expression vector carrying the SPCBP cassettes is no longer a limitation. Nevertheless, MAR elements as small as 1.3 kb have been described, thus multiple in cis inclusions are feasible. MARs have also been reported to be added both in cis and in trans, and in this configuration increase expression levels of antibodies in CHO cells 14-fold. One other function of these elements—besides their effect on stability—is that they will also increase the number of independently transformed cells that express the protein and promotes higher amounts of the recombinant protein. Clone isolation and production levels are overall higher, thus these elements may be used for making large collections of cell lines producing compositions comprising multiple functional binding sites.

8. Proteinaceous Mixtures with Multiple Effector Regions and Multiple Types of Binding Sites The methods can be used to create compositions of proteinaceous molecules that have multiple effector regions. In the case of antibodies, compositions are included that display one or more antigen binding regions in combination with two or more natural effector regions. Examples are the effector regions encoded by IgG1 and IgG4, which have, for example, different binding regions for Clq and the various Fc-receptors based within their encoding constant regions. Such mixtures may be clinically more effective than their mono-effector compounds: the mixture combines multiple and maximal natural effectors, which for various reasons are never present in the one natural antibody isotype, and the mixture thus mimics much more closely the natural pleiotropy of immune effectors that a single antigen/pathogen will evoke when our immune system encounters it. Some formats are IgG1 and IgG4, or IgG and IgM, or IgG1 and Fab, or IgG and IgA, or IgA and IgM, or IgG1-cytokine fusion and alike. Instead of making such proteins in different hosts, the co-expression of such different antibody formats, all associated with the same binding site (or possibly multiple binding sites but related to one target and, for example, to one disease or indication), allows the direct production of cocktails of antibodies with different effectors. Such mixtures are more efficacious in their biological activity.

Besides antibodies, recent protein engineering techniques have allowed the production of binding sites with predetermined specificity using similar but also sometimes using very different structures. For example, antigen-specific ligands have been created using phage, bacterial, ribosomal or yeast display methods, from libraries of protein variants, in which the protein at some positions was variegated using random or oligonucleotide-based mutagenesis, but the main scaffold of the native protein maintained in the variants. Proteins for which has been already applied include the protein Z domain of Protein A, a variety of Kunitz domains, lipocalins, Green Fluorescent protein, one of the fibronectin domains, other domains of the immunoglobulin superfamily, and ankryns. Such antibody mimics are thus proteinaceous molecules with a non-natural binding activity, obtained, for example, by engineering into the molecule one or more residues or regions with variegated sequences, at either defined or random positions, and identifying the molecule with appropriate antigen binding properties by screening or selection processes. Examples of the processes are high-throughput screening for antigen binding by ELISA, or selection methods described in the literature such as in vitro display methods such as ribosome and puromycin display, cellular or viral display methods such as filamentous phage, lambda phage, bacterial, yeast, or eukaryotic cell display. The resulting proteinaceous molecules with the new binding site is an antibody mimic in the sense that it will contain a binding region for antigen at the position where it was initially a variable region, similar to an antibody molecule with two variable regions.

9. Making Compositions of Multiple Proteinaceous Compounds with Different Binding Specificities.

Recombinant DNA technology provides methods well known in the art to clone the variable region genes, and produce cell lines expressing the recombinant form of the antibody. In particular, the properties of antibodies are being exploited in order to design agents that bind to human target molecules, so-called "self-antigens," and to antigens of viral or bacterial diseases. For example, a number of monospecific antibodies have been approved as human therapeutics. These include Orthoclone OKT3, which targets CD3 antigen; ReoPro, which targets glycoprotein IIb/IIIa; Rituxan, which targets CD20; Zenapax and Simulect, which target interleukin-2 receptors; Herceptin, which targets the HER2-receptor; Remicade and Humira, which target tumor necrosis factor; Synagis, which targets the F protein of respiratory syncytial virus; Mylotarg, which targets CD33; and Campath, which targets CD52.

For many clinical applications the efficacy of the treatment would increase if combinations of monoclonal antibodies are used. An oligoclonal preparation can be made by mixing individual recombinant antibodies which each have been made by conventional procedures, which includes the expression and purification of the individual recombinant or hybridoma-derived monoclonal antibodies, and the subsequent mixing of these molecules. The pharmaceutical development of separately produced and then mixed monoclonal antibodies is inhibitively expensive. Recombinant monoclonal antibodies of the IgG isotype are commonly made by co-expression of the nucleic acid sequences encoding the heavy and light chain of the antibody in the same host cell, yielding a monoclonal antibody, bearing two identical binding sites. The production of several antibodies from individual cell lines each making one antibody (and in which each cell line is controlled for stability of expression and consistency), is not economical with present biotechnological production methods.

One approach to combining monoclonals is to combine the binding sites in one molecule, hence creating a multispecific antibody. This allows the targeting of multiple epitopes on the same antigen, or of multiple antigens on the same target entity (e.g., a cell, a virus, a bacteria, an antigen), or of epitopes on different entities, providing a bridge between these entities. Of the multispecific antibodies, bispecific antibodies have been investigated the most, for targeting therapeutic or diagnostic entities to tumor cells, e.g., a cytotoxic T-cell, an NK cell, a chelator that carries a radionuclide. But in the bispecific antibody the two binding sites are always covalently coupled to one another, which limits the flexibility and use of such compounds. Further, many of the recombinant bispecific antibodies (e.g., Fab-scFv fusions, diabodies, double-single-chain Fvs) lack the provision of the antibody's Fc region. Since Fc-dependent effector mechanisms such as ADCC are important for the efficacy of many antibodies (e.g., Rituxan and Herceptin), it will be important to maintain this region in the multispecific molecule.

An alternative approach is to use polyclonal antibodies comprising the entire immune response of a host to an immunogen. Polyclonals derived from the pooled serum from immunized animals or from selected humans have been used therapeutically e.g., for passive or active immunization, e.g., anti-rhesus D, anti-digoxin, anti-rabies, anti-snake venom polyclonals, and in some instances, work more effectively than a comparable monoclonal, e.g., Sangstat's rabbit polyclonal against thymocytes versus SIMULECT®. Drawbacks for the use of polyclonal antibodies are the risk of infectious agents (viruses, prions, bacteria) in these often pooled preparations, but also the variability in efficacy, the limited availability, the immune response directed to the preparation if the polyclonal is non-human, and the abundance of non-relevant antibodies in these preparations. Polyclonals have also been made using recombinant methods, but again, the production of large arrays of antibodies from individual cell lines each making one antibody, is not economical with present biotechnological production methods. The production of the polyclonal antibody mixture by cultivating the many different cell lines in batch would be even more affected by differences in stability, growth and production rate, differences in purification yield, etc.

Provided are methods for producing mixtures of antibodies, for example, by expression from a single host cell, using antibodies with variable regions that appropriately pair with one another to yield essentially solely functional binding site combinations. The methods to obtain such antibodies were described herein earlier. The resulting variable regions can thus be co-expressed in biotechnologically viable and simple procedure, and a mixture of antibodies isolated using methods known in the art.

After selection of antibodies with the appropriate pairing behavior (such as antibodies with pairing-compatible variable regions, co-expression-compatible elements, etc., as described above), the antibody variable region genes are cloned into expression vectors that will direct the expression of an antigen binding fragment in, for example, the following format: Fab, Fab', Fab'2, IgG, IgM. In many instances the use of antibodies with, for example, pairing-compatible variable regions simplifies the DNA constructs that mediate the expression of the particular antibody format. For example, for the expression of two different antibodies as Fab'2 fragments in which one of the two antibody chains is the pairing-compatible variable region, only three antibody chains instead of the normal four have to be expressed to form two different binding sites. Such simplified expression constructs can lead to a more stable and more readily controlled expression system, and increase functional yields by minimizing problems associated with mispairing of heavy and light chain domains.

The mixture may contain a given selection of antibodies, recognizing epitopes on the same or different targets; examples are given below. A new application is the use of mixture containing antibodies specific for complexes formed by another antibody bound to a given target. Both of the antibodies can be provided in the mixture, providing a first antibody to bind the antigen, and a second one to "seal" the first interaction, providing the antibody mixture with an increase in overall affinity and specificity. Another embodiment is to use asymmetrically paired antibody molecules in the mixture such that the effector functions of the resulting mix are altered. The purpose of such mixing is to alter the properties of the effector mechanism of the individual antibodies in the mixture, in an antigen-specific/binding site directed manner, for example, the monospecific antibodies may each have a different effector from the bispecific components present in the mixture. Consider the next example, a mixture of two antibody binding sites formatted as OLIGOCLONICS® in the IgG-format, composed of the heavy chain gamma-1 heavy chain for one antibody variable region and the gamma-4 heavy chain for the other antibody variable region. The OLIGOCLONICS® mixture will contain the two monospecific antibodies, which will be either an IgG1 or an IgG4 isotype and display their respective effector functions, and also a hybrid dimer of gamma-1 and gamma-4, with altered or lost effector functions. Since many Fc receptors bind in an asymmetric manner to the symmetrically arranged Fc region, asymmetric Fc regions often will loose interactions with Fc receptors and thus ADCC or other activity. Mutants of Fc regions with, for example, mutations in the Fcgamma-Receptor motif (residues 233-238 in the CH2-lower hinge region), or mutants with reduced Clq binding, or mutants with exchanged or shortened hinge, or with domains exchanged by other domains of the immunoglobulin heavy chain family, or Fc regions optimized for their interaction with particular Fc regions (e.g., improved binding to the activating receptor FcgammaRIII and/or decreased binding to the inhibitory receptor FcgammaRIIb), can also be used for the assembly of such asymmetric Fc regions. Applications of such asymmetric pairs are provided in a mixture of one compound but not others with a particular effector function, or to remove an effector, for example, in the bispecific or monospecific compounds.

10. Examples of Uses of Compositions of Multiple Proteinaceous Compounds with Different Binding Specificities There are applications for mixtures of different binding sites on the same antigen, for mixtures of different binding sites on different antigens, for mixtures of different binding sites on different antigens on the same or different target. As an example of use of a mixture in the treatment of a viral disease, the example of hepatitis B virus (HBV) infection is discussed. Recombinant HBV vaccines provide a safe and effective means for prevention of HBV conferring long-term immunity through active immunization. In contrast to the slow onset of protection following this vaccination, passive immunotherapy with antibodies to HBV provides immediate but short-term protection against viral transmission and infection. Antibodies are believed to inhibit infection by blocking HBV from entering into cells. Such passive immunotherapy is advisable for individuals who were exposed to HBV-positive material (needle or cut injuries) and for newborns to mothers who are HBV carriers, for patients undergoing liver transplantation. At present, such treatment is carried out with hepatitis B immunoglobulin, a plasma derived, polyclonal antibody preparation obtained from donors who were anti-hepatitis B surface antigen antibody-positive. The availability of this serum is limited and further pricing and safety concerns regarding the use of blood products, make the development of an alternative treatment necessary. A human monoclonal antibody would be advantageous by presenting a stable and reproducible source for prolonged immunotherapy. However, studies show that a monoclonal antibody directed to the S antigen and neutralizing capacity against HBV in chimpanzees delayed but not prevented the infection with HBV. In part this may be caused by the emergence of escape variants, mutants in the S-antigen that can no longer be bound by the monoclonal antibody. Similarly, escape mutants arise in patients after liver transplantation in clinical trials with monoclonal antibodies. Therefore, treatment with a single monoclonal antibody may be inefficacious and insufficient. Follow-up studies have involved mixtures of human monoclonal antibodies. Studies carried out by XTL Biopharmaceuticals and colleagues show that a mixture of two antibodies is more effective in reducing viral load and inhibiting HBV infection in animal model systems than a polyclonal mixture. This indicates that the potency of a polyclonal humoral immune response can be deconvoluted to a few antibodies, and that a defined mixture of a few antibodies should work as well or better than some polyclonal preparations. A mixture of two antibodies recognizing different epitopes on the viral surface was thus shown to be more effective in the prevention of HBV reinfection.

In another example of use of a mixture of monoclonal antibodies in the treatment of a viral disease, the example of the Human Immunodeficiency Virus type-1 (HIV-1) is discussed. Infection with HIV-1 leads to the development of the Acquired Immunodeficiency Syndrome (AIDS) if left untreated. During infection with HIV-1, neutralizing antibodies that are directed against diverse epitopes on the HIV-1 envelope glycoprotein molecules gp41 and gp120 develop. In a clinical trial published in 1992, the administration of HIV-1 seropositive plasma containing high titers of HIV-neutralizing antibodies, was associated with a reduction in HIV-1 viremia and a number of opportunistic infections. Several groups have subsequently published that administration of HIV-1 seropositive plasma results in delay of the first AIDS-defining event and improvement of clinical symptoms. However, enthusiasm for passive immunotherapy declined when it was found that antibodies failed to eliminate the virus and resulted in the emergence of neutralization escape variants in patients. It was demonstrated that the antibodies that are induced during natural HIV-1 infection poorly neutralize the virus, resulting in a low potency of hyperimmune sera used for passive immunotherapy of HIV-1 infection. In addition, it was demonstrated that some antibodies that arise during natural infection can even enhance the infection. It was realized that for antibody therapy of HIV-1, potent and well-characterized neutralizing monoclonal antibodies were needed.

These early findings spurred the development of human monoclonal antibodies against HIV-1 envelope glycoproteins. In recent years, a number of human monoclonal antibodies against the HIV-1 gp41 and gp120 viral coat glycoproteins have been isolated and characterized for their virus-neutralizing activity in vitro. Subsequent experiments in non-human primate models of HIV infection and transmission have shown that human monoclonal antibodies targeting different HIV-1 envelope glycoprotein epitopes exhibit strong synergy when used in combination. It has been suggested that combinations of human anti-HIV monoclonal antibodies can be exploited clinically for passive immunoprophylaxis against HIV-1.

A third example relates to the rabies field. Rabies is an acute, neurological disease caused by the infection of the central nervous system with rabies virus, a member of the Lyssavirus genus of the family of Rhabdoviridae. Almost invariably fatal once clinical symptoms appear, rabies virus continues to be an important threat to human and veterinary infection because of the extensive reservoirs in diverse species of wildlife. Throughout the world, distinct variants of rabies virus are endemic, in particular, terrestrial animal species, with relatively little in common between them. Rabies virus is characteristically bullet-shaped, enveloped virion of single-stranded-negative sense RNA genome and five structural proteins. Of these, a suitable target for neutralization is the viral glycoprotein (G). Antigenic determinants on G vary substantially among the rabies virus strains. Prompt treatment after infection consists of passive and active immunotherapy. For passive immunotherapy mostly pooled serum of rabies immune individuals or immunized horses is used, but with a risk of contamination with known or unknown human pathogens, or the risk of anaphylactic reactions, respectively. In addition, anti-rabies immunoglobulin is expensive and may be either in short supply or non-existent in most developing countries where canine rabies is endemic. There is, therefore, a need for compositions and methods for producing mixes of antibodies, for example human antibodies, to use in passive immunotherapy of rabies infections. A number of human monoclonal antibodies made by fusion of Epstein-Barr Virus transformed, rabies-virus-specific human heterohybridomas have been made (Champion et al., *J. Immunol. Methods* (2000) 235:81-90). A number of virus-neutralizing antibodies derived from these antibodies have also been cloned (PCT/IS02/26584 and PCR/US01/14468 and Morimoto et al. (2001), *J. Immunol. Methods* 252:199-206). Several other rabies-neutralizing monoclonal antibodies have been described in the art, which could also be used in the experiments below. As indicated in these publications, a mix of different rabies-neutralizing human antibodies would be an ideal reagent for passive immunotherapy of rabies.

In general for viral diseases, the functional assembly of mixes of anti-viral antibodies may increase the clinical efficacy of the treatment when compared to monoclonal therapy, by decreasing the probability of viral escape mutants resistant to treatment, and by reducing the likelihood of viral resistance with prolonged therapy. In the mixture, antibodies may be included that bind to many different epitopes of the virus. It may also be feasible to include antibodies to different subtypes of the virus, to broaden the utility of the drug for a wider patient population. Further anti-viral antibodies directed to linear epitopes may be added, which may be less prone to the effect of escape mutants than conformation-dependent antibodies. The effect of multiple binding specificities present in the antibody mix can provide a stronger signal for viral clearance than when a monoclonal antibody is used. There are also applications for mixtures of essentially one binding site with different fine-specificities for binding its antigen. For example, when the antigen is prone to mutation as is the case with many viral antigens, in the course of a treatment the epitope on the antigen may be altered such that the binding of the original antibody is lost. When using a mixture, e.g., based on the same heavy chain paired with a small set of light chains that provide a range of fine-specificities, there is a possibility that the mutations will affect the binding of some species in the mixture, but not of others with a different binding chemistry mediated by the pairing-compatible variable region. In such a case, distinct binding chemistries for the interaction with the antigen may be used, thus the pairing-compatible variable regions should be as unrelated as possible in sequence. Alternatively, antibodies can be used that use very different binding site chemistries by having unrelated heavy and light chain variable regions, but display exclusively pairing behavior such that their production in the same cell yields mainly functional binding sites. Such mixtures are may be more active than the individual components, and in some case will act synergistically.

In the OLIGOCLONICS® format, antibodies of the IgG isotype are made by co-expression of the light and heavy chain genes with appropriate pairing behavior in the same host cell. The result of this process is a mixture of different proteins, the monospecific bivalent antibodies which carry two identical binding sites, and bispecific antibodies, carrying two different binding sites. There will be occasions where the presence of this bispecific antibody class will further enhance the efficacy of the antibody mixture. Only when there are multiple epitopes present on the antigen or microorganism, and these epitopes are presented in the correct positioning, will a monoclonal antibody of the IgG isotype, for example, be able to bind both of its binding Fab-arms to the antigen. In many instances where the antigen is a monomer or a small multimer, like cytokines, interleukins and interferons, mostly only one arm of a monoclonal IgG antibody will be binding the antigen. The bispecific component of the OLIGOCLONICS®, provides a new opportunity to bridge neighboring epitopes, and form a highly avid binding antibody. Pairs that have this behavior may be selected using the methodologies of screening mixtures of antibodies as disclosed herein. Besides this avidity advantage, bispecific molecules may also cross-link receptors that mono-specific yet bivalent antibodies in the same mixture cannot cross-link. OLIGOCLONICS® may thus provide an antibody mixture that per unit of mass will more effectively neutralize viruses, cytokines, toxins etc when compared to monoclonal antibodies, and in specific cases, for example, with an avidly binding bispecific component or receptor-cross-linking or other unique mechanism mediated by the bispecific antibody, also compared to mixtures of monoclonal antibodies. The bispecific compounds are also useful to explore routes traditionally developed with bispecific antibodies, such as the retargeting of immune effector molecules or cells such as T-cells, complement proteins and Fc-receptor expressing cells to tumor cells or pathogens.

Thus, mixtures of antibodies may be suitable to fight pathogens including viruses like HIV and rabies, bacteria, fungi, and parasites. Other examples where a polyclonal serum or gammaglobulin is currently used that could be replaced with a defined antibody mixture, include such diseases as rabies, hepatitis, varicella-zoster virus, herpes or rubella. Bacterial diseases that could be treated with antibody mixtures include Meningitis, diseases caused by *Staphylococcus, Streptococcus*, Hemophilus, Nesseria, *Pseudomonas* and the actinomycetes. Targets may also include those involved in bacterial sepsis such as lipopolysaccharide (LPS), lipid A, tumor necrosis factor alpha or LPS-binding proteins. Some of these pathogens occur in multiple serotypes and not one but multiple antibodies are required to neutralize the various serotypes. A mixture of antibodies will provide, by the choice of the binding specificities, a wider coverage of serotypes that may be treated and, therefore, more patients can be treated with the same antibody mixture. The mixtures for this and other reason can form also suitable diagnostics and part of diagnostic kits for the detection of a disease or disorder in patient.

Mixtures of antibodies may be more effective than monoclonal antibodies also in the treatment of oncological diseases such as non-Hodgkin's lymphoma (NHL) and epithelial cell tumors like breast and colon carcinoma. Targeting both CD20 and CD22 on NHL with antibodies has already been proven to be more effective than targeting the tumor cells with the individual antibodies. Suitable target antigens for antibody mixtures in oncological diseases are many, including CD19, CD20, CD22, CD25 (IL-2 receptor), CD33, the IL-4 receptor, EGF-receptor, mutant EGF receptor, Carcino-Embryonic Antigen, Prostate-specificAntigen, ErbB2IHER2, Lewis$^y$ carbohydrate, Mesothelin, Mucin-1, the transferrin receptor, Prostate-specificMembrane Antigen, VEGF and receptors, EpCAM and CTLA-4. Synergistic effects may be seen when using antibodies that bind different targets and pathways in the disease, such as antibodies with anti-angiogenesis and anti-proliferative effects. There are also applications in this field for a mixture of essentially one binding site with different affinities for binding its antigen. For example, the efficiency of in vivo solid tumor penetration is limited for high affinity antibodies due to the binding site barrier, yet a minimal affinity is required to achieve a substantial accumulation in the tumor. With the methods described in this document, a mixture of antibodies can be established, e.g., based on the same heavy chain paired with a small set of light chains yet appropriate pairing behavior that provide a range of affinities when paired with the heavy chain. Such mixtures can be used to increase the accumulation in the tumor, and the best balanced cocktail found by choosing the components and their expression levels. Such mixtures may be more active than the individual components, and may act synergistically.

Mixtures of antibodies may also be suitable to neutralize multiple different targets, for example, in the field of inflammatory diseases, where multiple factors are involved one way or another in mediating the disease or aggravating its symptoms. Examples of these diseases are rheumatoid arthritis, Crohn's disease, multiple sclerosis, insulin-dependent diabetes, mellitus and psoriasis. Optimal treatment of many of these diseases involves the neutralization or inhibition of circulating pathological agents and/or those on the surface on cells targeted in the specific inflammatory response in the patient. In autoimmunity and inflammatory diseases suitable targets are generally interferons, cytokines, interleukins, chemokines and specific markers on cells of the immune system, and, in particular, alpha interferon, alpha interferon receptor, gamma interferon, gamma interferon receptor, tumor necrosis factor alpha, tumor necrosis factor receptor, HLA-class II antigen receptor, interleukin-beta, interleukin-beta receptor, interleukin-6, interleukin-6 receptor, interleukin-15, interleukin-15 receptor, IgE or its receptor, CD4, CD2, and ICAM-1.

Mixtures are also suitable for the neutralization of effects mediated by agents of biological warfare, including toxins such as *Clostridium botulinum*-derived botulinum neurotoxin, anthrax, smallpox, hemorrhagic fever viruses, and the plague. The neutralization of the botulinum toxins is discussed here as an example. The botulinum toxins, the most poisonous substances known, cause the paralytic human disease botulism and are one of the high-risk threat agents of bioterrorism. Toxin-neutralizing antibody can be used for pre- or post-exposure prophylaxis or for treatment. Small quantities of both equine antitoxin and human botulinum immune globulin exist and are currently used to treat adult and infant botulism. Recombinant monoclonal antibody could provide an unlimited supply of antitoxin free of infectious disease risk and not requiring human donors for plasmapheresis. A panel of human and murine monoclonal antibodies was generated from the B lymphocytes of hyperimmune donors and immunized mice using phage antibody display technology. Single monoclonal antibodies and combinations were tested for their capacity to protect mice from lethal doses of neurotoxin (A. Nowakowski et al. (2002) *PNAS* 99:11346-11350.). Whereas single monoclonal antibodies showed no significant protection of the mice against lethal doses of toxin, combinations of only three monoclonal antibodies against different epitopes on the toxin gave very potent protection. The combination of three monoclonal antibodies neutralized 450,000 lethal doses of botulinum toxin, a potency 90 times greater then human hyperimmune globulin. Importantly, the potency of the monoclonal antibody mixture was primarily due to a large increase in functional antibody-binding affinity. Thus, methods that allow the cost-effective, controlled and efficient production of mixtures of monoclonal antibodies against botulinum neurotoxin provide a route to the treatment and prevention of botulism and other pathogens and biologic threat agents. As shown in this study, a mix of three antibodies that bound non-overlapping epitopes on botulinum neurotoxin, had a synergistic effect on toxin neutralization due to a increased overall avidity.

Mixtures of antibodies may be further applied to delay the onset of anti-idiotype responses in patients, by providing multiple idiotypes of an antibody family, all binding to the same target, in the simplest form amino acid mutants of the same antibody with a resulting similar binding specificity and affinity, to a more complex mixture of multiple antibodies directed to the same epitope.

Mixtures of antibodies can also be applied to develop derivatives of the protein mixtures, including immunotoxins, immunoliposomes, radio-isotope labeled versions, immunoconjugates, antibody-enzyme conjugates for prodrug-therapy (ADEPT), and immunopolymers (Allen, (2002) *Nat. Rev. Cancer* 2:750-783). The mixes of the antibodies can either be modified in batch with the appropriate substances, or may be genetically fused to a toxin or enzyme encoding gene as described in the art for monoclonal antibodies.

Having generally described the embodiments, the same will be more readily understood by reference to the following examples, which are provided by way of illustration and are not intended as limiting.

EXAMPLES

Example 1. Description of the Hybridoma-Derived Anti-Rabies Antibodies Used in the Studies This Example describes a number of rabies-neutralizing antibodies that are used in the further examples. The following antibodies are virus-neutralizing human antibodies: (1) JB.1 (abbreviated to JB in the next section), described in Champion et al., *J. Immunol. Methods* (2000) 235:81-90, and the cloning and sequence in PCT/IS02/26584; (2) JA-3.3A5 (abbreviated to JA in the next section), described in Champion et al., *J. Immunol. Methods* (2000) 235:81-90, the cloning in Morimoto et al. (2001), *J. Immunol. Methods* 252:199-206 and also in PCT/US01/14468; (3) M57, antibody and its cloning were described in Cheung et al. (1992), *J. Virol.* 66:6714-6720, and further in PCT/IS02/26584. The nucleotide sequences of the full heavy and light chain nucleotide sequences and also amino acid sequences of their variable regions are disclosed in the sequence listings (SEQ ID NOS: 103-114 of the incorporated Sequence Listing). On the basis of the data in the literature these antibodies all neutralize a variety or rabies isolates, but not all the same, providing a broader spectrum of neutralized isolates than when using a monoclonal.

Example 2. Production of Mixtures of scFv Antibody Fragments Based on Recloned Hybridoma-Derived Anti-Rabies Antibodies and Co-Expression This Example describes the production of a mixture of three binding sites as three proteins. Using as a template, the variable region genes of the three antibodies described in Example 1, cloning is used to construct three single-chain Fv expression cassettes, one for each of the antibodies, and to clone these in an appropriate expression vector.

First, the variable region genes are amplified with oligonucleotides that hybridize to the 5' and 3' ends of the nucleotide sequences and provide appropriate restriction enzyme sites for cloning. Standard cloning techniques are described in Sambrook et al., *Molecular cloning, second edition*, Cold Spring Harbor Laboratory Press (1987). Cloned variable regions genes are amplified by the polymerase chain reaction using methods well known in the art.

For antibody JA, the following procedure is used: primers are designed in the FR1 region and in the FR4 region of the variable heavy chain nucleotide sequence, such that the variable region is cloned downstream of a bacterial leader sequence and upstream of a continuation of the reading frame with a Gly-Ser encoding sequence. The polylinker into which the variable region heavy and light chains are cloned is indicated in FIG. 13. The primers are designed to maintain the amino-terminal sequence of the FR1 and FR4 regions, and to include a unique restriction enzyme site for cloning of the variable region into the polylinker region of pSCFV (FIG. 13). pSCFV is a pUC119 derivate which is essentially pHEN 1 (Hoogenboom et al. (1991) *Nucl. Acids Res.* 19:4133-4137) into which the SfiI-NotI fragment is replaced with the SfiI-NotI sequence depicted in FIG. 13, and in which the NotI site is followed by a c-myc tag, for detection and purification of the antibody fragment. Also the geneIII of filamentous phage is deleted in this plasmid. Several options for directional cloning are feasible, indicated by the restriction sites locations on the polylinker map on FIG. 13. For the VH of JA, the following oligonucleotides are used to amplify the VH regions: 5'-GTC CTC GCA ACT GCG GCC CAG CCG GCC ATG GCA GAG GTG CAG CTG TTG GAG TCT GGG GG-3' (SEQ ID NO: 120) and the reverse complement of 5'-ACC CGG GTC ACC GTC TCC TCC-3' (SEQ ID NO:121). The PCR reaction is carried out with the template antibody gene which was already cloned, plasmid SPBN-H (Morimoto et al. (2001), *J. Immunol. Methods* 252:199-206), for 25 cycles, denaturation at 94° C. for 30 seconds, annealing at 50° C. for 60 seconds, and elongation at 72° C. for 90 seconds, using Taq DNA polymerase (Promega, Madison, Wis.). The resulting product of approximately 400 bp is purified, digested with the restriction enzymes SfiI and BstEII, and cloned into pSCFV, resulting in pJA-VH. Similarly, the light chain of JA is amplified from pSPBN-L with appropriately designed oligonucleotides and is cloned into pJA-VH, to yield pSCFV-JA. The integrity of the sequences is confirmed by using the AmpliTaqs cycle sequencing kit (Perkin-Elmer, Foster City, US) with specific primers based in the vector backbone just adjacent to the variable region inserts. Similarly, the antibody variable regions from hybridomas JB and M57 are cloned into the single-chain Fv format.

The expression of the individual antibody fragments is done as follows. Soluble scFv fragments are expressed upon induction with isopropyl-β-D-thiogalactopyranoside (IPTG) from the lacZ promoter that drives the expression of the scFv in pSCFV-based plasmids, and harvested from the periplasmic space of *E. coli* TG1 cells. To confirm binding of the individual scFvs, an ELISA is performed using Polysorb plates (Nunc) coated with 5 micrograms/ml of rabies virus glycoprotein. Virus purification and glycoprotein purification have been described elsewhere (Dietzschold et al. (1996) *Laboratory Techniques in Rabies*, Eds Meslin, Kaplan and Korpowski), *World Health Organization, Geneva*, p. 175). Alternatively, a source of recombinant Rabies Glycoprotein (G) of the appropriate type is used for the coating. The sequence of rabies G is available to the person skilled in the art and so are cloning, expression and purification techniques.

In the next step, the scFv expression cassettes are cloned one after another in plasmid pSCFV-3 (depicted in FIG. 14A), which is a derivative of pSCFV carrying unique restriction sites for cloning scFv genes, two behind the same lacZ promoter and separated via a new ribosome-binding site (rbs) and signal sequence (S), and one behind an arabinose-inducible promoter, rbs and S (FIG. 14A). It also carries different tags, one for each of the scFv cassettes, c-myc (as in pSCFV; sequence EQKLISEEDL (SEQ ID NO: 122)), the VSV-tag (the sequence YTDIEMNRLGK (SEQ ID NO: 123)) and the influenza Hemagglutinin (HA)-tag (the sequence YPYDVPDYA (SEQ ID NO: 124)), and all followed by a stretch of three alanines and five histidines. This set-up provides a method for detection of the individual antibodies in the mix, and a generic method for purification, based on immobilized metal affinity chromatography (IMAC) using methods well known in the art. The plasmid is also used in Example 17 (with restriction inserts and cloning sites described in SEQ ID NOS: 118 and 119). The scFv genes are amplified with oligonucleotides that introduce the appropriate sites, and cloned into this plasmid. The finally resulting plasmid, pSCFV-JA-JB-M57 (FIG. 14B) is introduced into *E. coli* host TG1 cell, and expression of the scFvs induced with IPTG (for JA and JB) and/or arabinose (M57). By induction with IPTG, the expression of a mixture of two functional scFv fragments is achieved, in which the direct linkage favors the pairing between the intramolecularly linked variable regions. By further induction with arabinose, an additional scFv fragment is co-expressed. Alternatively, the three scFv expression cassettes are cloned in separate plasmids into compatible plasmids such as pBR322 and pACYC and maintained in the same host cell before induction. The binding of the mixture to rabies glycoprotein (G) is tested as before using ELISA. The contribution to the binding in the mix of each of the scFv fragments is confirmed using one of three anti-tag antibodies (the mouse monoclonal antibody 9E10 binding to human c-Myc epitope tag (product code from abcam, www.abcam.com: ab32), and polyclonal antibodies to the HA-tag (ab3413) or VSV-tag (ab3556). To verify whether the production is carried out by one bacterium and its progeny and not by three clones that each produce one of the antibody fragments, the culture is colony-purified after four hours in the induction phase and the production tested of three independent clones, confirming that the expression is clonal. To determine the percentage of correctly paired variable regions, the scFv mixture is first purified from the *E. coli* periplasmic extract using IMAC. Briefly, an IPTG and arabinose-induced 500 ml culture (kept for four hours at 30° C.), is spun at 4600×g for 20 minutes at 4° C., and the bacterial pellet resuspended in phosphate buffered saline (PBS) containing protease inhibitors (phenyl-methyl-sulfonyl fluoride and benzamidin). The solution is sonicated at 24° C. using an ultrasonic desintegrator (MSE Scientific Instruments), and the suspension centrifuged at 50,000×g for 30 minutes at 4° C. The supernatant fraction is incubated with TALON™ resin according to the instructions of the manufacturer (Clontech). After extensive washing, proteins are eluted using 100 mM imidazole. Following this procedure, scFv fragments are further purified by gel filtration using a Superdex 75 column (Amersham Pharmacia Biotech) connected to a Biologic instrument (Biorad). ScFv concentrations are quantitated using the bicinchoninic acid kit (Pierce). A fraction of the antibody mix is bound to a molar excess of biotinylated G protein in a 0.5 ml volume. The protein with bound scFvs is captured onto the surface of an excess of paramagnetic Streptavidin-coated beads (200 microliters of DYNAbeads, Dynal, Norway), in a way similar to what is described in Example 4 for phage selections. The supernatants of the mixture are then tested for the presence of scFv fragments in an SDS PAGE followed by Western blot analysis with the anti-tag antibodies to characterize the non-functional antibodies. The experiment provides evidence for the simultaneous production of three scFv fragments by the same host cell, and the efficient recovery of functional binding sites, thus correctly paired variable regions from this preparation.

Figure 15:
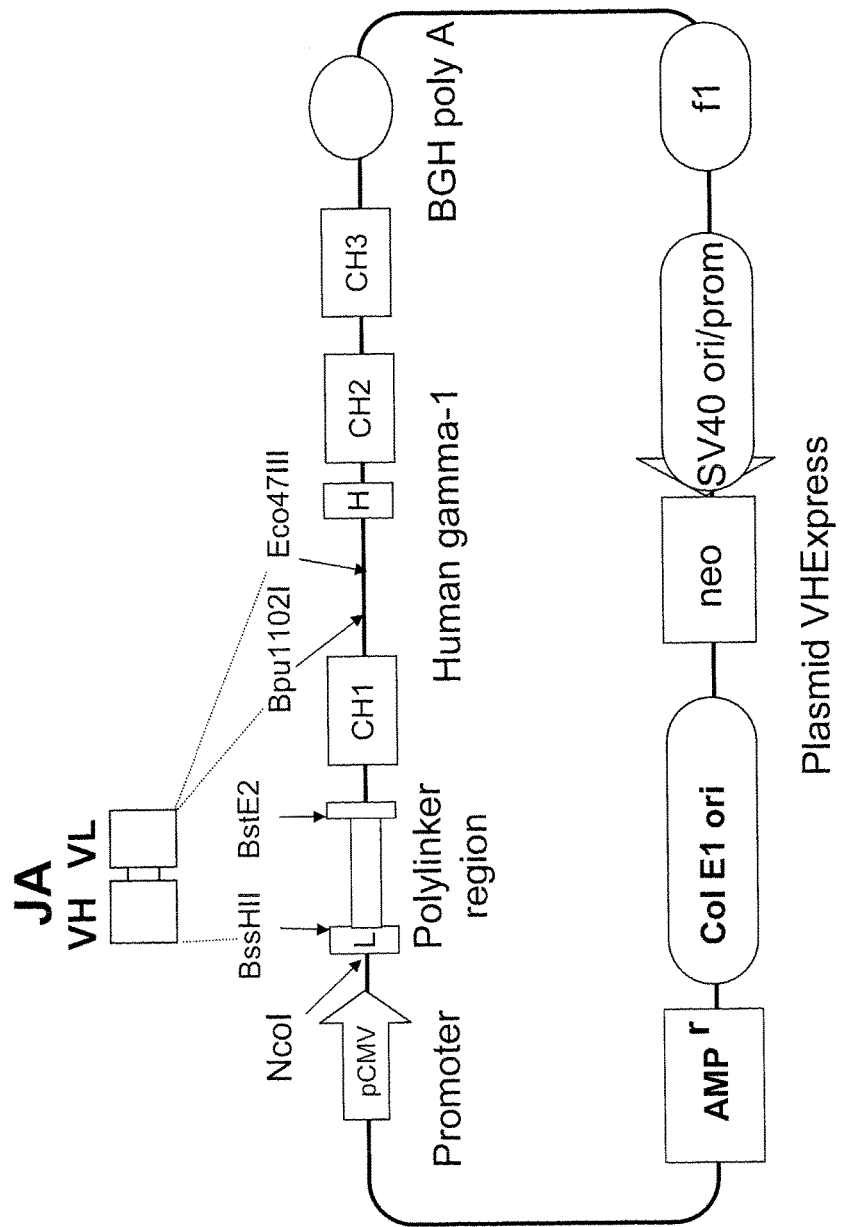
FIG. 15: Schematic depiction of the eukaryotic expression vector VHExpress as also described in (Persic et al. (1997) 187:9-18) except that this variant has a CMV promoter; its use for cloning scFv fragments (top, indicated for antibody JA) such that the expression of scFv-Fc fusions is achieved.

Example 3. Production of Mixtures of scFv-Fc Antibodies Based on Recloned Hybridoma-Derived Anti-Rabies Antibodies and Co-Expression in a Eukaryotic System This example describes the production of a mixture of three or six different proteins composed of variable regions paired to form two or three binding specificities. In a further example, the scFv genes are subcloned into a eukaryotic expression vector based on pCDNA3 which carries the human gamma-1 region. This plasmid, VHExpress, was extensively engineered to remove internal restriction enzyme sites (Persic et al. (1997) 187:9-18), and contains a promoter (CMV instead of EF-1alpha as in publication), a eukaryotic leader sequence, a polylinker with cloning sites for an antibody variable region, the human gamma-1 gene and the bovine growth hormone poly A site (FIG. 15). Further it contains the genes encoding amp and neo resistance, and the SV40 origin of replication. The full sequence is given in SEQ ID NO: 115. This vector is suitable for the expression of antibody variable region genes formatted as scFv fragments. The cloning of the scFv gene of antibody JA is carried out as follows. The scFv is used as a template in a PCR reaction with oligonucleotides 5'-TATC CGC GCG CAC TCC GAG GTG CAG CTG TTG GAG TCT GGG GG-3' (SEQ ID NO: 125) and the reverse complement of 5'-ACC CGG GTC ACC GTC TCC TCC GGT GAG TCC TAG CGC TTT TCG T-3' (SEQ ID NO: 126). The PCR fragment of approximately 750-800 bp is isolated, digested with BssHII and Eco47III and cloned into similarly cut plasmid VHExpress. Similarly, the scFv genes of antibodies JB and M57 are cloned into this plasmid; to avoid digestion at internal sites the other suitable site is used (Bpu1102I) or a three-way ligation which also yields the same plasmid. The resulting plasmids with correctly cloned scFv, called respectively pscFv-Fc-JA, pscFv-Fc-JB and pscFv-Fc-M57, are introduced into host cells, in this example PER. C6® cells.

For an initial analysis, these plasmids are transiently expressed either alone or in combinations of two or three scFv-Fc constructs. Cells grown to $5 \times 10^6$ cells/ml in culture medium with 10% Fetal calf serum (FCS) in 80 cm² flasks are transfected for four hours using lipofectamine (Invitrogen Life Technologies) according to the manufacturer's instructions (140 microliters Lipofectamine per 10 micrograms of DNA per flask) in serum-free medium at 37° C. After this incubation, cells are washed, resuspended in rich culture medium, and the cells grown for five days. The supernatant is harvested for analysis of the secreted scFv-Fc fusion protein. A sandwich ELISA is used to quantify the amount of IgG produced, using two antibodies directed to the Fc region. The scFv-Fc fusion proteins are purified using protein A affinity chromatography using a HighTrap column (Amersham Pharmacia) according to the manufacturer's instructions for IgG1), and the eluate concentrated via Microcon-YM30 concentrator (Amicon) and its buffer exchanged for PBS pH 7.0. The occurrence of different scFv-Fc mixtures, six in total for the cells transfected with the three scFv-Fc genes, are further characterized as described above in ELISA, and using viral isolates that are specifically recognized by the antibodies, including European bat virus 2 for antibody JB and Lagos bat virus and Mokoa virus for antibody JA, and strains CVS-11, CVS-24, PM, SHBRV and COSRV (Champion et al., *J. Immunol. Methods* (2000) 235:81-90). The presence of the M57 and JB binding sites is confirmed using an anti-Id antibody (see, also Examples 14 and 22). Following this, the viral neutralization activity of the mixture of three monospecific and three bispecific molecules (without purification) is assayed for the presence of rabies virus-neutralizing antibodies using the rapid fluorescent focus inhibition test (RFFIT) as described by Hooper et al., *ASM Pres, WA*, p. 1997. *Essentially, serial dilutions are made of the supernatant containing the antibody mixture in 96-well plates (Nunc), and a rabies virus dilution known to cause 70-80% infection of indicator cells added to each well. Controls are positive rabies-immune serum control samples and negative medium are also included. After one hour, to each well, 50,000 baby hamster kidney (BHK) cells are added and the culture incubated overnight at 37° C. Plates are then washed once with ice-cold PBS and the cells fixed with ice-cold 90% acetone for 20 minutes at −20° C. Acetone is removed and to the air-dried plates 50 microliters of FITC-labeled anti-rabies nucleoprotein monoclonal antibody (ab 1002 from abcam site or antibody from Centocor, Malvern) is added. After one hour incubation at 37° C., the plates are washed three times with water and analyzed under a fluorescence microscope. The activity of each of the scFv-components is studied by testing in this assay the neutralization of a variety of different rabies isolates, including the ones mentioned in Example 1.

The same plasmids, pscFv-Fc-JA, pscFv-Fc-JB and pscFv-Fc-M57, are also suitable for making stable transfectants. By selection using the neo-resistance gene and culturing and screening methods known to those in the art, stable PER. C6® derived cell lines expressing antibodies are obtained. Essentially $5 \times 10^6$ PER. C6® cells are transfected using Lipofectamine according to the manufacturer's instructions, and 3 micrograms of DNA per plasmid. Cells are transfected with the 3 micrograms of each plasmid separately, or with 1.5 micrograms each of pscFv-Fc-JA and pscFv-Fc-JB, or with 1.5 micrograms each of pscFv-Fc-JB and pscFv-Fc-M57, or with 1 microgram of each of pscFv-Fc-JA, pscFv-Fc-JB and pscFv-Fc-M57, or with a control LacZ vector. After five hours, the cells are washed and the medium is exchanged with non-selective medium. The next day the medium is replaced with fresh medium containing 500 micrograms/ml G418 (Sigma-Aldrich) and also every next two to three days, the culture medium is refreshed until clones appear (15 to 20 days after seeding). Clones are picked and cloned out to limiting dilution conditions, such that two to three weeks later, clonal cell lines start appearing. These are expanded to larger wells and flasks, and eventually the selective medium is omitted. The supernatant of these cell lines is harvested for analysis of the secreted scFv-Fc fusion protein. As before, a sandwich ELISA (as described in WO 00/63403) is used to quantify the amount of IgG produced, using two antibodies directed to the Fc region. The scFv-Fc fusion proteins are purified using protein A affinity chromatography using a HighTrap column (Amersham Pharmacia) according to the manufacturer's instructions for IgG1. Purified scFv-Ig from various clones is isolated, purified and tested in a series of assays. The first is to analyze the presence of the two or three different scFv genes of the cell lines created, by amplifying the genomic DNA of these cell lines with antibody JA/JB or M57 scFv or V-gene-specificoligonucleotides, and confirming the presence by sequencing the amplified material. The copy number of each of the integrated antibody constructs is determined with methods such as Southern blot or Fluorescent In Situ Hybridization (FISH). Second, the mixture is biochemically characterized using SDS-PAGE and iso-electric focusing. Alternatively, anti-idiotype antibodies or peptide mimitopes are used to delineate the compositions (see, Example 12). The stability of the expression level, of the ratios between the different scFv components, and of the composition of the antibody mixture produced by cell lines which produce the mix of three or six proteins is followed over time by these assays. Finally, binding and neutralization assays are carried out, including antigen binding in ELISA and in fluorescence microscopy with infected cells and tissues, and in the RFFIT virus neutralization assay as described above. The biological activity of the mixture is tested against a range of rabies isolates and the activity determined according to the international Units of Rabies Antibodies and referenced to WHO reference Rabies Immunoglobulin (WHO Technical Series Report (1994) vol 848, p. 8; and vol. 840). By testing the biological activity (virus neutralization) of a series of cell lines producing variable quantities of the three scFv-Fc fusions, the most optimal mixture is identified. The mixtures are compared to the activity of IMMOGAM® Rabies, the human immunoglobulin preparation used for passive immunotherapy (see, also www.aventispasteur.com/usa/product/pdffiles/!LE3439I.PDF). The effect of the bispecific component is tested by comparing the neutralization efficacy of the scFv-Fc protein mixture with the activity of comparable quantities of the (1) individual whole recombinant antibodies JA (IgG1), JB (IgG1) and M57 (IgG1), (2) mixtures of two or three of these antibodies. Due to the discrepancy observed sometimes between in vitro and in vivo neutralization data, besides in vitro neutralization tests, it may sometimes be necessary to carry out in vivo neutralization tests using mouse protection experiments as described in Dietzschold et al. (1992) *PNAS* 89:7252.

Figure 17A:
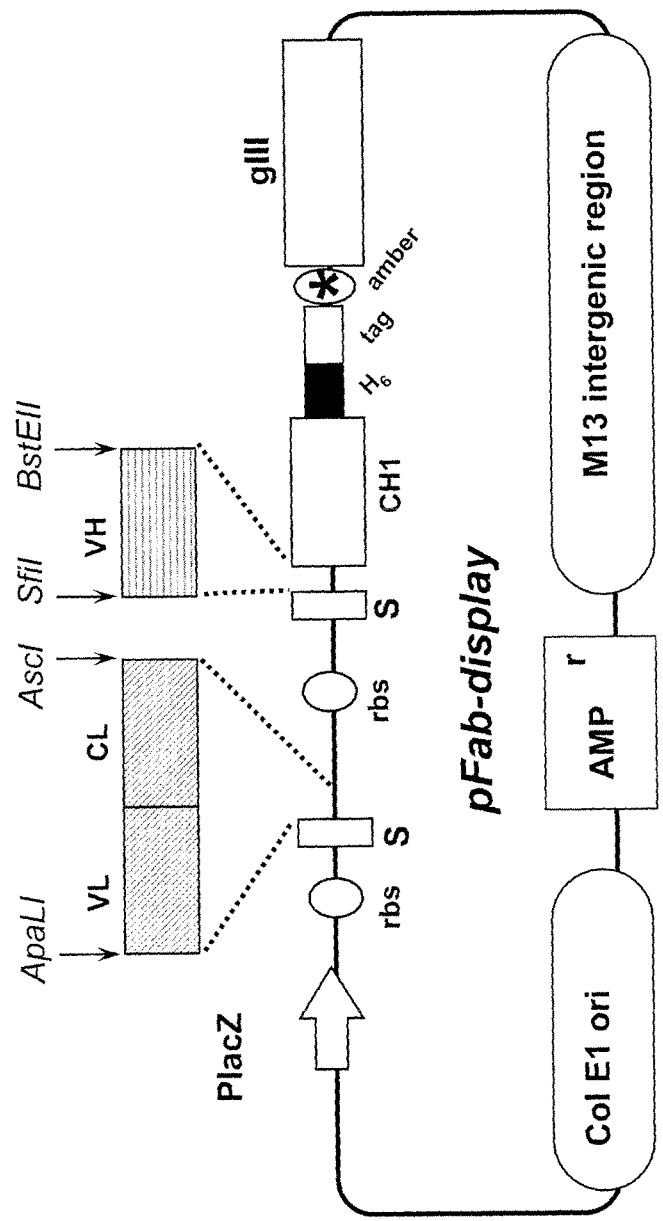
FIGS. 17A and 17B: pFAB-display: Schematic depiction of pFAb-display (top), and indication of cloning of VLCL and VH regions; the polylinker region (below). Legend as in FIG. 14.
Figure 17B:
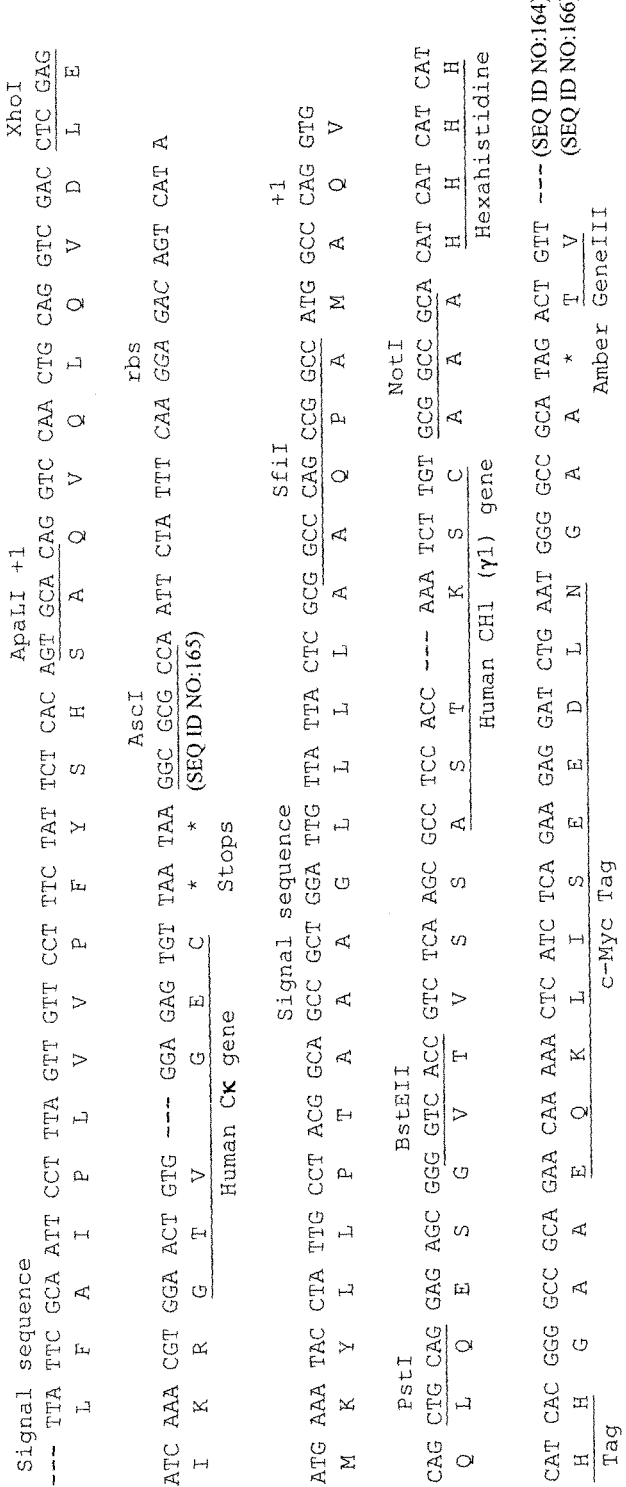
Figure 18B:
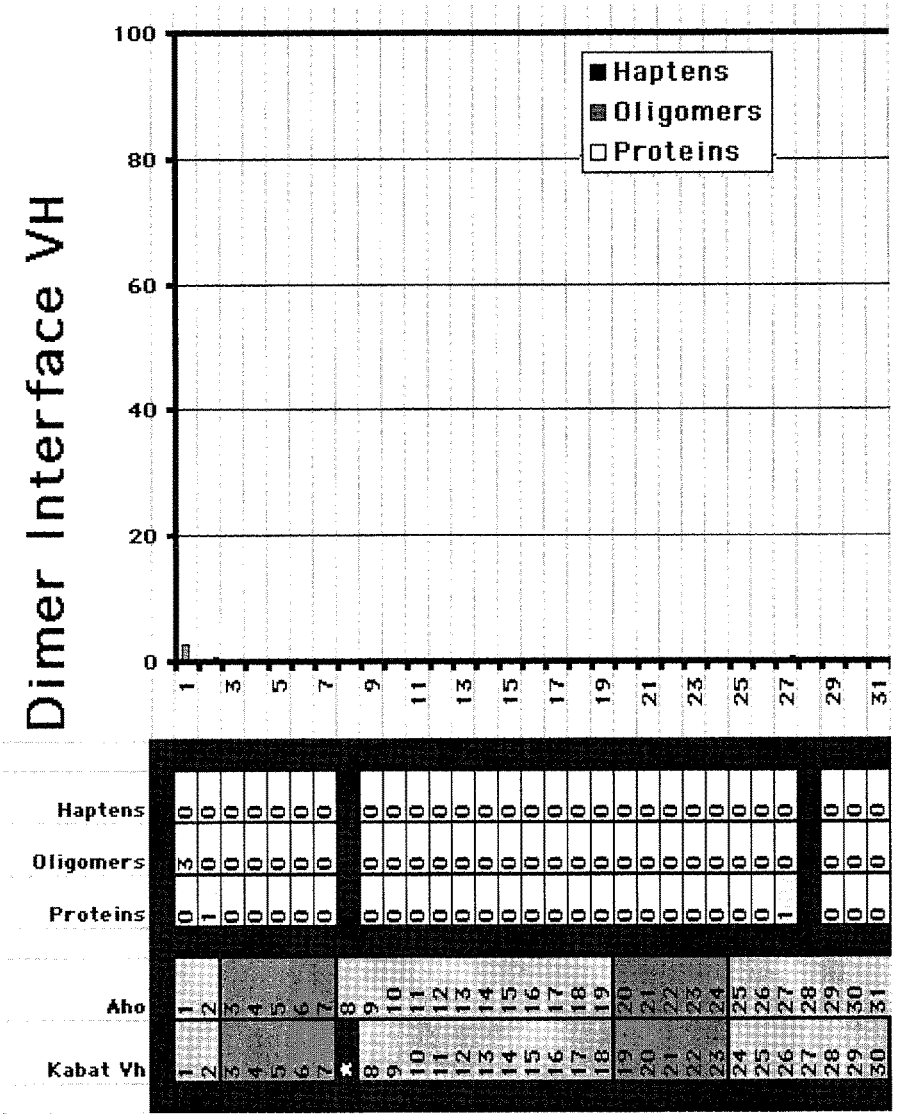
Figure 18C:
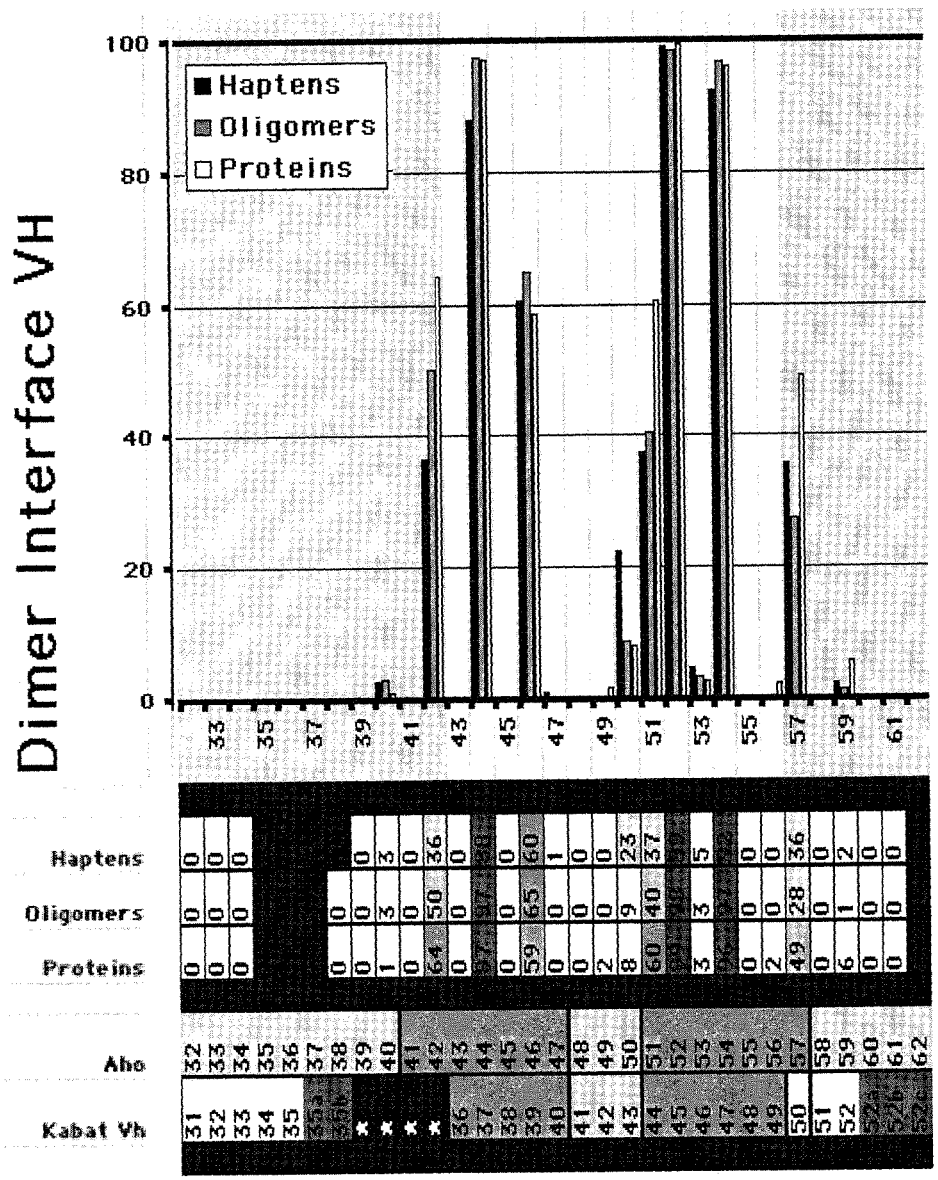
Figure 18D:
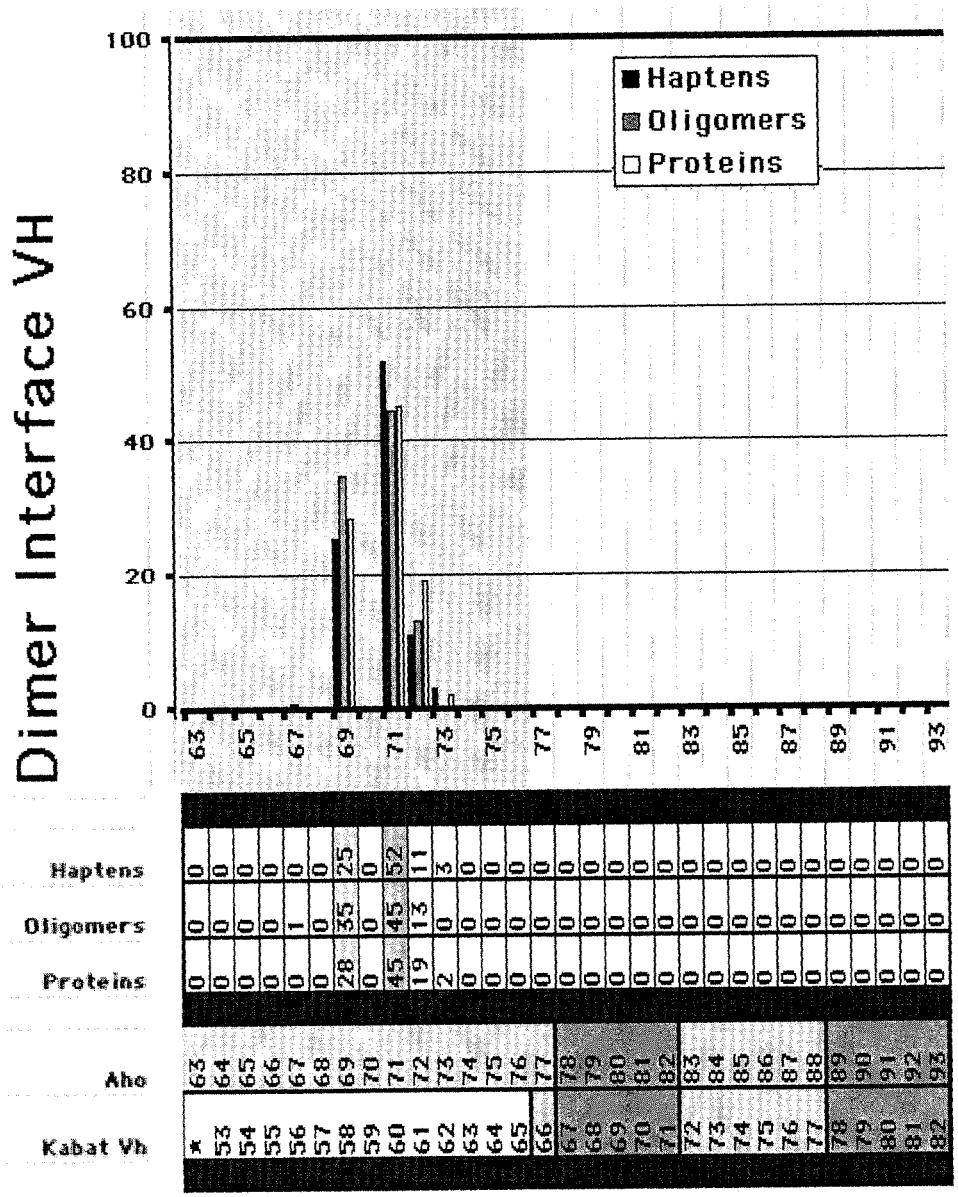
Figure 18E:
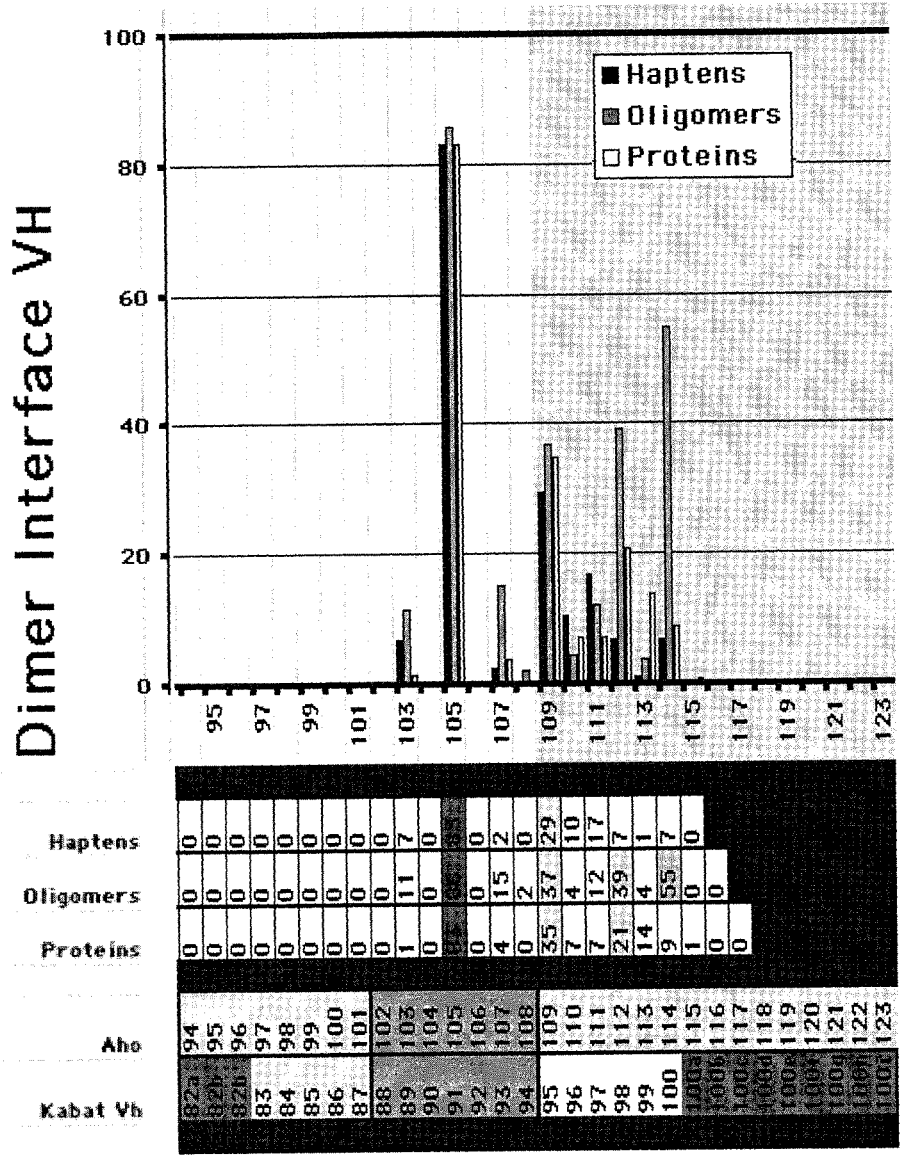
Figure 18F:
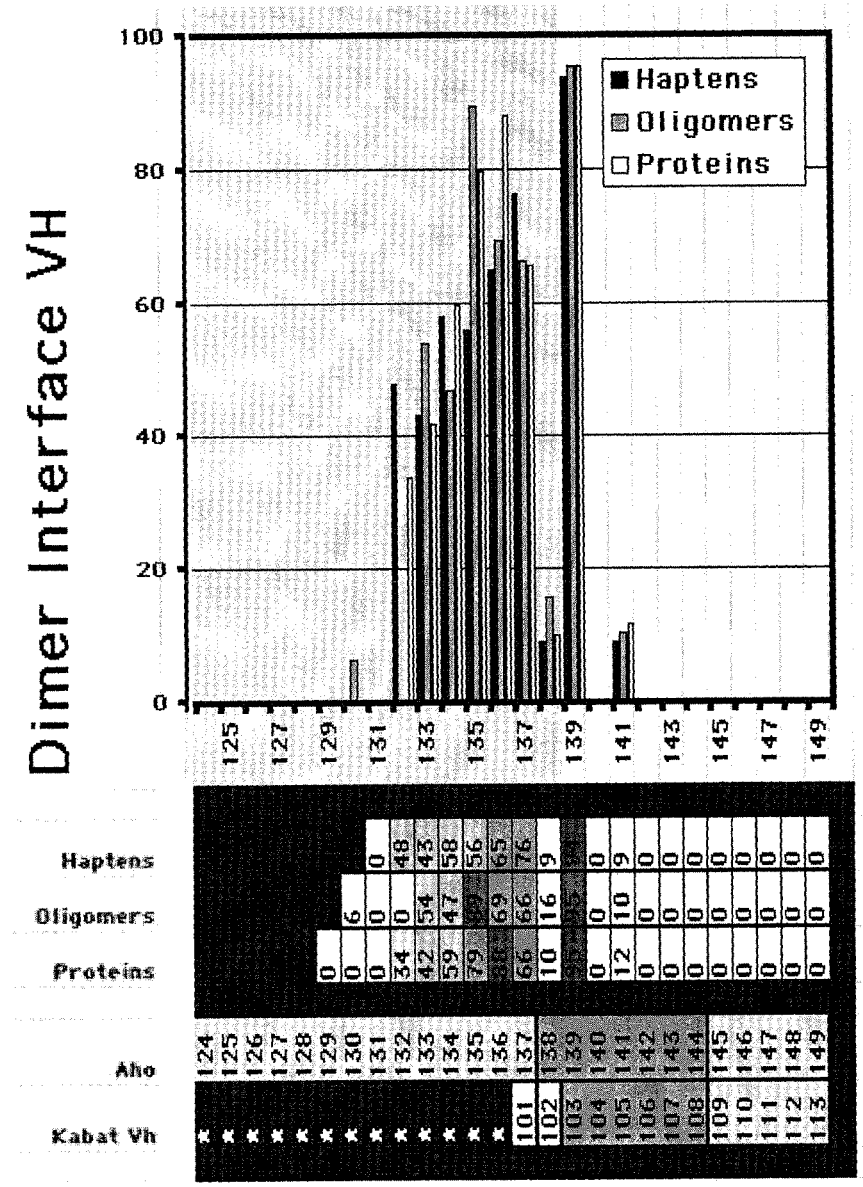

Example 4. Selection of Optimally Paired Variable Regions for Two Antibody Variable Region Pairs by Optimizing the Light Chain Variable Region Antibodies M57 and JB are used in this experiment. Both have a lambda light chain, of class I for JB and class II for M57, with homology between the two chains (FIG. 16). The antibody heavy chain variable region genes of these two antibodies are cloned into vector pFab-display, which resembles functionally pCES1 (H. J. de Haard et al. (1999) *J. Biol. Chem.* 274:18218-18230), and is a Fab fragment display and expression vector. In this vector system, the variable heavy chain region genes are cloned as VH-gene fragments; the vector supplies all Fabs with a human gamma-1 CH1 gene. The Fd fragment is fused to two tags for purification and detection: a histidine tail for Immobilized Metal Affinity Chromatography (IMAC) and a c-myc-derived tag, followed by an amber stop codon and the minor coat protein III of filamentous phage fd. The antibody light chain is cloned as full VLCL fragment, for directed secretion and assembly with the VHCH1 on the phage particle. Restriction enzyme sites and the sequence of the polylinker region is indicated in FIGS. 17A and 17B. The cloning of the variable regions is carried out similarly as described in Example 2, with oligonucleotides to amplify the VH region and that append appropriate restriction enzyme sites. The resulting plasmids are designated pVH-M57 and pVH-JB, respectively.

These plasmids are used as recipients for a collection of human lambda chains derived from human donors. B lymphocytes are isolated from 2-L of blood on a Ficoll-Pacque gradient. For RNA isolation, the cell pellet is immediately dissolved in 50 ml 8 M guanidinium thiocyanate/0.1 M 2-mercaptoethanol. Chromosomal DNA is sheared to completion by passing through a narrow syringe (1.2/0.5 mm gauge), and insoluble debris is removed by low speed centrifugation (15 minutes 2,934 xg at room temperature). RNA is pelleted by centrifugation through a CsCl-block gradient (12 ml supernatant on a layer of 3.5 ml 5.7 M CsCl/0.1 M EDTA; in total four tubes) during 20 hours at 125,000 xg at 20° C. in an SW41-rotor (Beckman). RNA is stored at −20° C. in ethanol. Random primed cDNA is prepared with 250 µg PBL RNA. RNA is heat denatured for five minutes at 65° C. in the presence of 20 µg random primer (Promega), subsequently buffer and DTT are added according to the suppliers instructions (Gibco-BRL), as well as 250 µM dNTP (Pharmacia), 800 U RNAsin (40 U/µl; Promega) and 2,000 U MMLV-RT (200 U/µl; Gibco-BRL) in a total volume of 500 µl. After two hours at 42° C., the incubation is stopped by a phenol/chloroform extraction; cDNA is precipitated and dissolved in 85 µl water. From this material, the variable region gene pools from the light chain lambda family are amplified using 4 Vλ-specific oligonucleotides that preferentially pair to the lambda I and II families (HuV11A/B/C-BACK and HuV12-BACK as in Table below) and with two primers based in the constant regions (HuCl2-FOR and HuC17-FOR as in the Table below, combined in each reaction), and with PCR in a volume of 50 µl, using AmpliTaq polymerase (Cetus) and 500 pM of each primer for 28 cycles (one minute at 94° C., one minute at 55° C. and two minutes at 72° C.). All products are purified from agarose gel with the QIAex-II extraction kit (Qiagen). As input for reamplification to introduce restriction sites, 100 to 200 ng purified DNA-fragment is used as template in a 100 µl reaction volume, using the oligonucleotides appropriately extended to provide the sites for cloning, ApaLI and AscI (last six primers of following Table). This amplified material is purified, digested with AscI and ApaLI and two samples cloned into the two different plasmids pVH-M57 and pVH-JB.

```
HuV11A-BACK
                                          (SEQ ID NO: 127)
5'-CAG TCT GTG CTG ACT CAG CCA CC-3'

HuV11B-BACK
                                          (SEQ ID NO: 128)
5'-CAG TCT GTG YTG ACG CAG CCG CC-3'

HuV11C-BACK
                                          (SEQ ID NO: 129)
5'-CAG TCT GTC GTG ACG CAG CCG CC-3'

HuV12-BACK
                                          (SEQ ID NO: 130)
5'-CAR TCT GCC CTG ACT CAG CCT-3'

HuC12-FOR
                                          (SEQ ID NO: 131)
5'-TGA ACA TTC TGT AGG GGC CAC TG-3'

HuC17-FOR
                                          (SEQ ID NO: 132)
5'-AGA GCA TTC TGC AGG GGC CAC TG-3'

HuV11A-BACK-APA
                                          (SEQ ID NO: 133)
5'-ACC GCC TC ACC AGT GCA CAG TCT GTG CTG ACT CAG
CCA CC-3'
```

-continued

HUV11B-BACK-APA
(SEQ ID NO: 134)
5'-ACC GCC TCC ACC AGT GCA CAG TCT GTG YTG ACG CAG

CCG CC-3'

HuV11C-BACK-A.PA
(SEQ ID NO: 135)
5'-ACC GCC TCC ACC AGT GCA CAG TCT GTC GTG ACG GAG

CCG CC-3'

HUV12-BACK-APA
(SEQ ID NO: 136)
5'-ACC GCC TCC ACC AGT GCA CAR TCT GCG CTG ACT CAG

CCT-3'

HuC12-FOR.ASC
(SEQ ID NO: 137)
5'-ACC GCC TCC ACC GGG CGC GCC TTA TTA TGA ACA TTC

TGT AGG GGC CAC TG-3'

HuC17-FOR-ASC
(SEQ ID NO: 138)
5-ACC GCC TCC ACC GGG CGC GCC TTA TTA AGA GCA TTC

TGC AGG GGC CAC TG-3'

This cloning results in two libraries designated as Fab-VH-M57-VLn and Fab-VH-JB-VLn.

Phage particles are made from cultures of these two libraries. The rescue of phagemid particles with helper phage M13-KO7 is performed according to (Marks et al. (1991), *J. Mol. Biol.* 222:581-597) on a 1-L scale, using representative numbers of bacteria from the library for inoculation, to ensure the presence of at least ten bacteria from each clone in the start inoculum. For selections, $10^{13}$ cfus (colony forming units) are used with 10 micrograms/ml Rabies glycoprotein coated in immunotubes (Maxisorp tubes, Nunc) or with 250 nM soluble biotinylated G protein. Antigen is biotinylated at a ratio of one to five molecules NHS-Biotin (Pierce) per molecule antigen according to the supplier's recommendations. Three rounds of selection are carried out with these libraries. Detailed protocols for culturing and selecting phage display libraries have been described elsewhere (as in Marks et al. (1991), *J. Mol. Biol.* 222:581-597) and are well known to those working in the art. Briefly, the selection with the biotinylated antigen is carried out as follows. Phage particles are incubated on a rotator wheel for one hour in 2% M-PBST (PBS supplied with 2% skimmed milk powder and 0.1% TWEEN®-20). Meanwhile, 100 μl Streptavidin-conjugated paramagnetic beads (Dynal, Oslo, Norway) are incubated on a rotator wheel for two hours in 2% M-PBST. Biotinylated antigen is added to the pre-incubated phage and incubated on a rotator wheel for 30 minutes. Next, beads are added and the mixture is left on the rotator wheel for 15 minutes. After 14 washes with 2% M-PBST and one wash with PBS, phage particles are eluted with 950 μl 0.1 M triethylamine for five minutes. The eluate is immediately neutralized by the addition of 0.5 ml Tris-HCl (pH 7.5) and is used for infection of long-phase *E. coli* TG1 cells. The TG1 cells are infected for 30 minutes at 37° C. and are plated on 2×TY (16 g Bacto-trypton, 10 g Yeast-extract and 5 g NaCl per liter) agar plates, containing 2% glucose and 100 μg/ml ampicillin. After overnight incubation at 30° C., the colonies are scraped from the plates and used for phage rescue as described (Marks et al. (1991), *J. Mol. Biol.* 222:581-597). Culture supernatants of individual selected clones harboring either rescued phage or soluble Fab fragments are tested in ELISA with directly coated antigen or indirectly captured biotinylated antigen via immobilized biotinylated BSA-streptavidin. Here described is the procedure with biotinylated antigen for the detection of soluble Fab fragments. For capture of biotinylated Rabies glycoprotein, first biotinylated BSA is coated at 2 μg/ml in PBS during one hour at 37° C. After three washes with PBS-0.1% (v/v) TWEEN®-20 (PBST), plates are incubated during one hour with streptavidin (10 μg/ml in PBS/0.5% gelatin) (24). Following washing as above, biotinylated antigen is added for an overnight incubation at 4° C. at a concentration of 3 μg/ml. The plates are blocked during 30 minutes at room temperature with 2% (w/v) semi-skimmed milk powder (Marvel) in PBS. The culture supernatant is transferred to these wells and diluted 1 or 5-fold in 2% (w/v) Marvel/PBS and incubated for two hours; bound Fab is detected with anti-myc antibody 9E10 (5 μg/ml) recognizing the myc-peptide tag at the carboxyterminus of the heavy Fd chain, and rabbit anti-mouse-HRP conjugate (DAKO). Following the last incubation, staining ms performed with tetramethylbenzidine (TMB) and $H_2O_2$ as substrate and stopped by adding half a volume of 2 N $H_2SO_4$ the optical density is measured at 450 nm. Clones giving a positive signal in ELISA (over 2× the background), are further analyzed by BstNI-fingerprinting of the PCR products obtained by amplification with the oligonucleotides M13-reverse and geneIII-forward (as in Marks et al. (1991), *J. Mol. Biol.* 222:581-597).

Large-scale induction of soluble Fab fragments from individual clones is performed on a 50 ml scale in 2×TY containing 100 μg/ml ampicillin and 2% glucose. After growth at 37° C. to an $OD_{600}$ of 0.9, the cells are pelleted (ten minutes at 2,934 xg) and resuspended in 2×TY with ampicillin and 1 mM IPTG. Bacteria are harvested after 3.5 hours growing at 30° C. by centrifugation (as before); periplasmic fractions are prepared by resuspending the cell pellet in 1 ml ice cold PBS. After 2 to 16 hours rotating head-over-head at 4° C., the spheroplasts are removed by two centrifugation steps: after spinning during ten minutes at 3,400 xg, the supernatant is clarified by an additional centrifugation step during ten minutes at 13,000 xg in an Eppendorf centrifuge. The periplasmic fraction obtained is directly used for determination of the affinity by surface plasmon resonance and of fine-specificity in western blot or virus neutralization studies.

Using the cited ELISA test, panels of antigen reactive Fabs are identified for both M57 and JB. The Fabs are purified and their relative affinity for the antigen compared to the native antibody as Fab determined. All clones that are in a ten-fold reach of the affinity are sequenced. For sequencing, plasmid DNA is prepared from 50 ml cultures grown at 30° C. in medium, containing 100 μg/ml ampicillin and 2% glucose, using the QIAGEN midi-kit (Qiagen). Sequencing is performed with the thermocycling kit (Amersham) with CY5-labeled primers CH1FOR (5'-GTC CTT GAC CAG GCA GCC CAG GGC-3' (SEQ ID NO:139)) and M13REV (5'-CAG GAA ACA GCT ATG AC-3' (SEQ ID NO:140)). The analysis is done as described above: the amino acid sequences of the two antibody VL sets, for M57 and JB, are compared to one another. Many of the selected variants are derived from the lambda 1 and lambda 2 family but carry somatic mutations throughout the sequence. In each collection, a set of 10 VLs are selected that are putative "common" candidates for pairing to both VHs, and these are cloned via the common restriction sites ApaLI and AscI into the plasmid carrying the other VH. Thus, the VLCL of a candidate clone of library Fab-VH-M57-VLn is isolated using gel-electrophoresis of the ApaLI-AscI digest and cloned into pVH-JB. This is carried out for all candidate VLs; the new combinations are all tested as before in ELISA for their pairing compatibility with the non-cognate VH. The clone with highest affinity in both antibodies is designated VL-M57=JB. This procedure leads to the identification of a lambda variable region light chain that in the Fab format can optimally pair with both the VH of JB and of M57.

Example 5. Selection of Optimally Paired Variable Regions for Two Antibody Variable Region Pairs by Optimizing the Heavy Chain Variable Region For occasions where the two light chains of two given antibodies are very different from one another, as is the case between antibodies of kappa and lambda families, it is also possible to follow an alternative strategy than the one described in Example 4. Herein described is the selection of an optimally paired VL that will be pairing in a compatible fashion with two VH variable regions. In the experiment, the major loop in the VH, the CDR3 that is both responsible for antigen binding and contributes to the interaction with the light chain, is diversified. Other schemes can be followed, in which other VH residues known to be structurally positioned at the VH-VL interface are mutated (exemplified in FIGS. 18A-18F). This procedure may also be applied to multiple variable region genes, using, for example, a chosen germ line encoded variable region gene and multiple partner variable regions which are then mutagenized and selected as in the following description.

The aim of the experiment is to find a JA-variant that will have optimally pairing behavior to VL-M57=JB. The JA antibody carries a kappa chain instead of a lambda (FIG. 16), and replacement of its cognate light chain with VL-M57-JB leads to a substantial loss of affinity. Therefore, it is the VH of this antibody that will be mutated, to compensate for loss of affinity with the antigen, and to provide also new potential interactions with the new VL. First, the VL-M57=JB is cloned as VLCL ApaLI-AscI fragment into pFab-display as described in Example 4; this yields plasmid pVL-M57=JB. The heavy chain of antibody JA is amplified from pVH-JA (Example 2) using two primers: 5'-GTC CTC GCA ACT GCG GCC CAG CCG GCC ATG GCA GAG GTG CAG CTG TTG GAG TCT GGG GG-3' (SEQ ID NO:141), and the reverse complement of the following sequence, which is a mutagenic oligonucleotide that is spiked with mutations in the two residues preceding the CDR3 and throughout the CDR3 region (in the underlined region; see also FIGS. 18A-18F):

```
                                      (SEQ ID NO: 142)
5'-C ACG GCC GTA TAT TAC TGT

GCG AAA GAT CGA GAG GTT ACT ATG ATA GTT GTA CTT

AAT GGA GGC TTT GAC TAC TGG GGC CAG GGA ACC CGGG

TCA CCG TCT CCT-3'.
```

The spiking is carried out by the inclusion during the oligonucleotide synthesis at the underlined residues, of mixes of 90% of the natural residue, and 10% of a mix with equimolar ratios of the four residues. The PCR is carried out as in Example 1 to yield a 350-400 bp fragment, which is gel-purified, digested with SiI and BstEII and cloned into pVL-M57=JB, to form a library of variants of JA, designated Fab-JA-YHmut.

This library is now rescued using helper phage and selections and screenings are carried out on Rabies glycoprotein according to the methods described in Example 4. The resulting Fab clones that maintain antigen binding contain a VH-JA variant that is pairing-compatible with VL-M57=JB. Candidate Fabs are produced and purified, and their affinity determined as described in Example 4. The variable heavy chain mutant of the highest affinity is designated VH-JA*.

Example 6. Isolation of Antibodies Against Rabies Glycoprotein from a Random Combinatorial Phage Library and Screening for Compatible VL Between Binding Clones Phage display libraries are a suitable source of antibodies. Libraries that are suitable for the assembly of the panels of antibodies include non-immune libraries (H. J. de Haard et al. (1999) *J. Biol. Chem.* 274:18218-18230), semi-synthetic libraries (de Kruif et al. (1995) *J. Mol. Biol.* 248:97, and Griffiths et al. (1994) *EMBO J.* 13:3245-3260) and also immune libraries, which often display a lower level of variable chain diversity. The first application presented is to select antibodies to one antigen only, providing a mixture of antibodies directed to the same antigen that can then be screened for pairing-compatible variable regions, and used to produce an antibody mixture. The second application concerns the selection of antibodies to two different antigens. Methods to carry out selections and screenings are well known in the art and are also described in Examples 4 and 5. Using selection on antigens, panels of antibody fragments specific for a given set of antigens are obtained. For each of the panels the sequence of VH and VL is determined. Thus, each antigen will have a set of reactive antibodies. It is then possible to identify by visual inspection in each of the panels those antibodies that share a given VL or have highly related VLs between the different sets. The cases described in Example 4 are also applicable here. In the best case each set has at least one antibody with an identical VL as at least one other antibody in the other sets. When this is not the case, a suitable VL that matches a given VH is found by the methods described in Example 4: the VH is paired with a repertoire of VLs, of which the composition is driven by the homology with a given VL or VLs. Alternatively, one VL is chosen and the non-matching VH is mutagenized as described in Example 5, to yield compatible pairs for all sets. The sequences are further inspected to find pairing-compatible variable regions that do not have sequence identity or homology. Variable heavy chains that pair with multiple variable light chains and vice versa are identified. Such “promiscuous” pairings imply that the variable region involved binds to the same antigen with any of several partner chains. To rapidly identify such variable regions, it is particularly useful to use semi-synthetic antibody libraries which have a limited number of positions which were diversified, as has been described for the human synthetic phage antibody library in Griffiths et al. (1994) *EMBO J.* 13:3245-3260.

In the first application, antibodies are selected against one antigen, the Rabies glycoprotein. The library described in Griffiths et al. (1994) *EMBO J.* 13:3245-3260, is selected on the Rabies glycoprotein antigen as described earlier. There are different sources of the antigen, including the material purified as in Dietzschold et al. (1996) *Laboratory Techniques in Rabies*, Eds Meslin, Kaplan and Korpowski, World Health Organization, Geneva, p. 175. Alternatively, a source of recombinant Rabies Glycoprotein (G) of the appropriate type is used for the coating. The sequence of rabies G is available to persons in the art and so are cloning, expression and purification techniques. A suitable format is to use an immuno-adhesion-type of molecules, in which the soluble part of the glycoprotein is genetically fused to an immunoglobulin Fc region, and the fusion protein expressed in eukaryotic cells (see, also Chamow and Ashkenazi, *Antibody Fusion Proteins,* 1999, Wiley-Liss, NY). For phage selection, the immuno-adhesion is biotinylated to be used in a selection as described in Example 4, or immobilized by coating. Alternatively, selections are carried out on immobilized (or biotinylated) Rabies virions, and selections are carried out each round on virions derived from different Rabies strains, to obtain a panel of antibodies that recognize the most common epitopes present in the different strains. These procedures yield a panel of antibodies directed to the Rabies antigen, but the compatibility of the pairing of variable regions of the individual candidates has to be tested.

Disclose herein are the use of the antibodies from the phage antibody library described by Griffiths et al. (1994) *EMBO J.* 13:3245-3260, but for the clones from other libraries the same principles apply. A panel of Fabs reactive with the Rabies glycoprotein is identified and the procedure to find optimally pairing VH and VL combinations as described above carried out. As an alternative, independent of sequencing, to identify optimally paired VH and VL pairs (that, for example, are missed in the sequencing analysis), the following empirical approach is followed. The variable light chains of a panel of 30 human antibodies are shuffled, and the new combinations tested in a binding assay. The shuffling is carried out by recloning the light chains present in the antigen reactive Fab clones which are based in the recombined fd-DOG-21ox-plasmid, as ApaLI-AscI fragment into the same Fab-containing phage genomes cut with the same (unique) enzymes. This is an experiment that is done in batch, with all 30 VL inserts and 30 VH-containing vectors mixed; sequencing is used to delineate the pairing of each VH-VL pair. ELISA is used to define which antibodies retain antigen binding activity and those clones are sequenced. The resulting combinations provide VH-VL which are pairing-compatible, the first class of which is formed by clones that share a VL or related VL; in that case one can be chosen plus the different VH genes for making OLIGOCLONICS® (see, Example 10). The second class contains clones with "promiscuous" pairing, and the VH genes of these are combined with the VH and VL pairs of those Fabs which are compatible with this tolerant VH.

The second application concerns the selection of phage antibodies on two different antigens, as indicated in FIG. 2. The same procedures as were just described for one antigen are followed, now to assemble two sets of antibodies, one for each antigen. The same procedures are followed also to identify clones with an identical or similar variable region sequence, or empirically, to demonstrate the existence of pairing-compatible antibodies between the two sets of antibodies.

Figure 3:
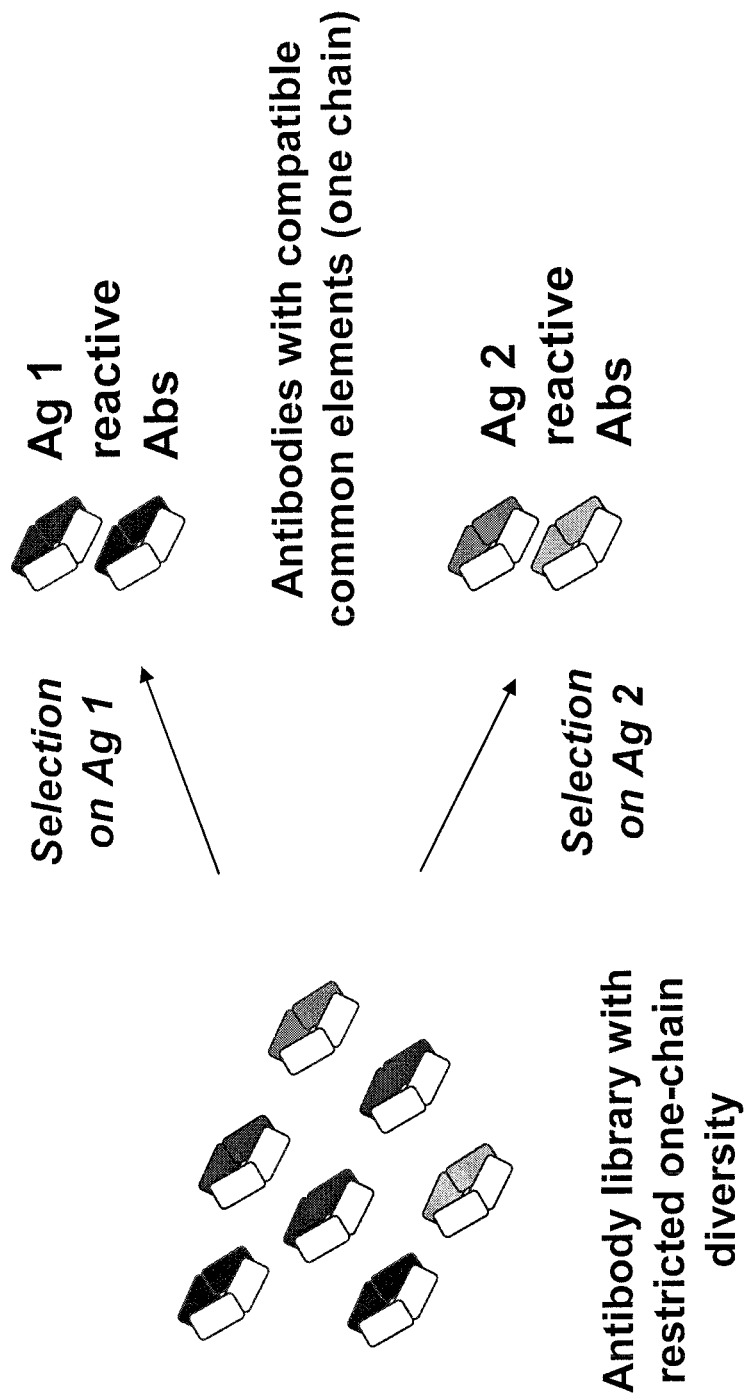
FIG. 3: Antibodies with similar light or heavy chain by selection from libraries with restricted diversity. In this example of a Fab library, one of the antibody chains is identical in all library members (the white chain), while the others contain amino acid diversity.

Example 7. Isolation of Antibodies Against Rabies Glycoprotein from a Phage Library with Limited Diversity and Screening Antibodies which are Non-Competitive Phage antibody scFv or Fab libraries that are formed by focusing the diversity in one variable region and keeping the other variable region invariable, for example a germ line sequence, are particularly relevant. From such libraries it is feasible to isolate antibodies with a different heavy chain yet identical light chain, or vice versa (FIG. 3). Such antibodies are readily reformatted into an OLIGOCLONICS® format. In the art, it has been described that antibodies that share the same VL gene but have different VH genes and widely varying specificities can be obtained from phage antibody display libraries (Nissim et al. (1994), *EMBO J.* 13:692-698).

A sub-library of the semi-synthetic scFv library (de Kruif et al. (1995) *J. Mol. Biol.* 248:97) is used in the following example. This sub-library contains antibodies with diversity in the VH region only. Selections on antigen are carried out as described in the previous examples. Using Rabies glycoprotein as the antigen as described in Example 6, ten human antibodies with different VH yet identical VL are identified. These are immediately suitable for inclusion into OLIGOCLONICS® (Example 10). In some instances it will be favorable to identify those antibodies that recognize different epitopes from the other antibodies in the mixture, and/or to obtain antibodies that recognize the same epitope recognized by a given monoclonal and polyclonal antibody. The competitive nature of the selected ten scFv antibodies with the Rabies monoclonal antibody M57 is determined in ELISA, using the set-up described in Example 2 (essentially, with bound antigen, adding sample, and detecting using an HRP-labeled anti-c-myc antibody) in the presence or absence of the M57 antibody. Competition experiments between the clones are readily performed using similar competition ELISAs with the phage-scFv particles and the soluble scFv fragments. Besides this procedure to screen clones for a particular competition-behavior, it is also possible to influence the selection outcome, either by using an antibody to block a site on the antigen during the selection (preventing antibodies to or competing with this epitope from being selected), or by using an antibody to competitively elute the fraction of phage antibodies that is bound to the same epitope. Examples of both are known in the art and methods are applicable here also to define suitable antibody combinations for inclusion in the OLIGOCLONICS® composition.

Example 8. Isolation of Single-Domain Antibodies Against Rabies Glycoprotein from a VL Phage Library, and Pairing with a Suitable Variable Region Antibodies made in two steps are also suitable for the inclusion in the OLIGOCLONICS® format and to make antibody mixtures. Rabies-specific single domain VL antibody fragments are selected from a phage displayed repertoire isolated from human PBLs and diversified by DNA-shuffling, as described in van den Beucken et al. (2001), *J. Mol. Biol.* 591-601 (libraries B and C). Selection and screening experiments are done as described in the previous examples. After the third round of selection, the pool of VLs is taken for combination with one VH segment (as depicted in FIG. 4, column (e)). For this, the VL pool is recloned by PCR as an ApaLI-XhoII fragment into pFab-display (FIGS. 17A and 17B) into which is cloned a single human VH. The latter is a DP-47 germ line encoded variable region with short CDR3 sequence designated VH-N(SEQ ID NO: 116), which is obtained by providing via PCR antibody clone FITC-B11 from Table IV in Griffiths et al. (1994) *EMBO J.* 13:3245.3260, with a short, five-residue CDR3 of amino acid sequence GGAVY (SEQ ID NO: 143), and cloning this as SfiI-BstEII fragment into pFab-display. This CDR3 is found in many different antibodies, and a short sequence with minimal length side chains (except for the tyrosine) is chosen to minimize effects on antigen binding and pairing. The resulting mini-library is screened for those antibody Fab fragments that maintain antigen binding. The three best Rabies glycoprotein-specific VL genes are designated VL-G1, G2 and G3. Similarly, the principles of this approach are applicable to building antigen-specific heavy chain fragments based on the VH domain, and providing these with a "neutral" VL, or even "neutral" partner VH.

Example 9. Selection of Antibodies with Pairing-Compatible Variable Regions by Intracellular Competition, and Expression of a Composition of Two or Three Fab Fragments with Pairing-Compatible Variable Regions Selections with phage libraries are carried out using monoclonal antibodies as competitors during the formation of new phage particles. The selection biases the library selection towards variable region pairs with compatible pairing in the context of multiple variable regions being expressed in the same host cell. The system relies on the simultaneous expression of two or more Fab fragments, the variable region of one of which is anchored onto a phage coat protein (FIG. 5).

First, the variable region genes of antibody M57 are cloned into pFab-Sol-pbr, a derivative of pFab-display (FIGS. 17A and 17B) with the same polylinker, but no gIII, no M13 intergenic region and instead of pUC119 the pBR322 backbone carrying the ampicillin resistance gene. The variable region genes of antibody JB are cloned in pFab-Sol-ACY-cat, similar in set-up as the previous one but carrying the Chloramphenicol resistance gene and based on the pACYC backbone. Both plasmids mediate the expression of the soluble non-tagged Fab fragment under control of the lacZ promoter, and they are compatible with one another and can be maintained in the same cell with antibiotic selection. Methods for the cloning have been described earlier; the sequences of these antibodies are also included in the sequence listings below, thus it will be possible for someone working in the art to clone these Fabs into these polylinkers such that upon induction with IPTG, both antibodies are expressed in the periplasm of the culture. These two antibody Fab fragments form the competitors in this method. *E. coli* TG1 cells harboring both plasmids are infected with phage harboring a library of human Fab fragments, in which the heavy chain is anchored to the phage coat and the light chain is provided as a soluble, non-anchored chain. The fd-based library from Griffiths et al. (1994) *EMBO J.* 13:3245-3260, which contains both VH and VL diversity is used for infection, the resulting bacteria start producing new phage particles and incorporate the L and Fd chains expressed from this genome. Cells are grown to an OD of 1.0, the cells washed to remove produced phage, and the cells incubated for four hours in 1 mM IPTG. During this time, competition will occur for pairing between the three variable heavy and light chains, and there are many opportunities for mispairing. The phage produced during this induction time will only recognize the native antigen, if the VH is tolerant to pair with any VL yet bind antigen, or when it exclusively pairs with the VL that is also encoded in the genome. The phage is harvested, PEG precipitated, dissolved in PBS, and is now selected for binding to Rabies glycoprotein. Methods for selection have been described earlier. In both case the phage will be able to bind antigen, and be enriched in a selection round with antigen. The phage resulting from the selection is used to infect cells harboring the two Fab-containing plasmids, and the cycle of induction, phage preparation and selection is repeated. After five rounds of this selection, the resulting Fab proteins are tested for antigen binding in a solid phage ELISA and recloned into the soluble expression vectors pFab-Sol-ACY-cata and pFab-Sol-pbr. *E. colis* are transfected with one of these plasmids and either the M57-containing vector or the JB-containing vector described above, or no additional vector. These cultures are induced with IPTG (inducing expression of one or two Fab fragments), and the resulting Fab fragments and Fab mixes analyzed for antigen binding in ELISA. To confirm exclusive or tolerant pairing, the Fab fragments are purified using IMAC and tested in a capture assay with antigen as described in Example 2. The selected variable region pair can be further used to build an OLIGOCLONICS® mixture with either M57 or JB variable region genes (but not together), as in Example 10.

For making a mix of these three antibodies, the experiment is repeated using the VL-M57=JB from Example 4 instead of the two original light chains VL-M57 and VL-JB. The result of the selection is a small number of Rabies antigen-specific VH-VL pairs derived from the phage library. The best candidate according to affinity, with designated variable regions VH-PO1 and VL-PO1, is further tested as above to confirm that it is pairing-compatible with the VH-57, the VH-JB and the VL-M57=JB. Next, the following expression cassettes are introduced in the same *E. coli* host cell using the two plasmids described earlier for producing the competing Fab, using cloning methods familiar to those working in the art: in cassette (1), on one plasmid, the VL-M57=JB-CL and VH-CH1 of M57; in cassette (2), the VL-M57=JB and VH-CH1 of JB (a second copy is provided to obtain an excess of light chain for pairing with the two heavy chains); and in cassette (3), on the other plasmid, the VL-PO1-CL and VH-PO1-CH1. Induction with IPTG leads to the production of a mixture of Fab fragments with paired variable regions, which is then recovered using IMAC purification. Alternatively, protein G purification is used. Using the binding and other assays described in the earlier examples for Rabies glycoprotein antibodies, the mixture is characterized. The contents of the mixture is dependent on the growth and induction conditions of the bacteria and the primary amino acid sequences of the Fab genes.

Example 10. Methods for Production of OLIGOCLONICS® in Eukaryotic Cells

Figure 19:
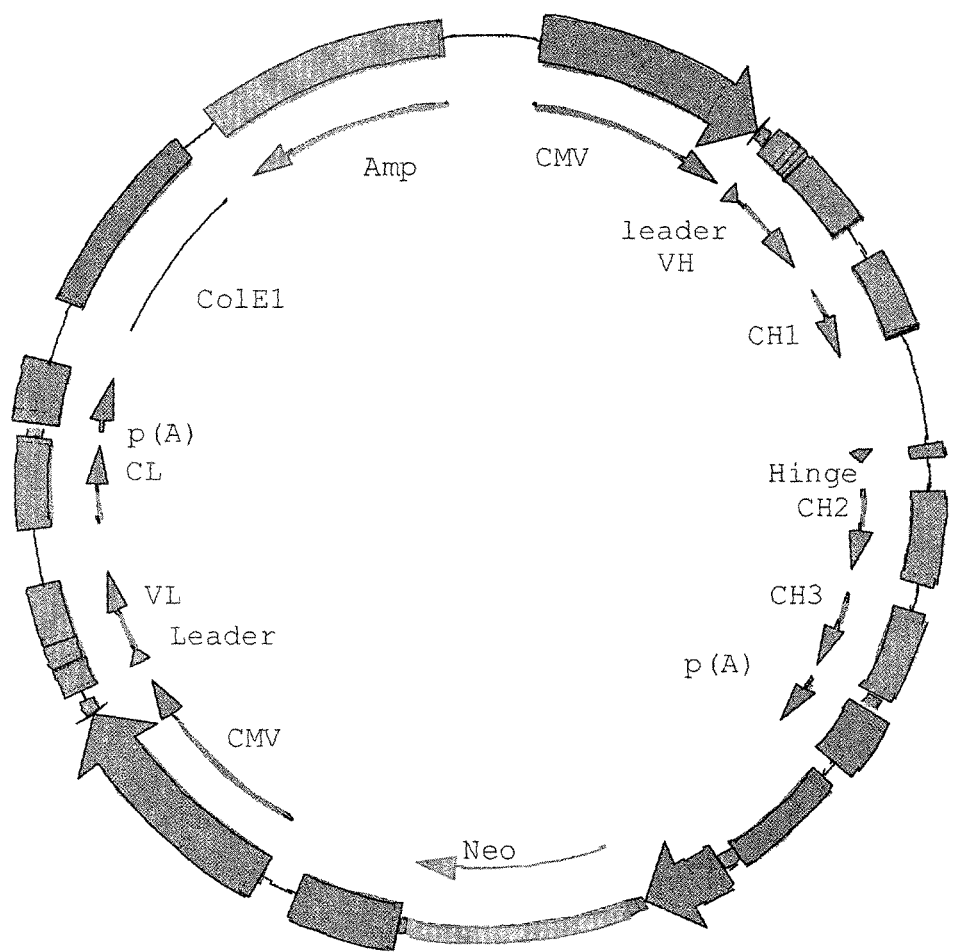
FIG. 19: Outline of an expression vector for human monoclonal antibodies in eukaryotic cells. CMV: CMV promoter; p(A): polyadenylation signal; Neo: neomycin resistance gene; Amp: ampicillin resistance gene.

A method for producing a mixture of antibodies in eukaryotic cells using expression in a recombinant host cell of multiple VH and VL genes resulting in the production of VH and VL proteins capable of pairing to form functional bivalent and bispecific antibodies, named OLIGOCLONICS®, is exemplified herein. The general format of a eukaryotic expression vector for human monoclonal antibodies is shown in FIG. 19.

The VH and VL regions of human monoclonal antibodies specific for rabies virus obtained by any of the methods described in the previous examples, can be inserted into an eukaryotic expression vector containing the HATV20 leader sequence and all the coding sequences of the constant regions of human immunoglobulin heavy (for example, IgG1) and light chains (for example, a kappa light chain) essentially as described (E. Boel et al. (2000), *J. Immunol. Methods,* 239:153-166). In this example, the following variable region genes optimized for pairing are used: VH-M57, VH-JB (non-modified variable region genes, from Example 2), VH-JA* (the optimized sequence of the VH of antibody JA, from Example 5), and only one light chain, VL=M57=JB (from Example 4). The resulting plasmids encoding heavy and light chains are transfected into eukaryotic cells such as the human cell line PER. C6® and in Chinese Hamster Ovary (CHO) to generate stable cell lines secreting antibodies. For this, published methods and methods known to persons skilled in the art are used (E. Boel et al. (2000), *J. Immunol. Methods*, 239:153-166 and WO 00/63403). For the generation of stable PER. C6® cells secreting antibodies, PER. C6® cells are seeded in DMEM plus 10% FCS and in tissue culture dishes (10 cm in diameter) or T80 flasks with approximately $2.5 \times 10^6$ cell per dish or flask and kept overnight in an incubator at 37° C. and 10% $CO_2$. The next day, transfections are preformed in separate dishes at 37° C. using Lipofectamine (Invitrogen Life Technologies) according to standard protocols provided by the manufacturer. The plasmids encoding the monoclonal antibodies can be mixed in various ratios and used at a concentration of 1-10 µg/ml. As controls, cells are subjected to the transfection procedure in the absence of plasmids.

After four to five hours, cells are washed twice with DMEM and fed with fresh culture medium. The next day, the culture medium is removed and cells are fed with fresh medium containing 500 µg/ml of the antibiotic G418. Cells are fed every two or three days with culture medium containing 500 µg/ml of G418. After about 20 to 22 days after initiation of the experiment, a large number of colonies is visible and from each transfection, 300 clones are picked and grown individually in 96-well plates and further expanded in 24-well, 6-well and T25 flasks. At this stage, cells are frozen in liquid nitrogen and production levels of recombinant immunoglobulin are determined in an ELISA according to standard procedures (e.g., E. Boel et al. (2000), *J. Immunol. Methods*, 239:153-166 and WO 00/63403). At this stage of the culture procedure, G418 is no longer added to the culture medium.

To establish the presence of anti-rabies antibodies in a mixture, a solid phase anti-rabies ELISA is performed. For the rabies virus ELISA, rabies virus glycoprotein is purified according to standard procedures (Dietzschold et al., in F.-X. Meslin et al. eds., *Laboratory techniques in Rabies*, World Health Organization, Geneva, page 175). Plates (Poly-Sorb™, Nunc) are coated with 5 µg/ml of glycoprotein diluted in PBS and 150 µl/well. The plates are then blocked with 5% powdered milk in PBS and washed in PBS containing 0.05% TWEEN®-20 (PBS-TWEEN®) prior to the addition of supernatant samples. Following incubation at room temperature for two hours, the plates are washed with PBS-TWEEN® to remove unbound antibody present in the supernatant samples. Enzyme-conjugated or biotinylated secondary antibodies specific for various human heavy chain isotypes are added for one hour at room temperature and the plates are subsequently washed with PBS-TWEEN®. Detection of secondary antibody is performed according to standard procedures (e.g., J. M. Champion et al. (2000), *J. Immunol. Methods* 235:81-90); see also previous examples. Other analysis methods are described in Examples 3, 4 and 12.

Next, it is demonstrated that a clonal cell line accounts for the production of each of the binding specificities encoded by the plasmids, i.e., proving that a single cell is able to produce a mixture of multiple anti-rabies antibodies. For a limited number of colonies that secrete a mixture of all monoclonal antibodies, 30 clones selected from the initial panel of approximately 300, clonality is further established by subcloning under limiting dilution known to persons skilled in the art. Picked and expanded colonies are seeded in a 96-well plate at a concentration of 0.3 cells/well in DMEM with 10% FCS and expanded. Colonies of cells are processed as described above and are referred to as subclones. Subclones are screened by PCR on genomic DNA for the presence or absence of each of the three constructs. Further confirmation of the presence of the constructs is obtained by nucleotide sequence analysis of the PCR products.

For a representative number of subclones, larger volumes are cultured to purify the recombinant human IgG1 fraction from the conditioned supernatant using Protein A affinity chromatography according to standard procedures. Purified human Ig from the various subclones is subsequently analyzed by SDS-PAGE, Iso-electric focusing (IEF) according to standard protocols (see, also, Examples 3 and 12).

Subclones that are shown to harbor the relevant plasmids are brought into culture for an extensive period of time to determine whether the presence of the plasmids is stable and whether expression of the antibody mixture remains the same, not only in terms of expression levels, but, in particular, the ratio between the various antibodies that are secreted from the cell. Therefore, the subclone culture is maintained for at least 25 population doubling times. At every four to six population doublings, a specific production test is performed using the human Ig-specificELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human Ig fraction as described. Purified human Ig obtained at the various population doublings is subsequently analyzed as described, i.e., by SDS-PAGE, Iso-electric focusing (IEF) and binding in the inhibition ELISA.

Example 11. Method for Selecting Antigen-Specificproteinaceous Compounds Using Mixtures of Encoding DNA The basis for the mixtures of antibodies present in OLIGOCLONICS® are immunoglobulin variable regions that encode human monoclonal antibodies that have been selected for their specificity, contain variable region genes with compatible pairing behavior and are thus compatible with the OLIGOCLONICS® format. For example, antibodies that are encoded by different VH genes and bind to different epitopes but share the same VL gene are suitable for the OLIGOCLONICS® format. Example 7 describes how such antibodies are obtained.

In this Example, methods using eukaryotic expression systems to obtain human monoclonal antibodies with desired specificities and that share the same VL gene are described. Such "repertoires" of human VH genes are PCR-amplified from the B lymphocytes of human individuals and typically harbor $10^8$ to $10^{10}$ members. The method is known to persons skilled in the art and has been described many times in the literature; the amplification of antibody genes is also exemplified for human V-lambda libraries in Example 4. The source of B lymphocytes may be any lymphoid organ including blood, bone marrow, tonsil, spleen, lymph node, etc. The individual may be pre-selected because it is expected that B lymphocytes producing the antibodies of interest are enriched in those individuals because of, e.g., a prior infection with a micro-organism or because of a prior immunization, or may be randomly picked. The VH genes may be used unaltered in their coding region or may be altered, particularly in the CDR3 region to introduce novel specificities. Such VH genes are known in the art as synthetic or semi-synthetic VH regions. In certain embodiments, primers are used that selectively amplify members of a few VH gene families such as the large VH3 and VH4 gene families. Primers that amplify members of more VH gene families may also be used in procedures known by persons skilled in the art.

Amplified VH regions are cloned into the eukaryotic expression vector for human monoclonal antibodies as described in Example 10 and subsequently introduced into eukaryotic cells such as CHO cells or PER. C6® cells. The expression plasmid shown in Example 10 that harbors a VL gene is used (FIG. 7). There are two alternatives: (1) the VL gene is co-transfected with the VH genes on a separate plasmid or (2) an approach particularly suitable when only one VL needs to be expressed the eukaryotic cells are already transfected with a human VL gene that is stably expressed. The eukaryotic cells are transfected with the repertoire of human VH genes cloned into the eukaryotic expression vector for human antibodies. High plasmid DNA concentrations are used to transfect the eukaryotic cells in order to introduce multiple copies of VH genes into a single cell. As a result a single cell will produce multiple antibodies, e.g., between 10 to 1000 different human antibodies. In the first approach, transfections are transient. In brief for PER. C6® cells, an 80 cm$^2$ tissue culture flask with cells is transfected by incubation for four hours with 140 µl lipofectamine+10 to 1000 µg plasmid DNA in serum-free DMEM medium. After four hours, the medium is replaced with DMEM+10% FCS, and the cells are grown overnight at 37° C. Cells are then washed with PBS and the medium is replaced with Excell 525 medium (JRH Bioscience). The cells are seeded at a concentration that results in the outgrowth of approximately 100 transfected cells/well of a 96-well culture plate. After five to six days, the cell culture supernatant is harvested and assayed for the presence of specific antibody by solid phase ELISA. The cells that correspond to the supernatants that score positive in ELISA are harvested and the VH genes are amplified by PCR. Subsequently, the amplified VH genes are cloned into the eukaryotic expression vector for human monoclonal antibodies, described in Example 10. Thus, a restricted repertoire of human VH genes is obtained. In this example, 100 cells that each harbors 100 VH genes yield a maximum of 10$^4$ VH genes. This repertoire is transiently transfected into PER. C6® cells that harbor the same VL gene using low plasmid DNA concentrations (0.1 to 1 µg/ml) such that on average a single cell harbors a single VH gene and transfected cells are plated out under conditions such that only approximately ten cells/well will grow out. After five to six days, supernatants are screened in ELISA for specific antibodies and the cells corresponding to positive supernatants are harvested and used for PCR amplification of the VH genes. In this example, the maximum number of VH genes obtained is approximately ten. Each VH gene is separately transfected into PER. C6® cells and the VH gene encoding the desired antibody specificity is identified by screening the supernatants of clones in ELISA.

In a second approach, the initial library of 10$^8$ to 10$^{10}$ VH genes cloned together with a single VL gene into the plasmid described in Example 10, is transfected into PER. C6® cells and plated out in T80 cell culture flasks. After four to six days, the cells are harvested and mixed with red blood cells coated with the antigen of interest and individual cells are monitored for the secretion of specific antibodies against the coated antigen by the reverse hemolytic plaque assay, well-known in the art (e.g., F. Dammacco et al. (1984) *Clin. Exp. Immunol.* 57:743-51). B lymphocytes inducing plaques are visualized under a light microscope and picked with a micromanipulator. The single transfected PER. C6® cell is transferred to an Eppendorf tube, lysed and subjected to single cell PCR to amplify the VH genes. The advantage of this approach is that only a few rounds of selection are needed to identify the VH gene of interest.

In a third approach, stable transfectants are used. After the transfection as described above, large collections of clones are grown essentially as described in Example 10, with the exception that clones are not plated out under limiting dilution conditions. Instead, the cells after transfection are plated in microtiter plates such that after growth in the selective medium multiple clones per well arise (e.g., 100 cell clones per well as indicated in FIG. 7). Each clone expresses multiple species of heavy chains, and each well contains multiple clones. The supernatant of these cultures are tested for antigen binding and the VH-genes are further enriched in cycles of PCR, cloning, transfection and screening, as described above.

Figure 22:
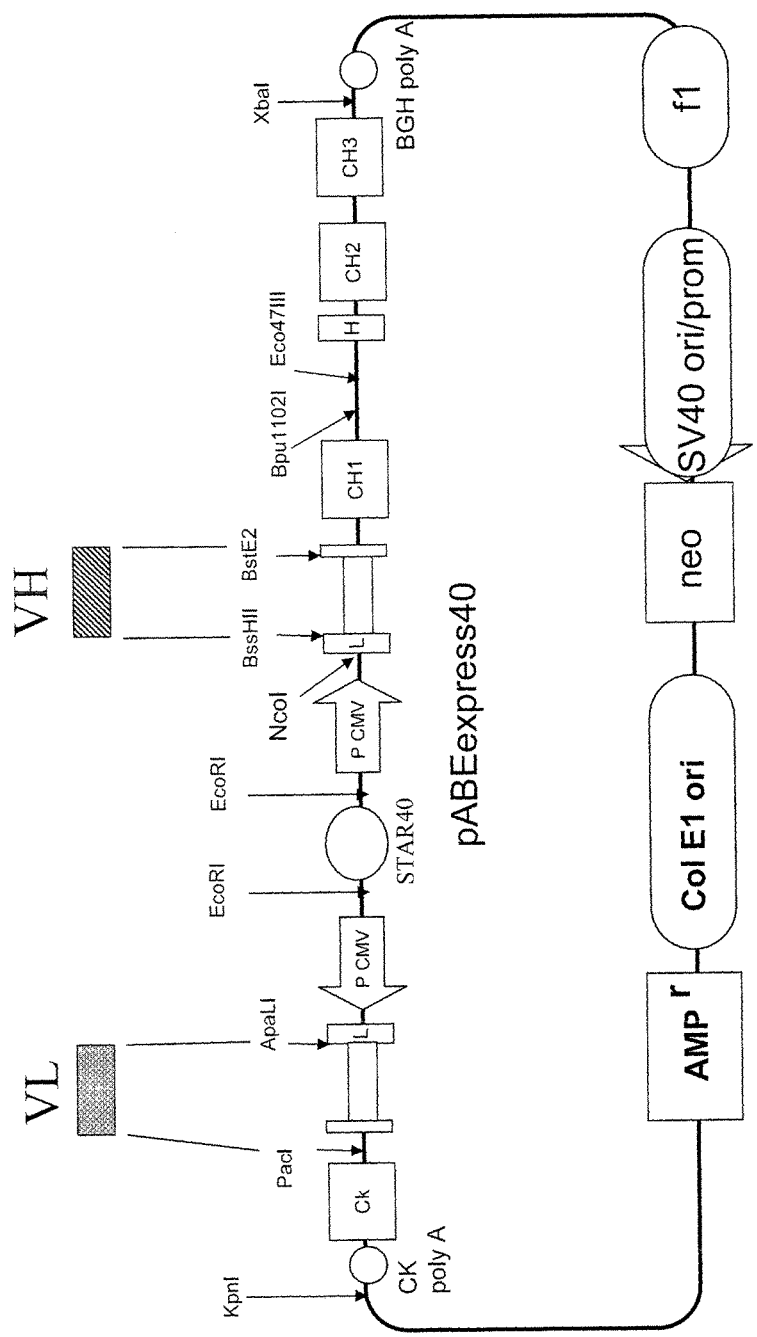
FIG. 22: Plasmid pABExpress40 for expression of libraries of pairing-compatible antibodies in mammalian cells. Cloning sites for directional insertion of antibody variable region genes are indicated. See Example 11 for details. Without the STAR40 insertion into the EcoRI site, this plasmid is called pABExpress.

The expression of multiple antibodies by a single transfected eukaryotic cell is improved in all of these approaches by introducing anti-repressor DNA elements in the plasmid constructs for the expression of human monoclonal antibodies. Anti-repressor elements confer high level and stable expression of proteins in mammalian cells in a copy number-dependent fashion (Kwaks et al. (2003), *Nat. Biotechnol.* 21:553-558). The DNA fragments responsible for this effect are amplified from the clones described in this citation and introduced upstream of the heavy chain expression cassette. The human anti-repressor element nr. 40 (SEQ ID NO: 117) is amplified from the pSDH vector containing the element (described in Kwaks et al.), using flanking oligonucleotides that also incorporate restriction sites suitable for cloning (5'-GTCCCTAGGAATTCGATCAAGAAA GCACTC-CGGG-3' (SEQ ID NO: 144) and the reverse complement of 5'-CCTCATGATGTACATTAGAT CGAATTCG-TAATACG-3' (SEQ ID NO: 145)). In this example, EcoRI (GAATTC (SEQ ID NO: 146)) which is not present in this segment, is appended at both ends of the segment in a PCR reaction, and the fragment digested with EcoRI and cloned into an EcoRI-digested acceptor plasmid. In this example, the latter is a chimeric plasmid of VHExpress and VLExpress, which is a composition made by cloning the full VHExpress plasmid (FIG. 15), cut with KpnI and EcoRI, and inserting the VK expression cassette that was digested with the same enzymes (described in Persic et al. (1997) 187:9-18). The resulting plasmid, pABExpress40 contains both heavy and light chain cassettes with their respective transcriptional orientation in opposite directions, and the anti-repressor element positioned in the middle of the two transcription units. A schematic map of the plasmid is shown in FIG. 22. This plasmid, pABExpress40 is used first in the cloning of the one chosen VL gene (using ApaLI and PacI cloning sites), resulting in pABExpress40-VL. This plasmid is used to receive the VH repertoire described above (as BssHII-BstEII fragment) (all of these four sites are unique in pABExpress40 and pABExpress40-VL). The cloning of the repertoire is carried out as described for the lambda repertoire in Example 4, using in the PCR of IgM-primed cDNA a set of nine oligonucleotides labeled "VH-back" and the mix of four "VH-forward" oligonucleotides described in Table 1 of H. J. de Haard et al. (1999), *J. Biol. Chem.* 274:18218-18230. The material is re-amplified using variants of the nine oligonucleotides appended with 5'-TATC CGC GCG CAC TCC-3' (SEQ ID NO: 147) and with the same VH forward mix, the product digested with BssHII and BstEII and cloned into pABExpress40-VL. The library is subsequently used as described in the previous examples to isolate panels of antigen-binding clones. Similarly the vector is used to construct the expression plasmid for given sets of antibodies, such as the ones described in Example 10, further confirming that the flanking variable region genes by anti-repressor elements facilitates the efficient and stable production of multiple antibodies by a single cell.

Example 12. Recovery and Analysis of Antibody Mixtures Using ELISA Including the Use of Anti-Idiotype and Peptide Mimotopes Antibody mixtures containing Fc regions are recovered as indicated in Example 3 using Protein A affinity chromatography. Antibody fragments with Histidine tags are isolated using IMAC as described in Example 2.

The resulting protein mixtures are analyzed as follows. Considered was the case of an antibody mixture composed of different binding sites directed to the same target antigen, with all antibodies being the same isotype, carrying the same light chain, and the mixture containing both monovalent bispecific and bivalent monospecific IgG-type antibodies. The following methods are available for analyzing the mixture. The heavy chain variable region genes will yield different amino acid compositions and allow the following non-antigen-dependent analysis: (1) Isoelectric focusing gel analysis: this analysis relies on a different pI value for the various forms of the antibodies. In a mixture of two IgGs and one bispecific, these three molecules will each display a unique isoelectric point. Proteins with a different pI are separated via electrophoresis in a pH gradient. The method is semi-quantitative. If two proteins of the complex have only a minimal difference in their pI value, it will be difficult to separate them using this test, and the other tests cited are used. (2) Mass-Spectrometry analysis: this analysis relies on the differential composition of the VH region, which, after digestion with proteolytic enzymes, yields a unique spectrum of peptides in MassSpec analysis. This method is predominantly qualitative. (3) Binding analysis based on anti-idiotype antibodies or peptide mimics: this analysis requires the availability of reagents that specifically recognize one antibody binding site in the presence of the other binding sites in the mixture. Suitable for this analysis are anti-idiotype antibodies which uniquely recognize the idiotype of the antibody. In this example where the antibodies share a common light chain, the unique features of the idiotype are formed mainly by the heavy chain determinants. Anti-idiotype antibodies are selected using the individual monoclonal antibodies as antigen in a selection of a large phage displayed antibody library using methods known to those in the art. Typically used are a non-immune antibody library (H. J. de Haard et al. (1999), *J. Biol. Chem.* 274: 18218-18230), which yields Fab fragments, and a semi-synthetic phage antibody library (de Kruif et al. (1995) *J. Mol. Biol.* 248:97). Anti-idiotype antibodies are selected on immobilized M57 and JB antibodies from the cited non-immune antibody library. Using ELISA screening of the selected phage antibodies on these two monoclonal antibodies used for the selection, anti-idiotype antibodies that uniquely recognize one of the two binding sites are identified. The respective Fab and scFv reagents selected from these library, are expressed as antibody fragments and purified using standard methods, for example, described in these citations and in *Antibody Engineering* (2001), Eds. Konterman and Dubel, Springer Lab Manual, and described in Example 2 for the scFv antibodies. The fragments are used in ELISA to determine which idiotype is present in the mixture, which is carried out in a quantitative assay. The anti-idiotype antibodies specific for the binding sites of M57 and JB are also used in virus competition experiments with the OLIGOCLONICS® preparation made in Example 10, to delineate the contribution of an individual binding site to the biological activity of the antibody mixture. Alternatively, the monoclonal antibodies are used to derive idiotype-associated peptides, linear or conformational peptides derived from the sequence of the antigen and still reactive with the antibody, for example, via PepScan analysis, as was demonstrated for the rabies virus ~neutralizing antibody MAb 6-15C4 (van der Heijden et al. (1993), *J. Gen. Virol.* 74:1539-45). An alternative is to isolate peptide mimotopes, with sequences unrelated to the original antigen yet specifically binding to the variable regions of the antibody. Provided the reaction is specific for a given antibody in the context of the other antibodies in the mixture, such peptides are also suitable for a specific analysis of the antibody mixture. Peptides with such unique reactivity to a given antibody are selected from phage display peptide libraries using methods essentially similar to those for phage antibody libraries. The binding test with the anti-idiotype antibodies and peptide-mimotopes is qualitatively or quantitatively, and a large series of binding tests are feasible, including ELISA, RIA, Flow cytometric analysis, BIAcore, etc.

Also disclosed is the analysis of an OLIGOCLONICS® mixture comprising multiple antibodies, in which each of the original antibodies binds to a different antigen. This resembles the situation in which the antibodies recognize the same antigen or target, and anti-idiotype reagents or peptide mimics are available. The analysis of multiple specificities in a mixture is carried out as follows, keeping in mind that antigen is synonymous for anti-idiotype. The reactivity to individual antigens is tested in ELISA on all antigens separately, with standardized assays using the monoclonal antibodies and quantitative IgG ELISA test. Antigen is coated directly or indirectly, the plates incubated with the antibody mixture, and bound antibody detected with an anti-IgG reagent. This leads to a "specific" activity of the preparation, that is a reactivity in relative units of activity per antibody quantity. The amount of bispecific antibody in the mixture is determined using a sandwich assay with one antigen coated and a second antigen, for example labeled with HRP, Alkaline Phosphatase or biotin, or detectable using another antibody specific for this antigen, provided to the plate after the antibody mixture was incubated with the first antigen.

If the antibodies present in the OLIGOCLONICS® mixture are binding different targets or different epitopes on the same target such that they are non-competitive, this feature can be used in an inhibition ELISA to determine the presence of the different antibodies in the mixtures produced by the transfected clonal cell lines. Consider an OLIGOCLONICS® made according to the methods of the previous examples using the antibodies specific for the Rabies glycoprotein isolated in Example 7 (which are non-competitive). For the inhibition ELISA, the same procedures as described for the standard anti-rabies ELISA as described above is used with some modifications. The OLIGOCLONICS® mixture produced by a clonal cell line is characterized as follows. Before addition to the wells coated with rabies glycoprotein, the supernatants of the transfected clonal cell line is diluted with an equal volume of a biotinylated rabies monoclonal antibody used to make the mixture. The biotinylated rabies monoclonal antibody is added in various concentrations, ranging from 0.1 to 10 µg/ml. Binding of the biotinylated monoclonal antibody to the coated rabies glycoprotein is inhibited when the same non-biotinylated antibody is present in the mixture produced by the clonal cell line. The binding of the biotinylated antibody is visualized with streptavidin, conjugated to an enzyme. As a control for binding and degree of inhibition, various concentrations of the biotinylated monoclonal antibodies diluted with an equal volume of culture medium without the mixture of antibodies or using the non-biotinylated antibody are used in the inhibition ELISA. This method is also suitable to screen the mixture of antibodies at a very early stage after transfection (as in Examples 10 and 11); thus, for each supernatant containing mixtures of antibodies, the presence of individual antibody specificities can be determined.

Example 13. Expression of Three Fab Fragments in the Same Eukaryotic Cell

For making a mix of these three antibodies, the expression experiment described in Example 10 is repeated using the following antibody genes, of the M57, JB and PO1 antibody (the latter is formed by the VH-PO1 and VL-PO1 genes of Example 9). Anti-idiotype reagents are separately selected on M57 and JB whole antibodies using a non-immune antibody library (see, also Example 12). This yields anti-idiotype antibodies that react with either M57 or JB; these antibodies are also tested on the PO1 to confirm specificity for either M57 or JB idiotypes. Similarly, the PO1 antibody is used in similar selections to obtain an anti-Id reagent for the PO1 binding site. Next, the heavy chains of these three antibodies, M57, JB and PO1, are cloned as VHCH1 fragments into VHExpress while deleting the gamma-1 gene (thus encoding an Fd chain only), yielding pEU-VH-M57, pEU-VH-JB and pEU-VH-PO1. The light chains VL-M57=JB-CL and VL-PO1-CL are cloned into VKexpress (Persic et al. (1997) 187:9-18), while deleting the CK gene from the cassette. First the light chain plasmids are introduced into PER. C6® cells and a clone is selected that stably produces over 2 micrograms/ml of both light chains (using methods described in Example 10). This cell line, designated PL2-2, is subsequently transfected with the three heavy chain containing plasmids, and a large collection of cell lines is obtained that produce a variety of levels of antibody L and Fd chains. The best candidate mixtures are purified on protein G affinity chromatography and tested for binding and composition as described in the previous examples, and also using the anti-Id reagents as described in Example 12. The experiments provide confirmation that multiple Fab fragments, with appropriately paired variable region genes, are expressed as highly functional mixtures.

Example 14. Cloning and Expression of Three Antibodies Directed to Different Antigens as an OLIGOCLONICS® Mixture Using the methods of the previous examples, antibodies with the same light chain are isolated against three different antigen, TNF-alpha, Interleukin-1beta (IL-1beta) and Interleukin-6 (IL-6), using a semi-synthetic library scFv library from Example 7 and described in (de Kruif et al. (1995) *J. Mol. Biol.* 248:97). In the selection, biotinylated recombinant cytokines (purchased from R&D Systems), are used, at decreasing concentrations during selection (250 nM, 100 nM and 50 nM). From the panels of antibodies generated against each of the targets after three rounds of selection, those scFv antibodies that neutralize the activity of the cytokine are identified. For this, the antibody fragments are recloned into pSCFV and purified using IMAC as in Example 2. Biological assays used are well known to those skilled in the art and include a L929 neutralization assay for TNF-alpha. Neutralizing clones are identified against TNF-alpha, IL-1beta or IL-6. The potency of neutralization can be improved by further affinity maturation techniques. For example, the CDR1 and CDR2 of the VH can be mutagenized and variants selected using phage display and tested for improved neutralization activity. These three antibodies have an identical light chain and have heavy chain variable regions that are distinct from one another, with most changes located in the CDR3.

The antibody variable regions are cloned into the eukaryotic expression described in Example 10, and essentially following the same procedure, CHO-cell lines identified that express mixture of the one light chain and three heavy chains. The analysis of the mixtures is carried out using ELISA to demonstrate binding to three antigens in a subset of the cell lines identified. A clone stably producing all three antibodies in an approximate ratio of heavy chains of 2:1:1 is identified using the techniques described in Examples 10 and 12. The cell lines are expanded and the mixture purified on Protein A and extensively tested to determine its composition. Using ELISA tests in various formats, with indirectly coated biotinylated antigen, with directly coated antigen 1, adding sample, followed by biotinylated antigen 2 and detection with Strep-HRP, and using samples of the mixture that have been depleted on TNF, IL-1beta or IL-6-coated beads, is it shown that the mixture contains three monospecific antibodies and three bispecific antibodies. The exact ratio between these six components is established by using quantitative ELISA tests and by IEF analysis of the mixture, as shown in Example 12. The neutralization efficacy of the mixture for the individual cytokines was confirmed with the assays as tested before. The neutralization of these cytokines in more complex systems, for example, using mixed cell populations, may establish a synergistic effect of the neutralization of these components by the OLIGOCLONICS® mixture.

Example 15. In Vitro Pairing of Antibody Chains Produced in Different Cells to Form Defined Antibody Mixtures Alternatively, to the expression in one host cell, antibody mixture can also be assembled ex vivo. The chains can be expressed separately and combined with a set of potential partner variable regions for pairing and assembly of the molecule.

In this prophetic example, a mixture of Fab fragments with pairing-compatible variable regions will be made as follows. The heavy chain variable regions of M57, JB and PO1 (Example 9) will first be cloned separately into an appropriate pET expression plasmid, such that this will mediate the expression of the Fd chain tagged with six Histidines inside the *E. coli*, as inclusion bodies. A suitable vector can be found in Novagen's pET Table, such as pET21d+(see, also www.novagen.com/Includes/wrapper.asp?href=/SharedImage s/Novagen/pETtable.htm§ion=TechResources&subsectjon=TechLit&strsubsection=techresources). The cloning will then be carried out by PCR of the VHCH1-containing templates (from Example 9) using oligonucleotides to provide appropriate cloning sites and also the C-terminal Histidine tag. These three plasmids will be introduced into separate *E. coli* host cells. The expression of the Fd fragments can then be induced and the protein demonstrated to be present in inclusion bodies. The two light chain variable regions, VL-M57=JB and YL-PO1 can also be suitably cloned into a suitable pET vector (although, alternatively, they could be obtained by secretion from a secretion vector like pFab-sol-pbr). After expression of the separate light chains, they should also be retrievable from the intracellular fraction. To assemble the mixture of three functional Fab fragments, the following procedure can then be followed. First the approximate and relative quantities of the individual L or Fd chains is estimated by gel-electrophoresis and Western blot. Then five 50-ml cultures of *E. coli* carrying one of five antibody variable regions are grown and induced as described in the pET manual from Novagen. After induction and growth, the pelleted cells of each of the chains can be resuspended in 8 ml 8 M urea (in PBS). After sonication, the five suspensions would be mixed in a ratio of approximately 1:1:1:4:2 for VH-M57, VH-JB, VH-PO1, VL-M57=JB, VL-PO1 (thus with a two-fold excess of light chain over heavy chain, and more of the twice needed VL). After this mixing of the denatured heavy and light chain variable regions, the mix will be rotated head over head for two hours. Insoluble material may then be removed by centrifugation for 30 minutes at 13,000 xg. The supernatant is dialyzed against PBS with four buffer changes, and insoluble protein further removed by centrifugation. The flow through fraction, obtained by filtration through a 0.2 µm membrane, should contain the refolded antibody mixture with pairing-optimized chains. The mixture may be further concentrated and purified, first using IMAC, which should retrieve all heavy chains and their paired light chains, followed by semi-preparative gel-filtration on a Superdex 75HR column (Pharmacia). The yield may be determined by measuring the optical density at 280 nm (using a molar extinction coefficient of 13 for Fabs). The mixture may be further characterized by analyzing the binding to the Rabies antigen. Since all functional Fabs should bind this antigen, a straightforward capture assay with antigen may be performed to determine the level of functional binding sites. There are many alternative protocols to this procedure, including the use of other extraction methods, other denaturation reagents, renaturation conditions and buffers, etc. Alternatively, to this procedure, both chains may also be secreted, and re-assembled using the conditions described by Figini et al. (1994) *J. Mol. Biol.* 239:68-78.

Figures 14A, 14B:
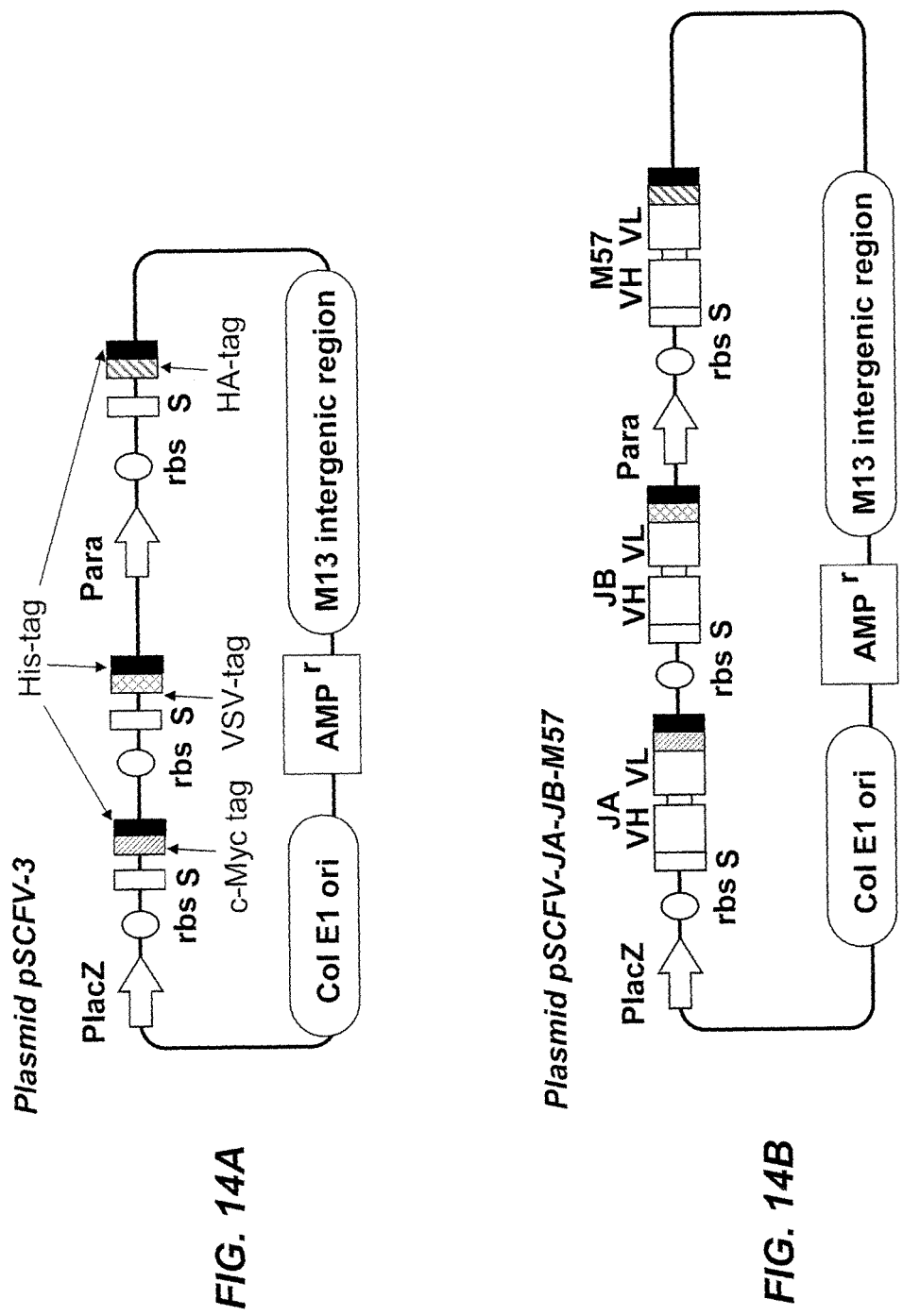
FIGS. 14A and 14B: Schematic depiction of plasmid pSCFV-3 (A) and pSCFV-3 with three cloned scFv fragments, in this case derived from the antibodies JA, JB and M57. The black box is a schematic depiction of the histidine stretch; other C-terminal-based tags are also indicated. S, signal sequence; rbs, ribosome binding site; AMPr, ampicillin resistance gene (beta-lactamase).

Example 16. Screening Antibody Mixtures Targeting Murine Vascular Endothelial Growth Factor The antibodies used in this example are described in WO 03102157A2 (inventors Fuh and Sidhu). The antibodies were derived by in vitro selection of a display library in which only the heavy chain was diversified. The repertoire with a fixed light chain and variable heavy chain was selected on murine vascular endothelial growth factor (mVEGF) and a large panel of antibodies binding mVEGF identified (Sidhu et al., *J. Mol. Biol.* 2004, 338:299-310). The source of the antibody heavy and light chain variable genes used in the repertoire was the humanized antibody 4D5. Antibody 4D5 is a humanized antibody specific for a cancer-associated antigen known as Her-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al., *PNAS* 54:4285 (1992); the variable region sequences of the heavy and light chains are also given in FIGS. 14A and 14B and SEQ ID NO:23 of WO 03102157A2; finally the crystal structure of 4D5 is shown in *J. Mol. Biol.* 229:969 (1993) and online at www.ncbi.nih.gov/structure, structure 1FVE.

An OLIGOCLONICS® mixture consisting of four different mVEGF-binding antibody binding sites is obtained as follows. Antibodies with clone numbers 4, 69, 73 and 74 as in Table 6, page 306 of Sidhu et al., *J. Mol. Biol.* 2004, 338:299-310, were selected on the basis of mVEGF binding as scFv on phage and as Fab protein (same Table 6). The antibodies share an identical light chain (of the Herceptin antibody, 4D5; as described in WO 03102157A2), but have differences in their heavy chain amino acid sequence as depicted in Table 6 of this paper.

The h4D5 antibody is a humanized antibody that specifically recognizes a cancer-associated antigen known as HER-2 (ErbB2) developed as described previously. The h4d5 VL gene is obtained by polymerase chain reaction using the humAb4D5 version 8 ("humAMD5-8"; Carter et al. (1992) *PNAS* 89:4285-4289) sequence and primers engineered to give rise to a 5' ApaLI site and a 3' PacI site in the PCR product. The PCR product was cleaved with ApaLI and PacI and ligated into the pABExpress vector (the vector described in Example 11 and in FIG. 23 but without the STAR40 sequence cloned into the EcoRI site). This yields plasmid pAb-4D5-VL, which encodes the expression of a functional 4D5 light chain (with human Ckappa constant region), and contains a polylinker region suitable for cloning VH regions. The VH regions from clones 4, 69, 73 and 74 are then cloned into this vector, using BssHII and BstEII restriction sites, and following the cloning route described in the previous examples (by providing the nucleotides encoding these restriction sites into the PCR primers in such manner that the cloning will yield an in-frame insertion encoding a fully functional antibody variable domain). This yields plasmids pAb-IgG-04, pAb-IgG-69, pAb-IgG-73 and pAb-IgG-74.

These plasmids encoding heavy and light chains are transfected into the human cell line PER. C6® to generate stable cell lines secreting multiple of the mVEGF-binding antibodies. For this, published methods and methods known to persons skilled in the art are used (E. Boel et al. (2000). *J. Immunol. Methods,* 239:153-166 and WO 00/63403). For the generation of stable PER. C6® cells secreting antibodies, PER. C6® cells are seeded in DMEM plus 10% FCS and in tissue culture dishes (10 cm in diameter) or T80 flasks with approximately $2.5 \times 10^6$ cell per dish or flask and kept overnight in an incubator at 37° C. and 10% $CO_2$. The next day, transfections are preformed in separate dishes at 37° C. using Lipofectamine (Invitrogen Life Technologies) according to standard protocols provided by the manufacturer. The plasmids pAb-IgG-04, pAb-IgG-69, pAb-IgG-73 and pAb-IgG-74 are mixed in a 1:1:1:1 ratios and used at a concentration of 2.5 µg/ml each. As controls, cells are subjected to the transfection procedure in the absence of plasmids, or with just a single plasmid. After four to five hours, cells are washed twice with DMEM and fed with fresh culture medium. The next day, the culture medium is removed and cells are fed with fresh medium containing 500 µg/ml of the antibiotic G418. Cells are fed every two to three days with culture medium containing 500 µg/ml of G418. After about 20 to 22 days after initiation of the experiment, a large number of colonies is visible and from each transfection, 400 clones are picked and grown individually in 96-well plates and further expanded in 24-well, 6-well and T25 flasks. At this stage, cells are frozen in liquid nitrogen and production levels of recombinant immunoglobulin are determined in an ELISA according to standard procedures (e.g., E. Boel et al. (2000), *J. Immunol. Methods,* 239:153-166 and WO 00/63403). At this stage of the culture procedure, G418 is no longer added to the culture medium.

To establish the presence of at least one functional anti-mVEGF antibody in a clone's culture supernatant, a solid phase ELISA is performed. Plates (PolySorb™, Nunc) are coated with 2.5 g/ml of mVEGF (R&D Systems, recombinant Mouse VEGF120 and VEG164, both carrier free) diluted in PBS and 100 µl/well overnight at 4° C. The plates are then blocked with 2% BSA in PBS for two hours and washed in PBS containing 0.05% TWEEN®-20 (PBS-TWEEN®) prior to the addition of cell supernatant samples containing antibodies. Following incubation at room temperature for two hours, the plates are washed with PBS-TWEEN® to remove unbound antibody present in the supernatant samples. Horseradish peroxidase-conjugated anti-human IgG is then added in PBS for one hour at room temperature and the plates are subsequently washed with PBS-TWEEN® (2×) and PBS (2×). Detection of secondary antibody is performed according to standard procedures and the absorbance determined spectrophotometrically (see, also previous examples). It is found that of the 400 clones screened, a substantial fraction produces a minimal IgG quantity.

Since only a limited number of colonies secrete a mixture of the four mVEGF antibodies, 50 clones selected from the initial panel of approximately 400, that are strongly reactive in the IgG-ELISA, clonality is further established by subcloning under limiting dilution. Picked and expanded colonies are seeded in a 96-well plate at a concentration of 0.3 cells/well in DMEM with 10% FCS and expanded. Colonies of cells are processed as described above and are referred to as subclones. While the initial transfection experiment used a ratio of DNA for the four plasmids pAb-IgG-04, pAb-IgG-69, pAb-IgG-73 and pAb-IgG-74 of 1:1:1:1, the cell subclones still display a variety in the expression levels for each of the antibodies. This is due to their independent expression regulation and their random integration into the genome. Further, since the same selection marker is used on all plasmids, the subclones express at the most four antibody binding sites, but not necessarily all four of them. The precise number depends on the transfection experiment; approximately 20-30% of the Ig-reactive clones express multiple antibody heavy chains, and of these, approximately 20% express more than two antibody heavy chains. The methods to increase these frequencies have been described earlier herein.

Screening to find the most optimal mixture of these four mVEGF-binding antibodies, as OLIGOCLONICS® mixture with bivalent and bispecific components, is done as follows. Optimal mixture here means with regards to which of the four antibody binding sites are optimally present in the mixture, and at which ratio they should be present. For the 50 subclones as well as for one IgG-reactive clone from the control transfectants made with just one antibody encoding plasmid, larger volumes are cultured to purify the recombinant human IgG1 fraction from the conditioned supernatant. This is done using Protein A affinity column chromatography according to standard procedures (Ed Harlow and David Lane, *Using Antibodies, A Laboratory Manual,* 1999, ISBN: 0879695447). These mixtures and the monoclonal antibody controls are tested for their neutralization activity on mVEGF in a $^3$H-thymidine incorporation assay using human umbilical vein endothelial cells (Conn et al., 1990, *Proc.*

*Natl. Acad. Sci. U.S.A.* 87:1323-1327). The inhibitory activity of each of the mixtures is compared to the inhibitory capacity of the four individual monoclonal antibodies. Mixtures that display a higher inhibitory activity on a molar basis compared to the activity of the monoclonal antibody controls putatively contain multiple antibodies that in combination mediate a synergic effect on the activity of VEGF. Next, assays that indicate the binding to mVEGF, the affinity of the interaction of the mix, the competition in binding with receptor (Flt-1 and KDR-1), are used. A binding assay is described above (solid phase ELISA). Assays to determine the relative affinity of the mixes are described in Sidhu et al., *J. Mol. Biol.* 2004, 338:299-310, page 308 (affinity measurements by competitive ELISA), with Fab and phage-displayed antibodies replaced with the mixtures of antibodies or the monoclonal antibodies as controls. An increase in relative affinity indicates a strong synergistic activity between the antibodies in the mixture, as described in Marks, *Movelent Disorders,* vol. 19, suppl. 8, 2004, p. S101-S108, for antibody mixtures binding to nonoverlapping epitopes of botulinum neurotoxins. Other assays to demonstrate the activity of the mixture of the antibodies on VEGF either in vivo or in vitro, are well established in the field and are, for example, described in WO 03102157A2, EP 0666868B1 and WO0044777A1.

Since VEGF displays activities in many processes, including mitogenesis, angiogenesis, endothelial cell survival, induction of metalloproteinases and growth factors, regulation of permeability/flow, recruitment of endothelial progenitor cells etc, any other single assays or combinations of assays can be used to determine the effect of the antibody mixtures on the activity of VEGF. The antibody mixtures can be screened in any of these assays, or combinations of assays, to find those compositions that have an effect in a defined set of assays, or have an effect in one but not in another assay. Further or instead of the in vitro assays, in vivo assays can be used to measure the overall effect of the antibody mixture on the pharmacokinetics of the antigen, and demonstrate improved clearance as mechanism of the synergic activity of the multiple antibodies in the OLIGO-CLONICS® mixture.

Mixtures are further characterized biochemically to find which antibodies are present and in which ratio, as described in Example 12.

Example 17: Pairing-Compatible Antibodies for Producing a Mixture of HER2/ErbB2-Targeting Molecules Trastuzumab (Herceptin, or h4D5, or hu4D5, see Example 16) and pertuzumab (Omnitarg, humanized 2C4) are both recombinant monoclonal antibodies that target different extracellular regions of the HER-2 tyrosine kinase receptor. Recently, it was shown that these antibodies synergistically inhibit the survival of breast cancer cells in vitro (Nahta et al., *Cancer Research* 64:2343-2346, 2004). Herceptin is active against HER-2 overexpressing metastatic breast cancers, leading to its approval in 1998 by the US FDA. In contrast to Herceptin, pertuzumab sterically blocks HER-2 dimerization with other HER receptors and blocks ligand-activated signaling from HER-2/EGFR and HER-2/HER-3 heterodimers. On the other hand, trastuzumab blocks ErbB2 shedding while pertuzumab does not. Mixtures of antibodies directed to the same target antigen but that display different or non-overlapping mechanisms of action will be very valuable in the therapeutic arsenal, and production of such multiple antibodies in a commercial manner will become very important. In this example, described is how pairing-compatible versions of these two antibodies are isolated, and used to build an OLIGOCLONICS® with an expected increase in potency and efficacy in tumor cell killing compared to the original monoclonal antibodies.

Anti-HER2 antibodies 4D5 and 2C4 are described in WO 0100245A2 and in Fendly et al., *Cancer Research* 50:1550-1558 (1990). The molecular structure and sequence of the humanized version of antibody 2C4 is described in Vajdos et al., *J. Mol. Biol.* 2002, 320, 415-428, in PDB database reference 1L7I, and in WO 0100245A2 (version 574 in Table 2 on page 54, or rhuMAb2C4 in continuation of this document). For simplicity here "2C4" is used to indicate the humanized version 574 of the murine 2C4 antibody. Its structure, in complex with the first three domains of ErbB2, was recently published (Franklin et al., *Cancer Cell*, 5, 2004, 317-328. The structure and sequence of h4D5 or Herceptin was described by Cho et al., *Nature* 2003, 421, 756-760, and is deposited as 1N8Z in the PDB database. Outside of the complementarity-determining regions (CDRs), pertuzumab is identical in sequence to trastuzumab (Carter et al., *Proc. Natl. Acad. Sci. U.S.A.* 89, 4285-4289, 1992); consequently, the local structure of the pertuzumab Fab in the ErbB2-pertuzumab complex is expected to be largely the same as that of the trastuzumab Fab. To build a pairing-compatible single light chain that will restore a functional binding site when paired with the h4D5 VH but also when paired with the 2C4 VH, the following route is followed.

Designing pairing-compatible light chains: The amino acid differences between the light chains of hu4D5v8 (the humanization variant described by Kelly et al., 1992, supra, indicated by hu4D5 or h4D5 in the next section) and 2C4 have been mapped to be 11 residues as highlighted in FIG. 23. In the CDR regions of the light chains, there are four differences in CDR1, three in CDR2 and four in CDR3. In most straight forward to follow in the absence of structural data on the antibodies and their interaction with antigen, is to build a library of light chain that have been diversified at these positions, and screen or select for variant light chain that maintain antigen-binding behavior when paired with the heavy chains of both antibodies, h4D5 and 2C4. The diversification can be chosen to contain all possible 20 amino acids or a subset thereof, for example, all residues but cysteine (which is not normally occurring at these 11 positions), or a selected set of amino acids that frequently occurs in antibodies at these positions. The design of a light chain repertoire based on all 11 amino acid differences between h4D5 and 2C4 is given in FIG. 23, in line HYB1.

A second approach to build a pairing-compatible variable hybrid light chain region for two antibodies, is to further employ structural information on the interaction of the antibodies with their respective antigen or antigens. In the example of h4D5 and 2C5, a wealth of structure-function information is available to guide the design of a hybrid light chain library. In this design, HYB2 in FIG. 23, all the light chains in the designed repertoire retain all of the common residues between the two original light chains of hu4D5 and 2C4, and a selection of residues at the positions where the original two light chains differ in composition, in which the selection is based on structural information on the antibody-antigen interaction. While some of the design may be based on this information, it is also noted that point mutations of h4D5 have been shown to dramatically effect the biological behavior of the antibody. The antiproliferative activities of the humanized variants of 4D5, which differ only in maximally seven amino acid residues, were found not to be strongly correlated with antigen affinity (Kelley et al., 1992, supra). Thus, it will be required to sample multiple versions of pairing-compatible light chains, and test the biological activity of the combinations after the antigen-selection and binding characterization to ensure maintenance of the biological activity.

The following HYB2 library design was made, based on the following observations:

CDR1. The sequence plasticity of the antigen-binding site of Herceptin was analyzed in a study by Gerstner et al. (*J. Mol. Biol.* 2002, 321:851-862). From these studies it appears that for trastuzumab residues N30 may be readily replaced by Serine (Table 1, Class 1 mutation VL30, of Gerstner et al., supra). Serine is the residue used at this position by 2C4. Thus, the pairing-compatible hybrid light chain is designed to contain Ser at position 30. The rest of the CDR1 is taken from the Herceptin light chain, as this region appears to be irrelevant for antigen binding in 2C4 (Franklin et al., supra).

CDR2. By alanine-scanning and homolog-scanning of the Fab2C4 antibody it was revealed that most of the side-chains that contribute to antigen binding are located in the heavy chain (Vajdos et al., supra). This was recently confirmed by the crystal structure of the antibody in complex with antigen: the light chain of pertuzumab Fab makes only a few contacts with ErbB2, mostly via CDR L2 (possibly via residue 55) and some via L3 (Franklin et al., supra). Some of 2C4's residues in this region may be converted to h4D5's residues without loss of affinity, as suggested by experiments with humanized versions of 2C4 described in WO 0100245A2 (page 54), in particular, what may be possible is to choose h4D5's VL's residues at positions 54 and 56. The Phe at position 53 in Herceptin appears to be relatively conserved, with some presence of Trp, while the other positions in this CDR region were not tested. Since some of these CDR2-based residues may also be important for positioning neighboring heavy-chain-based residues for antigen binding, in the hybrid light chain design, the three residues which are different between h4D5 and 2C4 are diversified fully, such that the selection process can identify which of the 8000 combinations will yield a pairing-compatible light chain.

CDR3. Tyrosine 91 of 2C4 is said to be important for antigen binding (Franklin et al., supra) but its substitution with phenylalanine (F) is acceptable (Vajdos et al., supra). Herceptin at this position in the light chain besides its original residue histidine tolerates several other aromatic side chains including Phe, Tyr and Trp (Table 1, page 854 in Gerstner et al., supra). Thus, the hybrid light chain is designed to contain Phe at position 91 (FIG. 23). For 2C4 antigen binding of the other residues of the H3 loop is relatively resistant to mutagenesis as in Gerstner et al., with the exception of the Pro at position 95. But this residue is shared between the Herceptin and 2C4 antibody light chains. In the interaction of Herceptin with antigen there are more likely interactions of the CDR3 regions with antigen, thus in the hybrid light chain, all but residue 91 is taken from Herceptin-VL (FIG. 23).

In the final HYB2 design, amino acids are taken for 6 out of 11 positions from the h4D5 VL, 1 out of 11 from the 2C4 VL (pos. 30), one is a residue not found in either VL (pos. 91) and the three are to be randomized (in CDR2).

HYB1 Library Construction and Selection of Pairing-Compatible VLs

The two libraries of light chains are constructed as follows. In the HYB1-designed VL library, 11 residues are randomized, implying that the total theoretical amino acid diversity (20exp11) is much larger than can be readily screened. To sample the diversity in this library, a powerful selection method is, therefore, used. The heavy chains (VH)

of h4D5 and 2C4 are cloned into the SfiI-BstEII cloning sites from pCES1 (de Haard et al., 1999, *J. Biol. Chem.* 274, 18218-30) using PCR and oligonucleotides binding to the 5' and 3' end of the nucleotide sequences of the VH genes and introducing SfiI and BstEII sites at appropriate sites for in-frame cloning (as described for antibody VH genes in de Haard et al., supra; the BstEII site is already present in the JH region of both h4D5-VH and 2C4-VH). The template for the PCR of the VH of h4D5 is plasmid pAK19 carrying the humanized 4D5 variant number 8, hu4D5-8, described in Kelly et al., 1992, *Biochemistry* 31:5435-5441, Table 1. The nucleotide sequence of this clone is essentially described in Carter et al. 1992, *P.N. A.S.,* 89:4285-4289, in FIG. 1, as huMAb4D5-5, with two alterations (V102Y in CDR3 of the VH, and E55Y in CDR2 of VL, as described in Kelly et al., 1992, supra). The VH sequence can also be extracted as SfiI-BstEII fragment from SEQ ID NO: 119 as described below. The template for the PCR reaction of the VH of 2C4 is plasmid pC2C4, described on page 425 of Vajdos et al., supra. The VH sequence can also be extracted from the NcoI-BstEII insertion inside the larger BssHII-NotI-fragment from SEQ ID NO: 119. The cloning of the PCR products into pCES1 is carried out as described for human antibody heavy chain VH pools and using standard cloning procedures. pCES1 is a phagemid vector that is suitable for the expression of Fab fragments in *E. coli* and for the display of Fab fragments on the surface of filamentous phage (de Haard et al., 1999, supra). Two plasmids with correct insert are identified by sequencing the insertion and junction region and the resulting plasmids named pCES-VH-h4D5 and pCES-VH-2C4. These are the acceptor plasmids for the light chain repertoire, HYB1. The VLCL coding region of hu4D5v8 is amplified using specific oligonucleotides priming in its 5' and 3' region and introducing ApaLI and AscI restriction sites as described in de Haard et al., supra, for human VLCL chains. As template pAK19 carrying the humanized 4D5 variant number 8 (hu4D5-8, described in Kelly et al., 1992, *Biochemistry* 31:5435-5441, Table 1) is used. The PCR product is cloned as ApaLI-AscI fragment in pCES-WI-h4D5, to yield pCES-Fab-h4D5. This encodes a functional h4D5 Fab fragment. HYB1 is produced using described methods with "stop" template versions of this plasmid. The stop template version is made by replacing one codon in each of the CDR1, CDR2 and CDR3 of the hu4D5-v8-VL with TAA stop codons. Methods to diversify the VL-template have been extensively described in the literature including in WO 03102157A2, in *Directed Mutagenesis, a Practical Approach*, Ed. M. J. McPerson, IRL Press 1991. The method used here is the Kunkel method; this yields the stop template of the VL in plasmid pCES-Fab-h4D5-3ST. The stop template version of h4D5-VL is used as a template for the Kunkel mutagenesis method (Kunkel et al. 1987, *Methods in Enzymol.* 154:367-382), using mutagenic oligonucleotides designed to simultaneously repair the stop codons and introduce mutations at the designed sites. Mutations in all three CDRs of the VL are introduced simultaneously in a single mutagenesis reaction. This is extensively described in Sidhu et al. 2000, *Methods Enzymol.* 328:333-363. The mutagenesis reaction is electroporated into *E. coli* SS320 (Sidhu et al., supra), and the transformed cells are grown overnight in the presence of M13-VCS helper phage to produce phage particles that encapsulated the phagemid DNA and displayed Fab fragments on their surfaces. Methods for phage-display library manipulation, selection and screening of clones have been described in the literature, for example, see de Haard et al., supra; Vajdos et al., supra and also the other examples). The resulting 4D5-HYB1 library contains greater than 1×10$^8$ unique members. This 4D5-HVB1 library is selected twice on HER2 antigen as described in Vajdos et al., supra, to yield a population of more than 65% of antibodies with antigen-binding activity. These antibodies share their VH region, but most carry different light chains. The light chains of this population are obtained as ApaLI-AscI fragment (VLCL), and cloned as a pool into pCES-VH-2C4. This new library now contains a subset of the light chains of HYB1 that are likely to be compatible with antigen binding in the context of h4D5. The library is selected once on antigen, and clones identified that mediate antigen binding. Light chains with identical amino acid sequence and that mediate antigen-binding when paired with the h4D5-VH and with the 2C4-VH are identified by sequencing a panel of Ag-reactive clones from the selected h4D5-HYB1 library, and of Ag-reactive clones from the selected 2C4 sublibrary, and comparing the sequences. Besides using antigen-reactivity in phage ELISA as readout, the reactivity of the Fab fragments is tested in ELISA (as described in de Haard et al., supra). This leads to the identification of a panel of VLs that display are functionally pair with both VH-h4D5 as well as VH-2C4. Within the panel the best VL is identified by determining the affinity of the interaction and the biological activity of the two respective Fab fragments. Methods for affinity determination and biological activity of anti-HER2 Fabs are described in Kelley et al., 1992, supra, and Gerstner et al., 2002, supra, and are described further below.

HYB2 library construction and screening of pairing-compatible VLs: The HYB2-designed VL library contains 8000 variants only. Here a different route is followed to allow simultaneous expression, and detection of antigen-binding variants, of h4D5 and 2C4 WI containing antibodies. First, the VL in pCES-Fab-h4D5 is mutated by Kunkel site-directed mutagenesis (Kunkel et al., supra) with Asparagine 30 changed to Serine (N30S), and Histidine 91 changed to Phenylalanine (H91F), according to the design depicted in FIG. 23. Of the resulting clone, p4D5-VLmut, phage and Fab are produced and tested for binding in a dilutions series for binding to Her-2 (extra-cellular domain) coated plate phage ELISA, to confirm that h4D5 maintains a minimal antigen-reactivity. Next a stop-template version is made from this plasmid, by replacing one codon in the CDR2 of the VL with a TAA stop codon (residue 55, tyrosine is mutated from "tat" to "taa"; this residue is said to be required in order to attain the antigen affinity of the humanized h4D5 antibody, Kelley et al., 1992, supra, thus will need to be fixed to "Y" to restore the reading frame and antigen-binding), This stop template version of the light chain of h4D5v8 is cloned into pSCFV-3 (Example 2 and FIG. 14B), by amplification of the VLCL region from the CDR2 stop-template. The design of the oligonucleotides used in this amplification is such that the whole VLCL segment is amplified and that after digestion the segment can be directionally cloned for in frame expression of the light chain under control of the arabinose promoter of pSCFV-3, and without any C-terminal tags. Briefly the VLCL is amplified with primers binding to the 5' and 3' end of the cassette and at the 5' providing a long overhang in two PCR reactions to encode a region of approximately 90 nucleotides encoding ribosome binding sites, start codon and bacterial leader sequence, to produce an EcoRV-EcoRI fragment that is cloned into the PacI-EcoRI sites bordering the third expression cassette in pSCFV-3. This plasmid, pVLmutST, is used as acceptor for the two heavy chains, after an internal BstEII site at position 143 of the insert was removed. The sequence of the final PacI-EcoRI insert is given in SEQ ID NO: 118.

Figure 24:
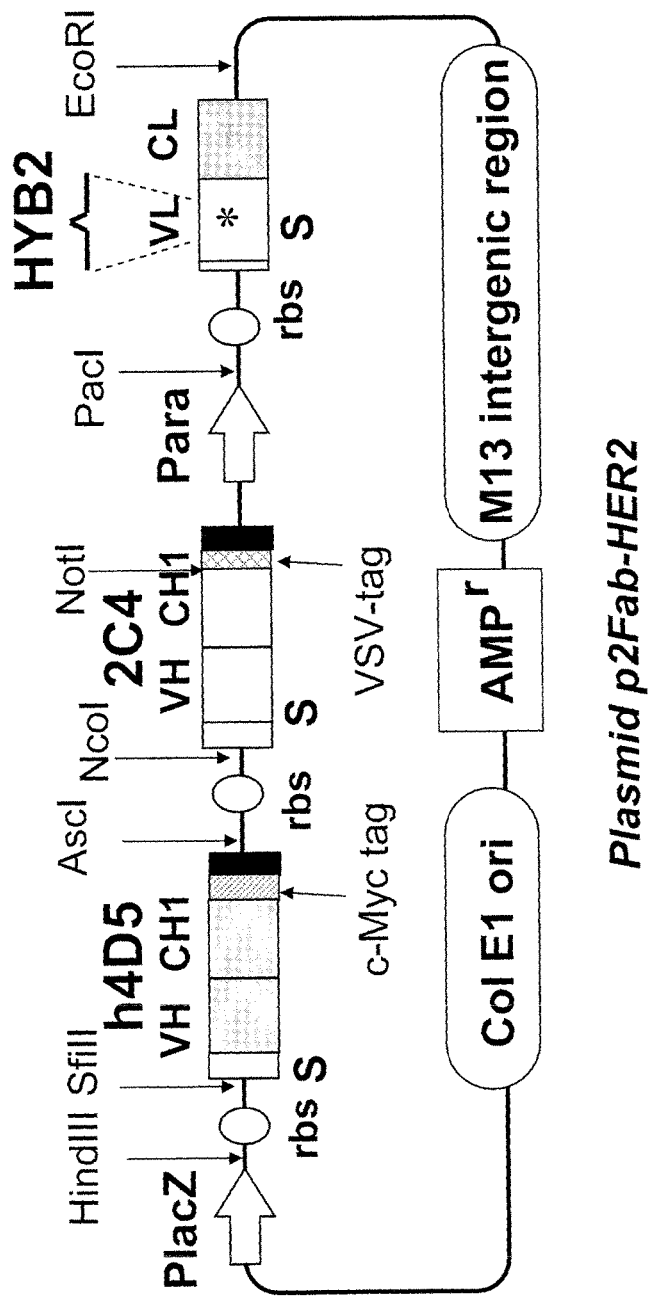
FIG. 24: Plasmid p2Fab-HER2 used for the identification of a light chain variable region that is pairing-compatible with two HER2-binding antibodies, h4D5v8, and 2C4. The black box is a schematic depiction of the histidine tag (six Histidines); other C-terminal-based tags are also indicated. S, signal sequence; rbs, ribosome binding site; $AMP^r$, ampicillin resistance gene (beta-lactamase). The version of the VL of h4D5 that is present in this vector carries two designed mutations in two CDR residues, and a stop codon (indicated with *) in the CDR2 region. By site-directed mutagenesis, the CDR2 is diversified using an oligonucleotide (designed according to approach HYB2) that simultaneously removes the stop codon as well as introduces diversity at three positions of the CDR2. This plasmid directs the expression of two antibody heavy chains (as Fd chains) and one antibody light chain, and thus allows simultaneous production, and individual detection, of two Fab fragments.

The heavy chains 2C4 and h4D5v8 are cloned in two steps as VH-CH1 fragments into pSCFV-3 (FIG. 14B) to yield plasmid p2Fab-HER2 as indicated in FIG. 24. First the h4D5 VHCH1 region is amplified from pCES-WI-h4D5 and cloned as SfiI-BssHII fragment into pVLmutST. The design of the primers is such that they, after cloning, arrange appropriate reading frames with leaders and tags in pSCFV3, to yield the final junctional sequences as depicted in SEQ ID NO:119. Second, the 2C4 heavy chain VHCH1 is amplified from pCES-VH-2C4 and cloned as BssHII-NotI fragment into this plasmid. Similarly, the design of the primers is such that they, after cloning, arrange appropriate reading frames with leaders and tags in pSCFV3, to yield the final junctional sequences as depicted in SEQ ID NO: 119. This final plasmid, p2Fab-Her2, provides the expression of both heavy chain variable domains as Fd chains (linked to human gamma-1), and the expression of a yet stop codon containing light chain. The sequence of the HindIII-NotI and PacI-EcoRI inserts of p2Fab-HER2 is given in SEQ ID NOS:119 and 118, respectively. The heavy chains of the two humanized antibodies, h4D5-version 8 and 2C4-version 574 are provided as fusions to the human CH1 domain, the Myc and VSV tag, respectively, and a HIS-tag for IMAC purification. The light chain in format VLCL is essentially derived from h4D5 but carries two designed VL mutations at positions 30 and 91, a stop codon in the CDR2, and has an internal BstEII site removed without amino acid change.

Plasmid p2Fab-HER2 is used as a template for the Kunkel mutagenesis method (Kunkel et al. 1987, *Methods in Enzymol.* 154:367-382), using mutagenic oligonucleotides designed to simultaneously repair the stop codon in the VL-CDR2 and introduce mutations at the three designed sites in CDR2, as indicated in FIG. 23. After electroporation and plating (as before), a small library of 50,000 clones is screened for pairing-compatible VL versions as follows. In the plasmid p2Fab-HER2, all three variable region genes are linked to a unique epitope tag that provides a way for their specific detection. Individual clones are picked into 96-well plates (Nunc) and induced to express both heavy chains and the one light chain, using conditions as described in Example 4, with the exception that arabinose is also added as inducer at the same time as the IPTG. The next day the supernatant of the cultures is tested for the presence of HER2 reactive Fabs, in an ELISA essentially as in Example 4. Multiple assays are carried out with the same sample, using either anti-myc or anti-VSV secondary reagents to detect the presence of the h4D5-Fab or the 2C4-Fab, respectively.

A dual-reactive clone designated 3-8E3, which binds HER-2 in ELISA with both the anti-VSV and anti-Myc tag reagents, is chosen for further analysis. The Fab mixture of this clone is expressed to 10-L scale level and purified from *E. coli* Supernatants according to Kelley et al., 1992, supra, page 5435-5436. Briefly, the culture supernatant is microfiltered by tangential flow filtration, concentrated by ultrafiltration and filtered over DEAE-Sepharose-FF. The antibody mixture in the flow-through fraction is subjected to affinity chromatography on Protein-G-Sepharose-FF. The Fab mixture is eluted with 0.1 M glycine, pH 3.0. The total protein concentration is determined by $A_{280}$ measurements using an $\epsilon_{280}$ of 67 $mM^{-1}$ $cm^{-1}$.

The binding constant of individual Fabs or the apparent binding constant of the Fab mix are measured by ELISA essentially as described by Vajdos et al., 2002, supra, on page 426. Briefly, NUNC 96-well maxisorb immunoplates are coated overnight at 4° C. with HER2-ECD (1 microgram/ml in 50 mM carbonate buffer, pH 9.6), and the plates blocked for one hour at room temperature with 0.5% BSA in PBS-0.05% TWEEN®-20. Serial dilutions of Fab protein are incubated on the HER2-ECD coated plates for two hours at room temperature, and the plates washed. Bound Fab is detected with biotinylated murine anti-human kappa chain antibody following by streptavidin—horseradish peroxidase conjugate (Sigma), using 3,3',5,5'-tetramethyl benzidine (TMB) as substrate (Kirsgaard and Perry Laboratories, Gaithersburg, Md.). The actual binding constant of one Fab in the mixture of two Fabs is measured by replacing the biotinylated murine anti-human kappa chain antibody of the above test with biotinylated anti-MYC-tag (for h4D5) or biotinylated anti-VSV tag (for 2C4) antibodies (antibodies similar to those described in Example 2). Titration curves are fit with a four-parameter non-linear regression curve-fitting program (KaledaGraph, Synergy Software) to determine the EC50 values, the Fab concentrations corresponding to half-maximal binding signals. Examples for h4D5, 2C4 and the 3-8E3 mixture is given in FIG. 25. The 3-8E3 mix is confirmed to contain two functional Fab antibody fragments, h4D5* and 2C4*, in which the * indicates that the light chain variable region is different from the two original humanized light chains of h4D5 and 2C4 (in FIG. 24), The ratio of the two Fab antibodies that are present in the 3-8E3 mix is analyzed by electrospray-ionization mass spectrometry essentially as described in Kelley et al., 1992, supra. There is a difference in the molecular weights of the Fabs on the basis of the heavy chains of 2C4 and h4D5 differing in approximately 68 dalton, well above the standard deviation of the assay (in the range of three to seven dalton).

Figure 25:
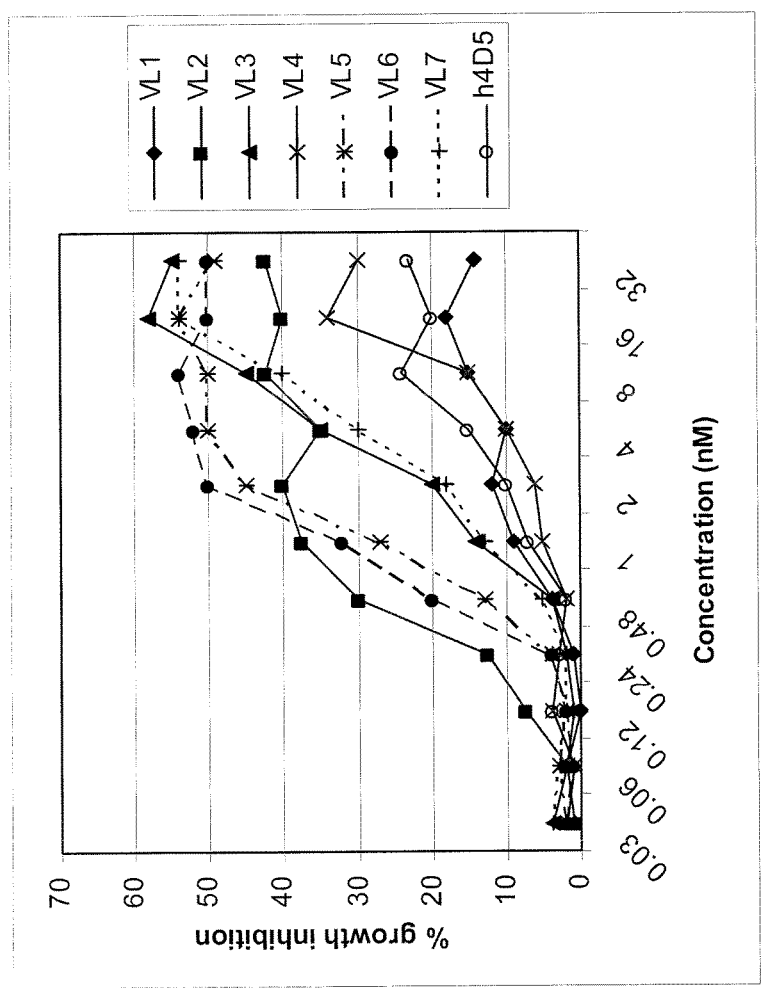
FIG. 25: Growth inhibition curves for h4D5 Fab and mixtures of 4D5* and 2C4* (see, Example 17) that utilize different light chains, indicated with VL1 to VL7. Different concentrations of these Fabs are incubated with HER2-positive cells sensitive to the growth inhibitory effect of HER2-targeting antibodies.

The biological activity of the Fab mixtures is compared with that of the individual monoclonal Fab fragments. The growth inhibitory characteristics are evaluated using the breast cancer cell line, SK-BR-3 (see, Hudziak et al., 1989, *Mol. Cell. Biol.* 9:1165-1172), using the assay conditions described on page 50 of WO 0100245A2. An exemplary graph in FIG. 25 shows the growth inhibition curves for h4D5 Fab and mixtures of 4D5* and 2C4* (see, Example 17) that utilize different pairing-compatible light chains, indicated with VL1 to VL7. The Fabs are further evaluated for their ability to inhibit HRG-stimulated tyrosine phosphorylation of proteins in the Mr 180,000 range from whole-cell lysates of MCR7 cells, which are known to express all known ErbB receptors (as in WO 0100245A2, page 50-51). As a control, 2C4 as Fab is used; this antibody is very effective in disrupting the formation of the high affinity HER2/HER3 binding site on MCF7 cells.

Once the activity of the Fabs in the mixture confirmed, the selected, pairing-compatible VL of 3-8E3, is used to build an OLIGOCLONICS® of the IgG format, essentially as described in the previous Example 10. This results in the production of 30 cell clones each producing a mixture of the bivalent h4D5* and 2C4* antibodies, and the bispecific combination; the IgGs are purified from the cell supernatants by protein A column chromatography as described above, and the concentration of the total IgG present in the mixtures determined. The biological activity of the resulting IgG-mixtures is tested as in Nahta et al., *Cancer Research* 64:2343-2346 (2004), using a growth inhibition assay of BT474 breast cancer cells as described on page 2343 of this paper. Briefly BT474 cells are treated in triplicate with two-fold serial dilutions of the IgG mixtures in the range of 0.1 to 25 ng/ml. After five days, cells are trypsinized and counted by trypan blue exclusion. The growth inhibition is calculated as the fraction of viable cells compared with untreated cultures. As controls, the original antibodies hu4D5-v8 (trastuzumab) and 2C4 (Pertuzumab) are used, as well as a 1:1 mixture of these monoclonal antibodies. The mixture with the most synergic activity between the two binding sites is identified based on the dose-effect plots as described in the legend of FIG. 1 on page 2344 in Nahta et al., 2004, supra. Other tests to confirm the synergistic activity are described in this paper (in vitro tests: apoptosis induction, Akt signaling), in WO 0100245 A2 (in vitro tests and in vivo tests, such as human tumor xenograft models described in Examples 5 to 7 and in FIGS. 10 to 13) and in Franklin et al., 2004, supra (in vitro HER2/HER3 heterodimerization using COS7 transfected cells).

Other examples of antibodies that can be combined with one or both of these anti-ErbB2 antibodies are antibodies with pairing-compatible chains that function as an anti-angiogenic agent (e.g., an anti-VEGF antibody); target the EGF-receptor (or ErbB1; e.g., C225 or ZD1839); or that are anti-ErbB2 antibody that strongly induce apoptosis, such as 7C2 or 7F3 (WO 0100245 A2). Pairing-compatible light chains are identified using the methods described herein.

Example 18. Pairing-Compatible Antibodies to Produce a Mixture of Hepatocyte Growth Factor/Scatter Factor (HGF/SF)-Targeting Antibodies that Block Multiple Biological Activities HGF/SF is a ligand that binds to the Met receptor tyrosine kinase. HGF/SF is composed of an α chain containing the N-terminal domain and four kringle domains covalently di-sulfide linked to the β chain. Binding of HGF/SF to the Met receptor tyrosine kinase induces multiple biological activities, including cell proliferation and cell invasion, and outgrowth of blood vessels (angiogenesis). In addition, binding of HGF/SF to Met prevents programmed cell death (reviewed in C. Birchmeier et. al. *Nat. Rev. Mol. Cell Biol.* 4:915-925 (2004). The Met receptor is expressed by many solid tumors and Met-HGF/SF signaling has been shown to be involved in tumor development, invasion and metastasis (J. M. Cherrington et al., *Adv. Cancer. Res.* 79:1-38 (2000); S. Rong et al., *Mol. Cell Biol.* 12, 5152-5158 (1992).

Monoclonal antibodies against HGF/SF have been produced to study their capacity to block the diverse biological activities of HGF/SC (B. Cao et al., *Proc. Natl. Acad. Sci. U.S.A.*, 98, 7443-7448 2001). The antibodies were produced by immunizing mice with human HGF/SF and generating hybridomas secreting monoclonal antibodies. The polyclonal serum from mice immunized with HGF/SC showed potent neutralizing activity of all biologic activities of HGF/SF. In contrast a large panel of monoclonal antibodies that bind to the human HGF/SCF was shown to lack the capacity to completely block all biological activities of HGF/SC (B. Cao et al., *Proc. Natl. Acad. Sci. USA*, 98, 7443-7448 2001). Combinations of two anti-HGF/SF monoclonal antibodies still lacked full blocking activity while several mixtures of three monoclonal antibodies potently neutralized all HGF/SF activity in in vitro assays. It was concluded that blocking of the biological activities of HGF/SF requires the simultaneous binding of multiple monoclonal antibodies against different epitopes of the HGF/SF ligand (B. Cao et. al., *Proc. Natl. Acad. Sci. USA*, 98, 7443-7448 2001).

Mixtures of monoclonal antibodies directed against the same target molecule that block the complete spectrum of biological activities of the molecule are very valuable contributions to the therapeutic arsenal, especially when such blocking activities can not be achieved with monoclonal antibodies. Production of such multiple antibodies in a pharmaceutical manner and in a commercially viable way will become very important. In this example, described is how mixtures of monoclonal antibodies against the HGF/SF ligand are isolated and used to construct an OLIGOCLONICS® that efficiently blocks all biological activities of this ligand.

Phage antibody scFv or Fab libraries that are formed by focusing the diversity in one variable region and keeping the other variable region invariable, for example a germ line sequence, are particularly relevant. From such libraries it is feasible to isolate antibodies with a different heavy chain yet identical light chain, or vice versa (FIG. 3). Such antibodies are readily reformatted into an OLIGOCLONICS® format. In the art, it has been described that antibodies that share the same VL gene but have different VH genes and widely varying specificities can be obtained from phage antibody display libraries (Nissim et al. (1994), *EMBO J.* 13:692-698). A sub-library of the semi-synthetic scFv library (de Kruif et al. (1995) *J. Mol. Biol.* 248:97) described in Example 7 is used to select antibodies against recombinant human HGF/SF.

The HGF/SF ligand is produced and purified from S-114 cells (NIH 3T3 cells transformed with human HGF/SF and Met) as described (S. Rong et al. (1993) *Cell Growth Differ.* 4, 563-569). For phage selections, 96-well plates are coated with 2.5 μg/ml HGF/SF in coating buffer (0.2 M $Na_2CO_3$/ $NaHCO_3$, pH 9.6; 50 μl per well) overnight at 4° C. The plates were then blocked with PBS containing 1% BSA (200 μl/well) overnight at 4° C. Selections of phages binding to human HGF/SF are performed as described in the previous examples. The binding of phages selected from the library is monitored by a HGF/SF ELISA using 96-well plates coated with 2.5 μg/ml HGF/SF in coating buffer (0.2 M $Na_2CO_3$/ $NaHCO_3$, pH 9.6; 50 μl per well) overnight at 4° C. The plates are then blocked with PBS containing 1% BSA (200 μl/well) overnight at 4° C.

The VH regions from individual monoclonal antibodies and the single VL region are cloned into the eukaryotic expression vector for human monoclonal antibodies as described in Example 10 and subsequently introduced into eukaryotic CHO cells by transfection. For each transfection, the plasmids encoding two or more different VH regions are mixed in various ratios and used at a concentration of 1 to 10 μg/ml. Clones secreting human antibodies are generated essentially as described in Example 10 and the supernatants monitored for HGF/SF-specific antibodies with an ELISA in 96-well plates coated with HGF/SF as described in the previous paragraph. Supernatants from clones secreting anti-HGF/SF antibodies are used to determine the capacity of mixtures to block the biological activities of HGF/SF.

Supernatants from transfectants are screened for neutralizing HGF/SF capacity in the Madin-Darby canine kidney (MDCK) scatter assay as described (B. Cao et. al., *Proc. Natl. Acad. Sci. USA*, 98, 7443-7448 2001). MDCK cells are plated at $7.5 \times 10^4$ cells per 100 μl per well with or without HGF (5 ng/well) in DMEM with 5% FBS. Three hundred microliters of supernatants at two-fold serial dilutions is then added to 96-well plates. A rabbit polyclonal-neutralizing antiserum (1 l/well; ref S. Koochekpour et. al. (1997) *Cancer Res.* 57, 5391-5398) is included as control. Following overnight incubation at 37° C., cells are then stained with 0.5% crystal violet in 50% ethanol (vol/vol) for ten minutes at room temperature, and scattering is viewed using a light microscope.

Supernatants from transfectants are also screened for neutralizing HGF/SF capacity in the Branching Morphogenesis Assay as described. Branching morphogenesis assay using SK-LMS-1 cells was conducted as described (M. Jeffers et al. (1996) *Mol. Cell. Biol.* 16, 1115-1125). Briefly, cell suspensions are mixed with an equal volume of GFR-Matrigel (Becton Dickinson), plated at 5×10⁴ cells per 125 μl per well in a 96-well culture plate, and incubated for 30 minutes at 37° C. HGF/SF, with or without neutralizing mAbs, is added along with DMEM containing 10% FBS on top of the gel. After 72 to 96 hours of incubation at 37° C., representative wells are photographed at ×400 magnification.

Example 19. Pairing-Compatible Antibodies to Produce a Mixture of Antibodies that Block Vascular Endothelial Cell Growth Factor Receptor 1 (VEGF-R1) and VEGF-R2

Vascular endothelial growth factor (VEGF) is a key regulator of angiogenic processes during adult life such as wound healing, diabetic retinopathy, rheumatoid arthritis, psoriasis, inflammatory disorders and tumor growth and metastasis (N. Ferrara et. al., *Curr Top. Microbiol. Immunol.* 237-1-30 (1999); M. Klagsbrun et al., *Cytokine Rev.* 7, 259-270 (1996); G. Neufeld et al. *FASEB J.* 13, 9-22 (1999)). VEGF binds to and mediates its activity mainly through two tyrosine kinase receptors, VEGF-R1 (also named Flt-1) and VEGF-R-2 (also named KDR). Numerous studies have shown that overexpression of VEGF and its receptors plays a role in associated-associated angiogenesis and hence in tumor growth and metastasis (J. Folkman, *J Nat. Med.* 1, 27-31 (1995); Z. Zhu et. al., *Invest. New Drugs* 17, 195-212 (1999)).

A human anti-VEGF monoclonal antibody binding to VEGF and blocking its binding to the VEGF-R1 has recently been approved by the FDA for the treatment of patients with metastatic colorectal cancer (www.fda.gov/cder/foi/applet-ter/2004/1250851tr.pdf). This shows that monoclonal antibodies that block angiogenesis provide an important tool in the treatment of solid tumors.

In WO 04003211 A1, Zhu describes bispecific antibodies with one part of the molecule blocking the binding of VEGF to VEGF-R1 and another part of the molecule blocking binding of VEGF to VEGF-R2. In addition, the bi-specific antibody prevents the homodimerization of the VEGF receptors and thus blocking VEGF-R-mediated cellular signaling. Compared to binding to a single VEGF-R, dual binding can result in more potent inhibition of VEGF-stimulated cellular functions such as, for example, proliferation of endothelial cells. The bispecific antibodies described by Zhu comprise single chain Fv antibody fragments fused to the heavy and light chain constant regions of an IgG molecule. Because of the nature of the bispecific molecules, they can be expected to be immunogenic upon injection in humans, impeding their clinical effectiveness. Mixtures of human antibodies as represented in the OLIGOCLONICS® format that block both the VEGF-R1 and VEGR-R2 while retaining optimal clinical efficacy may be an important addition to the arsenal of anti-solid tumor drugs. Such an OLIGOCLONICS® is obtained as follows:

The soluble fusion protein VEGF-R2 fused to alkaline phosphatase (VEGF-R2-AP) is expressed in stably-transfected NIH 3T3 cells and purified from cell culture supernatant by affinity chromatography as described (D. Lu et al., *J. Biol. Chem.* 275, 14321-14330 (2000)). VEGF-R1-Fc fusion protein is purchased from R&D Systems (Minneapolis, Minn.). VEGF-R2-AP is coated to Maxisorp Star tubes plates at a concentration of 10 μg/ml and subsequently, the tubes are blocked with 3% milk/PBS as described in WO 003211 and D. Lu et al., *Cancer Res.* 61:7002-7008 (2001). The phage library used for selection of scFv antibody fragments specific for VEGF-R2 contains a single light chain and is diversified in the heavy chain as described in the previous Example 7. Selection of phages is carried out as described in the previous examples. The specificity of selected scFv antibody fragments is determined in ELISA with 10 μg/ml VEGF-R2-AP coated to Maxisorp 96-well plates and scFv binding, washing and detection steps as described in the previous examples. As a control for binding to the AP moiety, scFv are assayed for binding to a control AP fusion proteins such as ELF2-AP (GenHunter Corp., Nashvflle, Tn). Selection of phages binding to the VEGF-R1 is carried out by coating Maxisorp Star tubes with 10 μg/ml VEGF-R1-Fc and performing rounds of selection as described in the previous examples. The specificity of selected scFv is analyzed in ELISA with 10 μg/ml VEGF-R1-Fc coated to 96-well plates. As a control for binding to the Fc portion VEGF-R1-Fc, plates are coated with the Fc fusion protein rhsThy-1:Fc (product number ALX-203-004, Alexis Biochemicals, Lausen, Switzerland).

The VH regions from individual monoclonal antibody fragments and the single VL region are cloned into the eukaryotic expression vector for human monoclonal antibodies as described in Example 10 and subsequently introduced into eukaryotic CHO cells by transfection. For each transfection, the plasmids encoding two or more different VH regions are mixed in various ratios and used at a concentration of 1 to 10 μg/ml. Clones secreting human antibodies are generated essentially as described in Example 10 and the supernatants monitored for VEGF-R1 and VEGF-R2-specific antibodies with an ELISA in 96-well plates coated with VEGF-R1-Fc and VEGF-R2-AP as described in the previous paragraph, and using secondary antibodies that specifically bind to the human antibodies. Supernatants from clones secreting antibodies to both receptors are used to determine the biological activity of the mixtures in VEGF-R1 and VEGF-R2 blocking assays and in an anti-mitotic and leukemia migration assays.

VEGF-R1 and VEGF-R2 blocking assays are performed as described (Z. Zhu et al., *Cancer Res.* 58:3209-14 (1998); D. Lu et al., *J. Immunol. Methods,* 230:159-71 (1999). The anti-mitotic and leukemia migration assays are performed as described in WO 04003211 A1. To measure whether these antibody mixtures compete with VEGF for binding to the receptors, assays are carried out that measure the level of antibody-induced inhibition of VEGF-associated effects. For example, the effect of the antibody cocktail on VEGF-induced endothelial cell proliferation is measured using a thymidine incorporation assay. Numerous in vitro and in vivo assays have been described to measure the effect of ligands interfering with the VEGF—VEGF-receptor interaction. Some suitable assays are described in Gerbert et al., *J. Biol. Chem.* 1998, 273:30336 (cell survival assay, endothelial cell apoptosis, Akt phosphorylation assay, as on page 30337); in Mendel et al., *Clin. Cancer Res.* 2000, 6:4848-4858 (s.c. xenograft model in athymic mice, surface expression of KDR, ¹²⁵I VEGF binding assay, and Flk-1 receptor kinase assay, as on pages 4849-4850). These and other suitable assays are reviewed in Auerbach et al., 2003, *Clin. Chemistry* 49(1):32-40.

Example 20: Human Light Chain V-Gene Clones

This Example describes the rationale behind the choice of two human light chain V-genes, one gene of the kappa type and one gene of the lambda type, that are used as a proof of concept for light chain expressing transgenic mice. De Wildt et al. 1999 (de Wildt et al. (1999), *J. Mol. Biol.* 285(3):895) analyzed the expression of human light chains in peripheral IgG-positive B-cells. Based on these data, IGKV1-39 (O12) and IGLV2-14 (2a2) were chosen as light chains as they were well represented in the B-cell repertoire. The J-segment sequence of the light chains has been chosen based upon sequences as presented in GenBank ABA26122 for IGKV1-39 (B. J. Rabquer, S. L. Smithson, A. K. Shriner and M. A. J. Westerink) and GenBank AAF20450 for IGLV2-14 (O. Ignatovich, I. M. Tomlinson, A. V. Popov, M. Bruggemann and G. J. Winter, *J. Mol. Biol.* 294 (2):457-465 (1999)).

All framework segments are converted into germline amino acid sequences to provide the lowest immunogenicity possible in potential clinical applications.

Example 21: Obtaining Mouse Heavy Chain V-Genes that Pair with Human IGKV1-39 Gene Segment to Form Functional Antibody Binding Sites This example describes the identification of mouse heavy chain V-genes that are capable of pairing with a single, rearranged human germline IGKV1-39/J region. A spleen VH repertoire from mice that were immunized with tetanus toxoid was cloned in a phage display Fab vector with a single human IGKV1-39-C kappa light chain and subjected to panning against tetanus toxoid. Clones obtained after a single round of panning were analyzed for their binding specificity. The murine VH genes encoding tetanus toxoid-specific Fab fragments were subjected to sequence analysis to identify unique clones and assign VH, DH and JH utilization.

Many of the protocols described here are standard protocols for the construction of phage display libraries and the panning of phages for binding to an antigen of interest and described in Antibody Phage Display: *Methods and Protocols* (editor(s): Philippa M. O'Brien and Robert Aitken).

Immunizations: BALB/c mice received one immunization with tetanus toxoid and were boosted after six weeks with tetanus toxoid.

Splenocyte isolation: Preparation of spleen cell suspension. After dissection, the spleen was washed with PBS and transferred to a 60 mm Petri dish with 20 ml PBS. A syringe capped with 20 ml PBS and a G20 needle was used to repeatedly flush the spleen. After washing the flushed cells with PBS, the cells were carefully brought into suspension using 20 ml PBS and left on a bench for five minutes to separate the splenocytes from the debris and cell clusters. The splenocytes suspension was transferred on top of a FICOLL-PAQUE® PLUS-filled tube and processed according to the manufacturer's procedures for lymphocyte isolation (Amersham Biosciences).

RNA isolation and cDNA synthesis: After isolation and pelleting of lymphocytes, the cells were suspended in TRIzol LS Reagent (Invitrogen) for the isolation of total RNA according to the accompanying manufacturer's protocol and subjected to reverse transcription reaction using 1 microgram of RNA, Superscript III RT in combination with dT20 according to manufacturer's procedures (Invitrogen).

PCR amplification of cDNA: The cDNA was amplified in a PCR reaction using primer combinations that allow the amplification of approximately 110 different murine V-genes belonging to 15 VH families (Table 1; RefSeq NG_005838; Thiebe et al. 1999, *European Journal of Immunology* 29:2072-2081). In the first round, primer combinations that bind to the 5' end of the V-genes and 3' end of the J regions were used. In the second round, PCR products that were generated with the MJH-Rev2 primer were amplified in order to introduce modifications in the 3' region to enable efficient cloning of the products. In the last round of amplification, all PCR products were amplified using primers that introduce a SfiI restriction site at the 5' end and a BstEII restriction site at the 3' end (see, FIGS. 26 and 27, and Table 1).

Figure 32:
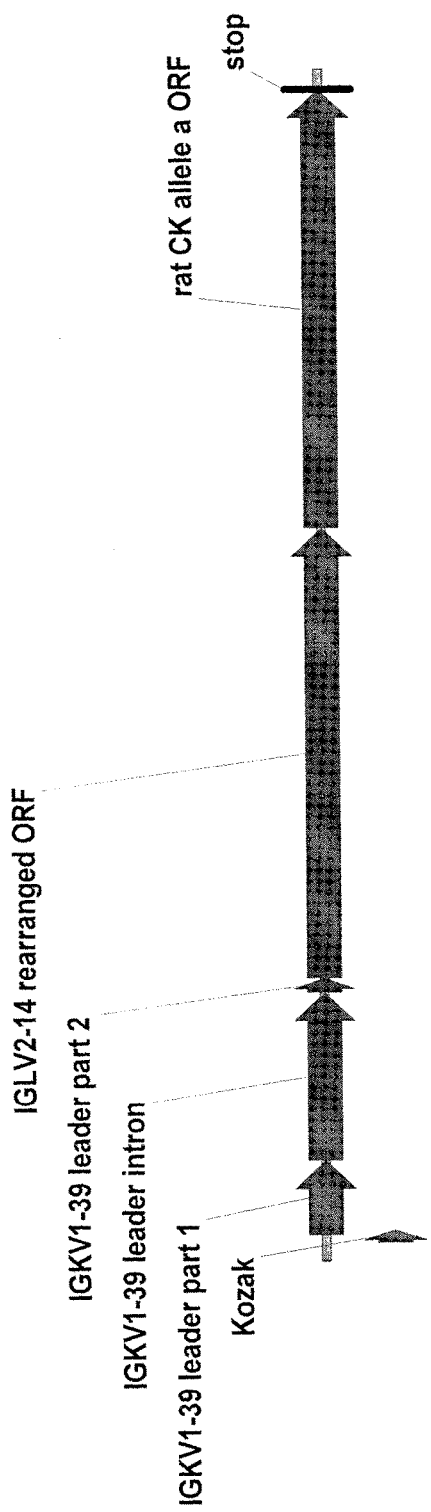
FIG. 32: Construct topology of IGLV2-14/J-Ck with an intron located in the leader open reading frame (ORF).

Reaction conditions for 1st round PCR: four different reactions combining all 25 forward primers (MVH1 to MVH25, Table 1 and FIG. 27) and one reverse primer per reaction (MJH-Rev1, MJH-Rev2, MJH-Rev3 or MJH-Rev4; see Table 1 and FIG. 32). Fifty microliters PCR volumes were composed of 2 microliters cDNA (from RT reactions), 10 microliters 5* Phusion polymerase HF buffer, 40 nM of each of the 25 forward primers (total concentration of 1 micromolar), 1 micromolar reverse primer, 1 microliter 10 mM dNTP stock, 1.25 unit Phusion polymerase and sterile MQ water. The thermocycler program consisted of a touch down program: one cycle 98° C. for 30 seconds, 30 cycles 98° C. for ten seconds, 58° C. decreasing 0.2° C. per cycle ten seconds, 72° C. 20 seconds and one cycle 72° C. for three minutes. The second round PCR program was set up only for the products of the first PCR that contain the MJH-Rev2 primer: two different reactions combining either the Ext-MVH-1 or ExtMVH-2 primers (Table 1 and FIG. 27) in combination with the reverse primer ExtMJH-Rev2int (Table 1 and FIG. 27). Fifty microliters PCR volumes were composed of 50 ng PCR product (from first PCR round), 10 microliters 5* Phusion polymerase HF buffer, 500 nM of each forward primer, 1 micromolar reverse primer, 1 microliter 10 mM dNTP stock, 1.25 unit Phusion polymerase and sterile MQ water. The thermocycler program consisted of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. The third round PCR program was setup as described in FIG. 27. Fifty microliters PCR volumes were composed of 50 ng PCR product (from earlier PCR rounds, FIG. 27), 10 microliters 5* Phusion polymerase HF buffer, 1 micromolar forward primer (Table 1 and FIG. 27), 1 micromolar reverse primer, 1 microliter 10 mM dNTP stock, 1.25 unit Phusion polymerase and sterile MQ water. The program consists of a touch down program followed by a regular amplification step: one cycle 98° C. for 30 seconds, ten cycles 98° C. for ten seconds, 65° C. decreasing 1.5° C. per cycle ten seconds, 72° C. 20 seconds, ten cycles 98° C. for ten seconds, 55° C. ten seconds, 72° C. 20 seconds and one cycle 72° C. for three minutes. After PCR amplifications, all PCR products were gel purified using Qiaex II according to the manufacturer's protocols.

Figure 27:
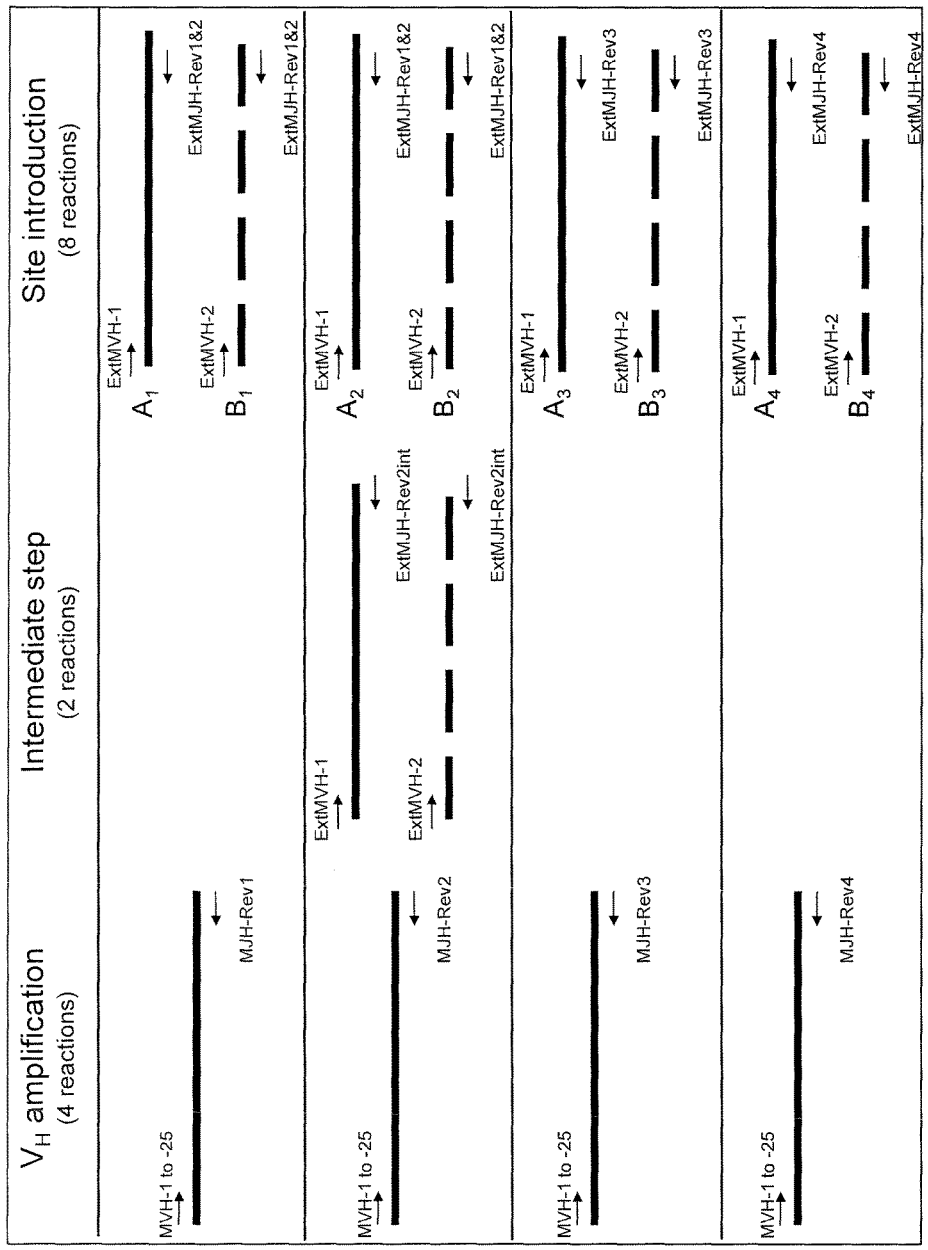
FIG. 27: PCR amplification steps (Amplification, Intermediate and Site introduction). The location and names of the mouse VH amplification primers (and mixtures of primers) are indicated per step.
Figure 28:
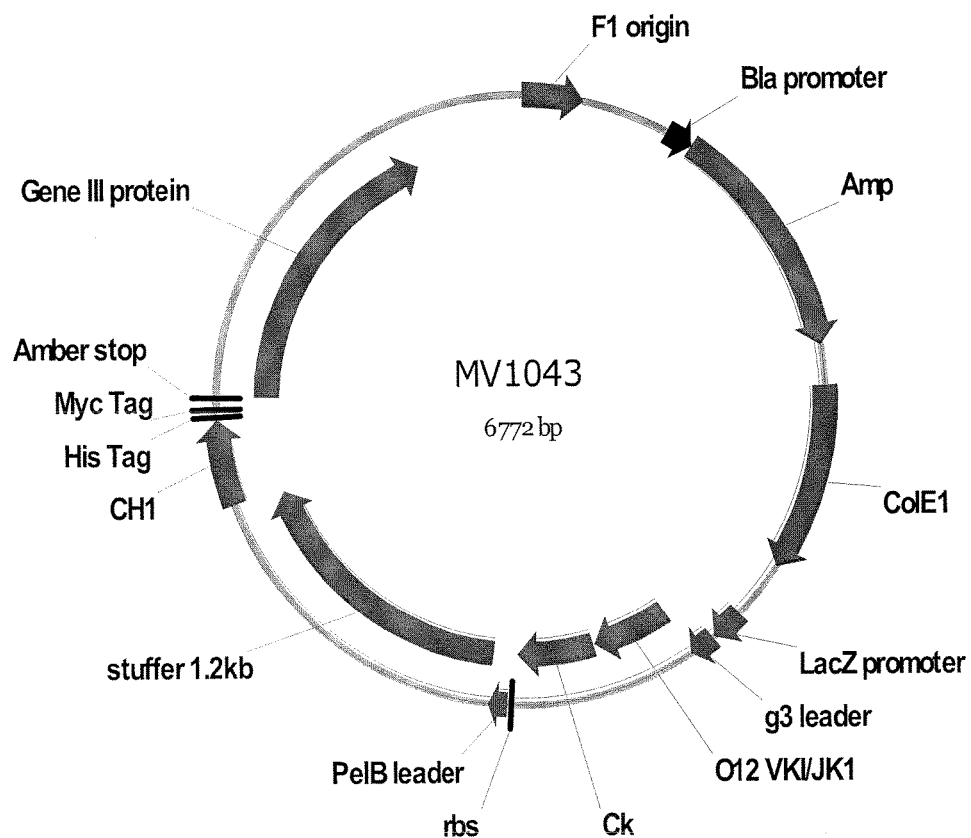
FIG. 28: Topology of the MV1043 vector. This vector is used for the cloning of human or murine VH fragments. O12 (IGKV1-39) is indicated as the VL gene. Products of this vector in combination with helper phages in *E. coli* cells allow the generation of phages that display Fab fragments on the surface of the phage particles as a fusion product to the g3 protein and presence of the vector in the phage as the genetic content (F1 ORI).

Restriction enzyme digestions: Purified products were digested with BstEII and SfiI in two steps. First 1 microgram of DNA was digested in 100 microliters reactions consisting of 10 microliters of 10*NEB buffer 3 (New England Biolabs), 1 microliter 100*BSA, 12.5 unit BstEII and sterile water for six hours at 60° C. in a stove. The products were purified using Qiaquick PCR Purification kit from Qiagen according to the manual instructions and eluted in 40 microliters water. Next, all products were further digested with SfiI in 100 microliters reactions consisting of 10 microliters of 10* NEB buffer 2 (New England Biolabs), 1 microliter 100*BSA, 12.5 unit SfiI and sterile water for 12 hours at 50° C. in a stove. The digested fragments were purified by Qiaquick Gel Extraction kit following gel separation on a 20 cm 1.5% agarose TBE plus ethidium bromide gel at 80 V. 100 micrograms of the acceptor vector (MV1043, FIGS. 28 and 27) was digested with 50 units Eco91I in 600 microliters under standard conditions (Tango buffer) and next purified on a 0.9% agarose gel. After a second digestion step under prescribed conditions with 400 units SfiI in 500 microliters for 12 hours, 100 units BsrGI were added for three hours at 50° C.

Ligations: Each PCR product was ligated separately according to the following scheme: 70 ng digested PCR products, 300 ng digested acceptor vector, 100 units T4 Ligase (NEB), 1*ligase buffer in 30 microliters for 16 hours at 12° C. The ligation reactions were purified with phenol/chloroform/isoamyl alcohol extractions followed by glycogen precipitations (Sigma Aldrich #G1767) according to the manufacturer's protocol and finally dissolved in 25 microliters sterile water.

Transformations and library storage: The purified ligation products were transformed by electroporation using 1200 microliters TG1 electrocompetent bacteria (Stratagene #200123) per ligation batch and plated on LB carbenicillin plates containing 4% glucose. Libraries were harvested by scraping the bacteria in 50 ml LB carbenicillin. After centrifugation at 2000 g for 20 minutes at 4° C., the bacterial pellets were resuspended carefully in 2 ml ice cold 2*TY/30% glycerol on ice water and frozen on dry ice/ethanol before storage at −80° C.

Library amplification: Libraries were grown and harvested according to procedures as described by Kramer et al. 2003 (Kramer et al. (2003), *Nucleic Acids Res.* 31(11):e59) using VCSM13 (Stratagene) as helper phage strain.

Selection of phages on coated immunotubes: Tetanus toxoid was dissolved in PBS in a concentration of 2 μg/ml and coated to MaxiSorp Nunc-Immuno Tube (Nunc 444474) overnight at 4° C. After discarding the coating solution, the tubes were blocked with 2% skim milk (ELK) in PBS (blocking buffer) for one hour at RT. In parallel, 0.5 ml of the phage library was mixed with 1 ml blocking buffer and incubated for 20 minutes at room temperature. After blocking the phages, the phage solution was added to the tetanus toxoid-coated tubes and incubated for two hours at RT on a slowly rotating platform to allow binding. Next, the tubes were washed ten times with PBS/0.05% TWEEN®-20 followed by phage elution by an incubation with 1 ml 50 mM glycine-HCl pH 2.2 ten minutes at RT on rotating wheel and directly followed by neutralization of the harvested eluent with 0.5 ml 1 M Tris-HCl pH 7.5.

Harvesting phage clones: Five ml XL1-Blue MRF (Stratagene) culture at O.D. 0.4 was added to the harvested phage solution and incubated for 30 minutes at 37° C. without shaking to allow infection of the phages. Bacteria were plated on Carbenicillin/Tetracycline 4% glucose 2*TY plates and grown overnight at 37° C.

Phage production: Phages were grown and processed as described by Kramer et al. 2003 (Kramer et al. 2003, *Nucleic Acids Res.* 31(11):e59) using VCSM13 as helper phage strain.

Phage ELISA: ELISA plates were coated with 100 microliters tetanus toxoid per well at a concentration of 2 micrograms/ml in PBS overnight at 4° C. Plates coated with 100 microliters thyroglobulin at a concentration of 2 micrograms/ml in PBS were used as a negative control. Wells were emptied, dried by tapping on a paper towel, filled completely with PBS-4% skimmed milk (ELK) and incubated for one hour at room temperature to block the wells. After discarding the block solution, phage minipreps premixed with 50 μl blocking solution were added and incubated for one hour at RT. Next five washing steps with PBS-0.05% TWEEN®-20 removed unbound phages. Bound phages were detected by incubating the wells with 100 microliters anti-M13-HRP antibody conjugate (diluted 1/5000 in blocking buffer) for one hour at room temperature. Free antibody was removed by repeating the washing steps as described above, followed by TMB substrate incubation until color development was visible. The reaction was stopped by adding 100 microliters of 2 M $H_2SO_4$ per well and analyzed on an ELISA reader at 450 nm emission wavelength (Table 2). Higher numbers indicate stronger signals and thus higher incidence of specific binding of the phage-Fab complex.

Figure 37C:
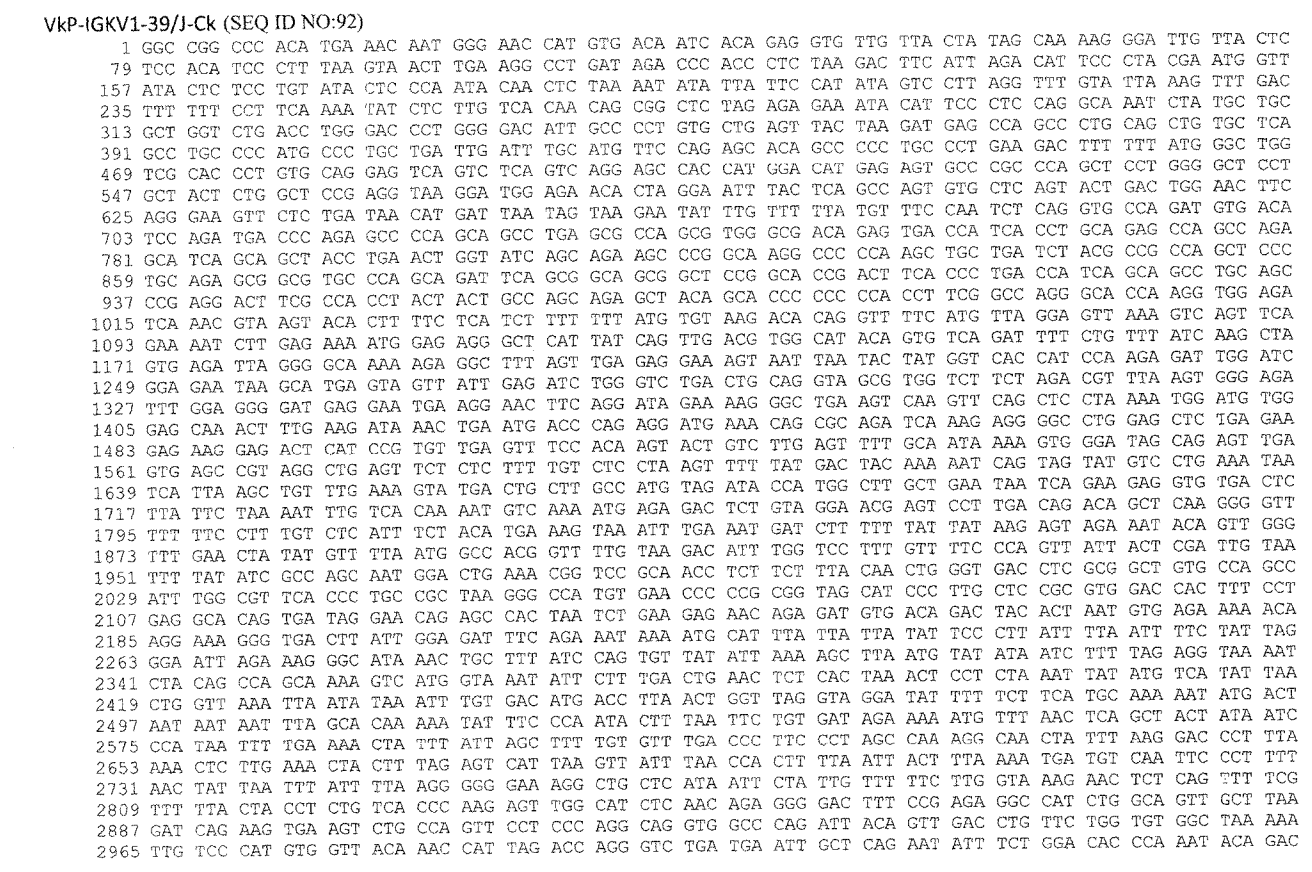
Figure 37D:
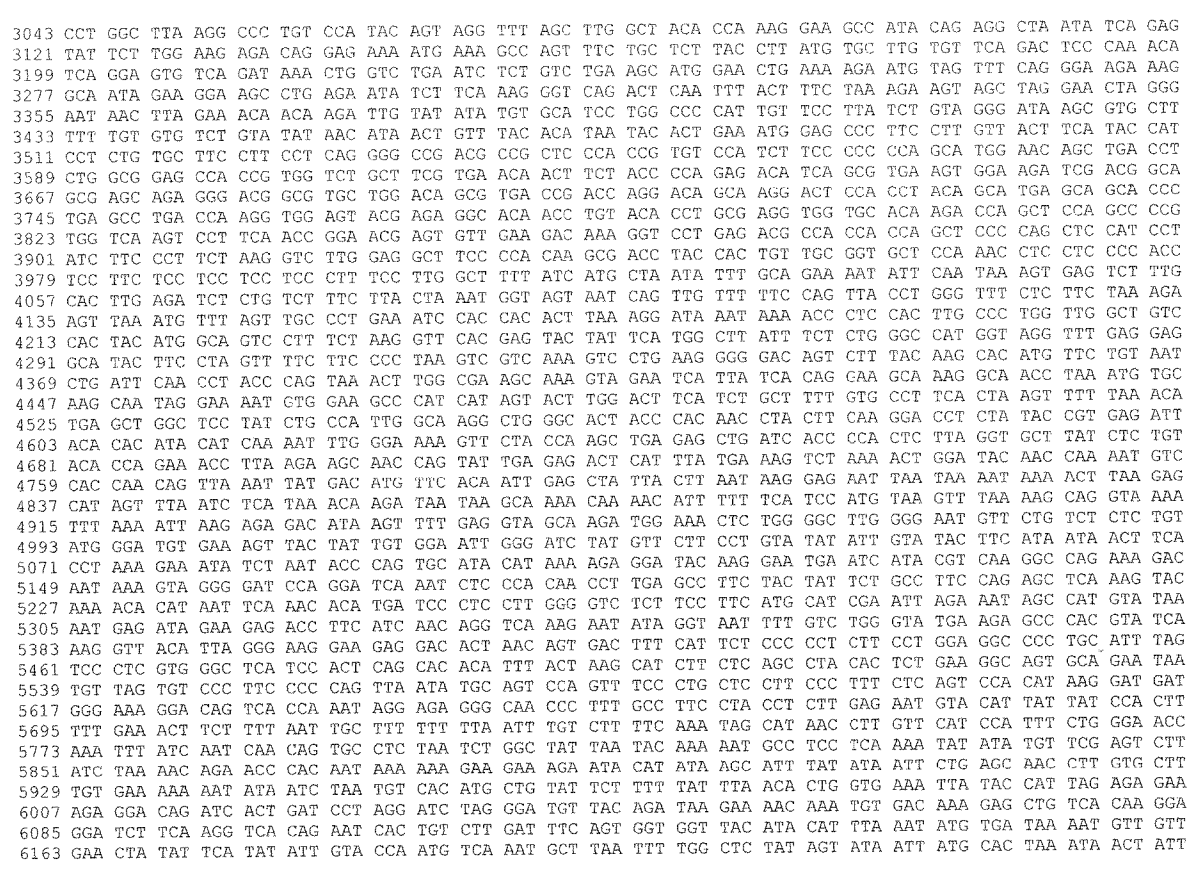
Figure 37E:
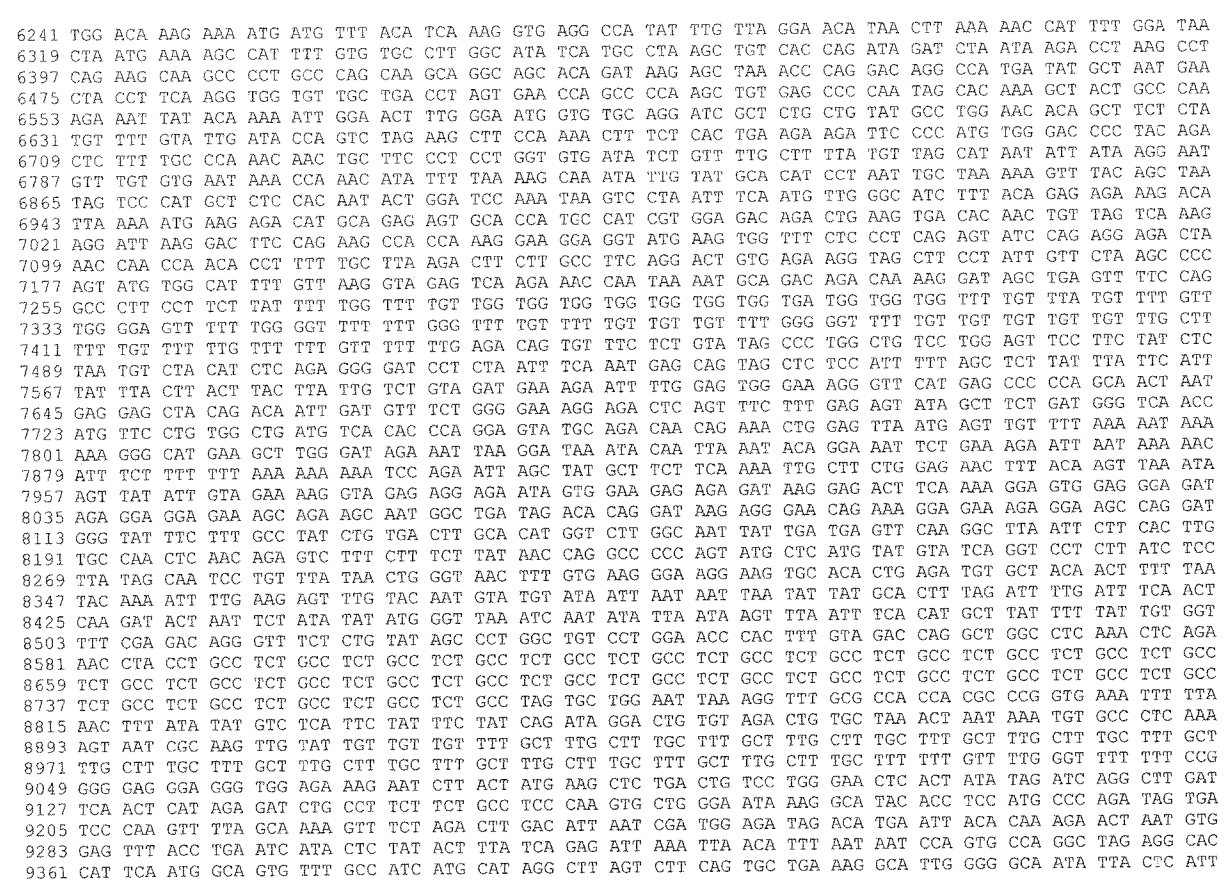
Figure 37F:
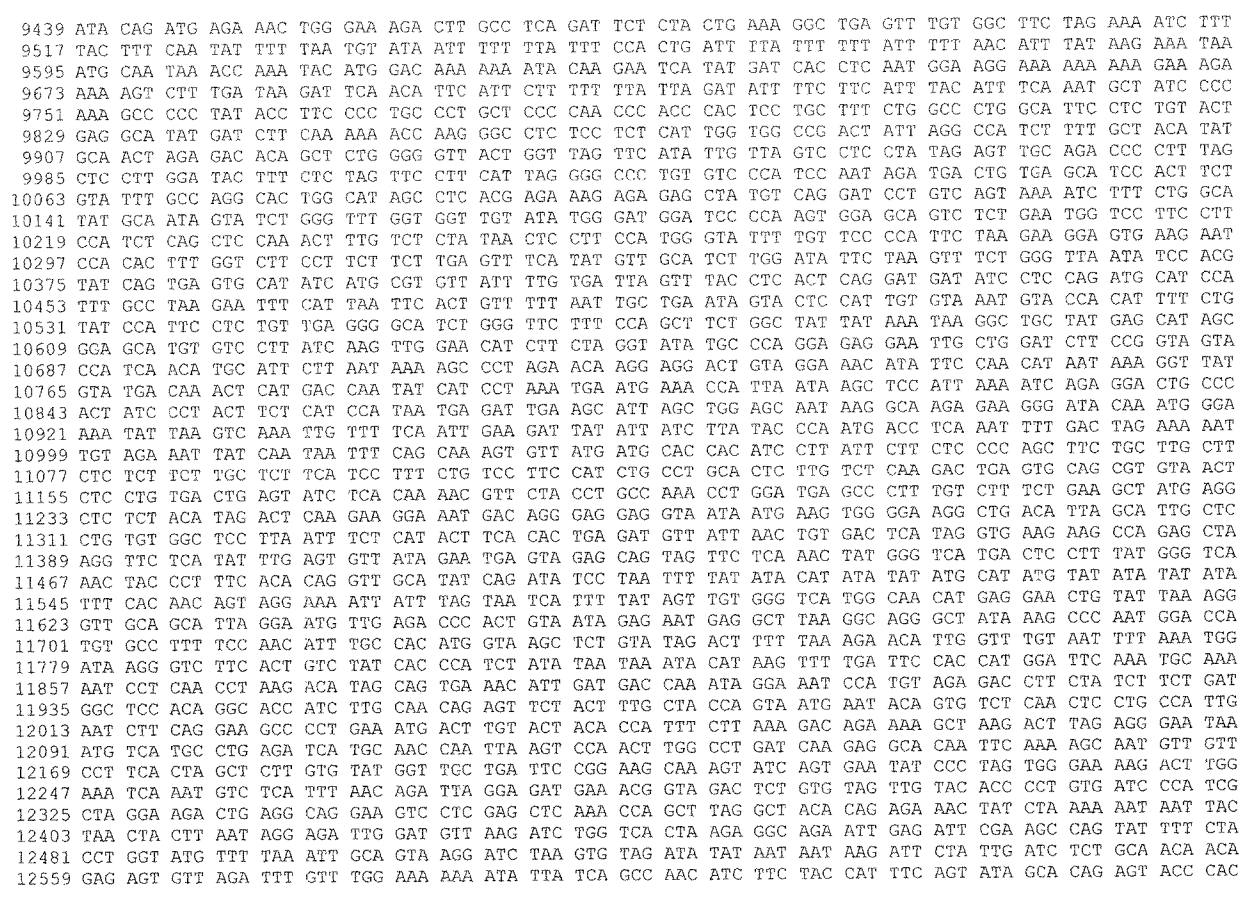
Figure 37H:
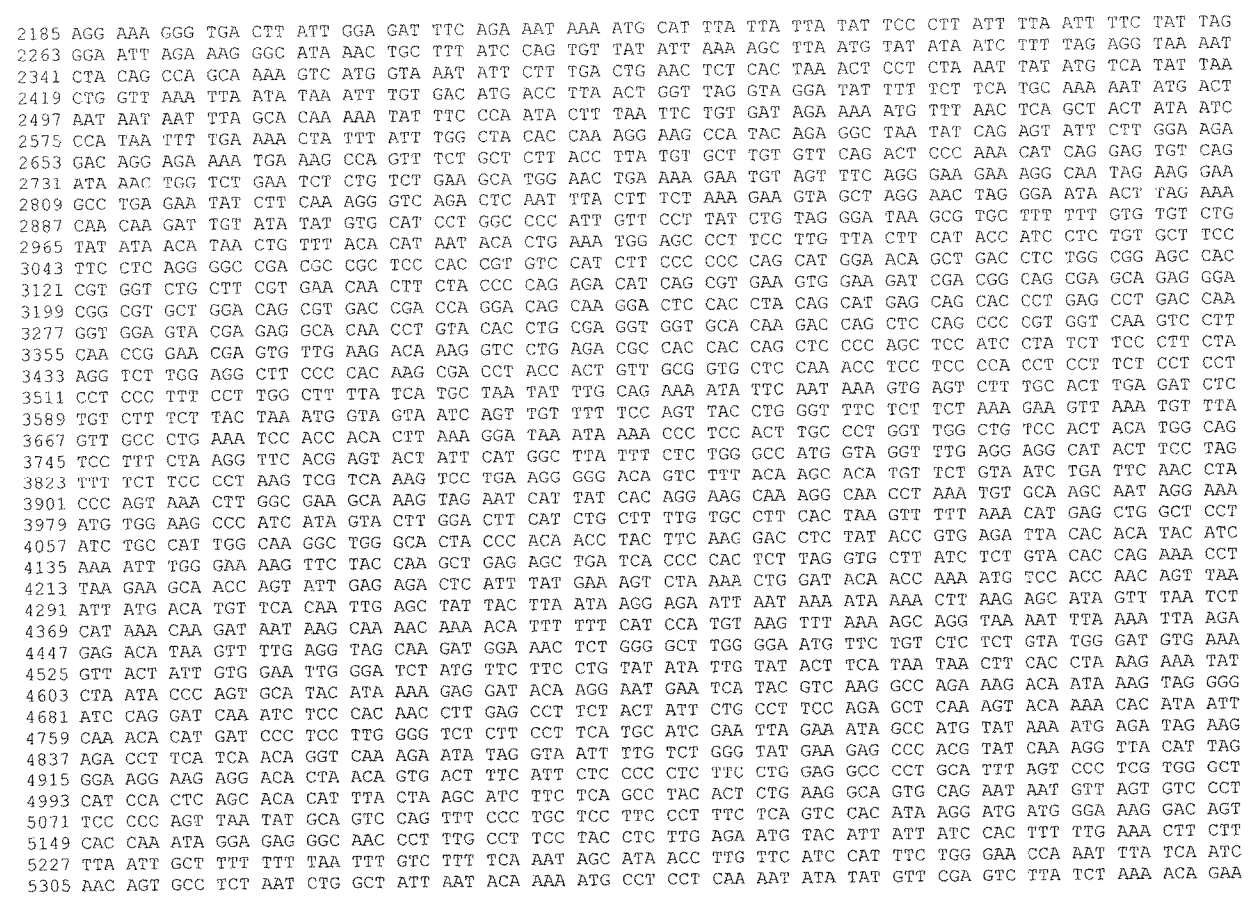
Figure 37I:
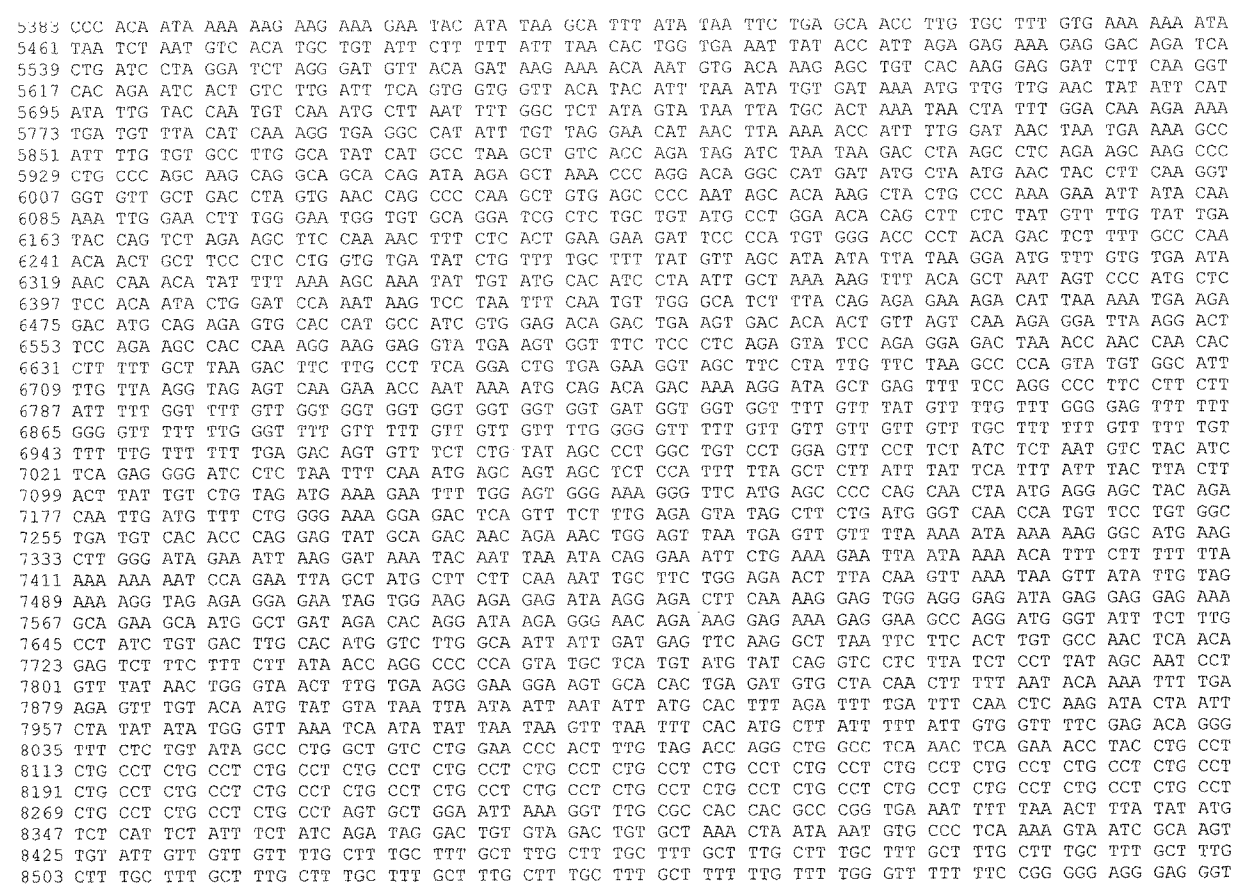
Figure 37J:
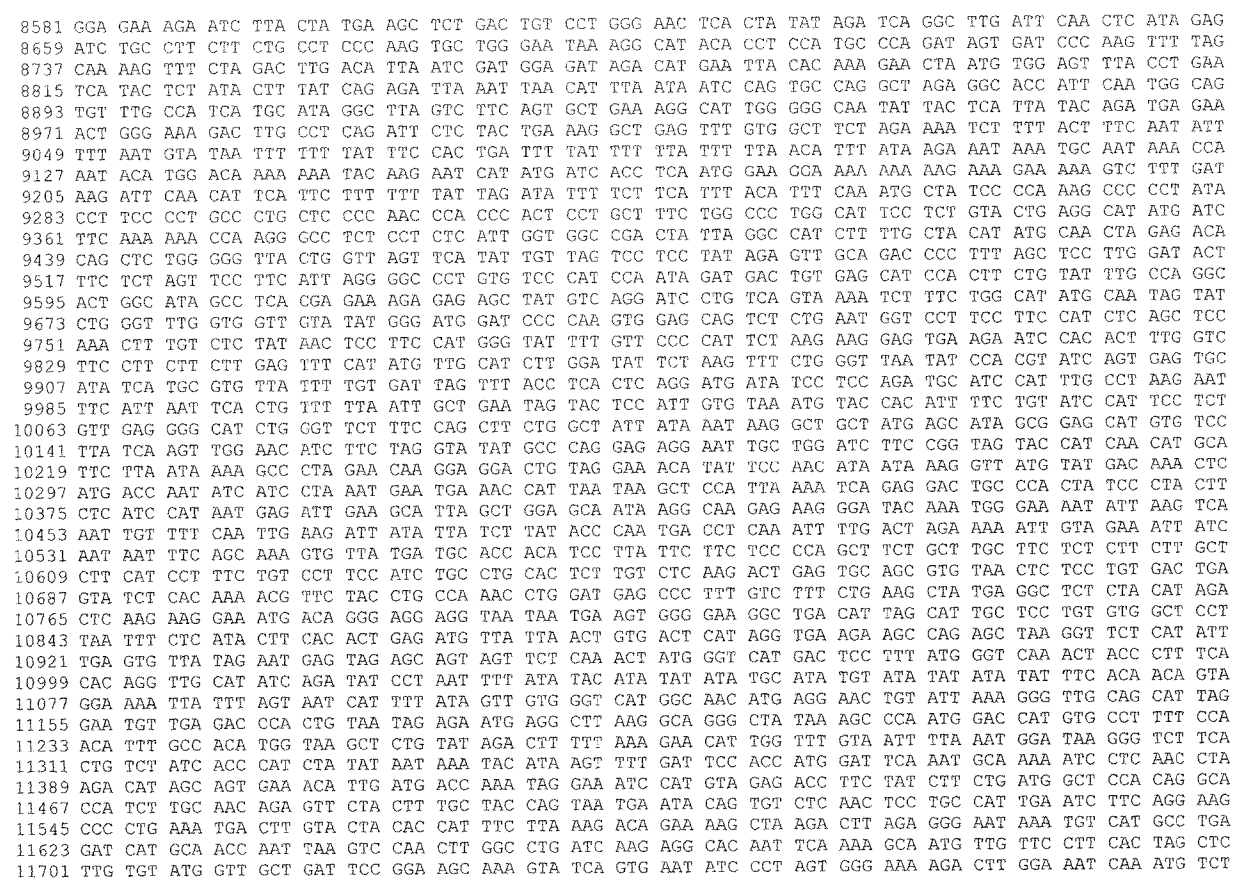
Figure 37K:
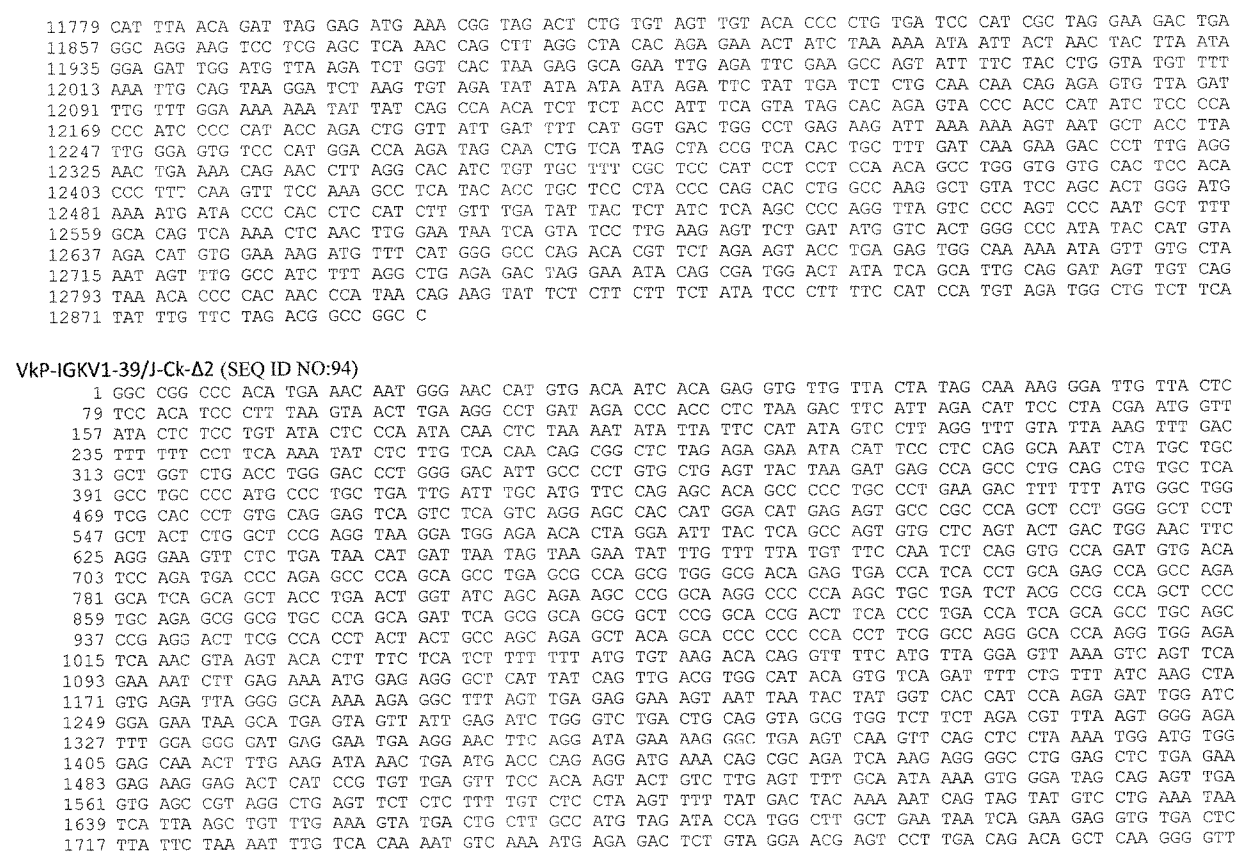
Figure 37L:
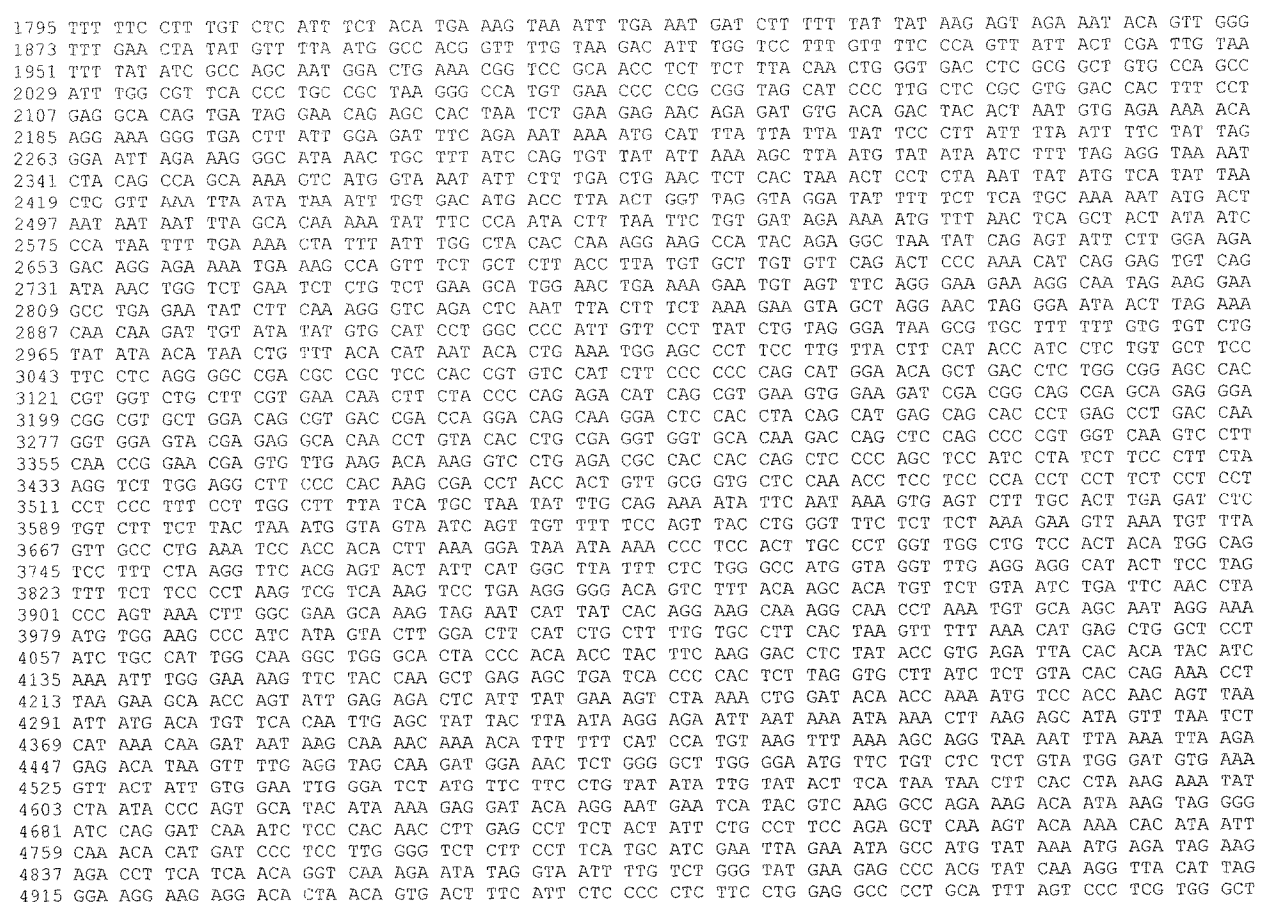
Figure 37M:
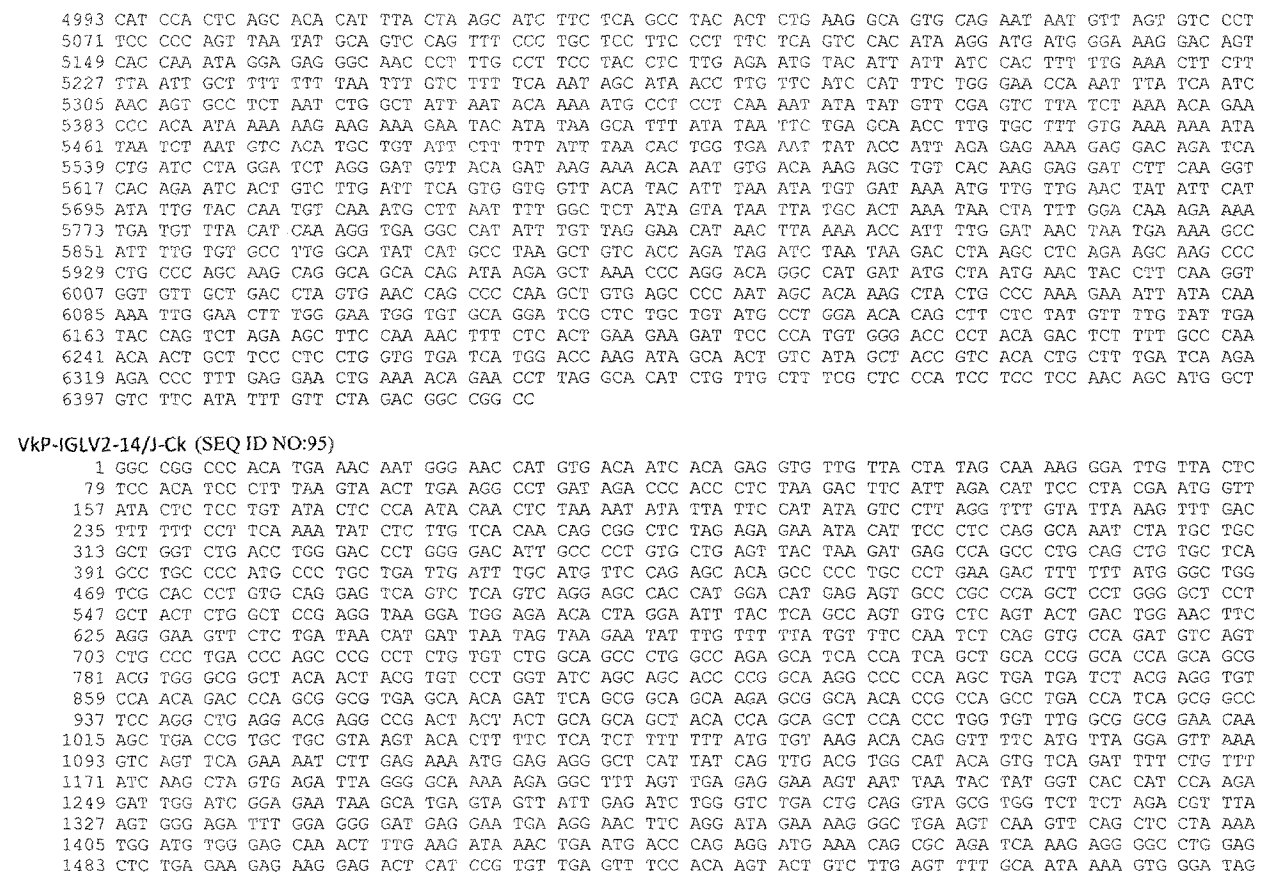
Figure 37N:
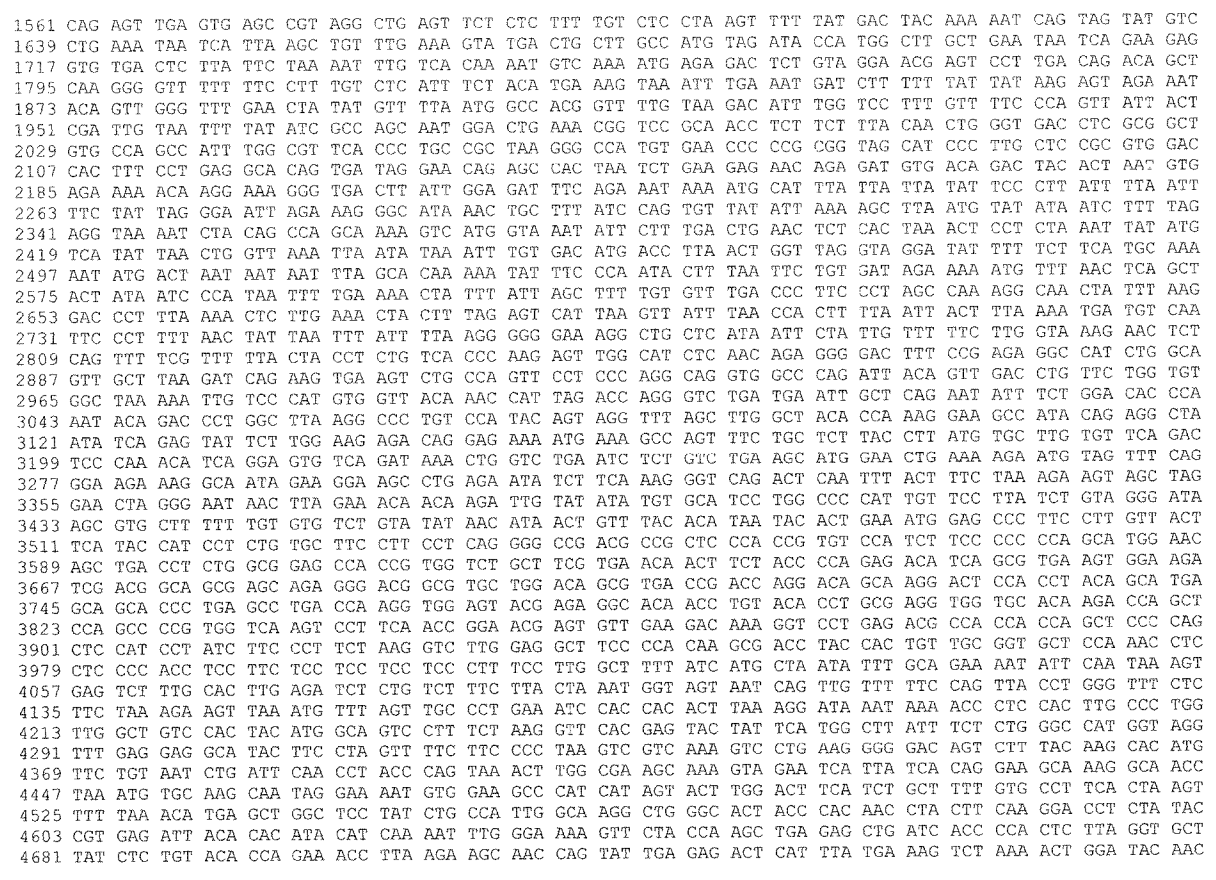
Figure 37O:
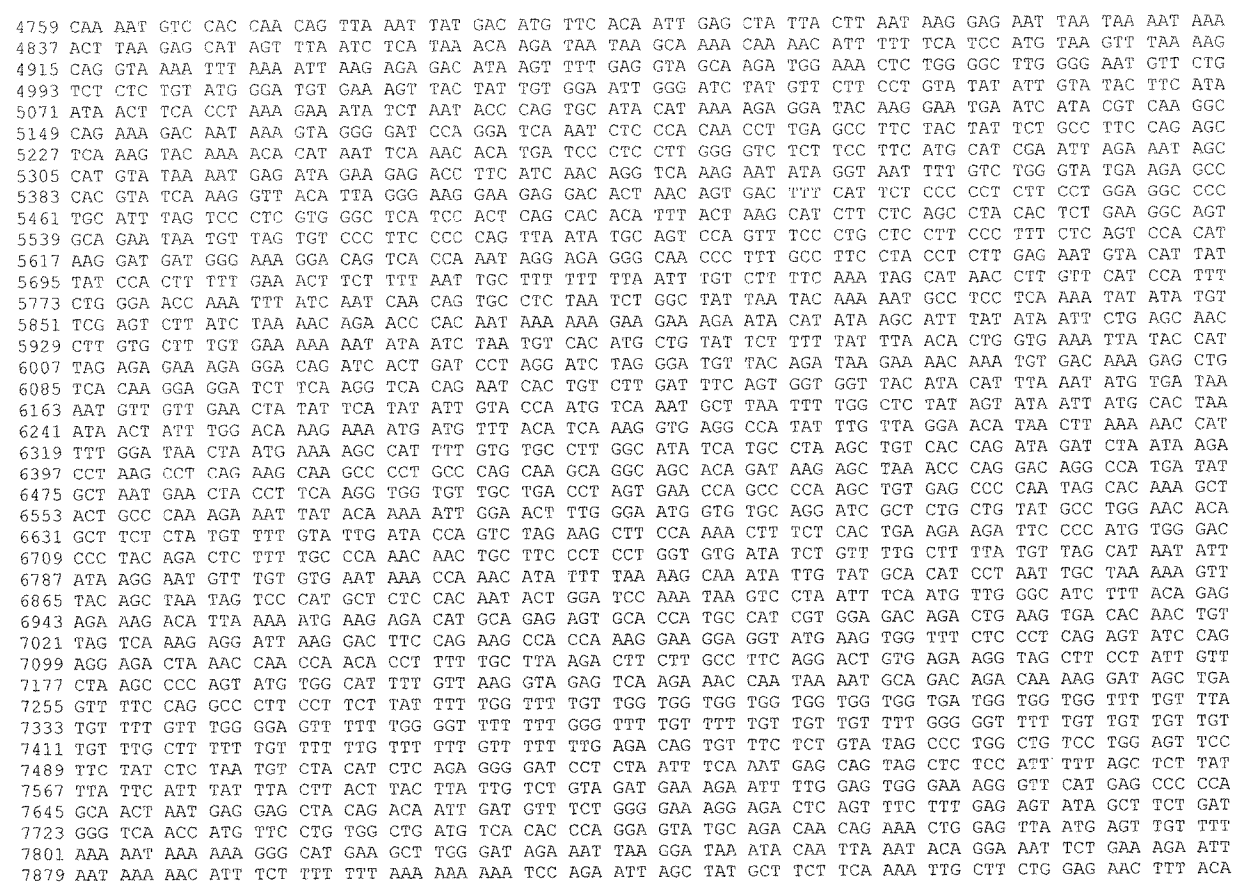
Figure 37Q:
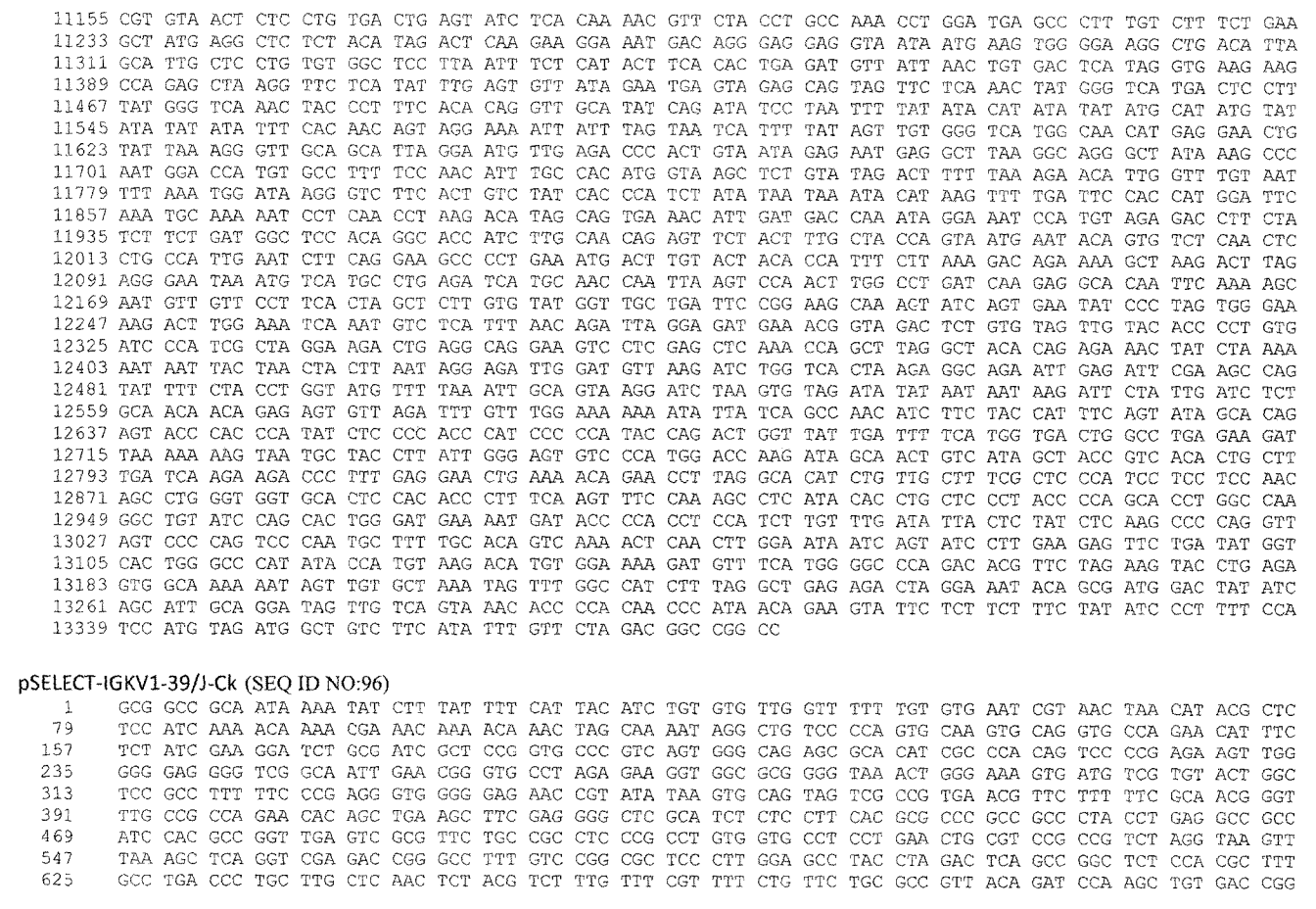
Figure 37R:
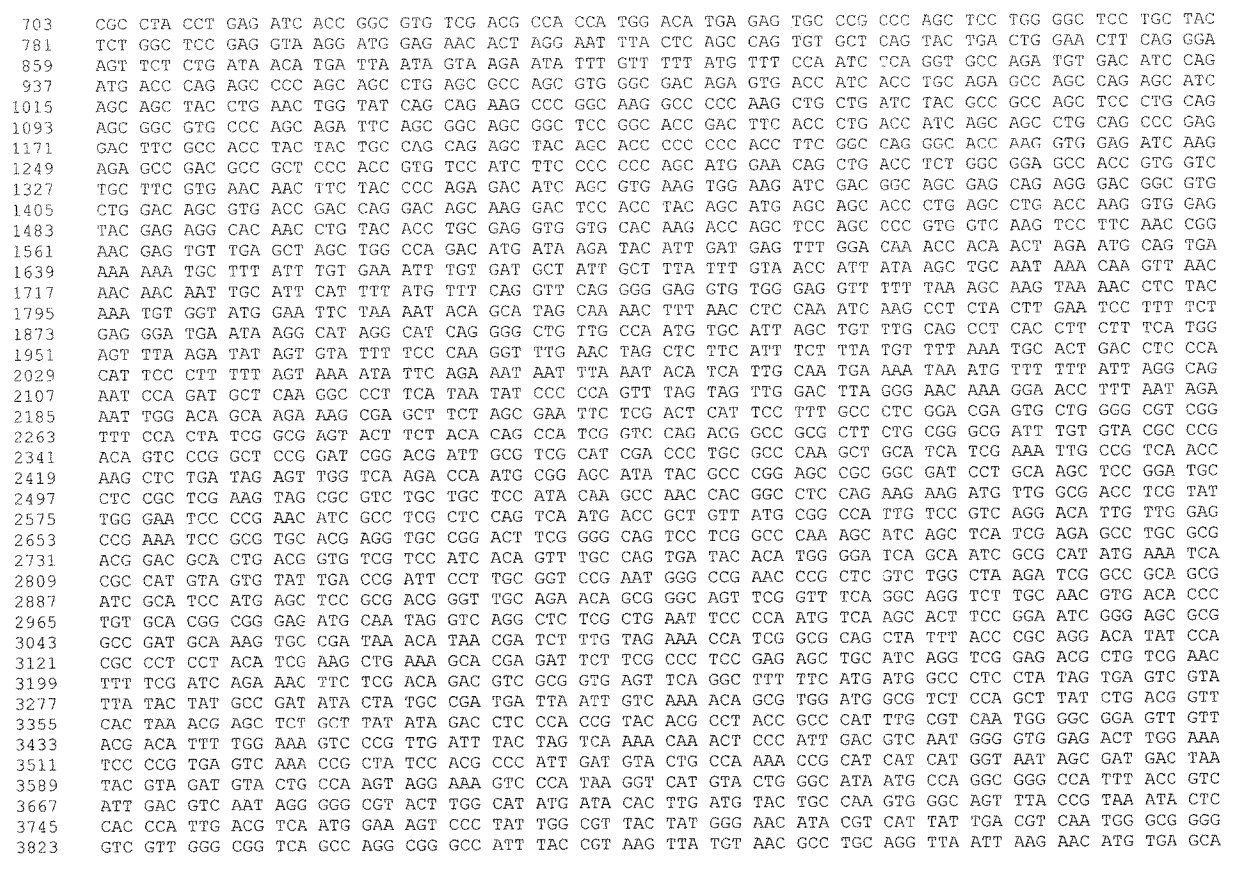
Figure 37T:
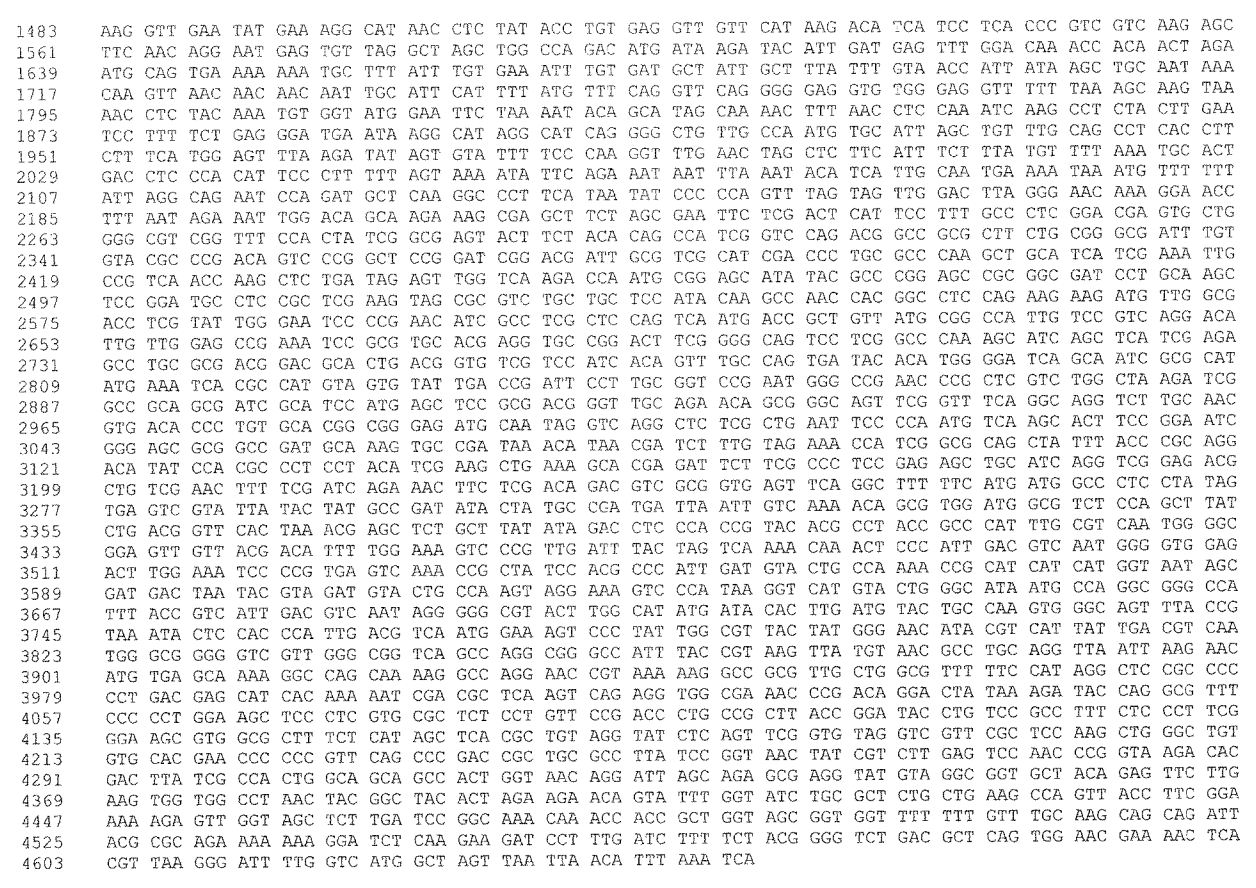
Figure 37V:
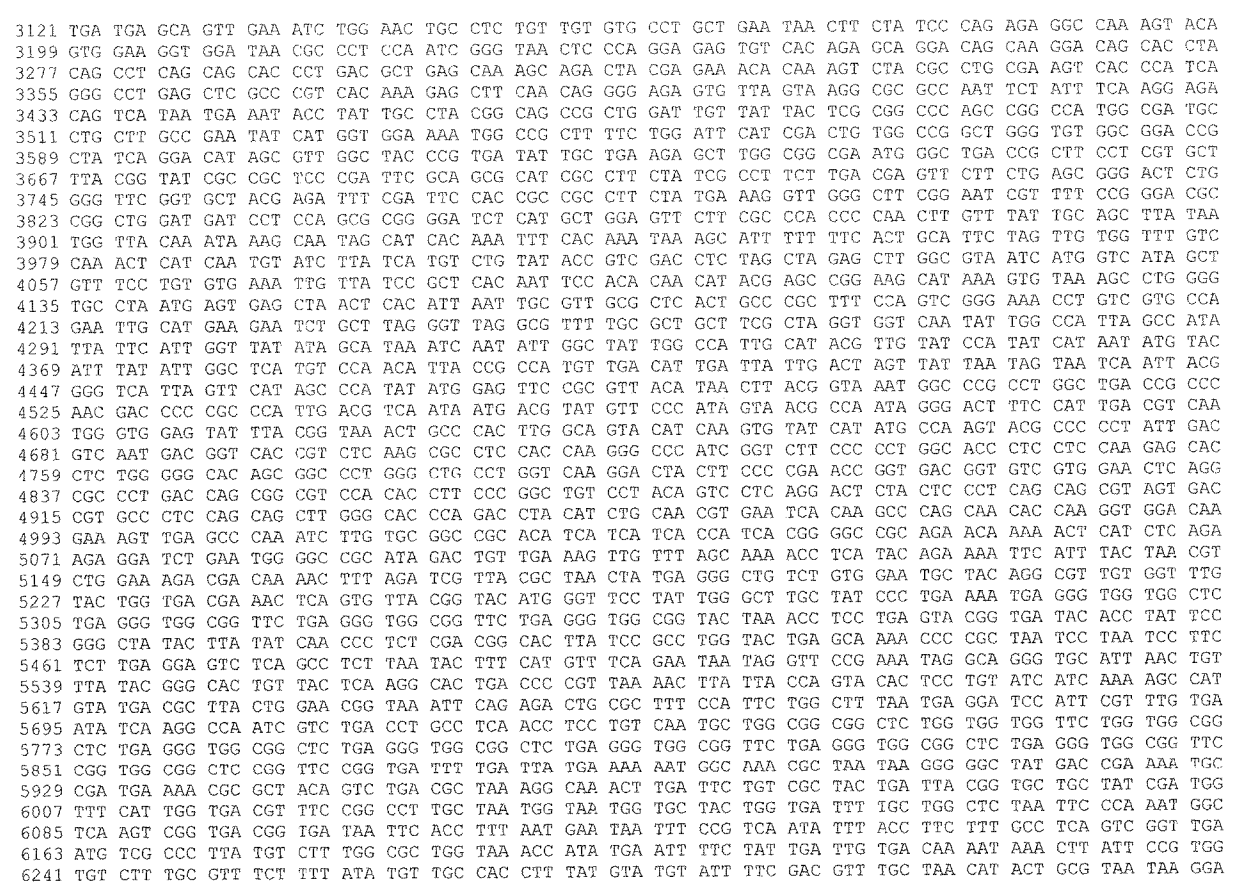
Figure 37W:
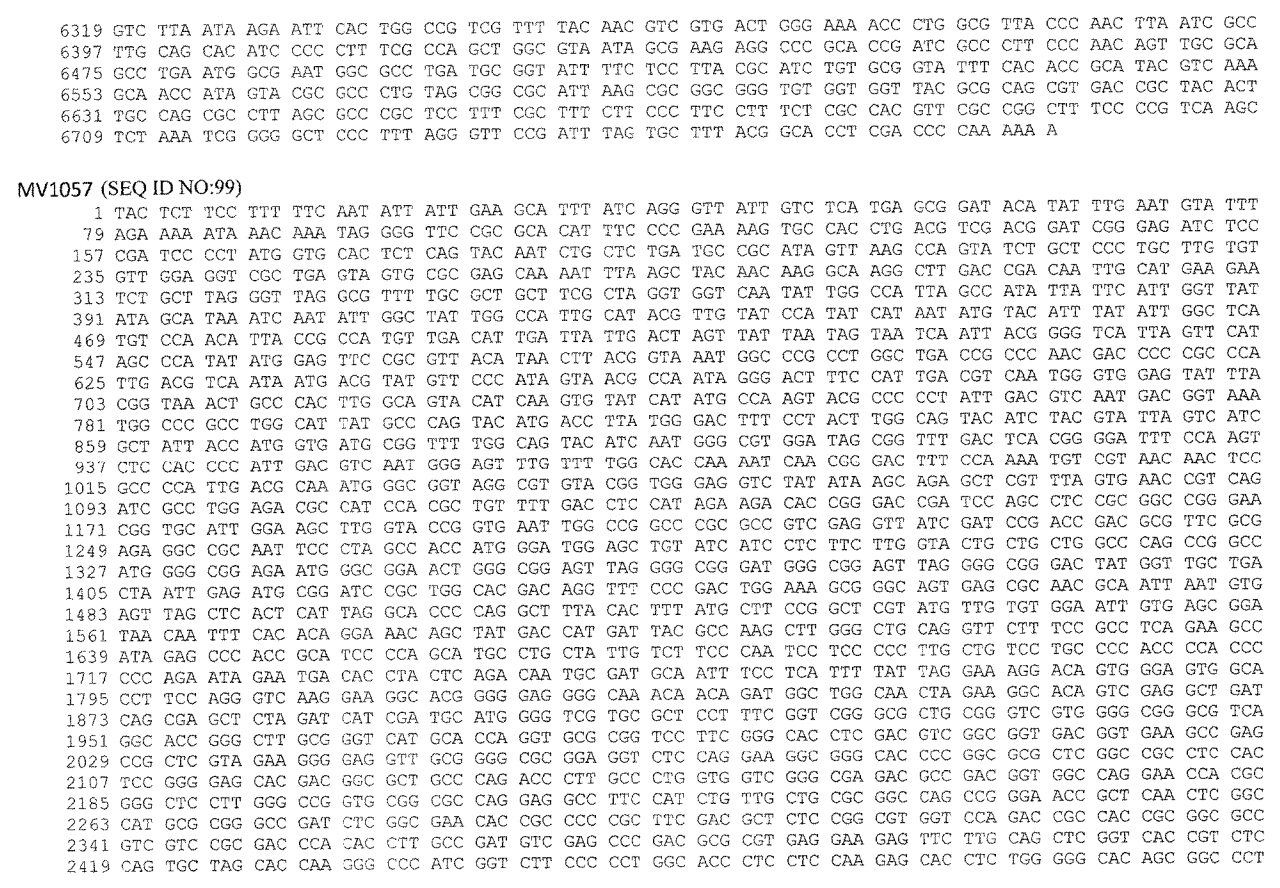
Figure 37X:
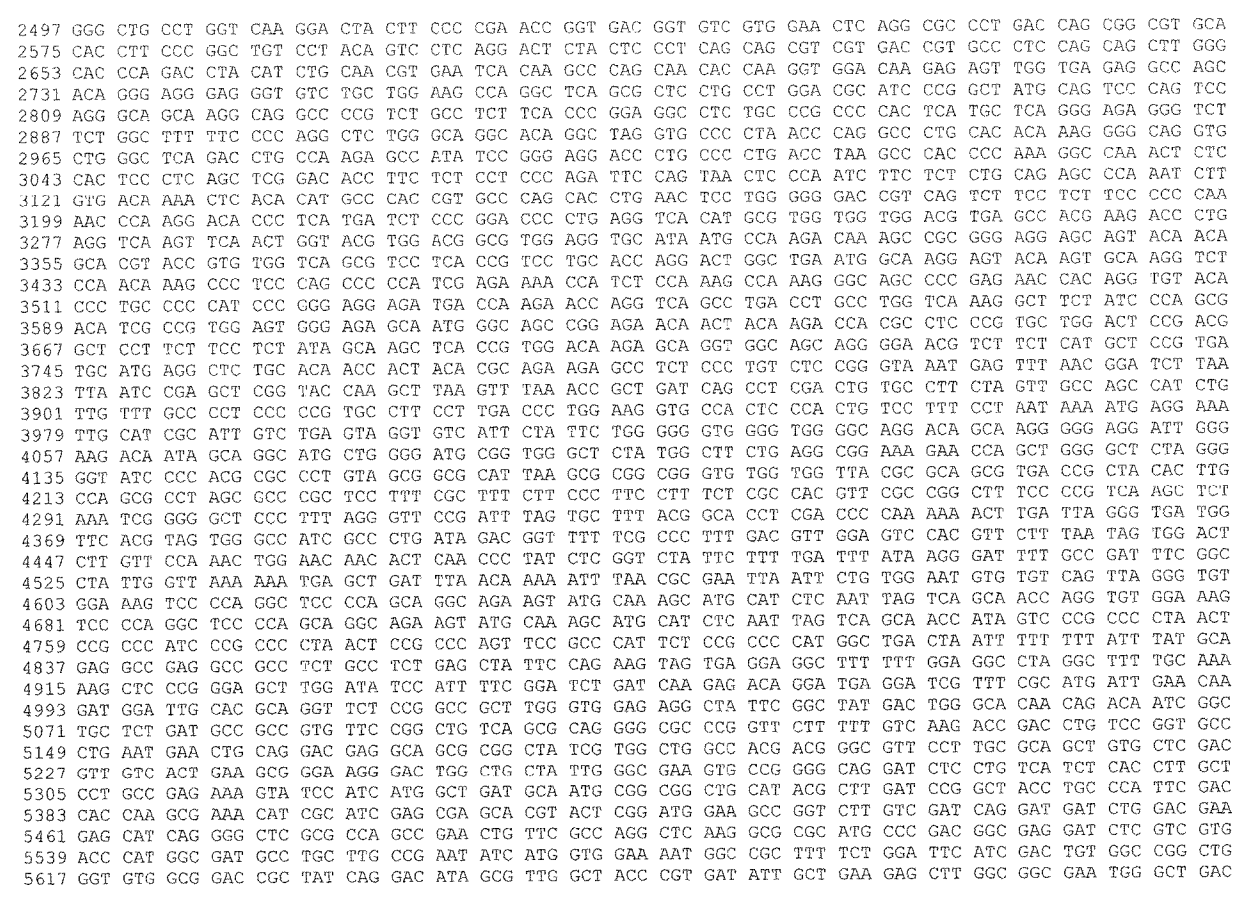
Figure 37Y:
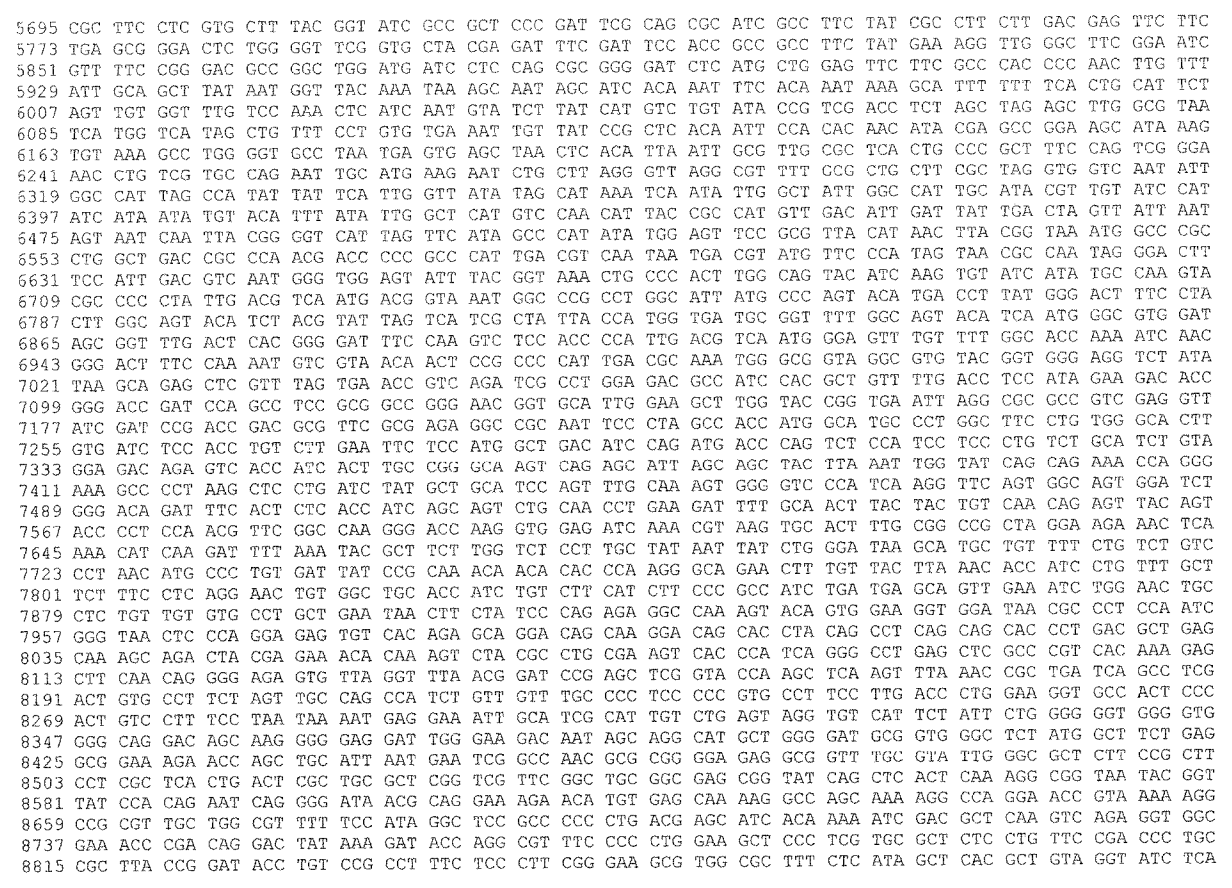

Sequencing: Clones that gave signals at least three times above the background signal (Table 2) were propagated, used for DNA miniprep procedures (see, procedures Qiagen miniPrep manual) and subjected to nucleotide sequence analysis. Sequencing was performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 28 and 37A-37Z). Mouse VH sequences of 28 tetanus toxoid binding clones are depicted in Table 3. The results show that the selected murine VH genes belong to different gene families, and different individual members from these gene families are able to pair with the rearranged human IGKV1-39/J VH region to form functional tetanus toxoid-specific antibody binding sites. From the sequence analyses, it was concluded that the murine VH regions utilize a diversity of DH and JH gene segments.

Example 27: Silencing of the Mouse Kappa Light Chain Locus

This example describes the silencing of the mouse endogenous kappa light chain locus. The endogenous kappa locus is modified by homologous recombination in ES cells, followed by the introduction of genetically modified ES cells in mouse embryos to obtain genetically adapted offspring.

Figure 29:
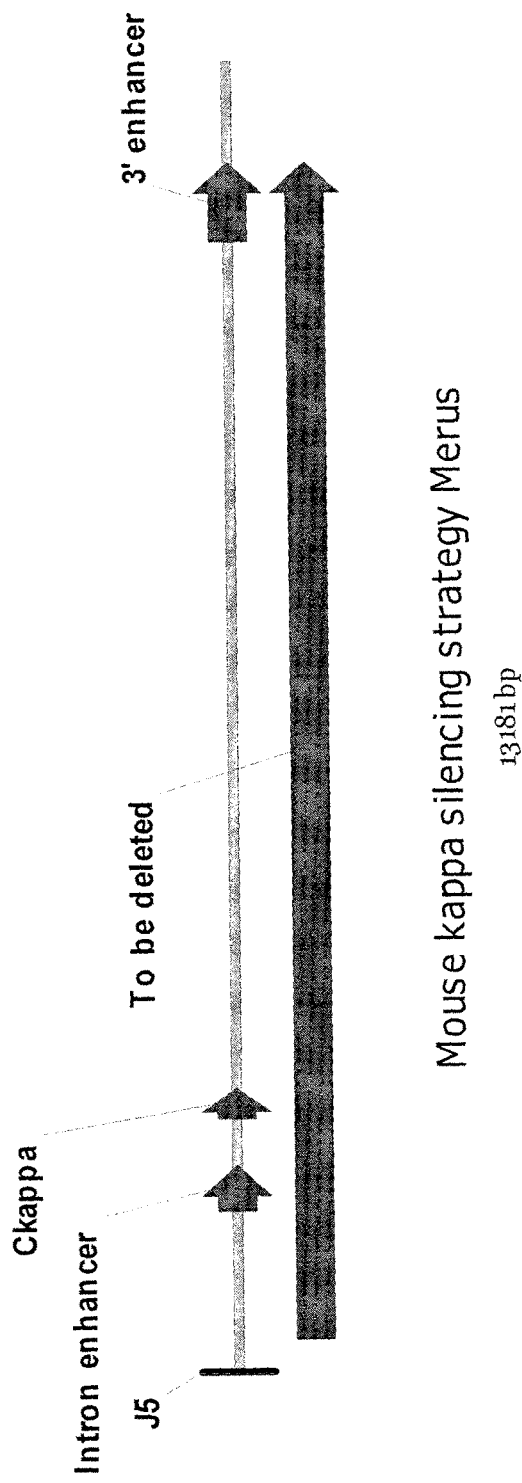
FIG. 29: The topology of the mouse Ckappa locus downstream of the J-segments. Both enhancers and Ckappa region are indicated. The lower arrow indicates the region that is removed in order to silence the locus.
Figure 43A:
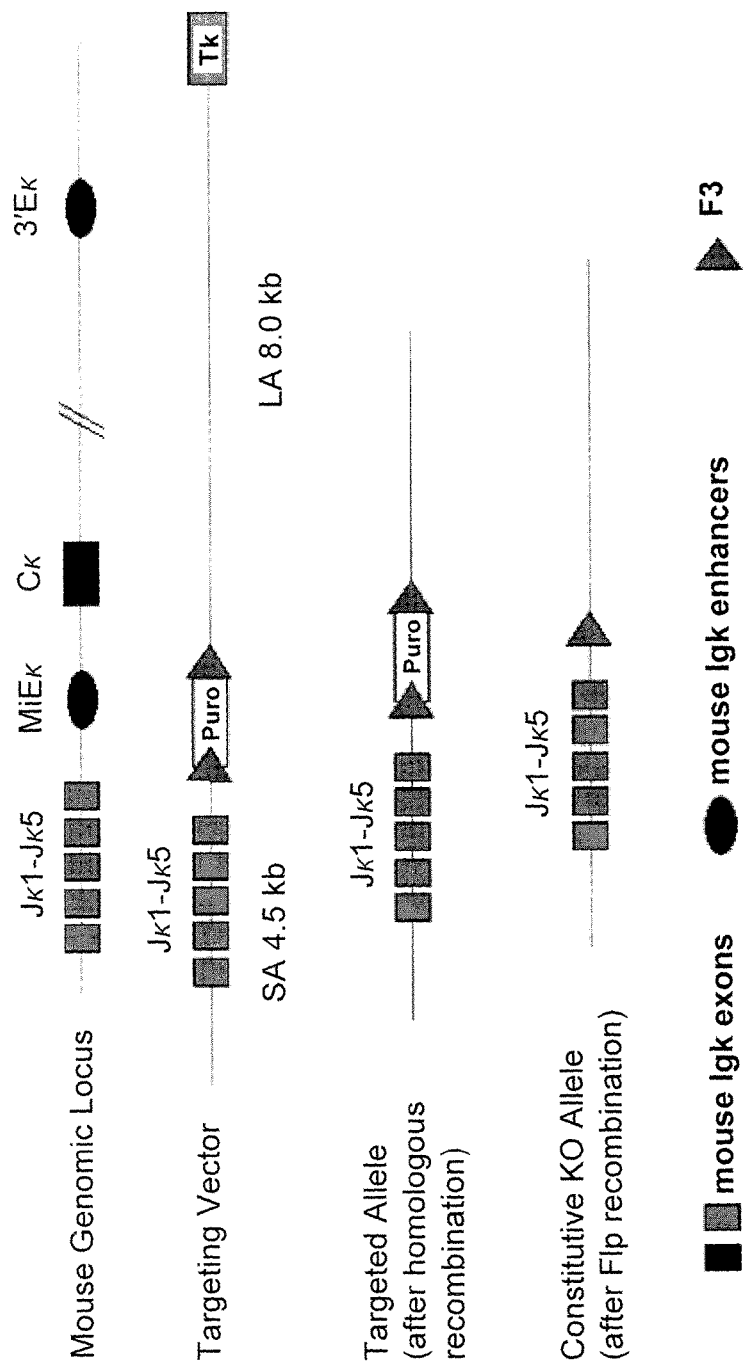
FIGS. 43A and 43B: Constitutive knock-out (KO) of the Ig kappa locus.
Figure 43B:
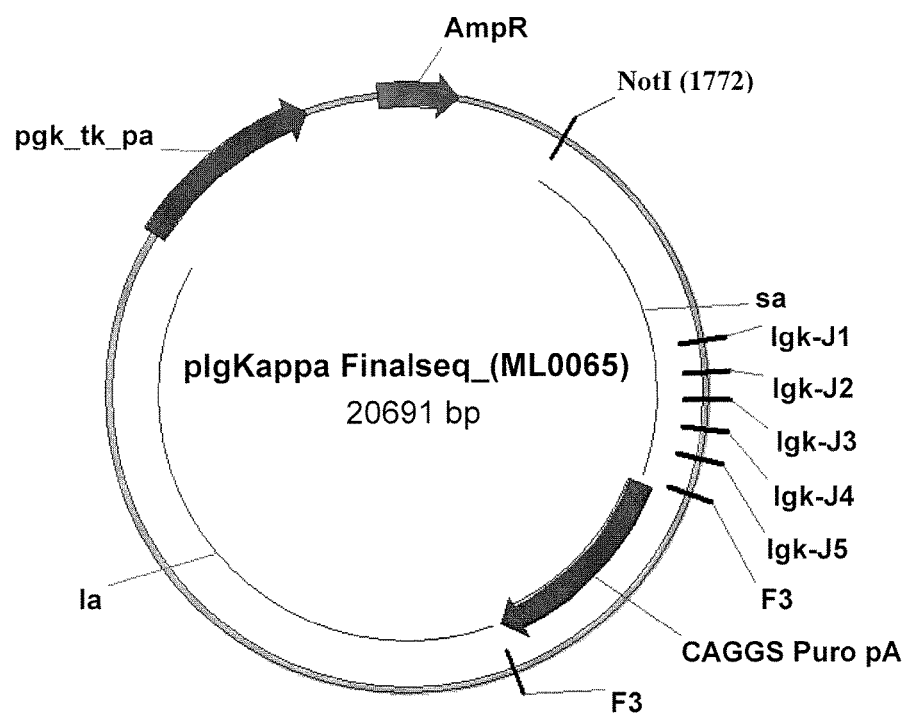

A vector that contains an assembled nucleotide sequence consisting of a part comprising the J-region to 338 bp downstream of the J5 gene segment fused to a sequence ending 3' of the 3' CK enhancer is used for homologous recombination in ES cells. The assembled sequence is used to delete a genomic DNA fragment spanning from 3' of the JK region to just 3' of the 3' CK enhancer. As a consequence of this procedure, the CK constant gene, the 3' enhancer and some intergenic regions are removed (see, FIGS. 29, 43A and 43B).

Construction of the targeting vector: A vector that received 4.5-8 kb flanking arms on the 3' and 5' end fused to the deletion segment was used for targeted homologous recombination in an ES cell line. Both arms were obtained by PCR means ensuring maximum homology. The targeting strategy allows generation of constitutive KO allele. The mouse genomic sequence encompassing the Igk intronic enhancer, Igk constant region and the Igk 3' enhancer was replaced with a PuroR cassette, which was flanked by F3 sites and inserted downstream of the Jk elements. Flp-mediated removal of the selection marker resulted in a constitutive KO allele. The replacement of the Igk MiEk-Igk C-Igk 3'E genomic region (approximately 10 kb) with a F3-Puro cassette (approx. 3 kb) was likely to decrease the efficiency of homologous recombination. Therefore, the arms of homology were extended accordingly and more ES cell colonies were analyzed after transfection in order to identify homologous recombinant clones.

Generation of ES cells bearing the deleted kappa fragment: The generation of genetically modified ES cells was essentially performed as described (Seibler et al. (2003), *Nucleic Acids Res.* February 15; 31(4):e12). See also Example 33 for a detailed description.

Generation of ES mice by tetraploid embryo complementation: The production of mice by tetraploid embryo complementation using genetically modified ES cells was essentially performed as described (Eggan et al., *PNAS* 98:6209-6214; J. Seibler et al. (2003), *Nucleic Acids Res.* February 15; 31(4):e12; Hogan et al. (1994), Summary of mouse development, *Manipulating the Mouse Embryo*, Cold Spring Harbor Laboratory Press, Cold Spring Harbor N. Y., pp. 253-289).

Example 23: Silencing of the Mouse Lambda Light Chain Locus

This Example describes the silencing of the mouse endogenous lambda light chain locus. The endogenous lambda locus is modified by homologous recombination in ES cells followed by the introduction of genetically modified ES cells in mouse embryos to obtain genetically adapted offspring.

Two regions of the murine lambda locus that together contain all functional lambda V regions are subject to deletion.

Figure 30:
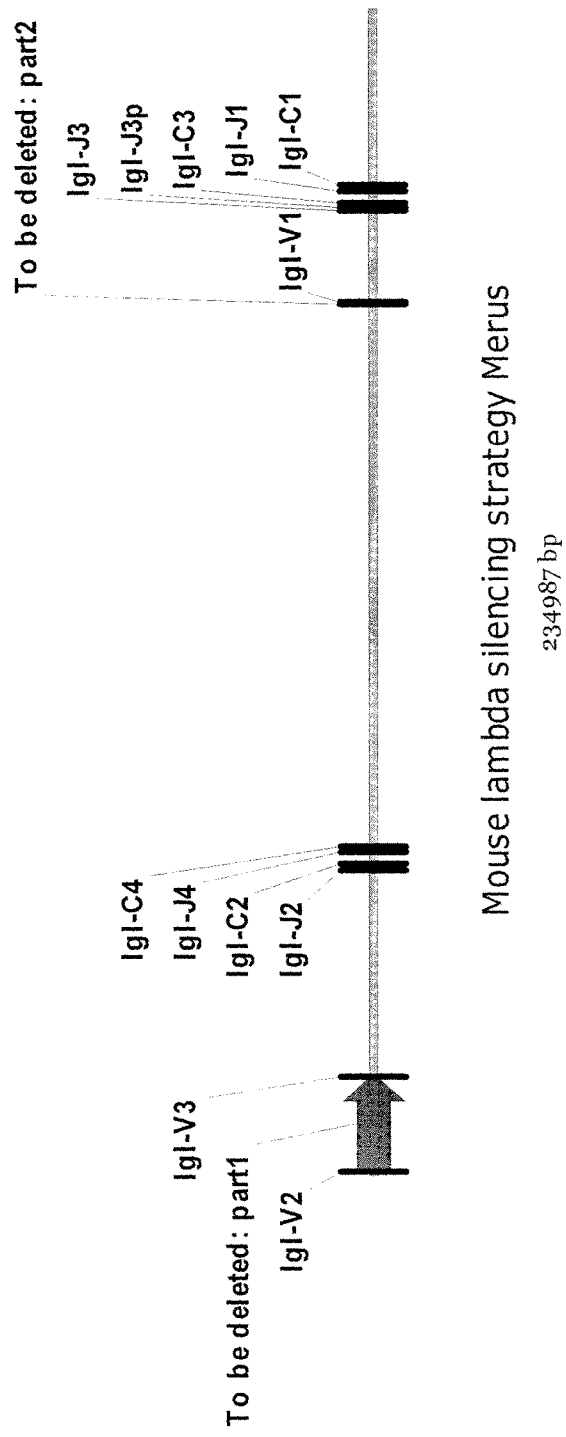
FIG. 30: The topology of the mouse C-lambda locus. All three active V-regions are indicated (Igl-V1, V2 and V3) as are the J-segments (Igl-J1, Igl-J2, Igl-J3, Igl-J4 and the pseudo segment Igl-J3p) and constant regions (Igl-C1, Igl-C2, Igl-C3 and Igl-C4). The regions that are deleted in order to silence the locus are indicated by deletion markers. These deletions include all active V genes (1, 2 and 3) and the intergenic segment between V2 and V3.
Figure 44A:
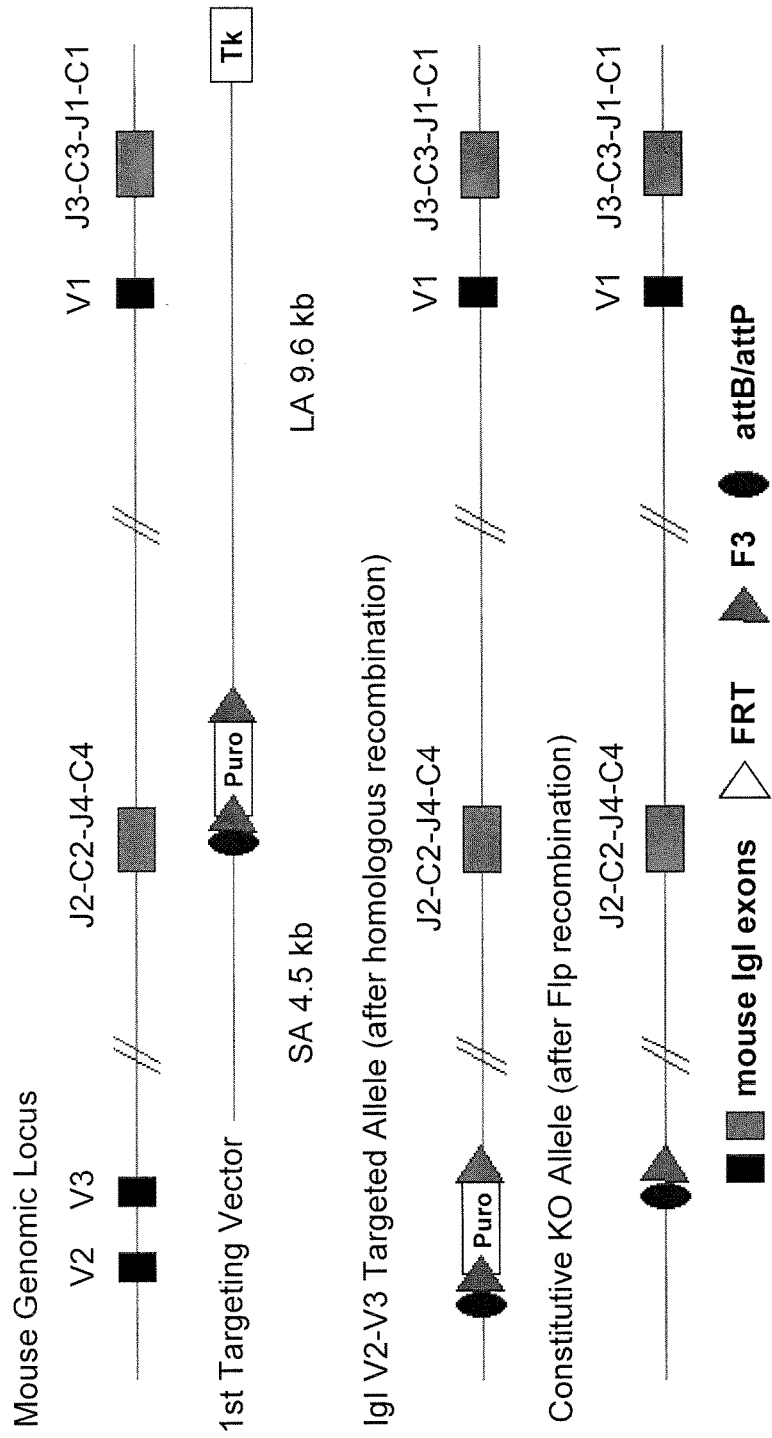
FIGS. 44A and 44B: Constitutive KO of the Ig lambda locus.
Figure 44B:
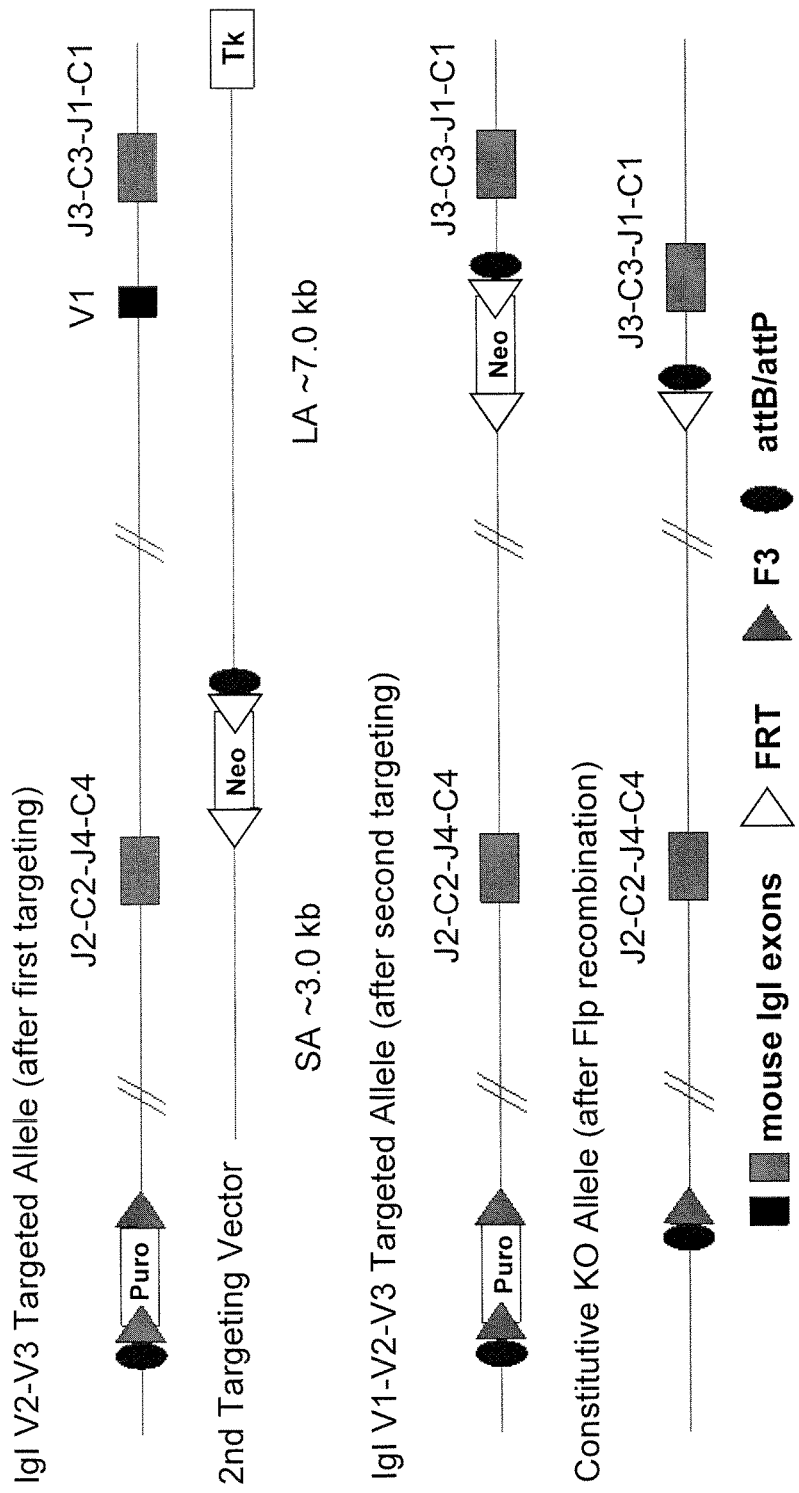

The first region targeted for homologous recombination-based deletion is a region that is located 408 bp upstream of the start site of the IGLV2 gene segment and ends 215 bp downstream of IGLV3 gene segment, including the intergenic sequence stretch between these IGLV gene segments. The second region that is subject to a deletion involves the IGLV1 gene segment consisting of a fragment spanning from 392 bp upstream to 171 bp downstream of the IGLV1 gene segment. As a consequence of these two deletion steps, all functional V-lambda genes segments are deleted, rendering the locus functionally inactive (FIGS. 30, 44A and 44B).

Construction of the Targeting Vectors

Vectors that received 3-9.6 kb flanking arms on the 3' and 5' end fused to the deletion segment were used for targeted homologous recombination in an ES cell line. Both arms were obtained by PCR means ensuring maximum homology. In a first step, the mouse genomic sequence encompassing the Igl V2-V3 regions were replaced with a PuroR cassette flanked by F3 sites, which yields a constitutive KO allele after Flp-mediated removal of selection marker (see, FIG. 44A). In a second step, the mouse genomic sequence encompassing the Igl V1 region was replaced with a Neo cassette in ES cell clones which already carried a deletion of the Igl V2-V3 regions (see, FIG. 44B). The selection marker (NeoR) was flanked by FRT sites. A constitutive KO allele was obtained after Flp-mediated removal of selection markers.

Generation of ES Cells Bearing the Deleted Lambda Fragment

The generation of genetically modified ES cells was essentially performed as described (J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Kühn, F. Schwenk (2003), *Nucleic Acids Res.*, February 15; 31(4):e12). See also, Example 33 for a detailed description. To show that both targeting events occurred on the same chromosome several double targeted clones were selected for the in vitro deletion with pCMV C31deltaCpG. The clones were expanded under antibiotic pressure on a mitotically inactivated feeder layer comprised of mouse embryonic fibroblasts in DMEM High Glucose medium containing 20% FCS (PAN) and 1200 µ/mL Leukemia Inhibitory Factor (Millipore ESG 1107). 1×10$^7$ cells from each clone were electroporated with 20 µg of circular pCMV C31deltaCpG at 240 V and 500 µF and plated on four 10 cm dishes each. Two to three days after electroporation, cells were harvested and analyzed by PCR. Primers used were:

| | | |
|---|---|---|
| 2005_5: | CCCTTTCCAATCTTTATGGG | (SEQ ID NO: 1) |
| 2005_7: | AGGTGGATTGGTGTCTTTTTCTC | (SEQ ID NO: 2) |
| 2005_9: | GTCATGTCGGCGACCCTACGCC | (SEQ ID NO: 3) |

PCR reactions were performed in mixtures comprising 5 µl PCR Buffer 10× (Invitrogen), 2 µl MgCl$_2$ (50 mM), 1 µl dNTPs (10 mM), 1 µl first primer (5 µM), 1 µl second primer (5 µM), 0.4 µl Taq (5 U/ul, Invitrogen), 37.6 µl H$_2$O, and 2 µl DNA. The program used was 95° C. for five minutes; followed by 35 cycles of 95° C. for 30 seconds; 60° C. for 30 seconds; 72° C. for 1 minute; followed by 72° C. for ten minutes.

Generation of ES mice by tetraploid embryo complementation: The production of mice by tetraploid embryo complementation using genetically modified ES cells was essentially performed as described (Eggan et al., *PNAS* 98:6209-6214; J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Kühn, and F. Schwenk (2003), *Nucleic Acids Res.*, February 15; 31(4):e12; Hogan et al. (Cold Spring Harbor Laboratory Press, Cold Spring Harbor N. Y.), pp. 253-289).

Example 24: Construction of the CAGGS Expression Insert Based on a Rearranged Human Germline IGKV1-39/J-Ck Gene (IGKV1-39/J-Ck)

Figure 31:
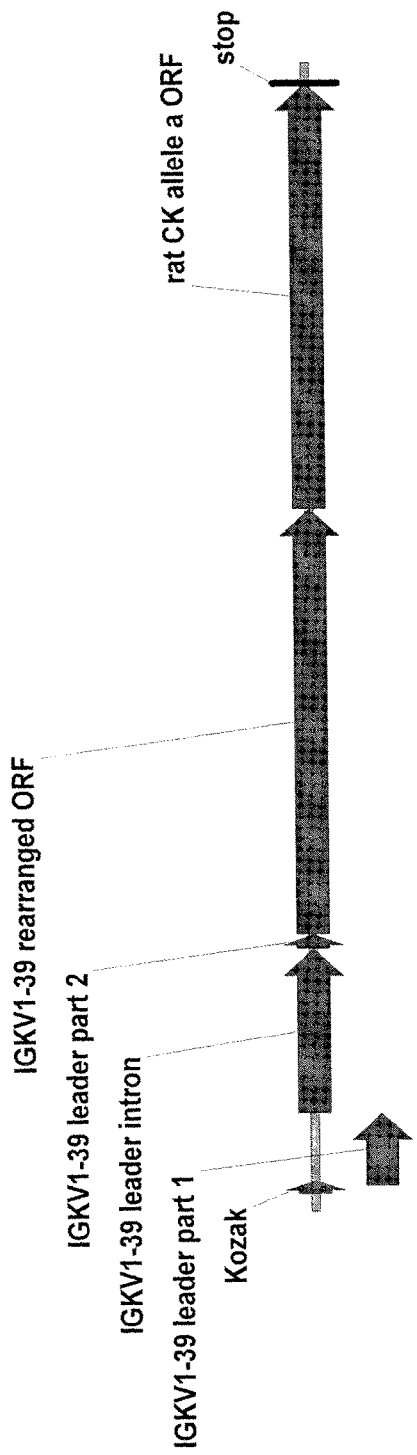
FIG. 31: Construct topology of IGKV1-39/J-Ck with an intron located in the leader open reading frame (ORF).

This example describes the construction of a CAGGS expression cassette incorporating the rearranged human germline IGKV1-39/J region. This insert expression cassette encompasses cloning sites, a Kozak sequence, a leader sequence containing an intron, an open reading frame of the rearranged IGKV1-39 region, a rat CK constant region from allele a and a translational stop sequence (IGKV1-39/J-Ck; FIG. 31). The primary construct consists of naturally occurring sequences and has been analyzed and optimized by removing undesired cis acting elements like internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions is optimized for expression in mice. The intron sequence is unchanged and thus represents the sequence identical to the coding part of the human IGKV1-39 leader intron.

Figure 38A:
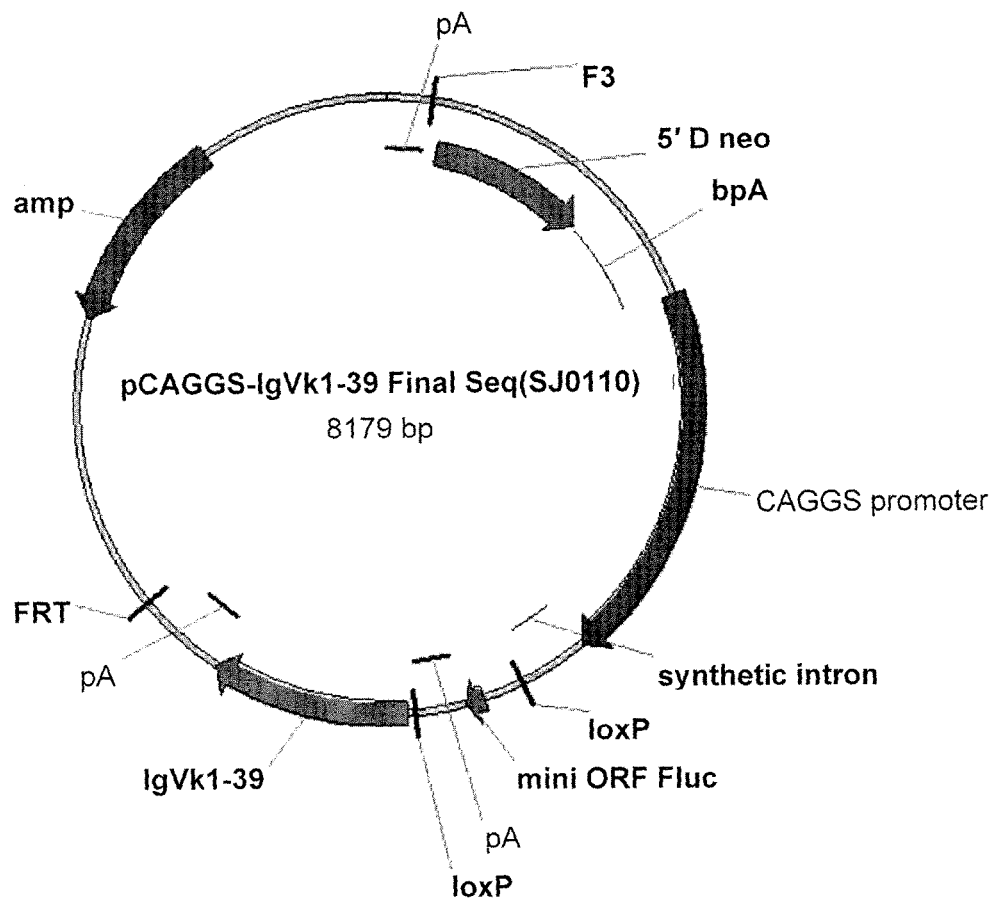
Figure 38C:
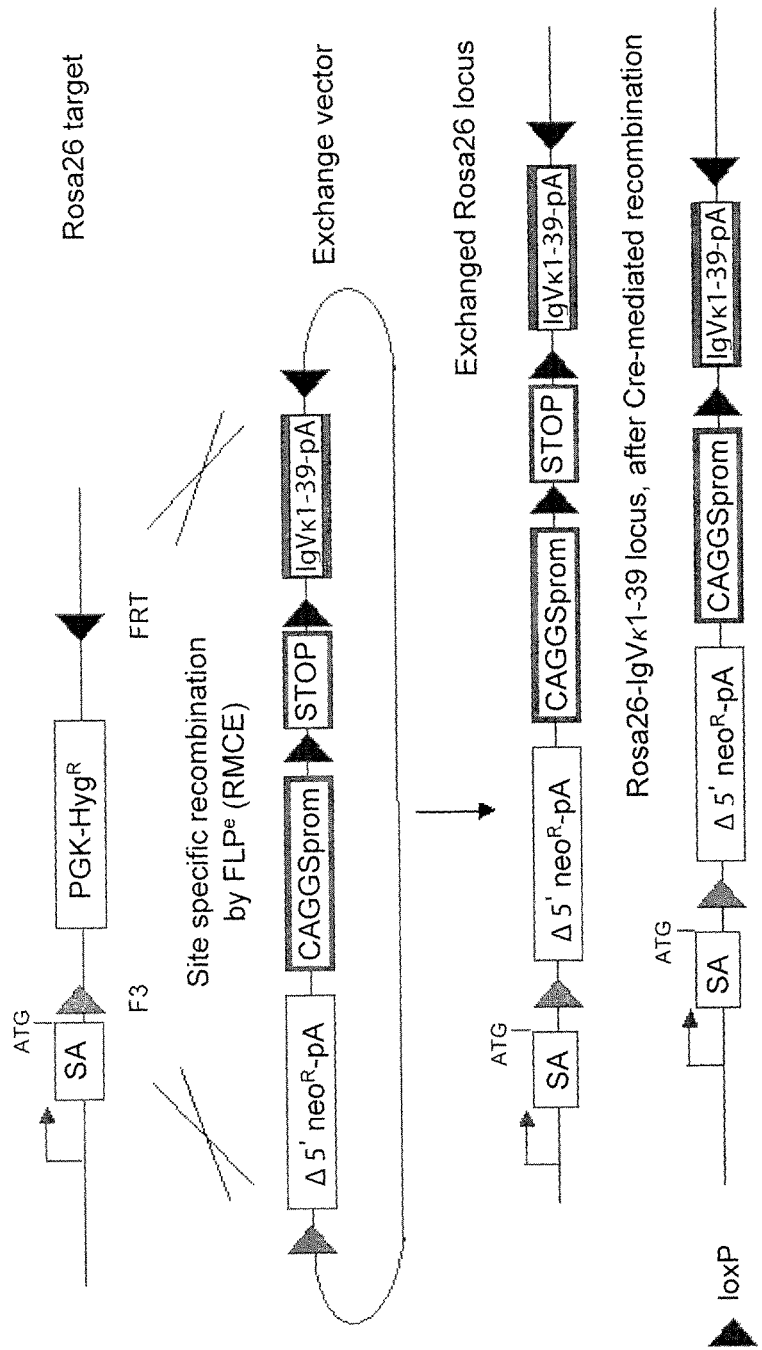

At the 5' end of the expression cassette, a NotI site was introduced and on the 3' site a NheI site. Both sites are used for cloning in the CAGGS expression module. After gene assembly according to methods used by GeneArt, the insert is digested with NotI-NheI and cloned into the expression module containing a CAGGS promoter, a stopper sequence flanked by LoxP sites ("floxed"), a polyadenylation signal sequence and, at the 5' and 3' end, sequences to facilitate homologous recombination into the Rosa26 locus of mouse ES cell lines. Promoter and/or cDNA fragments were amplified by PCR, confirmed by sequencing and/or cloned directly from delivered plasmids into an RMCE exchange vector harboring the indicated features. A schematic drawing and the confirmed sequence of the final targeting vector pCAGGS-IgVK1-39 are shown in FIGS. 38A-38B-4. The targeting strategy is depicted in FIG. 38C.

Example 25: CAGGS Expression Insert Based on the Rearranged Germline IGLV2-14/J V Lambda Region (IGLV2-14/J-Ck)

This example describes the sequence and insertion of an expression cassette incorporating the rearranged germline IGLV2-14/J V lambda region. This insert encompasses cloning sites, a Kozak sequence, a leader sequence containing an intron, an open reading frame of the rearranged IGLV2-14/J region, a rat CK constant region from allele a and a translational stop sequence (IGLV2-14/J-Ck; FIG. 32). The primary construct consists of naturally-occurring sequences and has been analyzed and optimized by removing undesired cis acting elements like: internal TATA-boxes, poly adenylation signals, chi-sites, ribosomal entry sites, AT-rich or GC-rich sequence stretches, ARE-, INS- and CRS sequence elements, repeat sequences, RNA secondary structures, (cryptic) splice donor and acceptor sites and splice branch points (GeneArt GmbH). In addition, the codon usage in the open reading frame regions was optimized for expression in mice. The intron sequence is unchanged and thus represents the sequence identical to the human IGKV1-39 leader intron.

Figure 40A:
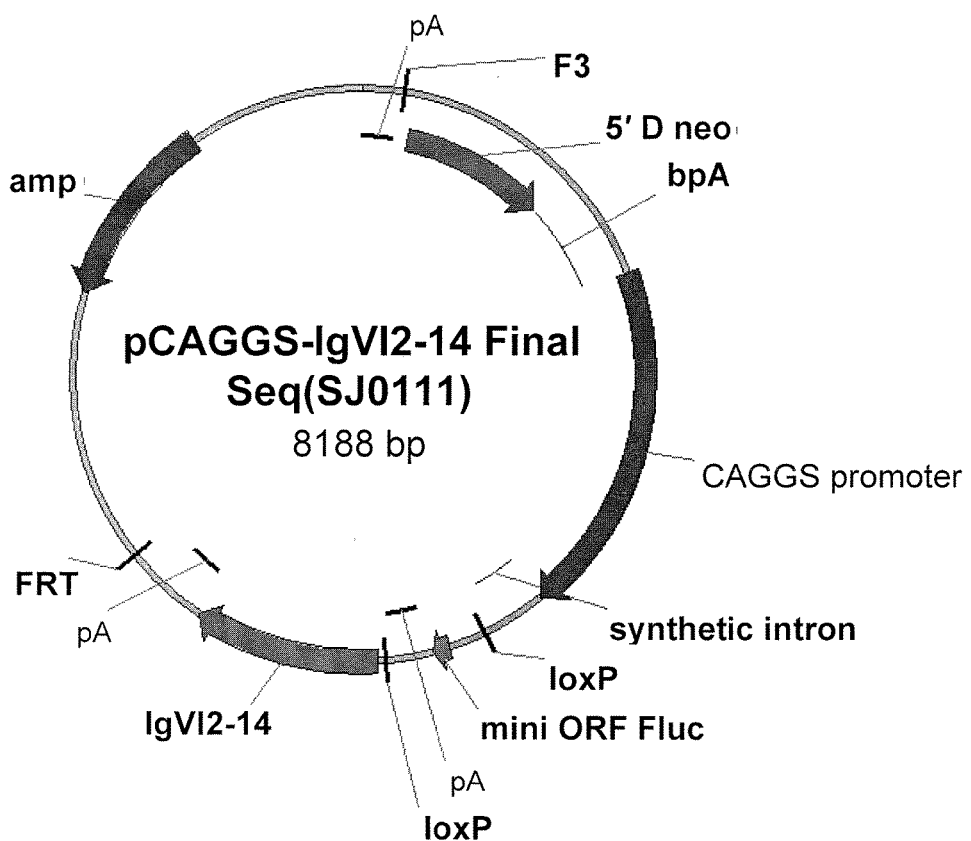
Figure 40C:
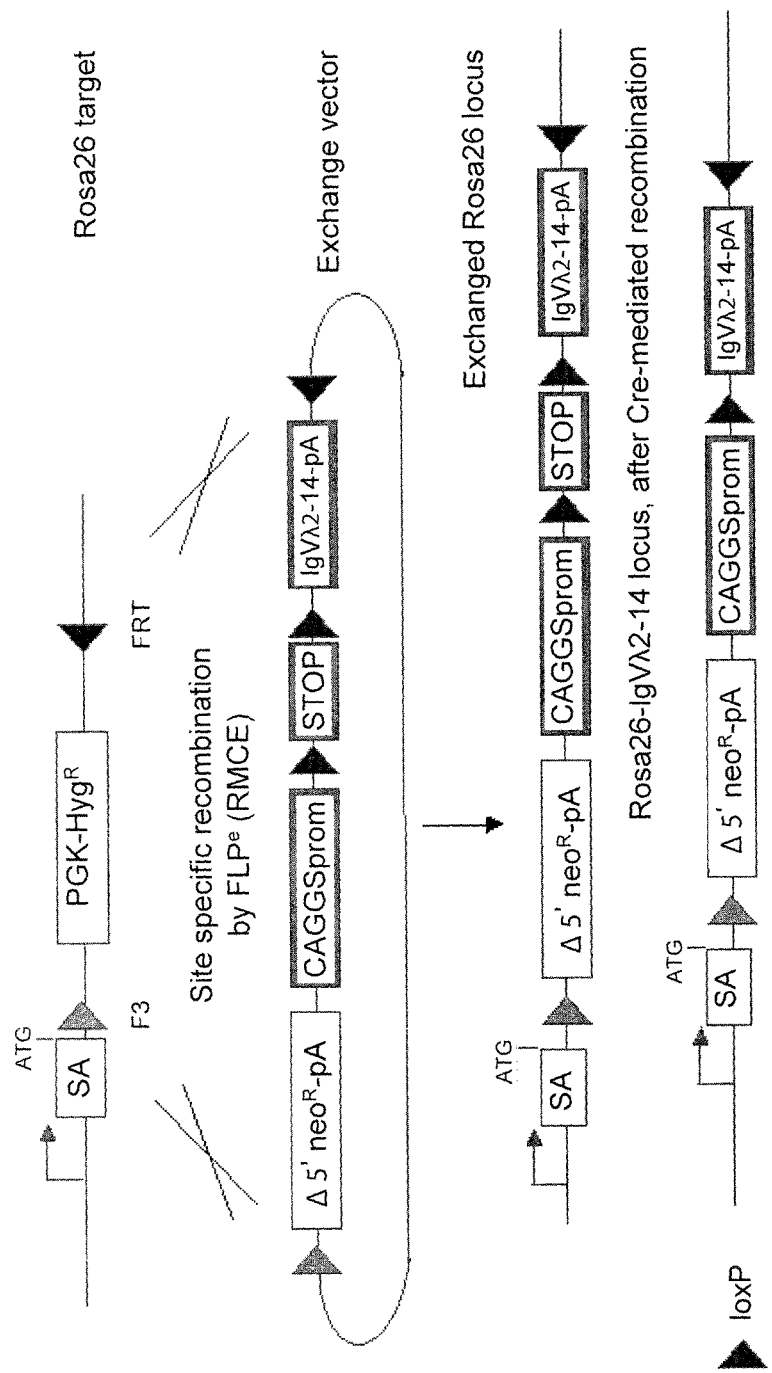
Figure 41A:
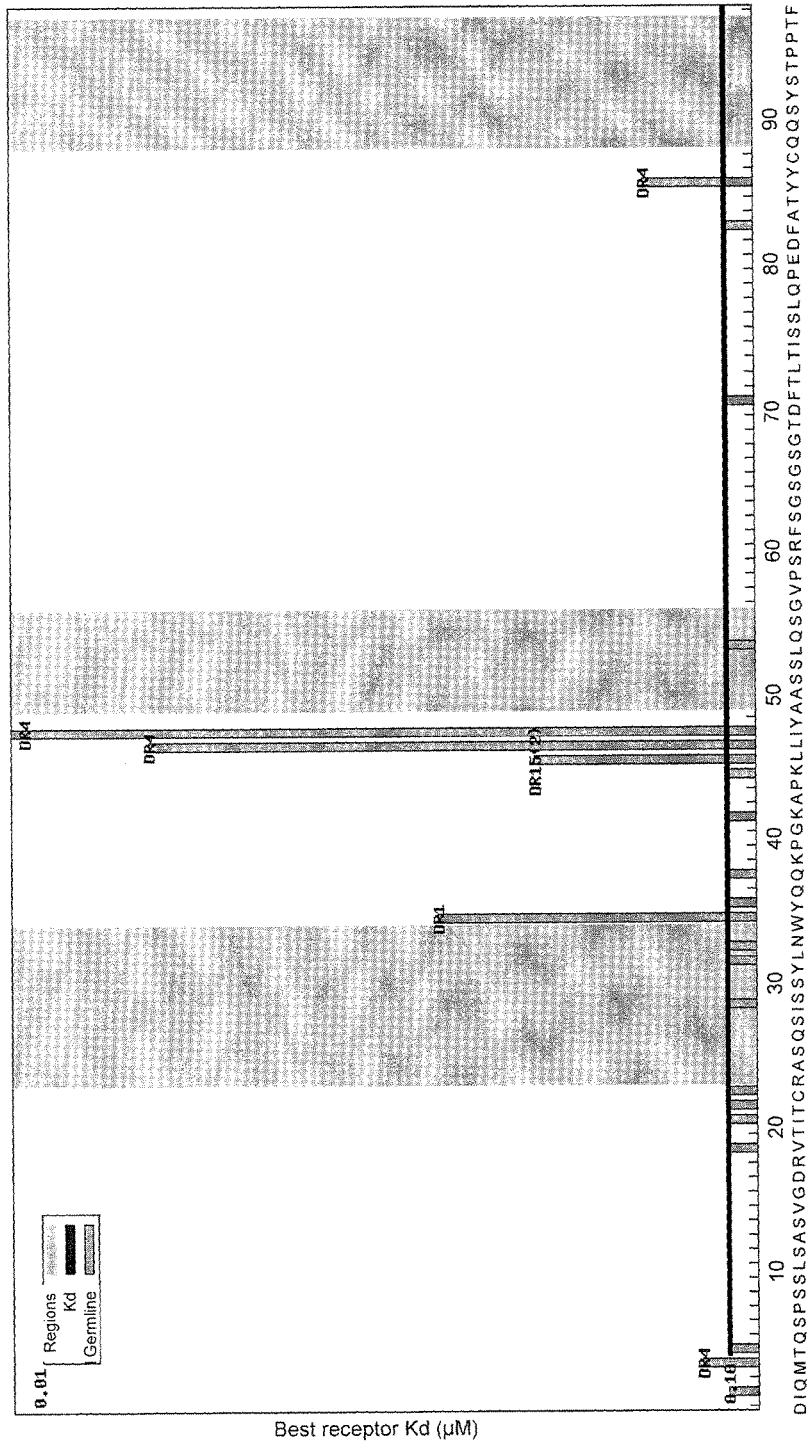
FIGS. 41A-41C: EPIBASE® profile of IGKV1-39 residues 1-107.
Figure 41B:
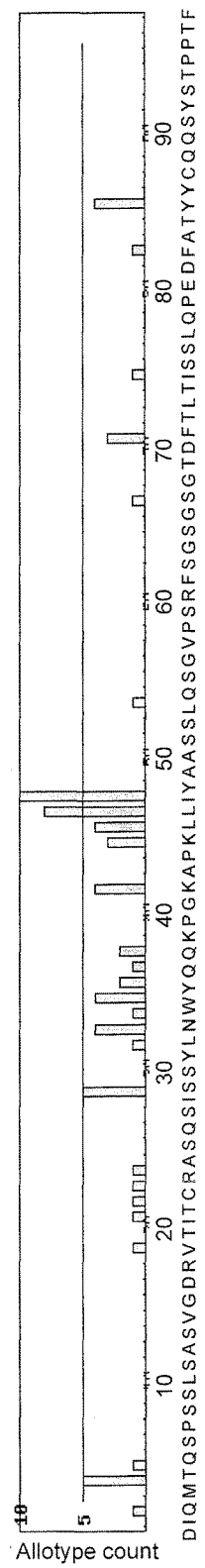
Figure 41C:
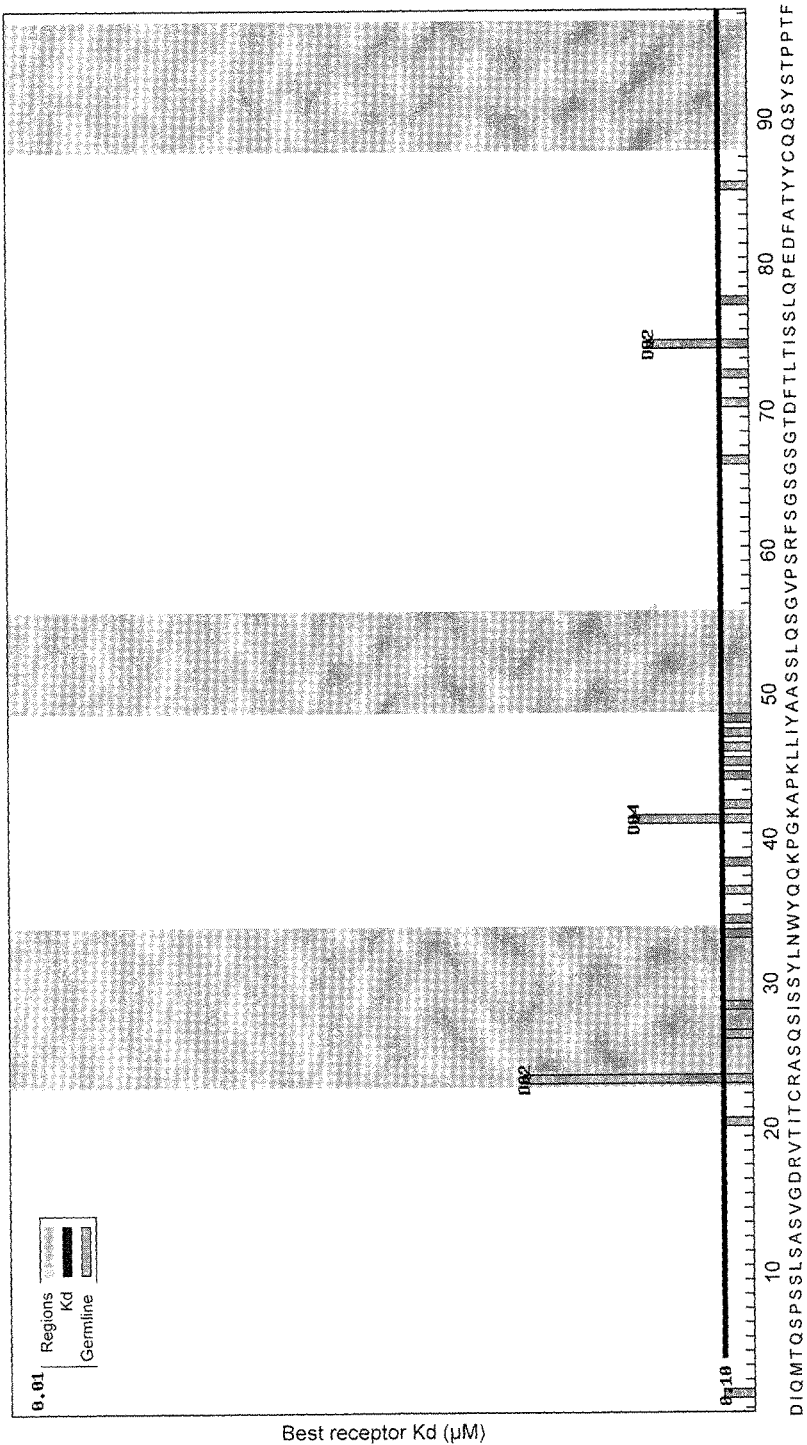
Figure 42:
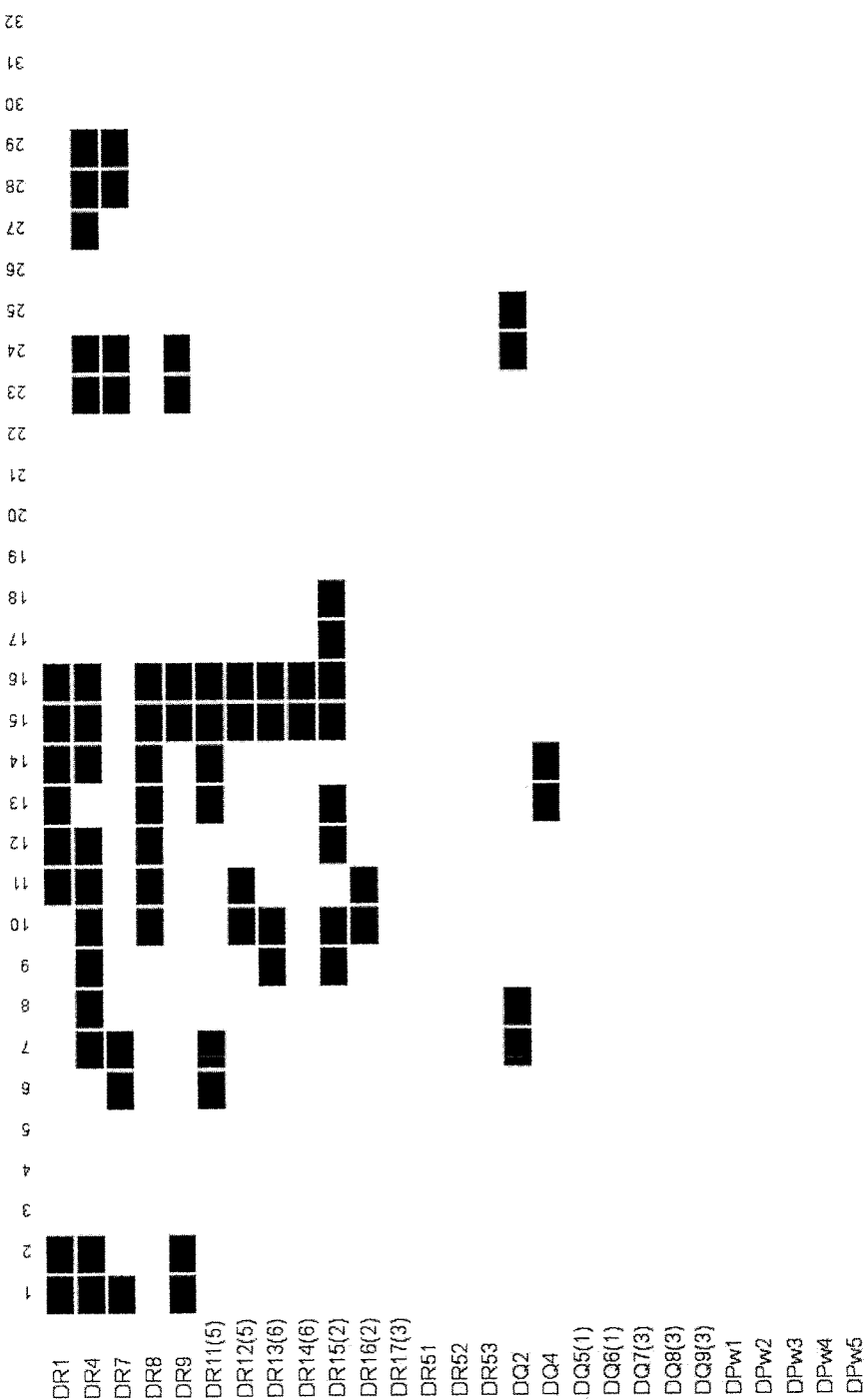
FIG. 42: Epitope map of IGKV1-39 showing the presence of peptide binders predicted in the sequence of IGKV1-39 by serotype in the 15-mer format. Each 15-mer is numbered as indicated in the top of the figure. The full sequence of the corresponding 15-mer is listed in Table 7. Black boxes indicate the presence of one or more critical self-epitopes in the 15-mer for the serotype listed on the left. Critical epitopes are operationally defined as strong or medium DRB1 binders and strong DRB3/4/5 or DP or DQ binders.

At the 5' end of the expression cassette, a NotI site was introduced and on the 3' site a NheI site. Both sites are used for cloning in the CAGGS expression module as described by TaconicArtemis. After gene assembly according to methods used by GeneArt, the insert was digested with NotI-NheI and cloned into the expression module containing a CAGGS promoter, a stopper sequence flanked by LoxP sites ("floxed"), a polyadenylation signal sequence and, at the 5' and 3' end, sequences to facilitate homologous recombination into the Rosa26 locus of mouse ES cell lines. To construct the final ROSA26 RMCE targeting vector, promoter and/or cDNA fragments were amplified by PCR. Amplified products were confirmed by sequencing and/or cloned directly from delivered plasmids into an RMCE exchange vector harboring the indicated features. A schematic drawing and the confirmed sequence of the final targeting vector pCAGGS-IgVL2-14 is shown in FIGS. 40A-40B-4. The targeting strategy is depicted in FIG. 40C.

Example 26: Expression of IGKV1-39/J-Ck in HEK293 Cell Lines (pSELECT-IGKV1-39/J-Ck)

This example describes a method to verify that the IGKV1-39/J-Ck constructs described in Example 24 enable expression and detection of the IGKV1-39/J-Ck L chain in HEK293 cells. The IGKV1-39/J insert (FIG. 31) was modified at the 5' end by changing the NotI site into a SalI site. This change is required for cloning of the product into the expression cassette plasmid pSELECT-hygro (InvivoGen). The CAGGS expression insert IGKV1-39/J-Ck and pSELECT-hygro were digested with SalI and NheI, ligated and used to transform competent XL1-Blue cells using standard techniques. Colonies were picked and DNA purified using Qiagen Midi-prep columns according to the manufacturer's procedures. The resulting light chain (LC) expressing vector named 0817676_pSELECT_0815426 was used to transfect HEK293 cells with Fugene6 (Roche) according to the manufacturer's protocols. Supernatants were screened for the presence of IGKV1-39/J-Ck light chains by ELISA and western blot using anti-rat-Ck antibodies (Beckton Dickinson #550336 and 553871) and protocols used in the art.

The VH of anti-tetanus toxoid (TT) IgG MG1494 was cloned into IgG expression vector MV1056 using restriction sites SfiI and BstEII. The resulting clone was sequence verified. HEK293T cells were transfected with five different vector combinations as shown in Table 4 (see, Example 27 for details of vector 0817678_pSELECT_0815427). Supernatants were harvested and IgG concentrations determined (see, Table 4). No IgG could be detected for supernatants A and B containing light chain only as expected (detection antibody recognized Fc part of IgG). IgG concentration in supernatants C and D was comparable to that of positive control supernatant E, indicating correct expression of the light chain constructs.

Binding to TT was analyzed by ELISA to check functionality of the produced antibodies, using hemoglobin as negative control antigen. No TT-specific binding could be detected for supernatants A and B containing light chain only, as expected. TT-specific binding for supernatants C and D was at least as good as for positive control supernatant E, confirming correct expression of the light chain constructs and functional assembly with heavy chain. Antibodies were detected not only using an anti-human IgG secondary antibody, but also an anti-rat Ckappa light chain secondary antibody. The results confirm that the anti-rat Ckappa antibody (BD Pharmingen #553871, clone MRK-1) recognizes the light chain expressed by the pSELECT vectors.

Supernatants were analyzed by non-reducing SDS-PAGE and Western blot (not shown). Detection using an anti-human IgG heavy chain antibody did not show bands for supernatants A and B containing light chain only, as expected. Results for supernatants C and D were comparable to positive control supernatant E, with a band close to the 170 kD marker as expected for intact IgG. Additional lower molecular weight bands were observed as well for supernatants C, D and E, which might represent degradation products, IgG fragments resulting from (partial) reduction and/or irrelevant protein bands due to non-specific binding of the detection antibody.

Detection using an anti-rat Ckappa light chain antibody showed a band close to the 26 kD marker for supernatants A and B, as expected for light chain only. This band was much more intense for A compared to B, indicating that the free IGKV1-39 light chain may be better expressed and/or more stable than the free IGLV2-14 light chain. No bands were detected for control supernatant E as expected, since the expressed IgG contains a human Ckappa light chain. For supernatants C and D, expected bands close to the 170 kD marker were observed; lower molecular weight bands were also observed, but to a lesser extent than above using the anti-human IgG antibody.

In conclusion, transfection of the light chain expression constructs combined with the heavy chain of anti-tetanus toxoid (TT) IgG MG1494 resulted in IgG production comparable to the positive control construct for both the pSELECT kappa and lambda light chain constructs. Both IgG productions yielded ELISA signals in a TT ELISA that were better than or comparable to the control IgG. SDS-PAGE and Western blot analysis confirmed the presence of intact IgG. The tested anti-rat Ckappa antibody worked efficiently in both ELISA and Western blot. Culture supernatant from cells transfected with light chain constructs only did not result in detectable IgG production nor in detectable TT-specific binding, while free light chain was detected on Western blot.

Example 27: Expression of IGLV2-14/J-Ck in HEK293 Cell Lines (pSELECT-IGLV2-14/J-Ck)

This Example describes a method to verify that the IGLV2-14/J constructs described in Example 25 enable expression and detection of the IGLV2-14/J-Ck L chain in HEK293 cells. The IGLV2-14/J-Ck insert (FIG. 32) was modified at the 5' end by changing the NotI site into a SalI site. This change is required for cloning of the product into the expression cassette plasmid pSELECT-hygro (Invivo-Gen). The CAGGS expression insert IGLV2-14/J-Ck and pSELECT-hygro were digested with SalI and NheI ligated and used to transform competentXL 1-Blue cells using standard techniques. Colonies were picked and DNA purified using Qiagen Midi-prep columns according to the manufacturer's procedures. The resulting light chain (LC) expressing vector named 0817678_pSELECT_0815427 was used to transfect HEK293 cells with Fugene6 (Roche) according to the manufacturer's protocols. Supernatants were screened for the presence of IGLV2-14/J-Ck light chains by ELISA and western blot using anti-rat-Ck antibodies (Becton Dickinson #550336 and 553871) and protocols used in the art. See Example 26 for details and results.

Example 28: Construction of a VK Promoter-Driven Expression Construct Containing an IGKV1-39/J Insert and Multiple Enhancer Elements Derived from the Murine CK Locus (VkP-IGKV1-39/J-Ck; VkP-O12)

This example describes the construction of an expression cassette that contains relevant elements to enable B-cell and developmental/differentiation stage-specific expression of the rearranged human IGKV1-39 VK region, based on the IGKV1-39 VK promoter region, leader containing an intron, germline V-gene, CDR3, IGKJ segment, mouse intergenic region located between Jk and CK, rat Ck allele a open reading frame, and a mouse intergenic fragment from the 3' end of the mouse CK gene ending just 3' of the 3' CK enhancer.

Optimized open reading frames of the leader, IGKV1-39 rearranged gene, and rat CK allele a gene, as described in Example 24, was used for the construction of the expression cassette. The VK promoter region was obtained by gene synthesis procedures (GeneArt, GmbH) and is almost identical to the sequence of the human IGKV1-39 region between −500 bp and the ATG (start site) of the gene. The only deviation from the natural sequence is the introduction of a GCCACCATGG Kozak sequence (SEQ ID NO:102) at the ATG (start) site in order to promote translation. A genomic fragment from a mouse BAC clone (TaconicArtemis) is used as the basis for the introduction of individual elements. This fragment is identical to the sequence of the mouse VK locus starting with the intron donor site located directly 3' of the JK5 region and ending just 3' of the 3' CK enhancer and covers approximately 12.5 kb.

Figure 33:
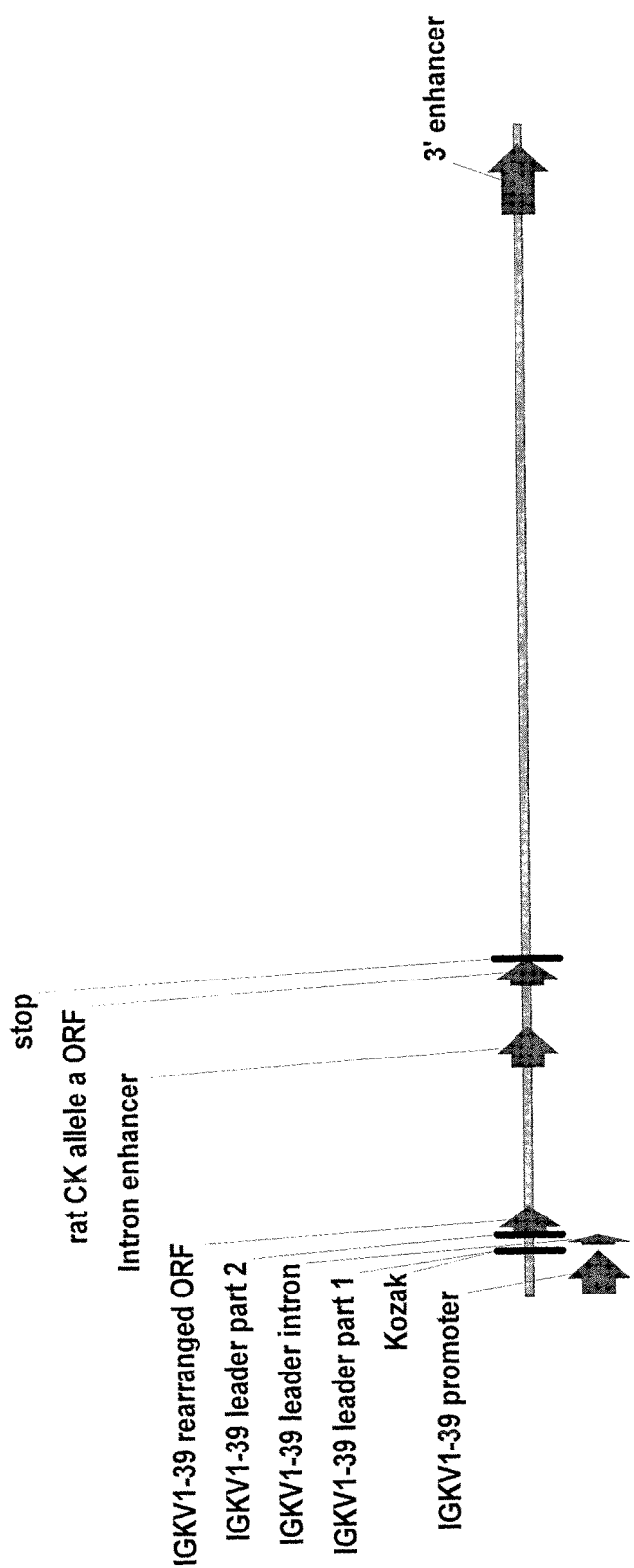
FIG. 33: Construct topology of VkP-IGKV1-39/J-Ck (VkP-O12). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.
Figure 45A:
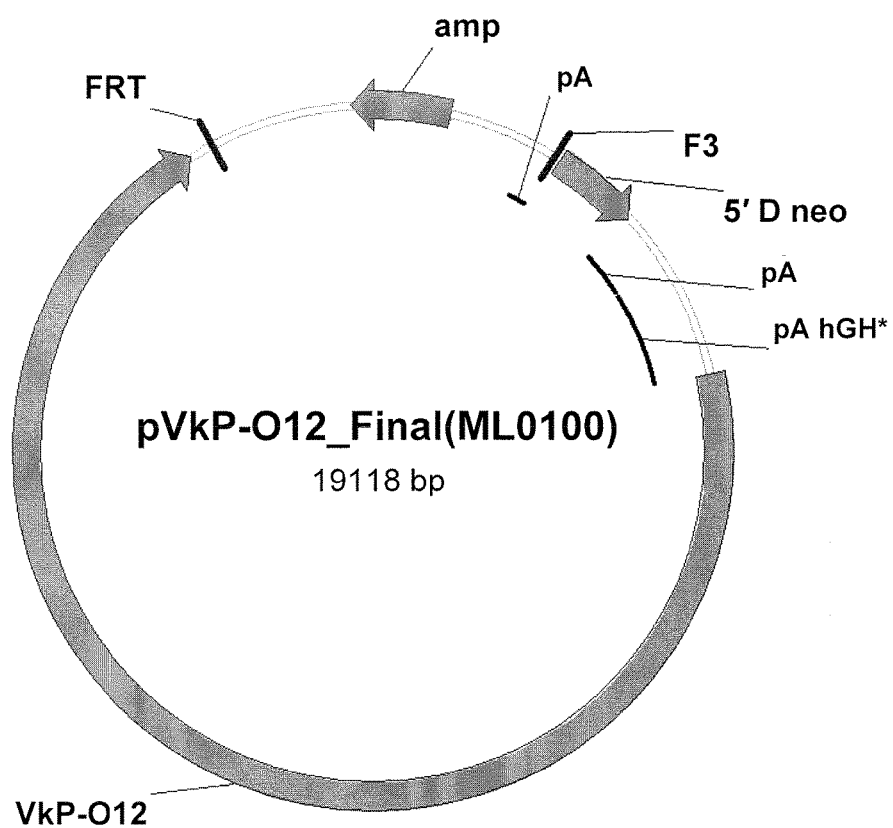
FIGS. 45A-45C: Schematic drawing of targeting vectors.
Figure 46A:
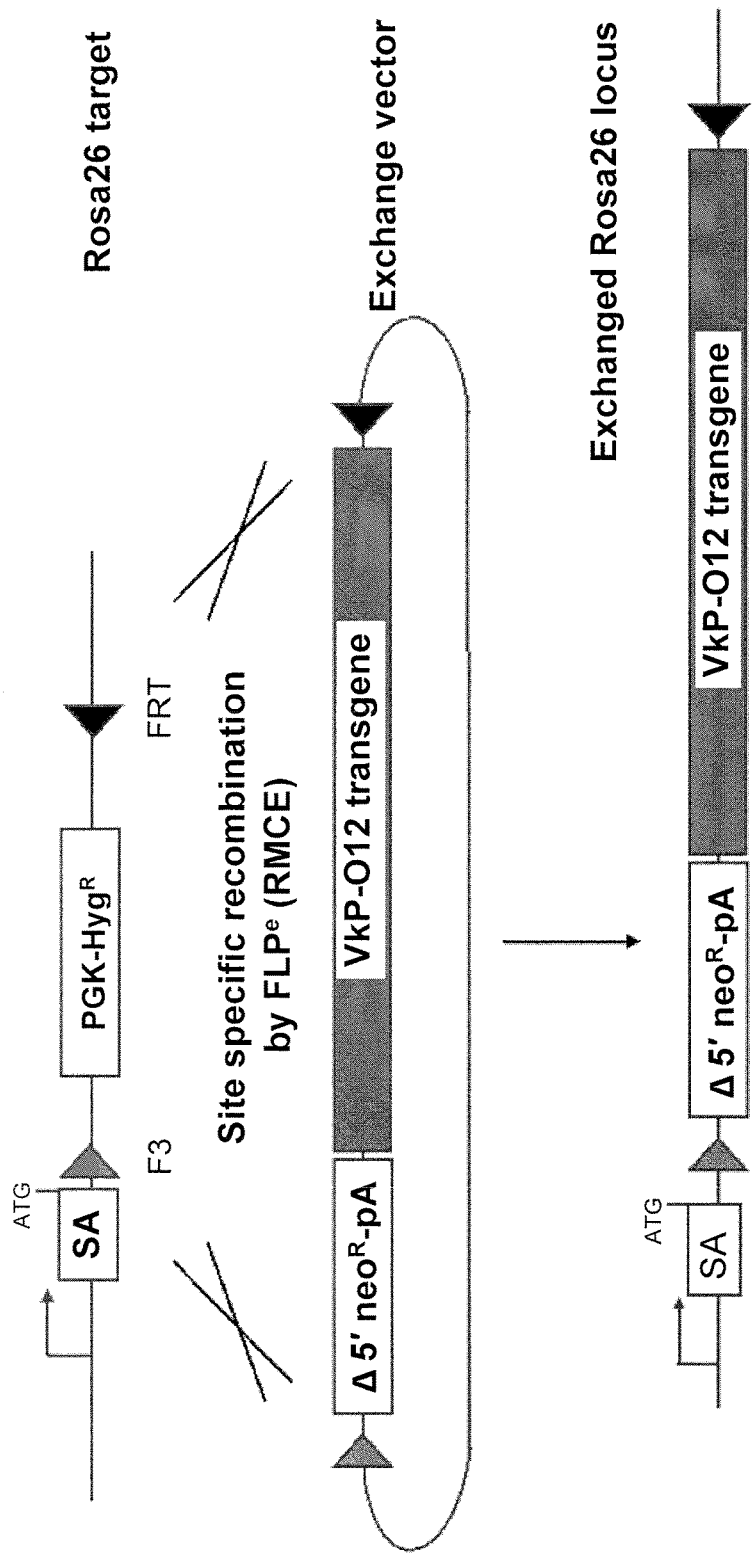
FIGS. 46A-46C: Targeting strategies for insertion of transgene into the Rosa26 locus by targeted transgenesis using RMCE.

The final construct contains from 5' to 3' end the following elements: human genomic IGKV1-39 promoter (500 bp), a Kozak sequence, a human IGKV1-39 leader part 1 (optimized), a human IGKV1-39 leader intron, a human IGKV1-39 leader part 2 (optimized), a human IGKV1-39 germline gene (optimized), a human J-region (optimized), a mouse intergenic region including the intron enhancer element, a rat (Rattus norvegicus) kappa constant region (optimized), and a mouse intergenic region including the 3' kappa enhancer. The elements of this expression cassette are shown in FIG. 33 and named VkP-IGKV1-39/J-Ck (VkP-O12). An outline of the pVkP-O12 vector and the targeting strategy is depicted in FIGS. 45A and 46A. The vector was introduced into ES cells following standard procedures (see, Example 33).

Example 29: Construction of a VK Promoter-Driven Expression Construct Containing an IGLV2-14/J Clone and Multiple CK Locus-Derived Enhancer Elements (VkP-IGLVL2-14/J-Ck; VkP-2a2)

Figure 34:
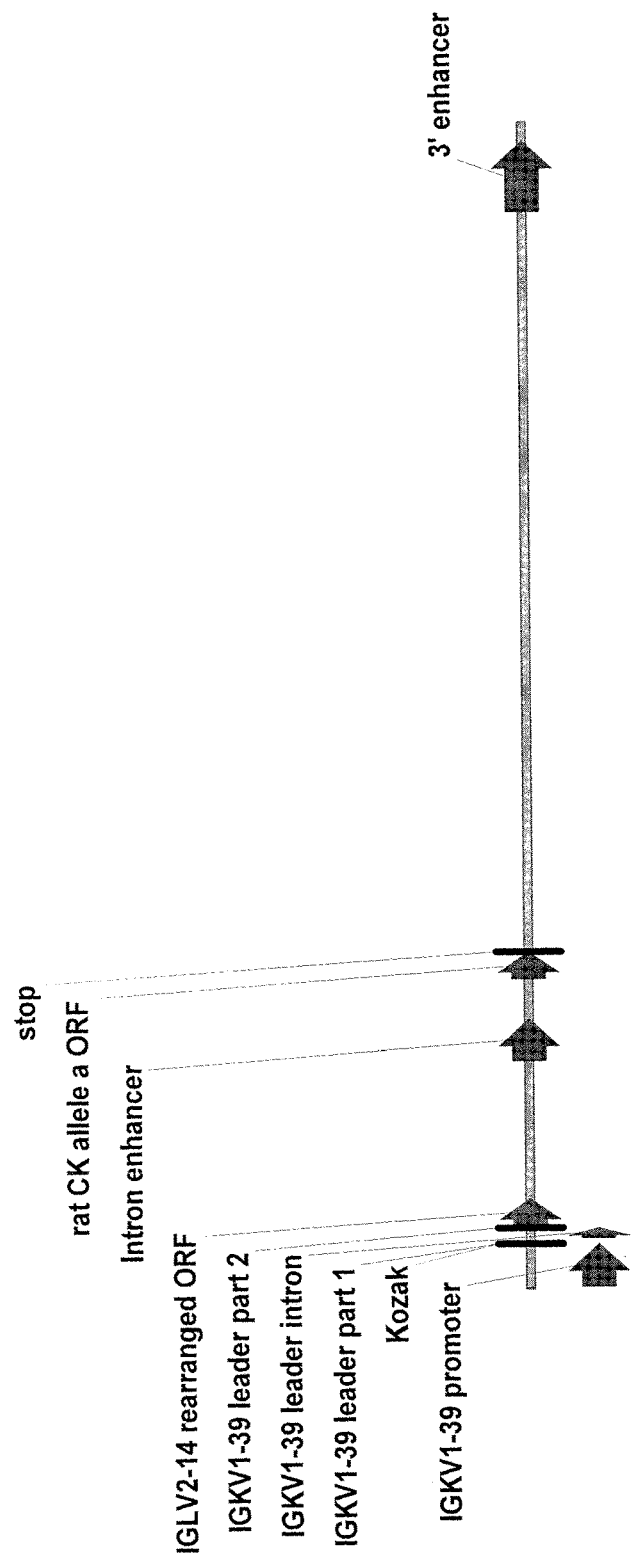
FIG. 34: Construct topology of VkP-IGLV2-14/J-Ck (VkP-2a2). The promoter originates from the IGKV1-39 gene and is placed directly in front of the required elements for efficient transcription and translation. Intergenic sequences (including the enhancers) are derived from mice and obtained from BAC clones. The C-kappa sequence codes for the kappa constant region of rat.

This example describes the same construct as described in Example 28, except that the IGKV1-39 gene and J-region are replaced by the optimized human IGLV2-14 germline gene including a unique V-J region (VkP-IGLV2-14/J-Ck; VkP-2a2; FIG. 34).

Example 30: Construction of a VK Promoter-Driven Expression Construct Containing an IGKV1-39 Clone Lacking the CK Intron Enhancer Element (VkP-IGKV1-39/J-Ck-Δ1; VkP-O12-Del1)

Figure 35:
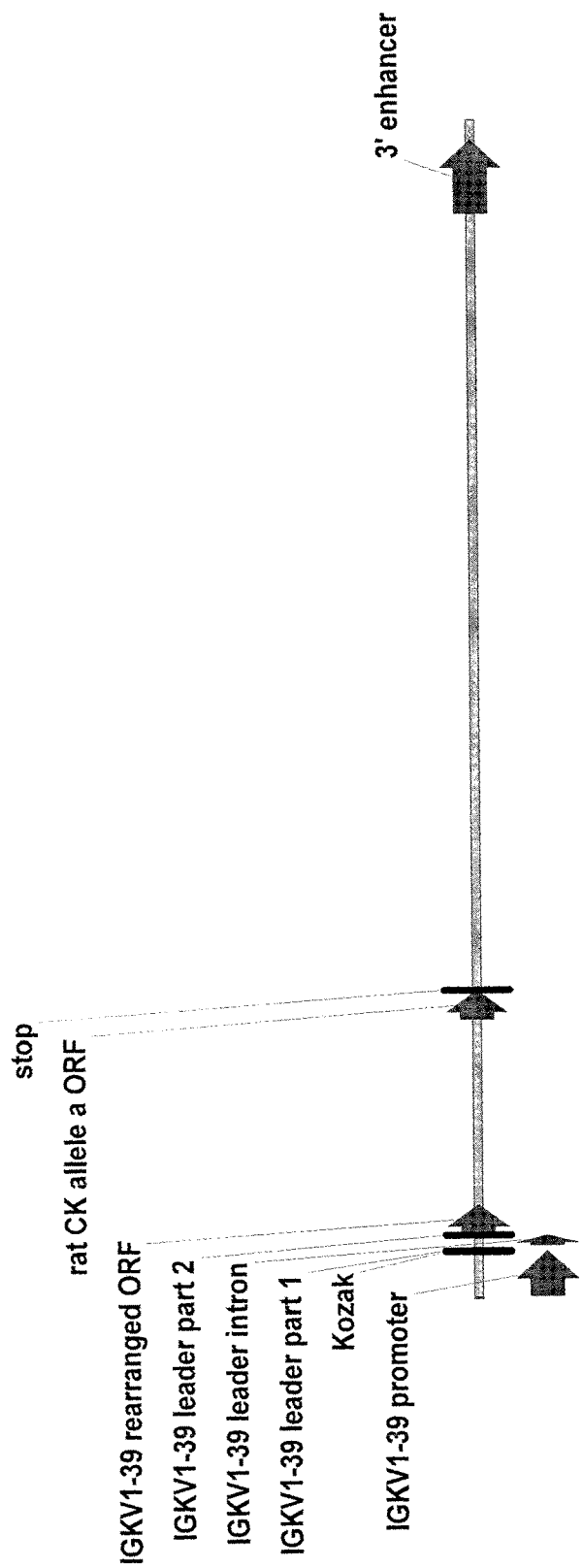
FIG. 35: Construct topology of VkP-IGKV1-39/J-Ck-Δ1 (VkP-O12-del1) is identical to VkP-IGKV1-39/J-Ck from FIG. 34 except that the intron enhancer region is removed.
Figure 36:
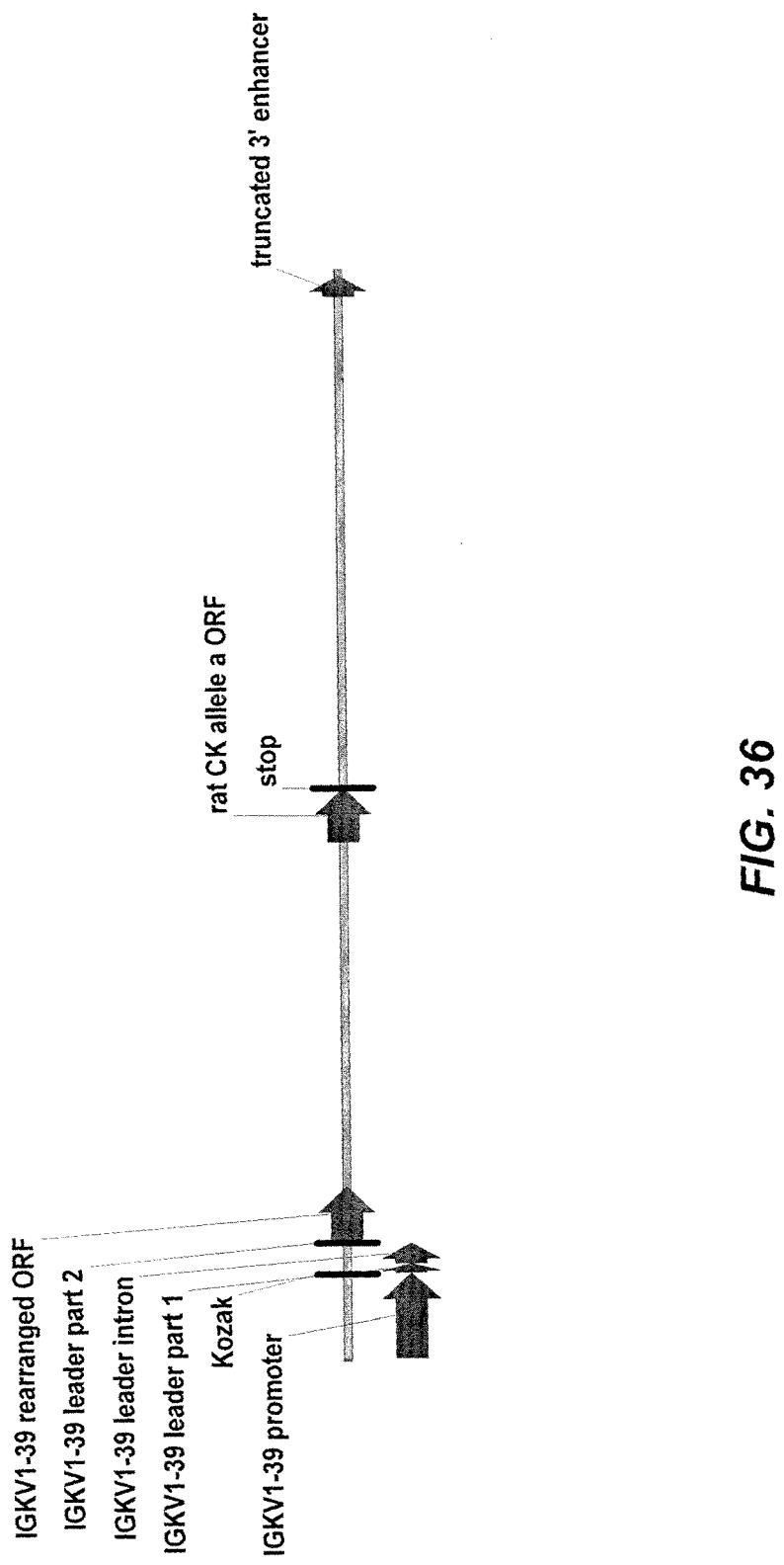
FIG. 36: Construct topology of VkP-IGKV1-39/J-Ck-Δ2 VkP-O12-del2) is identical to VkP-IGKV1-39/J-Ck-Δ1 from FIG. 35 except that a large piece of the intergenic region between the Ck gene and 3' enhancer is deleted. In addition, the 3' enhancer is reduced in size from 809 bp to 125 bp.

The construct described in Example 28 was modified by removing the CK intron enhancer element, located in the intergenic region between the human J region and the rat CK region by standard PCR modification and DNA cloning methodologies (GeneArt, GmBH). The resulting expression cassette is shown in FIG. 35 and named VkP-IGKV1-39/J-Ck-Δ1 (VkP-O12-del1).

Figure 45B:
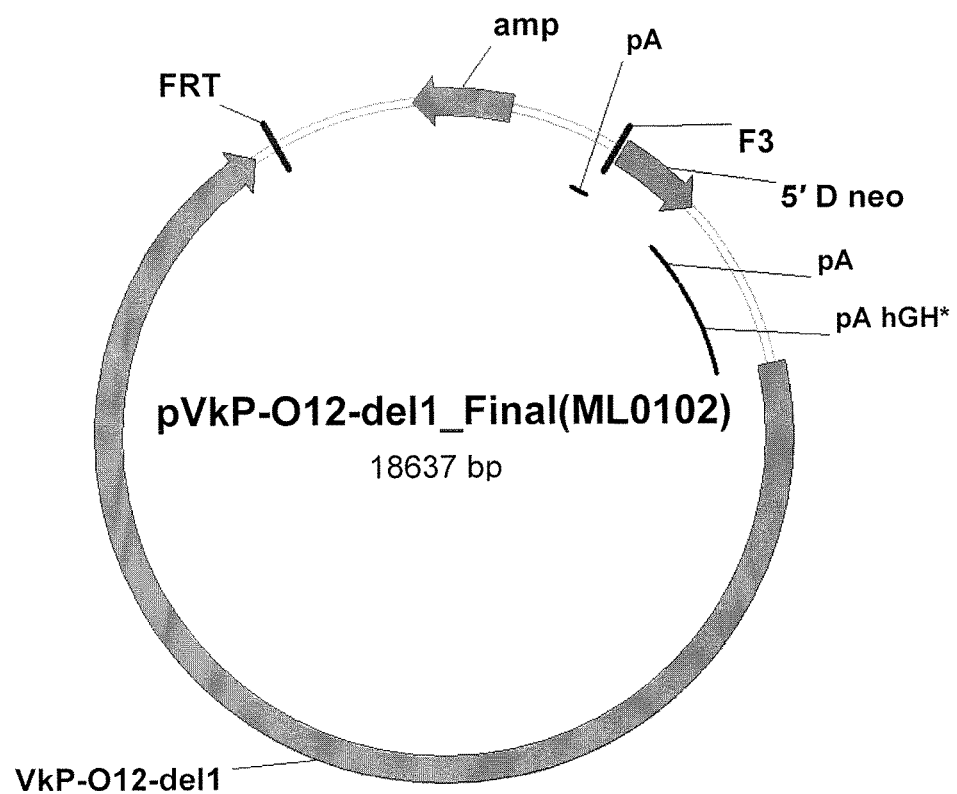
Figure 45C:
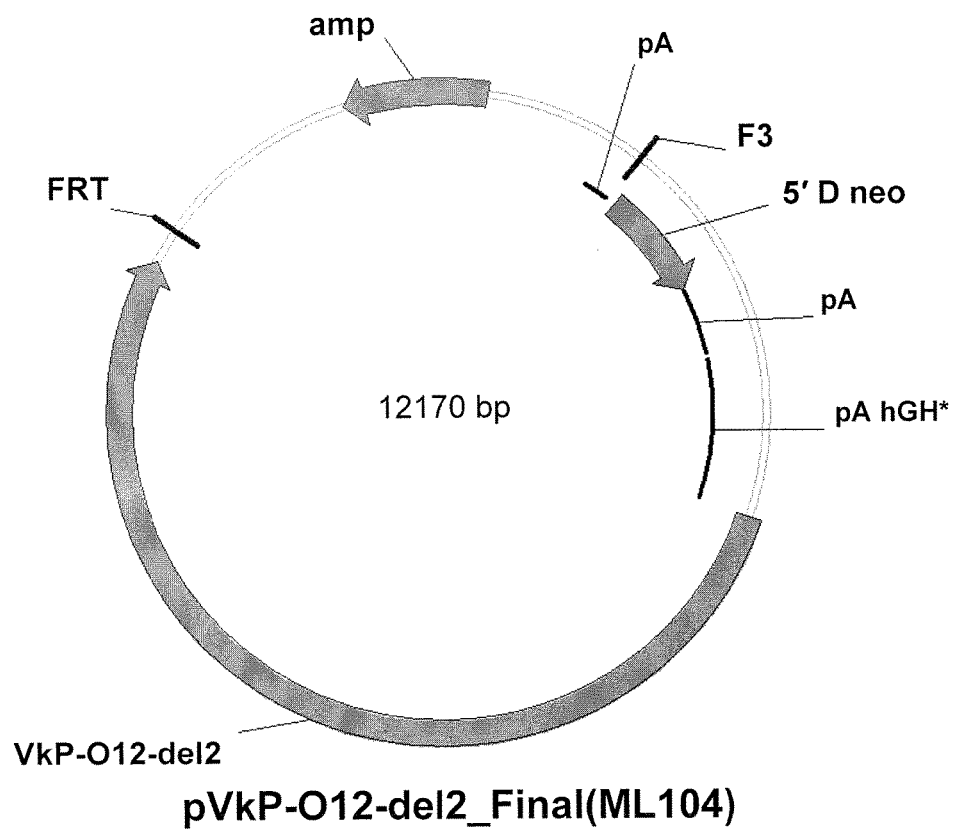
Figure 46B:
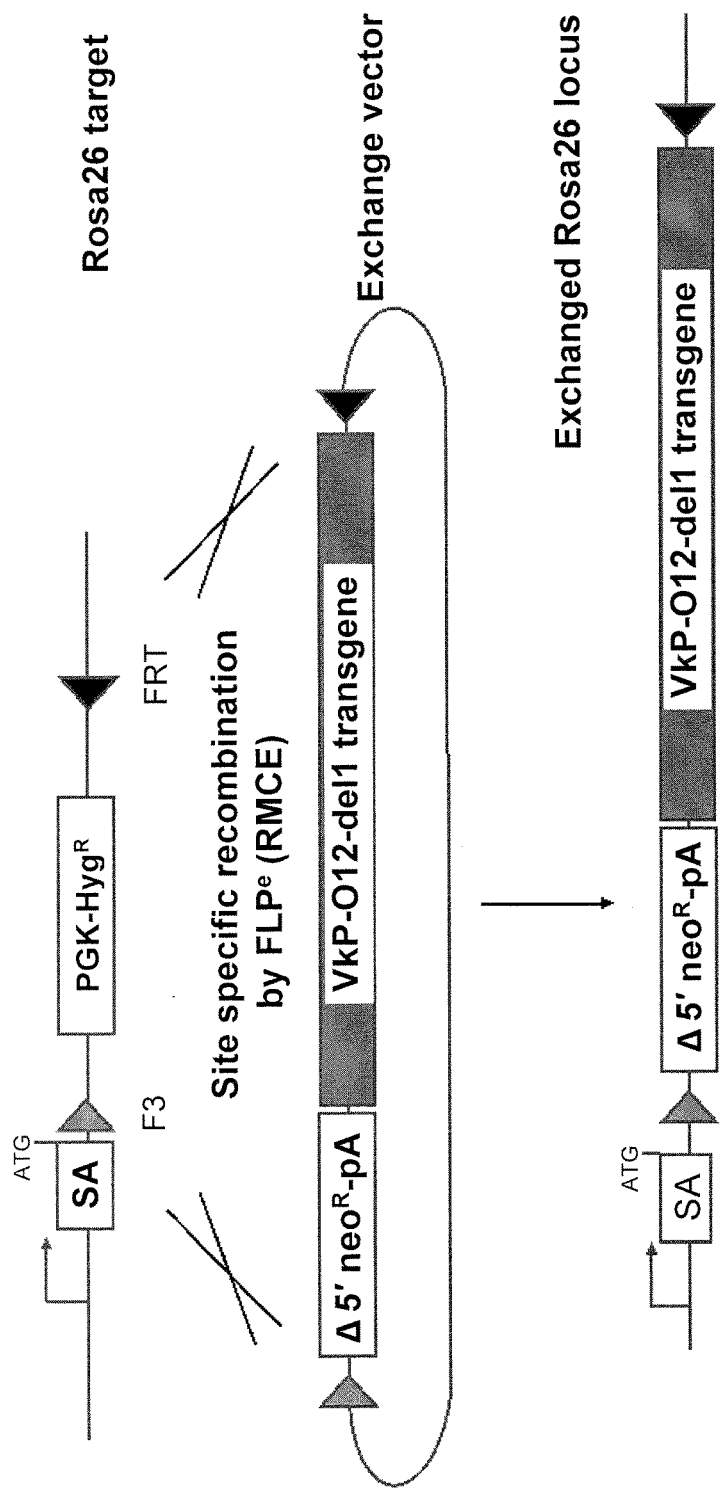
Figure 46C:
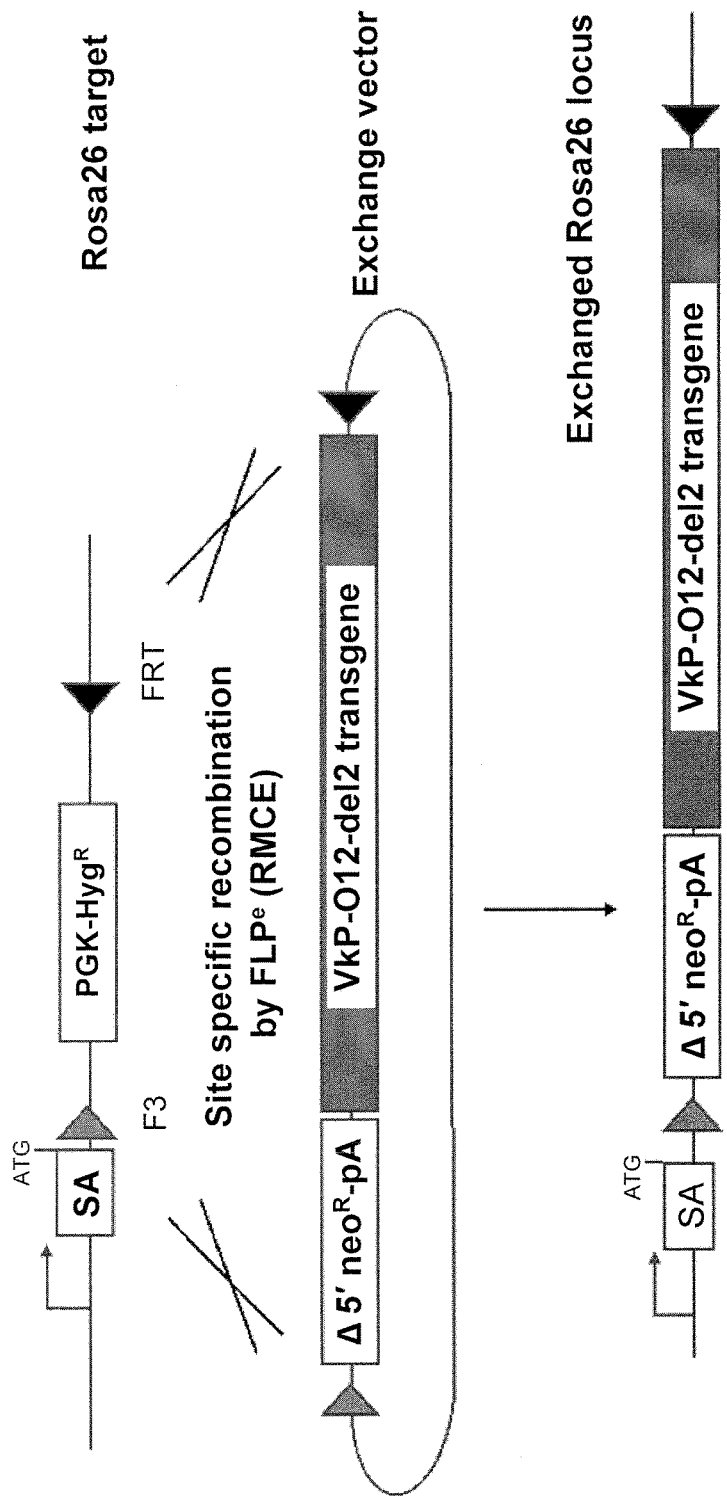

An outline of the pVkP-O12-del1 vector and the targeting strategy is depicted in FIGS. 45B and 46B. The vector was introduced into ES cells following standard procedures (see, Example 33).

Example 31: Construction of a VK Promoter-Driven Expression Construct Containing an IGKV1-39 Clone Lacking the CK Intron Enhancer Element and a Truncated 3' CK Enhancer Element (VkP-IGKV1-39/J-Ck-Δ2; VkP-O12-Del2)

Figure 26:
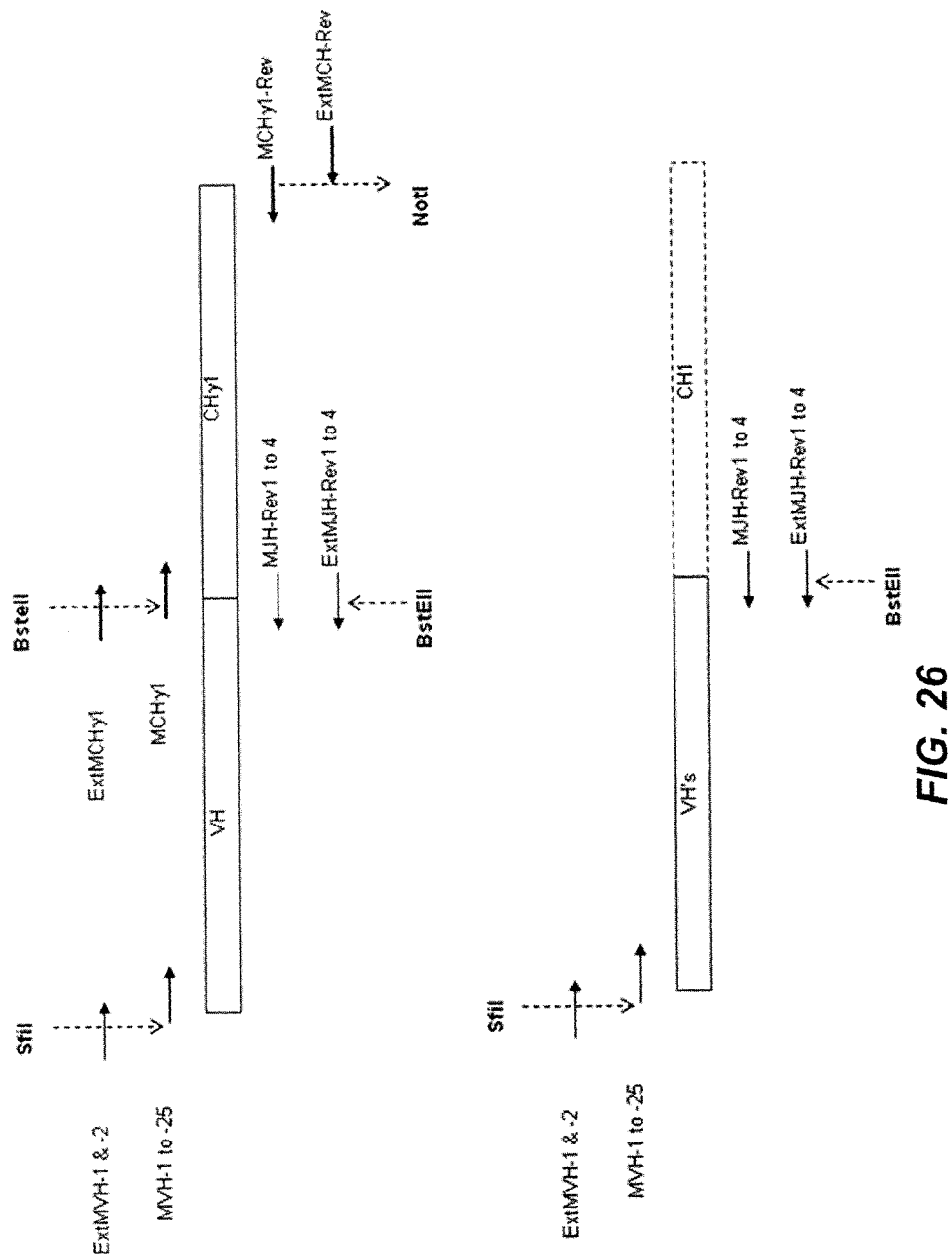
FIG. 26: A topology map of the annealing locations of mouse specific VH primers and the position of required restriction sites that are introduced by overhanging sequences at the 3' end of primers.

The construct described in Example 40 was modified by truncating the 3' CK enhancer element and deleting part of the intergenic region 3' of the rat Ck gene, to remove potential inhibitory elements. This was achieved by removing the intergenic sequence between an EcoRV site (located 3' of the rat Ck gene) and the NcoI site present in the 3' enhancer (5993 bp) and further removing the sequence between the 3' enhancer BstXI site and the BstXI site 3' of the 3' enhancer (474 bp) using standard methods. The resulting expression cassette is shown in FIG. 26 and named VkP-IGKV1-39/J-Ck-Δ2 (VkP-O12-del2).

An outline of the pVkP-O12-del2 vector and the targeting strategy is depicted in FIGS. 25C and 26C. The vector was introduced into ES cells following standard procedures (see, Example 33).

Example 32: Expression of Vk Constructs in Cell Lines

The constructs described in Examples 28-31 are tested for their ability to produce light chain proteins in the myeloma cell lines MPC11 (ATCC CCL167), B-cell lymphoma WEHI231 (ATCC CRL-1702), the T-cell lymphoma EL4 (ATCC TIB-39) and in HEK293 (ATCC CRL1573). The enhancer and promoter elements in the construct enable expression in the B-cell lines but not in cell lines derived from other tissues. After transfection of the cell lines using purified linearized DNA and Fugene6 (Roche) cells are cultured for transient expression. Cells and supernatant are harvested and subjected to SDS-PAGE analysis followed by western blotting using a specific anti-rat-C-kappa antibody. Supernatants are analyzed in ELISA for secreted L chains using the anti-rat CK antibody (Beckton Dickinson #550336).

Example 33: Generation of Transgenic ES Lines

All constructs as described in Examples 22, 23, 24, 25, 28, 29, 30 and 31 were used to generate individual stable transgenic ES lines by means of homologous recombination. The methods for generation of transgenic ES lines via homologous recombination are known in the field (e.g., Eggan et al., *PNAS* 98:6209-6214; J. Seibler, B. Zevnik, B. Küter-Luks, S. Andreas, H. Kern, T. Hennek, A. Rode, C. Heimann, N. Faust, G. Kauselmann, M. Schoor, R. Jaenisch, K. Rajewsky, R. Kühn, F. Schwenk (2003), *Nucleic Acids Res.*, February 15; 31(4):e12; Hogan et al. (Cold Spring Harbor Laboratory Press, Cold Spring Harbor N. Y.), pp. 253-289).

For all constructs described in Examples 5 and 6, and Examples 9-12, the RMCE ES cell line (derived from mouse strain 129S6B6F1-Gt(ROSA)26Sortm10Arte) was grown on a mitotically inactivated feeder layer comprised of mouse embryonic fibroblasts (MEF) in DMEM High Glucose medium containing 15% FBS (PAN 1302-P220821). Leukemia Inhibitory Factor (Chemicon ESG 1107) was added to the medium at a concentration of 900 U/mL. For manipulation, $2 \times 10^5$ ES-cells were plated on 3.5 cm dishes in 2 ml medium. Directly before transfection, 2 ml fresh medium was added to the cells. Three µl Fugene6 Reagent (Roche; Catalog No. 1 814 443) was mixed with 100 µl serum free medium (OptiMEM I with Glutamax I; Invitrogen; Catalog No. 51985-035) and incubated for five minutes. One hundred µl of the Fugene/OptiMEM solution was added to 2 µg circular vector and 2 µg CAGGS-Flp and incubated for 20 minutes. This transfection complex was added dropwise to the cells and mixed. Fresh medium was added to the cells the following day. From day 2 onwards, the medium was replaced daily with medium containing 250 µg/mL G418 (Geneticin; Invitrogen; Catalog No. 10131-019). Seven days after transfection, single clones were isolated, expanded, and molecular analyzed by Southern blotting according to standard procedures.

Figure 39A:
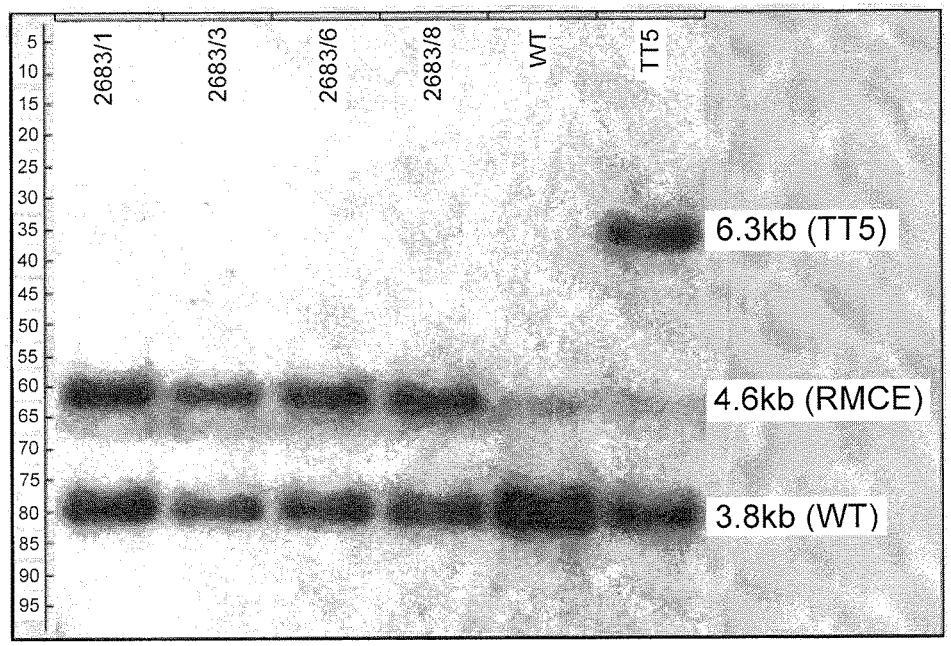
FIGS. 39A-39C.
Figure 39B:
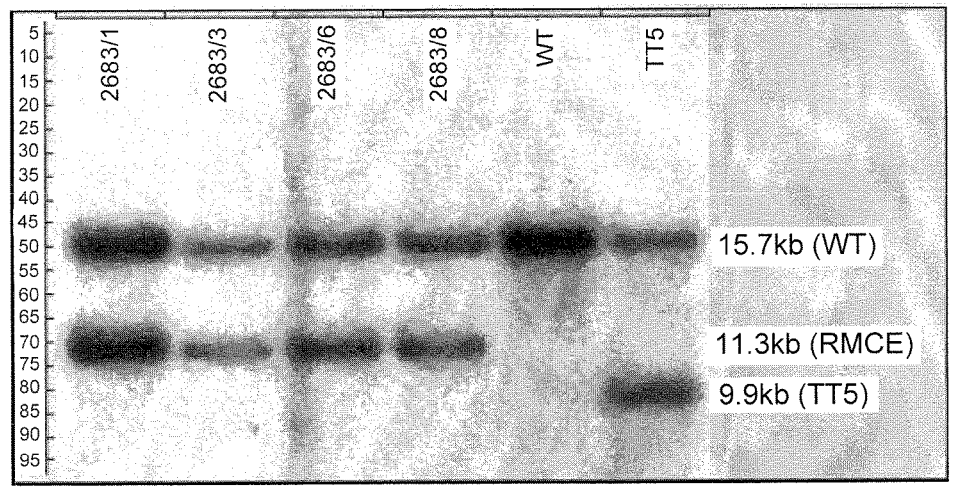
Figure 39C:
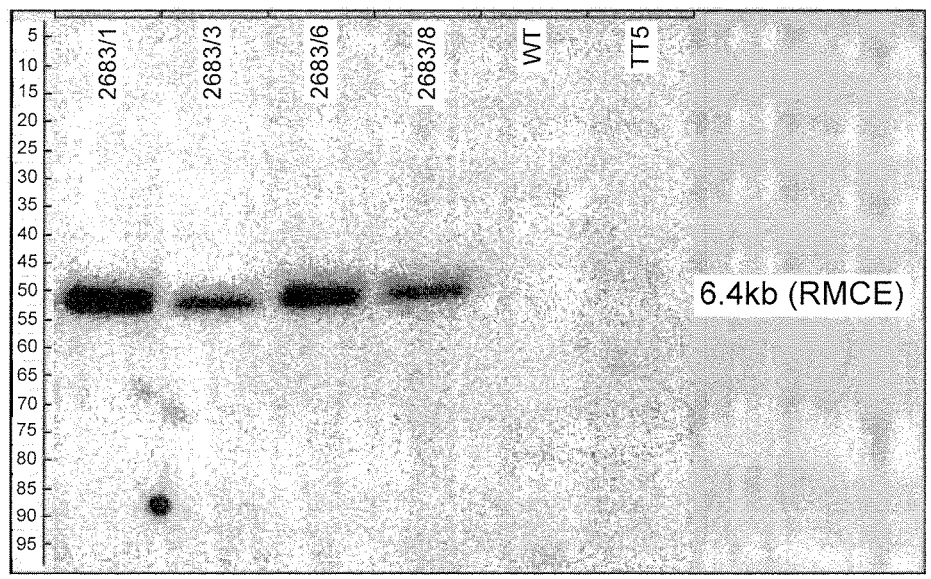

For each construct, analysis of multiple clones by restriction enzyme digestion of genomic DNA of single clones followed by hybridization with 5' probes, 3' probes, and internal probes resulted in clones that comprised a correct, single insertion at the correct position in the Rosa26 locus. An example is provided in FIGS. 39A-39C.

Example 34: Generation of Transgenic Mouse Strains

All ES cell lines that were generated and verified for their modifications as described in Example 33 were used to generate stable transgenic mice by means of tetraploid recombination. The methods are known in the field. In general, after administration of hormones, superovulated Balb/c females were mated with Balb/c males. Blastocysts were isolated from the uterus at dpc 3.5. For microinjection, blastocysts were placed in a drop of DMEM with 15% FCS under mineral oil. A flat tip, piezo actuated microinjection-pipette with an internal diameter of 12-15 micrometers was used to inject 10-15 targeted C57BL/6 N.tac ES cells into each blastocyst. After recovery, injected blastocysts were transferred to each uterine horn of 2.5 days post coitum, pseudopregnant NMRI females. Chimerism was measured in chimeras (G0) by coat color contribution of ES cells to the Balb/c host (black/white). Highly chimeric mice were bred to strain C57BL/6 females. Depending on the project requirements, the C57BL/6 mating partners are non-mutant (W) or mutant for the presence of a recombinase gene (Flp-Deleter or Cre-deleter or CreER inducible deleter or combination of Flp-deleter/CreER). Germline transmission was identified by the presence of black, strain C57BL/6, offspring (G1).

For example, ESC clone IgVK1-39 2683 8 (see, Examples 5 and 14) was injected in a total of 62 blastocysts in three independent experiments. Three litters were obtained with a total of six pups. All pups were chimeric. Three heterozygous offspring pups were obtained that were used for further crossing.

ESC Clone Kappa 2692 A-C10 (see, Examples 3 and 14) was injected in a total of 54 blastocysts in three independent experiments. Three litters were obtained with a total of eleven pups, of which ten were chimeric. Eight heterozygous offspring pups were obtained that were used for further crossing.

ESC Clone Kappa 2692 B-C1 (see, Examples 3 and 14) was injected in a total of 51 blastocysts in three independent experiments. Two litters were obtained with a total of six pups, of which four were chimeric. Three heterozygous offspring pups were obtained that were used for further crossing.

Example 35: Breeding

This example describes the breeding for obtaining mice that contain transgenic expression cassettes as described Example 33 and knock-out mice in which the endogenous lambda and kappa loci have been silenced. The localization of V-lambda on chromosome 16 and CD19 on chromosome 7 allow standard breeding procedures. The breeding of the co-localized Vk locus and Rosa26 locus on chromosome 6 with a distance of about 24 cM requires special attention during the screening as only a percentage of the offspring shows crossover in a way that both modifications are brought together on one chromosome.

All four loci have to be combined in a single mouse strain that is homo- or heterozygous for CD19-cre (not described) and modified Rosa26 transgene and homozygous for the other loci. Breeding is performed by standard breeding and screening techniques as appropriate and offered by commercial breeding companies (e.g., TaconicArtemis).

Example 36: Immunizations of Mice

Primary and booster immunization of mice are performed using standard protocols.

To validate the transgenic expression of human rearranged VK O12 (IGKV1-39)—rat CK light chains (see, Examples 5, 14-16) in B cells from CD19-HuVκ1 mice and to assess its impact on VH repertoire size, diversity of VH family usage and V(D)J recombination after immunization, the CD19-HuVκ1 transgenic mice are immunized with tetanus toxin vaccine (TT vaccine) and VH sequence diversity of randomly picked clones from CD19-HuVκ1 mice are compared with TT-immunized wt mice and CD19-Cre HuVκ1 negative littermates. Data on the SHM frequency of the human VκO12 transgene in the immunized mice are obtained. A diverse collection of at least 40 TT-specific, clonally-unrelated mAbs containing the human Vκ O12 are recovered from CD19-HuVκ1 mice by phage display.

For this, three adult CD19-HuVκ1 mice are vaccinated with TT vaccine using standard immunization procedures. After immunization, serum titers are measured using TT specific ELISA (TT: Statens Serum Institute, Art. no. 2674) and spleen suspensions subjected to cell sorting by the FACS procedure after staining with a rat Cκ-specific monoclonal antibody to isolate transgenic B cells (clone RG7/9.1; BD Pharmingen#553901, Lot#06548). RNA from rat Cκ-positive B cells are extracted and the resulting cDNA material used for library building and SHM analysis.

The standard monoclonal mouse anti-rat Cκ antibody (clone RG7/9.1; BD Pharmingen#553901, Lot#06548) is used in FACS analysis of transgene expressing B cells (Meyer et al. (1996), Int. Immunol. 8:1561). The clone RG7/9.1 antibody reacts with a monotypic (common) kappa chain determinant. This anti-rat CK antibody (clone RG7/9.1 (BD Pharmingen#553901, Lot#06548) is labeled with R-phycoerythrin (PE) using the LYNX rapid conjugation kit according to the manufacturer's instructions for FACS analysis and sorting. The labeled antibody is firstly tested by flow cytometry for binding to rat Cκ-containing functional light chain proteins produced into transiently transfected HEK-293T cells; the un-conjugated antibody serves as a positive control. Two other antibodies shown to bind to rat Cκ by ELISA and Western-blot (see, Example 26) are tested as well by flow cytometry.

Fab-phage display library building is carried out with a set of optimized degenerate PCR primers designed to amplify C57BL/6 VH genes; the minimal library size is $10^6$ clones, and minimal insert frequency is 80%. The vector used, MV1043 (FIGS. 28 and 37A-37Z), contains the human VκO12 fused to a human Cκ region. The rat Cκ is therefore exchanged for the human counterpart in the library generation process.

Before selection, VH sequencing of 96 randomly picked clones is performed to validate VH repertoire diversity that is compared to diversity obtained from an unselected library previously generated using the same procedures from BALB/c mice immunized with TT. A library from C57Bl/6 wt mice that are immunized in the same way allows diversity comparison between two preselected libraries sharing the same vaccine and the same genetic background.

Several independent selections are performed on TT coated in immunotubes. Variables that may be included are selections using biotinylated antigens in solution or selections on captured TT. Based on the number and diversity of ELISA-positive clones obtained in the first selections, decisions on additional rounds of selection are made. Clones are considered positive when >3× positive over a negative control clone. Positive clones are analyzed by ELISA against a panel of negative control antigens to verify antigen specificity. The aim is to identify at least 40 unique VH regions, as based on unique CDR3 sequences and $V_H DJ_H$ rearrangements.

Amplification of the cDNA material from rat Cκ-positive sorted B cells is performed with a PCR forward primer specific to the human leader sequence and a PCR reverse primer specific to the rat Cκ sequence, in a region not redundant with the mouse Cκ sequence, as reported in a recent study (Brady et al. (2006), JIM 315:61). Primer combinations and annealing temperatures are firstly tested on cDNA from HEK-293T cells transfected with 0817676_pSELECT_0815426=pSELECT vector with IGKV1-39 DNA cassette (see, Example 26).

The amplification products is cloned in pJET-1 vector and after XL1-blue transformation, 96 colonies are sequenced for assessing VL SHM frequency by direct comparison to the VκO12 (IGKV1-39) germline sequence. The R/S ratio method, as described in the study on human TT-specific antibodies (de Kruif et al. (2009), J. Mol. Biol. 387:548) allows discrimination between random mutations and antigen-driven mutations that occurred on VL sequences.

Example 37: Immunofluorescent Analysis of B Cell Populations in Transgenic Mouse Lines This example describes the use of antibodies and flow cytometry to analyze B cell populations in primary (bone marrow) and secondary (spleen, peritoneal) lymphoid organs and blood. Methods and reagents are described in Middendorp et al. (2002), J. Immunol. 168:2695; and Middendorp et al. (2004), J. Immunol. 172:1371. For analysis of early B cell development in bone marrow, cells were surface stained with combinations of antibodies (Becton Dickinson) specific for B220, CD19, CD25, IgM, IgD, mouse Ckappa, mouse Clambda and rat Ckappa to detect pro-B cells, pre-B cells, large pre-B cells, early and late immature B cells and recirculating B cell populations expressing the transgene on their surface. DAPI staining (Invitrogen) was included to exclude dead cells from the analysis and FC block (Becton Dickinson) to inhibit antibody interaction with Fc receptors on myeloid cells. For analysis of surface transgene expression on B cell populations in peripheral lymphoid organs and blood, cells were stained with combinations of antibodies (Becton Dickinson) specific for B220, CD5, CD19, CD21, CD23, IgM, IgD, mouse Ckappa, mouse Clambda and rat Ckappa. DAPI staining was included to exclude dead cells from the analysis and FC block to inhibit antibody interaction with Fc receptors on myeloid cells. In addition, combinations of antibodies (Becton Dickinson) specific for CD3, CD4, CD11b, CD11c and NK1.1 were included to determine if transgene expression occurred in cell types outside of the B cell compartment.

Three mice heterozygous for the human IGKV1-39/rat Ckappa transgene and heterozygous for the CD19-Cre transgene on a C57BL6 background (HuVk1/CD19-Cre) were analyzed. As controls for the FACS analysis, three littermate mice wild-type for the human IGKV1-39/rat Ckappa transgene and heterozygous for the CD19-Cre transgene on a C57BL6 background (CD19-Cre) and two C57BL6/NTac mice (Wt) were included. All animals were allowed to acclimatize in the animal facility for one week before analysis and all mice were male and six weeks of age. Lymphocytes were isolated from the femurs, spleens, peritoneal cavity and blood of mice using conventional techniques as previously described (Middendorp et al. (2002), J. Immunol. 168:2695; and Middendorp et al. (2004), J. Immunol. 172:1371). Antibodies were pre-combined as shown in Table 10 and staining was carried out in 96-well plates. Incubation with the PE-conjugated anti-rat C kappa (described above) was carried out before staining with the rat anti-murine antibodies to avoid non-specific binding. After completion of cell staining, labeled cells were analyzed on a Becton Dickinson LSR II FACS machine and the acquired data analyzed with FlowJo software (v6.4.7).

Transgenic mice were similar in weight, appearance and activity to wild-type mice. No gross anatomical alterations were observed during the harvesting of tissues. No difference was observed in the numbers of B cells in the bone marrow (BM) and spleen (Table 11) or in the numbers of B cells, T cells and myeloid cells in peripheral organs between transgenic and wild-type mice. In addition, the frequency or proportion of the cells in the different lymphocyte developmental pathways was not altered in transgenic mice when compared to wild-type mice. Thus in the double transgenic (HuVk1/CD19-Cre) and transgenic (CD19-Cre) mice lymphoid and most importantly B cell development was indistinguishable from wild-type mice.

Figure 48A:
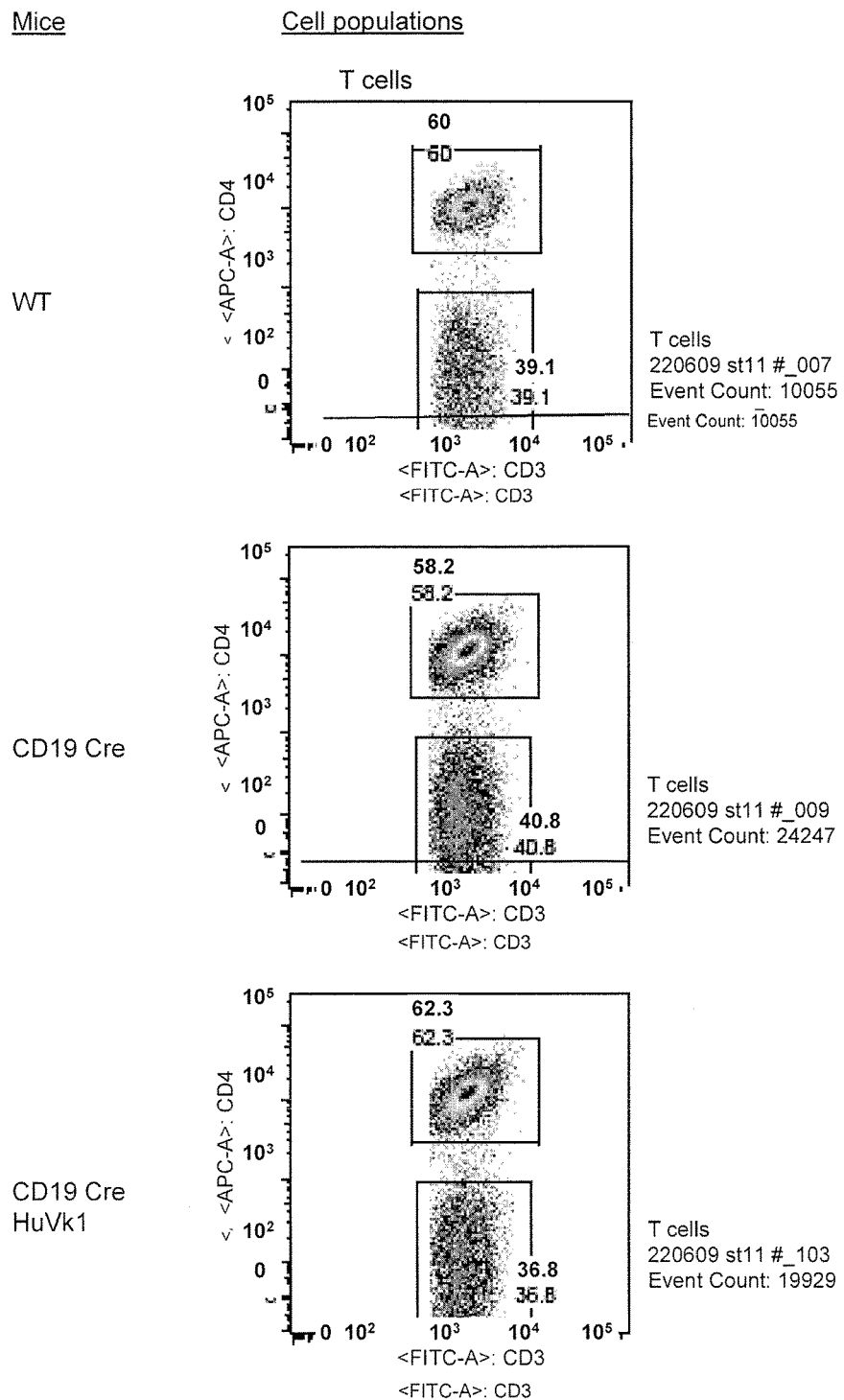
FIGS. 48A-48C: Lack of transgenic human Vk1 light chain expression in non-B cell populations of the spleen.
Figure 48B:
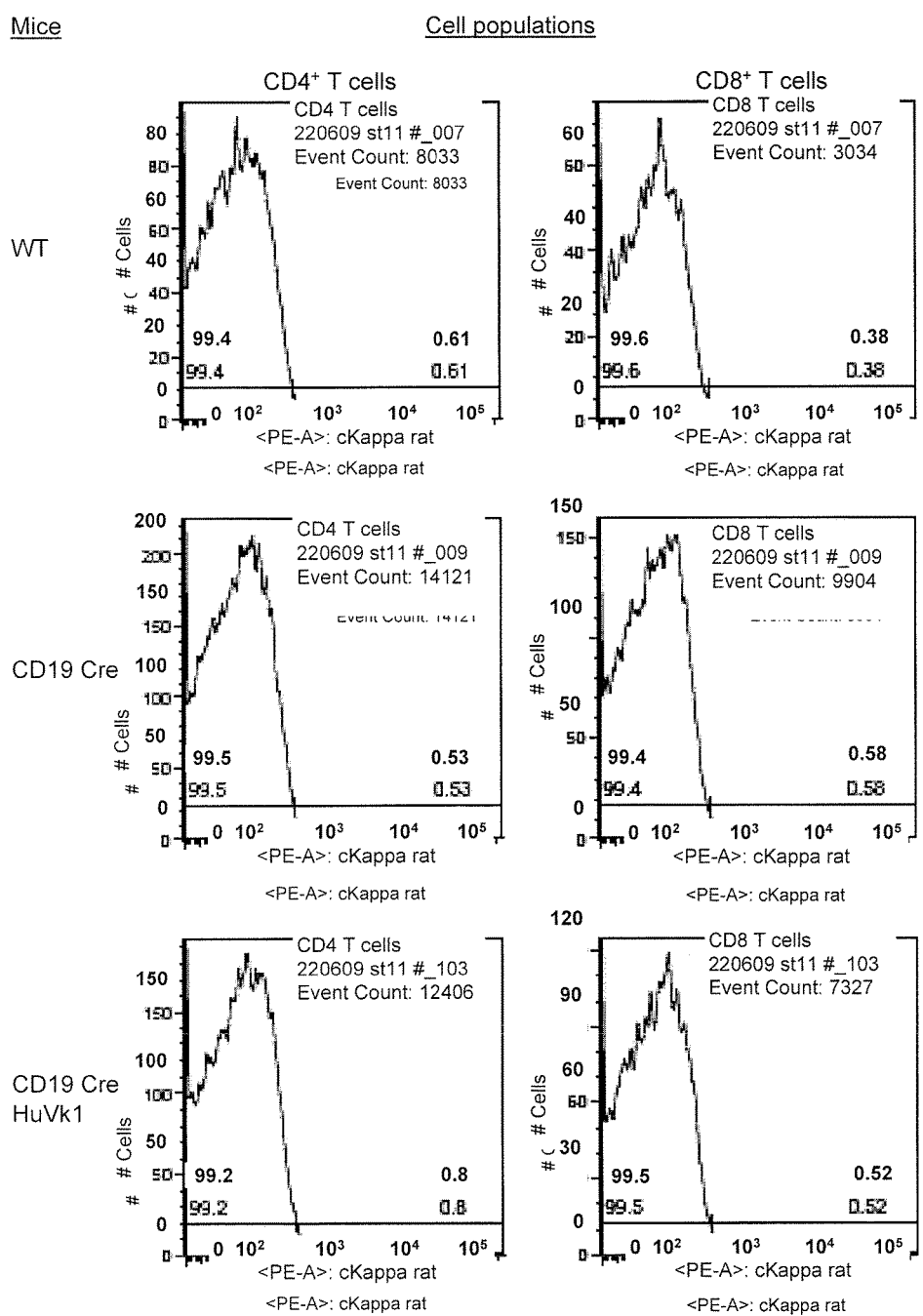
Figure 48C:
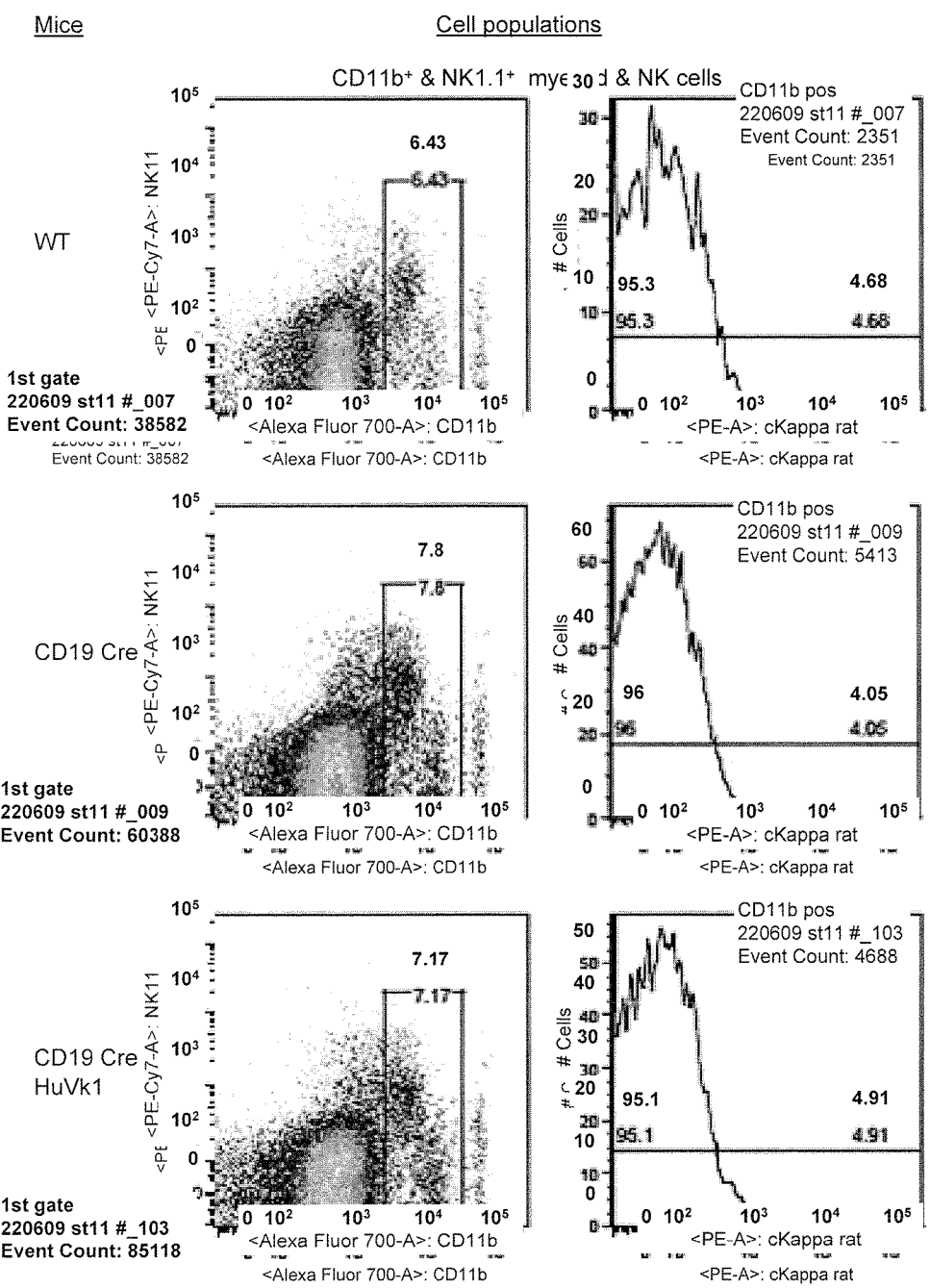
Figure 49A:
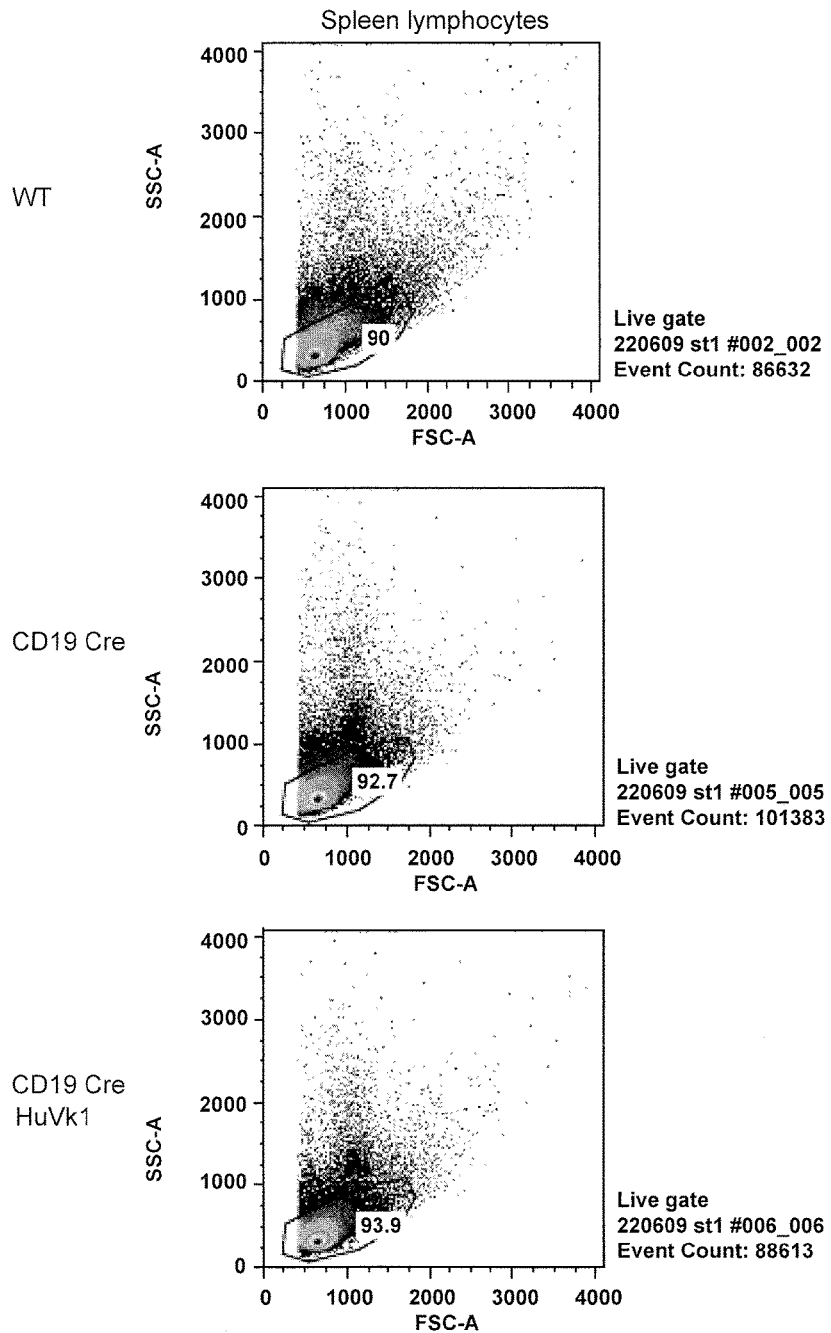
FIGS. 49A and 49B: Transgenic human Vk1 light chain is expressed in all B cell populations of the spleen.
Figure 49B:
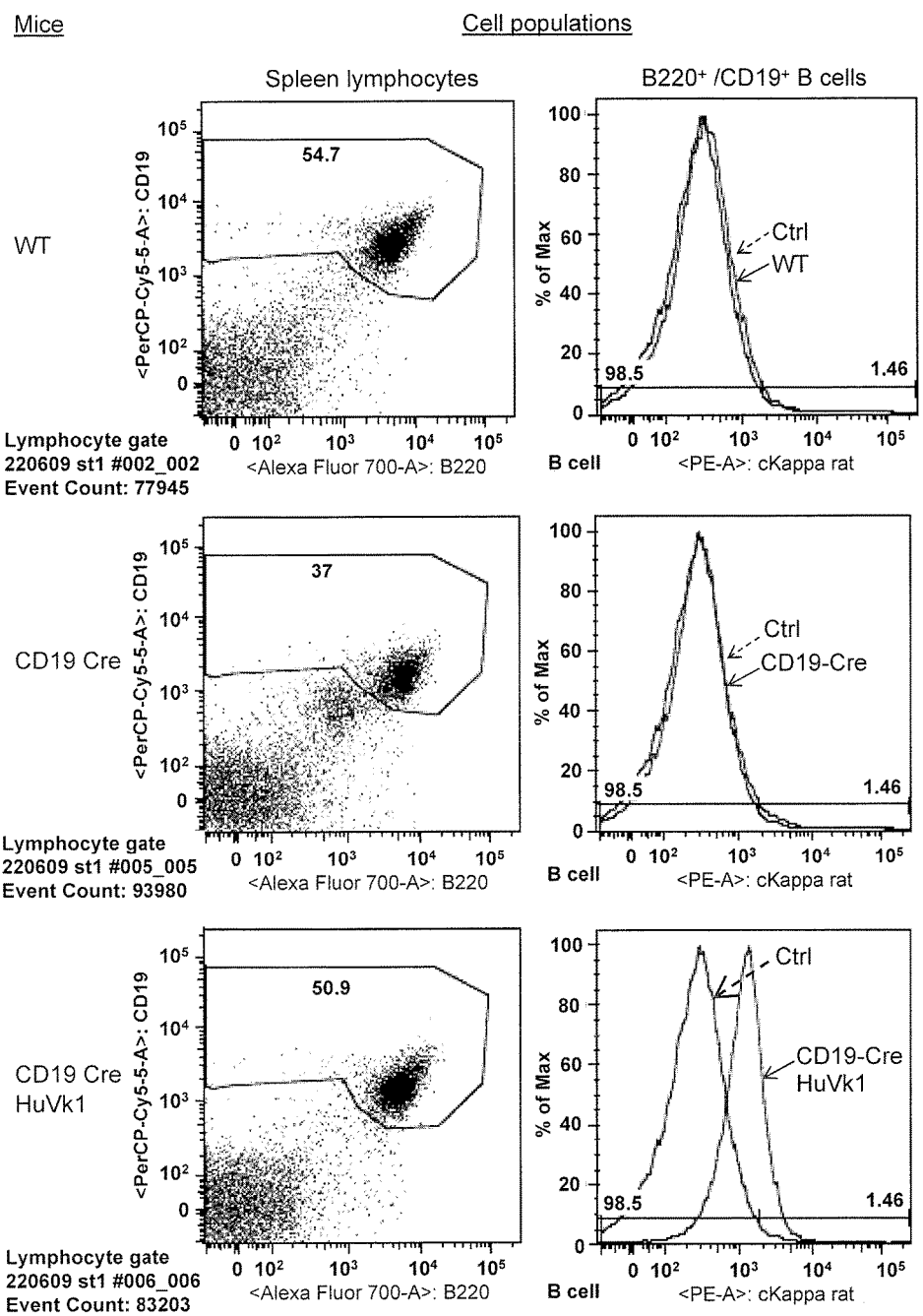
Figure 50A:
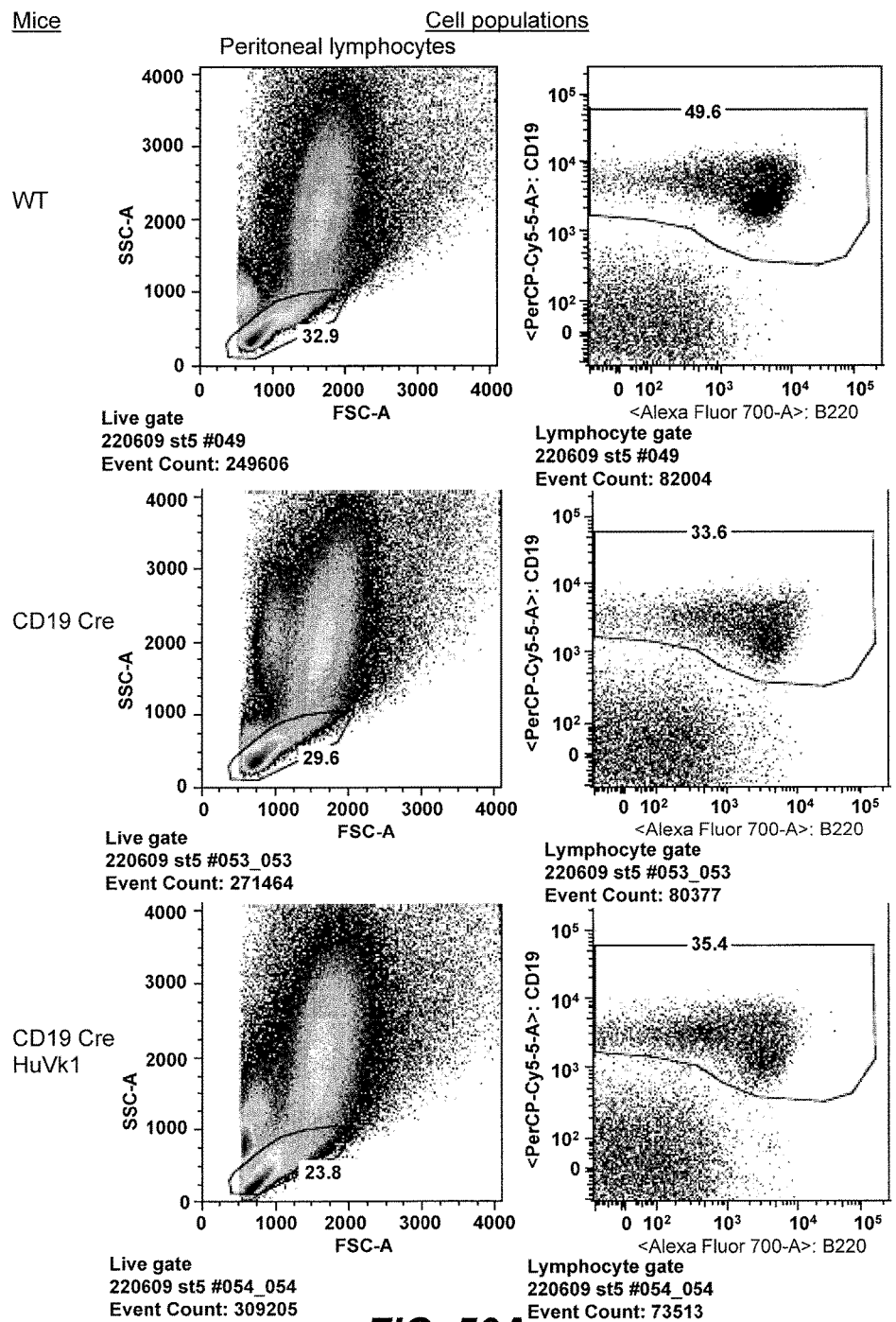
FIGS. 50A and 50B: Transgenic human Vk1 light chain is expressed in B1 cells of the peritoneal cavity.
Figure 50B:
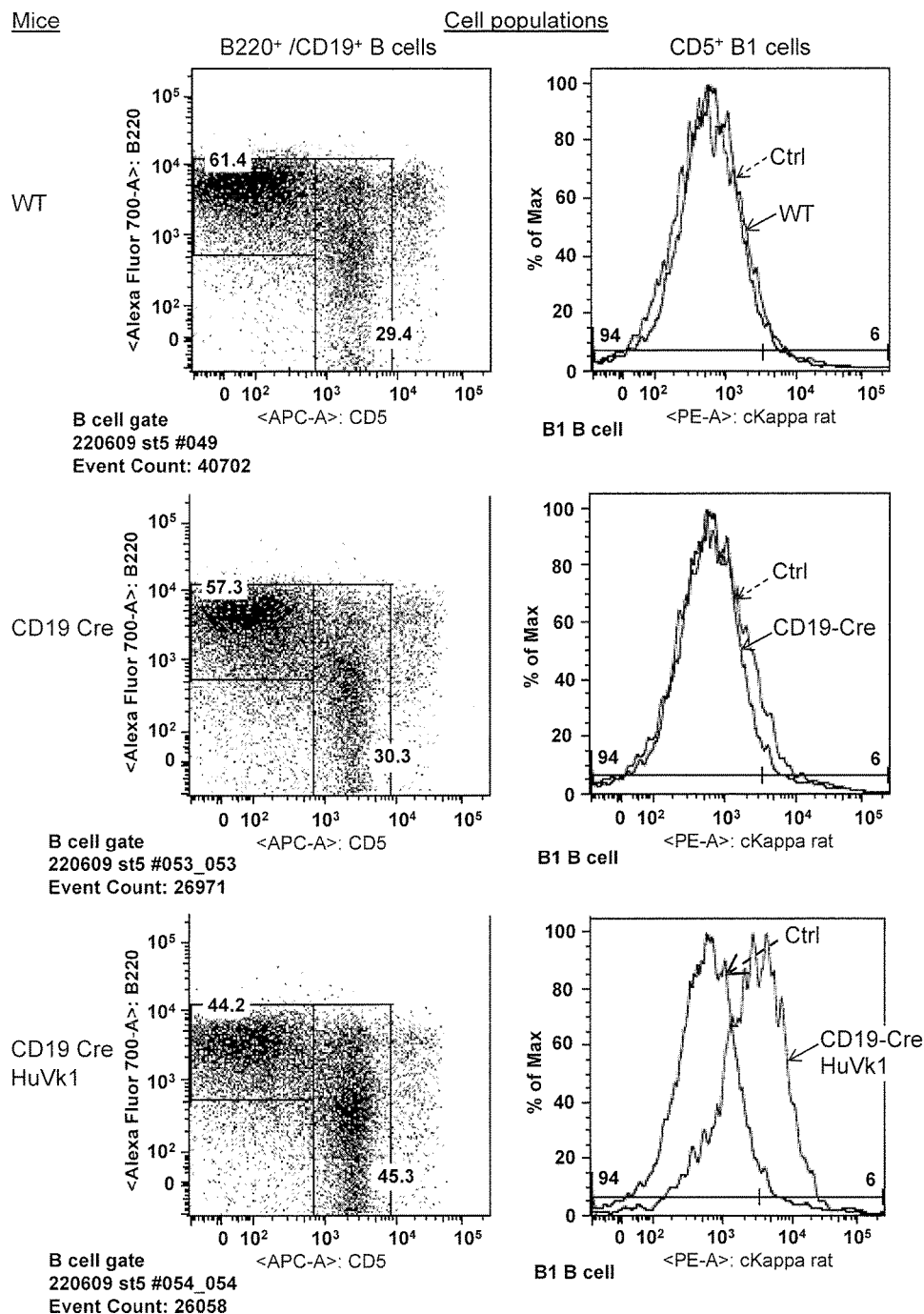
Figures 1, 51A:
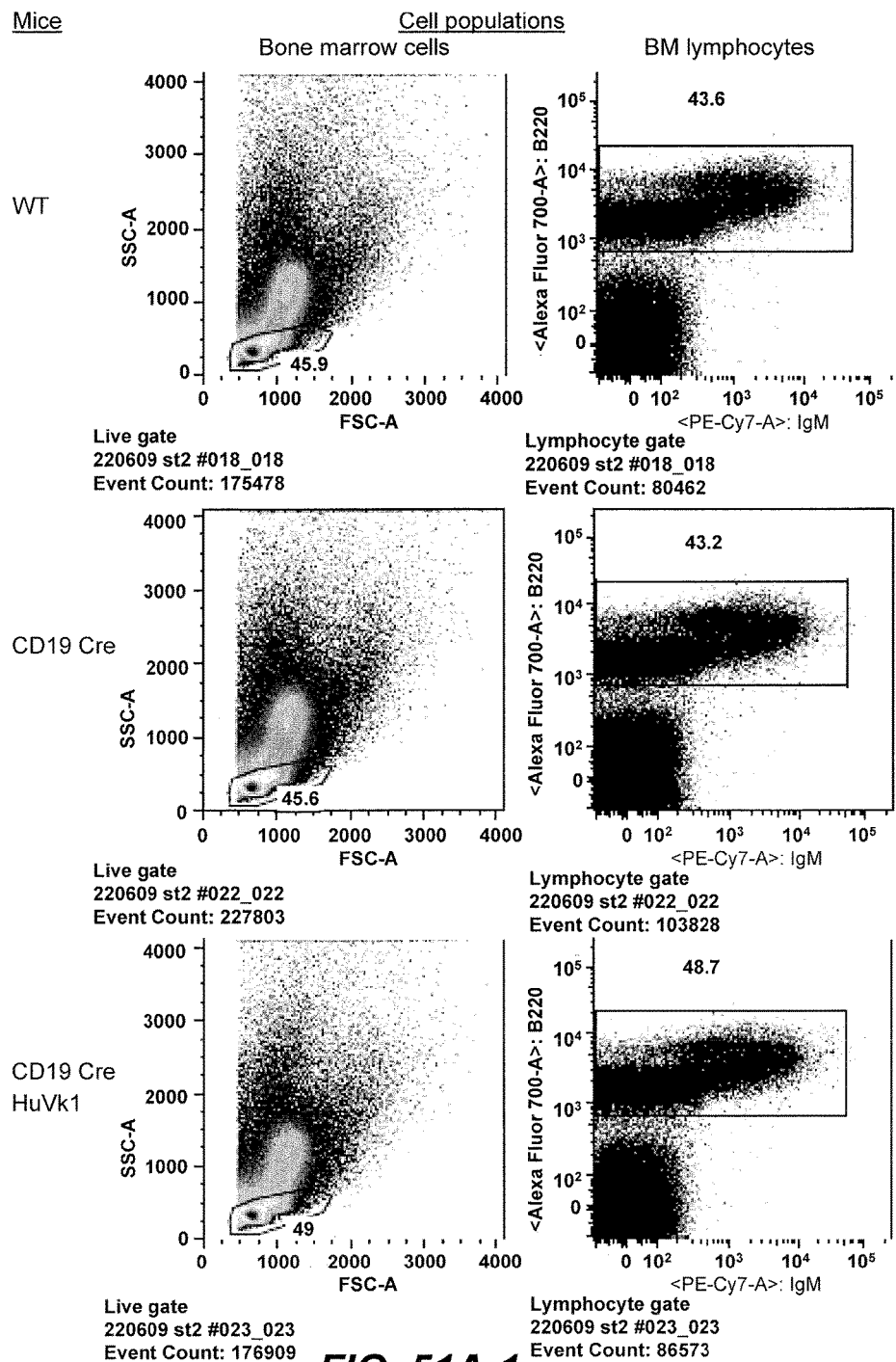
Figures 2, 51A:
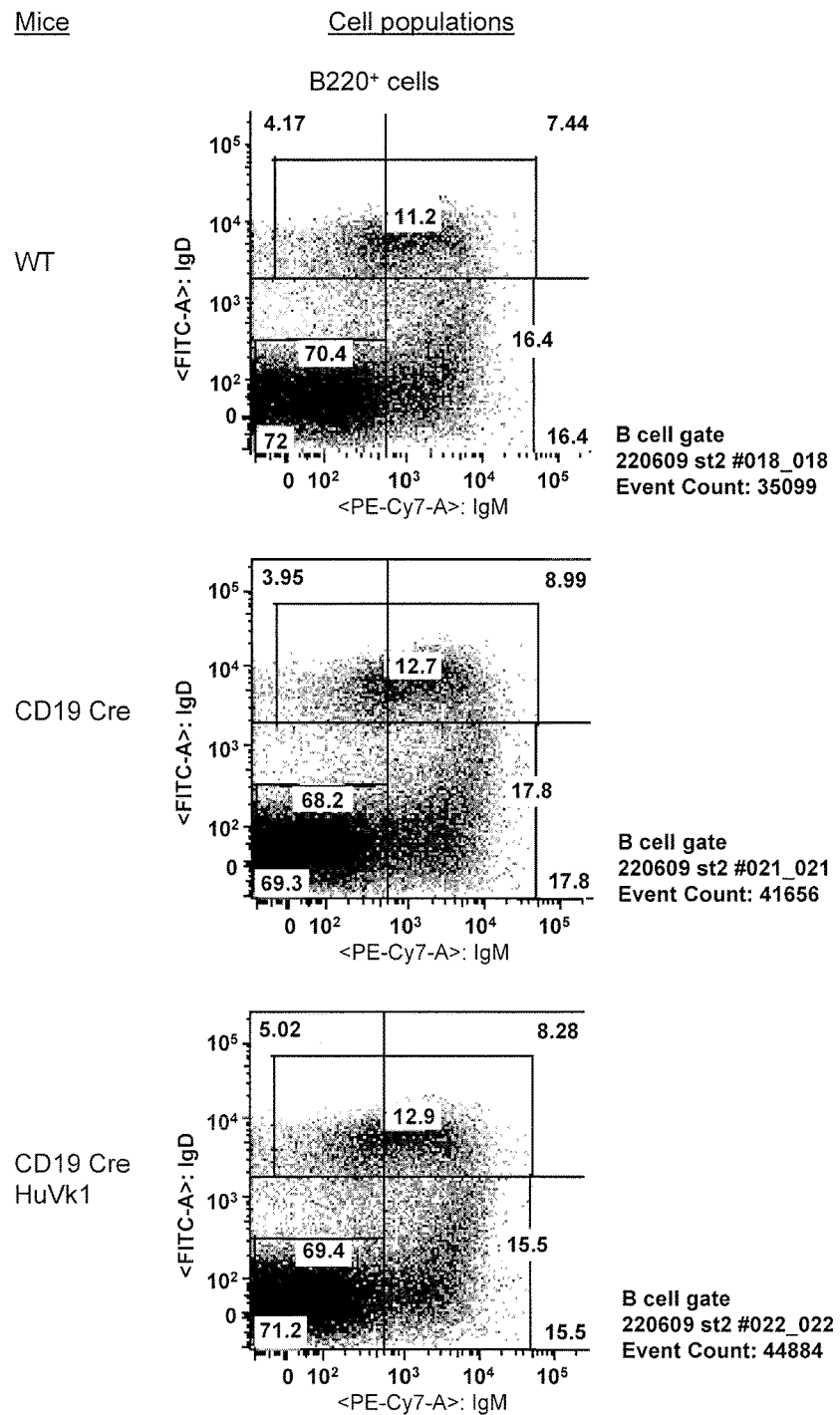
Figures 1, 51B:
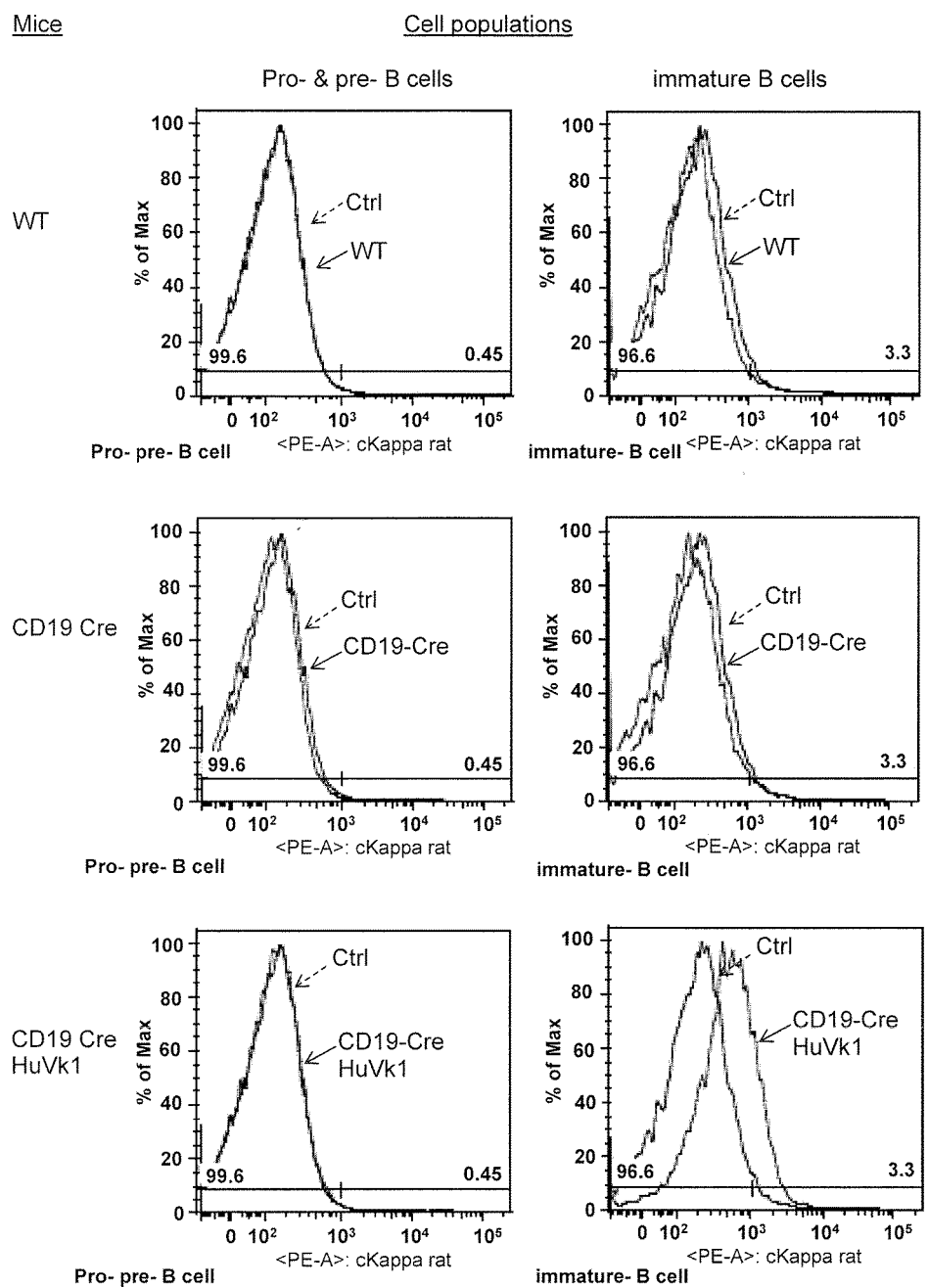
Figures 2, 51B:
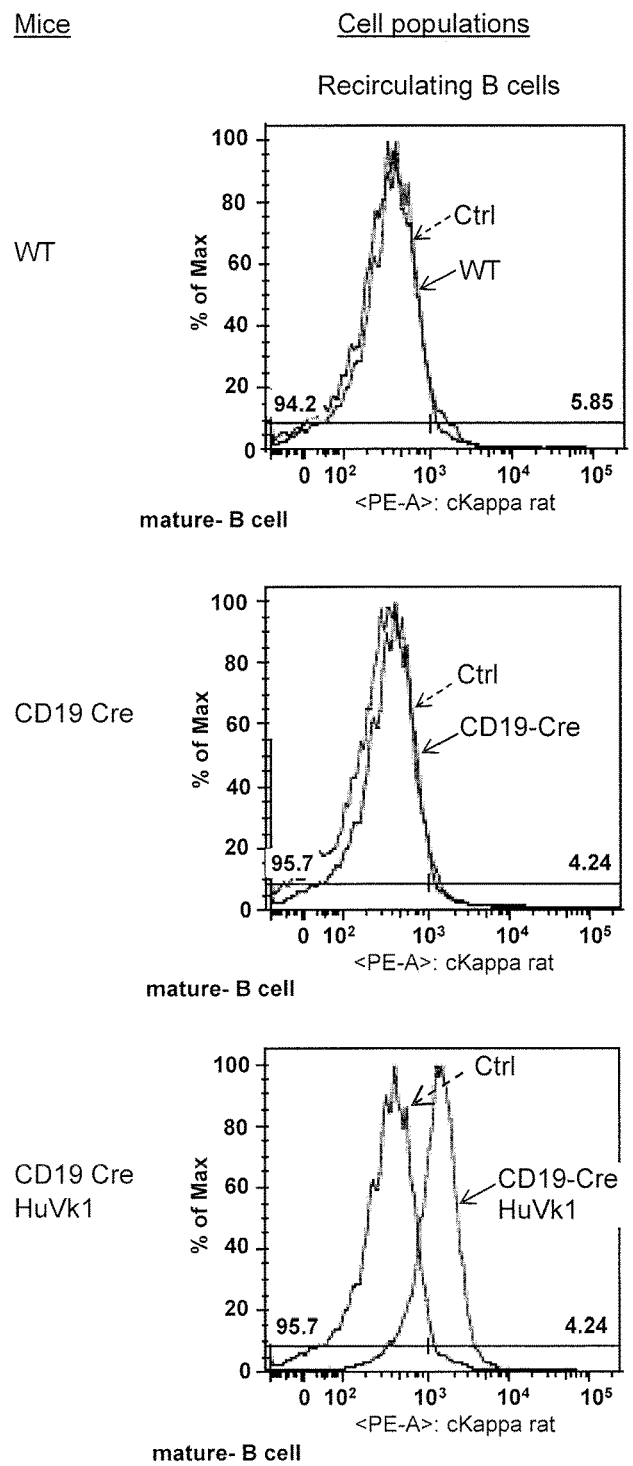

In the peripheral lymphoid organs, staining with the transgene specific antibody (anti-ratCkappa-PE) was only observed in the B cell populations. T cell, myeloid cell and NK cell populations were all negative for surface expression of the transgene in the spleen (FIGS. 48A-48C). In contrast, in cells stained with the pan B cell markers B220 and CD19 all cells were shifted to the right in the FACS plot indicating cell surface expression of the transgene (FIGS. 49A and 49B). A similar transgene-specific staining was measured in CD5+B1 cells of the peritoneum, a developmentally distinct population of B cells (FIGS. 50A and 50B).

Figure 52A:
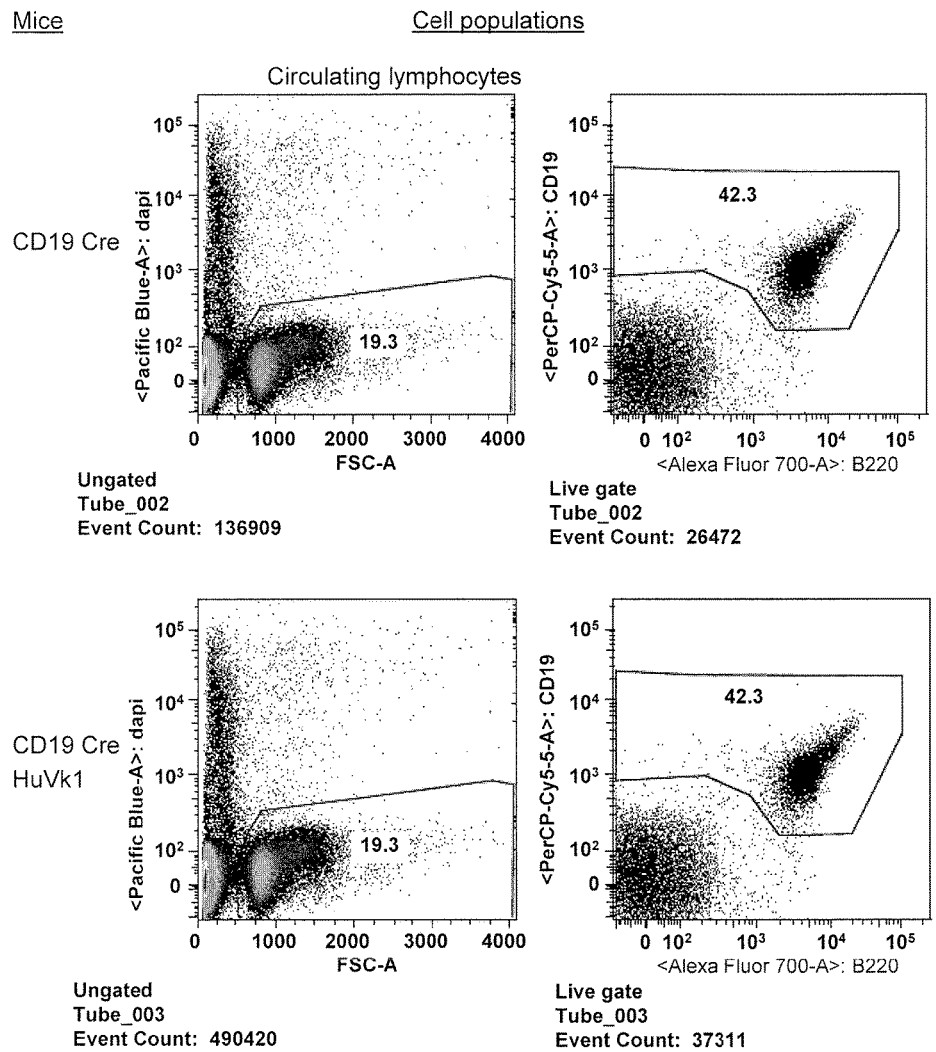
FIGS. 52A and 52B: Transgenic human Vk1 light chain is directly correlated with endogenous light chain and IgM expression in circulating B cells in the blood.
Figure 52B:
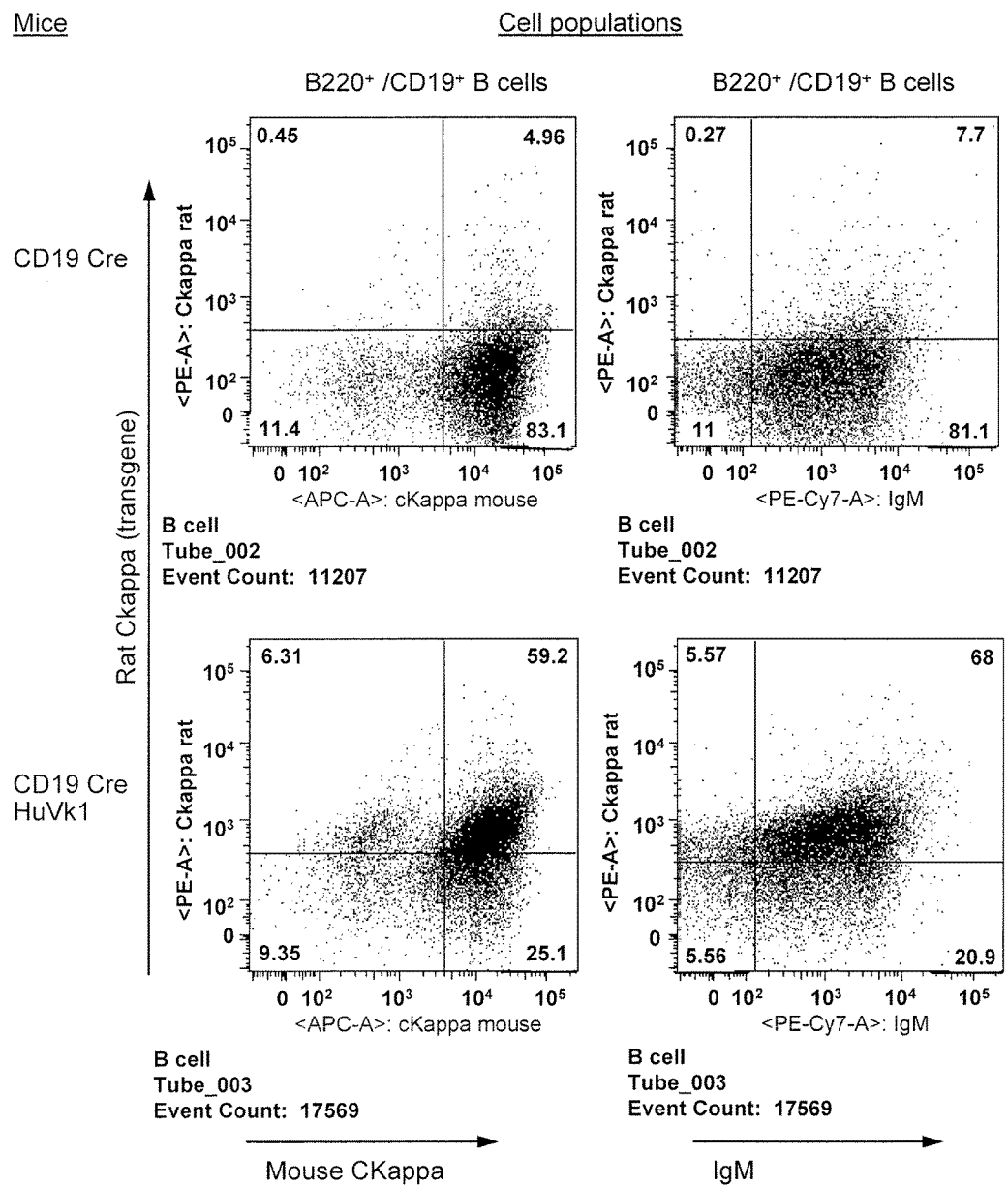

Differentiation of B cells from multilineage precursors to mature B cells occurs in the bone marrow. In the lymphocytes analyzed from the bone marrow, extracellular and transgene expression was not detectable in the earliest B cell progenitors the pro- and pre-B cell consistent with the pattern of normal light chain expression (FIGS. 51A-1-51B-2). Transgene expression first becomes detectable in immature B cells, the developmental stage at which the germline murine light chain undergoes rearrangement and is expressed at the cell surface in the context of the preselected heavy chain (FIGS. 51A-1-51B-2). Consistent with the staining in the spleen transgenic light chain expression is also detected on mature recirculating B cells (FIGS. 51A-1-51B-2). Thus the CD19-Cre driven expression of the transgene is consistent with the normal pattern of light chain expression. The staining with the endogenous light chain-specific antibody is more intense than that of the transgene-specific light chain antibody. This may indicate a higher expression level of the endogenous light chain, a more sensitive staining with the endogenous light chain-specific antibody or a combination of both. Importantly, the intensity of the surface expression of the transgenic light chain is correlated with both endogenous light chain and IgM surface expression as observed in staining of circulating B cells in the blood (FIGS. 52A and 52B).

Thus, overall this analysis demonstrates that expression of the human IGKV1-39/Ckappa transgene is restricted to the B cell compartment and the temporal regulation of its expression is similar to the endogenous kappa and lambda light chains resulting in normal development of all B cell populations. The apparent lower level of expression of the transgene could be explained by the strength of the promoter in comparison to the promoter and enhancers present on endogenous light chain genes or by a delay in transgene expression that gives the endogenous light chains a competitive advantage in pairing with the rearranged heavy chain. This is consistent with the observation that as B cells mature the relative intensity of transgene staining increases compared to the endogenous light chains. In addition, the observation that B cells numbers are normal and that every surface Ig+B cell co-expresses an endogenous and transgenic light chain supports the conclusion that the IGKV1-39 variable region is capable of pairing with a normal repertoire of different murine heavy chain variable regions. Concluded from this analysis was that insertion of the IGKV1-39/rat Ckappa transgene driven by the CD19-Cre activated CAGGS promoter in the Rosa locus facilitates timely and B cell-specific expression of the transgene and that the transgene is capable of pairing with a normal repertoire of murine heavy chains.

Example 38: EPIBASE® T-Cell Epitope Profile for IGKV1-39

The protein sequence of IGKV1-39 (FIGS. 37A-37Z, human germline IGKV1-39/J Protein) was scanned for the presence of putative HLA class II restricted epitopes, also known as $T_H$-epitopes. For this, Algonomics' EPIBASE® platform was applied to IGKV1-39. In short, the platform analyzes the HLA binding specificities of all possible 10-mer peptides derived from a target sequence (Desmet et al. (1992), Nature 356:539-542; Desmet et al. (1997), FASEB J. 11:164-172; Desmet et al. (2002), Proteins 48:31-43; Desmet et al. (2005), Proteins 58:53-69). Profiling is done at the allotype level for 20 DRB1, 7 DRB3/4/5, 13 DQ and 7 DP, i.e., 47 HLA class II receptors in total (see, Table 5). EPIBASE® calculates a quantitative estimate of the free energy of binding $\Delta G_{bind}$ of a peptide for each of the 47 HLA class II receptors. These data were then further processed as follows:

Free energies were converted into Kd-values through $\Delta G_{bind} = RT \ln(Kd)$.

Peptides were classified as strong (S), medium (M), weak and non (N) binders. The following cutoffs were applied:
S: strong binder: Kd<0.1 µM.
M: medium binder: 0.1 µM≤Kd≤0.8 µM.
N: weak and non-binder: 0.8 µM≤Kd.

Peptides corresponding to self-peptides were treated separately. The list of self-peptides was taken from 293 antibody germline sequences. They are referred to as "germline-filtered" peptides.

S- and M-peptides are mapped onto the target sequence in so-called epitope maps; S-affinities are plotted quantitatively; M-values are presented qualitatively. As a general overview of the results, Table 6 lists the number of strong and medium binders in the analyzed proteins, for the groups of HLA class II receptors corresponding to the DRB1, DQ, DP and DRB3/4/5 genes. Counting was done separately for strong and medium affinity binders. Peptides binding to multiple allotypes of the same group were counted as one. Values between brackets refer to germline-filtered peptides. In Table 7, the sequence is shown in a format suitable for experimental work. The sequence is broken down in consecutive 15-mers overlapping by 12 residues. For each 15-mer, the promiscuity is listed (the number of allotypes out of a total of 47 for which the 15-mer contains a critical binder), as well as the implied serotypes. The EPIBASE® profile and epitope maps are shown in FIGS. 41A-41C and 42.

It was concluded that IGKV1-39 contains no strong non-self DRB1 binders. Typically, significantly more binders were found for DRB1 than for other HLA genes. This is in agreement with experimental evidence that allotypes belonging to the DRB1 group are more potent peptide binders. Medium strength epitopes for DRB1 allotypes are expected to contribute to the population response, and cannot be disregarded. Again, no non-self DRB1 binders were found in IGKV1-39.

In the humoral response raised against an antigen, the observed $T_H$ cell activation/proliferation is generally interpreted in terms of the DRB1 specificity. However, one cannot ignore the possible contribution of the DRB3/4/5, DQ and DP genes. Given the lower expression levels of these genes as compared to DRB1, the focus was on the class of strong epitopes for DRB3/4/5, DQ and DP. "Critical epitopes" are those epitopes that are strong binders for any DRB1, DRB3/4/5, DQ or DP allotype or are medium binders for DRB1. IGKV1-39 contains no strong or medium non-self binders for DRB3/4/5, DQ, or DP.

A number of peptides are also present in germline sequences (values between brackets in Table 6). Such peptides may very well bind to HLA but they are assumed to be self and, hence, non-immunogenic. In total, six strong and 16 medium germline-filtered DRB1 binders were found in IGKV1-39. Framework region 1 up to framework region 3 is an exact match for germline V-segment VKI 2-1-(1) O12 (VBase), a.k.a. IGKV1-39*01 (IMGT). Framework region 4 is an exact match for germline J-segment JK1 (V-base) a.k.a. IGKJ1*01(IMGT). It is hardly surprising that these segments do not contain any non-self epitopes.

Example 39: Production Characteristics of IGKV1-39

There is a great demand for antibody discovery platforms that yield therapeutic antibodies that are thermodynamically stable and give good expression yields. These characteristics are important in ensuring the stability of the drug substance during production and after injection of the drug product into the patient. In addition good expression yields impact directly on the cost of drug manufacture and thus pricing, patient access and profitability. Virtually all therapeutic antibodies in clinical use today are composed of human IgG1 and kappa constant regions but use different heavy and light chain variable regions that confer specificity. Human variable heavy and light chain domains can be divided into families that have greater than 80% sequence divergence. When rearranged examples of these families in germline configuration are combined and compared for stability and yield it is clear that the gene families are not equal in terms of biophysical properties. In particular $V_H3$, $V_H1$ and $V_H5$ have favourable stability for the heavy chains and Vk1 and Vk3 have the best stability and yield of light chains. In addition when mutations are introduced as part of the somatic hypermutation process they can interfere with $V_H/V_L$ pairing. To assess the effect that different light chain genes with different rates of mutation have on the production characteristics of a fixed $V_H$ chain, a Fab phage display library was built of light chains (kappa and lambda) from six naïve healthy donors combined with a panel of 44 TT binding heavy chains from immunized donors. After one round of selection TT binding Fab clones were isolated. Several of these shared the same $V_H$ gene as the TT clone PG1433 in combination with different light chains. The Fab light chain fragments were recloned into a kappa expression vector and transfected in combination with DNA encoding the heavy chain of PG1433 into 293 cells and specific IgG production measured by ELISA. As demonstrated in Table 8 the selected clones containing PG1433 $V_H$ combined with different light chains had between five- and ten-fold lower protein expression PG1433 $V_H$ combined with IGKV1-39. Note that all of the light chains contained amino acid mutations within their coding regions that might disrupt $V_H$ paring and reduce production stability. Thus, in addition to reducing the chances of unwanted immunogenicity, it is expected that the use of the light chain IGKV1-39 without mutations contributes to improved production stability and yields of various specificity-contributing $V_H$ genes. Indeed stable clones generated by the transfection of different $V_H$ genes all paired with IGKV1-39 are able to be passaged extensively and still retain robust production characteristics as shown in Table 9.

Example 40: Generation of Mice Expressing Fully Human VH and VL Regions

Transgenic mice described herein are crossed with mice that already contain a human VH locus. Examples of appropriate mice comprising a human VH locus are disclosed in Taylor et al. (1992), *Nucleic Acids Res.* 20:6287-95; Lonberg et al. (1994), *Nature* 368:856-9; Green et al. (1994), *Nat. Genet.* 7:13-21; Dechiara et al. (2009), *Methods Mol. Biol.* 530:311-24.).

After crossing and selecting for mice that are at least heterozygous for the IGKV1-39 transgene and the human VH locus, selected mice are immunized with a target. VH genes are harvested as described hereinabove. This method has the advantage that the VH genes are already fully human and thus do not require humanization.

Example 41: Isolation, Characterization, OLIGOCLONICS® Formatting and Production of Antibodies Targeting Human IL6 for Treatment of Chronic Inflammatory Diseases Such as Rheumatoid Arthritis A spleen VH repertoire from transgenic mice that are immunized with human recombinant IL6 is cloned in a phage display Fab vector with a single human IGKV1-39-C kappa light chain (identical to the mouse transgene) and subjected to panning against the immunogen human IL6. Clones that are obtained after two to four rounds of panning are analyzed for their binding specificity. VH genes encoding IL6-specific Fab fragments are subjected to sequence analysis to identify unique clones and assign VH, DH and JH utilization. The Fab fragments are reformatted as IgG1 molecules and transiently expressed. Unique clones are then grouped based on non-competition in binding assays and subjected to affinity and functional analysis. The most potent anti-IL6 IgG1 mAbs are subsequently expressed as combinations of two, three, four or five heavy chains comprising different VH-regions in the OLIGOCLONICS® format, together with one IGKV1-39-C-based kappa light chain and tested in vitro for complex formation with IL-6. The OLIGOCLONICS® are also tested in vivo for clearance of human IL-6 from mice. An OLIGOCLONICS® with the most potent clearance activity is chosen and the murine VH genes humanized according to conventional methods. The humanized IgG1 are transfected into a mammalian cell line to generate a stable clone. An optimal subclone is selected for the generation of a master cell bank and the generation of clinical trial material.

Many of the protocols described here are standard protocols for the construction of phage display libraries and the panning of phages for binding to an antigen of interest and are described, for example, in *Antibody Phage Display: Methods and Protocols* (2002), Editor(s) Philippa M. O'Brien, Robert Aitken, Humana Press, Totowa, N.J., US.

Immunizations: Transgenic mice receive three immunizations with human IL6 every two weeks using the adjuvant Sigma titerMax according to manufacturer's instructions.

RNA isolation and cDNA synthesis: Three days after the last immunization, spleens and lymphnodes from the mice are removed and passed through a 70 micron filter into a tube containing PBS pH 7.4 to generate a single cell suspension. After washing and pelleting of lymphocytes, cells are suspended in TRIzol LS Reagent (Invitrogen) for the isolation of total RNA according to the manufacturer's protocol and subjected to reverse transcription reaction using 1 microgram of RNA, Superscript III RT in combination with dT20 according to manufacturer's procedures (Invitrogen).

The generation of Fab phage display libraries is carried out as described in Example 21.

Selection of phages on coated immunotubes: Human recombinant IL6 is dissolved in PBS in a concentration of 5 µg/ml and coated to MaxiSorp Nunc-Immuno Tube (Nunc 444474) overnight at 4° C. After discarding the coating solution, the tubes are blocked with 2% skim milk (ELK) in PBS (blocking buffer) for one hour at Room Temperature (RT). In parallel, 0.5 ml of the phage library is mixed with 1 ml blocking buffer and incubated for 20 minutes at room temperature. After blocking the phages, the phage solution is added to the IL6-coated tubes and incubated for two hours at RT on a slowly rotating platform to allow binding. Next, the tubes are washed ten times with PBS/0.05% TWEEN®-20 followed by phage elution by incubating with 1 ml 50 mM glycine-HCl pH 2.2 ten minutes at RT on rotating wheel and directly followed by neutralization of the harvested eluent with 0.5 ml 1 M Tris-HCl pH 7.5.

Harvesting phage clones: A 5 ml XL1-Blue MRF (Stratagene) culture at O.D. 0.4 is added to the harvested phage solution and incubated for 30 minutes at 37° C. without shaking to allow infection of the phages. Bacteria are plated on Carbenicillin/Tetracycline 4% glucose 2*TY plates and grown overnight at 37° C.

Phage production: Phages are grown and processed as described by Kramer et al. 2003 (Kramer et al. 2003, *Nucleic Acids Res.* 31(11):e59) using VCSM13 as helper phage strain.

Phage ELISA: ELISA plates are coated with 100 microliters human recombinant IL6 per well at a concentration of 2.5 micrograms/ml in PBS overnight at 4° C. Plates coated with 100 microliters thyroglobulin at a concentration of 2 micrograms/ml in PBS are used as a negative control. Wells are emptied, dried by tapping on a paper towel, filled completely with PBS-4% skimmed milk (ELK) and incubated for one hour at room temperature to block the wells. After discarding the block solution, phage minipreps premixed with 50 µl blocking solution are added and incubated for one hour at RT. Unbound phages are subsequently removed by five washing steps with PBS-0.05% TWEEN®-20. Bound phages are detected by incubating the wells with 100 microliters anti-M13-HRP antibody conjugate (diluted 1/5000 in blocking buffer) for one hour at room temperature. Free antibody is removed by repeating the washing steps as described above, followed by TMB substrate incubation until color development was visible. The reaction is stopped by adding 100 microliters of 2 M H2SO4 per well and analyzed on an ELISA reader at 450 nm emission wavelength.

Sequencing: Clones that give signals at least three times above the background signal are propagated, used for DNA miniprep procedures (see, procedures Qiagen miniPrep manual) and subjected to nucleotide sequence analysis. Sequencing is performed according to the Big Dye 1.1 kit accompanying manual (Applied Biosystems) using a reverse primer (CH1_Rev1, Table 1) recognizing a 5' sequence of the CH1 region of the human IgG1 heavy chain (present in the Fab display vector MV1043, FIGS. 28 and 37A-37Z).

The sequences of the murine VH regions are analyzed for diversity of DH and JH gene segments.

Figure 47:
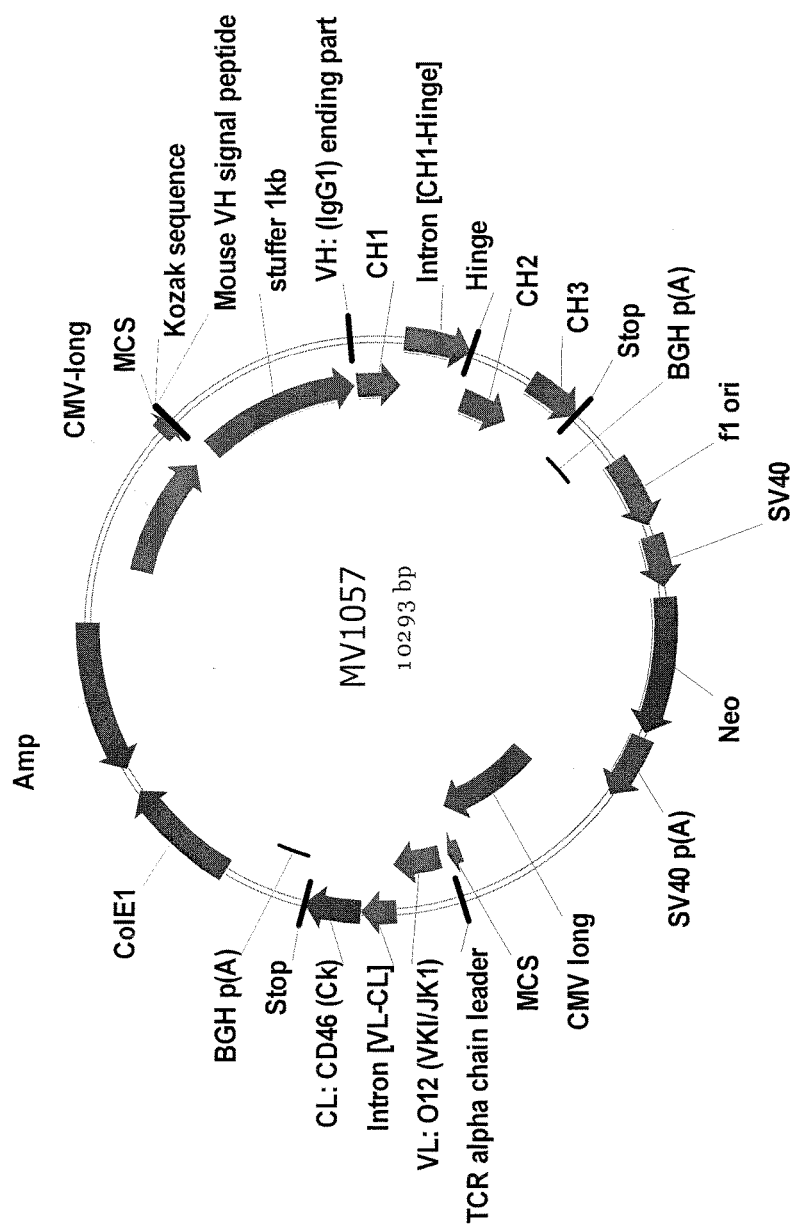
FIG. 47: Topology of the MV1057 vector. Replacing the indicated stuffer fragment with a VH fragment yields an expression vector that can be transfected to eukaryotic cells for the production of IgG1 antibodies with light chains containing an O12 (IGKV1-39) VL gene.

Construction and expression of chimeric IgG1: Vector MV1057 (FIGS. 37A-37Z and 47) was generated by cloning the transgene (IGKV1-39) L chain fragment into a derivative of vector pcDNA3000Neo (Crucell, Leiden, The Netherlands) that contains the human IgG1- and kappa constant regions. VH regions are cloned into MV1057 and nucleotide sequences for all constructs are verified according to standard techniques. The resulting constructs are transiently expressed in HEK293T cells and supernatants containing chimeric IgG1 are obtained and purified using standard procedures as described before (M. Throsby 2006, *J. Virol.* 80:6982-92).

IgG1 binding and competition analysis: IgG1 antibodies are titrated in ELISA using IL6-coated plates as described above and an anti-human IgG peroxidase conjugate. Competition ELISAs to group antibodies based on epitope recognition are performed by incubating Fab phages together with IgG1 or with commercial antibodies against IL6 (e.g., Abcam cat. no. ab9324) in IL6-coated plates, followed by detection of bound Fab phage using an anti-M13 peroxidase conjugate.

IgG1 affinity measurements: The affinities of the antibodies to IL6 are determined with the Quantitative kinetic protocol on the Octet (ForteBio). Antibodies are captured onto an Anti-Human IgG Fc Capture biosensor and exposed to free IL6 and analyzed using proprietary software to calculate the Kd of each antibody.

Functional activity of IL6 antibodies: To test the ability of the selected antibodies to inhibit binding between IL6 and IL6 receptor (IL6R), an ELISA based assay is used. Various concentrations of antibody are mixed with a fixed concentration (10 ng/ml) of biotinylated IL6 as described by Naoko et al. 2007, *Can. Res.* 67:817-875. The IL6-antibody immune complex is added to immobilized IL6R. The binding of biotinylated IL6 to IL6R is detected with horseradish peroxidase-conjugated streptavidin. The reduction of ELISA signal is a measurement of inhibition. As positive control for inhibition of binding between IL6 and IL6R either anti-IL6R antibody (Abcam cat. no. ab34351; clone B-R6) or anti IL6 antibody (Abcam cat. no. ab9324) is used.

In vitro blocking activity of the selected anti-IL6 antibodies is measured in a proliferation assay using the IL6-dependent cell line 7TD1. Briefly, cells are incubated with different concentrations of human IL6 with or without the anti-IL6 antibody. The available amount of IL6 determines the degree of proliferation. Thus if an added antibody blocks IL6 binding the proliferation readout is reduced compared to a non binding antibody control. Proliferation is measured by the incorporation of 5-bromo-2'-deoxy-uridine (BrdU) into the DNA using the BrdU proliferation kit (Roche cat. no. 11444611001) according to the manufacturer's instructions.

Generation of anti-IL6 OLIGOCLONICS®: The most potent anti-IL6 antibodies are selected from each epitope group. The expression constructs expressing these antibodies are transfected into HEK293T cells in non-competing groups of three in different ratios (1:1:1; 3:1:1; 1:3:1; 1:1:3; 3:3:1; 1:3:3; 3:1; 10:11; 1:10:1; 1:1:10; 10:10:1; 1:10:10; 10:1:10; 3:10:1; 10:3:1; 1:10:3; 3:1:10; 10:1:3; 1:3:10). Antibody containing supernatants are harvested and purified and characterized as above.

Complex formation and in vivo clearance of anti-IL6 OLIGOCLONICS®: To measure the ability of anti-IL6 OLIGOCLONICS® to form immune complexes and to analyze these complexes Size Exclusion Chromatography (SEC) is used according to the approach disclosed by Min-Soo Kim et al. (2007), *JMB* 374:1374-1388, to characterize the immune-complexes formed with different antibodies to TNFα. Different molar ratios of the anti-IL6 OLIGOCLONICS® are mixed with human IL6 and incubated for 20 hours at 4° C. or 25° C. The mixture is analyzed on an HPLC system fitted with a size exclusion column; different elution times are correlated to molecular weight using a molecular weight standards.

The ability of antibodies to form complexes with IL6 is correlated with their ability to rapidly clear the cytokine from the circulation in vivo. This is confirmed by measuring the clearance of radiolabelled IL6 from mice. Briefly, female, six- to eight-week-old Balb/c mice are obtained and 18 hours before the experiment, the animals are injected intravenously (IV) via the lateral tail vein with different doses of purified anti-IL6 OLIGOCLONICS®. On day 0, the mice are injected IV with 50 microliters of radiolabeled IL-6 (1×10E7 cpm/mL) under the same conditions. Blood samples (approximately 50 microliters) are collected at several time intervals and stored at 4° C. The samples are centrifuged for five minutes at 4000 xg and the radioactivity of the serum determined. All pharmacokinetic experiments are performed simultaneously with three animals for each treatment.

Generation of anti-IL6 OLIGOCLONICS® stable clones and preclinical development: A lead anti-IL6 OLIGOCLONICS® is selected based on the in vitro and in vivo potency as determined above. The murine VH genes are humanized according to standard methods and combined with the fully human IGKV1-39 light chain in an expression vector as described above. Examples of humanization methods include those based on paradigms such as resurfacing (E. A. Padlan et al. (1991), *Mol. Immunol.* 28:489), superhumanization (P. Tan, D. A., et al. (2002), *J. Immunol.* 169:1119) and human string content optimization (G. A. Lazar et al. (2007), *Mol. Immunol.* 44:1986). The three constructs are transfected into PER. C6® cells at the predetermined optimal ratio (described above) under the selective pressure of G418 according to standard methods. A stable high producing anti-IL6 OLIGOCLONICS® clone is selected and a working and qualified master cell bank generated.

U.S. patent application Ser. No. 12/931,955, filed Feb. 14, 2011, which is a continuation of U.S. patent application Ser. No. 11/282,414, filed Nov. 30, 2005, now U.S. Pat. No. 7,919,257, which is a continuation of PCT International Patent Application No. PCT/NL2004/000386, filed on May 28, 2004, designating the United States of America, and published in English, as PCT International Publication No. WO 2004/106375 A1 on Dec. 9, 2004, which application claims priority to European Patent Application No. 03076671.1 filed on May 30, 2003, are incorporated herein by this reference.

TABLE 1

List of primers

| DO- | Primer | Sequence |
|---|---|---|
| 0012 | CH1_Rev1 | TGCCAGGGGGAAGACCGATG (SEQ ID NO: 4) |
| 0656 | MVH-1 | GCCGGCCATGGCCGAGGTRMAGCTTCAGGAGTCAGGAC (SEQ ID NO: 5) |
| 0657 | MVH-2 | GCCGGCCATGGCCGAGGTSCAGCTKCAGCAGTCAGGAC (SEQ ID NO: 6) |
| 0658 | MVH-3 | GCCGGCCATGGCCCAGGTGCAGCTGAAGSASTCAGG (SEQ ID NO: 7) |
| 0659 | MVH-4 | GCCGGCCATGGCCGAGGTGCAGCTTCAGGAGTCSGGAC (SEQ ID NO: 8) |
| 0660 | MVH-5 | GCCGGCCATGGCCGARGTCCAGCTGCAACAGTCYGGAC (SEQ ID NO: 9) |
| 0661 | MVH-6 | GCCGGCCATGGCCCAGGTCCAGCTKCAGCAATCTGG (SEQ ID NO: 10) |
| 0662 | MVH-7 | GCCGGCCATGGCCCAGSTBCAGCTGCAGCAGTCTGG (SEQ ID NO: 11) |
| 0663 | MVH-8 | GCCGGCCATGGCCCAGGTYCAGCTGCAGCAGTCTGGRC (SEQ ID NO: 12) |
| 0664 | MVH-9 | GCCGGCCATGGCCCAGGTYCAGCTYCAGCAGTCTGG (SEQ ID NO: 13) |
| 0665 | MVH-10 | GCCGGCCATGGCCGAGGTCCARCTGCAACAATCTGGACC (SEQ ID NO: 14) |
| 0666 | MVH-11 | GCCGGCCATGGCCCAGGTCCACGTGAAGCAGTCTGGG (SEQ ID NO: 15) |
| 0667 | MVH-12 | GCCGGCCATGGCCGAGGTGAASSTGGTGGAATCTG (SEQ ID NO: 16) |
| 0668 | MVH-13 | GCCGGCCATGGCCGAVGTGAAGYTGGTGGAGTCTG (SEQ ID NO: 17) |
| 0669 | MVH-14 | GCCGGCCATGGCCGAGGTGCAGSKGGTGGAGTCTGGGG (SEQ ID NO: 18) |

TABLE 1-continued

List of primers

| DO- | Primer | Sequence |
|---|---|---|
| 0670 | MVH-15 | GCCGGCCATGGCCGAKGTGCAMCTGGTGGAGTCTGGG (SEQ ID NO: 19) |
| 0671 | MVH-16 | GCCGGCCATGGCCGAGGTGAAGCTGATGGARTCTGG (SEQ ID NO: 20) |
| 0672 | MVH-17 | GCCGGCCATGGCCGAGGTGCARCTTGTTGAGTCTGGTG (SEQ ID NO: 21) |
| 0673 | MVH-18 | GCCGGCCATGGCCGARGTRAAGCTTCTCGAGTCTGGA (SEQ ID NO: 22) |
| 0674 | MVH-19 | GCCGGCCATGGCCGAAGTGAARSTTGAGGAGTCTGG (SEQ ID NO: 23) |
| 0675 | MVH-20 | GCCGGCCATGGCCGAAGTGATGCTGGTGGAGTCTGGG (SEQ ID NO: 24) |
| 0676 | MVH-21 | GCCGGCCATGGCCCAGGTTACTCTRAAAGWGTSTGGCC (SEQ ID NO: 25) |
| 0677 | MVH-22 | GCCGGCCATGGCCCAGGTCCAACTVCAGCARCCTGG (SEQ ID NO: 26) |
| 0678 | MVH-23 | GCCGGCCATGGCCCAGGTYCARCTGCAGCAGTCTG (SEQ ID NO: 27) |
| 0679 | MVH-24 | GCCGGCCATGGCCGATGTGAACTTGGAAGTGTCTGG (SEQ ID NO: 28) |
| 0680 | MVH-25 | GCCGGCCATGGCCGAGGTGAAGGTCATCGAGTCTGG (SEQ ID NO: 29) |
| 0681 | ExtMVH-1 | CAGTCACAGATCCTCGCGAATT*GGCCCA GCCGGCC*ATGGCCSANG (SEQ ID NO: 30) |
| 0682 | ExtMVH-2 | CAGTCACAGATCCTCGCGAATT*GGCCCA GCCGGCC*ATGGCCSANC (SEQ ID NO: 31) |
| 0683 | MJH-Rev1 | GGGGGTGTCGTTTTGGCTGAGGAGAC *GGTGACC*GTGG (SEQ ID NO: 32) |
| 0684 | MJH-Rev2 | GGGGGTGTCGTTTTGGCTGAGGAGAC *TGTGAGA*GTGG (SEQ ID NO: 33) |
| 0685 | MJH-Rev3 | GGGGGTGTCGTTTTGGCTGCAGAGAC *AGTGACC*AGAG (SEQ ID NO: 34) |
| 0686 | MJH-Rev4 | GGGGGTGTCGTTTTGGCTGAGGAGAC *GGTGACT*GAGG (SEQ ID NO: 35) |
| 0687 | ExtMJH-Rev1 & | GGGGGTGTCGTTTTGGCTGAGGAGAC *GGTGACC*GTGG (SEQ ID NO: 36) |
| 0688 | ExtMJH-Rev2in | GGGGGTGTCGTTTTGGCTGAGGAGAC *GGTGACA*GTGG (SEQ ID NO: 37) |
| 0690 | ExtMJH-Rev3 | GGGGGTGTCGTTTTGGCTGAGGAGAC *GGTGACC*AGAG (SEQ ID NO: 38) |
| 0691 | ExtMJH-Rev4 | GGGGGTGTCGTTTTGGCTGAGGAGAC *GGTGACC*GAGG (SEQ ID NO: 39) |

TABLE 2

Phage ELISA signal levels as measured at 450 nm. TT-coated plates represent plates that were coated with tetanus toxoid. Thyroglobulin-coated plates are used as negative controls. 10/10 and 15/15 indicate the number of wash steps with PBS-TWEEN ® during panning procedures. The 10/10 tetanus toxoid and 10/10 thyroglobulin plates and the 15/15 tetanus toxoid and 15/15 thyroglobulin plates are duplicates from each other except for the coating agent. OD values higher than three times the background are assumed specific.

|   | 1 | 2 | 3 | 4 | 5 | 6 | 7 | 8 | 9 | 10 | 11 | 12 |
|---|---|---|---|---|---|---|---|---|---|----|----|----|
| TT-coated plate 10/10 washings | | | | | | | | | | | | |
| A | 0.139 | 0.093 | 0.089 | 0.121 | 0.117 | 0.598 | 0.146 | 0.115 | 0.18 | 0.155 | 0.543 | 0.601 |
| B | 0.136 | 0.404 | 0.159 | 0.187 | 0.489 | 0.134 | 0.216 | 0.092 | 0.222 | 0.108 | 0.181 | 0.484 |
| C | 0.197 | 0.526 | 0.09 | 0.213 | 0.395 | 0.155 | 0.108 | 0.12 | 0.183 | 0.136 | 0.092 | 0.866 |
| D | 0.143 | 0.258 | 0.101 | 0.422 | 0.088 | 0.243 | 0.485 | 0.251 | 0.304 | 0.198 | 0.478 | 0.091 |
| E | 0.445 | 0.169 | 0.526 | 0.481 | 0.206 | 0.285 | 0.111 | 0.119 | 0.128 | 0.2 | 0.118 | 0.098 |
| F | 0.237 | 0.291 | 0.594 | 0.139 | 0.206 | 0.565 | 0.543 | 0.091 | 0.136 | 0.227 | 0.228 | 0.099 |
| G | 0.459 | 0.102 | 0.152 | 0.659 | 0.203 | 0.452 | 0.152 | 0.133 | 0.094 | 0.102 | 0.375 | 0.098 |
| H | 0.341 | 0.623 | 0.745 | 0.415 | 0.682 | 0.527 | 0.655 | 0.114 | 0.258 | 0.284 | 0.685 | 0.113 |
| TT-coated plate 15/15 washings | | | | | | | | | | | | |
| A | 0.247 | 0.582 | 0.421 | 0.428 | 0.133 | 0.082 | 0.262 | 0.079 | 0.343 | 0.414 | 0.095 | 0.292 |
| B | 0.065 | 0.364 | 0.073 | 0.042 | 0.049 | 0.071 | 0.046 | 0.103 | 0.078 | 0.057 | 0.048 | 0.155 |
| C | 0.081 | 0.044 | 0.066 | 0.082 | 0.225 | 0.444 | 0.203 | 0.362 | 0.122 | 0.047 | 0.052 | 0.309 |
| D | 0.092 | 0.11 | 0.59 | 0.22 | 0.33 | 0.544 | 0.058 | 0.159 | 0.047 | 0.174 | 0.086 | 0.05 |
| E | 0.469 | 0.577 | 0.206 | 0.304 | 0.13 | 0.749 | 0.431 | 0.062 | 0.167 | 0.049 | 0.056 | 0.049 |
| F | 0.846 | 0.07 | 0.561 | 0.656 | 0.882 | 0.094 | 0.383 | 0.13 | 0.152 | 0.098 | 0.134 | 0.048 |
| G | 0.537 | 0.052 | 0.49 | 0.105 | 0.337 | 0.193 | 0.514 | 0.294 | 0.068 | 0.35 | 0.525 | 0.05 |
| H | 0.061 | 0.306 | 0.157 | 0.853 | 0.054 | 0.534 | 0.102 | 0.235 | 0.441 | 0.412 | 0.565 | 0.061 |
| Thyroglobulin-coated plate 10/10 washings | | | | | | | | | | | | |
| A | 0.047 | 0.051 | 0.045 | 0.043 | 0.051 | 0.044 | 0.046 | 0.042 | 0.047 | 0.048 | 0.049 | 0.05 |
| B | 0.042 | 0.042 | 0.042 | 0.042 | 0.043 | 0.041 | 0.041 | 0.042 | 0.043 | 0.045 | 0.042 | 0.046 |
| C | 0.044 | 0.043 | 0.043 | 0.044 | 0.043 | 0.044 | 0.043 | 0.042 | 0.043 | 0.041 | 0.044 | 0.046 |
| D | 0.045 | 0.044 | 0.044 | 0.044 | 0.045 | 0.046 | 0.045 | 0.056 | 0.045 | 0.049 | 0.048 | 0.73 |
| E | 0.046 | 0.045 | 0.046 | 0.044 | 0.045 | 0.044 | 0.044 | 0.044 | 0.047 | 0.046 | 0.047 | 0.926 |
| F | 0.048 | 0.045 | 0.044 | 0.046 | 0.044 | 0.043 | 0.044 | 0.046 | 0.046 | 0.046 | 0.046 | 0.792 |
| G | 0.051 | 0.048 | 0.045 | 0.045 | 0.044 | 0.043 | 0.048 | 0.045 | 0.048 | 0.051 | 0.045 | 0.053 |
| H | 0.064 | 0.05 | 0.049 | 0.047 | 0.05 | 0.051 | 0.047 | 0.046 | 0.047 | 0.047 | 0.047 | 0.056 |
| Thyroglobulin-coated plate 15/15 washings | | | | | | | | | | | | |
| A | 0.036 | 0.049 | 0.045 | 0.044 | 0.046 | 0.047 | 0.046 | 0.042 | 0.042 | 0.043 | 0.042 | 0.041 |
| B | 0.045 | 0.042 | 0.041 | 0.043 | 0.043 | 0.043 | 0.045 | 0.045 | 0.047 | 0.048 | 0.044 | 0.045 |
| C | 0.049 | 0.047 | 0.047 | 0.046 | 0.046 | 0.046 | 0.045 | 0.047 | 0.046 | 0.045 | 0.045 | 0.052 |
| D | 0.047 | 0.049 | 0.048 | 0.048 | 0.048 | 0.048 | 0.047 | 0.052 | 0.048 | 0.046 | 0.048 | 0.456 |
| E | 0.049 | 0.047 | 0.047 | 0.047 | 0.047 | 0.049 | 0.047 | 0.048 | 0.047 | 0.046 | 0.048 | 0.412 |
| F | 0.05 | 0.047 | 0.046 | 0.046 | 0.046 | 0.046 | 0.046 | 0.046 | 0.046 | 0.047 | 0.048 | 0.528 |
| G | 0.05 | 0.048 | 0.045 | 0.045 | 0.046 | 0.049 | 0.048 | 0.046 | 0.053 | 0.049 | 0.05 | 0.057 |
| H | 0.057 | 0.05 | 0.046 | 0.045 | 0.047 | 0.049 | 0.047 | 0.047 | 0.046 | 0.047 | 0.053 | 0.048 |

TABLE 3

Protein sequence analysis of ELISA positive tetanus toxoid binders. CDR3 sequence, CDR3 length, VH family members and specific name, JH origin and DH origin of of the clones is indicated.

| CDR3/ SEQ ID NO: | CDR3 length | VH | DH | JH | V Gene family |
|---|---|---|---|---|---|
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |

TABLE 3-continued

Protein sequence analysis of ELISA positive tetanus toxoid binders. CDR3 sequence, CDR3 length, VH family members and specific name, JH origin and DH origin of of the clones is indicated.

| CDR3/ SEQ ID NO: | CDR3 length | VH | DH | JH | V Gene family |
|---|---|---|---|---|---|
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAYYTYDEKAWFAY (SEQ ID NO: 40) | 15 | musIGHV192 | DSP2.11 | JH3 mouse | VH7183 |
| HGAFYTYDEKPWFAY (SEQ ID NO: 41) | 15 | musIGHV192 | IGHD2-14*01 | JH3 mouse | VH7183 |
| HISYYRYDEEVSFAY (SEQ ID NO: 42) | 15 | musIGHV192 | IGHD2-14*01 | JH3 mouse | VH7183 |
| HISYYRYDEEVSFAY (SEQ ID NO: 42) | 15 | musIGHV192 | IGHD2-14*01 | JH3 mouse | VH7183 |
| GWRAFAY (SEQ ID NO: 43) | 7 | musIGHV131 | DSP2.9 | JH3 mouse | VH7183 |
| GWRAFAY (SEQ ID NO: 43) | 7 | musIGHV131 | DSP2.9 | JH3 mouse | VH7183 |
| GWRAFAY (SEQ ID NO: 43) | 7 | musIGHV131 | DSP2.9 | JH3 mouse | VH7183 |
| DRGNYYGMDY (SEQ ID NO: 44) | 10 | musIGHV178 | DSP2.1 | JH4 mouse | VH7183 |
| LGDYYVDWFFAV (SEQ ID NO: 45) | 12 | musIGHV165 | DFL16.1 | JH1 mouse | VH7183 |
| NFPAWFAF (SEQ ID NO: 46) | 8 | musIGHV547 | DST4.3inv | JH3 mouse | VJH558 |
| NFPAWFAY (SEQ ID NO: 46) | 8 | musIGHV547 | DSP2.1 | JH3 mouse | VJH558 |
| NFPAWFVY (SEQ ID NO: 46) | 8 | musIGHV547 | DSP2.1 | JH3 mouse | VJH558 |
| SFTPVPFYYGYDWYFDV (SEQ ID NO: 47) | 17 | musIGHV532 | DSP2.3 | JH1 mouse | VJH558 |
| SFTPVPFYYGYDWYFDV (SEQ ID NO: 47) | 17 | musIGHV532 | DSP2.3 | JH1 mouse | VJH558 |
| SDYDWYFDV (SEQ ID NO: 48) | 9 | musIGHV286 | DSP2.2 | JH1 mouse | VJH558 |
| SDYDWYFDV (SEQ ID NO: 48) | 9 | musIGHV286 | DSP2.2 | JH1 mouse | VJH558 |
| DSKWAYYFDY (SEQ ID NO: 49) | 10 | musIGHV532 | DST4.3 | JH2 mouse | VJH558 |
| GDYTGYGMDY (SEQ ID NO: 50) | 10 | musIGHV125 | DSP2.13 | JH4 mouse | VHSM7 |
| GDYTGYGMDY (SEQ ID NO: 50) | 10 | musIGHV125 | DSP2.13 | JH4 mouse | VHSM7 |

TABLE 3-continued

Protein sequence analysis of ELISA positive tetanus toxoid binders. CDR3 sequence, CDR3 length, VH family members and specific name, JH origin and DH origin of of the clones is indicated.

| CDR3/ SEQ ID NO: | CDR3 length | VH | DH | JH | V Gene family |
|---|---|---|---|---|---|
| GGYDGYWFPY (SEQ ID NO: 51) | 10 | musIGHV125 | DSP2.9 | JH3 mouse | VHSM7 |

TABLE 4

Vector combinations that were transfected to HEK293T.

| Code | HC vector | LC vector | Combined vector | Prep name | Conc. (µg/ml) |
|---|---|---|---|---|---|
| A | x | 0817676_pSELECT_0815426 (IGKV1-39) | x | PIGKV1-39/P1 | — |
| B | x | 0817678_pSELECT_0815427 (IGLV2-14) | x | PIGLV2-14/P1 | — |
| C | MV1110 | 0817676_pSELECT_0815426 (IGKV1-39) | x | PMV1110/IGKV1-39/P1 | 11.0 |
| D | MV1110 | 0817678_pSELECT_0815427 (IGLV2-14) | x | PMV1110/IGLV2-14/P1 | 15.4 |
| E | x | x | MG1494 | MG1494/P2 | 16.1 |

TABLE 5

HLA allotypes considered in $T_H$-epitope profiling.

| HLA type | Serotype | Population % |
|---|---|---|
| DRB1*0101 | DR1 | 17.4 |
| DRB1*0102 | DR1 | 4.9 |
| DRB1*0301 | DR17(3) | 21.2 |
| DRB1*0401 | DR4 | 11.5 |
| DRB1*0402 | DR4 | 3.1 |
| DRB1*0404 | DR4 | 5.5 |
| DRB1*0405 | DR4 | 2.2 |
| DRB1*0407 | DR4 | <2 |
| DRB1*0701 | DR7 | 23.4 |
| DRB1*0801 | DR8 | 3.3 |
| DRB1*0802 | DR8 | <2 |
| DRB1*0901 | DR9 | <2 |
| DRB1*1101 | DR11(5) | 17 |
| DRB1*1104 | DR11(5) | 5.7 |
| DRB1*1201 | DR12(5) | 3.1 |
| DRB1*1301 | DR13(6) | 15.4 |
| DRB1*1302 | DR13(6) | 10.8 |
| DRB1*1401 | DR14(6) | 4.2 |
| DRB1*1501 | DR15(2) | 13.2 |
| DRB1*1601 | DR16(2) | 5.5 |
| DRB3*0101 | DR52 | 24.6 |
| DRB3*0202 | DR52 | 43 |
| DRB3*0301 | DR52 | 10 |
| DRB4*0101 | DR53 | 25.5 |
| DRB4*0103 | DR53 | 21 |
| DRB5*0101 | DR51 | 15.8 |
| DRB5*0202 | DR51 | 5.7 |
| DQA1*0101/DQB1*0501 | DQ5(1) | 20.5 |
| DQA1*0102/DQB1*0502 | DQ5(1) | 2.6 |
| DQA1*0102/DQB1*0602 | DQ6(1) | 26.5 |
| DQA1*0102/DQB1*0604 | DQ6(1) | 6.7 |
| DQA1*0103/DQB1*0603 | DQ6(1) | 11 |
| DQA1*0104/DQB1*0503 | DQ5(1) | 4 |
| DQA1*0201/DQB1*0202 | DQ2 | 20.9 |
| DQA1*0201/DQB1*0303 | DQ9(3) | 7.2 |
| DQA1*0301/DQB1*0301 | DQ7(3) | 12.5 |
| DQA1*0301/DQB1*0302 | DQ8(3) | 18.3 |
| DQA1*0401/DQB1*0402 | DQ4 | 4.5 |
| DQA1*0501/DQB1*0201 | DQ2 | 24.6 |
| DQA1*0501/DQB1*0301 | DQ7(3) | 20.9 |
| DPA1*0103/DPB1*0201 | DPw2 | 19.9 |
| DPA1*0103/DPB1*0401 | DPw4 | 65.1 |
| DPA1*0103/DPB1*0402 | DPw4 | 24.3 |
| DPA1*0201/DPB1*0101 | DPw1 | 6.3 |
| DPA1*0201/DPB1*0301 | DPw3 | <2 |
| DPA1*0201/DPB1*0501 | DPw5 | <2 |
| DPA1*0201/DPB1*0901 | — | 2.4 |

The corresponding serotypes are shown, as well as allotype frequencies in the Caucasian population (Klitz et al. (2003), *Tissue Antigens* 62: 296-307; Gjertson and Terasake (eds) in: *HLA* 1997; Gjertson and Terasake (eds) in: *HLA* 1998; Castelli et al. (2002), *J. Immunol.* 169: 6928-6934). Frequencies can add up to more than 100% since each individual has two alleles for each gene. If all allele frequencies of a single gene were known, they would add up to slightly less than 200% due to homozygous individuals.

TABLE 6

$T_H$ epitope counts for IGKV1-39. Peptides binding to multiple HLAs of the same group (DRB1, DRB3/4/5, DP, DQ) are counted as one. Values between brackets refer to germline-filtered peptides.

| | DRB1 | | DRB3/4/5 | | DQ | | DP | |
|---|---|---|---|---|---|---|---|---|
| | Strong | Medium | Strong | Medium | Strong | Medium | Strong | Medium |
| Menus IGKV1-39 | 0 (+ 6) | 0 (+ 16) | 0 (+ 0) | 0 (+ 5) | 0 (+ 3) | 0 (+ 9) | 0 (+ 0) | 0 (+ 9) |

TABLE 7

Mapping of EPIBASE ® predictions for Merus IGKV1-39 in the classical 15-mer peptide format. This table shows the allotype count of critical epitopes (SEQ ID NOs: 52-83) and implicated serotypes for each of the 15-mers spanning the Merus IGKV1-39 sequence.

| 15mer | Start position | 15-mer sequence | Allotype count | Implicated serotypes |
|---|---|---|---|---|
| 1 | 1 | DIQMTQSPSSLSASV | 6 | DR1, DR4, DR7, DR9 |
| 2 | 4 | MTQSPSSLSASVGDR | 5 | DR1, DR4, DR9 |
| 3 | 7 | SPSSLSASVGDRVTI | 0 | |
| 4 | 10 | SLSASVGDRVTITCR | 0 | |
| 5 | 13 | ASVGDRVTITCRASQ | 0 | |
| 6 | 16 | GDRVTITCRASQSIS | 2 | DR11(5), DR7 |
| 7 | 19 | VTITCRASQSISSYL | 4 | DQ2, DR11(5), DR4, DR7 |
| 8 | 22 | TCRASQSISSYLNWY | 2 | DQ2, DR4 |
| 9 | 25 | ASQSISSYLNWYQQK | 5 | DR13(6), DR15(2), DR4 |
| 10 | 28 | SISSYLNWYQQKPGK | 8 | DR12(5), DR13(6), DR15(2), DR16(2), DR4, DR8 |
| 11 | 31 | SYLNWYQQKPGKAPK | 10 | DR1, DR12(5), DR16(2), DR4, DR51, DR8 |
| 12 | 34 | NWYQQKPGKAPKLLI | 9 | DR1, DR15(2), DR4, DR51, DR8 |
| 13 | 37 | QQKPGKAPKLLIYAA | 7 | DQ4, DR1, DR11(5), DR15(2), DR51, DR8 |
| 14 | 40 | PGKAPKLLIYAASSL | 7 | DQ4, DR1, DR11(5), DR4, DR8 DR1, DR11(5), DR12(5), DR13(6), DR14(6), DR15(2), DR4, |
| 15 | 43 | APKLLIYAASSLQSG | 15 | DR51, DR8, DR9 DR1, DR11(5), DR12(5), DR13(6), DR14(6), DR15(2), DR4, |
| 16 | 46 | LLIYAAsSLQSGVPS | 15 | DR51, DR8, DR9 |
| 17 | 49 | YAASSLQSGVPSRFS | 1 | DR15(2) |
| 18 | 52 | SSLQSGVPSRFSGSG | 1 | DR15(2) |
| 19 | 55 | QSGVPSRFSGSGSGT | 0 | |
| 20 | 58 | VPSRFSGSGSGTDFT | 0 | |
| 21 | 61 | RFSGSGSGTDFTLTI | 0 | |
| 22 | 64 | GSGSGTDFTLTISSL | 1 | DR52 |
| 23 | 67 | SGTDFTLTISSLQPE | 4 | DR4, DR52, DR7, DR9 |
| 24 | 70 | DFTLTISSLQPEDFA | 4 | DQ2, DR4, DR7, DR9 |
| 25 | 73 | LTISSLQPEDFATYY | 1 | DQ2 |
| 26 | 76 | SSLQPEDFATYYCQQ | 0 | |
| 27 | 79 | QPEDFATYYCQQSYS | 1 | DR4 |
| 28 | 82 | DFATYYCQQSYSTPP | 5 | DR4, DR51, DR7 |
| 29 | 85 | TYYCQQSYSTPPTFG | 4 | DR4, DR51, DR7 |
| 30 | 88 | CQQSYSTPPTFGQGT | 0 | |
| 31 | 91 | SYSTPPTFGQGTKVE | 0 | |
| 32 | 94 | TPPTFGQGTKVEIK | 0 | |

TABLE 8

The $V_H$ gene from PG1433 paired with various light chain genes with differing rates of amino acid mutation were compared for production levels with the original clone containing the IGKV1-39 gene.

| IgG name | Light chain gene | Number of amino acid mutations | concentration (μg/ml) |
|---|---|---|---|
| PG1433 | 1-39 | 0 | 63, 45.5, 38.6 (avg = 49) |
| PG1631 | 1-12 | 4 | 10.5 |
| PG1632 | 1-27 | 7 | 9.3 |
| PG1634 | 1D-12 | 10 | 10.8 |
| PG1635 | 1D-33 | 6 | 10.2 |
| PG1642 | 1-5 | 8 | 7.1 |
| PG1644 | 1-9 | 3 | 7.8 |
| PG1650 | 1D-39 | 3 | 9.1 |
| PG1652 | 2D-28 | 3 | 7.1 |
| PG1653 | 3-15 | 14 | 7 |
| PG1654 | 3-20 | 2 | 5.2 |
| PG1674 | 1-40 | 7 | 8.2 |
| PG1678 | 2-11 | 2 | 8.1 |
| PG1680 | 2-14 | 15 | 10.8 |
| PG1682 | 3-1 | 13 | 9.9 |
| PG1683 | 6-57 | 6 | 13.9 |

TABLE 9

Parameters of stability for stable clones containing the germline IGKV1-39 gene.

| Subclone | Culture days at start batch run | Avg pdt in previous 14 days | ± SD | % avg | Batch started at population doublings | Maximum viable cell density (×10⁶ cells/ml) | % avg | IVC at maximum IgG concentration (10⁹ cells/ hr/L) | % avg | qAb (pg/ cell/ day) | % avg | Maximum IgG concentration (mg/L) | % avg | Correlation TF | correlation FH | correlation TH |
|---|---|---|---|---|---|---|---|---|---|---|---|---|---|---|---|---|
| B38.1 | 21 | 35 | 5.1 | 99 | 15 | 3 | 91 | 530 | 92 | 9.5 | 97 | 122 | 79 | 0.99 | 0.95 | 0.92 |
|  | 40 | 41 | 1.3 | 115 | 31 | 3.7 | 112 | 568 | 99 | 10.5 | 107 | 188 | 122 | 1 | 0.99 | 0.99 |
|  | 79 | 36 | 0.2 | 101 | 62 | 3.2 | 97 | 627 | 109 | 9.4 | 96 | 154 | 100 | 0.97 | 0.99 | 0.96 |
| avg |  | 36 |  |  |  | 3.3 |  | 575 |  | 9.8 |  | 155 |  |  |  |  |
| B38.4 | 21 | 35 | 1 | 101 | 15 | 2.2 | 114 | 424 | 134 | 14.2 | 116 | 141 | 127 | 1 | 0.96 | 0.97 |
|  | 40 | 35 | 0.3 | 101 | 29 | 1.9 | 98 | 247 | 78 | 12.5 | 102 | 96 | 86 | 1 | 1 | 1 |
|  | 79 | 34 | 0.2 | 99 | 59 | 1.7 | 88 | 278 | 88 | 9.9 | 81 | 97 | 87 | 0.99 | 1 | 0.99 |
| avg |  | 35 |  |  |  | 1.9 |  | 316 |  | 12.2 |  | 111 |  |  |  |  |
| B38.5 | 21 | 35 | 1.6 | 106 | 16 | 2.3 | 90 | 497 | 101 | 7.9 | 99 | 97 | 93 | 0.99 | 0.95 | 0.93 |
|  | 40 | 32 | 0.3 | 97 | 30 | 3.7 | 134 | 557 | 114 | 7.3 | 91 | 114 | 109 | 1 | 0.97 | 0.97 |
|  | 79 | 31 | 0.2 | 94 | 63 | 2.1 | 76 | 415 | 85 | 8.8 | 110 | 102 | 98 | 0.96 | 0.96 | 0.99 |
| avg |  | 33 |  |  |  | 2.8 |  | 490 |  | 8 |  | 104 |  |  |  |  |
| B38.30 | 21 | 38 | 9.2 | 97 | 15 | 1.6 | 81 | 335 | 89 | 14.5 | 112 | 100 | 71 | 0.99 | 1 | 0.99 |
|  | 40 | 51 | 2.7 | 131 | 30 | 2.7 | 137 | 472 | 125 | 13.9 | 107 | 205 | 147 | 1 | 0.99 | 0.99 |
|  | 79 | 40 | 0.7 | 103 | 64 | 1.6 | 81 | 325 | 86 | 10.6 | 82 | 114 | 81 | 0.98 | 0.98 | 0.99 |
| avg |  | 39 |  |  |  | 2.0 |  | 377 |  | 13 |  | 140 |  |  |  |  |
| B224.18 | 23 | 34 | 2.6 | 100 | 17 | 3.1 | 103 | 507 | 103 | 15.8 | 98 | 208 | 81 | 1 | 0.99 | 0.99 |
|  | 42 | 37 | 0.7 | 109 | 33 | 3.6 | 120 | 575 | 117 | 18.1 | 112 | 318 | 124 | 1 | 0.94 | 0.95 |
|  | 81 | 34 | 0.2 | 100 | 63 | 2.3 | 77 | 393 | 80 | 14.6 | 90 | 244 | 95 | 1 | 1 | 0.99 |
| avg |  | 34 |  |  |  | 3.0 |  | 492 |  | 16.2 |  | 257 |  |  |  |  |
| B224.47 | 23 | 32 | 0.4 | 102 | 17 | 3.5 | 98 | 695 | 109 | 22.5 | 114 | 387 | 122 | 0.99 | 0.93 | 0.89 |
|  | 42 | 33 | 0.3 | 105 | 31 | 3.6 | 101 | 578 | 91 | 20 | 101 | 357 | 112 | 0.99 | 0.92 | 0.95 |
|  | 81 | 31 | 0.2 | 98 | 64 | 3.6 | 101 | 634 | 100 | 16.8 | 85 | 209 | 66 | 1 | 0.99 | 0.99 |
| avg |  | 32 |  |  |  | 3.6 |  | 636 |  | 19.8 |  | 318 |  |  |  |  |
| B224.53 | 23 | 33 | 0.5 | 100 | 17 | 3.9 | 110 | 553 | 99 | 20.6 | 102 | 372 | 114 | 0.98 | 0.82 | 0.85 |
|  | 42 | 32 | 0.4 | 97 | 33 | 3.7 | 105 | 605 | 108 | 24.3 | 121 | 379 | 116 | 0.98 | 0.88 | 0.94 |
|  | 81 | 33 | 0.1 | 100 | 63 | 3 | 85 | 525 | 94 | 15.4 | 77 | 231 | 71 | 0.99 | 0.89 | 0.94 |
| avg |  | 33 |  |  |  | 3.5 |  | 561 |  | 20.1 |  | 327 |  |  |  |  |
| B224.53 | 23 | 36 | 0.6 | 104 | 16 | 4.3 | 115 | 750 | 107 | 16.4 | 106 | 301 | 104 | 0.99 | 0.78 | 0.84 |
|  | 42 | 34 | 0.2 | 99 | 30 | 4.4 | 118 | 779 | 111 | 14.6 | 95 | 344 | 119 | 0.98 | 0.92 | 0.96 |
|  | 81 | 33 | 0.3 | 96 | 61 | 2.5 | 67 | 583 | 83 | 15.2 | 99 | 224 | 77 | 0.97 | 0.99 | 0.96 |
| avg |  | 33 |  |  |  | 3.7 |  | 704 |  | 15.4 |  | 290 |  |  |  |  |
| B280.3 | 23 | 34 | 0.8 | 105 | 17 | 4.3 | 105 | 840 | 108 | 13 | 109 | 293 | 117 | 0.99 | 0.98 | 0.95 |
|  | 42 | 32 | 0.4 | 98 | 33 | 4 | 98 | 841 | 108 | 12.3 | 103 | 292 | 116 | 0.99 | 0.98 | 0.98 |
|  | 81 | 31 | 0.1 | 95 | 67 | 4 | 98 | 660 | 85 | 10.5 | 88 | 169 | 67 | 0.99 | 0.98 | 1 |
| avg |  | 33 |  |  |  | 4.1 |  | 780 |  | 11.9 |  | 251 |  |  |  |  |
| B280.12 | 23 | 36 | 1.7 | 104 | 15 | 2 | 72 | 426 | 77 | 5.8 | 95 | 64 | 81 | 0.98 | 0.98 | 0.98 |
|  | 42 | 37 | 0.7 | 107 | 30 | 3.2 | 116 | 673 | 122 | 6.2 | 101 | 96 | 121 | 1 | 0.97 | 0.97 |
|  | 81 | 33 | 0.2 | 96 | 64 | 3.1 | 112 | 552 | 100 | 6.4 | 104 | 78 | 98 | 0.98 | 0.98 | 0.98 |
| avg |  | 35 |  |  |  | 2.8 |  | 550 |  | 6.1 |  | 79 |  |  |  |  |
| B280.21 | 23 | 32 | 0.6 | 102 | 18 | 3.1 | 103 | 550 | 97 | 9.1 | 128 | 112 | 93 | 0.97 | 0.92 | 0.93 |
|  | 42 | 31 | 0.4 | 98 | 34 | 3.4 | 113 | 589 | 104 | 8.6 | 51 | 137 | 113 | 1 | 0.98 | 0.99 |
|  | 81 | 31 | 0.4 | 98 | 66 | 2.5 | 83 | 566 | 100 | 8.6 | 121 | 114 | 94 | 0.97 | 0.99 | 1 |
| avg |  | 32 |  |  |  | 3.0 |  | 568 |  | 7.1 |  | 121 |  |  |  |  |
| B280.36 | 23 | 33 | 1 | 99 | 17 | 3 | 81 | 596 | 75 | 10 | 186 | 143 | 156 | 1 | 0.99 | 0.98 |
|  | 42 | 36 | 0.5 | 107 | 30 | 4.6 | 124 | 1168 | 146 | 5.6 | 104 | 124 | 135 | 1 | 0.98 | 0.97 |
|  | 81 | 34 | 0.3 | 101 | 62 | 3.5 | 95 | 635 | 79 | 0.56 | 10 | 8 | 9 | 0.97 | 0.98 | 1 |
| avg |  | 34 |  |  |  | 3.7 |  | 800 |  | 5.4 |  | 92 |  |  |  |  |

TABLE 10

Antibody mixtures used for staining of lymphocyte populations.

| | Stainings | | | | Mixtures | | | |
|---|---|---|---|---|---|---|---|---|
| Facs # | tubes # | Monoclonal | Work dilution | Volume | 1st step | 2nd step | 3rd step | Final dilution |
| A Spleen | 1 | 1-8 | CD21$^{FITC}$ | 640 | 320 |  | 0.50 |  |  |
|  |  | Ckappa rat$^{PE}$ | 160 |  | 2.00 |  |  |  |
|  |  | CD19$^{PerCP-Cy5.5}$ | 640 |  |  | 0.50 |  |  |
|  |  | CD23$^{PE-Cy7}$ | 50 | 1:20 |  | 6.40 |  | 1000 |
|  |  | DAPI |  |  |  |  |  |  |
|  |  | Ckappa mouse$^{BIO-APC}$ | 100 | 1:50 |  | 3.20 | APC | 5000 |

TABLE 10-continued

Antibody mixtures used for staining of lymphocyte populations.

| | | | Stainings | | | Mixtures | | | |
|---|---|---|---|---|---|---|---|---|---|
| | Facs # | tubes # | Monoclonal | Work dilution | Volume | 1st step | 2nd step | 3rd step | Final diltion |
| Spleen<br>BM | 2 | 9-16<br>17-24 | Clamda mouse$^{BIO\text{-}APC}$<br>B220$^{Alex\text{-}700}$<br>FC block<br>IgD$^{FITC}$<br>Ckappa rat$^{PE}$<br>CD19$^{PerCP\text{-}Cy5.5}$<br>IgM$^{PE\text{-}Cy7}$<br>DAPI | 100<br>160<br>400<br>640<br>160<br>500<br>640 | 1:30<br><br><br>640 | <br><br><br><br>4.00 | 3.20<br>2.00<br>0.80<br>1.00<br>4.00<br>1.28<br>1.00 | APC | 3000 |
| Spleen | 3 | 25-32 | Ckappa mouse$^{BIO\text{-}APC}$<br>Clamda mouse$^{BIO\text{-}APC}$<br>B220$^{Alex\text{-}700}$<br>FC block<br>Ckappa mouse$^{FITC}$<br>Ckappa rat$^{PE}$<br>CD19$^{PerCP\text{-}Cy5.5}$<br>IgM$^{PE\text{-}Cy7}$<br>DAPI | 100<br>100<br>160<br>400<br>400<br>160<br>500<br>640 | 1:50<br>1:30<br><br><br><br><br> | <br><br><br><br>320<br><br> | <br><br><br><br><br>2.00 | 6.40<br>6.40<br>4.00<br>1.60<br>0.80<br>0.64<br>0.50 | APC<br>APC | 5000<br>3000 |
| Spleen<br>PP | 4 | 33-40<br>41-48 | Clamda mouse$^{BIO\text{-}APC}$<br>B220$^{Alex\text{-}700}$<br>FC block<br>Ckappa mouse$^{FITC}$<br>Iamda$^{FITC}$<br>Ckappa rat$^{PE}$<br>CD19$^{PerCP\text{-}Cy5.5}$<br>IgM$^{PE\text{-}Cy7}$<br>DAPI<br>IgD$^{A647}$<br>B220$^{Alex\text{-}700}$<br>PNA$^{BIO\text{-}SAV\text{-}APC\text{-}Cy7}$ | 100<br>160<br>400<br>400<br>600<br>160<br>500<br>640<br><br>1280<br>160<br>300 | 1:30<br><br><br><br><br><br><br><br><br><br><br> | <br><br><br>640<br><br><br><br><br><br><br><br> | <br><br><br><br><br>4.00<br><br><br><br><br><br> | 3.20<br>2.00<br>0.80<br>1.60<br>1.07<br><br>1.28<br>1.00<br><br>0.50<br>4.00<br>2.13 | APC<br><br><br><br><br><br><br><br><br><br><br>APC-Cy7 | 3000 |
| PC | 5 | 49-56 | FC block<br>IgM$^{FITC}$<br>Ckappa rat$^{PE}$<br>CD19$^{PerCP\text{-}Cy5.5}$<br>Ckappa mouse$^{BIO\text{-}PE\text{-}Cy7}$<br>Clamda mouse$^{BIO\text{-}PE\text{-}Cy7}$<br>DAPI<br>CD5$^{APC}$<br>B220$^{Alex\text{-}700}$ | 400<br>160<br>160<br>500<br>100<br>100<br><br>320<br>160 | <br><br><br><br>1:50<br>1:30 | 320 | <br><br>2.00 | 1.60<br>2.00<br><br>0.64<br>3.20<br>3.20<br><br>1.00<br>2.00 | <br><br><br><br>PE-Cy7<br>PE-Cy7 | 5000<br>3000 |
| BM | 6 | 57-64 | FC block<br>IgM$^{FITC}$<br>Ckappa rat$^{PE}$<br>CD19$^{PerCP\text{-}Cy5.5}$<br>Ckappa mouse$^{BIO\text{-}PE\text{-}Cy7}$<br>Clamda mouse$^{BIO\text{-}PE\text{-}Cy7}$<br>DAPI<br>CD25$^{APC}$<br>B220$^{Alex\text{-}700}$ | 400<br>160<br>160<br>500<br>100<br>100<br><br>80<br>160 | <br><br><br><br>1:50<br>1:30 | 640 | <br><br>4.00 | 0.80<br>4.00<br><br>1.28<br>6.40<br>6.40<br><br>8.00<br>4.00 | <br><br><br><br>PE-Cy7<br>PE-Cy7 | 5000<br>3000 |
| RAT spleen | 7 | 144 | FC block<br>Ckappa rat$^{PE}$<br>rat B220$^{FITC}$ | 400<br>160<br>160 | <br>80 | <br>0.5<br>0.5 | 1.60 | | |
| Spleen | 8 | 97-104 | cyt CD3$^{FITC}$<br>cyt Ckappa rat$^{PE}$<br>cyt CD11c$^{PE\text{-}TexasRED}$<br>cyt NK1.1$^{BIO\text{-}PE\text{-}Cy7}$<br>cyt CD19$^{PerCP\text{-}Cy5.5}$<br>cyt CD4$^{APC}$<br>cyt CD11b$^{Alex\text{-}700}$ | 320<br>80<br>75<br>200<br>320<br>500<br>50 | 320 | 4.00 | 1<br><br>4.27<br>1.6<br>1<br>0.64<br>6.40 | PE-Cy7 | |

BM = bone marrow,
PC = peritoneal cavity,
PP = Peyer's patches.

TABLE 11

Numbers of lymphocytes harvested from the bone marrow and spleen of wild-type and transgenic mice

| | *10e6/ml cells | total vol (ml) | total cells *10$^6$ |
|---|---|---|---|
| Bone Marrow | | | |
| Wt | 18.82 | 5.05 | 95.0 |
| Wt | 19.24 | 4.96 | 95.4 |
| CD19-Cre | 23.42 | 5.08 | 119.0 |
| CD19-Cre | 20.58 | 4.82 | 99.2 |
| CD19-Cre | 25.77 | 5.15 | 132.7 |
| CD19-Cre/HuVk1 | 17.71 | 5.06 | 89.6 |
| CD19-Cre/HuVk1 | 12.60 | 5.33 | 67.2 |
| CD19-Cre/HuVk1 | 18.13 | 5.27 | 95.5 |
| Spleen | | | |
| Wt | 41.70 | 5.36 | 223.5 |
| Wt | 37.85 | 4.71 | 178.3 |
| CD19-Cre | 60.19 | 3.77 | 226.9 |
| CD19-Cre | 35.06 | 3.66 | 128.3 |
| CD19-Cre | 80.69 | 4.60 | 371.2 |
| CD19-Cre/HuVk1 | 51.67 | 4.48 | 231.5 |
| CD19-Cre/HuVk1 | 58.80 | 6.24 | 366.9 |
| CD19-Cre/HuVk1 | 24.37 | 6.25 | 152.3 |

What is claimed is:

1. A method for selecting a single recombinant cell that produces a heterogeneous combination of monospecific and bispecific antibodies, or antibody fragments thereof, wherein the heterogeneous combination of antibodies has specific affinity for two target epitopes, the method comprising:

providing three different variable regions consisting of at least two different heavy chain regions and one light chain variable region from recombinant cells, wherein the sequence of the antigen binding parts of the variable regions originate from a single species and wherein one variable region is able to functionally pair with more than one other variable region, and under conditions allowing for pairing of variable regions and secretion of the paired regions from the recombinant cells resulting in the production of said heterogeneous combination, providing two target epitopes, and selecting a single recombinant cell from the recombinant cells that produces a heterogeneous combination that binds the two target epitopes, wherein the one light chain variable region comprises a rearranged human immunoglobulin light chain variable region consisting of a V and a J and is encoded by a human immunoglobulin light chain V gene segment joined to a human immunoglobulin light chain J gene segment, wherein the at least two different heavy chain variable regions are each encoded by nucleic acid sequences obtained from a transgenic mouse, wherein a first of the at least two different heavy chain variable regions encoded by nucleic acid sequences obtained from a transgenic mouse is produced by recombination of a heavy chain gene in a first transgenic mouse in response to challenge with a first antigen comprising at least one of the two target epitopes and wherein a second of the at least two different heavy chain variable regions encoded by nucleic acid sequences obtained from a transgenic mouse is produced by recombination of a heavy chain gene in a second transgenic mouse in response to challenge with a second antigen comprising at least one of the two target epitopes, wherein the first transgenic mouse and second transgenic mouse may be the same mouse or two different mice; and wherein the genome of each transgenic mouse comprises a transgene comprising the human immunoglobulin light chain V gene segment joined to the human immunoglobulin light chain J gene segment and wherein that mouse further comprises a human VH locus.

2. The method according to claim 1, wherein said two target epitopes are associated with a disease and/or disorder.

3. The method according to claim 2, further comprising:
subjecting a heterogeneous combination to a biological assay indicative of an effect of the combination on the disease and/or disorder.

4. The method according to claim 1, wherein the one variable region able to functionally pair with more than one other variable region does not significantly contribute to the resulting binding specificity of the resulting paired regions.

5. The method according to claim 1, wherein the combination comprises two monospecific antibodies produced in the single recombinant cell.

6. The method according to claim 1, wherein the human immunoglobulin light chain V gene segment joined to the human immunoglobulin light chain J gene segment is obtained from a transgenic mouse.

7. The method according to claim 1, wherein the transgenic mouse, in response to the two target epitopes, produces antibodies with immunoglobulin light chains comprising the rearranged human light chain variable region and murine light chain constant region, paired with a diversity of immunoglobulin heavy chains which bind the two target epitopes.

8. The method according to claim 1, wherein a first heavy chain of the two heavy chain regions is obtained by immunizing a first mouse with a first target epitope of the two target epitopes and wherein a second heavy chain of the two heavy chain regions is obtained by immunizing a second mouse with a second target epitope of the two target epitopes.

9. The method according to claim 1, further comprising:
isolating from the set of recombinant cells a single recombinant cell that produces the single heterogeneous combination.

* * * * *

SEQUENCE LISTING

<160> NUMBER OF SEQ ID NOS: 169

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ccctttccaa tctttatggg                                           20

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
aggtggattg gtgtctttt ctc                                        23

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gtcatgtcgg cgaccctacg cc                                        22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgccaggggg aagaccgatg                                           20

<210> SEQ ID NO 5
<211> LENGTH: 38
<212> TYPE: DNA
<213> ORGANISM: Artificial Sequence
<220> FEATURE:
<223> OTHER INFORMATION: primer -continued

```
<400> SEQUENCE: 5
gccggccatg gccgaggtrm agcttcagga gtcaggac                              38

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
gccggccatg gccgaggtsc agctkcagca gtcaggac                              38

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
gccggccatg gcccaggtgc agctgaagsa stcagg                                36

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
gccggccatg gccgaggtgc agcttcagga gtcsggac                              38

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
gccggccatg gccgargtcc agctgcaaca gtcyggac                              38

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10
gccggccatg gcccaggtcc agctkcagca atctgg                                36

<210> SEQ ID NO 11
<211> LENGTH: 36
<212> TYPE: DNA
<213> ORGANISM: Artificial Sequence
<220> FEATURE:
<223> OTHER INFORMATION: primer

<400> SEQUENCE: 11
gccggccatg gcccagstbc agctgcagca gtctgg                                36

<210> SEQ ID NO 12
```

```
<211> LENGTH: 38
<212> TYPE: DNA
<213> ORGANISM: Artificial Sequence
<220> FEATURE:
<223> OTHER INFORMATION: primer

<400> SEQUENCE: 12
gccggccatg gcccaggtyc agctgcagca gtctggrc                              38

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13
gccggccatg gcccaggtyc agctycagca gtctgg                                36

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
gccggccatg gccgaggtcc arctgcaaca atctggacc                             39

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
gccggccatg gcccaggtcc acgtgaagca gtctggg                               37

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
gccggccatg gccgaggtga asstggtgga atctg                                 35

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
gccggccatg gccgavgtga agytggtgga gtctg                                 35

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
```

```
gccggccatg gccgaggtgc agskggtgga gtctgggg                                    38

<210> SEQ ID NO 19
<211> LENGTH: 37
<212> TYPE: DNA
<213> ORGANISM: Artificial Sequence
<220> FEATURE:
<223> OTHER INFORMATION: primer

<400> SEQUENCE: 19
gccggccatg gccgakgtgc amctggtgga gtctggg                                     37

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
gccggccatg gccgaggtga agctgatgga rtctgg                                      36

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
gccggccatg gccgaggtgc arcttgttga gtctggtg                                    38

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
gccggccatg gccgargtra agcttctcga gtctgga                                     37

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
gccggccatg gccgaagtga arsttgagga gtctgg                                      36

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
gccggccatg gccgaagtga tgctggtgga gtctggg                                     37

<210> SEQ ID NO 25
<211> LENGTH: 38
<212> TYPE: DNA
```

<213> ORGANISM: Artificial Sequence
<220> FEATURE:
<223> OTHER INFORMATION: primer

<400> SEQUENCE: 25
gccggccatg gcccaggtta ctctraaagw gtstggcc            38

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
gccggccatg gcccaggtcc aactvcagca rcctgg              36

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
gccggccatg gcccaggtyc arctgcagca gtctg               35

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
gccggccatg gccgatgtga acttggaagt gtctgg              36

<210> SEQ ID NO 29
<211> LENGTH: 36
<212> TYPE: DNA
<213> ORGANISM: Artificial Sequence
<220> FEATURE:
<223> OTHER INFORMATION: primer

<400> SEQUENCE: 29
gccggccatg gccgaggtga aggtcatcga gtctgg              36

<210> SEQ ID NO 30
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 30
cagtcacaga tcctcgcgaa ttggcccagc cggccatggc csang    45

<210> SEQ ID NO 31
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (44)..(44)
<223> OTHER INFORMATION: n is a, c, g, or t

<400> SEQUENCE: 31
cagtcacaga tcctcgcgaa ttggcccagc cggccatggc csanc         45

<210> SEQ ID NO 32
<211> LENGTH: 37
<212> TYPE: DNA
<213> ORGANISM: Artificial Sequence
<220> FEATURE:
<223> OTHER INFORMATION: primer

<400> SEQUENCE: 32
gggggtgtcg ttttggctga ggagacggtg accgtgg              37

<210> SEQ ID NO 33
<211> LENGTH: 37
<212> TYPE: DNA
<213> ORGANISM: Artificial Sequence
<220> FEATURE:
<223> OTHER INFORMATION: primer

<400> SEQUENCE: 33
gggggtgtcg ttttggctga ggagactgtg agagtgg              37

<210> SEQ ID NO 34
<211> LENGTH: 37
<212> TYPE: DNA
<213> ORGANISM: Artificial Sequence
<220> FEATURE:
<223> OTHER INFORMATION: primer

<400> SEQUENCE: 34
gggggtgtcg ttttggctgc agagacagtg accagag              37

<210> SEQ ID NO 35
<211> LENGTH: 37
<212> TYPE: DNA
<213> ORGANISM: Artificial Sequence
<220> FEATURE:
<223> OTHER INFORMATION: primer

<400> SEQUENCE: 35
gggggtgtcg ttttggctga ggagacggtg actgagg              37

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
gggggtgtcg ttttggctga ggagacggtg accgtgg              37

<210> SEQ ID NO 37
<211> LENGTH: 37
<212> TYPE: DNA
<213> ORGANISM: Artificial Sequence
<220> FEATURE:
<223> OTHER INFORMATION: primer

<400> SEQUENCE: 37
gggggtgtcg ttttggctga ggagacggtg acagtgg    37

<210> SEQ ID NO 38
<211> LENGTH: 37
<212> TYPE: DNA
<213> ORGANISM: Artificial Sequence
<220> FEATURE:
<223> OTHER INFORMATION: primer

<400> SEQUENCE: 38
gggggtgtcg ttttggctga ggagacggtg accagag    37

<210> SEQ ID NO 39
<211> LENGTH: 37
<212> TYPE: DNA
<213> ORGANISM: Artificial Sequence
<220> FEATURE:
<223> OTHER INFORMATION: primer

<400> SEQUENCE: 39
gggggtgtcg ttttggctga ggagacggtg accgagg    37

<210> SEQ ID NO 40
<211> LENGTH: 15
<212> TYPE: PRT
<213> ORGANISM: Artificial Sequence
<220> FEATURE:
<223> OTHER INFORMATION: CDR3

<400> SEQUENCE: 40

His Gly Ala Tyr Tyr Thr Tyr Asp Glu Lys Ala Trp Phe Ala Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: CDR3

<400> SEQUENCE: 41

His Gly Ala Phe Tyr Thr Tyr Asp Glu Lys Pro Trp Phe Ala Tyr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: CDR3

<400> SEQUENCE: 42

His Ile Ser Tyr Tyr Arg Tyr Asp Glu Glu Val Ser Phe Ala Tyr
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: CDR3

<400> SEQUENCE: 43

Gly Trp Arg Ala Phe Ala Tyr
1               5

```
<210> SEQ ID NO 44
<211> LENGTH: 10
<212> TYPE: PRT
<213> ORGANISM: Artificial Sequence
<220> FEATURE:
<223> OTHER INFORMATION: CDR3

<400> SEQUENCE: 44

Asp Arg Gly Asn Tyr Tyr Gly Met Asp Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CDR3

<400> SEQUENCE: 45

Leu Gly Asp Tyr Tyr Val Asp Trp Phe Phe Ala Val
1               5                   10

<210> SEQ ID NO 46
<211> LENGTH: 8
<212> TYPE: PRT
<213> ORGANISM: Artificial Sequence
<220> FEATURE:
<223> OTHER INFORMATION: CDR3

<400> SEQUENCE: 46

Asn Phe Pro Ala Trp Phe Ala Phe
1               5

<210> SEQ ID NO 47
<211> LENGTH: 17
<212> TYPE: PRT
<213> ORGANISM: Artificial Sequence
<220> FEATURE:
<223> OTHER INFORMATION: CDR3

<400> SEQUENCE: 47

Ser Phe Thr Pro Val Pro Phe Tyr Tyr Gly Tyr Asp Trp Tyr Phe Asp
1               5                   10                  15

Val

<210> SEQ ID NO 48
<211> LENGTH: 9
<212> TYPE: PRT
<213> ORGANISM: Artificial Sequence
<220> FEATURE:
<223> OTHER INFORMATION: CDR3

<400> SEQUENCE: 48

Ser Asp Tyr Asp Trp Tyr Phe Asp Val
1               5

<210> SEQ ID NO 49
<211> LENGTH: 10
<212> TYPE: PRT
<213> ORGANISM: Artificial Sequence
<220> FEATURE:
<223> OTHER INFORMATION: CDR3

<400> SEQUENCE: 49

Asp Ser Lys Trp Ala Tyr Tyr Phe Asp Tyr
1               5                   10
```

```
<210> SEQ ID NO 50
<211> LENGTH: 10
<212> TYPE: PRT
<213> ORGANISM: Artificial Sequence
<220> FEATURE:
<223> OTHER INFORMATION: CDR3

<400> SEQUENCE: 50

Gly Asp Tyr Thr Gly Tyr Gly Met Asp Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: CDR3

<400> SEQUENCE: 51

Gly Gly Tyr Asp Gly Tyr Trp Phe Pro Tyr
1               5                   10

<210> SEQ ID NO 52
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 52

Asp Ile Gln Met Thr Gln Ser Pro Ser Ser Leu Ser Ala Ser Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 53

Met Thr Gln Ser Pro Ser Ser Leu Ser Ala Ser Val Gly Asp Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 54

Ser Pro Ser Ser Leu Ser Ala Ser Val Gly Asp Arg Val Thr Ile
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: epitope IGKV1-39

<400> SEQUENCE: 55

Ser Leu Ser Ala Ser Val Gly Asp Arg Val Thr Ile Thr Cys Arg
1               5                   10                  15
```

```
<210> SEQ ID NO 56
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 56

Ala Ser Val Gly Asp Arg Val Thr Ile Thr Cys Arg Ala Ser Gln
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 57

Gly Asp Arg Val Thr Ile Thr Cys Arg Ala Ser Gln Ser Ile Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 58

Val Thr Ile Thr Cys Arg Ala Ser Gln Ser Ile Ser Ser Tyr Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 59

Thr Cys Arg Ala Ser Gln Ser Ile Ser Ser Tyr Leu Asn Trp Tyr
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 60

Ala Ser Gln Ser Ile Ser Ser Tyr Leu Asn Trp Tyr Gln Gln Lys
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 61

Ser Ile Ser Ser Tyr Leu Asn Trp Tyr Gln Gln Lys Pro Gly Lys
1               5                   10                  15

<210> SEQ ID NO 62
```

```
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 62

Ser Tyr Leu Asn Trp Tyr Gln Gln Lys Pro Gly Lys Ala Pro Lys
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 63

Asn Trp Tyr Gln Gln Lys Pro Gly Lys Ala Pro Lys Leu Leu Ile
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 64

Gln Gln Lys Pro Gly Lys Ala Pro Lys Leu Leu Ile Tyr Ala Ala
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 65

Pro Gly Lys Ala Pro Lys Leu Leu Ile Tyr Ala Ala Ser Ser Leu
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 66

Ala Pro Lys Leu Leu Ile Tyr Ala Ala Ser Ser Leu Gln Ser Gly
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 67

Leu Leu Ile Tyr Ala Ala Ser Ser Leu Gln Ser Gly Val Pro Ser
1               5                   10                  15

<210> SEQ ID NO 68
<211> LENGTH: 15
```

```
<212> TYPE: PRT
<213> ORGANISM: Artificial Sequence
<220> FEATURE:
<223> OTHER INFORMATION: Epitope IGKV1-39

<400> SEQUENCE: 68

Tyr Ala Ala Ser Ser Leu Gln Ser Gly Val Pro Ser Arg Phe Ser
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 69

Ser Ser Leu Gln Ser Gly Val Pro Ser Arg Phe Ser Gly Ser Gly
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 70

Gln Ser Gly Val Pro Ser Arg Phe Ser Gly Ser Gly Ser Gly Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 71

Val Pro Ser Arg Phe Ser Gly Ser Gly Ser Gly Thr Asp Phe Thr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 72

Arg Phe Ser Gly Ser Gly Ser Gly Thr Asp Phe Thr Leu Thr Ile
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 73

Gly Ser Gly Ser Gly Thr Asp Phe Thr Leu Thr Ile Ser Ser Leu
1               5                   10                  15

<210> SEQ ID NO 74
<211> LENGTH: 15
<212> TYPE: PRT
```

-continued

```
<213> ORGANISM: Artificial Sequence
<220> FEATURE:
<223> OTHER INFORMATION: Epitope IGKV1-39

<400> SEQUENCE: 74

Ser Gly Thr Asp Phe Thr Leu Thr Ile Ser Ser Leu Gln Pro Glu
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 75

Asp Phe Thr Leu Thr Ile Ser Ser Leu Gln Pro Glu Asp Phe Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 76

Leu Thr Ile Ser Ser Leu Gln Pro Glu Asp Phe Ala Thr Tyr Tyr
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 77

Ser Ser Leu Gln Pro Glu Asp Phe Ala Thr Tyr Tyr Cys Gln Gln
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 78

Gln Pro Glu Asp Phe Ala Thr Tyr Tyr Cys Gln Gln Ser Tyr Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 79

Asp Phe Ala Thr Tyr Tyr Cys Gln Gln Ser Tyr Ser Thr Pro Pro
1               5                   10                  15

<210> SEQ ID NO 80
<211> LENGTH: 15
<212> TYPE: PRT
<213> ORGANISM: Artificial Sequence
```

```
<220> FEATURE:
<223> OTHER INFORMATION: Epitope IGKV1-39

<400> SEQUENCE: 80

Thr Tyr Tyr Cys Gln Gln Ser Tyr Ser Thr Pro Pro Thr Phe Gly
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 81

Cys Gln Gln Ser Tyr Ser Thr Pro Pro Thr Phe Gly Gln Gly Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Epitope IGKV1-39

<400> SEQUENCE: 82

Ser Tyr Ser Thr Pro Pro Thr Phe Gly Gln Gly Thr Lys Val Glu
1               5                   10                  15

<210> SEQ ID NO 83
<211> LENGTH: 14
<212> TYPE: PRT
<213> ORGANISM: Artificial Sequence
<220> FEATURE:
<223> OTHER INFORMATION: Epitope IGKV1-39

<400> SEQUENCE: 83

Thr Pro Pro Thr Phe Gly Gln Gly Thr Lys Val Glu Ile Lys
1               5                   10

<210> SEQ ID NO 84
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 84 gac atc cag atg acc cag agc ccc agc agc ctg agc gcc agc gtg ggc     48
Asp Ile Gln Met Thr Gln Ser Pro Ser Ser Leu Ser Ala Ser Val Gly
1               5                   10                  15 gac aga gtg acc atc acc tgc aga gcc agc cag agc atc agc agc tac     96
Asp Arg Val Thr Ile Thr Cys Arg Ala Ser Gln Ser Ile Ser Ser Tyr
            20                  25                  30 ctg aac tgg tat cag cag aag ccc ggc aag gcc ccc aag ctg ctg atc    144
Leu Asn Trp Tyr Gln Gln Lys Pro Gly Lys Ala Pro Lys Leu Leu Ile
        35                  40                  45 tac gcc gcc agc tcc ctg cag agc ggc gtg ccc agc aga ttc agc ggc    192
Tyr Ala Ala Ser Ser Leu Gln Ser Gly Val Pro Ser Arg Phe Ser Gly
    50                  55                  60 agc ggc tcc ggc acc gac ttc acc ctg acc atc agc agc ctg cag ccc    240
Ser Gly Ser Gly Thr Asp Phe Thr Leu Thr Ile Ser Ser Leu Gln Pro
65                  70                  75                  80 gag gac ttc gcc acc tac tac tgc cag cag agc tac agc acc ccc ccc    288
Glu Asp Phe Ala Thr Tyr Tyr Cys Gln Gln Ser Tyr Ser Thr Pro Pro
```

```
Glu Asp Phe Ala Thr Tyr Tyr Cys Gln Gln Ser Tyr Ser Thr Pro Pro
                85                  90                  95 acc ttc ggc cag ggc acc aag gtg gag atc aag                              321
Thr Phe Gly Gln Gly Thr Lys Val Glu Ile Lys
            100                 105

<210> SEQ ID NO 85
<211> LENGTH: 107
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 86
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 86 cag tct gcc ctg acc cag ccc gcc tct gtg tct ggc agc cct ggc cag        48
Gln Ser Ala Leu Thr Gln Pro Ala Ser Val Ser Gly Ser Pro Gly Gln
1               5                   10                  15 agc atc acc atc agc tgc acc ggc acc agc agc gac gtg ggc ggc tac        96
Ser Ile Thr Ile Ser Cys Thr Gly Thr Ser Ser Asp Val Gly Gly Tyr
            20                  25                  30 aac tac gtg tcc tgg tat cag cag cac ccc ggc aag gcc ccc aag ctg       144
Asn Tyr Val Ser Trp Tyr Gln Gln His Pro Gly Lys Ala Pro Lys Leu
        35                  40                  45 atg atc tac gag gtg tcc aac aga ccc agc ggc gtg agc aac aga ttc       192
Met Ile Tyr Glu Val Ser Asn Arg Pro Ser Gly Val Ser Asn Arg Phe
    50                  55                  60 agc ggc agc aag agc ggc aac acc gcc agc ctg acc atc agc ggc ctc       240
Ser Gly Ser Lys Ser Gly Asn Thr Ala Ser Leu Thr Ile Ser Gly Leu
65                  70                  75                  80 cag gct gag gac gag gcc gac tac tac tgc agc agc tac acc agc agc       288
Gln Ala Glu Asp Glu Ala Asp Tyr Tyr Cys Ser Ser Tyr Thr Ser Ser
                85                  90                  95 tcc acc ctg gtg ttt ggc ggc gga aca aag ctg acc gtg ctg               330
Ser Thr Leu Val Phe Gly Gly Gly Thr Lys Leu Thr Val Leu
            100                 105                 110

<210> SEQ ID NO 87
<211> LENGTH: 110
<212> TYPE: PRT
```

-continued

<213> ORGANISM: Homo sapiens

<400> SEQUENCE: 87

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu
            100                 105                 110

<210> SEQ ID NO 88
<211> LENGTH: 321
<212> TYPE: DNA
<213> ORGANISM: Rattus norvegicus
<220> FEATURE:
<221> NAME/KEY: CDS
<222> LOCATION: (1)..(321)

<400> SEQUENCE: 88 aga gcc gac gcc gct ccc acc gtg tcc atc ttc ccc cca agc atg gaa      48
Arg Ala Asp Ala Ala Pro Thr Val Ser Ile Phe Pro Pro Ser Met Glu
1               5                   10                  15 cag ctg acc tct ggc gga gcc acc gtg gtc tgc ttc gtg aac aac ttc      96
Gln Leu Thr Ser Gly Gly Ala Thr Val Val Cys Phe Val Asn Asn Phe
            20                  25                  30 tac ccc aga gac atc agc gtg aag tgg aag atc gac ggc agc gag cag     144
Tyr Pro Arg Asp Ile Ser Val Lys Trp Lys Ile Asp Gly Ser Glu Gln
        35                  40                  45 agg gac ggc gtg ctg gac agc gtg acc gac cag gac agc aag gac tcc     192
Arg Asp Gly Val Leu Asp Ser Val Thr Asp Gln Asp Ser Lys Asp Ser
    50                  55                  60 acc tac agc atg agc agc acc ctg agc ctg acc aag gtg gag tac gag     240
Thr Tyr Ser Met Ser Ser Thr Leu Ser Leu Thr Lys Val Glu Tyr Glu
65                  70                  75                  80 agg cac aac ctg tac acc tgc gag gtg gtg cac aag acc agc tcc agc     288
Arg His Asn Leu Tyr Thr Cys Glu Val Val His Lys Thr Ser Ser Ser
                85                  90                  95 ccc gtg gtc aag tcc ttc aac cgg aac gag tgt                         321
Pro Val Val Lys Ser Phe Asn Arg Asn Glu Cys
            100                 105

<210> SEQ ID NO 89
<211> LENGTH: 107
<212> TYPE: PRT
<213> ORGANISM: Rattus norvegicus

<400> SEQUENCE: 89

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln

```
                35                  40                  45
Arg Asp Gly Val Leu Asp Ser Val Thr Asp Gln Asp Ser Lys Asp Ser
    50                  55                  60

Thr Tyr Ser Met Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 90
<211> LENGTH: 865
<212> TYPE: DNA
<213> ORGANISM: Artificial Sequence
<220> FEATURE:
<223> OTHER INFORMATION: IGKV1-39/J-Ck

<400> SEQUENCE: 90

```
ggtaccgcgg ccgccaccat ggacatgaga gtgcccgccc agctcctggg gctcctgcta      60
ctctggctcc gaggtaagga tggagaacac taggaattta ctcagccagt gtgctcagta     120
ctgactggaa cttcagggaa gttctctgat aacatgatta atagtaagaa tatttgtttt     180
tatgtttcca atctcaggtg ccagatgtga catccagatg acccagagcc ccagcagcct     240
gagcgccagc gtgggcgaca gagtgaccat cacctgcaga gccagccaga gcatcagcag     300
ctacctgaac tggtatcagc agaagcccgg caaggccccc aagctgctga tctacgccgc     360
cagctccctg cagagcggcg tgcccagcag attcagcggc agcggctccg gcaccgactt     420
caccctgacc atcagcagcc tgcagcccga ggacttcgcc acctactact gccagcagag     480
ctacagcacc cccccacct tcggccaggg caccaaggtg gagatcaaga gaccgacgc      540
cgctcccacc gtgtccatct ccccccag catggaacag ctgacctctg cggagccac      600
cgtggtctgc ttcgtgaaca acttctaccc cagagacatc agcgtgaagt ggaagatcga     660
cggcagcgag cagagggacg gcgtgctgga cagcgtgacc gaccaggaca gcaaggactc     720
cacctacagc atgagcagca ccctgagcct gaccaaggtg gagtacgaga ggcacaacct     780
gtacacctgc gaggtggtgc acaagaccag ctccagcccc gtggtcaagt ccttcaaccg     840
gaacgagtgt tgagctagcg agctc                                         865
```

<210> SEQ ID NO 91
<211> LENGTH: 874
<212> TYPE: DNA
<213> ORGANISM: Artificial Sequence
<220> FEATURE:
<223> OTHER INFORMATION: IGLV2-14/J-Ck

<400> SEQUENCE: 91

```
ggtaccgcgg ccgccaccat ggacatgaga gtgcccgccc agctcctggg gctcctgcta      60
ctctggctcc gaggtaagga tggagaacac taggaattta ctcagccagt gtgctcagta     120
ctgactggaa cttcagggaa gttctctgat aacatgatta atagtaagaa tatttgtttt     180
tatgtttcca atctcaggtg ccagatgtca gtctgccctg acccagcccg cctctgtgtc     240
tggcagccct ggccagagca tcaccatcag ctgcaccggc accagcagcg acgtgggcgg     300
ctacaactac gtgtcctggt atcagcagca cccggcaag gcccccaagc tgatgatcta     360
cgaggtgtcc aacagaccca gcggcgtgag caacagattc agcggcagca agagcggcaa     420
caccgccagc ctgaccatca gcggcctcca ggctgaggac gaggccgact actactgcag     480
```

| | |
|---|---|
| cagctacacc agcagctcca ccctggtgtt tggcggcgga acaaagctga ccgtgctgag | 540 |
| agccgacgcc gctcccaccg tgtccatctt ccccccagc atggaacagc tgacctctgg | 600 |
| cggagccacc gtggtctgct tcgtgaacaa cttctacccc agagacatca gcgtgaagtg | 660 |
| gaagatcgac ggcagcgagc agagggacgg cgtgctggac agcgtgaccg accaggacag | 720 |
| caaggactcc acctacagca tgagcagcac cctgagcctg accaaggtgg agtacgagag | 780 |
| gcacaacctg tacacctgcg aggtggtgca caagaccagc tccagccccg tggtcaagtc | 840 |
| cttcaaccgg aacgagtgtt gagctagcga gctc | 874 |

<210> SEQ ID NO 92
<211> LENGTH: 13373
<212> TYPE: DNA
<213> ORGANISM: Artificial Sequence
<220> FEATURE:
<223> OTHER INFORMATION: VkP-IGKV1-39/J-Ck

<400> SEQUENCE: 92

| | |
|---|---|
| ggccggccca catgaaacaa tgggaaccat gtgacaatca cagaggtgtt gttactatag | 60 |
| caaaagggat tgttactctc cacatcccett taagtaactt gaaggcctga tagacccacc | 120 |
| ctctaagact tcattagaca ttccctacga atggttatac tctcctgtat actcccaata | 180 |
| caactctaaa atatattatt ccatatagtc cttaggtttg tattaaagtt tgactttttt | 240 |
| ccttcaaaat atctcttgtc acaacagcgg ctctagagag aaatacattc cctccaggca | 300 |
| aatctatgct gcgctggtct gacctgggac cctggggaca ttgcccctgt gctgagttac | 360 |
| taagatgagc cagccctgca gctgtgctca gcctgcccca tgccctgctg attgatttgc | 420 |
| atgttccaga gcacagcccc ctgccctgaa gactttttta tgggctggtc gcaccctgtg | 480 |
| caggagtcag tctcagtcag gagccaccat ggacatgaga gtgcccgccc agctcctggg | 540 |
| gctcctgcta ctctggctcc gaggtaagga tggagaacac taggaattta ctcagccagt | 600 |
| gtgctcagta ctgactggaa cttcagggaa gttctctgat aacatgatta atagtaagaa | 660 |
| tatttgtttt tatgtttcca atctcaggtg ccagatgtga catccagatg acccagagcc | 720 |
| ccagcagcct gagcgccagc gtgggcgaca gagtgaccat cacctgcaga gccagccaga | 780 |
| gcatcagcag ctacctgaac tggtatcagc agaagcccgg caaggccccc aagctgctga | 840 |
| tctacgccgc cagctccctg cagagcggcg tgcccagcag attcagcggc agcggctccg | 900 |
| gcaccgactt caccctgacc atcagcagcc tgcagcccga ggacttcgcc acctactact | 960 |
| gccagcagag ctacagcacc ccccccacct tcggccaggg caccaaggtg gagatcaaac | 1020 |
| gtaagtacac ttttctcatc tttttttatg tgtaagacac aggttttcat gttaggagtt | 1080 |
| aaagtcagtt cagaaaatct tgagaaaatg gagagggctc attatcagtt gacgtggcat | 1140 |
| acagtgtcag attttctgtt tatcaagcta gtgagattag gggcaaaaag aggctttagt | 1200 |
| tgagaggaaa gtaattaata ctatggtcac catccaagag attggatcgg agaataagca | 1260 |
| tgagtagtta ttgagatctg gtctgactg caggtagcgt ggtcttctag acgtttaagt | 1320 |
| gggagatttg gaggggatga ggaatgaagg aacttcagga tagaaaaggg ctgaagtcaa | 1380 |
| gttcagctcc taaaatggat gtgggagcaa actttgaaga taaactgaat gacccagagg | 1440 |
| atgaaacagc gcagatcaaa gaggggcctg gagctctgag aagagaagga gactcatccg | 1500 |
| tgttgagttt ccacaagtac tgtccttgagt tttgcaataa aagtgggata gcagagttga | 1560 |
| gtgagccgta ggctgagttc tctcttttgt ctcctaagtt tttatgacta caaaaatcag | 1620 |

```
tagtatgtcc tgaaataatc attaagctgt ttgaaagtat gactgcttgc catgtagata    1680
ccatggcttg ctgaataatc agaagaggtg tgactcttat tctaaaattt gtcacaaaat    1740
gtcaaaatga gagactctgt aggaacgagt ccttgacaga cagctcaagg ggttttttc     1800
ctttgtctca tttctacatg aaagtaaatt tgaaatgatc ttttttatta taagagtaga    1860
aatacagttg ggtttgaact atatgtttta atggccacgg ttttgtaaga catttggtcc    1920
tttgttttcc cagttattac tcgattgtaa ttttatatcg ccagcaatgg actgaaacgg    1980
tccgcaacct cttctttaca actgggtgac ctcgcggctg tgccagccat ttggcgttca    2040
ccctgccgct aagggccatg tgaaccccccg cggtagcatc ccttgctccg cgtggaccac   2100
tttcctgagg cacagtgata ggaacagagc cactaatctg aagagaacag agatgtgaca   2160
gactacacta atgtgagaaa aacaaggaaa gggtgactta ttggagattt cagaaataaa    2220
atgcatttat tattatattc ccttatttta attttctatt agggaattag aaagggcata   2280
aactgcttta tccagtgtta tattaaaagc ttaatgtata taatcttta gaggtaaaat     2340
ctacagccag caaaagtcat ggtaaatatt ctttgactga actctcacta aactcctcta    2400
aattatatgt catattaact ggttaaatta atataaattt gtgacatgac cttaactggt    2460
taggtaggat attttttcttc atgcaaaaat atgactaata ataatttagc acaaaaatat   2520
ttcccaatac tttaattctg tgatagaaaa atgtttaact cagctactat aatcccataa    2580
ttttgaaaac tatttattag ctttgtgtt tgacccttcc ctagccaaag caactattt      2640
aaggaccctt taaaactctt gaaactactt tagagtcatt aagttattta accacttta    2700
attactttaa aatgatgtca attccctttt aactattaat ttattttaag gggggaaagg    2760
ctgctcataa ttctattgtt tttcttggta aagaactctc agttttcgtt tttactacct    2820
ctgtcaccca agagttggca tctcaacaga ggggactttc cgagaggcca tctggcagtt   2880
gcttaagatc agaagtgaag tctgccagtt cctcccaggc aggtggccca gattacagtt   2940
gacctgttct ggtgtggcta aaaattgtcc catgtggtta caaaccatta gaccagggtc    3000
tgatgaattg ctcagaatat ttctggacac ccaaatacag accctggctt aaggccctgt    3060
ccatacagta ggtttagctt ggctacacca aaggaagcca tacagaggct aatatcagag    3120
tattcttgga agagacagga gaaatgaaa gccagtttct gctcttacct tatgtgcttg     3180
tgttcagact cccaaacatc aggagtgtca gataaactgg tctgaatctc tgtctgaagc    3240
atggaactga aaagaatgta gtttcaggga agaaaggcaa tagaaggaag cctgagaata    3300
tcttcaaagg gtcagactca atttactttc taaagaagta gctaggaact agggaataac    3360
ttagaaacaa caagattgta tatatgtgca tcctggcccc attgttcctt atctgtaggg    3420
ataagcgtgc tttttttgtgt gtctgtatat aacataactg tttacacata atacactgaa   3480
atggagccct tccttgttac ttcataccat cctctgtgct tccttcctca ggggccgacg    3540
ccgctcccac cgtgtccatc ttccccccca gcatggaaca gctgacctct ggcggagcca    3600
ccgtggtctg cttcgtgaac aacttctacc ccagagacat cagcgtgaag tggaagatcg    3660
acggcagcga gcagagggac ggcgtgctgg acagcgtgac cgaccaggac agcaaggact    3720
ccacctacag catgagcagc accctgagcc tgaccaaggt ggagtacgag aggcacaacc    3780
tgtacacctg cgaggtggtg cacaagacca gctccagccc cgtggtcaag tccttcaacc    3840
ggaacgagtg ttgaagacaa aggtcctgag acgccaccac cagctcccca gctccatcct    3900
atcttccctt ctaaggtctt ggaggcttcc ccacaagcga cctaccactg ttgcggtgct    3960
ccaaacctcc tccccaccct cttctcctcc tcctcccttt ccttggcttt tatcatgcta    4020
```

```
atatttgcag aaaatattca ataaagtgag tctttgcact tgagatctct gtctttctta    4080
ctaaatggta gtaatcagtt gttttttccag ttacctgggt ttctcttcta aagaagttaa   4140
atgtttagtt gccctgaaat ccaccacact taaaggataa ataaaaccct ccacttgccc    4200
tggttggctg tccactacat ggcagtcctt tctaaggttc acgagtacta ttcatggctt    4260
atttctctgg gccatggtag gtttgaggag gcatacttcc tagttttctt cccctaagtc    4320
gtcaaagtcc tgaaggggga cagtctttac aagcacatgt tctgtaatct gattcaacct    4380
acccagtaaa cttggcgaag caaagtagaa tcattatcac aggaagcaaa ggcaacctaa    4440
atgtgcaagc aataggaaaa tgtggaagcc catcatagta cttggacttc atctgctttt    4500
gtgccttcac taagttttta aacatgagct ggctcctatc tgccattggc aaggctgggc    4560
actacccaca acctacttca aggacctcta taccgtgaga ttacacacat acatcaaaat    4620
ttgggaaaag ttctaccaag ctgagagctg atcaccccac tcttaggtgc ttatctctgt    4680
acaccagaaa ccttaagaag caaccagtat tgagagactc atttatgaaa gtctaaaact    4740
ggatacaacc aaaatgtcca ccaacagtta aattatgaca tgttcacaat tgagctatta    4800
cttaataagg agaattaata aaataaaact taagagcata gtttaatctc ataaacaaga    4860
taataagcaa aacaaaacat ttttttcatcc atgtaagttt aaaagcaggt aaaatttaaa   4920
attaagagag acataagttt tgaggtagca agatggaaac tctggggctt ggggaatgtt    4980
ctgtctctct gtatgggatg tgaaagttac tattgtggaa ttgggatcta tgttcttcct    5040
gtatatattg tatacttcat aataacttca cctaaagaaa tatctaatac ccagtgcata    5100
cataaaagag gatacaagga atgaatcata cgtcaaggcc agaaagacaa taaagtaggg    5160
gatccaggat caaatctccc acaaccttga gccttctact attctgcctt ccagagctca    5220
aagtacaaaa cacataattc aaacacatga tccctccttg gggtctcttc cttcatgcat    5280
cgaattagaa atagccatgt ataaaatgag atagaagaga ccttcatcaa caggtcaaag    5340
aatataggta attttgtctg ggtatgaaga gcccacgtat caaaggttac attagggaag    5400
gaagaggaca ctaacagtga ctttcattct cccctcttc ctggaggccc ctgcatttag    5460
tccctcgtgg gctcatccac tcagcacaca tttactaagc atcttctcag cctacactct    5520
gaaggcagtg cagaataatg ttagtgtccc ttcccccagt taatatgcag tccagttccc   5580
ctgctccttc cctttctcag tccacataag gatgatggga aaggacagtc accaaatagg    5640
agagggcaac cctttgcctt cctacctctt gagaatgtac attattatcc acttttttgaa   5700
acttcttttta attgcttttt tttaatttgt cttttcaaat agcataacct tgttcatcca    5760
tttctgggaa ccaaatttat caatcaacag tgcctctaat ctggctatta atacaaaaat    5820
gcctcctcaa aatatatatg ttcgagtctt atctaaaaca gaacccacaa taaaaaagaa    5880
gaaagaatac atataagcat ttatataatt ctgagcaacc ttgtgctttg tgaaaaaaat    5940
ataatctaat gtcacatgct gtattctttt tatttaacac tggtgaaatt ataccattag    6000
agagaaagag gacagatcac tgatcctagg atctagggat gttacagata agaaaacaaa    6060
tgtgacaaag agctgtcaca aggaggatct tcaaggtcac agaatcactg tcttgatttc    6120
agtggtggtt acatacattt aaatatgtga taaaatgttg ttgaactata ttcatatatt    6180
gtaccaatgt caaatgctta attttggctc tatagtataa ttatgcacta ataactatt    6240
tggacaaaga aaatgatgtt tacatcaaag gtgaggccat atttgttagg aacataactt    6300
aaaaaccatt ttggataact aatgaaaagc cattttgtgt gccttggcat atcatgccta    6360
```

```
agctgtcacc agatagatct aataagacct aagcctcaga agcaagcccc tgcccagcaa    6420
gcaggcagca cagataagag ctaaacccag gacaggccat gatatgctaa tgaactacct    6480
tcaaggtggt gttgctgacc tagtgaacca gccccaagct gtgagcccca atagcacaaa    6540
gctactgccc aaagaaatta tacaaaaatt ggaactttgg gaatggtgtg caggatcgct    6600
ctgctgtatg cctggaacac agcttctcta tgttttgtat tgataccagt ctagaagctt    6660
ccaaaacttt ctcactgaag aagattcccc atgtgggacc cctacagact cttttgccca    6720
aacaactgct tccctcctgg tgtgatatct gttttgcttt tatgttagca taatattata    6780
aggaatgttt gtgtgaataa accaaacata ttttaaaagc aaatattgta tgcacatcct    6840
aattgctaaa aagtttacag ctaatagtcc catgctctcc acaatactgg atccaaataa    6900
gtcctaattt caatgttggg catctttaca gagagaaaga cattaaaaat gaagagacat    6960
gcagagagtg caccatgcca tcgtggagac agactgaagt gacacaactg ttagtcaaag    7020
aggattaagg acttccagaa gccaccaaag gaaggaggta tgaagtggtt tctccctcag    7080
agtatccaga ggagactaaa ccaaccaaca ccttttttgct taagacttct tgccttcagg    7140
actgtgagaa ggtagcttcc tattgttcta agcccagta tgtggcattt tgttaaggta    7200
gagtcaagaa accaataaaa tgcagacaga caaaaggata gctgagtttt ccaggcccct    7260
ccttcttatt tttggttttg ttggtggtgg tggtggtggt ggtgatggtg gtggttttgt    7320 ttatgtttg tttggggagt tttttggggt tttttgggt tttgttttg ttgttgtttt    7380 gggggttttt gttgttgttg ttgtttgctt ttttgttttt tgtttttgt tttttgaga    7440 cagtgtttct ctgtatagcc ctggctgtcc tggagttcct tctatctcta atgtctacat    7500
ctcagagggg atcctctaat ttcaaatgag cagtagctct ccatttttag ctcttattta    7560
ttcatttatt tacttactta cttattgtct gtagatgaaa gaattttgga gtgggaaagg    7620
gttcatgagc ccccagcaac taatgaggag ctacagacaa ttgatgtttc tggggaaagg    7680
agactcagtt tctttgagag tatagcttct gatgggtcaa ccatgttcct gtggctgatg    7740
tcacacccag gagtatgcag acaacagaaa ctggagttaa tgagttgttt taaaaataaa    7800
aaagggcatg aagcttggga tagaaattaa ggataaatac aattaaatac aggaaattct    7860
gaaagaatta ataaaaacat ttcttttttt aaaaaaaaat ccagaattag ctatgcttct    7920
tcaaaattgc ttctggagaa cttttacaagt taaataagtt atattgtaga aaaggtagag    7980
aggagaatag tggaagagag agataaggag acttcaaaag gagtggaggg agatagagga    8040
ggagaaagca gaagcaatgg ctgatagaca caggataaga gggaacagaa aggagaaaga    8100
ggaagccagg atgggtattt ctttgcctat ctgtgacttg cacatggtct tggcaattat    8160
tgatgagttc aaggcttaat tcttcacttg tgccaactca acagagtctt tctttcttat    8220
aaccaggccc ccagtatgct catgtatgta tcaggtcctc ttatctcctt atagcaatcc    8280
tgtttataac tgggtaactt tgtgaaggga aggaagtgca cactgagatg tgctacaact    8340
ttttaataca aaattttgaa gagtttgtac aatgtatgta taattaataa ttaatattat    8400
gcactttaga ttttgatttc aactcaagat actaattcta tatatatggg ttaaatcaat    8460
atattaataa gttaatttc acatgcttat ttttattgtg gttttcgaga cagggtttct    8520
ctgtatagcc ctggctgtcc tggaacccac tttgtagacc aggctggcct caaactcaga    8580
aacctacctg cctctgcctc tgcctctgcc tctgcctctg cctctgcctc tgcctctgcc    8640
tctgcctctg cctctgcctc tgcctctgcc tgcctctctg cctctgcctc tgcctctgcc    8700
tctgcctctg cctctgcctc tgcctctgcc tgcctctctg cctctgcctc tgcctctgcc    8760
```

```
tctgcctagt gctggaatta aaggtttgcg ccaccacgcc cggtgaaatt tttaaacttt    8820
atatatgtct cattctattt ctatcagata ggactgtgta gactgtgcta aactaataaa    8880
tgtgccctca aaagtaatcg caagttgtat tgttgttgtt ttgctttgct ttgctttgct    8940
ttgctttgct ttgctttgct ttgctttgct ttgctttgct ttgctttgct ttgctttgct    9000
ttgctttgct ttgctttgct ttgctttttt gttttgggtt ttttccgggg ggagggaggg    9060
tggagaaaga atcttactat gaagctctga ctgtcctggg aactcactat atagatcagg    9120
cttgattcaa ctcatagaga tctgccttct tctgcctccc aagtgctggg aataaaggca    9180
tacacctcca tgcccagata gtgatcccaa gttttagcaa aagtttctag acttgacatt    9240
aatcgatgga gatagacatg aattacacaa agaactaatg tggagtttac ctgaatcata    9300
ctctatactt tatcagagat taaattaaca tttaataatc cagtgccagg ctagaggcac    9360
cattcaatgg cagtgtttgc catcatgcat aggcttagtc ttcagtgctg aaaggcattg    9420
ggggcaatat tactcattat acagatgaga aactgggaaa gacttgcctc agattctcta    9480
ctgaaaggct gagtttgtgg cttctagaaa atcttttact ttcaatattt ttaatgtata    9540
atttttttat ttccactgat tttattttt atttttaaca tttataagaa ataaatgcaa    9600
taaaccaaat acatggacaa aaaaatacaa gaatcatatg atcacctcaa tggaaggaaa    9660
aaaaaagaaa gaaaaagtct tgataagat tcaacattca ttcttttttt attagatatt    9720
ttcttcattt acatttcaaa tgctatcccc aaagccccct ataccttccc ctgccctgct    9780
ccccaaccca cccactcctg ctttctggcc ctggcattcc tctgtactga ggcatatgat    9840
cttcaaaaaa ccaagggcct ctcctctcat tggtggccga ctattaggcc atcttttgct    9900
acatatgcaa ctagagacac agctctgggg gttactggtt agttcatatt gttagtcctc    9960
ctatagagtt gcagacccct ttagctcctt ggatactttc tctagttcct tcattagggg   10020
ccctgtgtcc catccaatag atgactgtga gcatccactt ctgtatttgc caggcactgg   10080
catagcctca cgagaaagag agagctatgt caggatcctg tcagtaaaat ctttctggca   10140
tatgcaatag tatctgggtt tggtggttgt atatgggatg gatccccaag tggagcagtc   10200
tctgaatggt ccttccttcc atctcagctc caaactttgt ctctataact ccttccatgg   10260
gtattttgtt ccccattcta agaaggagtg aagaatccac actttggtct tccttcttct   10320
tgagtttcat atgttgcatc ttggatattc taagtttctg ggttaatatc cacgtatcag   10380
tgagtgcata tcatgcgtgt tattttgtga ttagtttacc tcactcagga tgatatcctc   10440
cagatgcatc catttgccta agaatttcat taattcactg ttttaattg ctgaatagta   10500 ctccattgtg taaatgtacc acattttctg tatccattcc tctgttgagg ggcatctggg   10560
ttctttccag cttctggcta ttataaataa ggctgctatg agcatagcgg agcatgtgtc   10620
cttatcaagt tggaacatct tctaggtata tgcccaggag aggaattgct ggatcttccg   10680
gtagtaccat caacatgcat tcttaataaa agccctagaa caaggaggac tgtaggaaac   10740
atattccaac ataataaagg ttatgtatga caaactcatg accaatatca tcctaaatga   10800
atgaaaccat taataagctc cattaaaatc agaggactgc ccactatccc tacttctcat   10860
ccataatgag attgaagcat tagctggagc aataaggcaa gagaagggat acaaatggga   10920
aaatattaag tcaaattgtt ttcaattgaa gattatatta tcttataccc aatgacctca   10980
aattttgact agaaaaattg tagaaattat caataatttc agcaaagtgt tatgatgcac   11040
cacatcctta ttcttctccc cagcttctgc ttgcttctct cttcttgctc ttcatcctt    11100
```

```
ctgtccttcc atctgcctgc actcttgtct caagactgag tgcagcgtgt aactctcctg    11160
tgactgagta tctcacaaaa cgttctacct gccaaacctg gatgagccct ttgtctttct    11220
gaagctatga ggctctctac atagactcaa gaaggaaatg acagggagga ggtaataatg    11280
aagtggggaa ggctgacatt agcattgctc ctgtgtggct ccttaatttc tcatacttca    11340
cactgagatg ttattaactg tgactcatag gtgaagaagc cagagctaag gttctcatat    11400
ttgagtgtta tagaatgagt agagcagtag ttctcaaact atgggtcatg actccttat     11460
gggtcaaact acccttcac acaggttgca tatcagatat cctaattta tatacatata      11520
tatatgcata tgtatatata tatatttcac aacagtagga aaattattta gtaatcattt    11580
tatagttgtg ggtcatggca acatgaggaa ctgtattaaa gggttgcagc attaggaatg    11640
ttgagaccca ctgtaataga gaatgaggct taaggcaggg ctataaagcc caatggacca    11700
tgtgcctttt ccaacatttg ccacatggta agctctgtat agacttttta aagaacattg    11760
gtttgtaatt ttaaatggat aagggtcttc actgtctatc acccatctat ataataaata   11820
cataagtttt gattccacca tggattcaaa tgcaaaaatc ctcaacctaa gacatagcag   11880
tgaaacattg atgaccaaat aggaaatcca tgtagagacc ttctatcttc tgatggctcc   11940
acaggcacca tcttgcaaca gagttctact ttgctaccag taatgaatac agtgtctcaa   12000
ctcctgccat tgaatcttca ggaagcccct gaaatgactt gtactacacc atttcttaaa   12060
gacagaaaag ctaagactta gagggaataa atgtcatgcc tgagatcatg caaccaatta   12120
agtccaactt ggcctgatca agaggcacaa ttcaaaagca atgttgttcc ttcactagct   12180
cttgtgtatg gttgctgatt ccggaagcaa agtatcagtg aatatcccta gtgggaaaag   12240
acttggaaat caaatgtctc atttaacaga ttaggagatg aaacggtaga ctctgtgtag   12300
ttgtacaccc ctgtgatccc atcgctagga agactgaggc aggaagtcct cgagctcaaa   12360
ccagcttagg ctacacagag aaactatcta aaaaataatt actaactact taataggaga   12420
ttggatgtta agatctggtc actaagaggc agaattgaga ttcgaagcca gtattttcta   12480
cctggtatgt tttaaattgc agtaaggatc taagtgtaga tatataataa taagattcta   12540
ttgatctctg caacaacaga gagtgttaga tttgtttgga aaaaaatatt atcagccaac   12600
atcttctacc atttcagtat agcacagagt acccacccat atctccccac ccatccccca   12660
taccagactg gttattgatt ttcatggtga ctggcctgag aagattaaaa aaagtaatgc   12720
taccttattg ggagtgtccc atggaccaag atagcaactg tcatagctac cgtcacactg   12780
ctttgatcaa gaagaccctt tgaggaactg aaaacagaac cttaggcaca tctgttgctt   12840
tcgctcccat cctcctccaa cagcctgggt ggtgcactcc acaccctttc aagtttccaa   12900
agcctcatac acctgctccc taccccagca cctggccaag gctgtatcca gcactgggat   12960
gaaaatgata ccccacctcc atcttgtttg atattactct atctcaagcc ccaggttagt   13020
ccccagtccc aatgcttttg cacagtcaaa actcaacttg gaataatcag tatccttgaa   13080
gagttctgat atggtcactg ggcccatata ccatgtaaga catgtggaaa agatgtttca   13140
tggggcccag acacgttcta gaagtacctg agagtggcaa aaaatagttg tgctaaatag   13200
tttggccatc tttaggctga gagactagga aatacagcga tggactatat cagcattgca   13260
ggatagttgt cagtaaacac cccacaaccc ataacagaag tattctcttc tttctatatc   13320
ccttttccat ccatgtagat ggctgtcttc atatttgttc tagacggccg gcc           13373
```

<210> SEQ ID NO 93
<211> LENGTH: 12892

<212> TYPE: DNA
<213> ORGANISM: Artificial Sequence
<220> FEATURE:
<223> OTHER INFORMATION: VkP-IGKV1-39/J-Ck-delta1

<400> SEQUENCE: 93

| | | | | | |
|---|---|---|---|---|---|
| ggccggccca | catgaaacaa | tgggaaccat | gtgacaatca | cagaggtgtt | gttactatag | 60 |
| caaaagggat | tgttactctc | cacatccctt | taagtaactt | gaaggcctga | tagacccacc | 120 |
| ctctaagact | tcattagaca | ttccctacga | atggttatac | tctcctgtat | actcccaata | 180 |
| caactctaaa | atatattatt | ccatatagtc | cttaggtttg | tattaaagtt | tgactttttt | 240 |
| ccttcaaaat | atctcttgtc | acaacagcgg | ctctagagag | aaatacattc | cctccaggca | 300 |
| aatctatgct | gcgctggtct | gacctgggac | cctggggaca | ttgcccctgt | gctgagttac | 360 |
| taagatgagc | cagccctgca | gctgtgctca | gcctgcccca | tgccctgctg | attgatttgc | 420 |
| atgttccaga | gcacagcccc | ctgccctgaa | gacttttta | tgggctggtc | gcaccctgtg | 480 |
| caggagtcag | tctcagtcag | gagccaccat | ggacatgaga | gtgcccgccc | agctcctggg | 540 |
| gctcctgcta | ctctggctcc | gaggtaagga | tggagaacac | taggaattta | ctcagccagt | 600 |
| gtgctcagta | ctgactggaa | cttcaggaa | gttctctgat | aacatgatta | atagtaagaa | 660 |
| tatttgtttt | tatgtttcca | atctcaggtg | ccagatgtga | catccagatg | acccagagcc | 720 |
| ccagcagcct | gagcgccagc | gtgggcgaca | gagtgaccat | cacctgcaga | gccagccaga | 780 |
| gcatcagcag | ctacctgaac | tggtatcagc | agaagcccgg | caaggccccc | aagctgctga | 840 |
| tctacgccgc | cagctccctg | cagagcggcg | tgcccagcag | attcagcggc | agcggctccg | 900 |
| gcaccgactt | caccctgacc | atcagcagcc | tgcagcccga | ggacttcgcc | acctactact | 960 |
| gccagcagag | ctacagcacc | ccccccacct | tcggccaggg | caccaaggtg | gagatcaaac | 1020 |
| gtaagtacac | ttttctcatc | ttttttatg | tgtaagacac | aggttttcat | gttaggagtt | 1080 |
| aaagtcagtt | cagaaaatct | tgagaaaatg | gagagggctc | attatcagtt | gacgtggcat | 1140 |
| acagtgtcag | attttctgtt | tatcaagcta | gtgagattag | gggcaaaaag | aggctttagt | 1200 |
| tgagaggaaa | gtaattaata | ctatggtcac | catccaagag | attggatcgg | agaataagca | 1260 |
| tgagtagtta | ttgagatctg | ggtctgactg | caggtagcgt | ggtcttctag | acgtttaagt | 1320 |
| gggagatttg | gaggggatga | ggaatgaagg | aacttcagga | tagaaaaggg | ctgaagtcaa | 1380 |
| gttcagctcc | taaaatggat | gtgggagcaa | actttgaaga | taaactgaat | gacccagagg | 1440 |
| atgaaacagc | gcagatcaaa | gaggggcctg | gagctctgag | aagagaagga | gactcatccg | 1500 |
| tgttgagttt | ccacaagtac | tgtcttgagt | tttgcaataa | aagtgggata | gcagagttga | 1560 |
| gtgagccgta | ggctgagttc | tctcttttgt | ctcctaagtt | tttatgacta | caaaaatcag | 1620 |
| tagtatgtcc | tgaaataatc | attaagctgt | ttgaaagtat | gactgcttgc | catgtagata | 1680 |
| ccatggcttg | ctgaataatc | agaagaggtg | tgactcttat | tctaaaattt | gtcacaaaat | 1740 |
| gtcaaaatga | gagactctgt | aggaacgagt | ccttgacaga | cagctcaagg | ggtttttttc | 1800 |
| ctttgtctca | tttctacatg | aaagtaaatt | tgaaatgatc | tttttatta | taagagtaga | 1860 |
| aatacagttg | ggtttgaact | atatgtttta | atggccacgg | ttttgtaaga | catttggtcc | 1920 |
| tttgttttcc | cagttattac | tcgattgtaa | ttttatatcg | ccagcaatgg | actgaaacgg | 1980 |
| tccgcaacct | cttctttaca | actgggtgac | ctcgcggctg | tgccagccat | ttggcgttca | 2040 |
| ccctgccgct | aagggccatg | tgaaccccg | cggtagcatc | ccttgctccg | cgtgaccac | 2100 |
| tttcctgagg | cacagtgata | ggaacagagc | cactaatctg | aagagaacag | agatgtgaca | 2160 |

```
gactacacta atgtgagaaa acaaggaaa  gggtgactta ttggagattt cagaaataaa    2220
atgcatttat tattatattc ccttatttta attttctatt agggaattag aaagggcata    2280
aactgcttta tccagtgtta tattaaaagc ttaatgtata taatcttta  gaggtaaaat    2340
ctacagccag caaaagtcat ggtaaatatt ctttgactga actctcacta aactcctcta    2400
aattatatgt catattaact ggttaaatta atataaattt gtgacatgac cttaactggt    2460
taggtaggat attttctc   atgcaaaaat atgactaata ataatttagc acaaaaatat    2520
ttcccaatac tttaattctg tgatagaaaa atgtttaact cagctactat aatcccataa    2580
ttttgaaaac tatttatttg gctacaccaa aggaagccat acagaggcta atatcagagt    2640
attcttggaa gagacaggag aaaatgaaag ccagtttctg ctcttacctt atgtgcttgt    2700
gttcagactc ccaaacatca ggagtgtcag ataaactggt ctgaatctct gtctgaagca    2760
tggaactgaa aagaatgtag tttcagggaa gaaaggcaat agaaggaagc ctgagaatat    2820
cttcaaaggg tcagactcaa tttactttct aaagaagtag ctaggaacta gggaataact    2880
tagaaacaac aagattgtat atatgtgcat cctggcccca ttgttcctta tctgtaggga    2940
taagcgtgct ttttgtgtg  tctgtatata acataactgt ttacacataa tacactgaaa    3000
tggagcccct ccttgttact tcataccatc ctctgtgctt ccttcctcag gggccgacgc    3060
cgctcccacc gtgtccatct tcccccccag catggaacag ctgacctctg cggagccac    3120
cgtggtctgc ttcgtgaaca acttctaccc cagagacatc agcgtgaagt ggaagatcga    3180
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctcccag  ctccatccta    3420
tcttcccttc taaggtcttg gaggcttccc cacaagcgac ctaccactgt tgcggtgctc    3480
caaacctcct ccccacctcc ttctcctcct cctcccttc  cttggctttt atcatgctaa    3540
tatttgcaga aaatattcaa taaagtgagt ctttgcactt gagatctctg tctttcttac    3600
taaatggtag taatcagttg tttttccagt tacctgggtt tctcttctaa agaagttaaa    3660
tgtttagttg ccctgaaatc caccacactt aaaggataaa taaaaccctc cacttgccct    3720
ggttggctgt ccactacatg gcagtccttt ctaaggttca cgagtactat tcatggctta    3780
tttctctggg ccatggtagg tttgaggagg catacttcct agttttcttc ccctaagtcg    3840
tcaaagtcct gaaggggac  agtctttaca agcacatgtt ctgtaatctg attcaaccta    3900
cccagtaaac ttggcgaagc aaagtagaat cattatcaca ggaagcaaag gcaacctaaa    3960
tgtgcaagca ataggaaaat gtggaagccc atcatagtac ttggacttca tctgcttttg    4020
tgccttcact aagttttaa  acatgagctg gctcctatct gccattggca aggctgggca    4080
ctacccacaa cctacttcaa ggacctctat accgtgagat tacacacata catcaaaatt    4140
tgggaaaagt tctaccaagc tgagagctga tcaccccact cttaggtgct tatctctgta    4200
caccagaaac cttaagaagc aaccagtatt gagagactca tttatgaaag tctaaaactg    4260
gatcaaccaa aaatgtccac caacagttaa attatgacat gttcacaatt gagctattac    4320
ttaataagga gaattaataa aataaaactt aagagcatag tttaatctca taaacaagat    4380
aataagcaaa acaaaacatt ttttcatcca tgtaagttta aaagcaggta aaatttaaaa    4440
ttaagagaga cataagtttt gaggtagcaa gatgaaaact ctggggcttg gggaatgttc    4500
tgtctctctg tatgggatgt gaaagttact attgtggaat tgggatctat gttcttcctg    4560
```

```
tatatattgt atacttcata ataacttcac ctaaagaaat atctaatacc cagtgcatac    4620
ataaaagagg atacaaggaa tgaatcatac gtcaaggcca gaaagacaat aaagtagggg    4680
atccaggatc aaatctccca caaccttgag ccttctacta ttctgccttc cagagctcaa    4740
agtacaaaac acataattca aacacatgat ccctccttgg ggtctcttcc ttcatgcatc    4800
gaattagaaa tagccatgta taaaatgaga tagaagagac cttcatcaac aggtcaaaga    4860
atataggtaa ttttgtctgg gtatgaagag cccacgtatc aaaggttaca ttagggaagg    4920
aagaggacac taacagtgac tttcattctc ccctcttcc tggaggcccc tgcatttagt     4980
ccctcgtggg ctcatccact cagcacacat ttactaagca tcttctcagc ctacactctg    5040
aaggcagtgc agaataatgt tagtgtccct tcccccagtt aatatgcagt ccagtttccc    5100
tgctccttcc ctttctcagt ccacataagg atgatgggaa aggacagtca ccaaatagga    5160
gagggcaacc ctttgccttc ctacctcttg agaatgtaca ttattatcca cttttttgaaa   5220
cttcttttaa ttgctttttt ttaatttgtc ttttcaaata gcataacctt gttcatccat    5280
ttctgggaac caaatttatc aatcaacagt gcctctaatc tggctattaa tacaaaaatg    5340
cctcctcaaa atatatatgt tcgagtctta tctaaaacag acccacaat aaaaagaag      5400
aaagaataca tataagcatt tatataattc tgagcaacct tgtgctttgt gaaaaaaata    5460
taatctaatg tcacatgctg tattcttttt atttaacact ggtgaaatta taccattaga    5520
gagaaagagg acagatcact gatcctagga tctagggatg ttacagataa gaaacaaat    5580
gtgacaaaga gctgtcacaa ggaggatctt caaggtcaca gaatcactgt cttgatttca    5640
gtggtggtta catacattta aatatgtgat aaaatgttgt tgaactatat tcatatattg    5700
taccaatgtc aaatgcttaa ttttggctct atagtataat tatgcactaa ataactattt    5760
ggacaaagaa aatgatgttt acatcaaagg tgaggccata tttgttagga acataactta    5820
aaaaccattt tggataacta atgaaaagcc atttttgtgtg ccttggcata tcatgcctaa   5880
gctgtcacca gatagatcta ataagaccta agcctcagaa gcaagcccct gcccagcaag    5940
caggcagcac agataagagc taaacccagg acaggccatg atatgctaat gaactacctt    6000
caaggtggtg ttgctgacct agtgaaccag ccccaagctg tgagcccaa tagcacaaag     6060
ctactgccca aagaaattat acaaaaattg gaactttggg aatggtgtgc aggatcgctc    6120
tgctgtatgc ctggaacaca gcttctctat gtttttgtatt gataccagtc tagaagcttc   6180
caaaactttc tcactgaaga agattcccca tgtgggaccc ctacagactc ttttgcccaa    6240
acaactgctt ccctcctggt gtgatatctg ttttgctttt atgttagcat aatattataa    6300
ggaatgtttg tgtgaataaa ccaaacatat tttaaaagca aatattgtat gcacatccta    6360
attgctaaaa agtttacagc taatagtccc atgctctcca caatactgga tccaaataag    6420
tcctaatttc aatgttgggc atctttacag agagaaagac attaaaaatg aagagacatg    6480
cagagagtgc accatgccat cgtggagaca gactgaagtg acacaactgt tagtcaaaga    6540
ggattaagga cttccagaag ccaccaaagg aaggaggtat gaagtggttt ctccctcaga    6600
gtatccagag gagactaaac caaccaacac ctttttgctt aagacttctt gccttcagga    6660
ctgtgagaag gtagcttcct attgttctaa gccccagtat gtggcatttt gttaaggtag    6720
agtcaagaaa ccaataaaat gcagacagac aaaaggatag ctgagttttc caggcccttc    6780
cttcttattt ttggttttgt tggtggtggt ggtggtggtg gtgatggtgg tggttttgtt    6840
tatgttttgt ttggggagtt ttttgggtt ttttgggtt ttgttttgt tgttgttttg       6900
```

```
ggggttttg   ttgttgttgt   tgtttgcttt   tttgttttttt   gttttttgtt   tttttgagac   6960
agtgtttctc  tgtatagccc   tggctgtcct   ggagttcctt   ctatctctaa   tgtctacatc   7020
tcagagggga  tcctctaatt   tcaaatgagc   agtagctctc   cattttttagc  tcttatttat   7080
tcatttattt  acttacttac   ttattgtctg   tagatgaaag   aattttggag   tgggaaaggg   7140
ttcatgagcc  cccagcaact   aatgaggagc   tacagacaat   tgatgtttct   ggggaaagga   7200
gactcagttt  ctttgagagt   atagcttctg   atgggtcaac   catgttcctg   tggctgatgt   7260
cacacccagg  agtatgcaga   aacagaaac    tggagttaat   gagttgtttt   aaaaataaaa   7320
aagggcatga  agcttgggat   agaaattaag   gataaataca   attaaataca   ggaaattctg   7380
aaagaattaa  taaaaacatt   tcttttttta   aaaaaaaatc  cagaattagc   tatgcttctt   7440
caaaattgct  tctggagaac   tttacaagtt   aaataagtta   tattgtagaa   aaggtagaga   7500
ggagaatagt  ggaagagaga   gataaggaga   cttcaaaagg   agtggaggga   gatagaggag   7560
gagaaagcag  aagcaatggc   tgatagacac   aggataagag   ggaacagaaa   ggagaaagag   7620
gaagccagga  tgggtatttc   tttgcctatc   tgtgacttgc   acatggtctt   ggcaattatt   7680
gatgagttca  aggcttaatt   cttcacttgt   gccaactcaa   cagagtcttt   ctttcttata   7740
accaggcccc  cagtatgctc   atgtatgtat   caggtcctct   tatctcctta   tagcaatcct   7800
gtttataact  gggtaacttt   gtgaagggaa   ggaagtgcac   actgagatgt   gctacaactt   7860
tttaatacaa  aattttgaag   agtttgtaca   atgtatgtat   aattaataat   taatattatg   7920
cactttagat  tttgatttca   actcaagata   ctaattctat   atatatgggt   taaatcaata   7980
tattaataag  tttaatttca   catgcttatt   tttattgtgg   ttttcgagac   agggtttctc   8040
tgtatagccc  tggctgtcct   ggaacccact   ttgtagacca   ggctggcctc   aaactcagaa   8100
acctacctgc  ctctgcctct   gcctctgcct   ctgcctctgc   ctctgcctct   gcctctgcct   8160
ctgcctctgc  ctctgcctct   gcctctgcct   ctgcctctgc   ctctgcctct   gcctctgcct   8220
ctgcctctgc  ctctgcctct   gcctctgcct   ctgcctctgc   ctctgcctct   gcctctgcct   8280
ctgcctagtg  ctggaattaa   aggtttgcgc   caccacgccc   ggtgaaattt   ttaaacttta   8340
tatatgtctc  attctatttc   tatcagatag   gactgtgtag   actgtgctaa   actaataaat   8400
gtgccctcaa  aagtaatcgc   aagttgtatt   gttgttgttt   tgctttgctt   tgctttgctt   8460
tgctttgctt  tgctttgctt   tgctttgctt   tgctttgctt   tgctttgctt   tgctttgctt   8520
tgctttgctt  tgctttgctt   tgcttttttg   ttttgggttt   ttttccgggg   gagggagggt   8580
ggagaaagaa  tcttactatg   aagctctgac   tgtcctggga   actcactata   tagatcaggc   8640
ttgattcaac  tcatagagat   ctgccttctt   ctgcctccca   agtgctggga   ataaaggcat   8700
acacctccat  gcccagatag   tgatcccaag   ttttagcaaa   agtttctaga   cttgacatta   8760
atcgatggag  atagacatga   attacacaaa   gaactaatgt   ggagtttacc   tgaatcatac   8820
tctatacttt  atcagagatt   aaattaacat   ttaataatcc   agtgccaggc   tagaggcacc   8880
attcaatggc  agtgtttgcc   atcatgcata   ggcttagtct   tcagtgctga   aaggcattgg   8940
gggcaatatt  actcattata   cagatgagaa   actgggaaag   acttgcctca   gattctctac   9000
tgaaaggctg  agtttgtggc   ttctagaaaa   tcttttactt   tcaatatttt   taatgtataa   9060
ttttttttatt tccactgatt   ttatttttta   tttttaacat   ttataagaaa   taaatgcaat   9120
aaaccaaata  catggacaaa   aaaatacaag   aatcatatga   tcacctcaat   ggaaggaaaa   9180
aaaaagaaag  aaaaagtctt   tgataagatt   caacattcat   tctttttttta  ttagatattt   9240
tcttcattta  catttcaaat   gctatcccca   aagcccccta   taccttcccc   tgccctgctc   9300
```

```
cccaacccac ccactcctgc tttctggccc tggcattcct ctgtactgag gcatatgatc    9360
ttcaaaaaac caagggcctc tcctctcatt ggtggccgac tattaggcca tcttttgcta    9420
catatgcaac tagagacaca gctctggggg ttactggtta gttcatattg ttagtcctcc    9480
tatagagttg cagacccctt tagctccttg gatactttct ctagttcctt cattaggggc    9540
cctgtgtccc atccaataga tgactgtgag catccacttc tgtatttgcc aggcactggc    9600
atagcctcac gagaaagaga gagctatgtc aggatcctgt cagtaaaatc tttctggcat    9660
atgcaatagt atctgggttt ggtggttgta tatgggatgg atccccaagt ggagcagtct    9720
ctgaatggtc cttccttcca tctcagctcc aaactttgtc tctataactc cttccatggg    9780
tattttgttc cccattctaa gaaggagtga agaatccaca ctttggtctt ccttcttctt    9840
gagtttcata tgttgcatct tggatattct aagtttctgg gttaatatcc acgtatcagt    9900
gagtgcatat catgcgtgtt attttgtgat tagtttacct cactcaggat gatatcctcc    9960
agatgcatcc atttgcctaa gaatttcatt aattcactgt ttttaattgc tgaatagtac   10020
tccattgtgt aaatgtacca catttctgt atccattcct ctgttgaggg gcatctgggt   10080
tctttccagc ttctggctat tataaataag gctgctatga gcatagcgga gcatgtgtcc   10140
ttatcaagtt ggaacatctt ctaggtatat gcccaggaga ggaattgctg gatcttccgg   10200
tagtaccatc aacatgcatt cttaataaaa gccctagaac aaggaggact gtaggaaaca   10260
tattccaaca taataaaggt tatgtatgac aaactcatga ccaatatcat cctaaatgaa   10320
tgaaaccatt aataagctcc attaaaatca gaggactgcc cactatccct acttctcatc   10380
cataatgaga ttgaagcatt agctggagca ataaggcaag agaagggata caaatgggaa   10440
aatattaagt caaattgttt tcaattgaag attatattat cttatacccca atgacctcaa   10500
attttgacta gaaaaattgt agaaattatc aataatttca gcaaagtgtt atgatgcacc   10560
acatccttat tcttctcccc agcttctgct tgcttctctc ttcttgctct tcatcctttc   10620
tgtccttcca tctgcctgca ctcttgtctc aagactgagt gcagcgtgta actctcctgt   10680
gactgagtat ctcacaaaac gttctacctg ccaaacctgg atgagcccct tgtctttctg   10740
aagctatgag gctctctaca tagactcaag aaggaaatga cagggaggag gtaataatga   10800
agtggggaag gctgacatta gcattgctcc tgtgtggctc cttaatttct catacttcac   10860
actgagatgt tattaactgt gactcatagg tgaagaagcc agagctaagg ttctcatatt   10920
tgagtgttat agaatgagta gagcagtagt tctcaaacta tgggtcatga ctcctttatg   10980
ggtcaaacta cccttttcaca caggttgcat atcagatatc ctaattttat atacatatat   11040
atatgcatat gtatatatat atatttcaca acagtaggaa aattatttag taatcatttt   11100
atagttgtgg gtcatggcaa catgaggaac tgtattaaag ggttgcagca ttaggaatgt   11160
tgagacccac tgtaatagag aatgaggctt aaggcagggc tataaagccc aatggaccat   11220
gtgcctttc caacatttgc cacatggtaa gctctgtata gacttttaa agaacattgg   11280
tttgtaattt taaatggata agggtcttca ctgtctatca cccatctata aataaatac   11340
ataagttttg attccaccat ggattcaaat gcaaaaatcc tcaacctaag acatagcagt   11400
gaaacattga tgaccaaata ggaaatccat gtagagacct tctatcttct gatggctcca   11460
caggcaccat cttgcaacag agttctactt tgctaccagt aatgaataca gtgtctcaac   11520
tcctgccatt gaatcttcag gaagcccctg aaatgacttg tactacacca tttcttaaag   11580
acagaaaagc taagacttag agggaataaa tgtcatgcct gagatcatgc aaccaattaa   11640
```

-continued

| | |
|---|---|
| gtccaacttg gcctgatcaa gaggcacaat tcaaaagcaa tgttgttcct tcactagctc | 11700 |
| ttgtgtatgg ttgctgattc cggaagcaaa gtatcagtga atatccctag tgggaaaaga | 11760 |
| cttggaaatc aaatgtctca tttaacagat taggagatga aacggtagac tctgtgtagt | 11820 |
| tgtacacccc tgtgatccca tcgctaggaa gactgaggca ggaagtcctc gagctcaaac | 11880 |
| cagcttaggc tacacagaga aactatctaa aaaataatta ctaactactt aataggagat | 11940 |
| tggatgttaa gatctggtca ctaagaggca gaattgagat tcgaagccag tattttctac | 12000 |
| ctggtatgtt ttaaattgca gtaaggatct aagtgtagat atataataat aagattctat | 12060 |
| tgatctctgc aacaacagag agtgttagat ttgtttggaa aaaaatatta tcagccaaca | 12120 |
| tcttctacca tttcagtata gcacagagta cccacccata tctccccacc catcccccat | 12180 |
| accagactgg ttattgattt tcatggtgac tggcctgaga agattaaaaa aagtaatgct | 12240 |
| accttattgg gagtgtccca tggaccaaga tagcaactgt catagctacc gtcacactgc | 12300 |
| tttgatcaag aagacccttt gaggaactga aaacagaacc ttaggcacat ctgttgcttt | 12360 |
| cgctcccatc ctcctccaac agcctgggtg gtgcactcca cacctttca agtttccaaa | 12420 |
| gcctcataca cctgctccct accccagcac ctggccaagg ctgtatccag cactgggatg | 12480 |
| aaaatgatac cccacctcca tcttgtttga tattactcta tctcaagccc caggttagtc | 12540 |
| cccagtccca atgcttttgc acagtcaaaa ctcaacttgg aataatcagt atccttgaag | 12600 |
| agttctgata tggtcactgg gcccatatac catgtaagac atgtggaaaa gatgtttcat | 12660 |
| ggggcccaga cacgttctag aagtacctga gagtggcaaa aaatagttgt gctaaatagt | 12720 |
| ttggccatct ttaggctgag agactaggaa atacagcgat ggactatatc agcattgcag | 12780 |
| gatagttgtc agtaaacacc ccacaaccca taacagaagt attctcttct ttctatatcc | 12840 |
| cttttccatc catgtagatg gctgtcttca tatttgttct agacggccgg cc | 12892 |

<210> SEQ ID NO 94
<211> LENGTH: 6425
<212> TYPE: DNA
<213> ORGANISM: Artificial Sequence
<220> FEATURE:
<223> OTHER INFORMATION: VkP-IGKV1-39/J-Ck-delta2

<400> SEQUENCE: 94

| | |
|---|---|
| ggccggccca catgaaacaa tgggaaccat gtgacaatca cagaggtgtt gttactatag | 60 |
| caaaagggat tgttactctc cacatccctt taagtaactt gaaggcctga tagacccacc | 120 |
| ctctaagact tcattagaca ttccctacga atggttatac tctcctgtat actcccaata | 180 |
| caactctaaa atatattatt ccatatagtc cttaggtttg tattaaagtt tgactttttt | 240 |
| ccttcaaaat atctcttgtc acaacagcgg ctctagagag aaatacattc cctccaggca | 300 |
| aatctatgct gcgctggtct gacctgggac cctggggaca ttgcccctgt gctgagttac | 360 |
| taagatgagc cagccctgca gctgtgctca gcctgcccca tgccctgctg attgatttgc | 420 |
| atgttccaga gcacagcccc ctgccctgaa gactttttta tgggctggtc gcaccctgtg | 480 |
| caggagtcag tctcagtcag gagccaccat ggacatgaga gtgcccgccc agctcctggg | 540 |
| gctcctgcta ctctggctcc gaggtaagga tggagaacac taggaattta ctcagccagt | 600 |
| gtgctcagta ctgactggaa cttcagggaa gttctctgat aacatgatta atagtaagaa | 660 |
| tatttgtttt tatgtttcca atctcaggtg ccagatgtga catccagatg acccagagcc | 720 |
| ccagcagcct gagcgccagc gtgggcgaca gagtgaccat cacctgcaga gccagccaga | 780 |
| gcatcagcag ctacctgaac tggtatcagc agaagcccgg caaggccccc aagctgctga | 840 |

```
tctacgccgc cagctccctg cagagcggcg tgcccagcag attcagcggc agcggctccg    900
gcaccgactt caccctgacc atcagcagcc tgcagcccga ggacttcgcc acctactact    960
gccagcagag ctacagcacc ccccccacct tcggccaggg caccaaggtg gagatcaaac   1020
gtaagtacac ttttctcatc tttttttatg tgtaagacac aggttttcat gttaggagtt   1080
aaagtcagtt cagaaaatct tgagaaaatg gagagggctc attatcagtt gacgtggcat   1140
acagtgtcag attttctgtt tatcaagcta gtgagattag gggcaaaaag aggctttagt   1200
tgagaggaaa gtaattaata ctatggtcac catccaagag attggatcgg agaataagca   1260
tgagtagtta ttgagatctg ggtctgactg caggtagcgt ggtcttctag acgtttaagt   1320
gggagatttg gaggggatga ggaatgaagg aacttcagga tagaaaaggg ctgaagtcaa   1380
gttcagctcc taaaatggat gtgggagcaa actttgaaga taaactgaat gacccagagg   1440
atgaaacagc gcagatcaaa gagggcctg gagctctgag aagagaagga gactcatccg   1500
tgttgagttt ccacaagtac tgtcttgagt tttgcaataa aagtgggata gcagagttga   1560
gtgagccgta ggctgagttc tctcttttgt ctcctaagtt tttatgacta caaaaatcag   1620
tagtatgtcc tgaaataatc attaagctgt ttgaaagtat gactgcttgc catgtagata   1680
ccatggcttg ctgaataatc agaagaggtg tgactcttat tctaaaattt gtcacaaaat   1740
gtcaaaatga gagactctgt aggaacgagt ccttgacaga cagctcaagg ggttttttc    1800
ctttgtctca tttctacatg aaagtaaatt tgaaatgatc ttttttatta taagagtaga   1860
aatacagttg ggtttgaact atatgtttta atggccacgg ttttgtaaga catttggtcc   1920
tttgttttcc cagttattac tcgattgtaa ttttatatcg ccagcaatgg actgaaacgg   1980
tccgcaacct cttctttaca actgggtgac ctcgcggctg tgccagccat ttggcgttca   2040
ccctgccgct aagggccatg tgaaccccg cggtagcatc ccttgctccg cgtggaccac    2100
tttcctgagg cacagtgata ggaacagagc cactaatctg aagagaacag agatgtgaca   2160
gactacacta atgtgagaaa aacaaggaaa gggtgactta ttggagattt cagaaataaa   2220
atgcatttat tattatattc ccttatttta attttctatt agggaattag aaagggcata   2280
aactgcttta tccagtgtta tattaaaagc ttaatgtata taatcttta gaggtaaaat    2340
ctacagccag caaagtcat ggtaaatatt ctttgactga actctcacta aactcctcta    2400
aattatatgt catattaact ggttaaatta atataaattt gtgacatgac cttaactggt   2460
taggtaggat atttttcttc atgcaaaaat atgactaata ataatttagc acaaaaatat   2520
ttcccaatac tttaattctg tgatagaaaa atgtttaact cagctactat aatcccataa   2580
ttttgaaaac tatttatttg gctacaccaa aggaagccat acagaggcta atatcagagt   2640
attcttggaa gagacaggag aaaatgaaag ccagtttctg ctcttacctt atgtgcttgt   2700
gttcagactc ccaaacatca ggagtgtcag ataaactggt ctgaatctct gtctgaagca   2760
tggaactgaa aagaatgtag tttcagggaa gaaaggcaat agaaggaagc ctgagaatat   2820
cttcaaaggg tcagactcaa tttactttct aaagaagtag ctaggaacta gggaataact   2880
tagaaacaac aagattgtat atatgtgcat cctggcccca ttgttcctta tctgtaggga   2940
taagcgtgct ttttgtgtg tctgtatata acataactgt ttacacataa tacactgaaa    3000
tggagccctt ccttgttact tcataccatc ctctgtgctt ccttcctcag gggccgacgc   3060
cgctcccacc gtgtccatct tccccccag catggaacag ctgacctctg gcggagccac    3120
cgtggtctgc ttcgtgaaca acttctaccc cagagacatc agcgtgaagt ggaagatcga   3180
```

```
cggcagcgag cagagggacg gcgtgctgga cagcgtgacc gaccaggaca gcaaggactc    3240
cacctacagc atgagcagca ccctgagcct gaccaaggtg gagtacgaga ggcacaacct    3300
gtacacctgc gaggtggtgc acaagaccag ctccagcccc gtggtcaagt ccttcaaccg    3360
gaacgagtgt tgaagacaaa ggtcctgaga cgccaccacc agctcccag  ctccatccta    3420
tcttcccttc taaggtcttg gaggcttccc cacaagcgac ctaccactgt tgcggtgctc    3480
caaacctcct ccccacctcc ttctcctcct cctcccttc  cttggctttt atcatgctaa    3540
tatttgcaga aaatattcaa taaagtgagt ctttgcactt gagatctctg tctttcttac    3600
taaatggtag taatcagttg ttttccagt  tacctgggtt tctcttctaa agaagttaaa    3660
tgtttagttg ccctgaaatc caccacactt aaaggataaa taaaaccctc cacttgccct    3720
ggttggctgt ccactacatg gcagtccttt ctaaggttca cgagtactat tcatggctta    3780
tttctctggg ccatggtagg tttgaggagg catacttcct agttttcttc ccctaagtcg    3840
tcaaagtcct gaaggggac  agtctttaca agcacatgtt ctgtaatctg attcaaccta    3900
cccagtaaac ttggcgaagc aaagtagaat cattatcaca ggaagcaaag gcaacctaaa    3960
tgtgcaagca ataggaaaat gtggaagccc atcatagtac ttggacttca tctgcttttg    4020
tgccttcact aagttttaa  acatgagctg gctcctatct gccattggca aggctgggca    4080
ctacccacaa cctacttcaa ggacctctat accgtgagat tacacacata catcaaaatt    4140
tgggaaaagt tctaccaagc tgagagctga tcaccccact cttaggtgct tatctctgta    4200
caccagaaac cttaagaagc aaccagtatt gagagactca tttatgaaag tctaaaactg    4260
gatacaacca aaatgtccac caacagttaa attatgacat gttcacaatt gagctattac    4320
ttaataagga gaattaataa aataaaactt aagagcatag tttaatctca taaacaagat    4380
aataagcaaa acaaaacatt ttttcatcca tgtaagttta aaagcaggta aaatttaaaa    4440
ttaagagaga cataagtttt gaggtagcaa gatggaaact ctggggcttg gggaatgttc    4500
tgtctctctg tatgggatgt gaaagttact attgtgaat  tgggatctat gttcttcctg    4560
tatatattgt atacttcata ataacttcac ctaaagaaat atctaatacc cagtgcatac    4620
ataaaagagg atacaaggaa tgaatcatac gtcaaggcca gaaagacaat aaagtagggg    4680
atccaggatc aaatctccca caaccttgag ccttctacta ttctgccttc cagagctcaa    4740
agtacaaaac acataattca aacacatgat ccctccttgg ggtctcttcc ttcatgcatc    4800
gaattagaaa tagccatgta taaaatgaga tagaagagac cttcatcaac aggtcaaaga    4860
atataggtaa ttttgtctgg gtatgaagag cccacgtatc aaaggttaca ttagggaagg    4920
aagaggacac taacagtgac tttcattctc cccctcttcc tggaggcccc tgcatttagt    4980
ccctcgtggg ctcatccact cagcacacat ttactaagca tcttctcagc ctacactctg    5040
aaggcagtgc agaataatgt tagtgtccct tcccccagtt aatatgcagt ccagtttccc    5100
tgctccttcc ctttctcagt ccacataagg atgatgggaa aggacagtca ccaaatagga    5160
gagggcaacc ctttgccttc ctacctcttg agaatgtaca ttattatcca cttttgaaa    5220
cttctttaa  ttgctttttt ttaatttgtc ttttcaaata gcataacctt gttcatccat    5280
ttctgggaac caaatttatc aatcaacagt gcctctaatc tggctattaa tacaaaaatg    5340
cctcctcaaa atatatatgt tcgagtctta tctaaaacag aacccacaat aaaaaagaag    5400
aaagaataca tataagcatt tatataattc tgagcaacct tgtgctttgt gaaaaaaata    5460
taatctaatg tcacatgctg tattcttttt atttaacact ggtgaaatta taccattaga    5520
gagaaagagg acagatcact gatcctagga tctagggatg ttacagataa gaaaacaaat    5580
```

-continued

```
gtgacaaaga gctgtcacaa ggaggatctt caaggtcaca gaatcactgt cttgatttca    5640
gtggtggtta catacattta aatatgtgat aaaatgttgt tgaactatat tcatatattg    5700
taccaatgtc aaatgcttaa tttttggctct atagtataat tatgcactaa ataactattt    5760
ggacaaagaa aatgatgttt acatcaaagg tgaggccata tttgttagga acataactta    5820
aaaaccattt tggataacta atgaaaagcc attttgtgtg ccttggcata tcatgcctaa    5880
gctgtcacca gatagatcta ataagaccta agcctcagaa gcaagcccct gcccagcaag    5940
caggcagcac agataagagc taaacccagg acaggccatg atatgctaat gaactacctt    6000
caaggtggtg ttgctgacct agtgaaccag ccccaagctg tgagcccaa tagcacaaag     6060 ctactgccca agaaattat acaaaaattg gaactttggg aatggtgtgc aggatcgctc     6120
tgctgtatgc ctggaacaca gcttctctat gttttgtatt gataccagtc tagaagcttc    6180
caaaactttc tcactgaaga agattcccca tgtgggaccc ctacagactc ttttgcccaa    6240
acaactgctt ccctcctggt gtgatcatgg accaagatag caactgtcat agctaccgtc    6300
acactgcttt gatcaagaag acccttgag gaactgaaaa cagaaccttga ggcacatctg     6360 ttgctttcgc tcccatcctc ctccaacagc atggctgtct tcatatttgt tctagacggc    6420
cggcc                                                                6425
```

<210> SEQ ID NO 95
<211> LENGTH: 13382
<212> TYPE: DNA
<213> ORGANISM: Artificial Sequence
<220> FEATURE:
<223> OTHER INFORMATION: VkP-IGLV2-14/J-Ck

<400> SEQUENCE: 95

```
ggccggccca catgaaacaa tgggaaccat gtgacaatca cagaggtgtt gttactatag     60
caaaagggat tgttactctc cacatccctt taagtaactt gaaggcctga tagacccacc    120
ctctaagact tcattagaca ttccctacga atggttatac tctcctgtat actcccaata    180
caactctaaa atatattatt ccatatagtc cttaggtttg tattaaagtt tgactttttt    240
ccttcaaaat atctcttgtc acaacagcgg ctctagagag aaatacattc cctccaggca    300
aatctatgct gcgctggtct gacctgggac cctggggaca ttgccccgt gctgagttac     360 taagatgagc cagccctgca gctgtgctca gcctgcccca tgccctgctg attgatttgc    420
atgttccaga gcacagcccc ctgccctgaa gacttttta tgggctggtc gcaccctgtg    480
caggagtcag tctcagtcag gagccaccat ggacatgaga gtgcccgccc agctcctggg    540
gctcctgcta ctctggctcc gaggtaagga tggagaacac taggaattta ctcagccagt    600
gtgctcagta ctgactggaa cttcaggaa gttctctgat aacatgatta atagtaagaa     660
tatttgtttt tatgtttcca atctcaggtg ccagatgtca gtctgccctg acccagcccg    720
cctctgtgtc tggcagccct ggccagagca tcaccatcag ctgcaccggc accagcagcg    780
acgtgggcgg ctacaactac gtgtcctggt atcagcagca ccccggcaag gcccccaagc    840
tgatgatcta cgaggtgtcc aacagaccca gcggcgtgag caacagattc agcggcagca    900
agagcggcaa caccgccagc ctgaccatca gcggcctcca ggctgaggac gaggccgact    960
actactgcag cagctacacc agcagctcca ccctggtgtt tggcggcgga acaaagctga    1020
ccgtgctgcg taagtacact tttctcatct tttttttatgt gtaagacaca ggttttcatg    1080
ttaggagtta aagtcagttc agaaaatctt gagaaaatgg agagggctca ttatcagttg    1140
```

```
acgtggcata cagtgtcaga ttttctgttt atcaagctag tgagattagg ggcaaaaaga    1200
ggctttagtt gagaggaaag taattaatac tatggtcacc atccaagaga ttggatcgga    1260
gaataagcat gagtagttat tgagatctgg gtctgactgc aggtagcgtg gtcttctaga    1320
cgtttaagtg ggagatttgg aggggatgag gaatgaagga acttcaggat agaaaagggc    1380
tgaagtcaag ttcagctcct aaaatggatg tgggagcaaa ctttgaagat aaactgaatg    1440
acccagagga tgaaacagcg cagatcaaag aggggcctgg agctctgaga agagaaggag    1500
actcatccgt gttgagtttc cacaagtact gtcttgagtt ttgcaataaa agtgggatag    1560
cagagttgag tgagccgtag gctgagttct ctcttttgtc tcctaagttt ttatgactac    1620
aaaaatcagt agtatgtcct gaaataatca ttaagctgtt tgaaagtatg actgcttgcc    1680
atgtagatac catggcttgc tgaataatca aagaggtgt gactcttatt ctaaaatttg    1740
tcacaaaatg tcaaaatgag agactctgta ggaacgagtc cttgacagac agctcaaggg    1800
gtttttttcc tttgtctcat ttctacatga aagtaaattt gaaatgatct ttttttattat    1860 aagagtagaa atacagttgg gtttgaacta tatgttttaa tggccacggt tttgtaagac    1920
atttggtcct ttgttttccc agttattact cgattgtaat tttatatcgc cagcaatgga    1980
ctgaaacggt ccgcaacctc ttctttacaa ctgggtgacc tcgcggctgt gccagccatt    2040
tggcgttcac cctgccgcta agggccatgt gaaccccgc ggtagcatcc cttgctccgc    2100
gtggaccact ttcctgaggc acagtgatag gaacagagcc actaatctga agagaacaga    2160
gatgtgacag actacactaa tgtgagaaaa acaaggaaag ggtgactat tggagatttc    2220 agaaataaaa tgcatttatt attatattcc cttattttaa ttttctatta gggaattaga    2280
aagggcataa actgctttat ccagtgttat attaaaagct taatgtatat aatctttttag    2340 aggtaaaatc tacagccagc aaaagtcatg gtaaatattc tttgactgaa ctctcactaa    2400
actcctctaa attatatgtc atattaactg gttaaattaa tataaatttg tgacatgacc    2460
ttaactggtt aggtaggata ttttctttca tgcaaaaata tgactaataa taatttagca    2520
caaaaatatt tcccaatact ttaattctgt gatagaaaaa tgtttaactc agctactata    2580
atcccataat tttgaaaact atttattagc ttttgtgttt gacccttccc tagccaaagg    2640
caactattta aggacccttt aaaactcttg aaactactt agagtcatta agttatttaa    2700
ccacttttaa ttactttaaa atgatgtcaa ttccctttta actattaatt tatttaagg    2760 ggggaaaggc tgctcataat tctattgttt ttcttggtaa agaactctca gttttcgttt    2820
ttactacctc tgtcacccaa gagttggcat ctcaacagag gggactttcc gagaggccat    2880
ctggcagttg cttaagatca gaagtgaagt ctgccagttc ctcccaggca ggtggcccag    2940
attacagttg acctgttctg gtgtggctaa aaattgtccc atgtggttac aaaccattag    3000
accagggtct gatgaattgc tcagaatatt tctggacacc caaatacaga ccctggctta    3060
aggccctgtc catacagtag gtttagcttg gctacaccaa aggaagccat acagaggcta    3120
atatcagagt attcttggaa gagacaggag aaaatgaaag ccagtttctg ctcttacctt    3180
atgtgcttgt gttcagactc ccaaacatca ggagtgtcag ataaactggt ctgaatctct    3240
gtctgaagca tggaactgaa aagaatgtag tttcagggaa gaaaggcaat agaaggaagc    3300
ctgagaatat cttcaaaggg tcagactcaa tttactttct aaagaagtag ctaggaacta    3360 gggataact tagaaacaac aagattgtat atatgtgcat cctggcccca ttgttcctta    3420
tctgtaggga taagcgtgct ttttgtgtg tctgtatata acataactgt ttacacataa    3480
tacactgaaa tggagcccctt ccttgttact tcataccatc ctctgtgctt ccttcctcag    3540
```

-continued

```
gggccgacgc cgctcccacc gtgtccatct tcccccccag catggaacag ctgacctctg    3600
gcggagccac cgtggtctgc ttcgtgaaca acttctaccc cagagacatc agcgtgaagt    3660
ggaagatcga cggcagcgag cagagggacg gcgtgctgga cagcgtgacc gaccaggaca    3720
gcaaggactc cacctacagc atgagcagca ccctgagcct gaccaaggtg gagtacgaga    3780
ggcacaacct gtacacctgc gaggtggtgc acaagaccag ctccagcccc gtggtcaagt    3840
ccttcaaccg gaacgagtgt tgaagacaaa ggtcctgaga cgccaccacc agctccccag    3900
ctccatccta tcttcccttc taaggtcttg gaggcttccc cacaagcgac ctaccactgt    3960
tgcggtgctc caaacctcct ccccacctcc ttctcctcct cctcccttt cttggctttt     4020 atcatgctaa tatttgcaga aaatattcaa taaagtgagt ctttgcactt gagatctctg    4080
tctttcttac taaatggtag taatcagttg ttttccagt tacctgggtt tctcttctaa     4140
agaagttaaa tgtttagttg ccctgaaatc caccacactt aaaggataaa taaaaccctc    4200
cacttgccct ggttggctgt ccactacatg gcagtccttt ctaaggttca cgagtactat    4260
tcatggctta tttctctggg ccatggtagg tttgaggagg catacttcct agttttcttc    4320
ccctaagtcg tcaaagtcct gaaggggggac agtctttaca agcacatgtt ctgtaatctg    4380
attcaaccta cccagtaaac ttggcgaagc aaagtagaat cattatcaca ggaagcaaag    4440
gcaacctaaa tgtgcaagca ataggaaaat gtggaagccc atcatagtac ttggacttca    4500
tctgcttttg tgccttcact aagttttaa acatgagctg gctcctatct gccattggca     4560
aggctgggca ctaccacaa cctacttcaa ggacctctat accgtgagat tacacacata    4620
catcaaaatt tgggaaaagt tctaccaagc tgagagctga tcaccccact cttaggtgct    4680
tatctctgta caccgaaaac cttaagaagc aaccagtatt gagagactca tttatgaaag    4740
tctaaaactg gatacaacca aaatgtccac caacagttaa attatgacat gttcacaatt    4800
gagctattac ttaataagga gaattaataa aataaaactt aagagcatag tttaatctca    4860
taaacaagat aataagcaaa acaaaacatt ttttcatcca tgtaagttta aaagcaggta    4920
aaatttaaaa ttaagagaga cataagtttt gaggtagcaa gatggaaact ctggggcttg    4980
gggaatgttc tgtctctctg tatgggatgt gaaagttact attgtggaat tgggatctat    5040
gttcttcctg tatatattgt atacttcata ataacttcac ctaaagaaat atctaatacc    5100
cagtgcatac ataaaagagg atacaaggaa tgaatcatac gtcaaggcca gaaagacaat    5160
aaagtagggg atccaggatc aaatctccca caaccttgag ccttctacta ttctgccttc    5220
cagagctcaa agtacaaaac acataattca aacacatgat ccctccttgg ggtctcttcc    5280
ttcatgcatc gaattagaaa tagccatgta taaaatgaga tagaagagac cttcatcaac    5340
aggtcaaaga atataggtaa ttttgtctgg gtatgaagag cccacgtatc aaaggttaca    5400
ttagggaagg aagaggacac taacagtgac tttcattctc ccctcttcc tggaggcccc     5460 tgcatttagt ccctcgtggg ctcatccact cagcacacat ttactaagca tcttctcagc    5520
ctacactctg aaggcagtgc agaataatgt tagtgtccct tcccccagtt aatatgcagt    5580
ccagtttccc tgctccttcc ctttctcagt ccacataagg atgatgggaa aggacagtca    5640
ccaaatagga gagggcaacc ctttgccttc ctacctcttg agaatgtaca ttattatcca    5700 cttttgaaa cttcttttaa ttgcttttt taatttgtc ttttcaaata gcataacctt       5760
gttcatccat ttctgggaac caaatttatc aatcaacagt gcctctaatc tggctattaa    5820
tacaaaaatg cctcctcaaa atatatatgt tcgagtctta tctaaaacag aacccacaat    5880
```

```
aaaaaagaag aaagaataca tataagcatt tatataattc tgagcaacct tgtgctttgt    5940
gaaaaaaata taatctaatg tcacatgctg tattctttttt atttaacact ggtgaaatta    6000
taccattaga gagaaagagg acagatcact gatcctagga tctagggatg ttacagataa    6060
gaaaacaaat gtgacaaaga gctgtcacaa ggaggatctt caaggtcaca gaatcactgt    6120
cttgatttca gtggtggtta catacattta aatatgtgat aaaatgttgt tgaactatat    6180
tcatatattg taccaatgtc aaatgcttaa ttttggctct atagtataat tatgcactaa    6240
ataactattt ggacaaagaa aatgatgttt acatcaaagg tgaggccata tttgttagga    6300
acataactta aaaaccattt tggataacta atgaaaagcc attttgtgtg ccttggcata    6360
tcatgcctaa gctgtcacca gatagatcta ataagaccta agcctcagaa gcaagcccct    6420
gcccagcaag caggcagcac agataagagc taaacccagg acaggccatg atatgctaat    6480
gaactacctt caaggtggtg ttgctgacct agtgaaccag ccccaagctg tgagcccaa     6540 tagcacaaag ctactgccca agaaattat acaaaaattg gaactttggg aatggtgtgc     6600
aggatcgctc tgctgtatgc ctggaacaca gcttctctat gttttgtatt gataccagtc    6660
tagaagcttc caaaactttc tcactgaaga agattcccca tgtgggaccc ctacagactc    6720
ttttgcccaa acaactgctt ccctcctggt gtgatatctg ttttgctttt atgttagcat    6780
aatattataa ggaatgtttg tgtgaataaa ccaaacatat tttaaaagca aatattgtat    6840
gcacatccta attgctaaaa agtttacagc taatagtccc atgctctcca caatactgga    6900
tccaaataag tcctaatttc aatgttgggc atctttacag agagaaagac attaaaaatg    6960
aagagacatg cagagagtgc accatgccat cgtggagaca gactgaagtg acacaactgt    7020
tagtcaaaga ggattaagga cttccagaag ccaccaaagg aaggaggtat gaagtggttt    7080
ctccctcaga gtatccagag gagactaaac caaccaacac cttttttgctt aagacttctt    7140 gccttcagga ctgtgagaag gtagcttcct attgttctaa gccccagtat gtggcatttt    7200
gttaaggtag agtcaagaaa ccaataaaat gcagacagac aaaaggatag ctgagttttc    7260
caggcccttc cttcttattt ttggttttgt tggtggtggt ggtggtggtg gtgatggtgg    7320
tggttttgtt tatgttttgt ttggggagtt ttttggggtt ttttttgggtt ttgttttttgt   7380 tgttgtttttg ggggtttttg ttgttgttgt tgtttgcttt tttgttttttt gtttttttgtt   7440 tttttgagac agtgtttctc tgtatagccc tggctgtcct ggagttcctt ctatctctaa    7500
tgtctacatc tcagagggga tcctctaatt tcaaatgagc agtagctctc cattttttagc   7560 tcttatttat tcatttattt acttacttac ttattgtctg tagatgaaag aattttggag    7620
tgggaaaggg ttcatgagcc cccagcaact aatgaggagc tacagacaat tgatgtttct    7680
ggggaaagga gactcagttt ctttgagagt atagcttctg atgggtcaac catgttcctg    7740
tggctgatgt cacacccagg agtatgcaga caacagaaac tggagttaat gagttgtttt    7800
aaaaataaaa aagggcatga agcttgggat agaaattaag gataaataca attaaataca    7860
ggaaattctg aaagaattaa taaaaacatt tcttttttta aaaaaaaatc cagaattagc     7920
tatgcttctt caaaattgct tctggagaac tttacaagtt aaataagtta tattgtagaa    7980
aaggtagaga ggagaatagt ggaagagaga gataaggaga cttcaaaagg agtggaggga    8040
gatagaggag gagaaagcag aagcaatggc tgatagacac aggataagag ggaacagaaa    8100
ggagaaagag gaagccagga tgggtatttc tttgcctatc tgtgacttgc acatggtctt    8160
ggcaattatt gatgagttca aggcttaatt cttcacttgt gccaactcaa cagagtcttt    8220 cttctcttata accaggcccc cagtatgctc atgtatgtat caggtcctct tatctcctta   8280
```

```
tagcaatcct gtttataact gggtaacttt gtgaagggaa ggaagtgcac actgagatgt    8340
gctacaactt tttaatacaa aattttgaag agtttgtaca atgtatgtat aattaataat    8400
taatattatg cactttagat tttgatttca actcaagata ctaattctat atatatgggt    8460
taaatcaata tattaataag tttaatttca catgcttatt tttattgtgg ttttcgagac    8520
agggtttctc tgtatagccc tggctgtcct ggaacccact tgtagacca ggctggcctc    8580 aaactcagaa acctcctgc ctctgcctct gcctctgcct ctgcctctgc ctctgcctct    8640
gcctctgcct ctgcctctgc ctctgcctct gcctctgcct ctgcctctgc ctctgcctct    8700
gcctctgcct ctgcctctgc ctctgcctct gcctctgcct ctgcctctgc ctctgcctct    8760
gcctctgcct ctgcctagtg ctggaattaa aggtttgcgc caccacgccc ggtgaaattt    8820
ttaaacttta tatatgtctc attctatttc tatcagatag gactgtgtag actgtgctaa    8880
actaataaat gtgccctcaa agtaatcgc aagttgtatt gttgttgttt tgctttgctt    8940
tgctttgctt tgctttgctt tgctttgctt tgctttgctt tgctttgctt tgctttgctt    9000
tgctttgctt tgctttgctt tgctttgctt tgcttttttg ttttgggttt ttttccgggg    9060
gagggagggt ggagaaagaa tcttactatg aagctctgac tgtcctggga actcactata    9120
tagatcaggc ttgattcaac tcatagagat ctgccttctt ctgcctccca agtgctggga    9180
ataaaggcat acacctccat gcccagatag tgatcccaag ttttagcaaa agtttctaga    9240
cttgacatta atcgatggag atagacatga attacacaaa gaactaatgt ggagtttacc    9300
tgaatcatac tctatacttt atcagagatt aaattaacat ttaataatcc agtgccaggc    9360
tagaggcacc attcaatggc agtgtttgcc atcatgcata ggcttagtct tcagtgctga    9420
aaggcattgg gggcaatatt actcattata cagatgagaa actgggaaag acttgcctca    9480
gattctctac tgaaaggctg agtttgtggc ttctagaaaa tctttttactt tcaatatttt    9540 taatgtataa tttttttatt tccactgatt ttatttttta tttttaacat ttataagaaa    9600
taaatgcaat aaaccaaata catggacaaa aaaatacaag aatcatatga tcacctcaat    9660
ggaaggaaaa aaaagaaag aaaaagtctt tgataagatt caacattcat tcttttttta    9720
ttagatattt tcttcattta catttcaaat gctatcccca aagcccccta taccttcccc    9780
tgccctgctc cccaacccac ccactcctgc tttctggccc tggcattcct ctgtactgag    9840
gcatatgatc ttcaaaaaac caagggcctc tcctctcatt ggtggccgac tattaggcca    9900
tcttttgcta catatgcaac tagagacaca gctctggggg ttactggtta gttcatattg    9960
ttagtcctcc tatagagttg cagacccctt tagctccttg gatactttct ctagttcctt   10020
cattaggggc cctgtgtccc atccaataga tgactgtgag catccacttc tgtatttgcc   10080
aggcactggc atagcctcac gagaaagaga gagctatgtc aggatcctgt cagtaaaatc   10140
tttctggcat atgcaatagt atctgggttt ggtggttgta tatgggatgg atccccaagt   10200
ggagcagtct ctgaatggtc cttccttcca tctcagctcc aaactttgtc tctataactc   10260
cttccatggg tattttgttc cccattctaa gaaggagtga agaatccaca ctttggtctt   10320
ccttcttctt gagtttcata tgttgcatct tggatattct aagttctggg ttaatatcc   10380 acgtatcagt gagtgcatat catgcgtgtt attttgtgat tagtttacct cactcaggat   10440
gatatcctcc agatgcatcc atttgcctaa gaatttcatt aattcactgt ttttaattgc   10500
tgaatagtac tccattgtgt aaatgtacca cattttctgt atccattcct ctgttgaggg   10560
gcatctgggt tctttccagc ttctggctat tataaataag gctgctatga gcatagcgga   10620
```

```
gcatgtgtcc ttatcaagtt ggaacatctt ctaggtatat gcccaggaga ggaattgctg   10680
gatcttccgg tagtaccatc aacatgcatt cttaataaaa gccctagaac aaggaggact   10740
gtaggaaaca tattccaaca taataaaggt tatgtatgac aaactcatga ccaatatcat   10800
cctaaatgaa tgaaaccatt aataagctcc attaaaatca gaggactgcc cactatccct   10860
acttctcatc cataatgaga ttgaagcatt agctggagca ataaggcaag agaagggata   10920
caaatgggaa atattaagt caaattgttt tcaattgaag attatattat cttatacccca   10980
atgacctcaa attttgacta gaaaaattgt agaaattatc ataatttca gcaaagtgtt   11040
atgatgcacc acatcctat tcttctcccc agcttctgct tgcttctctc ttcttgctct   11100
tcatcctttc tgtccttcca tctgcctgca ctcttgtctc aagactgagt gcagcgtgta   11160
actctcctgt gactgagtat ctcacaaaac gttctacctg ccaaacctgg atgagccctt   11220
tgtctttctg aagctatgag gctctctaca tagactcaag aaggaaatga cagggaggag   11280
gtaataatga agtggggaag gctgacatta gcattgctcc tgtgtggctc cttaatttct   11340
catacttcac actgagatgt tattaactgt gactcatagg tgaagaagcc agagctaagg   11400
ttctcatatt tgagtgttat agaatgagta gagcagtagt tctcaaacta tgggtcatga   11460
ctcctttatg ggtcaaacta cccttttcaca caggttgcat atcagatatc ctaatttat   11520
atacatatat atatgcatat gtatatatat atatttcaca acagtaggaa aattatttag   11580
taatcatttt atagttgtgg gtcatggcaa catgaggaac tgtattaaag ggttgcagca   11640
ttaggaatgt tgagacccac tgtaatagag aatgaggctt aaggcagggc tataaagccc   11700
aatgaccat gtgccttttc caacatttgc cacatggtaa gctctgtata gactttttaa   11760
agaacattgg tttgtaattt taaatggata agggtcttca ctgtctatca cccatctata   11820
taataaatac ataagttttg attccaccat ggattcaaat gcaaaaatcc tcaacctaag   11880
acatagcagt gaaacattga tgaccaaata ggaaatccat gtagagacct tctatcttct   11940
gatggctcca caggcaccat cttgcaacag agttctactt tgctaccagt aatgaataca   12000
gtgtctcaac tcctgccatt gaatcttcag gaagcccctg aaatgacttg tactacacca   12060
tttcttaaag acagaaaagc taagacttag agggaataaa tgtcatgcct gagatcatgc   12120
aaccaattaa gtccaacttg gcctgatcaa gaggcacaat tcaaaagcaa tgttgttcct   12180
tcactagctc ttgtgtatgg ttgctgattc cggaagcaaa gtatcagtga atatccctag   12240
tgggaaaaga cttggaaatc aaatgtctca tttaacagat taggagatga aacggtagac   12300
tctgtgtagt tgtacacccc tgtgatccca tcgctaggaa gactgaggca ggaagtcctc   12360
gagctcaaac cagcttaggc tacacagaga aactatctaa aaaataatta ctaactactt   12420
aataggagat tggatgttaa gatctggtca ctaagaggca gaattgagat tcgaagccag   12480
tatttctac ctggtatgtt ttaaattgca gtaaggatct aagtgtagat atataataat   12540
aagattctat tgatctctgc aacaacagag agtgttagat ttgtttggaa aaaaatatta   12600
tcagccaaca tcttctacca tttcagtata gcacagagta cccacccata tctccccacc   12660
catcccccat accagactgg ttattgattt tcatggtgac tggcctgaga agattaaaaa   12720
aagtaatgct acccttattgg gagtgtccca tggaccaaga tagcaactgt catagctacc   12780
gtcacactgc tttgatcaag aagacccttt gaggaactga aaacagaacc ttaggcacat   12840
ctgttgcttt cgctcccatc ctcctccaac agcctgggtg gtgcactcca cacccttttca   12900
agtttccaaa gcctcataca cctgctccct accccagcac ctggccaagg ctgtatccag   12960
cactgggatg aaaatgatac cccacctcca tcttgtttga tattactcta tctcaagccc   13020
```

-continued

```
caggttagtc cccagtccca atgcttttgc acagtcaaaa ctcaacttgg aataatcagt    13080
atccttgaag agttctgata tggtcactgg gcccatatac catgtaagac atgtggaaaa    13140
gatgtttcat ggggcccaga cacgttctag aagtacctga gagtggcaaa aaatagttgt    13200
gctaaatagt ttggccatct ttaggctgag agactaggaa atacagcgat ggactatatc    13260
agcattgcag atagttgtc  agtaaacacc ccacaaccca taacagaagt attctcttct    13320
ttctatatcc cttttccatc catgtagatg gctgtcttca tatttgttct agacggccgg    13380
cc                                                                   13382
```

<210> SEQ ID NO 96
<211> LENGTH: 4638
<212> TYPE: DNA
<213> ORGANISM: Artificial Sequence
<220> FEATURE:
<223> OTHER INFORMATION: pSELECT-IGKV1-39/J-Ck

<400> SEQUENCE: 96

```
gcggccgcaa taaaatatct ttattttcat tacatctgtg tgttggtttt ttgtgtgaat      60
cgtaactaac atacgctctc catcaaaaca aaacgaaaca aaacaaacta gcaaaatagg     120
ctgtccccag tgcaagtgca ggtgccagaa catttctcta tcgaaggatc tgcgatcgct     180
ccggtgcccg tcagtgggca gagcgcacat cgcccacagt ccccgagaag ttgggggggag    240 gggtcggcaa ttgaacgggt gcctagagaa ggtggcgcgg ggtaaactgg aaagtgatg     300 tcgtgtactg gctccgcctt tttcccgagg gtgggggaga accgtatata agtgcagtag    360
tcgccgtgaa cgttcttttt cgcaacgggt ttgccgccag aacacagctg aagcttcgag    420
gggctcgcat ctctccttca cgcgcccgcc gccctacctg aggccgccat ccacgccggt    480
tgagtcgcgt tctccgcct  cccgcctgtg gtgcctcctg aactgcgtcc gccgtctagg    540
taagtttaaa gctcaggtcg agaccgggcc tttgtccggc gctcccttgg agcctaccta    600
gactcagccg gctctccacg ctttgcctga ccctgcttgc tcaactctac gtctttgttt    660
cgttttctgt tctgcgccgt tacagatcca agctgtgacc ggcgcctacc tgagatcacc    720
ggcgtgtcga cgccaccatg gacatgagag tgcccgccca gctcctgggg ctcctgctac    780
tctggctccg aggtaaggat ggagaacact aggaatttac tcagccagtg tgctcagtac    840
tgactggaac ttcagggaag ttctctgata acatgattaa tagtaagaat atttgttttt    900
atgtttccaa tctcaggtgc cagatgtgac atccagatga cccagagccc cagcagcctg    960
agcgccagcg tgggcgacag agtgaccatc acctgcagag ccagcagag catcagcagc   1020 tacctgaact ggtatcagca gaagcccggc aaggccccca gctgctgat  ctacgccgcc   1080 agctccctgc agagcggcgt gcccagcaga ttcagcggca gcggctccgg caccgacttc   1140
accctgacca tcagcagcct gcagcccgag gacttcgcca cctactactg ccagcagagc   1200
tacagcaccc cccccacctt cggccagggc accaaggtgg agatcaagag agccgacgcc   1260
gctcccaccg tgtccatctt cccccccagc atggaacagc tgacctctgg cggagccacc   1320
gtggtctgct tcgtgaacaa cttctacccc agagacatca gcgtgaagtg aagatcgac    1380 ggcagcgagc agagggacgg cgtgctggac agcgtgaccg accaggacag caaggactcc   1440
acctacagca tgagcagcac cctgagcctg accaaggtgg agtacgagag gcacaacctg   1500
tacacctgcg aggtggtgca caagaccagc tccagccccg tggtcaagtc cttcaaccgg   1560
aacgagtgtt gagctagctg gccagacatg ataagataca ttgatgagtt tggacaaacc   1620
```

```
acaactagaa tgcagtgaaa aaaatgcttt atttgtgaaa tttgtgatgc tattgcttta    1680
tttgtaacca ttataagctg caataaacaa gttaacaaca acaattgcat tcattttatg    1740
tttcaggttc agggggaggt gtgggaggtt ttttaaagca agtaaaacct ctacaaatgt    1800
ggtatggaat tctaaaatac agcatagcaa aactttaacc tccaaatcaa gcctctactt    1860
gaatcctttt ctgagggatg aataaggcat aggcatcagg ggctgttgcc aatgtgcatt    1920
agctgtttgc agcctcacct tctttcatgg agtttaagat atagtgtatt ttcccaaggt    1980
ttgaactagc tcttcatttc tttatgtttt aaatgcactg acctcccaca ttcccttttt    2040
agtaaaatat tcagaaataa tttaaataca tcattgcaat gaaataaaat gttttttatt    2100
aggcagaatc cagatgctca aggcccttca taatatcccc cagtttagta gttggactta    2160
gggaacaaag gaacctttaa tagaaattgg acagcaagaa agcgagcttc tagcgaattc    2220
tcgactcatt cctttgccct cggacgagtg ctggggcgtc ggtttccact atcggcgagt    2280
acttctacac agccatcggt ccagacggcg cgcttctgc gggcgatttg tgtacgcccg     2340
acagtcccgg ctccggatcg gacgattgcg tcgcatcgac cctgcgccca agctgcatca    2400
tcgaaattgc cgtcaaccaa gctctgatag agttggtcaa gaccaatgcg gagcatatac    2460
gcccggagcc gcggcgatcc tgcaagctcc ggatgcctcc gctcgaagta gcgcgtctgc    2520
tgctccatac aagccaacca cggcctccag aagaagatgt tggcgaccctc gtattgggaa   2580 tccccgaaca tcgcctcgct ccagtcaatg accgctgtta gcggccatt gtccgtcagg     2640 acattgttgg agccgaaatc cgcgtgcacg aggtgccgga cttcggggca gtcctcggcc    2700
caaagcatca gctcatcgag agcctgcgcg acggacgcac tgacggtgtc gtccatcaca    2760
gtttgccagt gatacacatg gggatcagca atcgcgcata tgaaatcacg ccatgtagtg    2820
tattgaccga ttccttgcgg tccgaatggg ccgaacccgc tcgtctggct aagatcggcc    2880
gcagcgatcg catccatgag ctccgcgacg ggttgcagaa cagcgggcag ttcggtttca    2940
ggcaggtctt gcaacgtgac accctgtgca cggcgggaga tgcaataggt caggctctcg    3000
ctgaattccc caatgtcaag cacttccgga atcgggagcg cggccgatgc aaagtgccga    3060
taaacataac gatctttgta gaaaccatcg gcgcagctat ttacccgcag gacatatcca    3120
cgccctccta catcgaagct gaaagcacga gattcttcgc cctccgagag ctgcatcagg    3180
tcggagacgt tgtcgaactt ttcgatcaga aacttctcga cagacgtcgc ggtgagttca    3240 ggcttttca tgatggccct cctatagtga gtcgtattat actatgccga tatactatgc     3300
cgatgattaa ttgtcaaaac agcgtggatg gcgtctccag cttatctgac ggttcactaa    3360
acgagctctg cttatataga cctcccaccg tacacgccta ccgcccattt gcgtcaatgg    3420
ggcggagttg ttacgacatt ttggaaagtc ccgttgattt actagtcaaa acaaactccc    3480
attgacgtca atggggtgga gacttggaaa tccccgtgag tcaaaccgct atccacgccc    3540
attgatgtac tgccaaaacc gcatcatcat ggtaatagcg atgactaata cgtagatgta    3600
ctgccaagta ggaaagtccc ataaggtcat gtactgggca taatgccagg cgggccattt    3660
accgtcattg acgtcaatag ggggcgtact ggcatatga tacacttgat gtactgccaa     3720
gtgggcagtt taccgtaaat actccaccca ttgacgtcaa tggaaagtcc ctattggcgt    3780
tactatggga acatacgtca ttattgacgt caatgggcgg gggtcgttgg gcggtcagcc    3840
aggcgggcca tttaccgtaa gttatgtaac gcctgcaggt taattaagaa catgtgagca    3900
aaaggccagc aaaaggccag gaaccgtaaa aaggccgcgt tgctggcgtt tttccatagg    3960
ctccgccccc ctgacgagca tcacaaaaat cgacgctcaa gtcagaggtg gcgaaacccg    4020
```

```
acaggactat aaagatacca ggcgtttccc cctggaagct ccctcgtgcg ctctcctgtt    4080
ccgaccctgc cgcttaccgg atacctgtcc gcctttctcc cttcgggaag cgtggcgctt    4140
tctcatagct cacgctgtag gtatctcagt tcggtgtagg tcgttcgctc caagctgggc    4200
tgtgtgcacg aaccccccgt tcagcccgac cgctgcgcct tatccggtaa ctatcgtctt    4260
gagtccaacc cggtaagaca cgacttatcg ccactggcag cagccactgg taacaggatt    4320
agcagagcga ggtatgtagg cggtgctaca gagttcttga agtggtggcc taactacggc    4380
tacactagaa gaacagtatt tggtatctgc gctctgctga agccagttac cttcggaaaa    4440
agagttggta gctcttgatc cggcaaacaa accaccgctg gtagcggtgg ttttttttgtt    4500 tgcaagcagc agattacgcg cagaaaaaaa ggatctcaag aagatccttt gatcttttct    4560
acggggtctg acgctcagtg gaacgaaaac tcacgttaag ggattttggt catggctagt    4620
taattaacat ttaaatca                                                  4638

<210> SEQ ID NO 97
<211> LENGTH: 5349
<212> TYPE: DNA
<213> ORGANISM: Artificial Sequence
<220> FEATURE:
<223> OTHER INFORMATION: pSelect-IGVL2-14/J-Ck

<400> SEQUENCE: 97
gcggccgcaa taaatatctc ttattttcat tacatctgtg tgttggtttt ttgtgtgaat      60
cgtaactaac atacgctctc catcaaaaca aaacgaaaca aaacaaacta gcaaaatagg     120
ctgtccccag tgcaagtgca ggtgccagaa catttctcta tcgaaggatc tgcgatcgct     180
ccggtgcccg tcagtgggca gagcgcacat cgcccacagt ccccgagaag ttgggggggag    240 gggtcggcaa ttgaacgggt gcctagagaa ggtggcgcgg ggtaaactgg gaaagtgatg     300
tcgtgtactg gctccgcctt tttcccgagg gtggggggaga accgtatata agtgcagtag    360
tcgccgtgaa cgttcttttt cgcaacgggt ttgccgccag aacacagctg aagcttcgag     420
gggctcgcat ctctccttca cgcgcccgcc gccctacctg aggccgccat ccacgccggt     480
tgagtcgcgt tctgccgcct cccgcctgtg gtgcctcctg aactgcgtcc gccgtctagg     540
taagtttaaa gctcaggtcg agaccggggcc tttgtccggc gctcccttgg agcctaccta     600
gactcagccg gctctccacg ctttgcctga ccctgcttgc tcaactctac gtctttgttt     660
cgttttctgt tctgcgccgt tacagatcca agctgtgacc ggcgcctacc tgagatcacc     720
ggcgtgtcga cgccaccatg gacatgagag tgcccgccca gctcctgggg ctcctgctac     780
tctggctccg aggtaaggat ggagaacact aggaatttac tcagccagtg tgctcagtac     840
tgactggaac ttcagggaag ttctctgata acatgattaa tagtaagaat atttgttttt     900
atgtttccaa tctcaggtgc cagatgtcag tctgccctga cccagcccgc ctctgtgtct     960
ggcagccctg gccagagcat caccatcagc tgcaccggca ccagcagcga cgtgggcggc    1020
tacaactacg tgtcctggta tcagcagcac cccggcaagg cccccaagct gatgatctac    1080
gaggtgtcca acagacccag cggcgtgagc aacagattca gcggcagcaa gagcggcaac    1140
accgccagcc tgaccatcag cggcctccag gctgaggacg aggccgacta ctactgcagc    1200
agctacacca gcagctccac cctggtgttt ggcggcggaa caaagctgac cgtgctgaga    1260
gccgacgccg ctcccaccgt gtccatcttc cccccagca tggaacagct gacctctggc    1320
ggagccaccg tggtctgctt cgtgaacaac ttctacccca gagacatcag cgtgaagtgg    1380
```

```
aagatcgacg gcagcgagca gagggacggc gtgctggaca gcgtgaccga ccaggacagc    1440
aaggactcca cctacagcat gagcagcacc ctgagcctga ccaaggtgga gtacgagagg    1500
cacaacctgt acacctgcga ggtggtgcac aagaccagct ccagcccgt  ggtcaagtcc    1560 ttcaaccgga acgagtgttg agctagctgg ccagacatga taagatacat tgatgagttt    1620
ggacaaacca caactagact gactcagcct gcctccgtgt ctgggtctcc tggacagtcg    1680
atcaccatct cctgcactgg aaccagcagt gacgttggtg gttataacta tgtctcctgg    1740
taccaacagc acccaggcaa agcccccaaa ctcatgattt atgaggtcag taatcggccc    1800
tcagggtttt ctaatcgctt ctctggctcc aagtctggca acacggcctc cctgaccatc    1860
tctgggctcc aggctgagga cgaggctgat tattactgca gctcatatac aagcagcagc    1920
actctcgtat tcggcggagg gaccaagctg accgtcctac gggctgatgc tgcaccaact    1980
gtatccatct tcccaccatc catggaacag ttaacatctg gaggtgccac agtcgtgtgc    2040
ttcgtgaaca acttctatcc cagagacatc agtgtcaagt ggaagattga tggcagtgaa    2100
caacgagatg gtgtcctgga cagtgttact gatcaggaca gcaaagacag cacgtacagc    2160
atgagcagca ccctctcgtt gaccaaggtt gaatatgaaa ggcataacct ctatacctgt    2220
gaggttgttc ataagacatc atcctcaccc gtcgtcaaga gcttcaacag gaatgagtgt    2280
taggctagct ggccagacat gataagatac attgatgagt ttggacaaac cacaactaga    2340
atgcagtgaa aaaaatgctt tatttgtgaa atttgtgatg ctattgcttt atttgtaacc    2400
attataagct gcaataaaca agttaacaac aacaattgca ttcattttat gtttcaggtt    2460
cagggggagg tgtgggaggt tttttaaagc aagtaaaacc tctacaaatg tggtatggaa    2520
ttctaaaata cagcatagca aaactttaac ctccaaatca agcctctact gaatcctttt    2580
tctgagggat gaataaggca taggcatcag gggctgttgc caatgtgcat tagctgtttg    2640
cagcctcacc ttctttcatg gagtttaaga tatagtgtat tttcccaagg tttgaactag    2700
ctcttcattt ctttatgttt taaatgcact gacctcccac attccctttt tagtaaaata    2760
ttcagaaata atttaaatac atcattgcaa tgaaaataaa tgttttttat taggcagaat    2820
ccagatgctc aaggcccttc ataatatccc ccagtttagt agttggactt agggaacaaa    2880 ggaacctta  atagaaattg gacagcaaga aagcgagctt ctagcgaatt ctcgactcat    2940
tcctttgccc tcggacgagt gctggggcgt cggtttccac tatcggcgag tacttctaca    3000
cagccatcgg tccagacggc cgcgcttctg cgggcgattt gtgtacgccc gacagtcccg    3060
gctccggatc ggacgattgc gtcgcatcga ccctgcgccc aagctgcatc atcgaaattg    3120
ccgtcaacca agctctgata gagttggtca agaccaatgc ggagcatata cgcccggagc    3180
cgcggcgatc ctgcaagctc cggatgcctc cgctcgaagt agcgcgtctg ctgctccata    3240
caagccaacc acggcctcca agaagatgt  tggcgacct  cgtattggga atccccgaac    3300
atcgcctcgc tccagtcaat gaccgctgtt atgcggccat tgtccgtcag gacattgttg    3360
gagccgaaat ccgcgtgcac gaggtgccgg acttcggggc agtcctcggc ccaaagcatc    3420
agctcatcga gagcctgcgc gacggacgca ctgacggtgt cgtccatcac agtttgccag    3480
tgatacacat ggggatcagc aatcgcgcat atgaaatcac gccatgtagt gtattgaccg    3540
attccttgcg gtccgaatgg gccgaacccg ctcgtctggc taagatcggc cgcagcgatc    3600
gcatccatga gctccgcgac gggttgcaga acagcgggca gttcggtttc aggcaggtct    3660
tgcaacgtga caccctgtgc acggcgggag atgcaatagg tcaggctctc gctgaattcc    3720
ccaatgtcaa gcacttccgg aatcgggagc gcggccgatg caaagtgccg ataaacataa    3780
```

```
cgatctttgt agaaaccatc ggcgcagcta tttacccgca ggacatatcc acgccctcct   3840
acatcgaagc tgaaagcacg agattcttcg ccctccgaga gctgcatcag gtcggagacg   3900
ctgtcgaact tttcgatcag aaacttctcg acagacgtcg cggtgagttc aggcttttc    3960 atgatggccc tcctatagtg agtcgtatta tactatgccg atatactatg ccgatgatta   4020
attgtcaaaa cagcgtggat ggcgtctcca gcttatctga cggttcacta aacgagctct   4080
gcttatatag acctcccacc gtacacgcct accgcccatt tgcgtcaatg gggcggagtt   4140
gttacgacat tttggaaagt cccgttgatt tactagtcaa aacaaactcc cattgacgtc   4200 aatgggtgg agacttggaa atccccgtga gtcaaaccgc tatccacgcc cattgatgta    4260
ctgccaaaac cgcatcatca tggtaatagc gatgactaat acgtagatgt actgccaagt   4320
aggaaagtcc cataaggtca tgtactgggc ataatgccag gcgggccatt taccgtcatt   4380
gacgtcaata gggggcgtac ttggcatatg atacacttga tgtactgcca agtgggcagt   4440
ttaccgtaaa tactccaccc attgacgtca atggaaagtc cctattggcg ttactatggg   4500
aacatacgtc attattgacg tcaatgggcg ggggtcgttg ggcggtcagc caggcgggcc   4560
atttaccgta agttatgtaa cgcctgcagg ttaattaaga acatgtgagc aaaaggccag   4620
caaaaggcca ggaaccgtaa aaaggccgcg ttgctggcgt ttttccatag gctccgcccc   4680
cctgacgagc atcacaaaaa tcgacgctca agtcagaggt ggcgaaaccc gacaggacta   4740
taaagatacc aggcgtttcc ccctggaagc tccctcgtgc gctctcctgt tccgaccctg   4800
ccgcttaccg gatacctgtc cgcctttctc ccttcgggaa gcgtggcgct ttctcatagc   4860
tcacgctgta ggtatctcag ttcggtgtag gtcgttcgct ccaagctggg ctgtgtgcac   4920
gaaccccccg ttcagcccga ccgctgcgcc ttatccggta actatcgtct tgagtccaac   4980
ccggtaagac acgacttatc gccactggca gcagccactg gtaacaggat tagcagagcg   5040
aggtatgtag gcggtgctac agagttcttg aagtggtggc ctaactacgg ctacactaga   5100
agaacagtat ttggtatctg cgctctgctg aagccagtta ccttcggaaa aagagttggt   5160
agctcttgat ccggcaaaca aaccaccgct ggtagcggtg gtttttttgt ttgcaagcag   5220
cagattacgc gcagaaaaaa aggatctcaa gaagatcctt tgatctttc tacggggtct    5280 gacgctcagt ggaacgaaaa ctcacgttaa gggattttgg tcatggctag ttaattaaca   5340
tttaaatca                                                           5349

<210> SEQ ID NO 98
<211> LENGTH: 6772
<212> TYPE: DNA
<213> ORGANISM: Artificial Sequence
<220> FEATURE:
<223> OTHER INFORMATION: MV1043

<400> SEQUENCE: 98
cttgatttgg gtgatggttc acgtagtggg ccatcgccct gatagacggt ttttcgccct     60
ttgacgttgg agtccacgtt ctttaatagt ggactcttgt tccaaactgg aacaacactc    120
aactctatct cgggctattc ttttgattta tagggatttt gccgatttc ggtctattgg     180 ttaaaaaatg agctgattta acaaaaattt aacgcgaatt ttaacaaaat attaacgttt    240 acaatttat ggtgcagtct cagtacaatc tgctctgatg ccgcatagtt aagccagccc     300
cgacacccgc caacacccgc tgacgcgccc tgacgggctt gtctgctccc ggcatccgct    360
tacagacaag ctgtgaccgt ctccgggagc tgcatgtgtc agaggttttc accgtcatca    420
```

```
ccgaaacgcg cgagacgaaa gggcctcgtg atacgcctat ttttataggt taatgtcatg    480
ataataatgg tttcttagac gtcaggtggc acttttcggg gaaatgtgcg cggaacccct    540
atttgtttat ttttctaaat acattcaaat atgtatccgc tcatgagaca ataaccctga    600
taaatgcttc aataatattg aaaaaggaag agtatgagta ttcaacattt ccgtgtcgcc    660
cttattccct tttttgcggc attttgcctt cctgttttttg ctcacccaga aacgctggtg    720
aaagtaaaag atgctgaaga tcagttgggt gcccgagtgg gttacatcga actggatctc    780
aacagcggta agatccttga gagttttcgc cccgaagaac gttttccaat gatgagcact    840
tttaaagttc tgctatgtgg cgcggtatta tcccgtattg acgccgggca agagcaactc    900
ggtcgccgca tacactattc tcagaatgac ttggttgagt actcaccagt cacagaaaag    960
catcttacgg atggcatgac agtaagagaa ttatgcagtg ctgccataac catgagtgat   1020
aacactgcgg ccaacttact tctgacaacg atcggaggac cgaaggagct aaccgctttt   1080
ttgcacaaca tgggggatca tgtaactcgc cttgatcgtt gggaaccgga gctgaatgaa   1140
gccataccaa acgacgagcg tgacaccacg atgcctgtag caatggcaac aacgttgcgc   1200
aaactattaa ctggcgaact acttactcta gcttcccggc aacaattaat agactggatg   1260
gaggcggata aagttgcagg accacttctg cgctcggccc ttccggctgg ctggtttatt   1320
gctgataaat ctggagccgg tgagcgtggg tctcgcggta tcattgcagc actggggcca   1380
gatggtaagc cctcccgtat cgtagttatc tacacgacgg ggagtcaggc aactatggat   1440
gaacgaaata gacagatcgc tgagataggt gcctcactga ttaagcattg gtaactgtca   1500
gaccaagttt actcatatat actttagatt gatttaaaac ttcatttttta atttaaaagg   1560
atctaggtga agatccttttt tgataatctc atgaccaaaa tcccttaacg tgagttttcg   1620
ttccactgag cgtcagaccc cgtagaaaag atcaaaggat cttcttgaga tccttttttt   1680
ctgcgcgtaa tctgctgctt gcaaacaaaa aaaccaccgc taccagcggt ggtttgtttg   1740
ccggatcaag agctaccaac tcttttttccg aaggtaactg gcttcagcag agcgcagata   1800
ccaaatactg ttcttctagt gtagccgtag ttaggccacc acttcaagaa ctctgtagca   1860
ccgcctacat acctcgctct gctaatcctg ttaccagtgg ctgctgccag tggcgataag   1920
tcgtgtctta ccgggttgga ctcaagacga tagttaccgg ataaggcgca gcggtcgggc   1980
tgaacggggg gttcgtgcat acagcccagc ttggagcgaa cgacctacac cgaactgaga   2040
tacctacagc gtgagctatg agaaagcgcc acgcttcccg aagggagaaa ggcggacagg   2100
tatccggtaa gcggcagggt cggaacagga gagcgcacga gggagcttcc agggggaaac   2160
gcctggtatc tttatagtcc tgtcgggttt cgccacctct gacttgagcg tcgatttttg   2220
tgatgctcgt cagggggggcg gagcctatgg aaaaacgcca gcaacgcggc ctttttacgg   2280
ttcctggcct tttgctggcc ttttgctcac atgttctttc ctgcgttatc ccctgattct   2340
gtggataacc gtattaccgc ctttgagtga gctgataccg ctcgccgcag ccgaacgacc   2400
gagcgcagcg agtcagtgag cgaggaagcg gaagagcgcc caatacgcaa accgcctctc   2460
cccgcgcgtt ggccgattca ttaatgcagc tggcacgaca ggtttcccga ctggaaagcg   2520
ggcagtgagc gcaacgcaat taatgtgagt tagctcactc attaggcacc ccaggcttta   2580
cactttatgc ttccggctcg tatgttgtgt ggaattgtga gcggataaca atttcacaca   2640
ggaaacagct atgaccatga ttacgccaag ctttggagcc ttttttttgg agattttcaa   2700
cgtgaaaaaa ttattattcg caattccttt agttgttcct ttctattctc acagtgcaca   2760
gatccaaatg acccagtctc catcctccct gtctgcatct gtaggagaca gagtcaccat   2820
```

```
cacttgccgg gcaagtcaga gcattagcag ctacttaaat tggtatcagc agaaaccagg    2880
gaaagcccct aagctcctga tctatgctgc atccagtttg caaagtgggg tcccatcaag    2940
gttcagtggc agtggatctg ggacagattt cactctcacc atcagcagtc tgcaacctga    3000
agattttgca acttactact gtcaacagag ttacagtacc cctccaacgt tcggccaagg    3060
gaccaagctc gagatcaaac gtactgtggc tgcaccatct gtcttcatct tcccgccatc    3120
tgatgagcag ttgaaatctg gaactgcctc tgttgtgtgc ctgctgaata acttctatcc    3180
cagagaggcc aaagtacagt ggaaggtgga taacgccctc caatcgggta actcccagga    3240
gagtgtcaca gagcaggaca gcaaggacag cacctacagc ctcagcagca ccctgacgct    3300
gagcaaagca gactacgaga acacaaagt ctacgcctgc gaagtcaccc atcagggcct    3360
gagctcgccc gtcacaaaga gcttcaacag gggagagtgt tagtaaggcg cgccaattct    3420
atttcaagga cagtcataa tgaaatacc tattgcctac ggcagccgct ggattgttat    3480
tactcgcggc ccagccggcc atggcgatgc ctgcttgccg aatatcatgg tggaaaatgg    3540
ccgcttttct ggattcatcg actgtggccg gctgggtgtg gcggaccgct atcaggacat    3600
agcgttggct acccgtgata ttgctgaaga gcttggcggc gaatgggctg accgcttcct    3660
cgtgctttac ggtatcgccg ctcccgattc gcagcgcatc gccttctatc gccttcttga    3720
cgagttcttc tgagcgggac tctggggttc ggtgctacga gatttcgatt ccaccgccgc    3780
cttctatgaa aggttgggct tcggaatcgt tttccgggac gccggctgga tgatcctcca    3840
gcgcggggat ctcatgctgg agttcttcgc ccaccccaac ttgtttattg cagcttataa    3900
tggttacaaa taaagcaata gcatcacaaa tttcacaaat aaagcatttt tttcactgca    3960
ttctagttgt ggtttgtcca aactcatcaa tgtatcttat catgtctgta taccgtcgac    4020
ctctagctag agcttggcgt aatcatggtc atagctgttt cctgtgtgaa attgttatcc    4080
gctcacaatt ccacacaaca tacgagccgg aagcataaag tgtaaagcct ggggtgccta    4140
atgagtgagc taactcacat taattgcgtt gcgctcactg cccgctttcc agtcgggaaa    4200
cctgtcgtgc cagaattgca tgaagaatct gcttagggtt aggcgttttg cgctgcttcg    4260
ctaggtggtc aatattggcc attagccata ttattcattg gttatatagc ataaatcaat    4320
attggctatt ggccattgca tacgttgtat ccatatcata atatgtacat ttatattggc    4380
tcatgtccaa cattaccgcc atgttgacat tgattattga ctagttatta atagtaatca    4440
attacggggt cattagttca tagcccatat atggagttcc gcgttacata acttacggta    4500
aatggcccgc ctggctgacc gcccaacgac ccccgcccat tgacgtcaat aatgacgtat    4560
gttcccatag taacgccaat agggactttc cattgacgtc aatgggtgga gtatttacgg    4620
taaactgccc acttggcagt acatcaagtg tatcatatgc caagtacgcc ccctattgac    4680
gtcaatgacg gtcaccgtct caagcgcctc caccaagggc ccatcggtct tccccctggc    4740
accctcctcc aagagcacct ctgggggcac agcggccctg gctgcctgg tcaaggacta    4800 cttccccgaa ccggtgacgg tgtcgtggaa ctcaggcgcc ctgaccagcg gcgtccacac    4860
cttcccggct gtcctacagt cctcaggact ctactccctc agcagcgtag tgaccgtgcc    4920
ctccagcagc ttgggcaccc agacctacat ctgcaacgtg aatcacaagc ccagcaacac    4980
caaggtggac aagaaagttg agcccaaatc ttgtgcggcc gcacatcatc atcaccatca    5040
cggggccgca gaacaaaaac tcatctcaga agaggatctg aatggggccg catagactgt    5100
tgaaagttgt ttagcaaaac ctcatacaga aaattcattt actaacgtct ggaaagacga    5160
```

| | |
|---|---:|
| caaaacttta gatcgttacg ctaactatga gggctgtctg tggaatgcta caggcgttgt | 5220 |
| ggtttgtact ggtgacgaaa ctcagtgtta cggtacatgg gttcctattg gcttgctat | 5280 |
| ccctgaaaat gagggtggtg gctctgaggg tggcggttct gagggtggcg gttctgaggg | 5340 |
| tggcggtact aaacctcctg agtacggtga tacacctatt ccgggctata cttatatcaa | 5400 |
| ccctctcgac ggcacttatc cgcctggtac tgagcaaaac cccgctaatc ctaatccttc | 5460 |
| tcttgaggag tctcagcctc ttaatacttt catgtttcag aataataggt tccgaaatag | 5520 |
| gcagggtgca ttaactgttt atacgggcac tgttactcaa ggcactgacc ccgttaaaac | 5580 |
| ttattaccag tacactcctg tatcatcaaa agccatgtat gacgcttact ggaacgtaa | 5640 |
| attcagagac tgcgctttcc attctggctt taatgaggat ccattcgttt gtgaatatca | 5700 |
| aggccaatcg tctgacctgc ctcaacctcc tgtcaatgct ggcggcggct ctggtggtgg | 5760 |
| ttctggtggc ggctctgagg gtggcggctc tgagggtggc ggctctgagg gtggcggttc | 5820 |
| tgagggtggc ggctctgagg gtggcggttc cggtggcggc tccggttccg gtgattttga | 5880 |
| ttatgaaaaa atggcaaacg ctaataaggg ggctatgacc gaaaatgccg atgaaaacgc | 5940 |
| gctacagtct gacgctaaag gcaaacttga ttctgtcgct actgattacg gtgctgctat | 6000 |
| cgatggtttc attggtgacg tttccggcct tgctaatggt aatggtgcta ctggtgattt | 6060 |
| tgctggctct aattcccaaa tggctcaagt cggtgacggt gataattcac ctttaatgaa | 6120 |
| taatttccgt caatatttac cttctttgcc tcagtcggtt gaatgtcgcc cttatgtctt | 6180 |
| tggcgctggt aaaccatatg aattttctat tgattgtgac aaaataaact tattccgtgg | 6240 |
| tgtctttgcg tttcttttat atgttgccac ctttatgtat gtattttcga cgtttgctaa | 6300 |
| catactgcgt aataaggagt cttaataaga attcactggc cgtcgtttta caacgtcgtg | 6360 |
| actgggaaaa ccctggcgtt acccaactta atcgccttgc agcacatccc ctttcgcca | 6420 |
| gctggcgtaa tagcgaagag gcccgcaccg atcgcccttc ccaacagttg cgcagcctga | 6480 |
| atggcgaatg cgcctgatg cggtatttc tccttacgca tctgtgcggt atttcacacc | 6540 |
| gcatacgtca aagcaaccat agtacgcgcc ctgtagcggc gcattaagcg cggcgggtgt | 6600 |
| ggtggttacg cgcagcgtga ccgctacact tgccagcgcc ttagcgcccg ctcctttcgc | 6660 |
| tttcttccct tcctttctcg ccacgttcgc cggctttccc cgtcaagctc taaatcgggg | 6720 |
| gctcccttta gggttccgat ttagtgcttt acggcacctc gaccccaaaa aa | 6772 |

<210> SEQ ID NO 99
<211> LENGTH: 10293
<212> TYPE: DNA
<213> ORGANISM: Artificial Sequence
<220> FEATURE:
<223> OTHER INFORMATION: MV1057

<400> SEQUENCE: 99

| | |
|---|---:|
| tactcttcct ttttcaatat tattgaagca tttatcaggg ttattgtctc atgagcggat | 60 |
| acatatttga atgtatttag aaaaataaac aaatagggg tccgcgcaca tttccccgaa | 120 |
| aagtgccacc tgacgtcgac ggatcgggag atctcccgat cccctatggt gcactctcag | 180 |
| tacaatctgc tctgatgccg catagttaag ccagtatctg ctccctgctt gtgtgttgga | 240 |
| ggtcgctgag tagtgcgcga gcaaaattta agctacaaca aggcaaggct tgaccgacaa | 300 |
| ttgcatgaag aatctgctta gggttaggcg ttttgcgctg cttcgctagg tggtcaatat | 360 |
| tggccattag ccatattatt cattggttat atagcataaa tcaatattgg ctattggcca | 420 |
| ttgcatacgt tgtatccata tcataatatg tacatttata ttggctcatg tccaacatta | 480 |

```
ccgccatgtt gacattgatt attgactagt tattaatagt aatcaattac ggggtcatta      540
gttcatagcc catatatgga gttccgcgtt acataactta cggtaaatgg cccgcctggc      600
tgaccgccca acgaccccg cccattgacg tcaataatga cgtatgttcc catagtaacg      660
ccaataggga ctttccattg acgtcaatgg gtggagtatt tacggtaaac tgcccacttg      720
gcagtacatc aagtgtatca tatgccaagt acgccccta ttgacgtcaa tgacggtaaa      780
tggcccgcct ggcattatgc ccagtacatg accttatggg actttcctac ttggcagtac      840
atctacgtat tagtcatcgc tattaccatg gtgatgcggt tttggcagta catcaatggg      900
cgtggatagc ggtttgactc acggggattt ccaagtctcc accccattga cgtcaatggg      960
agtttgtttt ggcaccaaaa tcaacgggac tttccaaaat gtcgtaacaa ctccgcccca     1020
ttgacgcaaa tgggcggtag gcgtgtacgg tgggaggtct atataagcag agctcgttta     1080
gtgaaccgtc agatcgcctg gagacgccat ccacgctgtt ttgacctcca tagaagacac     1140
cgggaccgat ccagcctccg cggccgggaa cggtgcattg gaagcttggt accggtgaat     1200
tggccggccc gcgccgtcga ggttatcgat ccgaccgacg cgttcgcgag aggccgcaat     1260
tccctagcca ccatgggatg gagctgtatc atcctcttct tggtactgct gctgccccag     1320
ccggccatgg ggcggagaat gggcggaact gggcggagtt aggggcggga tgggcggagt     1380
taggggcggg actatggttg ctgactaatt gagatgcgga tccgctggca cgacaggttt     1440
cccgactgga aagcgggcag tgagcgcaac gcaattaatg tgagttagct cactcattag     1500
gcacccagg ctttacactt tatgcttccg gctcgtatgt tgtgtggaat tgtgagcgga     1560
taacaatttc acacaggaaa cagctatgac catgattacg ccaagcttgg gctgcaggtt     1620
ctttccgcct cagaagccat agagcccacc gcatccccag catgcctgct attgtcttcc     1680
caatcctccc ccttgctgtc ctgccccacc ccaccccca gaatagaatg acacctactc     1740
agacaatgcg atgcaatttc ctcattttat taggaaagga cagtgggagt ggaccttcc     1800
agggtcaagg aaggcacggg ggaggggcaa acaacagatg gctggcaact agaaggcaca     1860
gtcgaggctg atcagcgagc tctagatcat cgatgcatgg ggtcgtgcgc tcctttcggt     1920
cgggcgctgc gggtcgtggg gcgggcgtca ggcaccgggc ttgcgggtca tgcaccaggt     1980
gcgcggtcct tcgggcacct cgacgtcggc ggtgacggtg aagccgagcc gctcgtagaa     2040
ggggaggttg cggggcgcgg aggtctccag gaaggcgggc accccggcgc gctcggccgc     2100
ctccactccg gggagcacga cggcgctgcc cagacccttg ccctggtggt cgggcgagac     2160
gccgacggtg gccaggaacc acgcgggctc cttgggccgg tgcggcgcca ggaggccttc     2220
catctgttgc tgcgcggcca gccgggaacc gctcaactcg ccatgcgcg gccgatctc     2280
ggcgaacacc gccccgcttc gacgctctcc ggcgtggtc cagaccgcca ccgcggcgcc     2340
gtcgtccgcg acccacacct tgccgatgtc gagcccgacg cgcgtgagga agagttcttg     2400
cagctcggtc accgtctcca gtgctagcac caagggccca tcggtcttcc ccctggcacc     2460
ctcctccaag agcacctctg ggggcacagc ggccctgggc tgcctggtca aggactactt     2520
ccccgaaccg gtgacggtgt cgtggaactc aggcgccctg accagcggcg tgcacacctt     2580
cccggctgtc ctacagtcct caggactcta ctccctcagc agcgtcgtga ccgtgccctc     2640
cagcagcttg ggcacccaga cctacatctg caacgtgaat cacaagccca gcaacaccaa     2700
ggtggacaag agagttggtg agaggccagc acagggaggg agggtgtctg ctggaagcca     2760
ggctcagcgc tcctgcctgg acgcatcccg gctatgcagt cccagtccag ggcagcaagg     2820
```

| | |
|---|---|
| caggccccgt ctgcctcttc acccggaggc ctctgcccgc cccactcatg ctcagggaga | 2880 |
| gggtcttctg gcttttccc caggctctgg gcaggcacag gctaggtgcc cctaacccag | 2940 |
| gccctgcaca caaaggggca ggtgctgggc tcagacctgc aagagccat atccgggagg | 3000 |
| accctgcccc tgacctaagc ccaccccaaa ggccaaactc tccactccct cagctcggac | 3060 |
| accttctctc ctcccagatt ccagtaactc ccaatcttct ctctgcagag cccaaatctt | 3120 |
| gtgacaaaac tcacacatgc ccaccgtgcc cagcacctga actcctgggg ggaccgtcag | 3180 |
| tcttcctctt ccccccaaaa cccaaggaca ccctcatgat ctcccggacc cctgaggtca | 3240 |
| catgcgtggt ggtggacgtg agccacgaag accctgaggt caagttcaac tggtacgtgg | 3300 |
| acggcgtgga ggtgcataat gccaagacaa agccgcggga ggagcagtac aacagcacgt | 3360 |
| accgtgtggt cagcgtcctc accgtcctgc accaggactg gctgaatggc aaggagtaca | 3420 |
| agtgcaaggt ctccaacaaa gccctcccag cccccatcga gaaaaccatc tccaaagcca | 3480 |
| aagggcagcc ccgagaacca caggtgtaca ccctgccccc atcccgggag gagatgacca | 3540 |
| agaaccaggt cagcctgacc tgcctggtca aaggcttcta tcccagcgac atcgccgtgg | 3600 |
| agtgggagag caatgggcag ccggagaaca actacaagac cacgcctccc gtgctggact | 3660 |
| ccgacggctc cttcttcctc tatagcaagc tcaccgtgga caagagcagg tggcagcagg | 3720 |
| ggaacgtctt ctcatgctcc gtgatgcatg aggctctgca caaccactac acgcagaaga | 3780 |
| gcctctccct gtctccgggt aaatgagttt aacggatctt aattaatccg agctcggtac | 3840 |
| caagcttaag tttaaaccgc tgatcagcct cgactgtgcc ttctagttgc cagccatctg | 3900 |
| ttgtttgccc ctcccccgtg ccttccttga ccctggaagg tgccactccc actgtccttt | 3960 |
| cctaataaaa tgaggaaatt gcatcgcatt gtctgagtag gtgtcattct attctggggg | 4020 |
| gtggggtggg gcaggacagc aagggggagg attgggaaga caatagcagg catgctgggg | 4080 |
| atgcggtggg ctctatggct tctgaggcgg aaagaaccag ctggggctct aggggggtatc | 4140 |
| cccacgcgcc ctgtagcggc gcattaagcg cggcgggtgt ggtggttacg cgcagcgtga | 4200 |
| ccgctacact tgccagcgcc tagcgcccgc tcctttcgct ttcttccctt cctttctcgc | 4260 |
| cacgttcgcc ggctttcccc gtcaagctct aaatcggggg ctccctttag ggttccgatt | 4320 |
| tagtgcttta cggcacctcg accccaaaaa acttgattag ggtgatggtt cacgtagtgg | 4380 |
| gccatcgccc tgatagacgg ttttcgccc tttgacgttg gagtccacgt tctttaatag | 4440 |
| tggactcttg ttccaaactg gaacaacact caaccctatc tcggtctatt cttttgattt | 4500 |
| ataagggatt ttgccgattt cggcctattg gttaaaaat gagctgattt aacaaaaatt | 4560 |
| taacgcgaat taattctgtg gaatgtgtgt cagttagggt gtggaaagtc cccaggctcc | 4620 |
| ccagcaggca gaagtatgca aagcatgcat ctcaattagt cagcaaccag gtgtggaaag | 4680 |
| tccccaggct ccccagcagg cagaagtatg caaagcatgc atctcaatta gtcagcaacc | 4740 |
| atagtcccgc ccctaactcc gcccatcccg cccctaactc cgcccagttc cgcccattct | 4800 |
| ccgccccatg gctgactaat ttttttatt tatgcagagg ccgaggccgc ctctgcctct | 4860 |
| gagctattcc agaagtagtg aggaggcttt tttggaggcc taggcttttg caaaaagctc | 4920 |
| ccgggagctt ggatatccat tttcggatct gatcaagaga caggatgagg atcgtttcgc | 4980 |
| atgattgaac aagatggatt gcacgcaggt tctccggccg cttgggtgga ggctattc | 5040 |
| ggctatgact gggcacaaca gacaatcggc tgctctgatg ccgccgtgtt ccggctgtca | 5100 |
| gcgcaggggc gcccggttct ttttgtcaag accgacctgt ccggtgccct gaatgaactg | 5160 |
| caggacgagg cagcgcggct atcgtggctg gccacgacgg gcgttccttg cgcagctgtg | 5220 |

```
ctcgacgttg tcactgaagc gggaagggac tggctgctat tgggcgaagt gccggggcag    5280
gatctcctgt catctcacct tgctcctgcc gagaaagtat ccatcatggc tgatgcaatg    5340
cggcggctgc atacgcttga tccggctacc tgcccattcg accaccaagc gaaacatcgc    5400
atcgagcgag cacgtactcg gatggaagcc ggtcttgtcg atcaggatga tctggacgaa    5460
gagcatcagg ggctcgcgcc agccgaactg ttcgccaggc tcaaggcgcg catgcccgac    5520
ggcgaggatc tcgtcgtgac ccatggcgat gcctgcttgc cgaatatcat ggtggaaaat    5580
ggccgctttt ctggattcat cgactgtggc cggctgggtg tggcggaccg ctatcaggac    5640
atagcgttgg ctacccgtga tattgctgaa gagcttggcg gcgaatgggc tgaccgcttc    5700
ctcgtgcttt acggtatcgc cgctcccgat tcgcagcgca tcgccttcta tcgccttctt    5760
gacgagttct tctgagcggg actctggggt tcggtgctac gagatttcga ttccaccgcc    5820
gccttctatg aaaggttggg cttcggaatc gttttccggg acgccggctg atgatcctc    5880 cagcgcgggg atctcatgct ggagttcttc gcccaccccca acttgtttat tgcagcttat    5940
aatggttaca aataaagcaa tagcatcaca aatttcacaa ataaagcatt ttttcactg    6000 cattctagtt gtggtttgtc caaactcatc aatgtatctt atcatgtctg tataccgtcg    6060
acctctagct agagcttggc gtaatcatgg tcatagctgt ttcctgtgtg aaattgttat    6120
ccgctcacaa ttccacacaa catacgagcc ggaagcataa agtgtaaagc ctggggtgcc    6180
taatgagtga gctaactcac attaattgcg ttgcgctcac tgcccgcttt ccagtcggga    6240
aacctgtcgt gccagaattg catgaagaat ctgcttaggg ttaggcgttt tgcgctgctt    6300
cgctaggtgg tcaatattgg ccattagcca tattattcat tggttatata gcataaatca    6360
atattggcta ttggccattg catacgttgt atccatatca taatatgtac atttatattg    6420
gctcatgtcc aacattaccg ccatgttgac attgattatt gactagttat taatagtaat    6480
caattacggg gtcattagtt catagcccat atatggagtt ccgcgttaca taacttacgg    6540
taaatggccc gcctggctga ccgcccaacg acccccgccc attgacgtca ataatgacgt    6600
atgttcccat agtaacgcca atagggactt tccattgacg tcaatgggtg gagtatttac    6660
ggtaaactgc ccacttggca gtacatcaag tgtatcatat gccaagtacg ccccctattg    6720
acgtcaatga cggtaaatgg cccgcctggc attatgccca gtacatgacc ttatgggact    6780
ttcctacttg gcagtacatc tacgtattag tcatcgctat taccatggtg atgcggtttt    6840
ggcagtacat caatgggcgt ggatagcggt ttgactcacg gggatttcca agtctccacc    6900
ccattgacgt caatgggagt ttgttttggc accaaaatca acgggacttt ccaaaatgtc    6960
gtaacaactc cgccccattg acgcaaatgg gcggtaggcg tgtacggtgg gaggtctata    7020
taagcagagc tcgtttagtg aaccgtcaga tcgcctggag acgccatcca cgctgttttg    7080
acctccatag aagacaccgg gaccgatcca gcctccgcgg ccgggaacgg tgcattggaa    7140
gcttggtacc ggtgaattag gcgcgccgtc gaggttatcg atccgaccga cgcgttcgcg    7200
agaggccgca attccctagc caccatggca tgccctggct tcctgtgggc acttgtgatc    7260
tccacctgtc ttgaattctc catggctgac atccagatga cccagtctcc atcctccctg    7320
tctgcatctg taggagacag agtcaccatc acttgccggg caagtcagag cattagcagc    7380
tacttaaatt ggtatcagca gaaaccaggg aaagccccta agctcctgat ctatgctgca    7440
tccagtttgc aaagtggggt cccatcaagg ttcagtggca gtggatctgg gacagatttc    7500
actctcacca tcagcagtct gcaacctgaa gattttgcaa cttactactg tcaacagagt    7560
```

```
tacagtaccc ctccaacgtt cggccaaggg accaaggtgg agatcaaacg taagtgcact   7620
ttgcggccgc taggaagaaa ctcaaaacat caagatttta aatacgcttc ttggtctcct   7680
tgctataatt atctgggata agcatgctgt tttctgtctg tccctaacat gccctgtgat   7740
tatccgcaaa caacacaccc aagggcagaa ctttgttact aaacaccat cctgtttgct    7800
tctttcctca ggaactgtgg ctgcaccatc tgtcttcatc ttcccgccat ctgatgagca   7860
gttgaaatct ggaactgcct ctgttgtgtg cctgctgaat aacttctatc ccagagaggc   7920
caaagtacag tggaaggtgg ataacgccct ccaatcgggt aactcccagg agagtgtcac   7980
agagcaggac agcaaggaca gcacctacag cctcagcagc accctgacgc tgagcaaagc   8040
agactacgag aaacacaaag tctacgcctg cgaagtcacc catcagggcc tgagctcgcc   8100
cgtcacaaag agcttcaaca ggggagagtg ttaggtttaa cggatccgag ctcggtacca   8160
agctcaagtt taaaccgctg atcagcctcg actgtgcctt ctagttgcca gccatctgtt   8220
gtttgcccct cccccgtgcc ttccttgacc ctggaaggtg ccactcccac tgtcctttcc   8280
taataaaatg aggaaattgc atcgcattgt ctgagtaggt gtcattctat tctggggggt   8340
ggggtggggc aggacagcaa gggggaggat tgggaagaca atagcaggca tgctggggat   8400
gcggtgggct ctatggcttc tgaggcggaa agaaccagct gcattaatga atcggccaac   8460
gcgcggggag aggcggtttg cgtattgggc gctcttccgc ttcctcgctc actgactcgc   8520
tgcgctcggt cgttcggctg cggcgagcgg tatcagctca ctcaaaggcg gtaatacggt   8580
tatccacaga atcaggggat aacgcaggaa agaacatgtg agcaaaaggc cagcaaaagg   8640
ccaggaaccg taaaaaggcc gcgttgctgg cgttttttcca taggctccgc cccccctgacg   8700
agcatcacaa aaatcgacgc tcaagtcaga ggtggcgaaa cccgacagga ctataaagat   8760
accaggcgtt tcccctgga agctccctcg tgcgctctcc tgttccgacc ctgccgctta    8820
ccggatacct gtccgccttt ctcccttcgg gaagcgtggc gctttctcat agctcacgct   8880
gtaggtatct cagttcggtg taggtcgttc gctccaagct gggctgtgtg cacgaacccc   8940
ccgttcagcc cgaccgctgc gccttatccg gtaactatcg tcttgagtcc aacccggtaa   9000
gacacgactt atcgccactg gcagcagcca ctggtaacag gattagcaga gcgaggtatg   9060
taggcggtgc tacagagttc ttgaagtggt ggcctaacta cggctacact agaagaacag   9120
tatttggtat ctgcgctctg ctgaagccag ttaccttcgg aaaaagagtt ggtagctctt   9180
gatccggcaa acaaaccacc gctggtagcg gtggtttttt tgtttgcaag cagcagatta   9240
cgcgcagaaa aaaaggatct caagaagatc ctttgatctt ttctacgggg tctgacgctc   9300
agtggaacga aaactcacgt taagggattt tggtcatgag attatcaaaa aggatcttca   9360
cctagatcct tttaaattaa aaatgaagtt ttaaatcaat ctaaagtata tatgagtaaa   9420
cttggtctga cagttaccaa tgcttaatca gtgaggcacc tatctcagcg atctgtctat   9480
ttcgttcatc catagttgcc tgactccccg tcgtgtagat aactacgata cgggagggct   9540
taccatctgg ccccagtgct gcaatgatac cgcgagaccc acgctcaccg gctccagatt   9600
tatcagcaat aaaccagcca gccggaaggg ccgagcgcag aagtggtcct gcaactttat   9660
ccgcctccat ccagtctatt aattgttgcc gggaagctag agtaagtagt tcgccagtta   9720
atagtttgcg caacgttgtt gccattgcta caggcatcgt ggtgtcacgc tcgtcgtttg   9780
gtatggcttc attcagctcc ggttcccaac gatcaaggcg agttacatga tcccccatgt   9840
tgtgcaaaaa agcggttagc tccttcggtc ctccgatcgt tgtcagaagt aagttggccg   9900
cagtgttatc actcatggtt atggcagcac tgcataattc tcttactgtc atgccatccg   9960
```

-continued

| | |
|---|---|
| taagatgctt ttctgtgact ggtgagtact caaccaagtc attctgagaa tagtgtatgc | 10020 |
| ggcgaccgag ttgctcttgc ccggcgtcaa tacgggataa taccgcgcca catagcagaa | 10080 |
| ctttaaaagt gctcatcatt ggaaaacgtt cttcggggcg aaaactctca aggatcttac | 10140 |
| cgctgttgag atccagttcg atgtaaccca ctcgtgcacc caactgatct tcagcatctt | 10200 |
| ttactttcac cagcgtttct gggtgagcaa aaacaggaag gcaaaatgcc gcaaaaaagg | 10260 |
| gaataagggc gacacggaaa tgttgaatac tca | 10293 |

<210> SEQ ID NO 100
<211> LENGTH: 8179
<212> TYPE: DNA
<213> ORGANISM: Artificial Sequence
<220> FEATURE:
<223> OTHER INFORMATION: pCAGGS-IgVK1-39 targeting vector

<400> SEQUENCE: 100

| | |
|---|---|
| atccaggcgc ggatcaataa aagatcatta ttttcaatag atctgtgtgt tggttttttg | 60 |
| tgtgccttgg gggaggggga ggccagaatg aggcgcggcc aaggggggagg gggaggccag | 120 |
| aatgaccttg ggggaggggg aggccagaat gaccttgggg gaggggggagg ccagaatgag | 180 |
| gcgcggatcc ggagaagttc ctattccgaa gttcctattc ttcaaatagt ataggaactt | 240 |
| cgctcgaggt atcggccatt gaacaagatg gattgcacgc aggttctccg gccgcttggg | 300 |
| tggagaggct attcggctat gactgggcac aacagacaat cggctgctct gatgccgccg | 360 |
| tgttccggct gtcagcgcag gggcgcccgg ttcttttgt caagaccgac ctgtccggtg | 420 |
| ccctgaatga actgcaggac gaggcagcgc ggctatcgtg gctggccacg acgggcgttc | 480 |
| cttgcgcagc tgtgctcgac gttgtcactg aagcgggaag ggactggctg ctattgggcg | 540 |
| aagtgccggg gcaggatctc ctgtcatctc accttgctcc tgccgagaaa gtatccatca | 600 |
| tggctgatgc aatgcggcgg ctgcatacgc ttgatccggc tacctgccca ttcgaccacc | 660 |
| aagcgaaaca tcgcatcgag cgagcacgta ctcggatgga agccggtctt gtcgatcagg | 720 |
| atgatctgga cgaagagcat caggggctcg cgccagccga actgttcgcc aggctcaagg | 780 |
| cgcgcatgcc cgacggcgag gatctcgtcg tgacccatgg cgatgcctgc ttgccgaata | 840 |
| tcatggtgga aaatggccgc ttttctggat tcatcgactg tggccggctg ggtgtggcgg | 900 |
| accgctatca ggacatagcg ttggctaccc gtgatattgc tgaagagctt ggcggcgaat | 960 |
| gggctgaccg cttcctcgtg ctttacggta tcgccgctcc cgattcgcag cgcatcgcct | 1020 |
| tctatcgcct tcttgacgag ttcttctgag gggatcgatc cgctgtaagt ctgcagaaat | 1080 |
| tgatgatcta ttaaacaata aagatgtcca ctaaaatgga agtttttcct gtcatacttt | 1140 |
| gttaagaagg gtgagaacag agtacctaca ttttgaatgg aaggattgga gctacggggg | 1200 |
| tgggggtggg gtgggattag ataaatgcct gctctttact gaaggctctt tactattgct | 1260 |
| ttatgataat gtttcatagt tggatatcat aatttaaaca agcaaaacca aattaagggc | 1320 |
| cagctcattc ctcccactca tgatctatag atctatagat ctctcgtggg atcattgttt | 1380 |
| ttctcttgat tcccactttg tggttctaag tactgtggtt tccaaatgtg tcagtttcat | 1440 |
| agcctgaaga acgagatcag cagcctctgt tccacataca cttcattctc agtattgttt | 1500 |
| tgccaagttc taattccatc agaagctgac tctagatggc gcgtatgcag gttttcgaca | 1560 |
| ttgattattg actagttatt aatagtaatc aattacgggg tcattagttc atagcccata | 1620 |
| tatggagttc cgcgttacat aacttacggt aaatggcccg cctggctgac cgcccaacga | 1680 |

```
cccccgccca ttgacgtcaa taatgacgta tgttcccata gtaacgccaa tagggacttt    1740
ccattgacgt caatgggtgg agtatttacg gtaaactgcc cacttggcag tacatcaagt    1800
gtatcatatg ccaagtacgc cccctattga cgtcaatgac ggtaaatggc ccgcctggca    1860
ttatgcccag tacatgacct tatgggactt tcctacttgg cagtacatct acgtattagt    1920
catcgctatt accatggtcg aggtgagccc cacgttctgc ttcactctcc ccatctcccc    1980
cccctcccca cccccaattt tgtatttatt tattttttaa ttattttgtg cagcgatggg    2040
ggcggggggg gggggggcgc gcgccaggcg gggcggggcg gggcgagggg cggggcgggg    2100
cgaggcggag aggtgcggcg gcagccaatc agagcggcgc gctccgaaag tttccttttta   2160
tggcgaggcg gcggcggcgg cggccctata aaaagcgaag cgcgcggcgg gcgggagtcg    2220
ctgcgttgcc ttcgcccgt gccccgctcc gcgccgcctc gcgccgcccg ccccggctct     2280
gactgaccgc gttactccca caggtgagcg ggcgggacgg cccttctcct ccgggctgta    2340
attagcgctt ggtttaatga cggctcgttt cttttctgtg gctgcgtgaa agccttaaag    2400
ggctccggga gggccctttg tgcgggggg agcggctcgg ggggtgcgtg cgtgtgtgtg    2460
tgcgtgggga gcgccgcgtg cggcccgcgc tgcccggcgg ctgtgagcgc tgcgggcgcg    2520
gcgcggggct ttgtgcgctc cgcgtgtgcg cgaggggagc gcggccgggg gcggtgcccc    2580
gcggtgcggg ggggctgcga ggggaacaaa ggctgcgtgc ggggtgtgtg cgtgggggg    2640
tgagcagggg gtgtgggcgc ggcggtcggg ctgtaacccc cccctgcacc cccctccccg    2700
agttgctgag cacggcccgg cttcgggtgc ggggctccgt gcggggcgtg gcgcggggct    2760
cgccgtgccg ggcggggggt ggcggcaggt ggggtgccg ggcggggcgg ggccgcctcg    2820
ggccggggag ggctcggggg aggggcgcgg cggccccgga gcgccggcgg ctgtcgaggc    2880
gcggcgagcc gcagccattg cctttttatgg taatcgtgcg agaggcgca gggacttcct    2940
ttgtcccaaa tctgtgcgga gccgaaatct gggaggcgcc gccgcacccc ctctagcggg    3000
cgcggggcga agcggtgcgg cgccggcagg aaggaaatgg gcggggaggg ccttcgtgcg    3060
tcgccgcgcc gccgtcccct tctccctctc cagcctcggg gctgtccgcg ggggacggc    3120
tgccttcggg ggggacgggg cagggcgggg ttcggcttct ggcgtgtgac cggcggctct    3180
agaagcgttg gggtgagtac tccctctcaa aagcgggcat gacttctgcg ctaagattgt    3240
cagtttccaa aaacgaggag gatttgatat tcacctggcc cgcggtgatg cctttgaggg    3300
tggccgcgtc catctggtca gaaaagacaa tctttttgtt gtcaagcttg aggtgtggca    3360
ggcttgagat ctggccatac acttgagtga cattgacatc cactttgcct ttctctccac    3420
aggtgtccac tcccagggcg gcctccggag cgatcgccga tccgcctagg caattgttta    3480
aatcggccgg ccataacttc gtataatgta tgctatacga agttatggat cctcacagta    3540
ggtggcatcg ttcctttctg actgcccgcc ccccgcatgc cgtcccgcga tattgagctc    3600
cgaacctctc gccctgccgc cgccggtgct ccgtcgccgc cgcgccgcca tggaatcgaa    3660
gccaccatgg atcttaccgg aaaactcgac gcaagaaaaa tcagagagat cctcataaag    3720
gtcaagaagg gcggaaagat cgccgtgtaa ttctagaccg gttcgagatc caggcgcgga    3780
tcaataaaag atcattattt tcaatagatc tgtgtgttgg ttttttgtgt gccttggggg    3840
aggggaggc cagaatgagg cgcggccaag ggggaggggg aggccagaat gaccttgggg    3900
gaggggagg ccagaatgac cttggggag gggaggcca gaatgaggcg cgccctccgt    3960
cgacctataa cttcgtataa tgtatgctat acgaagttat ggcggccgcc accatggaca    4020
tgagagtgcc cgcccagctc ctggggctcc tgctactctg gctccgaggt aaggatggag    4080
```

```
aacactagga atttactcag ccagtgtgct cagtactgac tggaacttca gggaagttct    4140
ctgataacat gattaatagt aagaatattt gtttttatgt ttccaatctc aggtgccaga    4200
tgtgacatcc agatgaccca gagccccagc agcctgagcg ccagcgtggg cgacagagtg    4260
accatcacct gcagagccag ccagagcatc agcagctacc tgaactggta tcagcagaag    4320
cccggcaagg ccccccaagct gctgatctac gccgccagct ccctgcagag cggcgtgccc    4380
agcagattca gcggcagcgg ctccggcacc gacttcaccc tgaccatcag cagcctgcag    4440
cccgaggact tcgccaccta ctactgccag cagagctaca gcaccccccc caccttcggc    4500
cagggcacca aggtggagat caagagagcc gacgccgctc ccaccgtgtc catcttcccc    4560
cccagcatgg aacagctgac ctctggcgga gccaccgtgg tctgcttcgt gaacaacttc    4620
taccccagag acatcagcgt gaagtggaag atcgacggca gcgagcagag ggacggcgtg    4680
ctggacagcg tgaccgacca ggacagcaag gactccacct acagcatgag cagcaccctg    4740
agcctgacca aggtggagta cgagaggcac aacctgtaca cctgcgaggt ggtgcacaag    4800
accagctcca gccccgtggt caagtccttc aaccggaacg agtgttgagc tagcttaaga    4860
tttaaatagg ccgccgcgt cgacctcgag atccaggcgc ggatcaataa aagatcatta    4920
ttttcaatag atctgtgtgt tggttttttg tgtgccttgg gggaggggga ggccagaatg    4980
aggcgcggcc aaggggagg gggaggccag aatgaccttg ggggaggggg aggccagaat    5040
gaccttgggg gaggggagg ccagaatgag gcgcgccccc gggtaccgag ctcgaattag    5100
tggatcctca cagtaggtgg catcgttcct ttctgactgc ccgccccccg catgccgtcc    5160
cgcgatattg agctccgaac ctctcgccct gccgccgccg gtgctccgtc gccgccgcgc    5220
cgccatggaa tcgcgccggt aaccgaagtt cctatacttt ctagagaata ggaacttcgg    5280
aataggaact tcaagccggt acccagcttt tgttcccttt agtgagggtt aatttcgagc    5340
ttggcgtaat catggtcata gctgtttcct gtgtgaaatt gttatccgct cacaattcca    5400
cacaacatac gagccgggag cataaagtgt aaagcctggg gtgcctaatg agtgagctaa    5460
ctcacattaa ttgcgttgcg ctcactgccc gctttccagt cgggaaacct gtcgtgccag    5520
ctgcattaat gaatcggcca acgcgcgggg agaggcggtt tgcgtattgg gcgctcttcc    5580
gcttcctcgc tcactgactc gctgcgctcg tcgttcggc tgcggcgagc ggtatcagct    5640
cactcaaagg cggtaatacg gttatccaca gaatcagggg ataacgcagg aaagaacatg    5700
tgagcaaaag gccagcaaaa ggccaggaac cgtaaaaagg ccgcgttgct ggcgtttttc    5760
cataggctcc gcccccctga cgagcatcac aaaaatcgac gctcaagtca gaggtggcga    5820
aacccgacag gactataaag ataccaggcg tttccccctg gaagctccct cgtgcgctct    5880
cctgttccga ccctgccgct taccggatac ctgtccgcct ttctcccttc gggaagcgtg    5940
gcgctttctc atagctcacg ctgtaggtat ctcagttcgg tgtaggtcgt tcgctccaag    6000
ctgggctgtg tgcacgaacc cccgttcag cccgaccgct cgccttatc cggtaactat    6060 cgtcttgagt ccaacccggt aagacacgac ttatcgccac tggcagcagc cactggtaac    6120
aggattagca gagcgaggta tgtaggcggt gctacagagt tcttgaagtg gtggcctaac    6180
tacggctaca ctagaaggac agtatttggt atctgcgctc tgctgaagcc agttaccttc    6240
ggaaaaagag ttggtagctc ttgatccggc aaacaaacca ccgctggtag cggtggtttt    6300
tttgtttgca agcagcagat tacgcgcaga aaaaaaggat ctcaagaaga tccttttgatc    6360 ttttctacgg ggtctgacgc tcagtggaac gaaaactcac gttaagggat tttggtcatg    6420
```

| | |
|---|---|
| agattatcaa aaaggatctt cacctagatc cttttaaatt aaaaatgaag ttttaaatca | 6480 |
| atctaaagta tatatgagta aacttggtct gacagttacc aatgcttaat cagtgaggca | 6540 |
| cctatctcag cgatctgtct atttcgttca tccatagttg cctgactccc cgtcgtgtag | 6600 |
| ataactacga tacgggaggg cttaccatct ggccccagtg ctgcaatgat accgcgagac | 6660 |
| ccacgctcac cggctccaga tttatcagca ataaaccagc cagccggaag ggccgagcgc | 6720 |
| agaagtggtc ctgcaacttt atccgcctcc atccagtcta ttaattgttg ccgggaagct | 6780 |
| agagtaagta gttcgccagt taatagtttg cgcaacgttg ttgccattgc tacaggcatc | 6840 |
| gtggtgtcac gctcgtcgtt tggtatggct tcattcagct ccggttccca acgatcaagg | 6900 |
| cgagttacat gatcccccat gttgtgcaaa aaagcggtta gctccttcgg tcctccgatc | 6960 |
| gttgtcagaa gtaagttggc cgcagtgtta tcactcatgg ttatggcagc actgcataat | 7020 |
| tctcttactg tcatgccatc cgtaagatgc ttttctgtga ctggtgagta ctcaaccaag | 7080 |
| tcattctgag aatagtgtat gcggcgaccg agttgctctt gcccggcgtc aatacgggat | 7140 |
| aataccgcgc cacatagcag aactttaaaa gtgctcatca ttggaaaacg ttcttcgggg | 7200 |
| cgaaaactct caaggatctt accgctgttg agatccagtt cgatgtaacc cactcgtgca | 7260 |
| cccaactgat cttcagcatc ttttactttc accagcgttt ctgggtgagc aaaaacagga | 7320 |
| aggcaaaatg ccgcaaaaaa gggaataagg gcgacacgga aatgttgaat actcatactc | 7380 |
| ttcctttttc aatattattg aagcatttat cagggttatt gtctcatgag cggatacata | 7440 |
| tttgaatgta tttagaaaaa taaacaaata ggggttccgc gcacatttcc ccgaaaagtg | 7500 |
| ccacctaaat tgtaagcgtt aatattttgt taaaattcgc gttaaatttt tgttaaatca | 7560 |
| gctcattttt taaccaatag gccgaaatcg gcaaaatccc ttataaatca aaagaataga | 7620 |
| ccgagatagg gttgagtgtt gttccagttt ggaacaagag tccactatta agaacgtgg | 7680 |
| actccaacgt caaagggcga aaaccgtct atcagggcga tggcccacta cgtgaaccat | 7740 |
| cacccctaatc aagttttttg gggtcgaggt gccgtaaagc actaaatcgg aaccctaaag | 7800 |
| ggagccccg atttagagct tgacggggaa agccggcgaa cgtggcgaga aggaaggga | 7860 |
| agaaagcgaa aggagcgggc gctagggcgc tggcaagtgt agcggtcacg ctgcgcgtaa | 7920 |
| ccaccacacc cgccgcgctt aatgcgccgc tacagggcgc gtcccattcg ccattcaggc | 7980 |
| tgcgcaactg ttgggaaggg cgatcggtgc gggcctcttc gctattacgc cagctggcga | 8040 |
| aagggggatg tgctgcaagg cgattaagtt gggtaacgcc agggttttcc cagtcacgac | 8100 |
| gttgtaaaac gacggccagt gagcgcgcgt aatacgactc actatagggc gaattggggg | 8160 |
| taactaagta aggatcgag | 8179 |

<210> SEQ ID NO 101
<211> LENGTH: 8188
<212> TYPE: DNA
<213> ORGANISM: Artificial Sequence
<220> FEATURE:
<223> OTHER INFORMATION: pCAGGS-IgVL2-14 targeting vector

<400> SEQUENCE: 101

| | |
|---|---|
| atccaggcgc ggatcaataa aagatcatta ttttcaatag atctgtgtgt tggttttttg | 60 |
| tgtgccttgg gggagggggga ggccagaatg aggcgcggcc aaggggggagg gggaggccag | 120 |
| aatgaccttg ggggaggggg aggccagaat gaccttgggg gagggggagg ccagaatgag | 180 |
| gcgcggatcc ggagaagttc ctattccgaa gttcctattc tcaaatagt ataggaactt | 240 |
| cgctcgaggg atcggccatt gaacaagatg gattgcacgc aggttctccg gccgcttggg | 300 |

```
tggagaggct attcggctat gactgggcac aacagacaat cggctgctct gatgccgccg      360
tgttccggct gtcagcgcag gggcgcccgg ttcttttttgt caagaccgac ctgtccggtg     420
ccctgaatga actgcaggac gaggcagcgc ggctatcgtg gctggccacg acgggcgttc     480
cttgcgcagc tgtgctcgac gttgtcactg aagcgggaag ggactggctg ctattgggcg     540
aagtgccggg gcaggatctc ctgtcatctc accttgctcc tgccgagaaa gtatccatca     600
tggctgatgc aatgcggcgg ctgcatacgc ttgatccggc tacctgccca ttcgaccacc     660
aagcgaaaca tcgcatcgag cgagcacgta ctcggatgga agccggtctt gtcgatcagg     720
atgatctgga cgaagagcat caggggctcg cgccagccga actgttcgcc aggctcaagg     780
cgcgcatgcc cgacggcgag gatctcgtcg tgacccatgg cgatgcctgc ttgccgaata     840
tcatggtgga aaatggccgc ttttctggat tcatcgactg tggccggctg ggtgtggcgg     900
accgctatca ggacatagcg ttggctaccc gtgatattgc tgaagagctt ggcggcgaat     960
gggctgaccg cttcctcgtg ctttacggta tcgccgctcc cgattcgcag cgcatcgcct    1020
tctatcgcct tcttgacgag ttcttctgag gggatcgatc cgctgtaagt ctgcagaaat    1080
tgatgatcta ttaaacaata aagatgtcca ctaaaatgga agttttttcct gtcatacttt    1140 gttaagaagg gtgagaacag agtacctaca ttttgaatgg aaggattgga gctacgggg     1200 tgggggtggg gtgggattag ataaatgcct gctctttact gaaggctctt tactattgct    1260
ttatgataat gtttcatagt tggatatcat aatttaaaca agcaaaacca aattaagggc    1320
cagctcattc ctcccactca tgatctatag atctatagat ctctcgtggg atcattgttt    1380
ttctcttgat tcccacttttg tggttctaag tactgtggtt tccaaatgtg tcagtttcat    1440
agcctgaaga acgagatcag cagcctctgt tccacataca cttcattctc agtattgttt    1500
tgccaagttc taattccatc agaagctgac tctagatggc gcgtatgcag gttttcgaca    1560
ttgattattg actagttatt aatagtaatc aattacgggg tcattagttc atagcccata    1620
tatggagttc cgcgttacat aacttacggt aaatggcccg cctggctgac cgcccaacga    1680
cccccgccca ttgacgtcaa taatgacgta tgttcccata gtaacgccaa tagggacttt    1740
ccattgacgt caatgggtgg agtatttacg gtaaactgcc cacttggcag tacatcaagt    1800
gtatcatatg ccaagtacgc cccctattga cgtcaatgac ggtaaatggc ccgcctggca    1860
ttatgcccag tacatgacct tatgggactt tcctacttgg cagtacatct acgtattagt    1920
catcgctatt accatggtcg aggtgagccc cacgttctgc ttcactctcc ccatctcccc    1980
cccctcccca ccccccaattt tgtatttatt tattttttaa ttattttgtg cagcgatggg    2040
ggcggggggg gggggggcgc gcgccaggcg gggcggggcg gggcgagggg cggggcgggg    2100 cgaggcgag aggtgcggcg gcagccaatc agagcggcgc gctccgaaag tttccttttta    2160 tggcgaggcg gcggcggcgg cggccctata aaagcgaag cgcgcggcgg cgggagtcg     2220 ctgcgttgcc ttcgccccgt gccccgctcc gcgccgcctc gcgccgcccg ccccggctct    2280
gactgaccgc gttactccca caggtgagcg ggcgggacgg cccttctcct ccgggctgta    2340
attagcgctt ggtttaatga cggctcgttt cttttctgtg gctgcgtgaa agccttaaag    2400
ggctccggga gggccctttg tgcgggggg agcggctcgg ggggtgcgtg cgtgtgtgtg     2460
tgcgtgggga gcgccgcgtg cggcccgcgc tgcccggcgg ctgtgagcgc tgcgggcgcg    2520
gcgcggggct ttgtgcgctc cgcgtgtgcg cgaggggagc gcggccgggg gcggtgcccc    2580
gcggtgcggg ggggctgcga ggggaacaaa ggctgcgtgc ggggtgtgtg cgtggggggg    2640
```

```
tgagcagggg gtgtgggcgc ggcggtcggg ctgtaacccc ccccctgcacc cccctccccg    2700 agttgctgag cacggcccgg cttcgggtgc ggggctccgt gcggggcgtg gcgcggggct    2760
cgccgtgccg ggcggggggt ggcggcaggt gggggtgccg ggcggggcgg ggccgcctcg    2820
ggccggggag ggctcggggg aggggcgcgg cggcccgga gcgccggcgg ctgtcgaggc    2880
gcggcgagcc gcagccattg cctttatgg taatcgtgcg agagggcgca gggacttcct    2940
ttgtcccaaa tctgtgcgga gccgaaatct ggggaggcgcc gccgcacccc ctctagcggg    3000
cgcggggcga agcggtgcgg cgccggcagg aaggaaatgg gcggggaggg ccttcgtgcg    3060
tcgccgcgcc gccgtcccct tctccctctc cagcctcggg gctgtccgcg ggggacggc    3120 tgccttcggg ggggacgggg cagggcgggg ttcggcttct ggcgtgtgac cggcggctct    3180
agaagcgttg gggtgagtac tccctctcaa aagcgggcat gacttctgcg ctaagattgt    3240
cagtttccaa aaacgaggag gatttgatat tcacctggcc cgcggtgatg cctttgaggg    3300
tggccgcgtc catctggtca gaaaagacaa tcttttttgtt gtcaagcttg aggtgtggca    3360
ggcttgagat ctggccatac acttgagtga cattgacatc cactttgcct ttctctccac    3420
aggtgtccac tcccagggcg gcctccggag cgatcgccga tccgcctagg caattgttta    3480
aatcggccgg ccataacttc gtataatgta tgctatacga agttatggat cctcacagta    3540
ggtggcatcg ttcctttctg actgcccgcc ccccgcatgc cgtcccgcga tattgagctc    3600
cgaacctctc gccctgccgc cgccggtgct ccgtcgccgc cgcgccgcca tggaatcgaa    3660
gccaccatgg atcttaccgg aaaactcgac gcaagaaaaa tcagagagat cctcataaag    3720
gtcaagaagg gcgaaaagat cgccgtgtaa ttctagaccg gttcgagatc caggcgcgga    3780
tcaataaaag atcattattt tcaatagatc tgtgtgttgg ttttttgtgt gccttggggg    3840
agggggaggc cagaatgagg cgcggccaag ggggaggggg aggccagaat gaccttggg    3900 gaggggagg ccagaatgac cttggggag ggggaggcca gaatgaggcg cgccctccgt    3960
cgacctataa cttcgtataa tgtatgctat acgaagttat ggcggccgcc accatggaca    4020
tgagagtgcc cgcccagctc ctggggctcc tgctactctg gctccgaggt aaggatggag    4080
aacactagga atttactcag ccagtgtgct cagtactgac tggaacttca gggaagttct    4140
ctgataacat gattaatagt aagaatattt gtttttatgt ttccaatctc aggtgccaga    4200
tgtcagtctg ccctgaccca gcccgcctct gtgtctggca gccctggcca gagcatcacc    4260
atcagctgca ccggcaccag cagcgacgtg ggcggctaca actacgtgtc ctggtatcag    4320
cagcaccccg gcaaggcccc caagctgatg atctacgagg tgtccaacag acccagcggc    4380
gtgagcaaca gattcagcgg cagcaagagc ggcaacaccg ccagcctgac catcagcggc    4440
ctccaggctg aggacgaggc cgactactac tgcagcagct acaccagcag ctccaccctg    4500
gtgtttggcg gcggaacaaa gctgaccgtg ctgagagccg acgccgctcc caccgtgtcc    4560
atcttccccc ccagcatgga acagctgacc tctggcggag ccaccgtggt ctgcttcgtg    4620
aacaacttct accccagaga catcagcgtg aagtggaaga tcgacggcag cgagcagagg    4680
gacggcgtgc tggacagcgt gaccgaccag gacagcaagg actccaccta cagcatgagc    4740
agcaccctga gcctgaccaa ggtggagtac gagaggcaca acctgtacac ctgcgaggtg    4800
gtgcacaaga ccagctccag ccccgtggtc aagtccttca accggaacga gtgttgagct    4860
agcttaagat ttaaataggc cggccgcgtc gacctcgaga tccaggcgcg gatcaataaa    4920
agatcattat tttcaataga tctgtgtgtt ggttttttgt gtgccttggg ggagggggag    4980
gccagaatga ggcgcggcca aggggaggg ggaggccaga atgaccttgg gggagggga    5040
```

```
ggccagaatg accttggggg aggggaggc cagaatgagg cgcgcccccg ggtaccgagc    5100
tcgaattagt ggatcctcac agtaggtggc atcgttcctt tctgactgcc cgccccccgc    5160
atgccgtccc gcgatattga gctccgaacc tctcgccctg ccgccgccgg tgctccgtcg    5220
ccgccgcgcc gccatggaat cgcgccggta accgaagttc ctatactttc tagagaatag    5280
gaacttcgga ataggaactt caagccggta cccagctttt gttcccttta gtgagggtta    5340
atttcgagct tggcgtaatc atggtcatag ctgtttcctg tgtgaaattg ttatccgctc    5400
acaattccac acaacatacg agccgggagc ataaagtgta aagcctgggg tgcctaatga    5460
gtgagctaac tcacattaat tgcgttgcgc tcactgcccg ctttccagtc gggaaacctg    5520
tcgtgccagc tgcattaatg aatcggccaa cgcgcgggga gaggcggttt gcgtattggg    5580
cgctcttccg cttcctcgct cactgactcg ctgcgctcgg tcgttcggct gcggcgagcg    5640
gtatcagctc actcaaaggc ggtaatacgg ttatccacag aatcagggga taacgcagga    5700
aagaacatgt gagcaaaagg ccagcaaaag gccaggaacc gtaaaaaggc cgcgttgctg    5760 gcgttttttcc ataggctccg cccccctgac gagcatcaca aaaatcgacg ctcaagtcag    5820
aggtggcgaa acccgacagg actataaaga taccaggcgt ttccccctgg aagctccctc    5880
gtgcgctctc ctgttccgac cctgccgctt accggatacc tgtccgcctt tctcccttcg    5940
ggaagcgtgg cgctttctca tagctcacgc tgtaggtatc tcagttcggt gtaggtcgtt    6000
cgctccaagc tgggctgtgt gcacgaaccc cccgttcagc ccgaccgctg cgccttatcc    6060
ggtaactatc gtcttgagtc aacccggta agacacgact tatcgccact ggcagcagcc    6120
actggtaaca ggattagcag agcgaggtat gtaggcggtg ctacagagtt cttgaagtgg    6180
tggcctaact acggctacac tagaaggaca gtatttggta tctgcgctct gctgaagcca    6240
gttaccttcg gaaaaagagt tggtagctct tgatccggca acaaaccac cgctggtagc    6300 ggtggttttt ttgtttgcaa gcagcagatt acgcgcagaa aaaaaggatc tcaagaagat    6360
cctttgatct tttctacggg gtctgacgct cagtggaacg aaaactcacg ttaagggatt    6420
ttggtcatga gattatcaaa aaggatcttc acctagatcc ttttaaatta aaaatgaagt    6480
tttaaatcaa tctaaagtat atatgagtaa acttggtctg acagttacca atgcttaatc    6540
agtgaggcac ctatctcagc gatctgtcta tttcgttcat ccatagttgc ctgactcccc    6600
gtcgtgtaga taactacgat acgggagggc ttaccatctg gccccagtgc tgcaatgata    6660
ccgcgagacc cacgctcacc ggctccagat ttatcagcaa taaaccagcc agccggaagg    6720
gccgagcgca gaagtggtcc tgcaacttta tccgcctcca tccagtctat taattgttgc    6780
cgggaagcta gagtaagtag ttcgccagtt aatagtttgc gcaacgttgt tgccattgct    6840
acaggcatcg tggtgtcacg ctcgtcgttt ggtatggctt cattcagctc cggttcccaa    6900
cgatcaaggc gagttacatg atcccccatg ttgtgcaaaa aagcggttag ctccttcggt    6960
cctccgatcg ttgtcagaag taagttggcc gcagtgttat cactcatggt tatggcagca    7020
ctgcataatt ctcttactgt catgccatcc gtaagatgct tttctgtgac tggtgagtac    7080
tcaaccaagt cattctgaga atagtgtatg cggcgaccga gttgctcttg cccggcgtca    7140
atacgggata taccgcgcc acatagcaga actttaaaag tgctcatcat ggaaaacgt    7200 tcttcgggc gaaaactctc aaggatctta ccgctgttga gatccagttc gatgtaaccc    7260
actcgtgcac ccaactgatc ttcagcatct tttactttca ccagcgtttc tgggtgagca    7320
aaaacaggaa ggcaaaatgc cgcaaaaaag ggaataaggg cgacacggaa atgttgaata    7380
```

-continued

| | |
|---|---|
| ctcatactct tcctttttca atattattga agcatttatc agggttattg tctcatgagc | 7440 |
| ggatacatat ttgaatgtat ttagaaaaat aaacaaatag gggttccgcg cacatttccc | 7500 |
| cgaaaagtgc cacctaaatt gtaagcgtta atattttgtt aaaattcgcg ttaaattttt | 7560 |
| gttaaatcag ctcatttttt aaccaatagg ccgaaatcgg caaaatccct tataaatcaa | 7620 |
| aagaatagac cgagataggg ttgagtgttg ttccagtttg gaacaagagt ccactattaa | 7680 |
| agaacgtgga ctccaacgtc aaagggcgaa aaaccgtcta tcagggcgat ggcccactac | 7740 |
| gtgaaccatc accctaatca agttttttgg ggtcgaggtg ccgtaaagca ctaaatcgga | 7800 |
| accctaaagg agcccccga tttagagctt gacggggaaa gccggcgaac gtggcgagaa | 7860 |
| aggaagggaa gaaagcgaaa ggagcgggcg ctagggcgct ggcaagtgta gcggtcacgc | 7920 |
| tgcgcgtaac caccacccc gccgcgctta atgcgccgct acagggcgcg tcccattcgc | 7980 |
| cattcaggct gcgcaactgt tgggaagggc gatcggtgcg ggcctcttcg ctattacgcc | 8040 |
| agctggcgaa aggggatgt gctgcaaggc gattaagttg ggtaacgcca gggttttccc | 8100 |
| agtcacgacg ttgtaaaacg acggccagtg agcgcgcgta atacgactca ctatagggcg | 8160 |
| aattgggggt aactaagtaa ggatcgag | 8188 |

<210> SEQ ID NO 102
<211> LENGTH: 10
<212> TYPE: DNA
<213> ORGANISM: Artificial Sequence
<220> FEATURE:
<223> OTHER INFORMATION: Kozak sequence

<400> SEQUENCE: 102

| | |
|---|---|
| gccaccatgg | 10 |

<210> SEQ ID NO 103
<211> LENGTH: 1425
<212> TYPE: DNA
<213> ORGANISM: Artificial Sequence
<220> FEATURE:
<223> OTHER INFORMATION: heavy chain nucleotide sequence of the JA
    hybridoma

<400> SEQUENCE: 103

| | |
|---|---|
| atggagtttg ggctgagctg gcttttctt gtggctattt taaaaggtgt ccagtgtgag | 60 |
| gtgcagctgt tggagtctgg gggaggcttg gtacagcctg gggggtccct gagactctcc | 120 |
| tgtgcagcct ctggattcac ctttagcaac tatgccatga gctgggtccg ccaggctcca | 180 |
| gggaaggggc tggagtgggt ctcagctatt agtgctagtg gtcatagcac atatttggca | 240 |
| gactccgtga agggccggtt caccatctcc agagacaatt ccaagaacac gctgtatctg | 300 |
| caaatgaaca gcctgagagc cgaggacacg gccgtatatt actgtgcgaa agatcgagag | 360 |
| gttactatga tagttgtact taatggaggc tttgactact ggggccaggg aacccgggtc | 420 |
| accgtctcct ccgcctccac caagggccca tcggtcttcc cctggcacc ctcctccaag | 480 |
| agcacctctg ggggcacagc ggccctgggc tgcctggtca aggactactt ccccgaaccg | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc cagcagcttg | 660 |
| ggcacccaga cctacatctg caacgtgaat cacaagccca gcaacaccaa ggtggacaag | 720 |
| agagttgagc ccaaatcttg tgacaaaact cacacatgcc caccgtgccc agcacctgaa | 780 |
| ctcctggggg gaccgtcagt cttcctcttc cccccaaaac ccaaggacac cctcatgatc | 840 |

```
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggagg agatgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct atagcaagct caccgtggac   1320
aagagcaggt ggcagcaggg gaacgtcttc tcatgctccg tgatgcatga ggctctgcac   1380
aaccactaca cgcagaagag cctctccctg tccccgggta aatga                   1425
```

<210> SEQ ID NO 104
<211> LENGTH: 705
<212> TYPE: DNA
<213> ORGANISM: Artificial Sequence
<220> FEATURE:
<223> OTHER INFORMATION: light chain nucleotide sequence of the JA hybridoma

<400> SEQUENCE: 104

```
atggaagccc cagctcagct tctcttcctc ctgctactct ggctcccaga taccaccgga     60
gaaattgtgt tgacacagtc tccagccacc ctgtctttgt ctccagggga aagagccacc    120
ctcgcctgca gggccagtca gactgctagc aggtacttag cctggtacca acagaaacct    180
ggccaggctc ccagactcct catctatgat acatccaaca gggccactgg catcccagcc    240
aggttcagtg gcagtgggtc tgggacagac ttcactctct ccatcagcag cctggagcct    300
gaagattttg cagtttatta ctgtcagcag cgtttcaact ggccgtggac gttcggccaa    360
gggaccaagg tggaattcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 105
<211> LENGTH: 1557
<212> TYPE: DNA
<213> ORGANISM: Artificial Sequence
<220> FEATURE:
<223> OTHER INFORMATION: heavy chain nucleotide sequence of the JB.1 hybridoma

<400> SEQUENCE: 105

```
atggacacac tttgctccac gctcctgctg ctgaccatcc cttcatgggt cttgtcccaa     60
attaccttga aggagactgg tcctacgctg gtgaaaccca cacagaccct cacgctgacc    120
tgcaccttct cggggttctc actcagcact agtggagtgg gtgtgggctg gatccgtcag    180
cccccaggaa aggccctgga gtgggttaca ctcatttatt gggatgatga taagcgttac    240
agtccatctc tggagaacag ggtcaccatc aggaaggaca cctccaaaaa ccaggtggct    300
cttacaatga cgaacatgga cccctttgac acagcacact actactgtgc gcacagacaa    360
catatcagca gcttcccgtg gttcgattcc tggggccagg gaaccctggt caccgtctcc    420
```

```
tcagcttcca ccaagggccc atcggtcttc ccctggcgc cctgctccag gagcacctct       480
gggggcacag cggccctggg ctgcctggtc aaggactact ccccgagcc ggtgacggtg       540 tcgtggaact caggcgccct gaccagcggc gtgcacacct tccggctgt cctacagtcc       600 tcaggactct actccctcag cagcgtggtg accgtgccct ccagcagctt gggcacccag       660
acctacacct gcaacgtgaa tcacaagccc agcaacacca aggtggacaa gagagttgag       720
ctcaaaaccc cacttggtga cacaactcac acatgcccac ggtgcccaga gcccaaatct       780
tgtgacacac ctccccgtg cccacggtgc ccagagccca atcttgtga cacacctccc       840 ccgtgcccac ggtgcccaga gcccaaatct tgtgacacac ctccccatg cccacggtgc       900 ccagcacctg aactcctggg aggaccgtca gtcttcctct tcccccaaa acccaaggat       960 acccttatga tttcccggac ccctgaggtc acgtgcgtgg tggtggacgt gagccacgaa      1020
gaccccgagg tccagttcaa gtggtacgtg gacggcgtgg aggtgcataa tgccaagaca      1080
aagccgcggg aggagcagtt caacagcacg ttccgtgtgg tcagcgtcct caccgtcctg      1140
caccaggact ggctgaacgg taaggagtac aagtgcaagg tctccaacaa agccctccca      1200
gcccccatcg agaaaaccat ctccaaaacc aaaggacagc cccgagaacc acaggtgtac      1260
accctgcccc catcccggga ggagatgacc aagaaccagg tcagcctgac ctgcctggtc      1320
aaaggcttct accccagcga catcgccgtg gagtgggaga gcagcgggca gccggagaac      1380
aactacaaca ccacgcctcc catgctggac tccgacggct ccttcttcct ctacagcaag      1440
ctcaccgtgg acaagagcag gtggcagcag gggaacatct tctcatgctc cgtgatgcat      1500
gaggctctgc acaaccgctt cacgcagaag agcctctccc tgtctccggg taaatga       1557

<210> SEQ ID NO 106
<211> LENGTH: 699
<212> TYPE: DNA
<213> ORGANISM: Artificial Sequence
<220> FEATURE:
<223> OTHER INFORMATION: light chain nucleotide sequence of the JB.1
      hybridoma

<400> SEQUENCE: 106
atggcctgga ccgttctcct cctcggcctc ctctctcact gcacagggtc tgtgacgtcc        60
tatgtgctga ctcagccacc ctcggtgtca gtggccccag gaaagacggc caggattaac       120
tgtgggggaa acaacattga atatagaagt gtgcactggt accagcagaa gtcaggccag       180
gcccctgtag cggtcatcta tgataatagt gaccggccct cagggatccc tgagcgattc       240
tctggttcca atctgggaa cacggccacc ctgaccatca gcagggtcga agccggggat       300
gaggccgact attactgtca ggtgtgggat attagtagtg atgtggtctt cggcggaggg       360
accaagctga ccgtcctagg tcagcccaag gctgccccct cggtcactct gttcccgccc       420
tcctctgagg agcttcaagc caacaaggcc acactggtgt gtctcataag tgacttctac       480
ccgggagccg tgacagtggc ctggaaggca gatagcagcc cgtcaaggc gggagtggag       540 accaccacac cctccaaaca aagcaacaac aagtacgcgg ccagcagcta tctgagcctg       600
acgcctgagc agtggaagtc ccacagaagc tacagctgcc aggtcacgca tgaagggagc       660
accgtggaga agacagtggc ccctacagaa tgttcatag                             699

<210> SEQ ID NO 107
<211> LENGTH: 1431
<212> TYPE: DNA
<213> ORGANISM: Artificial Sequence
```

<220> FEATURE:
<223> OTHER INFORMATION: heavy chain nucleotide sequence of the M57 hybridoma

<400> SEQUENCE: 107

```
atggactgga cctggaggtt cctctttgtg gtggcagcag ctacaggtgt ccagtcccag      60
gtgcagctgg tgcagtctgg ggctgaggtg aagaagcctg gtcctcggt gaaggtctcc     120
tgcaaggctt ctggaggcac cttcaacagg tatactgtca actgggtgcg acaggcccct    180
ggacaagggc ttgagtggat gggaggcatc atccctatct ttggtacagc aaactacgca    240
cagaggttcc agggcagact caccattacc gcggacgaat ccacgagcac agcctacatg    300
gagctgagca gcctgagatc tgatgacacg gccgtgtatt tctgtgcgag agaatctc     360
gataattcgg ggacttatta ttatttctca ggctggttcg accctggg ccagggaacc     420
ctggtcaccg tctcctcagc ctccaccaag ggcccatcgg tcttcccct ggcaccctcc     480
tccaagagca cctctggggg cacagcggcc ctgggctgcc tggtcaagga ctacttcccc    540
gaaccggtga cggtgtcgtg gaactcaggc gccctgacca gcggcgtgca ccttcccg     600
gctgtcctac agtcctcagg actctactcc ctcagcagcg tggtgaccgt gcctccagc     660
agcttgggca cccagaccta catctgcaac gtgaatcaca agcccagcaa caccaaggtg    720
gacaagagag ttgagcccaa atcttgtgac aaaactcaca catgcccacc gtgcccagca    780
cctgaactcc tggggggacc gtcagtcttc ctcttcccc caaaacccaa ggacaccctc    840
atgatctccc ggaccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca caaagccct cccagccccc   1080
atcgagaaaa ccatctccaa agccaaaggg cagccccgag aaccacaggt gtacaccctg   1140
cccccatccc gggaggagat gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct cctctatag caagctcacc   1320
gtggacaaga gcaggtggca gcaggggaac gtcttctcat gctccgtgat gcatgaggct   1380
ctgcacaacc actacacgca gaagagcctc tccctgtccc cgggtaaatg a           1431
```

<210> SEQ ID NO 108
<211> LENGTH: 729
<212> TYPE: DNA
<213> ORGANISM: Artificial Sequence
<220> FEATURE:
<223> OTHER INFORMATION: light chain nucleotide sequence of the M57 hybridoma

<400> SEQUENCE: 108

```
atgagtgtcc ccaccatggc ctgggctctg ctcctcctca gcctcctcac tcagggcaca     60
ggatcctggg ctcagtctgc cctgactcag cctcgctcag tgtccgggtc tcctggacag    120
tcagtcacca tctcctgcac tggaaccagc agtgatattg gtggttataa ctttgtctcc    180
tggtaccaac aacacccagg caaagccccc aaactcatga tttatgatgc actaagcgg    240
ccctcagggg tccctgatcg cttctctggc tccaagtctg gcaacacggc ctccctgacc    300
atctctgggc tccaggctga ggatgaggct gattattact gctgctcata tgcaggcgac    360
tacacccgg gcgtggtttt cggcggaggg accaagctga ccgtcctagg tcagcccaag    420
```

```
gctgcccct cggtcactct gttcccgccc tcctctgagg agcttcaagc caacaaggcc    480
acactggtgt gtctcataag tgacttctac ccgggagccg tgacagtggc ctggaaggca    540
gatagcagcc ccgtcaaggc gggagtggag accaccacac cctccaaaca agcaacaac    600 aagtacgcgg ccagcagcta cctgagcctg acgcctgagc agtggaagtc ccacagaagc    660
tacagctgcc aggtcacgca tgaagggagc accgtggaga agacagtggc ccctacagaa    720
tgttcatag                                                             729
```

<210> SEQ ID NO 109
<211> LENGTH: 125
<212> TYPE: PRT
<213> ORGANISM: Artificial Sequence
<220> FEATURE:
<223> OTHER INFORMATION: heavy chain variable region amino acid sequence of the JA hybridoma

<400> SEQUENCE: 109

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly His Ser Thr Tyr Leu Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Glu Val Thr Met Ile Val Val Leu Asn Gly Gly Phe
            100                 105                 110

Asp Tyr Trp Gly Gln Gly Thr Arg Val Thr Val Ser Ser
        115                 120                 125
```

<210> SEQ ID NO 110
<211> LENGTH: 109
<212> TYPE: PRT
<213> ORGANISM: Artificial Sequence
<220> FEATURE:
<223> OTHER INFORMATION: light chain variable region amino acid sequence of the JA hybridoma

<400> SEQUENCE: 110

```
Glu Ile Val Leu Thr Gln Ser Pro Ala Thr Leu Ser Leu Ser Pro Gly
1               5                   10                  15

Glu Arg Ala Thr Leu Ala Cys Arg Ala Ser Gln Thr Ala Ser Arg Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Ser Ile Ser Ser Leu Glu Pro
65                  70                  75                  80

Glu Asp Phe Ala Val Tyr Tyr Cys Gln Gln Arg Phe Asn Trp Pro Trp
                85                  90                  95

Thr Phe Gly Gln Gly Thr Lys Val Glu Phe Lys Arg Thr
            100                 105
```

<210> SEQ ID NO 111
<211> LENGTH: 122
<212> TYPE: PRT
<213> ORGANISM: Artificial Sequence
<220> FEATURE:
<223> OTHER INFORMATION: heavy chain variable region amino acid sequence of the JB.1 hybridoma

<400> SEQUENCE: 111

```
Gln Ile Thr Leu Lys Glu Thr Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Val Thr Leu Ile Tyr Trp Asp Asp Lys Arg Tyr Ser Pro Ser
    50                  55                  60

Leu Glu Asn Arg Val Thr Ile Arg Lys Asp Thr Ser Lys Asn Gln Val
65                  70                  75                  80

Ala Leu Thr Met Thr Asn Met Asp Pro Leu Asp Thr Gly Thr Tyr Tyr
                85                  90                  95

Cys Ala His Arg Gln His Ile Ser Ser Phe Pro Trp Phe Asp Ser Trp
            100                 105                 110

Gly Gln Gly Thr Leu Val Thr Val Ser Ser
        115                 120
```

<210> SEQ ID NO 112
<211> LENGTH: 107
<212> TYPE: PRT
<213> ORGANISM: Artificial Sequence
<220> FEATURE:
<223> OTHER INFORMATION: light chain variable region amino acid sequence of the JB.1 hybridoma

<400> SEQUENCE: 112

```
Ser Tyr Val Leu Thr Gln Pro Pro Ser Val Ser Val Ala Pro Gly Lys
1               5                   10                  15

Thr Ala Arg Ile Asn Cys Gly Gly Asn Asn Ile Glu Tyr Arg Ser Val
            20                  25                  30

His Trp Tyr Gln Gln Lys Ser Gly Gln Ala Pro Val Ala Val Ile Tyr
        35                  40                  45

Asp Asn Ser Asp Arg Pro Ser Gly Ile Pro Glu Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Ser Ser Asp Val
                85                  90                  95

Val Phe Gly Gly Gly Thr Lys Leu Thr Val Leu
            100                 105
```

<210> SEQ ID NO 113
<211> LENGTH: 127
<212> TYPE: PRT
<213> ORGANISM: Artificial Sequence
<220> FEATURE:
<223> OTHER INFORMATION: heavy chain variable region amino acid sequence of the M57 hybridoma

<400> SEQUENCE: 113

```
Gln Val Gln Leu Val Gln Ser Gly Ala Glu Val Lys Lys Pro Gly Ser
```

```
1               5                   10                  15
Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Arg Phe
        50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
            85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser
            115                 120                 125

<210> SEQ ID NO 114
<211> LENGTH: 112
<212> TYPE: PRT
<213> ORGANISM: Artificial Sequence
<220> FEATURE:
<223> OTHER INFORMATION: light chain variable region amino acid sequence
      of the M57 hybridoma

<400> SEQUENCE: 114

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
            35                  40                  45

Met Ile Tyr Asp Ala Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
            85                  90                  95

Tyr Thr Pro Gly Val Val Phe Gly Gly Gly Thr Lys Leu Thr Val Leu
            100                 105                 110

<210> SEQ ID NO 115
<211> LENGTH: 6720
<212> TYPE: DNA
<213> ORGANISM: Artificial Sequence
<220> FEATURE:
<223> OTHER INFORMATION: VHExpress with the CMV promotor

<400> SEQUENCE: 115
gtggccacca tgggatggag ctgtatcatc ctcttcttgg tagcaacagc tacaggtaag      60
gggttaacag tagcaggctt gaggtctgga catatatatg ggtgacaatg acatccactt     120
tgcctttctc tccacaggcg cgcactccca ggtccaactg caggagagcg gggtcaccgt     180
ctcctcaggt gagtcctgtc gacggatcca cccaatgccc atgagcccag acactggacg     240
ctgaacctcg cggacagtta agaacccagg ggcctctgcg ccctgggccc agctctgtcc     300
cacaccgcgg tcatggca ccacctctct tgcagcctcc accaagggcc catcggtctt     360 cccctggca ccctcctcca agagcacctc tgggggcaca gcggccctgg gctgcctggt     420
```

```
caaggactac ttccccgaac cggtgacggt gtcgtggaac tcaggcgccc tgaccagcgg    480
cgtccacacc ttcccggctg tcctacagtc ctcaggactc tactccctca gcagcgtagt    540
gaccgtgccc tccagcagct tgggcaccca gacctacatc tgcaacgtga atcacaagcc    600
cagcaacacc aaggtggaca agaaagttgg tgagaggcca gcacagggag ggagggtgtc    660
tgctggaagc caggctcagc gctcctgcct ggacgcatcc cggctatgca gccccagtcc    720
agggcagcaa ggcaggcccc gtctgcctct cacccggag gcctctgccc gccccactca    780
tgctcaggga gagggtcttc tggcttttc cccaggctct gggcaggcac aggctaggtg    840
cccctaaccc aggccctgca cacaaagggg caggtgctgg gctcagacct gccaagagcc    900
atatccggga ggaccctgcc cctgacctaa gcccacccca aaggccaaac tctccactcc    960
ctcagctcgg acaccttctc tcctcccaga ttccagtaac tcccaatctt ctctctccag   1020
agcccaaatc ttgtgacaaa actcacacat gcccaccgtg cccaggtaag ccagcccagg   1080
cctcgccctc cagctcaagg cgggacaggt gccctaggt agcctgcatc cagggacagg   1140
ccccagccgg gtgctgacac gtccacctcc atctcttcct cagcacctga actcctgggg   1200
ggaccgtcag tcttcctctt ccccccaaaa cccaaggaca ccctcatgat ctcccggacc   1260
cctgaggtca catgcgtggt ggtggacgtg agccacgaag accctgaggt caagttcaac   1320
tggtacgtgg acggcgtgga ggtgcataat gccaagacaa agccgcggga ggagcagtac   1380
aacagcacgt accgtgtggt cagcgtcctc accgtcctgc accaggactg gctgaatggc   1440
aaggagtaca agtgcaaggt ctccaacaaa gccctcccag cccccatcga gaaaaccatc   1500
tccaaagcca aggtgggac ccgtggggtg cgagggccac atggacagag gccggctcgg   1560 cccacccctct gccctgagag tgaccgctgt accaacctct gtccctacag ggcagccccg   1620
agaaccacag gtgtacaccc tgcccccatc ccgggatgag ctgaccaaga accaggtcag   1680
cctgacctgc ctggtcaaag gcttctatcc cagcgacatc gccgtggagt gggagagcaa   1740
tgggcagccg gagaacaact acaagaccac gcctcccgtg ctggactccg acggctcctt   1800
cttcctctac agcaagctca ccgtggacaa gagcaggtgg cagcagggga acgtcttctc   1860
atgctccgtg atgcatgagg ctctgcacaa ccactacacg cagaagagcc tctccttaag   1920
tccgggaaaa taatctagaa gctcgctgat cagcctcgac tgtgccttct agttgccagc   1980
catctgttgt ttgcccctcc cccgtgcctt ccttgaccct ggaaggtgcc actcccactg   2040 tccttttccta ataaaatgag gaaattgcat cgcattgtct gagtaggtgt cattctattc   2100
tggggggtgg ggtggggcag gacagcaagg ggaggattg gaagacaat agcaggcatg   2160 ctggggatgg cccgggctct atggcttctg aggcggaaag aaccagctgg ggctctaggg   2220
ggtatcccca cgcgccctgt agcggcgcat taagcgcggc gggtgtggtg gttacgcgca   2280
gcgtgaccgc tacacttgcc agcgccctag cgcccgctcc tttcgctttc ttcccttcct   2340
ttctcgccac gttcgccggc tttccccgtc aagctctaaa tcggggcatc cctttagggt   2400
tccgatttag tgctttacgg cacctcgacc ccaaaaaact tgattagggt gatggttcac   2460
gtagtgggcc atcgccctga tagacggttt ttcgcccttt gacgttggag tccacgttct   2520
ttaatagtgg actcttgttc caaactggaa caacactcaa ccctatctcg gtctattctt   2580
ttgatttata agggattttg gggatttcgg cctattggtt aaaaaatgag ctgatttaac   2640
aaaaatttaa cgcgaattaa ttctgtggaa tgtgtgtcag ttagggtgtg gaaagtcccc   2700
aggctcccca ggcaggcaga agtatgcaaa gcatgcatct caattagtca gcaaccaggt   2760
gtggaaagtc cccaggctcc ccagcaggca gaagtatgca aagcatgcat ctcaattagt   2820
```

```
cagcaaccat agtcccgccc ctaactccgc ccatcccgcc cctaactccg cccagttccg    2880
cccattctcc gccccctaggc tgactaattt tttttattta tgcagaggcc gaggccgcct    2940
ctgcctctga gctattccag aagtagtgag gaggcttttt tggaggccta ggcttttgca    3000
aaaagctccc gggaggtcca caatgattga acaagatgga ttgcacgcag gttctccggc    3060
cgcttgggtg gagaggctat tcggctatga ctgggcacaa cagacaatcg gctgctctga    3120
tgccgccgtg ttccggctgt cagcgcaggg gcgcccggtt cttttttgtca agaccgacct    3180 gtccggtgcc ctgaatgaac tccaggacga ggcagcgcgg ctatcgtggc tggccacgac    3240
gggcgttcct tgcgcagctg tgctcgacgt tgtcactgaa gcgggaaggg actggctgct    3300
attgggcgaa gtgccggggc aggatctcct gtcatctcac cttgctcctg ccgagaaagt    3360
atccatcatg gctgatgcaa tgcggcggct gcatacgctt gatccggcta cctgcccatt    3420
cgaccaccaa gcgaaacatc gcatcgagcg agcacgtact cggatggaag ccggtcttgt    3480
cgatcaggat gatctggacg aagagcatca ggggctcgcg ccagccgaac tgttcgccag    3540
gctcaaggcg cgtatgcccg acggcgagga tctcgtcgtg actcatggcg atgcctgctt    3600
gccgaatatc atggtggaaa atggccgctt ttctggattc atcgactgtg gccggctggg    3660
tgtggcggac cgctatcagg acatagcgtt ggctacccgt gatattgctg aagagcttgg    3720
cggcgaatgg gctgaccgct tcctcgtgct ttacggtatc gccgctcccg attcgcagcg    3780
catcgccttc tatcgccttc ttgacgagtt cttctgagcg ggactctggg gttcgaaatg    3840
accgaccaag cgacgccaa cctgccatca cgagatttcg attccaccgc cgccttctat    3900
gaaaggttgg gcttcggaat cgttttccgg gacgccggct ggatgatcct ccagcgcggg    3960
gatctcatgc tggagttctt cgcccacccc aacttgttta ttgcagctta taatggttac    4020
aaataaagca atagcatcac aaatttcaca aataaagcat ttttttcact gcattctagt    4080
tgtggtttgt ccaaactcat caatgtatct tatcatgtct gtataccgga tctttccgct    4140
tcctcgctca ctgactcgct gcgctcggtc gttcggctgc ggcgagcggt atcagctcac    4200
tcaaaggcgg taatacggtt atccacagaa tcaggggata acgcaggaaa gaacatgtga    4260
gcaaaaggcc agcaaaaggc caggaaccgt aaaaaggccg cgttgctggc gttttttccat    4320 aggctccgcc cccctgacga gcatcacaaa aatcgacgct caagtcagag gtggcgaaac    4380
ccgacaggac tataaagata ccaggcgttt ccccctggaa gctccctcgt gcgctctcct    4440
gttccgaccc tgccgcttac cggatacctg tccgcctttc tcccttcggg aagcgtggcg    4500
ctttctcaat gctcacgctg taggtatctc agttcggtgt aggtcgttcg ctccaagctg    4560
ggctgtgtgc acgaaccccc cgttcagccc gaccgctgcg ccttatccgg taactatcgt    4620
cttgagtcca acccggtaag acacgactta tcgccactgg cagcagccac tggtaacagg    4680
attagcagag cgaggtatgt aggcggtgct acagagttct tgaagtggtg gcctaactac    4740
ggctacacta gaaggacagt atttggtatc tgcgctctgc tgaagccagt taccttcgga    4800
aaaagagttg gtagctcttg atccggcaaa caaaccaccg ctggtagcgg tggtttttt    4860 gtttgcaagc agcagattac gcgcagaaaa aaaggatctc aagaagatcc tttgatcttt    4920
tctacggggt ctgacgctca gtggaacgaa aactcacgtt aagggatttt ggtcatgaga    4980
ttatcaaaaa ggatcttcac ctagatcctt ttaaattaaa aatgaagttt taaatcaatc    5040
taaagtatat atgagtaaac ttggtctgac agttaccaat gcttaatcag tgaggcacct    5100
atctcagcga tctgtctatt tcgttcatcc atagttgcct gactccccgt cgtgtagata    5160
```

-continued

| | |
|---|---|
| actacgatac gggagggctt accatctggc cccagtgctg caatgatacc gcgagaccca | 5220 |
| cgctcaccgg ctccagattt atcagcaata aaccagccag ccggaagggc cgagcgcaga | 5280 |
| agtggtcctg caactttatc cgcctccatc cagtctatta attgttgccg ggaagctaga | 5340 |
| gtaagtagtt cgccagttaa tagtttgcgc aacgttgttg ccattgctac aggcatcgtg | 5400 |
| gtgtcacgct cgtcgtttgg tatggcttca ttcagctccg gttcccaacg atcaaggcga | 5460 |
| gttacatgat cccccatgtt gtgcaaaaaa gcggttagct ccttcggtcc tcgatcgtt | 5520 |
| gtcagaagta agttggccgc agtgttatca ctcatggtta tggcagcact gcataattct | 5580 |
| cttactgtca tgccatccgt aagatgcttt tctgtgactg gtgagtactc aaccaagtca | 5640 |
| ttctgagaat agtgtatgcg gcgaccgagt tgctcttgcc cggcgtcaat acgggataat | 5700 |
| accgcgccac atagcagaac tttaaaagtg ctcatcattg gaaaacgttc ttcggggcga | 5760 |
| aaactctcaa ggatcttacc gctgttgaga tccagttcga tgtaacccac tcgtgcaccc | 5820 |
| aactgatctt cagcatcttt tactttcacc agcgtttctg ggtgagcaaa aacaggaagg | 5880 |
| caaaatgccg caaaaaaggg aataagggcg acacggaaat gttgaatact catactcttc | 5940 |
| cttttcaat attattgaag catttatcag ggttattgtc tcatgagcgg atacatattt | 6000 |
| gaatgtattt agaaaaataa acaaataggg gttccgcgca catttccccg aaaagtgcca | 6060 |
| cctgacgtca gatcgacgga tcgggagatc aggtaccgaa ttcacattga ttattgagta | 6120 |
| gttattaata gtaatcaatt acgggtcat tagttcatag cccatatatg gagttccgcg | 6180 |
| ttacataact tacggtaaat ggcccgcctg gctgaccgcc caacgacccc gcccattga | 6240 |
| cgtcaataat gacgtatgtt cccatagtaa cgccaatagg gactttccat tgacgtcaat | 6300 |
| gggtggacta tttacggtaa actgcccact tggcagtaca tcaagtgtat catatgccaa | 6360 |
| gtacgccccc tattgacgtc aatgacggta aatggcccgc ctggcattat gcccagtaca | 6420 |
| tgaccttatg ggactttcct acttggcagt acatctacgt gttagtcatc gctattacca | 6480 |
| tagtgatgcg gttttggcag tacatcaatg ggcgtggata gcggtttgac tcacggggat | 6540 |
| ttccaagtct ccaccccatt gacgtcaatg ggagtttgtt ttggcaccaa aatcaacggg | 6600 |
| actttccaaa atgtcgtaac aactccgccc cattgacgca aatgggcggt aggcgtgtac | 6660 |
| ggtgggaggt ctatataagc agagcttct ggctaactag agaacccact gcttactggc | 6720 |

<210> SEQ ID NO 116
<211> LENGTH: 340
<212> TYPE: DNA
<213> ORGANISM: Artificial Sequence
<220> FEATURE:
<223> OTHER INFORMATION: VH-N, DP-47 based coding sequence

<400> SEQUENCE: 116

| | |
|---|---|
| gaggtgcagc tgttggagtc tgggggaggc ttggtacagc ctggggggtc cctgagactc | 60 |
| tcctgtgcag cctctggatt cacctttagc agctatgcca tgagctgggt ccgccaggct | 120 |
| ccagggaagg ggctggagtg gtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtat attactgtgc gaaaggcggt | 300 |
| gcagtctact ggggccaggg aaccctggtc accgtctcct | 340 |

<210> SEQ ID NO 117
<211> LENGTH: 1031
<212> TYPE: DNA
<213> ORGANISM: Artificial Sequence

```
<220> FEATURE:
<223> OTHER INFORMATION: anti-repressor element 40 (accession number
      AY190756)

<400> SEQUENCE: 117
gatcaagaaa gcactccggg ctccagaagg agccttccag gccagctttg agcataagct      60
gctgatgagc agtgagtgtc ttgagtagtg ttcagggcag catgttacca ttcatgcttg     120
acttctagcc agtgtgacga gaggctggag tcaggtctct agagagttga gcagctccag     180
ccttagatct cccagtctta tgcggtgtgc ccattcgctt tgtgtctgca gtccctggc     240
cacacccagt aacagttctg ggatctatgg gagtagcttc cttagtgagc tttcccttca     300
aatactttgc aaccaggtag agaagtttgg agtgaaggtt ttgttcttcg tttcttcaca     360
atatggatat gcatcttctt ttgaaaatgt taaagtaaat tacctctctt ttcagatact     420
gtcttcatgc gaacttggta tcctgtttcc atcccagcct tctataaccc agtaacatct     480
tttttgaaac cagtgggtga gaaagacacc tggtcaggaa cgcggaccac aggacaactc     540
aggctcaccc acggcatcag actaaaggca aacaaggact ctgtataaag taccggtggc     600
atgtgtatta gtggagatgc agcctgtgct ctgcagacag ggagtcacac agacactttt     660
ctataatttc ttaagtgctt tgaatgttca agtagaaagt ctaacattaa atttgattga     720
acaattgtat attcatggaa tattttggaa cggaatacca aaaaatggca atagtggttc     780
tttctggatg gaagacaaac ttttcttctt taaaataaat tttattttat atatttgagg     840
ttgaccacat gaccttaagg atacatatag acagtaaact ggttactaca gtgaagcaaa     900
ttaacatatc taccatcgta catagttaca ttttttgtg tgacaggaac agctaaaatc     960
tacgtattta acaaaactcc taaagacaat acattttat taactatagc cctcatgatg    1020
tacattagat c                                                         1031

<210> SEQ ID NO 118
<211> LENGTH: 748
<212> TYPE: DNA
<213> ORGANISM: Artificial Sequence
<220> FEATURE:
<223> OTHER INFORMATION: PacI-EcoRI insert containing VLCL in p2Fab-HER2

<400> SEQUENCE: 118
ttaattaaaa ttctatttca aggagacagt cataatgaaa aaattattat tcgcaattcc      60
tttagttgtt cctttctatt ctcacagtgc agatatccag atgacccagt ccccgagctc     120
cctgtccgcc tctgtgggcg atagggtcac tatcacctgc cgtgccagtc aggatgtgag     180
tactgctgta gcctggtatc aacagaaacc aggaaaagct ccgaaactac tgatttactc     240
ggcatccttc tctaatctg gagtcccttc tcgcttctct ggatccagat ctgggacgga     300
tttcactctg accatcagca gtctgcagcc ggaagacttc gcaacttatt actgtcagca     360
attctatact actcctccca cgttcggaca gggtaccaag gtggagatca aacgtggaac     420
tgtggctgca ccatctgtct tcatcttccc gccatctgat gagcagttga aatctggaac     480
tgcctctgtt gtgtgcctgc tgaataactt ctatcccaga gaggccaaag tacagtggaa     540
ggtggataac gccctccaat cgggtaactc ccaggagagt gtcacagagc aggacagcaa     600
ggacagcacc tacagcctca gcagcaccct gacgctgagc aaagcagact acgagaaaca     660
caaagtctac gcctgcgaag tcacccatca gggcctgagt tcaccggtga caaagagctt     720
caacagggga gagtgttaat aagaattc                                        748
```

<210> SEQ ID NO 119
<211> LENGTH: 1609
<212> TYPE: DNA
<213> ORGANISM: Artificial Sequence
<220> FEATURE:
<223> OTHER INFORMATION: HindIII-NotI insert containing two VHCH1 in p2Fab-HER2

<400> SEQUENCE: 119

```
aagctttgga gcctttttt tggagatttt caacatgaaa tacctattgc ctacggcagc      60
cgctggattg ttattactcg cggcccagcc ggccatggcc gaggttcagc tggtggagtc     120
tggcggtggc ctggtgcagc caggggggctc actccgtttg tcctgtgcag cttctggctt    180
caacattaaa gacacctata tacactgggt gcgtcaggcc ccgggtaagg gcctggaatg     240
ggttgcaagg atttatccta cgaatggtta tactagatat gccgatagcg tcaagggccg     300
tttcactata agcgcagaca catccaaaaa cacagcctac ctgcagatga acagcctgcg     360
tgctgaggac actgccgtct attattgttc tagatgggga ggggacggct tctatgctat     420
ggacgtgtgg ggtcaaggaa ccctggtcac cgtctcaagc gcctccacca agggcccatc     480
ggtcttcccc ctggcaccct cctccaagag cacctctggg ggcacagcgg ccctgggctg     540
cctggtcaag gactacttcc ccgaaccggt gacggtgtcg tggaactcag gcgccctgac     600
cagcggcgtc cacaccttcc cggctgtcct acagtcctca ggactctact ccctcagcag     660
cgtagtgacc gtgccctcca gcagcttggg cacccagacc tacatctgca acgtgaatca     720
caagcccagc aacaccaagg tggacaagaa agttgagccc aaatcttgtg cggcagcaga     780
acaaaaactc atctcagaag aggatctgaa tgacgccgca caccatcatc atcaccatta     840
ataaggcgcg ccaattctat ttcaaggaga cagtcataat gaaaaaatta ttattcgcaa     900
ttcctttagt tgttcctttc tattctcaca gtgcagaggt tcagctggtg gagtctggcg     960
gtggcctggt gcagccaggg ggctcactcc gtttgtcctg tgcagcttct ggcttcacct    1020
tcacagacta tcatggac tgggtgcgtc aggccccggg taagggcctg aatgggttg       1080
cagacgtgaa cccaaactct ggggggctcta tctacaacca gcgcttcaag ggtcgtttca    1140
ctctgagcgt agacagatcc aaaaacacac tgtacctgca gatgaacagc ctgcgtgctg    1200
aggacactgc cgtctattat tgtgctagaa acctgggacc ctctttctac ttcgattact    1260
ggggtcaagg aaccctggtc accgtctcaa gcgcctccac caagggccca tcggtcttcc    1320
ccctggcacc ctcctccaag agcacctctg ggggcacagc ggccctgggc tgcctggtca    1380
aggactactt ccccgaaccg gtgacggtgt cgtggaactc aggcgccctg accagcggcg    1440
tccacacctt cccggctgtc ctacagtcct caggactcta ctccctcagc agcgtagtga    1500
ccgtgccctc agcagcttg gcacccaga cctacatctg caacgtgaat cacaagccca      1560
gcaacaccaa ggtggacaag aaagttgagc ccaaatcttg tgcggccgc                1609
```

<210> SEQ ID NO 120
<211> LENGTH: 59
<212> TYPE: DNA
<213> ORGANISM: Artificial Sequence
<220> FEATURE:
<223> OTHER INFORMATION: primer

<400> SEQUENCE: 120

```
gtcctcgcaa ctgcggccca gccggccatg gcagaggtgc agctgttgga gtctggggg      59
```

<210> SEQ ID NO 121
<211> LENGTH: 21

<212> TYPE: DNA
<213> ORGANISM: Artificial Sequence
<220> FEATURE:
<223> OTHER INFORMATION: primer

<400> SEQUENCE: 121
acccgggtca ccgtctcctc c                                              21

<210> SEQ ID NO 122
<211> LENGTH: 10
<212> TYPE: PRT
<213> ORGANISM: Artificial Sequence
<220> FEATURE:
<223> OTHER INFORMATION: c-myc tag

<400> SEQUENCE: 122

Glu Gln Lys Leu Ile Ser Glu Glu Asp Leu
1               5                   10

<210> SEQ ID NO 123
<211> LENGTH: 11
<212> TYPE: PRT
<213> ORGANISM: Artificial Sequence
<220> FEATURE:
<223> OTHER INFORMATION: VSV-tag

<400> SEQUENCE: 123

Tyr Thr Asp Ile Glu Met Asn Arg Leu Gly Lys
1               5                   10

<210> SEQ ID NO 124
<211> LENGTH: 9
<212> TYPE: PRT
<213> ORGANISM: Artificial Sequence
<220> FEATURE:
<223> OTHER INFORMATION: influenz Hemagglutinin (HA)-tag

<400> SEQUENCE: 124

Tyr Pro Tyr Asp Val Pro Asp Tyr Ala
1               5

<210> SEQ ID NO 125
<211> LENGTH: 42
<212> TYPE: DNA
<213> ORGANISM: Artificial Sequence
<220> FEATURE:
<223> OTHER INFORMATION: primer

<400> SEQUENCE: 125
tatccgcgcg cactccgagg tgcagctgtt ggagtctggg gg                       42

<210> SEQ ID NO 126
<211> LENGTH: 43
<212> TYPE: DNA
<213> ORGANISM: Artificial Sequence
<220> FEATURE:
<223> OTHER INFORMATION: primer

<400> SEQUENCE: 126
acccgggtca ccgtctcctc cggtgagtcc tagcgctttt cgt                      43

<210> SEQ ID NO 127
<211> LENGTH: 23
<212> TYPE: DNA
<213> ORGANISM: Artificial Sequence
<220> FEATURE:
<223> OTHER INFORMATION: primer HuVl1A-BACK

<400> SEQUENCE: 127
cagtctgtgc tgactcagcc acc                                              23

<210> SEQ ID NO 128
<211> LENGTH: 23
<212> TYPE: DNA
<213> ORGANISM: Artificial Sequence
<220> FEATURE:
<223> OTHER INFORMATION: primer HuV11B-BACK

<400> SEQUENCE: 128
cagtctgtgy tgacgcagcc gcc                                              23

<210> SEQ ID NO 129
<211> LENGTH: 23
<212> TYPE: DNA
<213> ORGANISM: Artificial Sequence
<220> FEATURE:
<223> OTHER INFORMATION: primer HuV11C-BACK

<400> SEQUENCE: 129
cagtctgtcg tgacgcagcc gcc                                              23

<210> SEQ ID NO 130
<211> LENGTH: 21
<212> TYPE: DNA
<213> ORGANISM: Artificial Sequence
<220> FEATURE:
<223> OTHER INFORMATION: primer HuV12-BACK

<400> SEQUENCE: 130
cartctgccc tgactcagcc t                                                21

<210> SEQ ID NO 131
<211> LENGTH: 23
<212> TYPE: DNA
<213> ORGANISM: Artificial Sequence
<220> FEATURE:
<223> OTHER INFORMATION: primer HuCl2-FOR

<400> SEQUENCE: 131
tgaacattct gtaggggcca ctg                                              23

<210> SEQ ID NO 132
<211> LENGTH: 23
<212> TYPE: DNA
<213> ORGANISM: Artificial Sequence
<220> FEATURE:
<223> OTHER INFORMATION: primer HuCL7-FOR

<400> SEQUENCE: 132
agagcattct gcaggggcca ctg                                              23

<210> SEQ ID NO 133
<211> LENGTH: 41
<212> TYPE: DNA
<213> ORGANISM: Artificial Sequence
<220> FEATURE:
<223> OTHER INFORMATION: primer HuV11A-BACK-APA

<400> SEQUENCE: 133
accgcctcca ccagtgcaca gtctgtgctg actcagccac c                          41

<210> SEQ ID NO 134

<211> LENGTH: 41
<212> TYPE: DNA
<213> ORGANISM: Artificial Sequence
<220> FEATURE:
<223> OTHER INFORMATION: primer HuVl1B-BACK-APA

<400> SEQUENCE: 134
accgcctcca ccagtgcaca gtctgtgytg acgcagccgc c                41

<210> SEQ ID NO 135
<211> LENGTH: 41
<212> TYPE: DNA
<213> ORGANISM: Artificial Sequence
<220> FEATURE:
<223> OTHER INFORMATION: primer HuVl1C-BACK-APA

<400> SEQUENCE: 135
accgcctcca ccagtgcaca gtctgtcgtg acgcagccgc c                41

<210> SEQ ID NO 136
<211> LENGTH: 39
<212> TYPE: DNA
<213> ORGANISM: Artificial Sequence
<220> FEATURE:
<223> OTHER INFORMATION: primer HuVl2-BACK-APA

<400> SEQUENCE: 136
accgcctcca ccagtgcaca rtctgccctg actcagcct                  39

<210> SEQ ID NO 137
<211> LENGTH: 50
<212> TYPE: DNA
<213> ORGANISM: Artificial Sequence
<220> FEATURE:
<223> OTHER INFORMATION: primer HuCl2-FOR-ASC

<400> SEQUENCE: 137
accgcctcca ccgggcgcgc cttattatga acattctgta ggggccactg      50

<210> SEQ ID NO 138
<211> LENGTH: 50
<212> TYPE: DNA
<213> ORGANISM: Artificial Sequence
<220> FEATURE:
<223> OTHER INFORMATION: primer HuCl7-FOR-ASC

<400> SEQUENCE: 138
accgcctcca ccgggcgcgc cttattaaga gcattctgca ggggccactg      50

<210> SEQ ID NO 139
<211> LENGTH: 24
<212> TYPE: DNA
<213> ORGANISM: Artificial Sequence
<220> FEATURE:
<223> OTHER INFORMATION: primer CH1FOR

<400> SEQUENCE: 139
gtccttgacc aggcagccca gggc                                  24

<210> SEQ ID NO 140
<211> LENGTH: 17
<212> TYPE: DNA
<213> ORGANISM: Artificial Sequence
<220> FEATURE:
<223> OTHER INFORMATION: primer M13REV

<400> SEQUENCE: 140

```
caggaaacag ctatgac                                                    17

<210> SEQ ID NO 141
<211> LENGTH: 59
<212> TYPE: DNA
<213> ORGANISM: Artificial Sequence
<220> FEATURE:
<223> OTHER INFORMATION: primer

<400> SEQUENCE: 141
gtcctcgcaa ctgcggccca gccggccatg gcagaggtgc agctgttgga gtctggggg    59

<210> SEQ ID NO 142
<211> LENGTH: 104
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(104)
<223> OTHER INFORMATION: /Note="mutagenic oligonucleotide"

<400> SEQUENCE: 142
cacggccgta tattactgtg cgaaagatcg agaggttact atgatagttg tacttaatgg    60
aggctttgac tactggggcc agggaacccg ggtcaccgtc tcct                    104

<210> SEQ ID NO 143
<211> LENGTH: 5
<212> TYPE: PRT
<213> ORGANISM: Artificial Sequence
<220> FEATURE:
<223> OTHER INFORMATION: part of antibody CDR3

<400> SEQUENCE: 143

Gly Gly Ala Val Tyr
1               5

<210> SEQ ID NO 144
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(34)
<223> OTHER INFORMATION: oligo incorporating restriction sites

<400> SEQUENCE: 144
gtccctagga attcgatcaa gaaagcactc cggg                                34

<210> SEQ ID NO 145
<211> LENGTH: 35
<212> TYPE: DNA
<213> ORGANISM: Artificial Sequence
<220> FEATURE:
<223> OTHER INFORMATION: oligo incorporating restriction sites

<400> SEQUENCE: 145
cctcatgatg tacattagat cgaattcgta atacg                               35

<210> SEQ ID NO 146
<211> LENGTH: 6
<212> TYPE: DNA
<213> ORGANISM: Artificial Sequence
```

```
<220> FEATURE:
<223> OTHER INFORMATION: restriction site

<400> SEQUENCE: 146 gaattc                                                                6

<210> SEQ ID NO 147
<211> LENGTH: 16
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(16)
<223> OTHER INFORMATION: /Note="sequence appended to primer"

<400> SEQUENCE: 147
tatccgcgcg cactcc                                                    16

<210> SEQ ID NO 148
<211> LENGTH: 168
<212> TYPE: DNA
<213> ORGANISM: Artificial Sequence
<220> FEATURE:
<223> OTHER INFORMATION: polylinker sequence of pSCFV
<220> FEATURE:
<221> NAME/KEY: CDS
<222> LOCATION: (1)..(168)

<400> SEQUENCE: 148 gcg gcc cag ccg gcc atg gca cag gtc caa ctg cag gtc acc gtc tcg    48
Ala Ala Gln Pro Ala Met Ala Gln Val Gln Leu Gln Val Thr Val Ser
1               5                   10                  15 agt ggt gga ggc ggt tca ggc gga ggt ggc tct ggc ggt ggc gga tcg    96
Ser Gly Gly Gly Gly Ser Gly Gly Gly Gly Ser Gly Gly Gly Gly Ser
                20                  25                  30 gat atc gag ctc act gag atc aaa cgg gcg gcc gca gaa caa aaa ctc   144
Asp Ile Glu Leu Thr Glu Ile Lys Arg Ala Ala Ala Glu Gln Lys Leu
            35                  40                  45 atc tca gaa gag gat ctg aat taa                                   168
Ile Ser Glu Glu Asp Leu Asn
        50                  55

<210> SEQ ID NO 149
<211> LENGTH: 55
<212> TYPE: PRT
<213> ORGANISM: Artificial Sequence
<220> FEATURE:
<223> OTHER INFORMATION: Synthetic Construct

<400> SEQUENCE: 149

Ala Ala Gln Pro Ala Met Ala Gln Val Gln Leu Gln Val Thr Val Ser
1               5                   10                  15

Ser Gly Gly Gly Gly Ser Gly Gly Gly Gly Ser Gly Gly Gly Gly Ser
                20                  25                  30

Asp Ile Glu Leu Thr Glu Ile Lys Arg Ala Ala Ala Glu Gln Lys Leu
            35                  40                  45

Ile Ser Glu Glu Asp Leu Asn
        50                  55

<210> SEQ ID NO 150
<211> LENGTH: 13
<212> TYPE: DNA
<213> ORGANISM: Artificial Sequence
```

```
<220> FEATURE:
<223> OTHER INFORMATION: enzyme site SfiI
<220> FEATURE:
<221> NAME/KEY: misc_feature
<222> LOCATION: (5)..(9)
<223> OTHER INFORMATION: "N" stands for any nucleic acid

<400> SEQUENCE: 150
ggccnnnnng gcc                                                       13

<210> SEQ ID NO 151
<211> LENGTH: 8
<212> TYPE: DNA
<213> ORGANISM: Artificial Sequence
<220> FEATURE:
<223> OTHER INFORMATION: enzyme site NotI

<400> SEQUENCE: 151 gcggccgc                                                              8

<210> SEQ ID NO 152
<211> LENGTH: 6
<212> TYPE: DNA
<213> ORGANISM: Artificial Sequence
<220> FEATURE:
<223> OTHER INFORMATION: enzyme site ApaLI

<400> SEQUENCE: 152 gtgcac                                                                6

<210> SEQ ID NO 153
<211> LENGTH: 6
<212> TYPE: DNA
<213> ORGANISM: Artificial Sequence
<220> FEATURE:
<223> OTHER INFORMATION: enzyme site XhoI

<400> SEQUENCE: 153 ctcgag                                                                6

<210> SEQ ID NO 154
<211> LENGTH: 6
<212> TYPE: DNA
<213> ORGANISM: Artificial Sequence
<220> FEATURE:
<223> OTHER INFORMATION: enzyme site SacI

<400> SEQUENCE: 154 gagctc                                                                6

<210> SEQ ID NO 155
<211> LENGTH: 6
<212> TYPE: DNA
<213> ORGANISM: Artificial Sequence
<220> FEATURE:
<223> OTHER INFORMATION: enzyme site PstI

<400> SEQUENCE: 155 ctgcag                                                                6

<210> SEQ ID NO 156
<211> LENGTH: 6
<212> TYPE: DNA
<213> ORGANISM: Artificial Sequence
<220> FEATURE:
<223> OTHER INFORMATION: enzyme site NcoI
```

```
<400> SEQUENCE: 156 ccatgg                                                              6

<210> SEQ ID NO 157
<211> LENGTH: 6
<212> TYPE: DNA
<213> ORGANISM: Artificial Sequence
<220> FEATURE:
<223> OTHER INFORMATION: enzyme site SalI

<400> SEQUENCE: 157 gtcgac                                                              6

<210> SEQ ID NO 158
<211> LENGTH: 7
<212> TYPE: DNA
<213> ORGANISM: Artificial Sequence
<220> FEATURE:
<223> OTHER INFORMATION: enzyme site BstEII
<220> FEATURE:
<221> NAME/KEY: misc_feature
<222> LOCATION: (4)..(4)
<223> OTHER INFORMATION: "N" stands for any nucleic acid

<400> SEQUENCE: 158 ggtnacc                                                             7

<210> SEQ ID NO 159
<211> LENGTH: 6
<212> TYPE: DNA
<213> ORGANISM: Artificial Sequence
<220> FEATURE:
<223> OTHER INFORMATION: enzyme site EcoRV

<400> SEQUENCE: 159 gatatc                                                              6

<210> SEQ ID NO 160
<211> LENGTH: 355
<212> TYPE: DNA
<213> ORGANISM: Artificial Sequence
<220> FEATURE:
<223> OTHER INFORMATION: part of plasmid comprising 3 antibody-regions
<220> FEATURE:
<221> NAME/KEY: CDS
<222> LOCATION: (1)..(102)
<220> FEATURE:
<221> NAME/KEY: misc_feature
<222> LOCATION: (91)..(93)
<223> OTHER INFORMATION: "n" stands for unknown nucleic acid
<220> FEATURE:
<221> NAME/KEY: CDS
<222> LOCATION: (143)..(355)
<220> FEATURE:
<221> NAME/KEY: misc_feature
<222> LOCATION: (257)..(259)
<223> OTHER INFORMATION: "n" stands for unknown nucleic acid

<400> SEQUENCE: 160 tta ttc gca att cct tta gtt gtt cct ttc tat tct cac agt gca cag     48
Leu Phe Ala Ile Pro Leu Val Val Pro Phe Tyr Ser His Ser Ala Gln
1               5                   10                  15 gtc caa ctg cag gtc gac ctc gag atc aaa cgt gga act gtg nnn gga     96
Val Gln Leu Gln Val Asp Leu Glu Ile Lys Arg Gly Thr Val Xaa Gly
                20                  25                  30 gag tgt taataaggcg cgccaattct atttcaagga gacagtcata atg aaa tac    151
Glu Cys                                                Met Lys Tyr
                                                       35
```

```
cta ttg cct acg gca gcc gct gga ttg tta tta ctc gcg gcc cag ccg      199
Leu Leu Pro Thr Ala Ala Ala Gly Leu Leu Leu Leu Ala Ala Gln Pro
        40                  45                  50 gcc atg gcc cag gtg cag ctg cag gag agc ggg gtc acc gtc tca agc      247
Ala Met Ala Gln Val Gln Leu Gln Glu Ser Gly Val Thr Val Ser Ser
 55                  60                  65 gcc tcc acc nnn aaa tct tgt gcg gcc gca cat cat cat cat cat cac      295
Ala Ser Thr Xaa Lys Ser Cys Ala Ala Ala His His His His His His
 70              75                  80                  85 ggg gcc gca gaa caa aaa ctc atc tca gaa gag gat ctg aat ggg gcc      343
Gly Ala Ala Glu Gln Lys Leu Ile Ser Glu Glu Asp Leu Asn Gly Ala
                90                  95                 100 gca tag act gtt                                                       355
Ala     Thr Val
```

<210> SEQ ID NO 161
<211> LENGTH: 34
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 161

```
Leu Phe Ala Ile Pro Leu Val Val Pro Phe Tyr Ser His Ser Ala Gln
1               5                  10                  15

Val Gln Leu Gln Val Asp Leu Glu Ile Lys Arg Gly Thr Val Xaa Gly
            20                  25                  30

Glu Cys
```

<210> SEQ ID NO 162
<211> LENGTH: 68
<212> TYPE: PRT
<213> ORGANISM: Artificial Sequence
<220> FEATURE:
<221> NAME/KEY: misc_feature
<222> LOCATION: (39)..(39)
<223> OTHER INFORMATION: The 'Xaa' at location 39 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 162

```
Met Lys Tyr Leu Leu Pro Thr Ala Ala Ala Gly Leu Leu Leu Leu Ala
1               5                  10                  15

Ala Gln Pro Ala Met Ala Gln Val Gln Leu Gln Glu Ser Gly Val Thr
            20                  25                  30

Val Ser Ser Ala Ser Thr Xaa Lys Ser Cys Ala Ala Ala His His His
        35                  40                  45

His His His Gly Ala Ala Glu Gln Lys Leu Ile Ser Glu Glu Asp Leu
    50                  55                  60

Asn Gly Ala Ala
65
```

<210> SEQ ID NO 163
<211> LENGTH: 108
<212> TYPE: PRT

```
<213> ORGANISM: Artificial Sequence
<220> FEATURE:
<223> OTHER INFORMATION: Hybrid light chain

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 164
<211> LENGTH: 108
<212> TYPE: PRT
<213> ORGANISM: Artificial Sequence
<220> FEATURE:
<223> OTHER INFORMATION: Hybrid light chain

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg
            100                 105

<210> SEQ ID NO 165
<211> LENGTH: 108
<212> TYPE: PRT
<213> ORGANISM: Artificial Sequence
<220> FEATURE:
<223> OTHER INFORMATION: Hybrid light chain
<220> FEATURE:
<221> NAME/KEY: MISC_FEATURE
<222> LOCATION: (24)..(96)
<223> OTHER INFORMATION: "X" means positions to be targeted for
      diversification in a library approach

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Xaa Xaa Xaa
            20                  25                  30
```

```
Val Ala Trp Tyr Gln Gln Lys Pro Gly Lys Ala Pro Lys Leu Leu Ile
            35                  40                  45

Tyr Ser Ala Ser Xaa Xaa Tyr Xaa Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Xaa Tyr Xaa Xaa Pro Xaa
                 85                  90                  95

Thr Phe Gly Gln Gly Thr Lys Val Glu Ile Lys Arg
            100                 105
```

<210> SEQ ID NO 166
<211> LENGTH: 108
<212> TYPE: PRT
<213> ORGANISM: Artificial Sequence
<220> FEATURE:
<223> OTHER INFORMATION: Hybrid light chain
<220> FEATURE:
<221> NAME/KEY: MISC_FEATURE
<222> LOCATION: (53)..(56)
<223> OTHER INFORMATION: "X" means positions to be targeted for
      diversification in a library approach

<400> SEQUENCE: 166

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Xaa Xaa Tyr Xaa Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Thr Thr Pro Pro
                 85                  90                  95

Thr Phe Gly Gln Gly Thr Lys Val Glu Ile Lys Arg
            100                 105
```

<210> SEQ ID NO 167
<211> LENGTH: 55
<212> TYPE: PRT
<213> ORGANISM: Artificial Sequence
<220> FEATURE:
<223> OTHER INFORMATION: polylinker sequence of pSCFV

<400> SEQUENCE: 167

```
Ala Ala Gln Pro Ala Met Ala Gln Val Gln Leu Gln Val Thr Val Ser
 1               5                  10                  15

Ser Gly Gly Gly Gly Ser Gly Gly Gly Gly Ser Gly Gly Gly Gly Ser
            20                  25                  30

Asp Ile Glu Leu Thr Glu Ile Lys Arg Ala Ala Ala Glu Gln Lys Leu
            35                  40                  45

Ile Ser Glu Glu Asp Leu Asn
     50                  55
```

<210> SEQ ID NO 168
<211> LENGTH: 34
<212> TYPE: PRT
<213> ORGANISM: Artificial Sequence
<220> FEATURE:

```
<223> OTHER INFORMATION: part of plasmid comprising 3 antibody-regions
<220> FEATURE:
<221> NAME/KEY: MISC_FEATURE
<222> LOCATION: (31)..(31)
<223> OTHER INFORMATION: Xaa stands for Lys, Asn, Arg, Ser, Thr, Ile,
      Met, Glu, Asp, Gly, Ala, Val, Gln, His, Pro, Leu, a stop codon,
      Tyr, Trp, Cys, or Phe.

<400> SEQUENCE: 168

Leu Phe Ala Ile Pro Leu Val Val Pro Phe Tyr Ser His Ser Ala Gln
1               5                   10                  15

Val Gln Leu Gln Val Asp Leu Glu Ile Lys Arg Gly Thr Val Xaa Gly
            20                  25                  30

Glu Cys

<210> SEQ ID NO 169
<211> LENGTH: 68
<212> TYPE: PRT
<213> ORGANISM: Artificial Sequence
<220> FEATURE:
<223> OTHER INFORMATION: part of plasmid comprising 3 antibody-regions
<220> FEATURE:
<221> NAME/KEY: misc_feature
<222> LOCATION: (39)..(39)
<223> OTHER INFORMATION: Xaa can be any naturally occurring amino acid

<400> SEQUENCE: 169

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Val Thr
            20                  25                  30

Val Ser Ser Ala Ser Thr Xaa Lys Ser Cys Ala Ala Ala His His His
        35                  40                  45

His His His Gly Ala Ala Glu Gln Lys Leu Ile Ser Glu Glu Asp Leu
    50                  55                  60

Asn Gly Ala Ala
65
```